US007772247B2

(12) United States Patent
Vaisburg et al.

(10) Patent No.: US 7,772,247 B2
(45) Date of Patent: Aug. 10, 2010

(54) SUBSTITUTED THIENO[3,2-D]PYRIDINES AS INHIBITORS OF THE VEGF RECEPTOR AND HGF RECEPTOR

(75) Inventors: Arkadii Vaisburg, Kirkland (CA); Stephen William Claridge, Montreal (CA); Franck Raeppel, Montreal (CA); Oscar Mario Saavedra, Outremont (CA); Naomy Berstein, Cote Saint-Luc (CA); Marie-Claude Granger, Lapraine (CA); Lijie Zhan, Montreal (CA); Amal Wahhab, Laval (CA); David Llewellyn, Vancouver (CA)

(73) Assignee: Methylgene Inc., St. Laurent, Quebec (CA)

( * ) Notice: Subject to any disclaimer, the term of this patent is extended or adjusted under 35 U.S.C. 154(b) by 1022 days.

(21) Appl. No.: 11/191,617

(22) Filed: Jul. 28, 2005

(65) Prior Publication Data
US 2006/0074056 A1 Apr. 6, 2006

Related U.S. Application Data

(60) Provisional application No. 60/592,913, filed on Jul. 30, 2004, provisional application No. 60/683,038, filed on May 20, 2005.

(51) Int. Cl.
C07D 495/04 (2006.01)
A61K 31/4365 (2006.01)
C07D 413/04 (2006.01)
C07D 413/06 (2006.01)
C07D 413/12 (2006.01)
C07D 413/10 (2006.01)
C07D 223/04 (2006.01)
A61P 35/04 (2006.01)
A61P 9/10 (2006.01)
A61K 31/519 (2006.01)
C07D 487/04 (2006.01)
C07D 401/04 (2006.01)
C07D 471/04 (2006.01)

(52) U.S. Cl. .................. 514/301; 546/114; 546/113; 546/15; 544/278; 544/280; 544/127; 544/362; 544/117; 544/333; 514/260.1; 514/265.1; 514/233.8; 514/253.04; 514/217.07; 514/300; 514/256; 540/607

(58) Field of Classification Search .................. 546/114; 514/301
See application file for complete search history.

(56) References Cited

U.S. PATENT DOCUMENTS 6,232,320 B1  5/2001   Stewart et al.
6,448,261 B1  9/2002   Bakthavatchalam et al.
6,492,383 B1  12/2002  Munchhof et al.
6,833,456 B2  12/2004  Romines, III et al.
6,995,171 B2  2/2006   Autry et al.
2002/0004511 A1  1/2002   Luzzio et al.
2005/0239820 A1  10/2005  Borzilleri et al.
2005/0245547 A1  11/2005  Kim et al.
2005/0288290 A1  12/2005  Borzilleri et al.
2006/0004006 A1  1/2006   Borzilleri et al.
2006/0211695 A1  9/2006   Borzilleri et al.

FOREIGN PATENT DOCUMENTS

| CA | 2309690 | 10/1998 |
|----|---------|---------|
| CA | 2451678 | 1/2003 |
| CA | 2477651 | 10/2003 |
| CA | 2502614 | 6/2004 |
| WO | WO9924440 | 5/1999 |
| WO | WO9962908 | 12/1999 |
| WO | WO0075145 | 12/2000 |
| WO | WO0194353 | 12/2001 |
| WO | WO03000194 | 1/2003 |
| WO | WO03000688 | 1/2003 |
| WO | WO03074529 | 9/2003 |
| WO | WO2004048386 | 6/2004 |
| WO | WO2005014325 | 2/2005 |
| WO | WO2005021554 | 3/2005 |
| WO | WO2005073224 | 8/2005 |
| WO | 2005/116028 | 12/2005 |
| WO | WO2005117867 | 12/2005 |
| WO | WO2005121125 | 12/2005 |
| WO | WO 2005121125 | * 12/2005 |
| WO | WO2006004636 | 1/2006 |
| WO | WO2006004833 | 1/2006 |
| WO | WO 2006/014325 | 2/2006 |
| WO | WO2006036266 | 4/2006 |
| WO | WO2006104161 | 10/2006 |
| WO | WO2006116713 | 11/2006 |

OTHER PUBLICATIONS

Vippagunta et. al. (Advanced Drug Delivery Reviews, 2001, 48, 3-26.*
Fan et al., "Controlling the Vasculature: Angiogenesis . . . ", Trends Pharmacol. Sci. 16:57-66 (1995).
Folkman, J., Angiogenesis in Cancer, Vascular, Rheumatoid and Other . . . , Nat. Med. 1:27-31 (1995).
Jakeman et al., "Developmental Expression of Binding Sites . . . ", Endocrinology, 133:848-859 (1993).
Connolly et al., "Human Vascular Permeability Factor . . . ", J. Biol. Chem. 264:20017-20024 (1989).
Plowman et al., "Receptor Tyrosine Kinases as Targets for . . . ", Drug News Perspect. 7:334-339 (1994).
Strawn et al., "Tyrosine Kinases in Disease: Overview . . . ", Exp. Opin. Invest. Drugs 7:553-573 (1998).
Shawver et al., "Receptor Tyrosine Kinases as Targets for . . . ", Drug Discov. Today 2:50-63 (1997).

(Continued)

Primary Examiner—Susanna Moore
(74) Attorney, Agent, or Firm—Wood, Phillips, Katz, Clark & Mortimer

(57) ABSTRACT

The invention relates to the inhibition of VEGF receptor signaling and HGF receptor signaling. The invention provides compounds and methods for inhibiting VEGF receptor signaling and HGF receptor signaling. The invention also provides compositions and methods for treating cell proliferative diseases and conditions 77 Claims, No Drawings

OTHER PUBLICATIONS

De Vries et al., "The FMS-Like Tyrosine Kinases, a Receptor . . . " Science 255:989-991 (1992).

Terman et al., "identification of the KDR . . . ", Biochem. Biophys. Res. Commun. 187:1579-1586 (1992).

Plate et al., "Vascular Endothelial Growth Factor and Glioma . . . ", Int. J. Cancer 59:520-529 (1994).

Fuh et al., "Requirements for Binding and Signaling of the . . . ", J. Biol. Chem. 273:11197-11204 (1998).

Wheeler-Jones et al., "Vascular Endothelial Growth . . . ", FEBS Lett. 420:28-32 (1997).

Kim et al., "Inhibition of Vascular Endothelial Growth..", Nature (Lond.) 362:841-844 (1993).

Kanai et al., "Anti-Tumor and Anti-Metastatic Effects . . . ", Int. J. Cancer 77:933-936 (1998).

Zhu et al., "Inhibition of Vascular Endothelial Growth Factor..", Cancer Res. 58:3209-3214 (1998).

Siemeister et al., "An Antagonistic Vascular Endo . . . ", Proc. Natl. Acad. Sci. USA 95:4625-4629 (1998).

Lin, P. et al. "Inhibition of Tumor Growth by Targeting . . . ", Cell Growth Differ. 9:49-58 (1998).

Cheng et al., "Suppression of Glioblastoma Angiogenicity . . . ", Proc. Natl. Acad. Sci. USA 93:8502-8507 (1996).

Millauer et al. "Dominant-Negative Inhibition of Flk-1 Suppresses..", Cancer Res. 56:1615-1620 (1996).

Pennacchietti et al., "Hypoxia Promotes Invasive Growth by Transcriptional Activation of the Met Protooncogene", Cancer Cell. 3(4):347-361 (2003).

Camps et al., "Fibroblast-Mediate Acceleration of Human Epithelial Tumor Growth in Vivo", Proc. Natl. Acad. Sci. USA 87:75-9 (1990).

Nakamura et al., "Induction of Hepatocyte Growth Factor in Fibroblasts by Tumor-Derived Factors Affects Invasive Growth of Tumor Cells: in Vitro Analysis of Tumor-Stromal Interactions", Cancer Res. 57:3305-3313 (1997).

Nishimura et al., "Regulation of Invasive Potential of Human . . . ", Int. J. Urol. 5:276-281 (1998).

Bae-Jump et al., "Hepatocyte Growth Factor (HGF) Induces . . . ", Gynecol. Oncol. 73:265-272 (1999).

Nakamura et al., "A Partial Purification and Characterization . . . ",Bioch. Bio. Res. Com. 122:1450-9 (1984).

Nakamura et al., "Molecular Cloning and Expression of Human ", Nature 342:440-443 (1989).

Ebert et al., "Coexpression of the C-Met Proto-oncogene and . . . ", Cancer Res. 54:5775-5778 (1994).

DiRenzo et al., "Expression of the Met-HGF Receptor in normal . . . ", Oncogene 6:1997-2003 (1991).

DiRenzo et al., "Expression of the Met/Hepatocyte Growth Factor." Cancer Res. 11:1129-1138 (1995).

Delehedde et al., "Hepatocyte Growth Factor/Scatter Factor . . . " Eur. J. Biochem. 269:4423-4429 (2001).

Bardelli et al., "Concomitant Activation of Pathways Downstream . . . ", Oncogene 18:1139-1146 (1999).

Saucier et al., "The SHC Adaptor Protein is Critical for . . . " Nat. Acad. Sci. USA 101(8):2345-2350 (2004).

Evans et al., "Addition of Lithiated 9-Deazapurine Derivatives", J. Org. Chem.,66(17):5723-5730 (2001).

Tsou et al., "6-Substituted-4-(3-bromophenylamino) Quinazolines..", J. Med. Chem. 44:2719-2734 (2001).

Cliff et al., "Synthesis of 4,4'-Biimidazoles", Synthesis pp. 681-682 (1994).

He et al., "A Convenient Synthesis of 1,4-Disubstituted . . . ", Tetrahedron Lett. 45(28):5529-5532 (2004).

O'Connell et al., "Convenient Synthesis of Methyl 1-Methyl-2,4-Dibromo..", Synthesis pp. 767-771 (1988).

Gutschow et al., "2-(Diethylamino)Thieno[1,3]Oxazin-4..", J. Med. Chem. 42(26):5437-5447 (1999).

Robba et al., "Thienopyrimidines", Bull Soc. Chem. Fr. 587-591 (1975).

Hodgson et al., "The Nitrosation of Phenols. Part VII. . . . ", J. Chem. Soc. pp. 2775-2778 (1929).

Smith et al., "Cyclization of Isothiocyanates as a Route to . . . ", J. Org. Chem. pp. 2261-2265 (1964).

Evans et al., "Addition of Lithiated 9-Deazapurine . . . ", J. Org. Chem. 66(17):5723-5730 (2001).

Antilla et al., "The Copper-Catalyzed N-Arylation of Indoles", JACS 124:11684-11688 (2002).

Zhang et al., "A General Method for the Preparation of . . . ", J. Org. Chem. 67:2345-2347 (2002).

Almansa et al., "Synthesis and SAR of a New Series of COX-2 . . . ", J. med. Chem. 44:350-361 (2001).

Hill et al., "Dialkylacetyl Biurets", JACS 62:1595-1596 (1940).

* cited by examiner

SUBSTITUTED THIENO[3,2-D]PYRIDINES AS INHIBITORS OF THE VEGF RECEPTOR AND HGF RECEPTOR

RELATED APPLICATIONS

This application claims the benefit of U.S. Provisional Patent Application Ser. No. 60/592,913, filed on Jul. 30, 2004, and U.S. Provisional Patent Application Ser. No. 60/683,038, filed on May 20, 2005, the contents of which are incorporated herein by reference in their entirety.

BACKGROUND OF THE INVENTION

1. Field of the Invention

This invention relates to the inhibition of VEGF receptor signaling and HGF receptor signaling. More particularly, the invention relates to compounds and methods for the inhibition of VEGF receptor signaling and HGF receptor signaling.

2. Summary of the Related Art

Angiogenesis is an important component of certain normal physiological processes such as embryogenesis and wound healing, but aberrant angiogenesis contributes to some pathological disorders and in particular to tumor growth.[1,2] VEGF-A (vascular endothelial growth factor A) is a key factor promoting neovascularization (angiogenesis) of tumors.[3-7] VEGF induces endothelial cell proliferation and migration by signaling through two high affinity receptors, the fms-like tyrosine kinase receptor, Flt-1, and the kinase insert domain-containing receptor, KDR.[8,9,10] These signaling responses are critically dependent upon receptor dimerization and activation of intrinsic receptor tyrosine kinase (RTK) activity. The binding of VEGF as a disulfide-linked homodimer stimulates receptor dimerization and activation of the RTK domain [11]. The kinase activity autophosphorylates cytoplasmic receptor tyrosine residues, which then serve as binding sites for molecules involved in the propagation of a signaling cascade. Although multiple pathways are likely to be elucidated for both receptors, KDR signaling is most extensively studied, with a mitogenic response suggested to involve ERK-1 and ERK-2 mitogen-activatedprotein kinases [12].

Disruption of VEGF receptor signaling is a highly attractive therapeutic target in cancer, as angiogenesis is a prerequisite for all solid tumor growth, and that the mature endothelium remains relatively quiescent (with the exception of the female reproductive system and wound healing). A number of experimental approaches to inhibiting VEGF signaling have been examined, including use of neutralizing antibodies [13,14,15], receptor antagonists [16], soluble receptors [17], antisense constructs [18] and dominant-negative strategies [19].

Despite the attractiveness of anti-angiogenic therapy by VEGF inhibition alone, several issues may limit this approach. VEGF expression levels can themselves be elevated by numerous diverse stimuli and perhaps most importantly, the hypoxic state of tumors resulting from VEGFr inhibition, can lead to the induction of factors that themselves promote tumor invasion and metastasis thus, potentially undermining the impact of VEGF inhibitors as cancer therapeutics [20].

The HGF (hepatocyte growth factor) and the HGF receptor, c-met, are implicated in the ability of tumor cells to undermine the activity of VEGF inhibition [20]. HGF derived from either stromal fibroblasts surrounding tumor cells or expressed from the tumor itself has been suggested to play a critical role in tumor angiogenesis, invasion and metastasis [21,22]. For example, invasive growth of certain cancer cells is drastically enhanced by tumor-stromal interactions involving the HGF/c-Met (HGF receptor) pathway [21,24,25]. HGF, which was originally identified as a potent mitogen for hepatocytes [26,27] is primarily secreted from stromal cells, and the secreted HGF can promote motility and invasion of various cancer cells that express c-Met in a paracrine manner [28,29,30]. Binding of HGF to c-Met leads to receptor phosphorylation and activation of Ras/mitogen-activated protein kinase (MAPK) signaling pathway, thereby enhancing malignant behaviors of cancer cells [30,31]. Moreover, stimulation of the HGF/c-met pathway itself can lead to the induction of VEGF expression, itself contributing directly to angiogenic activity[32].

Thus, anti-tumor anti-angiogenic strategies or approaches that target both VEGF/VEGFr signaling and HGF/c-met signaling may circumvent the ability of tumor cells to overcome VEGF inhibition alone and may represent improved cancer therapeutics.

Here we describe small molecules that are potent inhibitors of both the VEGF receptor KDR and the HGF receptor c-met.

BRIEF SUMMARY OF THE INVENTION

The present invention provides new compounds and methods for treating cell proliferative diseases. The compounds of the invention are dual function inhibitors, capable of inhibiting both VEGF and HGF. Accordingly, the invention provides new inhibitors of VEGF receptor signaling and HGF receptor signaling, including the VEGF receptor KDR and the HGF receptor c-met.

In a first aspect, the invention provides compounds of formula A that are useful as inhibitors of VEGF receptor signaling and HGF receptor signaling.

In a second aspect, the invention provides compounds of formula B that are useful as inhibitors of VEGF receptor signaling and HGF receptor signaling.

In a third aspect, the invention provides compositions comprising a compound of the present invention that is an inhibitor of VEGF receptor signaling and HGF receptor signaling, or a pharmaceutically acceptable salt thereof, and a pharmaceutically acceptable carrier, excipient, or diluent.

In a fourth aspect, the invention provides a method of simultaneously inhibiting VEGF receptor signaling and HGF receptor signaling in a cell, comprising contacting a cell in which inhibition of VEGF receptor signaling and HGF receptor signaling is desired with a compound of the invention.

The foregoing merely summarizes certain aspects of the invention and is not intended to be limiting in nature. These aspects and other aspects and embodiments are described more fully below.

DETAILED DESCRIPTION OF THE PREFERRED EMBODIMENTS

The invention provides compounds and methods for inhibiting the VEGF receptor KDR and the HGF receptor c-met. The invention also provides compositions and methods for treating cell proliferative diseases and conditions. The patent and scientific literature referred to herein establishes knowledge that is available to those with skill in the art. The issued patents, applications, and references that are cited herein are hereby incorporated by reference to the same extent as if each was specifically and individually indicated to be incorporated by reference. In the case of inconsistencies, the present disclosure will prevail.

For purposes of the present invention, the following definitions will be used (unless expressly stated otherwise):

The terms "inhibitor of VEGF receptor signaling" and "inhibitor of HGF receptor signaling" are used to identify a compound having a structure as defined herein, which is capable of interacting with a HGF receptor and a VEGF receptor and inhibiting the activity of HGF and VEGF. In some preferred embodiments, such reduction of activity is at least about 50%, more preferably at least about 75%, and still more preferably at least about 90%.

For simplicity, chemical moieties are defined and referred to throughout primarily as univalent chemical moieties (e.g., alkyl, aryl, etc.). Nevertheless, such terms are also used to convey corresponding multivalent moieties under the appropriate structural circumstances clear to those skilled in the art. For example, while an "alkyl" moiety generally refers to a monovalent radical (e.g. $CH_3$-$CH_2$—), in certain circumstances a bivalent linking moiety can be "alkyl," in which case those skilled in the art will understand the alkyl to be a divalent radical (e.g., —$CH_2$-$CH_2$—), which is equivalent to the term "alkylene." (Similarly, in circumstances in which a divalent moiety is required and is stated as being "aryl," those skilled in the art will understand that the term "aryl" refers to the corresponding divalent moiety, arylene.) All atoms are understood to have their normal number of valences for bond formation (i.e., 4 for carbon, 3 for N, 2 for O, and 2, 4, or 6 for S, depending on the oxidation state of the S). On occasion a moiety may be defined, for example, as $(A)_a$—B—, wherein a is 0 or 1. In such instances, when a is 0 the moiety is B—and when a is 1 the moiety is A-B—. Also, a number of moieties disclosed herein exist in multiple tautomeric forms, all of which are intended to be encompassed by any given tautomeric structure.

The term "hydrocarbyl" refers to a straight, branched, or cyclic alkyl, alkenyl, or alkynyl, each as defined herein. A "$C_0$" hydrocarbyl is used to refer to a covalent bond. Thus, "$C_0$-$C_3$-hydrocarbyl" includes a covalent bond, methyl, ethyl, ethenyl, ethynyl, propyl, propenyl, propynyl, and cyclopropyl.

The term "alkyl" as employed herein refers to straight and branched chain aliphatic groups having from 1 to 12 carbon atoms, preferably 1-8 carbon atoms, and more preferably 1-6 carbon atoms, which is optionally substituted with one, two or three substituents. Preferred alkyl groups include, without limitation, methyl, ethyl, propyl, isopropyl, butyl, isobutyl, sec-butyl, tert-butyl, pentyl, and hexyl. A "$C_0$" alkyl (as in "$C_0$-$C_3$-alkyl") is a covalent bond (like "$C_0$" hydrocarbyl).

The term "alkenyl" as used herein means an unsaturated straight or branched chain aliphatic group with one or more carbon-carbon double bonds, having from 2 to 12 carbon atoms, preferably 2-8 carbon atoms, and more preferably 2-6 carbon atoms, which is optionally substituted with one, two or three substituents. Preferred alkenyl groups include, without limitation, ethenyl, propenyl, butenyl, pentenyl, and hexenyl.

The term "alkynyl" as used herein means an unsaturated straight or branched chain aliphatic group with one or more carbon-carbon triple bonds, having from 2 to 12 carbon atoms, preferably 2-8 carbon atoms, and more preferably 2-6 carbon atoms, which is optionally substituted with one, two or three substituents. Preferred alkynyl groups include, without limitation, ethynyl, propynyl, butynyl, pentynyl, and hexynyl.

An "alkylene," "alkenylene," or "alkynylene" group is an alkyl, alkenyl, or alkynyl group, as defined hereinabove, that is positioned between and serves to connect two other chemical groups. Preferred alkylene groups include, without limitation, methylene, ethylene, propylene, and butylene. Preferred alkenylene groups include, without limitation, ethenylene, propenylene, and butenylene. Preferred alkynylene groups include, without limitation, ethynylene, propynylene, and butynylene.

The term "cycloalkyl" as employed herein includes saturated and partially unsaturated cyclic hydrocarbon groups having 3 to 12 carbons, preferably 3 to 8 carbons, and more preferably 3 to 6 carbons, wherein the cycloalkyl group additionally is optionally substituted. Preferred cycloalkyl groups include, without limitation, cyclopropyl, cyclobutyl, cyclopentyl, cyclopentenyl, cyclohexyl, cyclohexenyl, cycloheptyl, and cyclooctyl.

The term "heteroalkyl" refers to an alkyl group, as defined hereinabove, wherein one or more carbon atoms in the chain are replaced by a heteroatom selected from the group consisting of O, S, NH, N-alkyl, SO, $SO_2$, $SO_2NH$, or $NHSO_2$.

An "aryl" group is a $C_6$-$C_{14}$ aromatic moiety comprising one to three aromatic rings, which is optionally substituted. Preferably, the aryl group is a $C_6$-$C_{10}$ aryl group. Preferred aryl groups include, without limitation, phenyl, naphthyl, anthracenyl, and fluorenyl. An "aralkyl" or "arylalkyl" group comprises an aryl group covalently linked to an alkyl group, either of which may independently be optionally substituted or unsubstituted. Preferably, the aralkyl group is ($C_1$-$C_6$)alk ($C_6$-$C_{10}$)aryl, including, without limitation, benzyl, phenethyl, and naphthylmethyl.

A "heterocyclyl" or "heterocyclic" group is a ring structure having from about 3 to about 12 atoms, wherein one or more atoms are selected from the group consisting of N, O, S, SO, and $SO_2$. The heterocyclic group is optionally substituted on carbon at one or more positions. The heterocyclic group is also independently optionally substituted on nitrogen with alkyl, aryl, aralkyl, alkylcarbonyl, alkylsulfonyl, arylcarbonyl, arylsulfonyl, alkoxycarbonyl, or aralkoxycarbonyl. Preferred heterocyclic groups include, without limitation, epoxy, aziridinyl, tetrahydrofuranyl, pyrrolidinyl, piperidinyl, piperazinyl, thiazolidinyl, oxazolidinyl, oxazolidinonyl, and morpholino. In certain preferred embodiments, the heterocyclic group is fused to an aryl, heteroaryl, or cycloalkyl group. Examples of such fused heterocycles include, without limitation, tetrahydroquinoline and dihydrobenzofuran. Specifically excluded from the scope of this term are compounds where an annular O or S atom is adjacent to another O or S atom.

As used herein, the term "heteroaryl" refers to groups having 5 to 14 ring atoms, preferably 5, 6, 9, or 10 ring atoms; having 6, 10, or 14 π-electrons shared in a cyclic array; and having, in addition to carbon atoms, from one to three heteroatoms per ring selected from the group consisting of N, O, and S. The term "heteroaryl" is also meant to encompass monocyclic and bicyclic groups. For example, a heteroaryl group may be pyrimidinyl, pyridinyl, benzimidazolyl, thienyl, benzothiazolyl, benzofuranyl and indolinyl. A "heteroaralkyl" or "heteroarylalkyl" group comprises a heteroaryl group covalently linked to an alkyl group, either of which is independently optionally substituted or unsubstituted. Preferred heteroalkyl groups comprise a $C_1$-$C_6$ alkyl group and a heteroaryl group having 5, 6, 9, or 10 ring atoms. Specifically excluded from the scope of this term are compounds having adjacent annular O and/or S atoms. Examples of preferred heteroaralkyl groups include pyridylmethyl, pyridylethyl, pyrrolylmethyl, pyrrolylethyl, imidazolylmethyl, imidazolylethyl, thiazolylmethyl, and thiazolylethyl. Specifically excluded from the scope of this term are compounds having adjacent annular O and/or S atoms.

For simplicity, reference to a "$C_n$-$C_m$" heterocyclyl or heteroaryl means a heterocyclyl or heteroaryl having from "n" to "m" annular atoms, where "n" and "m" are integers. Thus, for example, a $C_5$-$C_6$-heterocyclyl is a 5- or 6-membered ring having at least one heteroatom, and includes pyrrolidinyl ($C_5$) and piperidinyl ($C_6$); $C_6$-hetoaryl includes, for example, pyridyl and pyrimidyl.

An "arylene," "heteroarylene," or "heterocyclylene" group is an aryl, heteroaryl, or heterocyclyl group, as defined hereinabove, that is positioned between and serves to connect two other chemical groups.

Preferred heterocyclyls and heteroaryls include, but are not limited to, acridinyl, azocinyl, benzimidazolyl, benzofuranyl, benzothiophenyl, benzoxazolyl, benzthiazolyl, benztriazolyl, pyridotriazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,3,4-triazolyl, and xanthenyl.

As employed herein, when a moiety (e.g., cycloalkyl, hydrocarbyl, aryl, heteroaryl, heterocyclic, urea, etc.) is described as "optionally substituted" it is meant that the group optionally has from one to four, preferably from one to three, more preferably one or two, non-hydrogen substituents. Suitable substituents include, without limitation, halo, hydroxy, oxo (e.g., an annular —CH— substituted with oxo is —C(O)—) nitro, halohydrocarbyl, hydrocarbyl, aryl, aralkyl, alkoxy, aryloxy, amino, acylamino, alkylcarbamoyl, arylcarbamoyl, aminoalkyl, acyl, carboxy, hydroxyalkyl, alkanesulfonyl, arenesulfonyl, alkanesulfonamido, arenesulfonamido, aralkylsulfonamido, alkylcarbonyl, acyloxy, cyano, and ureido groups. Preferred substituents, which are themselves not further substituted (unless expressly stated otherwise) are:

(a) halo, hydroxy, cyano, oxo, carboxy, formyl, nitro, amino, amidino, guanidino, (b) $C_1$-$C_5$ alkyl or alkenyl or arylalkyl imino, carbamoyl, azido, carboxamido, mercapto, hydroxy, hydroxyalkyl, alkylaryl, arylalkyl, $C_1$-$C_8$ alkyl, $C_1$-$C_8$ alkenyl, $C_1$-$C_8$ alkoxy, $C_1$-$C_8$ alkoxycarbonyl, aryloxycarbonyl, $C_2$-$C_8$ acyl, $C_2$-$C_8$ acylamino, $C_1$-$C_8$ alkylthio, arylalkylthio, arylthio, $C_1$-$C_8$ alkylsulfinyl, arylalkylsulfinyl, arylsulfinyl, $C_1$-$C_8$ alkylsulfonyl, arylalkylsulfonyl, arylsulfonyl, $C_0$-$C_6$ N-alkyl carbamoyl, $C_2$-$C_{15}$ N,N-dialkylcarbamoyl, $C_3$-$C_7$ cycloalkyl, aroyl, aryloxy, arylalkyl ether, aryl, aryl fused to a cycloalkyl or heterocycle or another aryl ring, $C_3$-$C_7$ heterocycle, $C_5$-$C_{14}$ heteroaryl, or any of these rings fused or spiro-fused to a cycloalkyl, heterocyclyl, or aryl, wherein each of the foregoing is further optionally substituted with one more moieties listed in (a), above; and (c) —$(CH_2)_s$—$NR^{30}R^{31}$, wherein s is from 0 (in which case the nitrogen is directly bonded to the moiety that is substituted) to 6, and $R^{30}$ and $R^{31}$ are each independently hydrogen, cyano, oxo, carboxamido, amidino, $C_1$-$C_8$ hydroxyalkyl, $C_1$-$C_3$ alkylaryl, aryl-$C_1$-$C_3$ alkyl, $C_1$-$C_8$ alkyl, $C_1$-$C_8$ alkenyl, $C_1$-$C_8$ alkoxy, $C_1$-$C_8$ alkoxycarbonyl, aryloxycarbonyl, aryl-$C_1$-$C_3$ alkoxycarbonyl, $C_2$-$C_8$ acyl, $C_1$-$C_8$ alkylsulfonyl, arylalkylsulfonyl, arylsulfonyl, aroyl, aryl, cycloalkyl, heterocyclyl, or heteroaryl, wherein each of the foregoing is further optionally substituted with one more moieties listed in (a), above; or $R^{30}$ and $R^{31}$ taken together with the N to which they are attached form a heterocyclyl or heteroaryl, each of which is optionally substituted with from 1 to 3 substituents, from (a), above.

Especially preferred substituents on alkyl groups include halogen and hydroxy.

Especially preferred substituents or ring groups, such as aryl, heteroaryl, cycloalkyl and heterocyclyl, include halogen, alkoxy and alkyl.

A "halohydrocarbyl" is a hydrocarbyl moiety in which from one to all hydrogens have been replaced with one or more halo.

The term "halogen" or "halo" as employed herein refers to chlorine, bromine, fluorine, or iodine. As herein employed, the term "acyl" refers to an alkylcarbonyl or arylcarbonyl substituent. The term "acylamino" refers to an amide group attached at the nitrogen atom (i.e., R—CO—NH—). The term "carbamoyl" refers to an amide group attached at the carbonyl carbon atom (i.e., $NH_2$—CO—). The nitrogen atom of an acylamino or carbamoyl substituent is additionally substituted. The term "sulfonamido" refers to a sulfonamide substituent attached by either the sulfur or the nitrogen atom. The term "amino" is meant to include $NH_2$, alkylamino, arylamino, and cyclic amino groups. The term "ureido" as employed herein refers to a substituted or unsubstituted urea moiety.

The term "radical" as used herein means a chemical moiety comprising one or more unpaired electrons.

A moiety that is substituted is one in which one or more hydrogens have been independently replaced with another chemical substituent. As a non-limiting example, substituted phenyls include 2-flurophenyl, 3,4-dichlorophenyl, 3-chloro-4-fluoro-phenyl, 2-fluoro-3-propylphenyl. As another non-limiting example, substituted n-octyls include 2,4-dimethyl-5-ethyl-octyl and 3-cyclopentyl-octyl. Included within this definition are methylenes (—$CH_2$—) substituted with oxygen to form carbonyl —CO—).

An "unsubstituted" moiety as defined above (e.g., unsubstituted cycloalkyl, unsubstituted heteroaryl, etc.) means that moiety as defined above that does not have any of the optional substituents for which the definition of the moiety (above) otherwise provides. Thus, for example, while an "aryl" includes phenyl and phenyl substituted with a halo, "unsubstituted aryl" does not include phenyl substituted with a halo.

Throughout the specification, preferred embodiments of one or more chemical substituents are identified. Also preferred are combinations of preferred embodiments. For example, preferred embodiments of X and $X^1$ in the compounds of formula (A) and preferred embodiments of $R^1$ in the compounds of formula (A). Thus, also contemplated as within the scope of the invention are compounds of formula (A) in which X and $X^1$ and $R^1$. Furthermore, compounds excluded from any one particular genus of compounds (e.g., through a proviso clause) are intended to be excluded from the scope of the invention entirely, including from other disclosed genera, unless expressly stated to the contrary.

Compounds

In the first aspect, the invention comprises compounds of formula (A), that are inhibitors of VEGF receptor signaling and HGF receptor signaling:

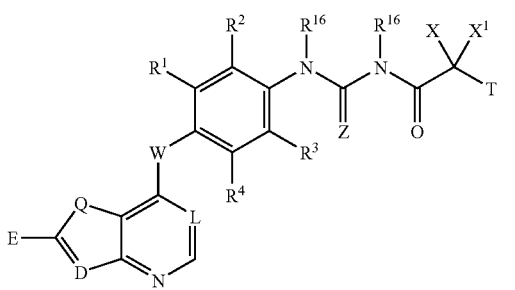

and pharmaceutically acceptable salts and complexes thereof, wherein

T is selected from the group consisting of arylalkyl, cycloalkyl, heterocyclyl, aryl and heteroaryl, wherein each of said arylalkyl, cycloalkyl, heterocyclyl, aryl and heteroaryl is optionally substituted with 1 to 3 independently selected $R^{20}$;

each $R^{20}$ is independently selected from the group consisting of —H, halogen, trihalomethyl, —CN, —NO$_2$, —NH$_2$, —OR$^{17}$, —OCF$_3$, —NR$^{17}$R$^{18}$, —S(O)$_{0-2}$R$^{17}$, —S(O)$_2$NR$^{17}$R$^{17}$, —C(O)OR$^{17}$, —C(O)NR$^{17}$R$^{17}$, —N(R$^{17}$)SO$_2$R$^{17}$, —N(R$^{17}$)C(O)R$^{17}$, —N(R$^{17}$)C(O)OR$^{17}$, —C(O)R$^{17}$, —C(O)SR$^{17}$, $C_1$-$C_4$ alkoxy, $C_1$-$C_4$ alkylthio, —O(CH$_2$)$_n$aryl, —O(CH$_2$)$_n$heteroaryl, —(CH$_2$)$_{0-5}$(aryl), —(CH$_2$)$_{0-5}$(heteroaryl), $C_1$-$C_6$ alkyl, $C_2$-$C_6$ alkenyl, $C_2$-$C_6$ alkynyl, —CH$_2$(CH$_2$)$_{0-4}$-T$^2$, an optionally substituted $C_{1-4}$ alkylcarbonyl, $C_{1-4}$ alkoxy, an amino optionally substituted by $C_{1-4}$ alkyl optionally substituted by $C_{1-4}$ alkoxy and a saturated or unsaturated three- to seven-membered carboxyclic or heterocyclic group, wherein T$^2$ is selected from the group consisting of —OH, —OMe, —OEt, —NH$_2$, —NHMe, —NMe$_2$, —NHEt and —NEt$_2$, and wherein the aryl, heteroaryl, $C_1$-$C_6$ alkyl, $C_2$-$C_6$ alkenyl, and $C_2$-$C_6$ alkynyl are optionally substituted;

W is selected from the group consisting of O, S, NH and NMe;

Z is selected from the group consisting of O, or S and NH;

X and X$^1$ are independently selected from the group consisting of H, $C_1$-$C_6$ alkyl, halo, cyano, or nitro, wherein $C_1$-$C_6$ alkyl is optionally substituted, or X and X$^1$ taken together with the atom to which they are attached, form a $C_3$-$C_7$ cycloalkyl;

R$^1$, R$^2$, R and R$^4$ independently represent hydrogen, halo, trihalomethyl, —CN, —NO$_2$, —NH$_2$, —OR$^{17}$, —NR$^{17}$R$^{18}$, —C(O)OR$^{17}$, —C(O)R$^{17}$, $C_1$-$C_4$ alkoxy, $C_1$-$C_4$ alkylthio, $C_1$-$C_6$ alkyl, $C_2$-$C_6$ alkenyl or $C_2$-$C_6$ alkynyl, wherein $C_1$-$C_6$ alkyl, $C_2$-$C_6$ alkenyl and $C_2$-$C_6$ alkynyl are optionally substituted;

R$^{17}$ is selected from the group consisting of H and R$^{18}$;

R$^{18}$ is selected from the group consisting of a ($C_1$-$C_6$)alkyl, an aryl, a aryl($C_1$-$C_6$)alkyl, a heterocyclyl and a heterocyclyl ($C_1$-$C_6$)alkyl, each of which is optionally substituted, or R$^{17}$ and R$^{18}$, taken together with a common nitrogen to which they are attached, form an optionally substituted five- to seven-membered heterocyclyl, the optionally substituted five- to seven-membered heterocyclyl optionally containing at least one additional annular heteroatom selected from the group consisting of N, O, S and P;

R$^{16}$ is selected from the group consisting of —H, —CN, —(CH$_2$)$_{0-5}$(aryl), —(CH$_2$)$_{0-5}$(heteroaryl), $C_1$-$C_6$ alkyl, $C_2$-$C_6$ alkenyl, $C_2$-$C_6$ alkynyl, —CH$_2$(CH$_2$)$_{0-4}$-T$^2$, an optionally substituted $C_{1-4}$alkylcarbonyl, and a saturated or unsaturated three- to seven-membered carboxyclic or heterocyclic group, wherein T$^2$ is selected from the group consisting of —OH, —OMe, —OEt, —NH$_2$, —NHMe, —NMe$_2$, —NHEt and —NEt$_2$, and wherein the aryl, heteroaryl, $C_1$-$C_6$ alkyl, $C_2$-$C_6$ alkenyl, and $C_2$-$C_6$ alkynyl are optionally substituted;

Q is selected from the group consisting of CH$_2$, O, S, N(H), N($C_1$-$C_6$ alkyl), N—Y-(aryl), —N—OMe, —NCH$_2$OMe and —N—Bn;

D is selected from the group consisting of C-E and N;

L is N, or CR, wherein R is selected from the group consisting of —H, halo, —CN, $C_1$-$C_6$ alkyl, $C_2$-$C_6$ alkenyl, and $C_2$-$C_6$ alkynyl, wherein $C_1$-$C_6$ alkyl, $C_2$-$C_6$ alkenyl, and $C_2$-$C_6$ alkynyl are optionally substituted; and E is selected from the group consisting of E$^1$, E$^2$ and E$^3$, wherein E$^1$ is selected from the group consisting of —H, halogen, nitro, azido, $C_1$-$C_6$ alkyl, $C_3$-$C_{10}$ cycloalkyl, —C(O)NR$^{42}$R$^{43}$, —Y—NR$^{42}$R$^{43}$, —NR$^{42}$C(=O)R$^{43}$, —SO$_2$R$^{42}$, —SO$_2$NR$^{42}$R$^{43}$, —NR$^{37}$SO$_2$R$^{42}$, —NR$^{37}$SO$_2$NR$^{42}$R$^{43}$, —C(=N—OR$^{42}$)R$^{43}$, —C(=NR$^{42}$)R$^{43}$, —C(=NR$^{42}$)NR$^{37}$R$^{43}$, —NR$^{37}$C(=NR$^{42}$)NR$^{37}$R$^{43}$, —C(O)R$^{42}$, —CO$_2$R$^{42}$, —C(O)(heterocyclyl), —C(O)($C_6$-$C_{10}$ aryl), —C(O)(heteroaryl), —Y—($C_6$-$C_{10}$ aryl), —Y-(heteroaryl), —Y—(5-10 membered heterocyclic), —NR$^{6a}$R$^{6b}$, —NR$^{6a}$SO$_2$R$^{6b}$, —NR$^{6a}$C(O)R$^{6b}$, —OC(O)R$^{6b}$, —NR$^{6a}$C(O)OR$^{6b}$, —OC(O)NR$^{6a}$R$^{6b}$, —OR$^{6a}$, —SR$^{6a}$, —S(O)R$^{6a}$, —SO$_2$R$^{6a}$, —SO$_3$R$^{6a}$, —SO$_2$NR$^{6a}$R$^{6b}$, —SO$_2$NR$^{42}$R$^{43}$, —COR$^{6a}$, —CO$_2$R$^{6a}$, —CONR$^{6a}$R$^{6b}$, —(C$_1$-C$_4$)fluoroalkyl, —(C$_1$-C$_4$)fluoroalkoxy, —(CZ$^3$Z$^4$)$_a$CN, wherein n is an integer ranging from 0 to 6, and the aforementioned E$^1$ groups other than —H and halogen are optionally substituted by 1 to 5 independently selected R$^{38}$, or E$^1$ is selected from a moiety selected from the group consisting of —(CZ$^3$Z$_4$)$_a$-aryl, —(CZ$^3$Z$^4$)$_a$-heterocycle, (C$_2$-C$_6$)alkynyl, —(CZ$^3$Z$^4$)$_a$—(C$_3$-C$_6$)cycloalkyl, —(CZ$^3$Z$^4$)$_a$—(C$_5$-C$_6$)cycloalkenyl, (C$_2$-C$_6$) alkenyl and (C$_1$-C$_6$)alkyl, which is optionally substituted with 1 to 3 independently selected Y$^2$ groups, where a is 0, 1, 2, or 3, and wherein when a is 2 or 3, the CZ$^3$Z$^4$ units may be the same or different; wherein each R$^{38}$ is independently selected from halo, cyano, nitro, trifluoromethoxy, trifluoromethyl, azido, —C(O)R$^{40}$, —C(O)OR$^{40}$, —OC(O)R$^{40}$, —OC(O)OR$^{40}$, —NR$^{36}$C(O)R$^{39}$, —C(O)NR$^{36}$R$^{39}$, —NR$^{36}$R$^{39}$, —OR$^{37}$, —SO$_2$NR$^{36}$R$^{39}$, C$_1$-C$_6$ alkyl, —(CH$_2$)$_j$O(CH$_2$)$_i$NR$^{36}$R$^{39}$, —(CH$_2$)$_n$O(CH$_2$)$_i$OR$^{37}$, —(CH$_2$)$_n$OR$^{37}$, —S(O)$_j$(C$_1$-C$_6$ alkyl), —(CH$_2$)$_n$(C$_6$-C$_{10}$aryl), —(CH$_2$)$_n$(C$_5$C$_{10}$ heteroaryl), —(CH$_2$)$_n$(5-10 membered heterocyclyl); —C(O)(CH$_2$)$_n$(C$_6$-C$_{10}$ aryl), —(CH$_2$)$_n$O(CH$_2$)$_j$(C$_6$-C$_{10}$ aryl), —(CH$_2$)$_n$O(CH$_2$)$_i$(5-10 membered heterocyclyl), —C(O) (CH$_2$)$_n$(5-10 membered heterocyclyl), —(CH$_2$)NR$^{39}$(CH$_2$)$_i$NR$^{36}$R$^{39}$, —(CH$_2$)$_j$NR$^{39}$CH$_2$C(O)NR$^{36}$R$^{39}$, —(CH$_2$)$_j$NR$^{39}$(CH$_2$)$_i$NR$^{37}$C(O)R$^{40}$, —(CH$_2$)$_n$NR$^{39}$(CH$_2$)$_n$O(CH$_2$)$_j$OR$^{37}$, —(CH$_2$)$_n$NR$^{39}$(CH$_2$)$_i$S(O)$_j$(C$_1$-C$_6$ alkyl), —(CH$_2$)$_j$NR$^{39}$(CH$_2$)$_n$R$^{36}$, —SO$_2$(CH$_2$)$_n$(C$_6$-C$_{10}$ aryl), —SO$_2$(CH$_2$)$_n$(5-10 membered heterocyclyl), —(CH$_2$)$_n$NR$^{36}$R$^{39}$, —NR$^{37}$SO$_2$NR$^{36}$R$^{39}$, SO$_2$R$^{36}$, C$_2$-C$_6$ alkenyl, C$_3$-C$_{10}$ cycloalkyl and C$_1$-C$_6$ alkylamino, wherein j is an integer ranging from 0 to 2, n is an integer ranging from 0 to 6, i is an integer ranging from 0 to 6, the —(CH$_2$)$_i$— and —(CH$_2$)$_n$— moieties of the foregoing R$^{38}$ groups optionally include a carbon-carbon double or triple bond where n is an integer between 2 and 6, and the alkyl, aryl, heteroaryl and heterocyclyl moieties of the foregoing R$^{38}$ groups are optionally substituted by one or more substituents independently selected from the group consisting of halo, cyano, nitro, trifluoromethyl, azido, —OH, —C(O)R$^{40}$, —C(O)OR$^{40}$, —OC(O)R$^{40}$, —OC(O)OR$^{40}$, —NR$^{36}$C(O)R$^{39}$, —C(O)NR$^{36}$R$^{39}$, —(CH$_2$)$_n$NR$^{36}$R$^{39}$, C$_1$-C$_6$ alkyl, C$_3$-C$_{10}$ cycloalkyl, —(CH$_2$)$_n$(C$_6$-C$_{10}$ aryl), —(CH$_2$)$_n$(5-10 membered heterocyclyl), —(CH$_2$)$_n$O (CH$_2$)$_i$OR$^{37}$, and —(CH$_2$)$_n$OR$^{37}$, wherein n is an integer ranging from 0 to 6 and i is an integer ranging from 2 to 6;

each R$^{42}$ and R$^{43}$ is independently selected from the group consisting of H, C$_1$-C$_6$ alkyl, C$_1$-C$_6$ heteroalkyl, —Y—(C$_3$-C$_{10}$ cycloalkyl), —Y—(C$_6$-C$_{10}$ aryl), —Y—(C$_6$-C$_{10}$ heteroaryl), —Y—(5-10 membered heterocyclic), —Y—O—Y$^1$—OR$^{37}$, —Y$^1$—CO$_2$—R$^{37}$, and —Y—OR$^{37}$, wherein the alkyl, heteroalkyl, cycloalkyl, aryl, heteroaryl and heterocyclic moieties of the foregoing R$^{42}$ and R$^{43}$ groups are optionally substituted by 1 or more substituents independently selected from R$^{44}$, wherein Y is a bond or is —(C(R$^{37}$)(H))$_n$, n is an integer ranging from 1 to 6, and Y$^1$ is —(C(R$^{37}$)(H))$_n$, or R$^{42}$ and R$^{43}$ taken together with the nitrogen to which they are attached form a C$_5$-C$_9$ heterocyclyl ring or a heteroaryl ring, wherein said ring is optionally substituted by 1 to 5 independently selected R$^{44}$ substituents, with the proviso that R$^{42}$ and R$^{43}$ are not both bonded to the nitrogen directly through an oxygen;

each R$^{44}$ is independently selected from the group consisting of halo, cyano, nitro, trifluoromethoxy, trifluoromethyl, azido, —C(O)R$^{40}$, —C(O)OR$^{40}$, —OC(O)R$^{40}$, —OC(O)OR$^{40}$, —NR$^{36}$C(O)R$^{39}$, —C(O)NR$^{36}$ R$^{39}$, —NR$^{36}$ R$^{39}$, —OR$^{37}$, —SO$_2$NR$^{36}$ R$^{39}$, —SO$_2$R$^{36}$, —NR$^{36}$SO$_2$R$^{39}$, —NR$^{36}$SO$_2$NR$^{37}$R$^{41}$, C$_1$-C$_6$ alkyl, C$_2$-C$_6$ alkenyl, C$_2$-C$_6$ alkynyl, C$_3$-C$_{10}$ cycloalkyl, —C$_1$-C$_6$ alkylamino, —(CH$_2$)$_j$O(CH$_2$)$_i$NR$^{36}$ R$^{39}$, —(CH$_2$)$_n$O(CH$_2$)$_i$OR$^{37}$, —(CH$_2$)$_n$ OR$^{37}$, —S(O)$_j$(C$_1$-C$_6$ alkyl), —(CH$_2$)$_n$(C$_6$-C$_{10}$ aryl), —(CH$_2$)$_n$(5-10 membered heterocyclic), —C(O)(CH$_2$)$_n$(C$_6$-C$_{10}$ aryl), —(CH$_2$)$_n$O(CH$_2$)j(C$_6$-C$_{10}$ aryl), —(CH$_2$)$_n$O (CH$_2$)$_i$(5 to 10 membered heterocyclic), —C(O)(CH$_2$)$_n$(5 to 10 membered heterocyclic), —(CH$_2$)$_j$NR$^{39}$(CH$_2$)$_i$ NR$^{36}$R$^{39}$, —(CH$_2$)$_j$NR$^{39}$CH$_2$C(O)NR$^{36}$R$^{39}$, —(CH$_2$)$_j$ NR$^{39}$(CH$_2$)$_i$NR$^{37}$C(O)R$^{40}$, —(CH$_2$)$_j$NR$^{39}$(CH$_2$)$_n$O(CH$_2$)$_i$ OR$^{37}$, —(CH$_2$)$_j$NR$^{39}$(CH$_2$)$_i$S(O)$_j$(C$_1$-C$_6$ alkyl), —(CH$_2$)$_j$ NR$^{39}$(CH$_2$)$_i$R$^{36}$, —SO$_2$(CH$_2$)$_n$(C$_6$-C$_{10}$ aryl), and —SO$_2$ (CH$_2$)$_n$(5 to 10 membered heterocyclic) wherein, j is an integer from 0 to 2, n is an integer from 0 to 6 and i is an integer ranging from 2 to 6, the —(CH$_2$)$_i$— and —(CH$_2$)$_{n1}$— moieties of the foregoing R$^{44}$ groups optionally include a carbon-carbon double or triple bond wherein n is an integer from 2 to 6, and the alkyl, aryl and heterocyclic moieties of the foregoing R$^{44}$ groups are optionally substituted by 1 or more substituents independently selected from the group consisting of halo, cyano, nitro, trifluoromethyl, azido, —OH, —C(O)R$^{40}$, —C(O)OR$^{40}$, —OC(O)R$^{40}$, —OC(O)OR$^{40}$, —NR$^{36}$C(O)R$^{39}$, —C(O) NR$^{36}$R$^{39}$, —(CH$_2$)$_n$NR$^{36}$R$^{39}$, —SO$_2$R$^{36}$, —SO$_2$NR$^{36}$R$^{39}$, C$_1$-C$_6$ alkyl, C$_3$-C$_{10}$ cycloalkyl, —(CH$_2$)$_n$(C$_6$-C$_{10}$ aryl), —(CH$_2$)$_n$(5 to 10 membered heterocyclic), —(CH$_2$)$_n$O (CH$_2$)$_i$OR$^{37}$ and —(CH$_2$)$_n$OR$^{37}$, wherein n is an integer from 0 to 6 and i is an integer from 2 to 6; and each R$^{40}$ is independently selected from H, C$_1$-C$_{10}$ alkyl, —(CH$_2$)$_n$(C$_6$-C$_{10}$ aryl), C$_3$-C$_{10}$ cycloalkyl, and —(CH$_2$)$_n$ (5-10 membered heterocyclic), wherein n is an integer ranging from 0 to 6;

each R$^{36}$ and R$^{39}$ is independently selected from the group consisting of H, —OH, C$_1$-C$_6$ alkyl, C$_3$-C$_{10}$ cycloalkyl, —(CH$_2$)$_n$(C$_6$-C$_{10}$ aryl), —(CH$_2$)$_n$(5-10 membered heterocyclic), —(CH$_2$)$_n$O(CH$_2$)$_i$OR$^{37}$, —(CH$_2$)$_n$CN(CH$_2$)$_n$ OR$^{37}$, —(CH$_2$)$_n$CN(CH$_2$)$_n$R$^{37}$, and —(CH$_2$)$_n$OR$^{37}$, wherein n is an integer ranging from 0 to 6 and i is an integer ranging from 2 to 6, and the alkyl, aryl and heterocyclic moieties of the foregoing R$^{36}$ and R$^{39}$ groups are optionally substituted by one or more substituents independently selected from —OH, halo, cyano, nitro, trifluoromethyl, azido, —C(O)R$^{40}$, —C(O)OR$^{40}$, —CO(O)R$^{40}$, —OC(O)OR$^{40}$, —NR$^{37}$C(O)R$^{41}$, —C(O)NR$^{37}$R$^{41}$, —NR$^{37}$R$^{41}$, —C$_1$-C$_6$ alkyl, —(CH$_2$)$_n$(C$_6$-C$_{10}$ aryl), —(CH$_2$)$_n$(5 to 10 membered heterocyclic), —(CH$_2$)$_n$O (CH$_2$)$_i$OR$^{37}$, and —(CH$_2$)$_n$OR$^{37}$, wherein n is an integer ranging from 0 to 6 and i is an integer ranging from 2 to 6, with the proviso that when R$^{36}$ and R$^{39}$ are both attached to the same nitrogen, then R$^{36}$ and R$^{39}$ are not both bonded to the nitrogen directly through an oxygen;

each R$^{37}$ and R$^{41}$ is independently selected from the group consisting of H, OR$^{36}$, C$_1$-C$_6$ alkyl and C$_3$-C$_{10}$ cycloalkyl;

each R$^{6a}$ and R$^{6b}$ is independently selected from the group consisting of hydrogen, —(CZ$^5$Z$^6$)$_u$—(C$_3$-C$_6$)cycloalkyl, —(CZ$^5$Z$^6$)$_u$—(C$_5$-C$_6$)cycloalkenyl, —(CZ$^5$Z$^6$)$_u$-aryl, —(CZ$^5$Z$^6$)$_u$-heteroaryl, —(CZ$^5$Z$^6$)$_u$-heterocycle, (C$_2$-C$_6$) alkenyl, and (C$_1$-C$_6$)alkyl, each of which is optionally substituted with 1 to 3 independently selected Y$^3$ groups, where u is 0, 1, 2, or 3, and wherein when u is 2 or 3, the CZ$^5$Z$^6$ units may be the same or different, or R$^{6a}$ and R$^{6b}$ taken together with adjacent atoms can form a heterocycle;

each Z$^3$, Z$^4$, Z$^5$ and Z$^6$ is independently selected from the group consisting of H, F and (C$_1$-C$_6$)alkyl, or each Z$^3$ and Z$^4$, or Z$^5$ and Z$^6$ are selected together to form a carbocycle, or two Z$^3$ groups on adjacent carbon atoms are selected together to optionally form a carbocycle;

each Y$^2$ and Y$^3$ is independently selected from the group consisting of halogen, cyano, nitro, tetrazolyl, guanidino, amidino, methylguanidino, azido, —C(O)Z$^7$, —OC(O) NH$_2$, —OC(O) NHZ$^7$, —OC(O)NZ$^7$Z$^8$, —NHC(O)Z$^7$, —NHC(O)NH$_2$, —NHC(O)NHZ$^7$, —NHC(O)NZ$^7$Z$^8$, —C(O)OH, —C(O)OZ$^7$, —C(O)NH$_2$, —C(O)NHZ$^7$, —C(O)NZ$^7$Z$^8$, —P(O)$_3$H$_2$, —P(O)$_3$(Z$^7$)$_2$, —S(O)$_3$H, —S(O)Z$^7$, —S(O)$_2$Z$^7$, —S(O)$_3$Z$^7$, -Z$^7$, —OZ$^7$, —OH, —NH$_2$, —NHZ$^7$, —NZ$^7$Z$^8$, —C(=NH)NH$_2$, —C(=NOH)NH$_2$, —N-morpholino, (C$_1$-C$_6$)alkyl, (C$_2$-C$_6$)alkenyl, (C$_2$-C$_6$)alkynyl, (C$_1$-C$_6$)haloalkyl, (C$_2$-C$_6$)haloalkenyl, (C$_2$-C$_6$)haloalkynyl, (C$_1$-C$_6$)haloalkoxy, —(CZ$^9$Z$^{10}$)$_r$NH$_2$, —(CZ$^9$Z$^{10}$)$_r$NHZ$^3$, —(CZ$^9$Z$^{10}$)$_r$ NZ$^7$Z$^8$, —X$^6$(CZ$^9$Z$^{10}$)$_r$—(C$_3$-C$_8$)cycloalkyl, —X$^6$ (CZ$^9$Z$^{10}$)$_r$—(C$_1$-C$_8$)cycloalkenyl, —X$^6$(CZ$^9$Z$^{10}$)$_r$-aryl and —X$^6$(CZ$^9$Z$^{10}$)$_r$—heterocycle, wherein r is 1, 2, 3 or 4;

X$^6$ is selected from the group consisting of O, S, NH, —C(O)—, —C(O)NH—, —C(O)O—, —S(O)—, —S(O)$_2$— and —S(O)$_3$—;

Z$^7$ and Z$^8$ are independently selected from the group consisting of an alkyl of 1 to 12 carbon atoms, an alkenyl of 2 to 12 carbon atoms, an alkynyl of 2 to 12 carbon atoms, a cycloalkyl of 3 to 8 carbon atoms, a cycloalkenyl of 5 to 8 carbon atoms, an aryl of 6 to 14 carbon atoms, a heterocycle of 5 to 14 ring atoms, an aralkyl of 7 to 15 carbon atoms, and a heteroaralkyl of 5 to 14 ring atoms, or $Z^7$ and $Z^8$ together may optionally form a heterocycle;

$Z^9$ and $Z^{10}$ are independently selected from the group consisting of H, F, a $(C_1-C_{12})$alkyl, a $(C_6-C_{14})$aryl, a $(C_5-C_{14})$heteroaryl, a $(C_7-C_{15})$aralkyl and a $(C_5-C_{14})$heteroaralkyl, or $Z^9$ and $Z^{10}$ are taken together form a carbocycle, or two $Z^9$ groups on adjacent carbon atoms are taken together to form a carbocycle; or any two $Y^2$ or $Y^3$ groups attached to adjacent carbon atoms may be taken together to be $-O[C(Z^9)(Z^{10})]_rO$ or $-O[C(Z^9)(Z^{10})]_{r+1}$, or any two $Y^2$ or $Y^3$ groups attached to the same or adjacent carbon atoms may be selected together to form a carbocycle or heterocycle; and wherein any of the above-mentioned substituents comprising a $CH_3$ (methyl), $CH_2$ (methylene), or CH (methine) group which is not attached to a halogen, SO or $SO_2$ group or to a N, O or S atom optionally bears on said group a substituent selected from hydroxy, halogen, $(C_1-C_4)$alkyl, $(C_1-C_4)$alkoxy and an $-N[(C_1-C_4)$alkyl][$(C_1-C_4)$alkyl];

$E^2$ is $-C{\equiv}CH$ or $-C{\equiv}C-(CR^{45}R^{45})_n-R^{46}$;

$R^{45}$ is independently selected from the group consisting of H, a $(C_1-C_6)$alkyl and a $(C_3-C_8)$cycloalkyl;

$R^{46}$ is selected from the group consisting of heterocyclyl, $-N(R^{47})-C(O)-N(R^{47})(R^{48})$, $-N(R^{47})-C(S)-N(R^{47})(R^{48})$, $-N(R^{47})-C(O)-OR^{48}$, $-N(R^{47})-C(O)-(CH_2)_n-R^{48}$, $-N(R^{47})-SO_2R^{47}$, $-(CH_2)_nNR^{47}R^{48}$, $-(CH_2)_nOR^{48}$, $-(CH_2)_nSR^{49}$, $-(CH_2)_nS(O)R^{49}$, $-(CH_2)_nS(O)_2R^{49}$, $-OC(O)R^{49}$, $-OC(O)OR^{49}$, $-C(O)NR^{47}R^{48}$, heteroaryl optionally substituted with one or more substituents selected from the group consisting of halo, $-CF_3$, $(C_1-C_6)$alkoxy, $-NO_2$, $(C_1-C_6)$alkyl, $-CN$, $-SO_2R^{50}$ and $-(CH_2)_nNR^{50}R^{51}$, and aryl optionally substituted with one or more substituents selected from the group consisting of halo, $-CF_3$, $(C_1-C_6)$alkoxy, $-NO_2$, $(C_1-C_6)$alkyl, $-CN$, $-SO_2R^{50}$ and $-(CH_2)_nNR^{50}R^{51}$;

$R^{47}$ and $R^{48}$ are independently selected from the group consisting of H, $(C_1-C_6)$alkyl, $(C_3-C_8)$cycloalkyl, heterocyclyl, $-(CH_2)_nNR^{50}R^{51}$, $-(CH_2)_nOR^{50}$, $-(CH_2)_nC(O)R^{49}$, $-C(O)_2R^{49}$, $-(CH_2)_nSR^{49}$, $-(CH_2)_nS(O)R^{49}$, $-(CH_2)_nS(O)_2R^{49}$, $-(CH_2)_nR^{49}$, $-(CH_2)_nCN$, aryl optionally substituted with one or more substituents selected from the group consisting of halo, $-CF_3$, $(C_1-C_6)$alkoxy, $-NO_2$, $(C_1-C_6)$alkyl, $-CN$, $-(CH_2)_nOR^{49}$, $-(CH_2)_n$heterocyclyl, $-(CH_2)_n$heteroaryl, $-SO_2R^{50}$ and $-(CH_2)_nNR^{50}R^{51}$, and heteroaryl optionally substituted with one or more substituents selected from the group consisting of halo, $-CF_3$, $(C_1-C_6)$alkoxy, $-NO_2$, $(C_1-C_6)$alkyl, $-CN$, $-(CH_2)_nOR^{49}$, $-(CH_2)_n$heterocyclyl, $-(CH_2)_n$heteroaryl, $-SO_2R^{50}$ and $-(CH_2)_nNR^{50}R^{51}$, or $R^{47}$ and $R^{48}$, together with the atom to which they are attached, form a 3-8 membered ring;

$R^{49}$ is selected from the group consisting of $(C_1-C_6)$alkyl, $(C_3-C_8)$cycloalkyl, heterocyclyl$(C_1-C_6)$alkylene, aryl$(C_1-C_6)$alkylene wherein the aryl is optionally substituted with one or more substituents selected from the group consisting of halo, $-CF_3$, $(C_1-C_6)$alkoxy, $-NO_2$, $(C_1-C_6)$alkyl, $-CN$, $-SO_2R^{50}$ and $-(CH_2)_nNR^{50}R^{51}$, heteroaryl$(C_1-C_6)$alkylene wherein the heteroaryl is optionally substituted with one or more substituents selected from the group consisting of halo, $-CF_3$, $(C_1-C_6)$alkoxy, $-NO_2$, $(C_1-C_6)$alkyl, $-CN$, $-SO_2R^{50}$ and $-(CH_2)_nNR^{50}R^{51}$, aryl optionally substituted with one or more substituents selected from the group consisting of halo, $-CF_3$, $(C_1-C_6)$alkoxy, $-NO_2$, $(C_1-C_6)$alkyl, $-CN$, $-SO_2R^{50}$ and $-(CH_2)_nNR^{50}R^{51}$, and heteroaryl optionally substituted with one or more substituents selected from the group consisting of halo, $-CF_3$, $(C_1-C_6)$alkoxy, $-NO_2$, $(C_1-C_6)$alkyl, $-CN$, $-SO_2R^{50}$ and $-(CH_2)_nNR^{50}R^{51}$;

$R^{50}$ and $R^{51}$ are independently selected from the group consisting of H, $(C_1-C_6)$alkyl, $(C_3-C_8)$cycloalkyl and $-C(O)R^{45}$, or $R^{50}$ and $R^{51}$, together with the atom to which they are attached, form a 3-8 membered ring; and $E^3$ is the group defined by $-(Z^{11})-(Z^{12})_m-(Z^{13})_{m1}$, wherein $Z^{11}$ is heterocyclyl or heterocyclylene;

$Z^{12}$ is selected from the group consisting of OC(O), OC(S) and C(O);

$Z^{13}$ is selected from the group consisting of heterocyclyl, aralkyl, $N(H)R^{52}$, $(C_1-C_3)$alkyl, $-OR^{52}$, halo, $S(O)_2R^{56}$, $(C_1-C_3)$hydroxyalkyl and $(C_1-C_3)$haloalkyl;

m is 0 or 1;

m1 is 0 or 1;

$R^{52}$ is selected from the group consisting of H, $-(CH_2)_gS(O)_2R^{54}$, $R^{55}NR^{53}R^{53}$, $(C_1-C_3)$alkyl, $-(CH_2)_qOR^{53}$, $-C(O)R^{54}$ and $-C(O)OR^{53}$;

q is 0, 1, 2, 3 or 4;

$R^{53}$ is $(C_1-C_3)$alkyl;

$R^{54}$ is $(C_1-C_3)$alkyl or $N(H)R^{53}$;

$R^{55}$ is $(C_1-C_6)$ alkyl; and $R^{56}$ is selected from the group consisting of $NH_2$, $(C_1-C_3)$alkyl and $OR^{52}$.

In a preferred embodiment of the compounds, T is aryl or heteroaryl, wherein each of said aryl and heteroaryl is optionally substituted with 1 to 3 independently selected $R^{20}$.

In a preferred embodiment of the compounds, T is selected from the group consisting of arylalkyl, cycloalkyl and heterocyclyl, wherein each of said arylalkyl, cycloalkyl and heterocyclyl is optionally substituted with 1 to 3 independently selected $R^{20}$.

In a preferred embodiment of the compounds, $R^{20}$ is selected from the group consisting of H, halogen, $-OR^{17}$ and $-C(O)OR^{17}$.

In a preferred embodiment of the compounds, $R^{20}$ is fluorine or chloride.

In a preferred embodiment of the compounds, W is O.

In a preferred embodiment of the compounds, Z is S or O.

In a preferred embodiment of the compounds, Z is S.

In a preferred embodiment of the compounds, X and $X^1$ are independently selected from the group consisting of H and $C_1-C_6$alkyl, wherein the $C_1-C_6$alkyl is optionally substituted.

In a preferred embodiment of the compounds, X and $X^1$ are both H.

In a preferred embodiment of the compounds, X and $X^1$ taken together with the atom to which they are attached, form a $C_3-C_7$cycloalkyl.

In a preferred embodiment of the compounds, $R^1$, $R^2$, $R^3$ and $R^4$ are independently selected from the group consisting of H, halogen, trihalomethyl, $OR^{17}$, $-NR^{17}R^{18}$ and $C_1-C_6$alkyl.

In a preferred embodiment of the compounds, $R^1$, $R^2$ and $R^4$ are independently selected from the group consisting of H, halo and $-OR^{17}$.

In a preferred embodiment of the compounds, $R^1$ is H or halogen.

In a preferred embodiment of the compounds, $R^1$ is halogen.

In a preferred embodiment of the compounds, $R^2$, $R^3$ and $R^4$ are each H.

In a preferred embodiment of the compounds, $R^{17}$ is a $C_1$-$C_6$alkyl.

In a preferred embodiment of the compounds, $R^{16}$ is H or $C_1$-$C_6$alkyl.

In a preferred embodiment of the compounds, Q is selected from the group consisting of $CH_2$, S, —N—($C_1$-$C_6$alkyl), N—Y-(aryl) and —N—OMe.

In a preferred embodiment of the compounds, Q is S.

In a preferred embodiment of the compounds, Q is $CH_2$.

In a preferred embodiment of the compounds, Q is —N—($C_1$-$C_6$alkyl).

In a preferred embodiment of the compounds, Q is —N—Y-(aryl).

In a preferred embodiment of the compounds, Q is —N—OMe.

In a preferred embodiment of the compounds, D is C-E.

In a preferred embodiment of the compounds, D is CH.

In a preferred embodiment of the compounds, L is C—R.

In a preferred embodiment of the compounds, R is H or halogen.

In a preferred embodiment of the compounds, L is N.

In a preferred embodiment of the compounds, E is selected from the group consisting of $E^1$ and $E^2$.

In a preferred embodiment of the compounds, E is $E^1$.

In a preferred embodiment of the compounds, E is $E^1$, wherein $E^1$ is selected from the group consisting of H, halogen, —C(O)$NR^{42}R^{43}$, —$SO_2NR^{42}R^{43}$, C(=$NR^{42}$)$NR^{37}R^{43}$, —$CO_2R^{42}$, —C(O)(heterocyclyl), —C(O)(heteroaryl), —Y—($C_6$-$C_{10}$ aryl), —Y-(heteroaryl), —Y-(5 to 10 membered heterocyclic), —$SR^{6a}$, —S(O)$R^{6a}$, —$SO_2R^{6a}$, wherein each of said $E^1$ other than H and halogen are optionally substituted with 1 to 5 independently selected $R^{38}$, or E1 is (C1-C6)alkyl, which is optionally substituted with 1 to 3 independently selected Y2 groups.

In a preferred embodiment of the compounds, $R^{38}$ is selected from the group consisting of halogen, —C(O)$OR^{40}$, —$NR^{36}C(O)R^{39}$, —C(O)$NR^{36}R^{39}$, —$NR^{36}R^{39}$, —$OR^{37}$, $C_1$-$C_6$alkyl, —C($CH_2$)$_j$O($CH_2$)$_iNR^{36}R^{39}$, —($CH_2$)$_nOR^{37}$, —S(O)$_j$($C_1$-$C_6$alkyl), —($CH_2$)$_n$-(5 to 10 membered heterocyclic), —($CH_2$)O($CH_2$)$_i$(5 to 10 membered heterocyclic), —($CH_2$)$_n$(5 to 10 membered heteroaryl), —($CH_2$)$_jNR^{39}$($CH_2$)$_jNR^{36}R^{39}$, —($CH_2$)$_jNR^{39}$($CH_2$)$_nR^{36}$, —($CH_2$)$_nNR^{36}R^{39}$, wherein j is an integer ranging from 0 to 2, n is an integer ranging from 0 to 6, i is an integer ranging from 1 to 6, the —($CH_2$)$_i$— and —($CH_2$)$_n$— moieties of the foregoing $R^{38}$ groups optionally include a carbon-carbon double or triple bond where n is an integer between 2 and 6, and the alkyl, aryl, heteroaryl, and heterocyclic moieties of the foregoing $R^{38}$ groups are optionally substituted by one or more substituents independently selected from the group consisting of halo, cyano, nitro, trifluoromethyl, azido, —OH, —C(O)$R^{40}$, —C(O)$OR^{40}$, —OC(O)$R^{40}$, —OC(O)$OR^{40}$, —$NR^{36}C(O)R^{39}$, —C(O)$NR^{36}R^{39}$, —($CH_2$)$_nNR^{36}R^{39}$, $C_1$-$C_6$ alkyl, $C_3$-$C_{10}$ cycloalkyl, —($CH_2$)$_n$($C_6$-$C_{10}$ aryl), —($CH_2$)$_n$(5-10 membered heterocyclyl), —($CH_2$)$_nO(CH_2)_iOR^{37}$, and —($CH_2$)$_nOR^{37}$, wherein n is an integer ranging from 0 to 6 and i is an integer ranging from 2 to 6.

In a preferred embodiment of the compounds, the alkyl, aryl, heteroaryl, and heterocyclic moieties of the foregoing $R^{38}$ groups are optionally substituted by one or more substituents independently selected from the group consisting of —OH and —C(O)$OR^{40}$.

In a preferred embodiment of the compounds, each $R^{42}$ and $R^{43}$ is independently selected from the group consisting of H, —Y—($C_3$-$C_{10}$ cycloalkyl), —Y—($C_6$-$C_{10}$ aryl), —Y—($C_6$-$C_{10}$ heteroaryl) and —Y-(5 to 10 membered heterocyclic), wherein the cycloalkyl, aryl, heteroaryl and heterocyclic moieties of the foregoing $R^{42}$ and $R^{43}$ groups are optionally substituted by 1 or more substituents independently selected from $R^{44}$.

In a preferred embodiment of the compounds, each $R^{42}$ and $R^{43}$ is independently selected from the group consisting of H, $C_1$-$C_6$ alkyl, $C_1$-$C_6$ heteroalkyl, —$Y^1$—$CO_2$—$R^{37}$ and —Y—$OR^{37}$.

In a preferred embodiment of the compounds, one of $R^{42}$ and $R^{43}$ is H.

In a preferred embodiment of the compounds, one of $R^{42}$ and $R^{43}$ is —($C_6$-$C_{10}$ heteroaryl) or —Y-(5 to 10 membered heterocyclic).

In a preferred embodiment of the compounds, Y is a bond.

In a preferred embodiment of the compounds Y is —(C($R^{37}$)(H))$_n$.

In a preferred embodiment of the compounds, $R^{42}$ and $R^{43}$ taken together with the nitrogen to which they are attached form a $C_5$-$C_9$ heterocyclyl ring or a heteroaryl ring, wherein said ring is optionally substituted by 1 to 5 independently selected $R^{44}$ substituents, with the proviso that $R^{42}$ and $R^{43}$ are not both bonded to the nitrogen directly through an oxygen.

In a preferred embodiment of the compounds, $R^{44}$ is independently selected from the group consisting of —C(O)$NR^{36}R^{39}$, —$OR^{37}$ and $C_1$-$C_6$alkyl.

In a preferred embodiment of the compounds, each $R^{40}$ is independently selected from the group consisting of H and $C_1$-$C_{10}$ alkyl.

In a preferred embodiment of the compounds, each $R^{36}$ and $R^{39}$ is independently selected from the group consisting of H, $C_1$-$C_6$alkyl, —($CH_2$)$_n$(5 to 10 membered heterocyclic), —($CH_2$)$_nOR^{37}$ and —C(O)$OR^{40}$, wherein n is an integer ranging from 0 to 6 and i is an integer ranging from 2 to 6, with the proviso that when $R^{36}$ and $R^{39}$ are both attached to the same nitrogen, then $R^{36}$ and $R^{39}$ are not both bonded to the nitrogen directly through an oxygen.

In a preferred embodiment of the compounds, each $R^{37}$ and $R^{41}$ is independently selected from the group consisting of H and $C_1$-$C_6$alkyl.

In a preferred embodiment of the compounds, $R^{6a}$ is selected from the group consisting of —(C$Z^5Z^6$)$_u$-aryl, —(C$Z^5Z^6$)$_u$-heteroaryl and $C_1$-$C_6$alkyl, each of which is optionally substituted with 1 to 3 independently selected $Y^3$ groups, wherein u is 0, 1, 2 or 3, and wherein when u is 2 or 3, the C$Z^5Z^6$ units may be the same or different.

In a preferred embodiment of the compounds, $R^{6a}$ is selected from the group consisting of —(C$Z^5Z^6$)$_u$-aryl and —(C$Z^5Z^6$)$_u$-heteroaryl, each of which is optionally substituted with 1 to 3 independently selected $Y^3$ groups, wherein u is 0.

In a preferred embodiment of the compounds, $Y^2$ is —OH.

In a preferred embodiment of the compounds, $Y^3$ is —OH.

In a preferred embodiment of the compounds, $E^2$ is —C≡C—(C$R^{45}R^{45}$)$_n$—$R^{46}$, wherein n is an integer ranging from 1 to 6.

In a preferred embodiment of the compounds, $R^{45}$ is H.

In a preferred embodiment of the compounds, $R^{46}$ is a heterocyclyl.

In a preferred embodiment of the compounds, the compounds are represented by the formula A-0:

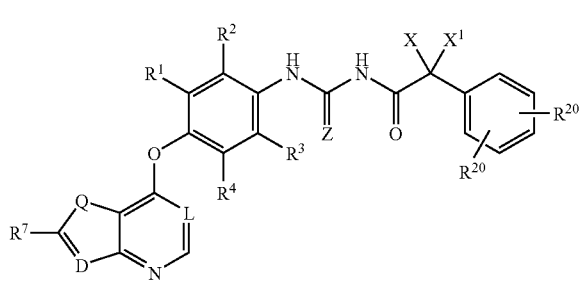

and pharmaceutically acceptable salts and complexes thereof, wherein

Z is O or S;

X and $X^1$ are independently selected from the group consisting of H, $C_1$-$C_6$ alkyl, halo, cyano and nitro, wherein $C_1$-$C_6$ alkyl is optionally substituted;

$R^1$, $R^2$, $R^3$ and $R^4$ are independently selected from the group consisting of hydrogen, halo, trihalomethyl, —$OR^{17}$, $C_1$-$C_6$ alkyl, $C_2$-$C_6$ alkenyl or $C_2$-$C_6$ alkynyl, wherein $C_1$-$C_6$ alkyl, $C_2$-$C_6$ alkenyl and $C_2$-$C_6$ alkynyl are optionally substituted;

Q is O, S, NH, N($C_1$-$C_6$ alkyl), or N—Y-(aryl);

D is $CR^{11}$, or N;

L is N, or CR, wherein R is H, halo, —CN, $C_1$-$C_6$ alkyl, $C_2$-$C_6$ alkenyl, or $C_2$-$C_6$ alkynyl, wherein $C_1$-$C_6$ alkyl, $C_2$-$C_6$ alkenyl, and $C_2$-$C_6$ alkynyl are optionally substituted; and $R^7$ is H, halogen, $C_1$-$C_6$ alkyl, —C(=O)$NR^9R^{10}$, —C(=O)(aryl), —C(=O)(heterocyclyl), —C(=O)(heteroaryl), —Y-(aryl), —Y-(heterocyclyl), —Y-(heteroaryl), —S-aryl, —S—$C_1$-$C_6$ alkyl, —SO—$C_1$-$C_6$ alkyl, —$SO_2$—$C_1$-$C_6$ alkyl, —Y—$NR^9R^{10}$, —$SO_2NR^9R^{10}$ or $CO_2R^9$, wherein $C_1$-$C_6$ alkyl, aryl, heterocycle and heteroaryl are each independently optionally substituted;

$R^9$ and $R^{10}$ are independently selected from H, $C_1$-$C_6$ alkyl, —Y-(cycloalkyl), —Y-(aryl), —Y-(heterocyclyl), —Y-(heteroaryl), —Y—o—$Y^1$—O—$R^{11}$, —$Y^1$—$CO_2$—$R^{11}$, and —Y—O—$R^{11}$, wherein $C_1$-$C_6$ alkyl, cycloalkyl, aryl, heterocycle, and heteroaryl are each optionally substituted, or $R^9$ and $R^{10}$ taken together with the nitrogen to which they are attached form a $C_5$-$C_9$ heterocyclyl ring or a heteroaryl ring, wherein said ring is optionally substituted;

Y is a bond or is —(C($R^{11}$)(H))$_t$—, wherein t is an integer from 1 to 6;

$Y^1$ is —(C($R^{11}$)(H))$_t$—, $R^{11}$ at each occurrence is independently H or $C_1$-$C_6$ alkyl, wherein $C_1$-$C_6$ alkyl is optionally substituted, each $R^{20}$ is independently selected from the group consisting of hydrogen, halo, trihalomethyl, $OR^{17}$, $C_1$-$C_6$ alkyl, $C_2$-$C_6$ alkenyl or $C_2$-$C_6$ alkynyl, wherein $C_1$-$C_6$ alkyl, $C_2$-$C_6$ alkenyl and $C_2$-$C_6$ alkynyl are optionally substituted, and each $R^{17}$ is an independently selected $C_1$-$C_6$alkyl, wherein said $C_1$-$C_6$alkyl is optionally substituted.

In a preferred embodiment of the compounds, X and $X^1$ are both hydrogen.

In a preferred embodiment of the compounds, $R^1$ is hydrogen or halogen.

In a preferred embodiment of the compounds, $R^1$ is fluorine.

In a preferred embodiment of the compounds, $R^4$ is hydrogen or halogen.

In a preferred embodiment of the compounds, $R^4$ is fluorine.

In a preferred embodiment of the compounds, $R^2$ is selected from the group consisting of H, halogen, trihalomethyl and —$OR^{17}$.

In a preferred embodiment of the compounds, $R^3$, and $R^{20}$ are each hydrogen.

In a preferred embodiment of the compounds, $R^{20}$ is —$OR^{17}$.

In a preferred embodiment of the compounds, Q is S, N($C_1$-$C_6$ alkyl), or N—Y-(aryl).

In a preferred embodiment of the compounds, Q is NH.

In a preferred embodiment of the compounds, D is $CR^{11}$.

In a preferred embodiment of the compounds, L is CH or N.

In a preferred embodiment of the compounds, $R^7$ is H, halogen, $C_1$-$C_6$ alkyl, —$CONR^9R^{10}$, —$SO_2NH_2$, —$SO_2NR^9R^{10}$, -Y-heterocyclyl, —Y-heteroaryl, —S-aryl, —S—$C_1$-$C_6$ alkyl, —SO—$C_1$-$C_6$ alkyl, or —$SO_2$—$C_1$-$C_6$ alkyl, wherein $C_1$-$C_6$ alkyl, is unsubstituted or is substituted with one or two of hydroxy or halogen, and heterocyclyl, and heteroaryl are unsubstituted or substituted with one or two of alkoxy, alkyl, or haloalkyl.

In a preferred embodiment of the compounds, $R^7$ is —$CONR^9R^{10}$.

In a preferred embodiment of the compound, $R^7$ is Y-heteroaryl.

In a preferred embodiment of the compounds, $R^9$ and $R^{10}$ are independently H, $C_1$-$C_6$ alkyl, —Y—O—$R^{11}$, —Y-(heterocycle), —$Y^1$—$CO_2$—$R^{11}$, or —Y-(aryl), wherein $C_1$-$C_6$ alkyl is unsubstituted or is substituted with one or two of hydroxy or halogen, and heterocyclyl, and aryl are unsubstituted or are substituted with one or two of alkoxy, alkyl, or haloalkyl.

In a preferred embodiment of the compounds, $R^9$ and $R^{10}$ are taken together with the nitrogen to which they are attached to form a pyrrolidinyl, piperidinyl, piperazinyl, morpholinyl, or thiomorpholinyl ring, wherein said ring is unsubstituted or is substituted with one or two of alkoxy, alkyl, or haloalkyl.

In a preferred embodiment of the compounds, $R^7$ is H, halogen, $C_1$-$C_6$ alkyl, —$SO_2NR^9R^{10}$, —C(=O)(heterocyclyl),13 Y-(heterocyclyl), or —Y-(heteroaryl), wherein $C_1$-$C_6$ alkyl is unsubstituted or is substituted with one or two of hydroxy or halogen, and heterocyclyl, and heteroaryl are unsubstituted or are substituted with one or two of alkoxy, alkyl, or haloalkyl.

In a preferred embodiment of the compounds, Z is sulfur.

In a preferred embodiment of the compounds, the compounds are represented by the formula A-1:

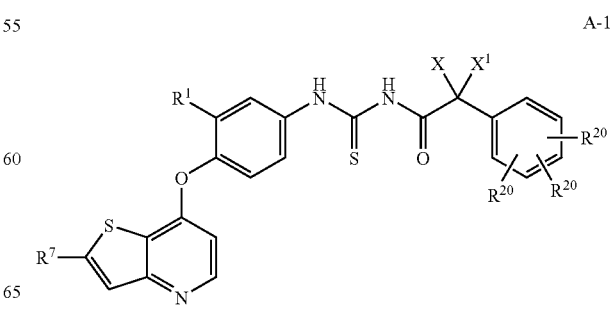

and pharmaceutically acceptable salts and complexes thereof, wherein $R^1$ is selected from the group consisting of hydrogen, halo, $C_1$-$C_6$ alkyl, $C_2$-$C_6$ alkenyl or $C_2$-$C_6$ alkynyl, wherein $C_1$-$C_6$ alkyl, $C_2$-$C_6$ alkenyl and $C_2$-$C_6$ alkynyl are optionally substituted;

X and $X^1$ are independently selected from the group consisting of H and $C_1$-$C_6$ alkyl, wherein $C_1$-$C_6$ alkyl is optionally substituted, or X and $X^1$ taken together with the atom to which they are attached, form a $C_3$-$C_7$ cycloalkyl;

$R^7$ is H, halogen, $C_1$-$C_6$ alkyl, —C(=O)$NR^9R^{10}$, —C(=O)(aryl), —C(=O)(heterocyclyl), —C(=O)(heteroaryl), —Y-(aryl), —Y-(heterocyclyl), —Y-(heteroaryl), —$SR^{6a}$, —S-aryl, —S-(heteroaryl), —S—$C_1$-$C_6$ alkyl, —SO—$C_1$-$C_6$ alkyl, —$SO_2$—$C_1$-$C_6$ alkyl, -Y—$NR^9R^{10}$, —$SO_2NR^9R^{10}$, $CO_2R^9$, —C≡C—$(CR^{45}R^{45})_n$—$R^{46}$ and —C(=$NR^{42}$)$NR^{37}R^{43}$, wherein n is an integer ranging from 0 to 6 and wherein $C_1$-$C_6$ alkyl, aryl, heterocycle and heteroaryl are each independently optionally substituted with 1 to 5 independently selected $R^{38}$;

$R^9$ and $R^{10}$ are independently selected from H, $C_1$-$C_6$ alkyl, —Y-(cycloalkyl), —Y—($C_1$-$C_6$ heteroalkyl), —Y-(aryl), —Y-(heterocyclyl), —Y-(heteroaryl), —Y—O—$Y^1$—O—$R^{11}$, —$Y^1$—$CO_2$—$R^{11}$, Y—C(O)$OR^{37}$ and —Y—O—$R^{11}$, wherein said $C_1$-$C_6$ alkyl, heteroalkyl, cycloalkyl, aryl, heterocycle, and heteroaryl are each optionally substituted with one or more independently selected $R^{44}$, or $R^9$ and $R^{10}$ taken together with the nitrogen to which they are attached form a $C_5$-$C_9$ heterocyclyl ring or a heteroaryl ring, wherein said ring is optionally substituted with 1 to 5 independently selected $R^{44}$;

each $R^{20}$ is independently selected from the group consisting of H, halo, —$OR^{17}$ and —C(O)$OR^{17}$;

Y is a bond or is —$(C(R^{11})(H))_t$—, wherein t is an integer from 1 to 6;

$Y^1$ is —$(C(R^{11})(H))_t$—, and $R^{11}$ at each occurrence is independently H or $C_1$-$C_6$ alkyl, wherein $C_1$-$C_6$ alkyl is optionally substituted.

In a preferred embodiment of the compounds, $R^1$ is hydrogen or halogen.

In a preferred embodiment of the compounds, $R^1$ is fluorine.

In a preferred embodiment of the compounds, $R^7$ is selected from the group consisting of H, —C(=O)$NR^9R^{10}$, —Y-(aryl), —Y-(heteroaryl) and —S—$C_1$-$C_6$ alkyl, wherein said —Y-(aryl), —Y-(heteroaryl) and —S—$C_1$-$C_6$ alkyl are optionally substituted with 1 to 5 independently selected $R^{38}$.

In a preferred embodiment of the compounds, $R^7$ is —C(=O)$NR^9R^{10}$, optionally substituted with one or more independently selected $R^{44}$.

In a preferred embodiment of the compounds, $R^7$ is —Y-(aryl), optionally substituted with 1 to 5 independently selected $R^{38}$.

In a preferred embodiment of the compounds, $R^7$ is —Y-(heteroaryl), optionally substituted with 1 to 5 independently selected $R^{38}$.

In a preferred embodiment of the compounds, $R^{38}$ is selected from the group consisting of halogen, —$OR^{37}$, $C_1$-$C_6$alkyl, —$(CH_2)_n$-(5 to 10 membered heterocyclyl), —$(CH_2)_j NR^{39}(CH_2)_n R^{36}$, —$(CH_2)_j NR^{39}(CH_2)_j NR^{36}R^{39}$, —$(CH_2)_n$—heteroaryl, —C(O)$NR^{36}R^{39}$, —$(CH_2)_n O(CH_2)_i$ (5 to 10 membered heterocyclyl) and —$(CH_2)_j O(CH_2)_i NR^{36}R^{39}$, wherein n is an integer ranging from 0 to 6, j is an integer ranging from 0 to 2, j is an integer ranging from 1 to 6 and wherein the alkyl, heteroaryl and heterocyclyl moieties of the foregoing $R^{38}$ groups are optionally substituted by one or more substituents independently selected from the group consisting of halo, cyano, nitro, trifluoromethyl, azido, —OH, —C(O)$R^{40}$, —C(O)$OR^{40}$, —OC(O)$R^{40}$, —OC(O)$OR^{40}$, —$NR^{36}$C(O)$R^{39}$, —C(O)$NR^{36}R^{39}$, —$(CH_2)_n NR^{36}R^{39}$, $C_1$-$C_6$ alkyl, $C_3$-$C_{10}$ cycloalkyl, —$(CH_2)_n(C_6$-$C_{10}$ aryl), —$(CH_2)_n$(5-10 membered heterocyclyl), —$(CH_2)_n O(CH_2)_i OR^{37}$, and —$(CH_2)_n OR^{37}$, wherein n is an integer ranging from 0 to 6 and i is an integer ranging from 2 to 6.

In a preferred embodiment of the compounds, $R^{38}$ is selected from the group consisting of —$OR^{37}$, $C_1$-$C_6$alkyl, —$(CH_2)_n$(5 to 10 membered heterocyclyl) and —$(CH_2)_n O(CH_2)_i$(5 to 10 membered heterocyclyl).

In a preferred embodiment of the compounds, $R^9$ and $R^{10}$ are independently selected from the group consisting of H, $C_1$-$C_6$ alkyl, —$C_1$-$C_6$ heteroalkyl, —Y-(aryl), —Y-(heterocyclyl), —Y-(heteroaryl), —Y—O—$R^{11}$ and Y—C(O)$OR^{37}$, wherein a $C_1$-$C_6$ alkyl, $C_1$-$C_6$ heteroalkyl, aryl, heterocyclcyl and heteroaryl are each optionally substituted with 1 or more independently selected $R^{44}$.

In a preferred embodiment of the compounds, $R^{44}$ is selected from the group consisting of $C_1$-$C_6$ alkyl, —$OR^{37}$, —C(O)$NR^{36}R^{39}$ and —C(O)$OR^{46}$.

In a preferred embodiment of the compounds, $R^{36}$ is selected from the group consisting of H, $C_1$-$C_6$ alkyl, —$(CH_2)_n OR^{37}$ and —$(CH_2)_n$(heterocyclyl).

In a preferred embodiment of the compounds, $R^{39}$ is H or $C_1$-$C_6$ alkyl.

In a preferred embodiment of the compounds, $R^{37}$ is H or $C_1$-$C_6$ alkyl.

In a preferred embodiment of the compounds, $R^{20}$ is selected from the group consisting of H, halogen, —$OR^{17}$ and —C(O)$OR^{17}$.

In a preferred embodiment of the compounds, $R^{17}$ is H or $C_1$-$C_6$ alkyl.

In a preferred embodiment of the compounds, $R^{20}$ is halogen.

In a preferred embodiment of the compounds, $R^{20}$ is Cl or F.

In a preferred embodiment of the compounds, $R^{6a}$ is —$(CZ^5Z^6)_u$-aryl.

In a preferred embodiment of the compounds, $R^7$ is selected from the group consisting of H, halogen, $C_1$-$C_6$ alkyl, —$CONR^9R^{10}$, —$SO_2NH_2$, —$SO_2NR^9R^{10}$, —Y-heterocyclyl, —Y-heteroaryl, —S-aryl, —S—$C_1$-$C_6$ alkyl, —SO—$C_1$-$C_6$ alkyl, or —$SO_2$—$C_1$-$C_6$ alkyl, wherein $C_1$-$C_6$ alkyl is unsubstituted or is substituted with one or two of hydroxy or halogen, and the heterocyclyl, and heteroaryl are unsubstituted or are substituted with one or two of alkoxy, alkyl, or haloalkyl.

In a preferred embodiment of the compounds, $R^7$ is selected from the group consisting of H, halogen, $C_1$-$C_6$ alkyl, —$SO_2NR^9R^{10}$, —C(=O)(heterocyclyl), —Y-(heterocyclyl), —Y-(heteroaryl), —S-aryl, —S—$C_1$-$C_6$ alkyl, —SO—$C_1$-$C_6$ alkyl, or —$SO_2$—$C_1$-$C_6$ alkyl, wherein $C_1$-$C_6$ alkyl is unsubstituted or is substituted with one or two of hydroxy or halogen, and the heterocyclyl, and heteroaryl are unsubstituted or are substituted with one or two of alkoxy, alkyl, or haloalkyl.

In a preferred embodiment of the compounds, $R^9$ and $R^{10}$ are independently selected from the group consisting of H, $C_1$-$C_6$ alkyl, $C_1$-$C_6$ heteroalkyl, —Y—O—$R^{11}$, —Y-(heterocycle), —Y—$CO_2$—$R^{11}$, —Y-(aryl) and —Y-(heteroaryl), wherein $C_1$-$C_6$ alkyl is unsubstituted or is substituted with one or two of hydroxy or halogen, and the heterocyclyl, aryl and heteroaryl are unsubstituted or are substituted with one or two of alkoxy, alkyl, or haloalkyl.

In a preferred embodiment of the compounds, $R^9$ and $R^{10}$ are taken together with the nitrogen to which they are attached to form a pyrrolidinyl, piperidinyl, piperazinyl, morpholinyl, or thiomorpholinyl ring, wherein said ring is unsubstituted or is substituted with one or two of alkoxy, alkyl, or haloalkyl.

In a preferred embodiment of the compounds, $NR^9R^{10}$ is selected from:

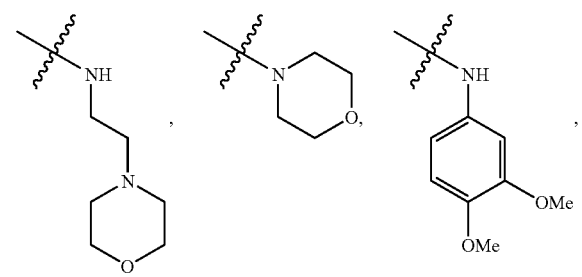
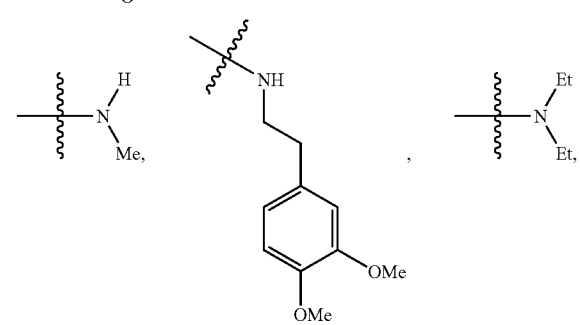
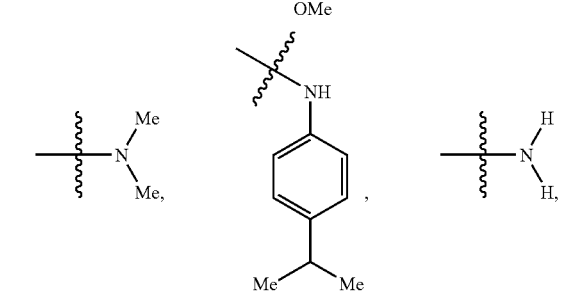
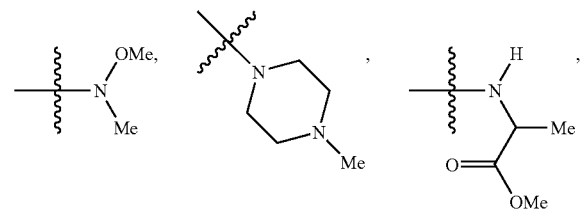
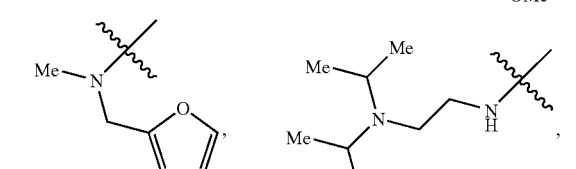
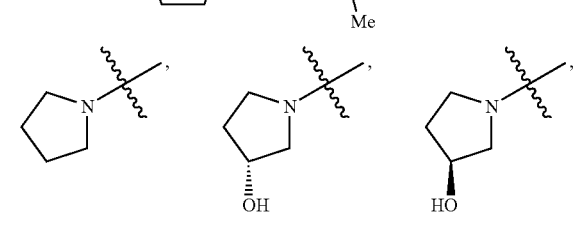

-continued

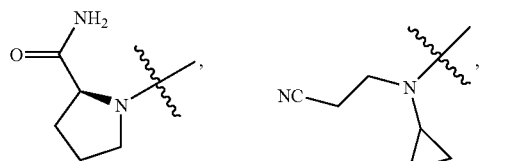
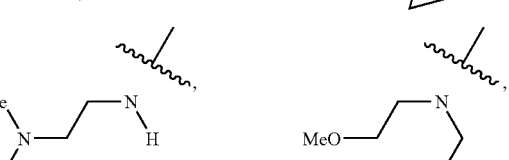
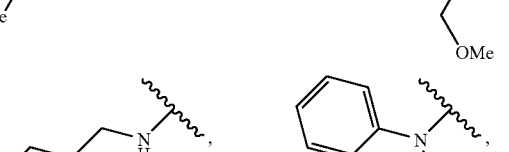
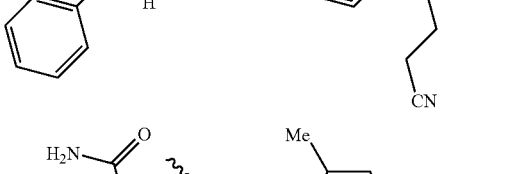
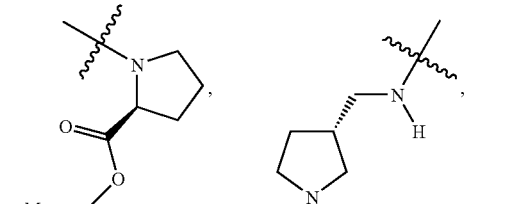
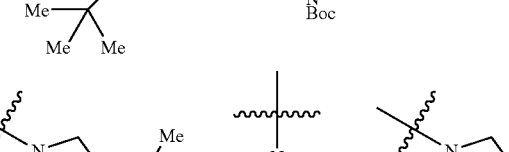
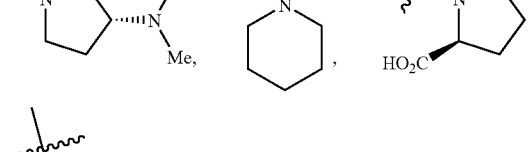
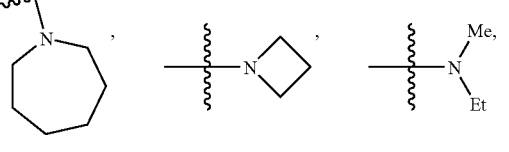
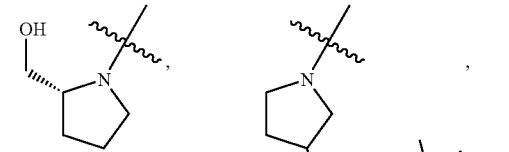
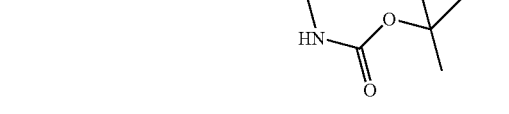

-continued

In a preferred embodiment of the compounds $R^7$ is unsubstituted heteroaryl.

In a preferred embodiment of the compounds, $R^7$ is thiazolyl, pyridinyl, pyrimidinyl, and imidazolyl, each of which is preferably unsubstituted or is substituted with one or two of alkoxy, or alkyl.

In a preferred embodiment of the compounds, $R^7$ is $C_1$-$C_6$ alkyl, unsubstituted or substituted with hydroxy.

In a preferred embodiment of the compounds, X and $X^1$ are both H.

In a preferred embodiment of the compounds, $R^{17}$ is selected from the group consisting of H and $C_1$-$C_6$ alkyl.

In a preferred embodiment of the compounds, $R^{38}$ is selected from the group consisting of —$OR^{37}$, $C_1$-$C_6$ alkyl and —$(CH_2)_n$(5 to 10 membered heterocylic), wherein n is an integer ranging from 0 to 6.

In a preferred embodiment of the compounds, $R^{37}$ is selected from the group consisting of H and $C_1$-$C_6$ alkyl.

In a preferred embodiment of the compounds, the compounds are represented by the formula A-2:

A-2 and pharmaceutically acceptable salts and complexes thereof, wherein $R^1$ is selected from the group consisting of hydrogen, halo, $C_1$-$C_6$ alkyl, $C_2$-$C_6$ alkenyl or $C_2$-$C_6$ alkynyl, wherein $C_1$-$C_6$ alkyl, $C_2$-$C_6$ alkenyl and $C_2$-$C_6$ alkynyl are optionally substituted;

$R^7$ is selected from the group consisting of H, halogen, $C_1$-$C_6$ alkyl, —C(=O)$NR^9R^{10}$, —C(=O)(aryl), —C(=O)(heterocyclyl), —C(=O)(heteroaryl), —Y-(aryl), —Y-(heterocyclyl), —Y-(heteroaryl), —S-aryl, —S—$C_1$-$C_6$ alkyl, —SO—$C_1$-$C_6$ alkyl, —$SO_2$—$C_1$-$C_6$ alkyl, —Y—$NR^9R^{10}$, —$SO_2NR^9R^{10}$ and $CO_2R^9$, wherein $C_1$-$C_6$ alkyl, aryl, heterocycle and heteroaryl are each independently optionally substituted with 1 to 5 independently selected $R^{38}$;

$R^9$ and $R^{10}$ are independently selected from the group consisting of H, $C_1$-$C_6$ alkyl, —Y-(cycloalkyl), —Y-(aryl), —Y-(heterocyclyl), —Y-(heteroaryl), —Y—O—$Y^1$—O—$R^{11}$, —$Y^1$—$CO_2$—$R^{11}$ and —Y—O—$R^{11}$, wherein $C_1$-$C_6$ alkyl, cycloalkyl, aryl, heterocycle, and heteroaryl are each optionally substituted with one or more independently selected $R^{44}$, or $R^9$ and $R^{10}$ taken together with the nitrogen to which they are attached form a $C_5$-$C_9$ heterocylyl ring or a heteroaryl ring, wherein said ring is optionally substituted;

Y is a bond or is —$(C(R^{11})(H))_t$—, wherein t is an integer from 1 to 6;

$Y_1$ is —$(C(R^{11})(H))_t$—, and $R^{11}$ at each occurrence is independently H or $C_1$-$C_6$ alkyl, wherein $C_1$-$C_6$ alkyl is optionally substituted.

In a preferred embodiment of the compounds, $R^1$ is hydrogen or halogen.

In a preferred embodiment of the compounds, $R^1$ R1 is fluorine.

In a preferred embodiment of the compounds, $R^4$ is selected from the group consisting of H and halogen.

In a preferred embodiment of the compounds, $R^4$ is fluorine.

In a preferred embodiment of the compounds, $R^7$ is selected from the group consisting of H, halogen, $C_1$-$C_6$ alkyl, —C(=O)$NR^9R^{10}$, —$SO_2NH_2$, —$SO_2NR^9R^{10}$, —Y-heterocyclyl —Y-heteroaryl, —S-aryl, —S—$C_1$-$C_6$ alkyl, —SO—$C_1$-$C_6$ alkyl and —$SO_2$—$C_1$-$C_6$ alkyl, wherein $C_1$-$C_6$ alkyl, heterocyclyl, heteroaryl and aryl are each optionally substituted with 1 to 5 independently selected $R^{38}$.

In a preferred embodiment of the compounds, $R^7$ is selected from the group consisting of H, halogen, $C_1$-$C_6$ alkyl, —C(=O)$NR^9R^{10}$, —$SO_2NH_2$, —$SO_2NR^9R^{10}$, —Y-heterocyclyl —Y-heteroaryl, —S-aryl, —S—$C_1$-$C_6$ alkyl, —SO—$C_1$-$C_6$ alkyl and —$SO_2$—$C_1$-$C_6$ alkyl, wherein $C_1$-$C_6$ alkyl is unsubstituted or is substituted with one or two of hydroxy or halogen, and the heterocyclyl, and heteroaryl are unsubstituted or are substituted with one or two of alkoxy, alkyl, haloalkyl or $(CH_2)_jNR^{39}(CH_2)_nO(CH_2)_iOR^{37}$.

In a preferred embodiment of the compounds, $R^7$ is selected from the group consisting of H, halogen, $C^1$-$C^6$ alkyl, —$SO_2NR^9R^{10}$, —C(=O)(heterocyclyl), —Y-(heterocyclyl), —Y-(heteroaryl), —S-aryl, —S—$C_1$-$C_6$ alkyl, —SO—$C_1$-$C_6$ alkyl, or —$SO_2$—$C_1$-$C_6$ alkyl, wherein $C_1$-$C_6$ alkyl is unsubstituted or is substituted with one or two of hydroxy or halogen, and the heterocyclyl, and heteroaryl are unsubstituted or are substituted with one or two of alkoxy, alkyl, haloalkyl or $(CH_2)_jNR^{39}(CH_2)_nO(CH_2)_iOR^{37}$.

In a preferred embodiment of the compounds, $R^7$ is selected from the group consisting of $C_1$-$C_6$ alkyl, —C(=O)$NR^9R^{10}$, —Y-(heterocyclyl, —Y-(heteroaryl), —S—$C_1$-$C_6$ alkyl and —SO—$C_1$-$C_6$ alkyl, wherein $C_1$-$C_6$ alkyl is unsubstituted or is substituted with one or two of hydroxy or halogen, and the heterocyclyl, and heteroaryl are unsubstituted or are substituted with one or two of alkoxy, alkyl, haloalkyl or $(CH_2)_jNR_{39}(CH_2)_nO(CH_2)_iOR^{37}$.

In a preferred embodiment of the compounds, $R_7$ is $CONR^9R^{10}$.

In a preferred embodiment of the compounds, $R^9$ and $R^{10}$ are independently selected from the group consisting of H, $C_1$-$C_6$ alkyl, —Y—O—$R_{11}$, —Y-(heterocycle), —$Y^1$—$CO_2$—$R^{11}$ and —Y-(aryl), wherein the alkyl, heterocyclyl and aryl moieties of the foregoing $R_9$ and $R_{10}$ groups are optionally substituted with 1 or more substituents independently selected from $R^{44}$.

In a preferred embodiment of the compounds, $R^9$ and $R^{10}$ are independently selected from the group consisting of H, $C_1$-$C_6$ alkyl, —Y—O—$R^{11}$, —Y-(heterocycle), —$Y^1$—$CO_2$—$R^{11}$ and —Y-(aryl), wherein $C^1$-$C^6$ alkyl, is unsubstitued or is substituted with one or two of hydroxy or halogen, and the heterocyclyl, and aryl are unsubstitued or are substituted with one or two of alkoxy, alkyl, haloalkyl or $(CH_2)_jNR_{39}(CH_2)_nO(CH_2)_iOR^{37}$.

In a preferred embodiment of the compounds, $R^9$ and $R^{10}$ taken together with the nitrogen to which they are attached form a $C_5$-$C_9$ heterocyclyl ring or a heteroaryl ring, wherein said ring is optionally substituted.

In a preferred embodiment of the compounds, $R_9$ $R_{10}$ are taken together with the nitrogen to which they are attached to form a pyrrolidinyl, piperidinyl, piperazinyl, morpholinyl, or thiomorpholinyl ring, wherein said ring is unsubstituted or is substituted with one or two of alkoxy, alkyl, or haloalkyl.

In a preferred embodiment of the compounds, $NR^9R^{10}$ is selected from the group consisting of:

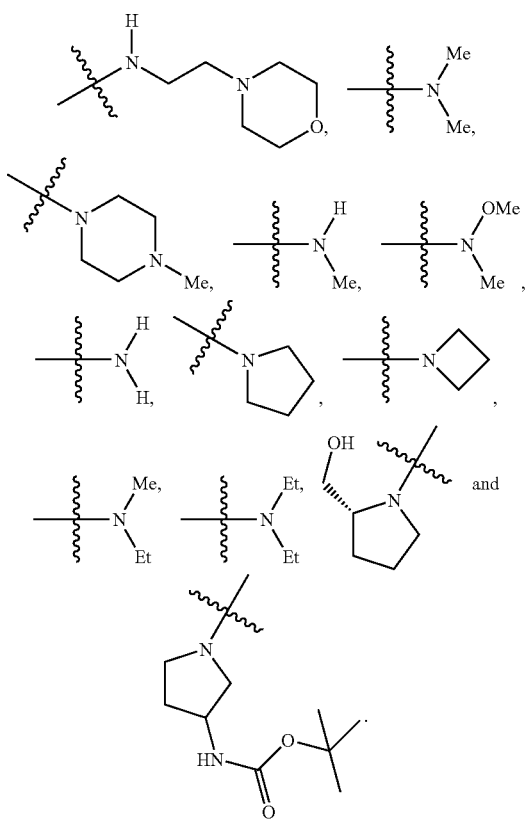

In a preferred embodiment of the compounds, the compounds are represented by the formula A-3:

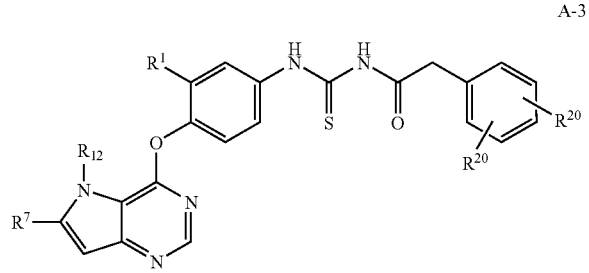

and pharmaceutically acceptable salts and complexes thereof, wherein $R^7$ is selected from the group consisting of H, —Y-(aryl) and —Y-(heteroaryl), wherein —Y-(aryl) and —Y-(heteroaryl) are optionally substituted with 1 to 5 independently selected $R^{38}$;

$R^1$ is selected from the group consisting of hydrogen, halo, $C_1$-$C_6$ alkyl, $C_2$-$C_6$ alkenyl and $C_2$-$C_6$ alkynyl, wherein $C_1$-$C_6$ alkyl, $C_2$-$C_6$ alkenyl and $C_2$-$C_6$ alkynyl are optionally substituted;

$R^{12}$ is selected from the group consisting of H, $C_1$-$C_6$ alkyl, —O($C_1$-$C_6$ alkyl) and —Y-(aryl), wherein $C_1$-$C_6$ alkyl and aryl are optionally substituted;

Y is a bond or is —$(C(R^{11})(H))_t$—, wherein t is an integer from 1 to 6;

$R^{11}$ is H or $C_1$-$C_6$ alkyl, wherein $C_1$-$C_6$ alkyl is optionally substituted; and each $R_{20}$ is independently selected from the group consisting of H and halogen.

In a preferred embodiment of the compounds, $R^1$ is hydrogen or halogen.

In a preferred embodiment of the compounds, $R^1$ is fluorine.

In a preferred embodiment of the compounds, $R^{12}$ is unsubstituted $C_1$-$C_3$ alkyl or unsubstituted —Y-phenyl.

In a preferred embodiment of the compounds, $R^{20}$ is Cl.

In a preferred embodiment of the compounds, the compounds are represented by the formula A-4:

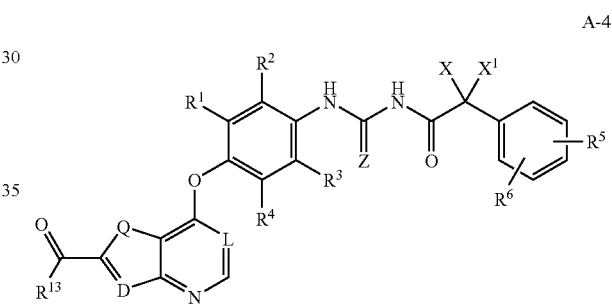

and pharmaceutically acceptable salts and complexes thereof, wherein

Z is O or S;

X and $X^1$ are independently selected from the group consisting of H, $C_1$-$C_6$ alkyl, halo, cyano and nitro, wherein $C_1$-$C_6$ alkyl is optionally substituted;

$R^1$, $R^2$, $R^3$, $R^4$, $R^5$ and $R^6$ are independently selected from the group consisting of hydrogen, halo, $C_1$-$C_6$ alkyl, $C_2$-$C_6$ alkenyl, $C_2$-$C_6$ alkynyl and $NR^{17}R^{18}$, wherein $C_1$-$C_6$ alkyl, $C_2$-$C_6$ alkenyl and $C_2$-$C_6$ alkynyl are optionally substituted;

$R^{17}$ and $R^{18}$ are independently $C_1$-$C_6$ alkyl;

Q is O, S, NH, N($C_1$-$C_6$ alkyl), or N—Y-(aryl);

D is $CR^{11}$, or N;

L is N, or CR, wherein R is selected from the group consisting of H, halo, —CN, $C_1$-$C_6$ alkyl, $C_2$-$C_6$ alkenyl and $C_2$-$C_6$ alkynyl, wherein $C_1$-$C_6$ alkyl, $C_2$-$C_6$ alkenyl, and $C_2$-$C_6$ alkynyl are optionally substituted; and $R^{13}$ is heterocyclyl or heteroaryl, wherein heterocyclyl and heteroaryl are optionally substituted with 1 to 5 independently selected $R^{38}$;

Y is a bond or is —$(C(R^{11})(H))_t$—, wherein t is an integer from 1 to 6; and $R^{11}$ at each occurrence is independently H or $C_1$-$C_6$ alkyl, wherein $C_1$-$C_6$ alkyl is optionally substituted.

In a preferred embodiment of the compounds, X and $X^1$ are both hydrogen.

In a preferred embodiment of the compounds, $R^1$, $R^2$, $R^3$ and $R^4$ are independently H or halogen.

In a preferred embodiment of the compounds, $R^1$ is hydrogen or halogen.

In a preferred embodiment of the compounds, $R^1$ is fluorine or chlorine.

In a preferred embodiment of the compounds, $R^4$ is hydrogen or halogen.

In a preferred embodiment of the compounds, $R^4$ is fluorine or chlorine.

In a preferred embodiment of the compounds, $R^2$, $R^3$, $R^5$, and $R^6$ are each hydrogen.

In a preferred embodiment of the compounds, Q is selected from the group consisting of S, $N(C_1$-$C_6$ alkyl) and N—Y—(aryl).

In a preferred embodiment of the compounds, Q is S.

In a preferred embodiment of the compounds, D is $CR^{11}$.

In a preferred embodiment of the compounds, $R^{11}$ is H.

In a preferred embodiment of the compounds, L is CH or N.

In a preferred embodiment of the compounds, L is CH.

In a preferred embodiment of the compounds, Z is sulfur.

In a preferred embodiment of the compounds, $R^{38}$ is selected from $C(O)OR^{40}$ and $NR^{36}R^{39}$.

In a preferred embodiment of the compounds, $R^{40}$ is H or $C_1$-$C_{10}$ alkyl.

In a preferred embodiment of the compounds, $R^{36}$ and $R^{39}$ are independently $C_1$-$C_6$ alkyl.

In a preferred embodiment of the compounds, the compounds are represented by the formula A-5:

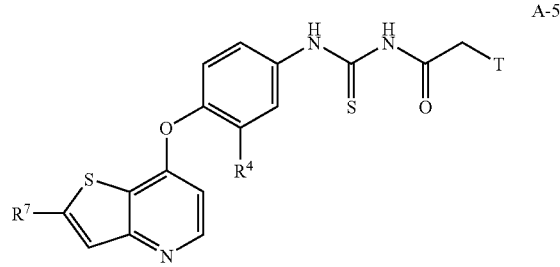

A-5 and pharmaceutically acceptable salts and complexes thereof, wherein $R^7$ is selected from the group consisting of H, —C(O)$NR^{42}R^{43}$, —Y-(aryl), —Y-(heteroaryl), —C(O)—($C_3$-$C_{10}$ cycloalkyl), —C(O)-(heterocyclyl), —C(O)—($C_6$-$C_{10}$ aryl) and —C(O)-(heteroaryl), wherein the aforementioned $R^7$ groups other than H are optionally substituted with 1 to 5 independently selected $R^{38}$;

$R^4$ is selected from the group consisting of H and halogen; and

T is selected from the group consisting of cycloalkyl, heterocyclyl, aryl, heteroaryl and arylalkyl, each of which is optionally substituted with 1 to 3 independently selected $R^{20}$;

In a preferred embodiment of the compounds, $R^7$ is selected from the group consisting of H, $C(O)NR^{42}R^{43}$ and —Y-(heteroaryl), wherein —Y-(heteroaryl) is optionally substituted with 1 to 5 independently selected $R^{38}$;

In a preferred embodiment of the compounds, $R^7$ is $C(O)NR^{42}R^{43}$;

In a preferred embodiment of the compounds, $R^{42}$ and $R^{43}$ taken together with the nitrogen to which they are attached form a $C_5$-$C_9$ heterocyclyl ring, wherein said ring is optionally substituted with 1 to 5 independently selected $R^{44}$ substituents, with the proviso that $R^{42}$ and $R^{43}$ are not both bonded to the nitrogen directly through and oxygen.

In a preferred embodiment of the compounds, $R^4$ is halogen.

In a preferred embodiment of the compounds, $R^4$ is fluorine.

In a preferred embodiment of the compounds, the compounds are represented by the formula A-6:

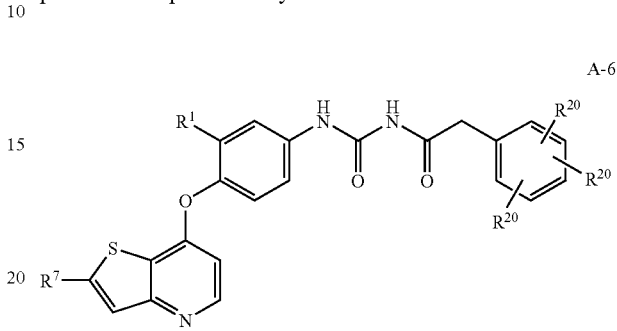

A-6 and pharmaceutically acceptable salts and complexes thereof, wherein $R^1$ is selected from the group consisting of hydrogen, halo, $C_1$-$C_6$ alkyl, $C_2$-$C_6$ alkenyl or $C_2$-$C_6$ alkynyl, wherein $C_1$-$C_6$ alkyl, $C_2$-$C_6$ alkenyl and $C_2$-$C_6$ alkynyl are optionally substituted;

$R^7$ is selected from the group consisting of H, halogen, $C_1$-$C_6$ alkyl, —C(=O)$NR^9R^{10}$, —C(=O)(aryl), —C(=O)(heterocyclyl), —C(=O)(heteroaryl), —Y-(aryl), —Y-(heterocyclyl), —Y-(heteroaryl), —$SR^{6a}$, —S-aryl, —S-(heteroaryl), —S—$C_1$-$C_6$ alkyl, —SO—$C_1$-$C_6$ alkyl, —$SO_2$—$C_1$-$C_6$ alkyl, —Y—$NR^9R^{10}$, —$SO_2NR^9R^{10}$, $CO_2R^9$, —C≡C—$(CR^{45}R^{45})_n$—$R^{46}$ and —C(=$NR^{42}$)$NR^{37}R^{43}$, wherein n is an integer ranging from 0 to 6 and wherein $C_1$-$C_6$ alkyl, aryl, heterocycle and heteroaryl are each independently optionally substituted with 1 to 5 independently selected $R^{38}$;

$R^9$ and $R^{10}$ are independently selected from the group consisting of H, $C_1$-$C_6$ alkyl, —Y-(cycloalkyl), —Y—($C_1$-$C_6$ heteroalkyl), —Y-(aryl), —Y-(heterocyclyl), —Y-(heteroaryl), —Y—O—$Y^1$—O—$R^{11}$, —$Y^1$—$CO_2$—$R^{11}$, Y—C(O)$OR^{37}$ and —Y—O—$R^{11}$, wherein said $C_1$-$C_6$ alkyl, heteroalkyl, cycloalkyl, aryl, heterocycle, and heteroaryl are each optionally substituted with one or more independently selected $R^{44}$, or $R^9$ and $R^{10}$ taken together with the nitrogen to which they are attached form a $C_5$-$C_9$ heterocyclyl ring or a heteroaryl ring, wherein said ring is optionally substituted with 1 to 5 independently selected $R^{44}$;

each $R^{20}$ is independently selected from the group consisting of H, halo, —$OR^{17}$ and —$C(O)OR^{17}$;

Y is a bond or is —$(C(R^{11})(H))_t$—, wherein t is an integer from 1 to 6;

$Y^1$ is —$(C(R^{11})(H))_t$—; and $R^{11}$ at each occurrence is independently H or $C_1$-$C_6$ alkyl, wherein $C_1$-$C_6$ alkyl is optionally substituted.

In a preferred embodiment of the compounds, $R^7$ is selected from the group consisting of H, $C(O)NR^9R^{10}$ and —Y-(heteroaryl), wherein —Y-(heteroaryl) is optionally substituted with 1 to 5 independently selected $R^{38}$;

In a preferred embodiment of the compounds, $R^7$ is $C(O)NR^9R^{10}$;

In a preferred embodiment of the compounds, $R^9$ and $R^{10}$ taken together with the nitrogen to which they are attached form a $C_5$-$C_9$ heterocyclyl ring, wherein said ring is optionally substituted with 1 to 5 independently selected $R^{44}$ substituents.

In a preferred embodiment of the compounds, $R^7$ is —Y-(heteroaryl), wherein said —Y-(heteroaryl) is optionally substituted with 1 to 5 independently selected $R^{38}$.

In a preferred embodiment of the compounds, $R^7$ is —Y-(heteroaryl), wherein said —Y-(heteroaryl) is optionally substituted with one $C_1$-$C_6$ alkyl.

In a preferred embodiment of the compounds, $R^1$ is halogen.

In a preferred embodiment of the compounds, $R^1$ is fluorine.

In a preferred embodiment of the compounds, $R^{17}$ is selected from the group consisting of H and $C_1$-$C_6$ alkyl.

In a preferred embodiment of the compounds, $R^{38}$ is selected from the group consisting of —$OR^{37}$, $C_1$-$C_6$ alkyl and —$(CH_2)_n$(5 to 10 membered heterocylic), wherein n is an integer ranging from 0 to 6.

In a preferred embodiment of the compounds, $R^{37}$ is selected from the group consisting of H and $C_1$-$C_6$ alkyl.

In a preferred embodiment of the compounds, each $R^{20}$ is independently selected from the group consisting of H, halogen and —O—($C_1$-$C_6$)alkyl.

In a preferred embodiment of the compounds, two $R^{20}$ are H and the third $R^{20}$ is selected from the group consisting of H, halogen and —O—($C_1$-$C_6$ alkyl).

In a second aspect, the invention comprises compounds of formula (B), which are inhibitors of VEGF receptor signaling and HGF receptor signaling:

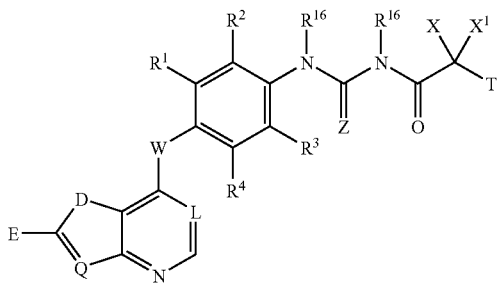

B and pharmaceutically acceptable salts and complexes thereof, wherein

T is selected from the group consisting of cycloalkyl, heterocyclyl, aryl and heteroaryl, wherein each of said cycloalkyl, heterocyclyl, aryl and heteroaryl is optionally substituted with 1 to 3 $R^{20}$;

each $R^{20}$ is independently selected from the group consisting of —H, halogen, trihalomethyl, —CN, —$NO_2$, —$NH_2$, —$OR^{17}$, —$OCF_3$, —$NR^{17}R^{18}$, —$S(O)_{0-2}R^{17}$, —$S(O)_2NR^{17}R^{17}$, —$C(O)OR^{17}$, —$C(O)NR^{17}R^{17}$, —$N(R^{17})SO_2R^{17}$, —$N(R^{17})C(O)R^{17}$, —$N(R^{17})C(O)OR^{17}$, —$C(O)R^{17}$, —$C(O)SR^{17}$, $C_1$-$C_4$ alkoxy, $C_1$-$C_4$ alkylthio, —$O(CH_2)_n$aryl, —$O(CH_2)_n$heteroaryl, —$(CH_2)_{0-5}$(aryl), —$(CH_2)_{0-5}$(heteroaryl), $C_1$-$C_6$ alkyl, $C_2$-$C_6$ alkenyl, $C_2$-$C_6$ alkynyl, —$CH_2(CH_2)_{0-4}$-$T^2$, an optionally substituted $C_{1-4}$ alkylcarbonyl, $C_{1-4}$ alkoxy, an amino optionally substituted by $C_{1-4}$ alkyl optionally substituted by $C_{1-4}$ alkoxy and a saturated or unsaturated three- to seven-membered carboxyclic or heterocyclic group, wherein $T^2$ is selected from the group consisting of —OH, —OMe, —OEt, —$NH_2$, —NHMe, —$NMe_2$, —NHEt and —$NEt_2$, and wherein the aryl, heteroaryl, $C_1$-$C_6$ alkyl, $C_2$-$C_6$ alkenyl, and $C_2$-$C_6$ alkynyl are optionally substituted;

W is selected from the group consisting of O, S and NH;

Z is selected from the group consisting of O, or S and NH;

X and $X^1$ are independently selected from the group consisting of H, $C_1$-$C_6$ alkyl, halo, cyano, or nitro, wherein $C_1$-$C_6$ alkyl is optionally substituted, or X and $X^1$ taken together with the atom to which they are attached, form a $C_3$-$C_7$ cycloalkyl;

$R^1$, $R^2$, $R^3$ and $R^4$ are independently selected from the group consisting of hydrogen, halo, trihalomethyl, —CN, —$NO_2$, —$NH_2$, —$OR^{17}$, —$NR^{17}R^{18}$, —$C(O)OR^{17}$, —$C(O)R^{17}$, $C_1$-$C_4$ alkoxy, $C_1$-$C_4$ alkylthio, $C_1$-$C_6$ alkyl, $C_2$-$C_6$ alkenyl or $C_2$-$C_6$ alkynyl, wherein $C_1$-$C_6$ alkyl, $C_2$-$C_6$ alkenyl and $C_2$-$C_6$ alkynyl are optionally substituted;

$R^{17}$ is selected from the group consisting of H and $R^{18}$;

$R^{18}$ is selected from the group consisting of a $C_1$-$C_6$ alkyl, an aryl, an aryl($C_1$-$C_6$ alkyl), a heterocyclyl and a heterocyclyl ($C_1$-$C_6$ alkyl), each of which is optionally substituted, or $R^{17}$ and $R^{18}$, taken together with a common nitrogen to which they are attached, form an optionally substituted five- to seven-membered heterocyclyl, the optionally substituted five- to seven-membered heterocyclyl optionally containing at least one additional annular heteroatom selected from the group consisting of N, O, S and P;

$R^{16}$ is selected from the group consisting of —H, —CN, —$(CH_2)_{0-5}$(aryl), —$(CH_2)_{0-5}$(heteroaryl), $C_1$-$C_6$ alkyl, $C_2$-$C_6$ alkenyl, $C_2$-$C_6$ alkynyl, —$CH_2(CH_2)_{0-4}$-$T^2$, an optionally substituted $C_{1-4}$ alkylcarbonyl, and a saturated or unsaturated three- to seven-membered carboxyclic or heterocyclic group, wherein $T^2$ is selected from the group consisting of —OH, —OMe, —OEt, —$NH_2$, —NHMe, —$NMe_2$, —NHEt and —$NEt_2$, and wherein the aryl, heteroaryl, $C_1$-$C_6$ alkyl, $C_2$-$C_6$ alkenyl, and $C_2$-$C_6$ alkynyl are optionally substituted;

Q is selected from the group consisting of $CH_2$, O, S, NH, N—($C_1$-$C_6$ alkyl), or N—Y-(aryl), —N—OMe, —$NCH_2$OMe and —N—Bn;

D is selected from the group consisting of C-E and N;

L is N, or CR, wherein R is selected from the group consisting of —H, halo, —CN, $C_1$-$C_6$ alkyl, $C_2$-$C_6$ alkenyl, and $C_2$-$C_6$ alkynyl, wherein $C_1$-$C_6$ alkyl, $C_2$-$C_6$ alkenyl, and $C_2$-$C_6$ alkynyl are optionally substituted; and E is selected from the group consisting of $E^1$, $E^2$ and $E^3$, wherein $E^1$ is selected from the group consisting of —H, halogen, nitro, azido, $C_1$-$C_6$ alkyl, $C_3$-$C_{10}$ cycloalkyl, —$C(O)NR^{42}R^{43}$, —Y—$NR^{42}R^{43}$, —$NR^{42}C(=O)R^{43}$, —$SO_2R^{42}$, —$SO_2NR^{42}R^{43}$, —NR $^{37}SO_2R^{42}$, —$NR^{37}SO_2NR^{42}R^{43}$, —$C(=N$—$OR^{42})R^{43}$, —$C(=NR^{42})R^{43}$, —C $(=NR^{42})N^{37}R^{43}$, $NR^{37}C$ $(=NR^{42})NR^{37}R^{43}$, —$C(O)R^{42}$, —$CO_2R^{42}$, —$C(O)$(heterocyclyl), —C $(O)(C_6$-$C_{10}$aryl), —$C(O)$(heteroaryl), —Y—($C_6$-$C_{10}$ aryl), —Y-(heteroaryl), —Y-(5-10 membered heterocyclic), —$NR^{6a}R^{6b}$, —$NR^{6a}SO_2R^{6b}$, —$NR^{6a}C(O)R^{6b}$, —$OC(O)R^{6b}$, —NR $^{6a}C(O)OR^{6b}$, —$OC(O)NR^{6a}R^{6b}$, —$OR^{6a}$, —$SR^{6a}$, —$S(O)R^{6a}$, —$SO_2R^{6a}$, —$SO_3R^{6a}$, —$SO_2NR^{6a}R^{6b}$, —$SO_2NR^{42}R^{43}$, —$COR^{6a}$, —$CO_2R^{6a}$, —$CONR^{6a}R^{6b}$, —($C_1$-$C_4$)fluoroalkyl, —($C_1$-$C_4$)fluoroalkoxy, —($C\ Z^3Z^4)_a$CN, wherein n is an integer ranging from 0 to 6, and the aforementioned $E^1$ groups other than —H and halogen are optionally substituted by 1 to 5 independently selected $R^{38}$, or $E^1$ is selected from a moiety selected from the group consisting of —(CZ$^3$Z$_4$)$_a$-aryl, —(CZ$^3$Z$^4$)$_a$-heterocycle, (C$_2$-C$_6$)alkynyl, —(CZ$^3$Z$^4$)$_a$—(C$_3$-C$_6$)cycloalkyl, —(CZ$^3$Z$^4$)$_a$—(C$_5$-C$_6$)cycloalkenyl, (C$_2$-C$_6$) alkenyl and (C$_1$-C$_6$)alkyl, which is optionally substituted with 1 to 3 independently selected Y$^2$ groups, where a is 0, 1, 2, or 3, and wherein when a is 2 or 3, the CZ$^3$Z$^4$ units may be the same or different; wherein each R$^{38}$ is independently selected from halo, cyano, nitro, trifluoromethoxy, trifluoromethyl, azido, —C(O)R$^{40}$, —C(O)OR$^{40}$, —OC(O)R$^{40}$, —OC(O)OR$^{40}$, —NR$^{36}$C(O)R$^{39}$, —C(O)NR$^{36}$R$^{39}$, —NR$^{36}$R$^{39}$, —OR$^{37}$, —SO$_2$NR$^{36}$R$^{39}$, C$_1$-C$_6$ alkyl, —(CH$_2$)$_j$O(CH$_2$)$_i$NR$^{36}$R$^{39}$, —(CH$_2$)$_n$O(CH$_2$)$_i$OR$^{37}$, —(CH$_2$)$_n$OR$^{37}$, —S(O)$_j$(C$_1$-C$_6$ alkyl), —(CH$_2$)$_n$(C$_6$-C$_{10}$ aryl), —(CH$_2$)$_n$(C$_5$-C$_{10}$ heteroaryl), —(CH$_2$)$_n$(5-10 membered heterocyclyl); —C(O)(CH$_2$)$_n$(C$_6$-C$_{10}$ aryl), —(CH$_2$)$_n$O(CH$_2$)$_j$(C$_6$-C$_{10}$ aryl), —(CH$_2$)$_n$O(CH$_2$)$_i$(5-10 membered heterocyclyl), —C(O)(CH$_2$)$_n$(5-10 membered heterocyclyl), —(CH$_2$)$_j$NR$^{39}$(CH$_2$)$_i$NR$^{36}$R$^{39}$, —(CH$_2$)$_j$NR$^{39}$CH$_2$C(O)NR$^{36}$R$^{39}$, —(CH$_2$)$_j$NR$^{39}$(CH$_2$)$_i$NR$^{37}$C(O)R$^{40}$, —(CH$_2$)$_j$NR$^{39}$(CH$_2$)$_n$O(CH$_2$)$_i$OR$^{37}$, —(CH$_2$)$_j$NR$^{39}$(CH$_2$)$_i$S(O)$_j$(C$_1$-C$_6$ alkyl), —(CH$_2$)$_j$NR$^{39}$(CH$_2$)$_n$R$^{36}$, —SO$_2$(CH$_2$)$_n$(C$_6$-C$_{10}$ aryl), —SO$_2$(CH$_2$)$_n$(5-10 membered heterocyclyl), —(CH$_2$)$_n$NR$^{36}$R$^{39}$, —NR$^{37}$SO$_2$NR$^{36}$R$^{39}$, SO$_2$R$^{36}$, C$_2$-C$_6$ alkenyl, C$_3$-C$_{10}$ cycloalkyl and C$_1$-C$_6$ alkylamino, wherein j is an integer ranging from 0 to 2, n is an integer ranging from 0 to 6, i is an integer ranging from 0 to 6, the —(CH$_2$)$_i$— and —(CH$_2$)$_n$—moieties of the foregoing R$^{38}$ groups optionally include a carbon-carbon double or triple bond where n is an integer between 2 and 6, and the alkyl, aryl, heteroaryl and heterocyclyl moieties of the foregoing R$^{38}$ groups are optionally substituted by one or more substituents independently selected from halo, cyano, nitro, trifluoromethyl, azido, —OH, —C(O)R$^{40}$, —C(O)OR$^{40}$, —OC(O)R$^{40}$, —OC(O)OR$^{40}$, —NR$^{36}$C(O)R$^{39}$, —C(O)NR$^{36}$R$^{39}$, —(CH$_2$)$_n$NR$^{36}$R$^{39}$, C$_1$-C$_6$ alkyl, C$_3$-C$_{10}$ cycloalkyl, —(CH$_2$)$_n$(C$_6$-C$_{10}$ aryl), —(CH$_2$)$_n$(5-10 membered heterocyclyl), —(CH$_2$)$_n$O(CH$_2$)$_i$OR$^{37}$, and —(CH$_2$)$_n$OR$^{37}$, wherein n is an integer ranging from 0 to 6 and i is an integer ranging from 2 to 6;

each R$^{42}$ and R$^{43}$ is independently selected from the group consisting of H, C$_1$-C$_6$ alkyl, C$_1$-C$_6$ heteroalkyl, —Y—(C$_3$-C$_{10}$ cycloalkyl), —Y—(C$_6$-C$_{10}$ aryl), —Y—(C$_6$-C$_{10}$ heteroaryl), —Y— (5-10 membered heterocyclic), —Y—O—Y—OR$^{37}$, —Y$^1$—CO$_2$—R$^{37}$, and —Y—OR$^{37}$, wherein the alkyl, heteroalkyl, cycloalkyl, aryl, heteroaryl and heterocyclic moieties of the foregoing R$^{42}$ and R$^{43}$ groups are optionally substituted by I or more substituents independently selected from R$^{44}$, wherein Y is a bond or is —(C(R$^{37}$)(H))$_n$, n is an integer ranging from 1 to 6, and Y$^1$ is —(C(R$^{37}$)(H))$_n$, or R$^{42}$ and R$^{43}$ taken together with the nitrogen to which they are attached form a C$_5$-C$_9$ heterocyclyl ring or a heteroaryl ring, wherein said ring is optionally substituted by 1 to 5 R$^{44}$ substituents, with the proviso that R$^{42}$ and R$^{43}$ are not both bonded to the nitrogen directly through an oxygen;

each R$^{44}$ is independently selected from the group consisting of halo, cyano, nitro, trifluoromethoxy, trifluoromethyl, azido, —C(O)R$^{40}$, —C(O)OR$^{40}$, —OC(O)R$^{40}$, —OC(O)OR$^{40}$, —NR$^{36}$C(O)R$^{39}$, —C(O)NR$^{36}$R$^{39}$, —NR$^{36}$R$^{39}$, —OR$^{37}$, —SO$_2$NR$^{36}$R$^{39}$, —SO$_2$R$^{36}$, —NR$^{36}$SO$_2$R$^{39}$, —NR$^{36}$SO$_2$NR$^{37}$R$^{41}$, C1-C$_6$ alkyl, C$_2$-C$_6$ alkenyl, C$_2$-C$_6$ alkynyl, C$_3$-C$_{10}$ cycloalkyl, —C$_1$-C$_6$ alkylamino, —(CH$_2$)$_j$O(CH$_2$)$_i$NR$^{36}$R$^{39}$, —(CH$_2$)$_n$O(CH$_2$)$_i$OR$^{37}$, —(CH$_2$)$_n$OR$^{37}$, —S(O)$_j$(C$_1$-C$_6$ alkyl), —(CH$_2$)$_n$(C$_6$-C$_{10}$ aryl), —(CH$_2$)$_n$(5-10 membered heterocyclic), —C(O)(CH$_2$)$_n$(C$_6$-C$_{10}$ aryl), —(CH$_2$)$_n$O(CH$_2$)j(C$_6$-C$_{10}$ aryl), —(CH$_2$)$_n$O(CH$_2$)$_i$(5 to 10 membered heterocyclic), —C(O)(CH$_2$)$_n$(5 to 10 membered heterocyclic), —(CH$_2$)$_j$NR$^{39}$(CH$_2$)$_i$NR$^{36}$R$^{39}$, —(CH$_2$)$_j$NR$^{39}$CH$_2$C(O)NR$^{36}$R$^{39}$, —(CH$_2$)$_j$NR$^{39}$(CH$_2$)$_i$NR$^{37}$C(O)R$^{40}$, —(CH$_2$)$_j$NR$^{39}$(CH$_2$)$_n$O(CH$_2$)$_i$OR$^{37}$, —(CH$_2$)$_j$NR$^{39}$(CH$_2$)$_i$S(O)$_j$(C$_1$-C$_6$ alkyl), —(CH$_2$)$_j$NR$^{39}$(CH$_2$)$_n$R$^{36}$, —SO$_2$(CH$_2$)$_n$(C$_6$-C$_{10}$ aryl), and —SO$_2$(CH$_2$)$_n$(5 to 10 membered heterocyclic) wherein, j is an integer from 0 to 2, n is an integer from 0 to 6 and i is an integer ranging from 2 to 6, the —(CH$_2$)$_i$— and —(CH$_2$)$_{n1}$— moieties of the foregoing R$^{44}$ groups optionally include a carbon-carbon double or triple bond wherein n is an integer from 2 to 6, and the alkyl, aryl and heterocyclic moieties of the foregoing R$^{44}$ groups are optionally substituted by 1 or more substituents independently selected from the group consisting of halo, cyano, nitro, trifluoromethyl, azido, —OH, —C(O)R$^{40}$, —C(O)OR$^{40}$, —O C(O)R$^{40}$, —OC(O)OR$^{40}$, —NR$^{36}$C(O)R$^{39}$, —C(O)NR$^{36}$R$^{39}$, —(CH$_2$)$_n$NR$^{36}$R$^{39}$, —SO$_2$R$^{36}$, —SO$_2$NR$^{36}$R$^{39}$, C$_1$-C$_6$ alkyl, C$_3$-C$_{10}$ cycloalkyl, —(CH$_2$)$_n$(C$_6$-C$_{10}$ aryl), —(CH$_2$)$_n$(5 to 10 membered heterocyclic), —(CH$_2$)$_n$O(CH$_2$)$_i$OR$^{37}$ and —(CH$_2$)$_n$OR$^{37}$, wherein n is an integer from 0 to 6 and i is an integer from 2 to 6; and each R$^{40}$ is independently selected from H, C$_1$-C$_{10}$ alkyl, —(CH$_2$)$_n$(C$_6$-C$_{10}$ aryl), C$_3$-C$_{10}$ cycloalkyl, and —(CH$_2$)$_n$ (5-10 membered heterocyclic), wherein n is an integer ranging from 0 to 6;

each R$^{36}$ and R$^{39}$ is independently selected from the group consisting of H, —OH, C$_1$-C$_6$ alkyl, C$_3$-C$_{10}$ cycloalkyl, —(CH$_2$)$_n$(C$_6$-C$_{10}$ aryl), —(CH$_2$)$_n$(5-10 membered heterocyclic), —(CH$_2$)$_n$O(CH$_2$)$_i$OR$^{37}$, —(CH$_2$)$_n$CN(CH$_2$)$_n$OR$^{37}$, —(CH$_2$)$_n$CN(CH$_2$)$_n$R$^{37}$, and —(CH$_2$)$_n$OR$^{37}$, wherein n is an integer ranging from 0 to 6 and i is an integer ranging from 2 to 6, and the alkyl, aryl and heterocyclic moieties of the foregoing R$^{36}$ and R$^{39}$ groups are optionally substituted by one or more substituents independently selected from —OH, halo, cyano, nitro, trifluoromethyl, azido, —C(O)R$^{40}$, —C(O)OR$^{40}$, —CO(O)R$^{40}$, —OC(O)OR$^{40}$, —NR$^{37}$C(O)R$^{41}$, —C(O)NR$^{37}$R$^{41}$, —NR$^{37}$R$^{41}$, —C$_1$-C$_6$ alkyl, —(CH$_2$)$_n$(C$_6$-C$_{10}$ aryl), —(CH$_2$)$_n$(5 to 10 membered heterocyclic), —(CH$_2$)$_n$O(CH$_2$)$_i$OR$^{37}$, and —(CH$_2$)$_n$OR$^{37}$, wherein n is an integer ranging from 0 to 6 and i is an integer ranging from 2 to 6, with the proviso that when R$^{36}$ and R$^{39}$ are both attached to the same nitrogen, then R$^{36}$ and R$^{39}$ are not both bonded to the nitrogen directly through an oxygen;

each R$^{37}$ and R$^{41}$ is independently selected from the group consisting of H, OR$^{36}$, C$_1$-C$_6$ alkyl and C$_3$-C$_{10}$ cycloalkyl;

each R$^{6a}$ and R$^{6b}$ is independently selected from the group consisting of hydrogen, —(CZ$^5$Z$^6$)$_u$—(C$_3$-C$_6$)cycloalkyl, —(CZ$^5$Z$^6$)$_u$—(C$_5$-C$_6$)cycloalkenyl, —(CZ$^5$Z$^6$)$_u$-aryl, —(CZ$^5$Z$^6$)$_u$-heterocycle, (C$_2$-C$_6$)alkenyl, and (C$_1$-C$_6$) alkyl, which is optionally substituted with 1 to 3 independently selected Y$^3$ groups, where u is 0, 1, 2, or 3, and wherein when u is 2 or 3, the CZ$^5$Z$^6$ units may be the same or different, or R$^{6a}$ and R$^{6b}$ taken together with adjacent atoms can form a heterocycle;

each Z$^3$, Z$^4$, Z$^5$ and Z$^6$ is independently selected from the group consisting of H, F and (C$_1$-C$_6$)alkyl, or each Z$^3$ and Z$^4$, or Z$^5$ and Z$^6$ are selected together to form a carbocycle, or two Z$^3$ groups on adjacent carbon atoms are selected together to optionally form a carbocycle;

each Y$^2$ and Y$^3$ is independently selected from the group consisting of halogen, cyano, nitro, tetrazolyl, guanidino, amidino, methylguanidino, azido, —C(O)Z$^7$, —OC(O)NH$_2$, —OC(O) NHZ$^7$, —OC(O)NZ$^7$Z$^8$, —NHC(O)Z$^7$, —NHC(O)NH$_2$, —NHC(O)NHZ$^7$, —NHC(O)NZ$^7$Z$^8$, —C(O)OH, —C(O)OZ$^7$, —C(O)NH$_2$, —C(O)NHZ$^7$, —C(O)NZ$^7$Z$^8$, —P(O)$_3$H$_2$, —P(O)$_3$(Z$^7$)$_2$, —S(O)$_3$H, —S(O)Z$^7$, —S(O)$_2$Z$^7$, —S(O)$_3$Z$^7$, —Z$^7$, —OZ$^7$, —OH, —NH$_2$, —NHZ$^7$, —NZ$^7$Z$^8$, —C(=NH)NH$_2$, —C(=NOH)NH$_2$, —N-morpholino, (C$_2$-C$_6$)alkenyl, (C$_2$-C$_6$)alkynyl, (C$_1$-C$_6$)haloalkyl, (C$_2$-C$_6$) haloalkenyl, (C$_2$-C$_6$)haloalkynyl, (C$_1$-C$_6$)haloalkoxy, —(CZ$^9$Z$^{10}$)$_r$NH$_2$, —(CZ$^9$Z$^{10}$)$_r$NHZ$^3$, —(CZ$^9$Z$^{10}$)$_r$NZ$^7$Z$^8$, —X$^6$(CZ$^9$Z$^{10}$)$_r$—(C$_3$-C$_8$)cycloalkyl, —X$^6$(CZ$^9$Z$^{10}$)$_r$—(C$_5$-C$_8$)cycloalkenyl, —X$^6$(CZ$^9$Z$^{10}$)$_r$-aryl and —X$^6$(CZ$^9$Z$^{10}$)$_r$-heterocycle, wherein r is 1, 2, 3 or 4;

X$^6$ is selected from the group consisting of O, S, NH, —C(O)—, —C(O)NH—, —C(O)O—, —S(O)—, —S(O)2— and —S(O)$_3$—;

Z$^7$ and Z$^8$ are independently selected from the group consisting of an alkyl of 1 to 12 carbon atoms, an alkenyl of 2 to 12 carbon atoms, an alkynyl of 2 to 12 carbon atoms, a cycloalkyl of 3 to 8 carbon atoms, a cycloalkenyl of 5 to 8 carbon atoms, an aryl of 6 to 14 carbon atoms, a heterocycle of 5 to 14 ring atoms, an aralkyl of 7 to 15 carbon atoms, and a heteroaralkyl of 5 to 14 ring atoms, or Z$^7$ and Z$^8$ together may optionally form a heterocycle;

Z$^9$ and Z$^{10}$ are independently selected from the group consisting of H, F, a (C$_1$-C$_{12}$)alkyl, a (C$_6$-C$_{14}$)aryl, a (C$_5$-C$_{14}$) heteroaryl, a (C$_7$-C$_{15}$)aralkyl and a (C$_5$-C$_{14}$)heteroaralkyl, or Z$^9$ and Z$^{10}$ are taken together form a carbocycle, or two Z$^9$ groups on adjacent carbon atoms are taken together to form a carbocycle; or any two Y$^2$ or Y$^3$ groups attached to adjacent carbon atoms may be taken together to be —O[C(Z$^9$)(Z$^{10}$)]$_r$O or —O[C(Z$^9$)(Z$^{10}$)]$_{r+1}$, or any two Y$^2$ or Y$^3$ groups attached to the same or adjacent carbon atoms may be selected together to form a carbocycle or heterocycle; and wherein any of the above-mentioned substituents comprising a CH$_3$ (methyl), CH$_2$ (methylene), or CH (methine) group which is not attached to a halogen, SO or SO$_2$ group or to a N, O or S atom optionally bears on said group a substituent selected from hydroxy, halogen, (C$_1$-C$_4$)alkyl, (C$_1$-C$_4$) alkoxy and an —N[(C$_1$-C$_4$)alkyl][(C$_1$-C$_4$) alkyl];

E$^2$ is —C≡CH or —C≡C—(CR$^{45}$R$^{45}$)$_n$—R$^{46}$;

R$^{45}$ is independently selected from the group consisting of H, a (C$_1$-C$_6$)alkyl and a (C$_3$-C$_8$)cycloalkyl;

R$^{46}$ is selected from the group consisting of heterocyclyl, —N(R$^{47}$)—C(O)—N(R$^{47}$)(R$^{48}$), —N(R$^{47}$)—C(S)—N(R$^{47}$)(R$^{48}$), —N(R$^{47}$)—C(O)—OR$^{48}$, —N(R$^{47}$)—C(O)—(CH$_2$)$_n$—R$^{48}$, —N(R$^{47}$)—SO$_2$R$^{47}$, —(CH$_2$)$_n$NR$^{47}$R$^{48}$, —(CH$_2$)$_n$OR$^{48}$, —(CH$_2$)$_n$SR$^{49}$, —(CH$_2$)$_n$S(O)R$^{49}$, —(CH$_2$)$_n$S(O)$_2$R$^{49}$, —OC(O)R$^{49}$, —OC(O)OR$^{49}$, —C(O)NR$^{47}$R$^{48}$, heteroaryl optionally substituted with one or more substituents selected from the group consisting of halo, —CF$_3$, (C$_1$-C$_6$)alkoxy, —NO$_2$, (C$_1$-C$_6$)alkyl, —CN, —SO$_2$R$^{50}$ and —(CH$_2$)$_n$NR$^{50}$R$^{51}$, and aryl optionally substituted with one or more substituents selected from the group consisting of halo, —CF$_3$, (C$_1$-C$_6$)alkoxy, —NO$_2$, (C$_1$-C$_6$)alkyl, —CN, —SO$_2$R$^{50}$ and —(CH$_2$)$_n$NR$^{50}$R$^{51}$;

R$^{47}$ and R$^{48}$ are independently selected from the group consisting of H, (C$_1$-C$_6$)alkyl, (C$_3$-C$_8$)cycloalkyl, heterocyclyl, —(CH$_2$)$_n$NR$^{50}$R$^{51}$, —(CH$_2$)$_n$OR$^{50}$, —(CH$_2$)$_n$C(O)R$^{49}$, —C(O)$_2$R$^{49}$, —(CH$_2$)$_n$SR$^{49}$, —(CH$_2$)$_n$S(O)R$^{49}$, —(CH$_2$)$_n$S(O)$_2$R$^{49}$, —(CH$_2$)$_n$R$^{49}$, —(CH$_2$)$_n$CN, aryl optionally substituted with one or more substituents selected from the group consisting of halo, —CF$_3$, (C$_1$-C$_6$) alkoxy, —NO$_2$, (C$_1$-C$_6$)alkyl, —CN, —(CH$_2$)$_n$OR$^{49}$, —(CH$_2$)$_n$heterocyclyl, —(CH$_2$)$_n$heteroaryl, —SO$_2$R$^{50}$ and —(CH$_2$)$_n$NR$^{50}$R$^{51}$, and heteroaryl optionally substituted with one or more substituents selected from the group consisting of halo, —CF$_3$, (C$_1$-C$_6$)alkoxy, —NO$_2$, (C$_1$-C$_6$) alkyl, —CN, —(CH$_2$)$_n$OR$^{49}$, —(CH$_2$)$_n$heterocyclyl, —(CH$_2$)$_n$heteroaryl, —SO$_2$R$^{50}$ and —(CH$_2$)$_n$NR$^{50}$R$^{51}$, or R$^{47}$ and R$^{48}$, together with the atom to which they are attached, form a 3-8 membered ring;

R$^{49}$ is selected from the group consisting of (C$_1$-C$_6$)alkyl, (C$_3$-C$_8$)cycloalkyl, heterocyclyl(C$_1$-C$_6$)alkylene, aryl(C$_1$-C$_6$)alkylene wherein the aryl is optionally substituted with one or more substituents selected from the group consisting of halo, —CF$_3$, (C$_1$-C$_6$)alkoxy, —NO$_2$, (C$_1$-C$_6$)alkyl, —CN, —SO$_2$R$^{50}$ and —(CH$_2$)$_n$NR$^{50}$R$^{51}$ heteroaryl(C$_1$-C$_6$)alkylene wherein the heteroaryl is optionally substituted with one or more substituents selected from the group consisting of halo, —CF$_3$, (C$_1$-C$_6$)alkoxy, —NO$_2$, (C$_1$-C$_6$) alkyl, —CN, —SO$_2$R$^{50}$ and —(CH$_2$)$_n$NR$^{50}$R$^{51}$, aryl optionally substituted with one or more substituents selected from the group consisting of halo, —CF$_3$, (C$_1$-C$_6$) alkoxy, —NO$_2$, (C$_1$-C$_6$)alkyl, —CN, —SO$_2$R$^{50}$ and —(CH$_2$)$_n$NR$^{50}$R$^{51}$, and heteroaryl optionally substituted with one or more substituents selected from the group consisting of halo, —CF$_3$, (C$_1$-C$_6$)alkoxy, —NO$_2$, (C$_1$-C$_6$) alkyl, —CN, —SO$_2$R$^{50}$ and —(CH$_2$)$_n$NR$^{50}$R$^{51}$;

R$^{50}$ and R$^{51}$ are independently selected from the group consisting of H, (C$_1$-C$_6$)alkyl, (C$_3$-C$_8$)cycloalkyl and —C(O)R$^{45}$, or R$^{50}$ and R$^{51}$, together with the atom to which they are attached, form a 3-8 membered ring; and E$^3$ is the group defined by -(Z$^{11}$)-(Z$^{12}$)$_m$-(Z$^{13}$)$_{m1}$, wherein Z$^{11}$ is heterocyclyl or heterocyclylene;

Z$^{12}$ is selected from the group consisting of OC(O), OC(S) and C(O);

Z$^{13}$ is selected from the group consisting of heterocyclyl, aralkyl, N(H)R$^{52}$, (C$_1$-C$_3$)alkyl, —OR$^{52}$, halo, S(O)$_2$R$^{56}$, (C$_1$-C$_3$)hydroxyalkyl and (C$_1$-C$_3$)haloalkyl;

m is 0 or 1;

m1 is 0 or 1;

R$^{52}$ is selected from the group consisting of H, —(CH$_2$)$_q$S(O)$_2$R$^{54}$, R$^{55}$NR$^{53}$R$^{53}$, (C$_1$-C$_3$)alkyl, —(CH$_2$)$_q$OR$^{53}$, —C(O)R$^{54}$ and —C(O)OR$^{53}$;

q is 0, 1, 2, 3 or 4;

R$^{53}$ is (C$_1$-C$_3$)alkyl;

R$^{54}$ is (C$_1$-C$_3$)alkyl or N(H)R$^{53}$;

R$^{55}$ is (C$_1$-C$_6$) alkyl; and

R$^{56}$ is selected from the group consisting of NH$_2$, (C$_1$-C$_3$) alkyl and OR$^{52}$.

In a preferred embodiment of the compounds, the compounds are represented by the formula B-0:

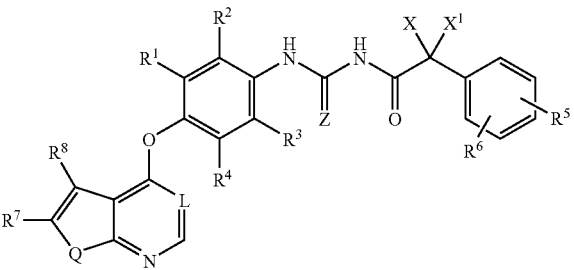

B-0 and pharmaceutically acceptable salts and complexes thereof, wherein

Z is O or S;

X and $X^1$ are independently selected from the group consisting of H, $C_1$-$C_6$ alkyl, halo, cyano, or nitro, wherein $C_1$-$C_6$ alkyl is optionally substituted;

$R^1$, $R^2$, $R^3$, $R^4$, $R^5$ and $R^6$ are independently selected from the group consisting of hydrogen, halo, $C_1$-$C_6$ alkyl, $C_2$-$C_6$ alkenyl and $C_2$-$C_6$ alkynyl, wherein $C_1$-$C_6$ alkyl, $C_2$-$C_6$ alkenyl and $C_2$-$C_6$ alkynyl are optionally substituted;

Q is O, S, NH, N($C_1$-$C_6$ alkyl), or N—Y-(aryl);

L is N, or CR, wherein R is halo, —CN, $C_1$-$C_6$ alkyl, $C_2$-$C_6$ alkenyl, or $C_2$-$C_6$ alkynyl, wherein $C_1$-$C_6$ alkyl, $C_2$-$C_6$ alkenyl, and $C_2$-$C_6$ alkynyl are optionally substituted; and $R^7$ is selected from the group consisting of H, halogen, $C_1$-$C_6$ alkyl, —C(=O)$NR^9R^{10}$, —C(=O)(aryl), —C(=O)(heterocyclyl), —C(=O)(heteroaryl), —Y-(aryl), —Y-(heterocyclyl), —Y-(heteroaryl), —Y—$NR^9R^{10}$, —$SO_2NR^9R^{10}$ and $CO_2R^9$, wherein $C_1$-$C_6$ alkyl, aryl, heterocyclyl and heteroaryl are each optionally substituted;

$R^9$ and $R^{10}$ are independently selected from the group consisting of H, $C_1$-$C_6$ alkyl, —Y-(cycloalkyl), —Y-(aryl), —Y-(heterocyclyl), —Y-(heteroaryl), —Y—O—$Y^1$—O—$R^{11}$, —$Y^1$—$CO_2$—$R^{11}$, and —Y—O—$R^{11}$, wherein $C_1$-$C_6$ alkyl, cycloalkyl, aryl, heterocyclyl, and heteroaryl are each optionally substituted, or $R^9$ and $R^{10}$ are taken together with the nitrogen to which they are attached to form a $C_5$-$C_9$ heterocyclyl ring or a heteroaryl ring, wherein said ring is optionally substituted;

$R^8$ is selected from the group consisting of H, halo and $C_1$-$C_6$ alkyl, wherein $C_1$-$C_6$ alkyl is optionally substituted;

Y is a bond or is —$(C(R^{11})(H))_t$—, wherein t is an integer from 1 to 6;

$Y^1$ is —$(C(R^{11})(H))_t$—, and $R^{11}$ at each occurrence is independently H or $C_1$-$C_6$ alkyl, wherein $C_1$-$C_6$ alkyl is optionally substituted.

In a preferred embodiment of the compounds, X and $X^1$ are both hydrogen.

In a preferred embodiment of the compounds, $R^1$ is hydrogen or halogen.

In a preferred embodiment of the compounds, $R^1$ is fluorine.

In a preferred embodiment of the compounds, $R^4$ is hydrogen or halogen.

In a preferred embodiment of the compounds $R^4$ is fluorine.

In a preferred embodiment of the compounds, $R^2$, $R^3$, $R^5$, and $R^6$ are each hydrogen.

In a preferred embodiment of the compounds, Q is S, N($C_1$-$C_6$ alkyl), or N—Y-(aryl).

In a preferred embodiment of the compounds, L is CH or N.

In a preferred embodiment of the compounds, $R^8$ is selected from the group consisting of H, halo and $C_1$-$C_6$ alkyl, wherein $C_1$-$C_6$ alkyl is optionally substituted with OH or $NR^{14}R^{15}$, where $R^{14}$ and $R^{15}$ are independently H or $C_1$-$C_6$ alkyl, or $R^{14}$ and $R^{15}$ are taken together with the nitrogen to which they are attached to form a $C_5$-$C_9$ heterocyclyl ring or a heteroaryl ring, wherein said ring is optionally substituted.

In a preferred embodiment of the compounds, $R^7$ is selected from the group consisting of H, halogen, $C_1$-$C_6$ alkyl, —$CONR^9R^{10}$, —$SO_2NH_2$, —$SO_2NR^9R^{10}$, —Y-heterocycle —Y-heteroaryl, —S-aryl, —S—$C_1$-$C_6$ alkyl, —SO—$C_1$-$C_6$ alkyl and —$SO_2$—$C_1$-$C_6$ alkyl, wherein $C_1$-$C_6$ alkyl is unsubstituted or is substituted with one or two of hydroxy or halogen, and the heterocycle, and heteroaryl are unsubstituted or are substituted with one or two of alkoxy, alkyl, or haloalkyl.

In a preferred embodiment of the compounds, $R^7$ is —$CONR^9R^{10}$.

In a preferred embodiment of the compounds, $R^9$ and $R^{10}$ are independently selected from the group consisting of H, $C_1$-$C_6$ alkyl, —Y—O—$R^{11}$, —Y-(heterocycle), —$Y^1$—$CO_2$—$R^{11}$ and —Y-(aryl), wherein $C_1$-$C_6$ alkyl is unsubstituted or is substituted with one or two of hydroxy or halogen, and the heterocycle, and aryl are unsubstituted or are substituted with one or two of alkoxy, alkyl, or haloalkyl.

In a preferred embodiment of the compounds, $R^9$ and $R^{10}$ are taken together with the nitrogen to which they are attached to form a pyrrolidinyl, piperidinyl, piperazinyl, morpholinyl, or thiomorpholinyl ring, wherein said ring is unsubstituted or is substituted with one or two of alkoxy, alkyl, or haloalkyl.

In a preferred embodiment of the compounds, $R^7$ is selected from the group consisting of H, halogen, $C_1$-$C_6$ alkyl, —$SO_2NR^9R^{10}$, —C(=O)(heterocyclyl), —Y-(heterocyclyl), —Y-(heteroaryl), —S-aryl, —S—$C_1$-$C_6$ alkyl, —SO—$C_1$-$C_6$ alkyl and —$SO_2$—$C_1$-$C_6$ alkyl, wherein $C_1$-$C_6$ alkyl is unsubstituted or is substituted with one or two of hydroxy or halogen, and the heterocyclyl, and heteroaryl are unsubstituted or are substituted with one or two of alkoxy, alkyl, or haloalkyl.

In a preferred embodiment of the compounds, Z is sulfur.

In a preferred embodiment of the compounds, the compounds are represented by the formula B-1:

B-1 and pharmaceutically acceptable salts and complexes thereof, wherein $R^1$ is selected from the group consisting of hydrogen, halo, $C_1$-$C_6$ alkyl, $C_2$-$C_6$ alkenyl and $C_2$-$C_6$ alkynyl, wherein $C_1$-$C_6$ alkyl, $C_2$-$C_6$ alkenyl and $C_2$-$C_6$ alkynyl are optionally substituted;

$R^7$ is selected from the group consisting of H, halogen, $C_1$-$C_6$ alkyl, —C(=O)$NR_9R_{10}$, —C(=O)(aryl), —C(=O)(heterocyclyl), —C(=O)(heteroaryl), —Y-(aryl), —Y-(heterocyclyl), —Y-(heteroaryl), —Y—$NR^9R^{10}$, —$SO_2NR^9R^{10}$ and $CO_2R^9$, wherein $C_1$-$C_6$ alkyl, aryl, heterocycle and heteroaryl are each independently optionally substituted;

$R^9$ and $R^{10}$ are independently selected from the group consisting of H, $C_1$-$C_6$ alkyl, —Y-(cycloalkyl), —Y-(aryl), —Y-(heterocyclyl), —Y-(heteroaryl), —Y—O—$Y^1$—O—$R^{11}$, —$Y^1$—$CO_2$—$R^{11}$, and —Y—O—$R^{11}$, wherein $C_1$-$C_6$ alkyl, cycloalkyl, aryl, heterocycle, and heteroaryl are each optionally substituted, or $R^9$ and $R^{10}$ taken together with the nitrogen to which they are attached form a $C_5$-$C_9$ heterocyclyl ring or a heteroaryl ring, wherein said ring is optionally substituted;

Y is a bond or is —$(C(R^{11})(H))_t$—, wherein t is an integer from 1 to 6;

$Y_1$ is —$(C(R^{11})(H))_t$—;

$R^{11}$ at each occurrence is independently H or $C_1$-$C_6$ alkyl, wherein $C_1$-$C_6$ alkyl is optionally substituted; and $R^{12}$ is selected from the group consisting of H, $C_1$-$C_6$ alkyl and —Y-(aryl), wherein $C_1$-$C_6$ alkyl and aryl are optionally substituted.

In a preferred embodiment of the compounds, $R^1$ is hydrogen or halogen.

In a preferred embodiment of the compounds, $R^1$ is fluorine.

In a preferred embodiment of the compounds, $R^{12}$ is unsubstituted $C_1$-$C_3$ alkyl or unsubstituted benzyl.

In a preferred embodiment of the compounds, $R^7$ is —C(O)NR$^9$R$^{10}$.

In a preferred embodiment of the compounds $R^7$ is selected from the group consisting of

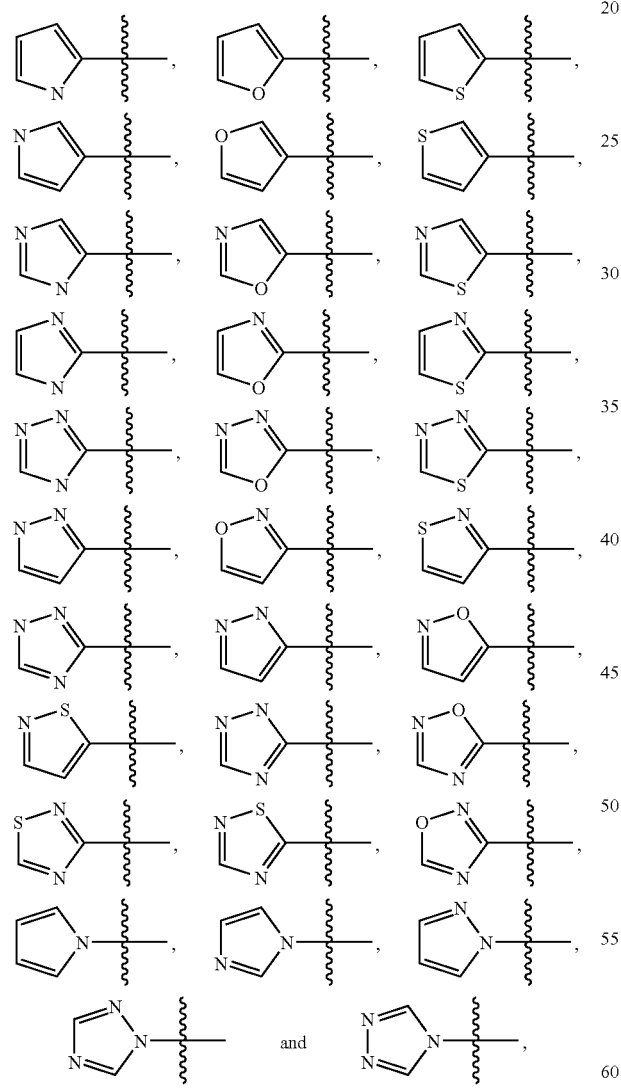

wherein the members of said group are optionally substituted by 1 to 3 independently selected $R^{38}$.

In a preferred embodiment of the compounds $R^7$ is selected from the group consisting of

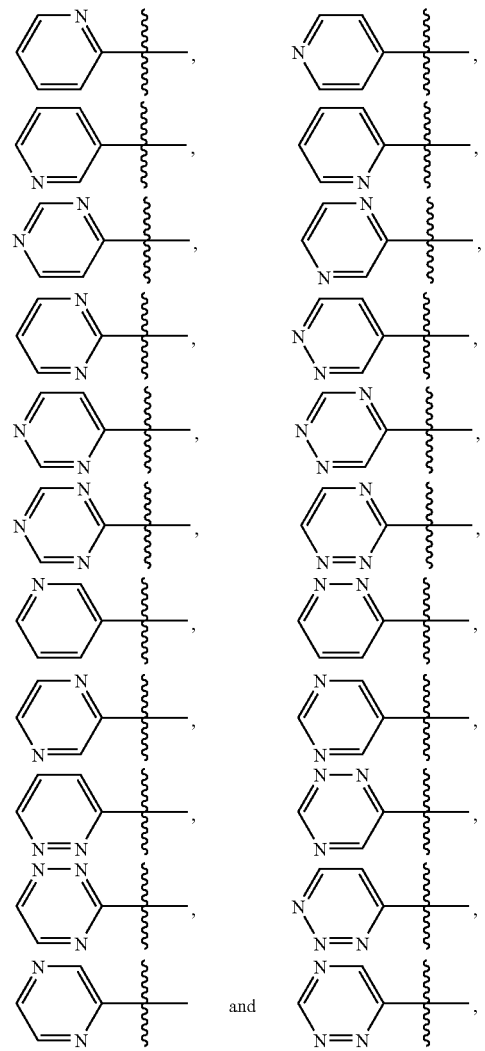

wherein the members of said group are optionally substituted with 1 to 3 independently selected $R^{38}$.

In the third aspect, the invention provides a composition comprising a compound or as depicted in any of the tables and examples herein together with a pharmaceutically acceptable excipient.

The fourth aspect of the invention provides a method of inhibiting VEGF receptor signaling and HGF receptor signaling, the method comprising contacting the receptor with a compound or as depicted in any of the tables herein, or with a composition. Inhibition of VEGF and HGF activity can be in a cell or a multicellular organism. If in a multicellular organism, the method according to this aspect of the invention comprises administering to the organism a compound or as depicted in any of the tables herein, or a composition. Preferably the organism is a mammal, more preferably a human.

The data presented herein demonstrate the inhibitory effects of the VEGF and HGF inhibitors of the invention. These data lead one to reasonably expect that the compounds of the invention are useful not only for inhibition of VEGF receptor signaling and HGF receptor signaling, but also as therapeutic agents for the treatment of proliferative diseases, including cancer and tumor growth.

Preferred compounds according to the invention include those described in the examples below. Compounds were named using Chemdraw Ultra version 6.0.2 or version 8.0.3, which are available through Cambridgesoft.com, 100 Cambridge Park Drive, Cambridge, Mass. 02140, Namepro version 5.09, which is available from ACD labs, 90 Adelaide Street West, Toronto, Ontario, M5H, 3V9, Canada, or were derived therefrom.

Synthetic Schemes and Experimental Procedures

The compounds of the invention can be prepared according to the reaction schemes or the examples illustrated below utilizing methods known to one of ordinary skill in the art. These schemes serve to exemplify some procedures that can be used to make the compounds of the invention. One skilled in the art will recognize that other general synthetic procedures may be used. The compounds of the invention can be prepared from starting components that are commercially available. Any kind of substitutions can be made to the starting components to obtain the compounds of the invention according to procedures that are well known to those skilled in the art.

I. SYNTHESIS (GENERAL SCHEMES)

Thieno[3,2-b]pyridine based compounds of formula A-0 may be prepared according to the procedures illustrated in the scheme A. Thus, thieno[3,2-b]pyridine-7-ol (I) upon treatment with $POCl_3$ is converted to the chloride II. Treatment of this material with a strong base such as n-BuLi followed by an addition of carbon dioxide affords the carboxylate III which is used without purification in the next step, providing the acyl chloride IV (presumably as a hydrochloride salt) upon its reaction with oxalyl chloride. The acyl chloride IV is used for the next step without further purification as well: upon its reaction with different primary and secondary amines the compound IV is converted to a variety of primary and secondary amides V which can further be derivatized via a substitution of the chlorine atom in the pyridine ring.

Thus, V reacting with substituted 4-nitrophenols in a high boiling point solvent, such as diphenyl ether in the presence of a base such as potassium carbonate, produced the nitro derivatives VI which then are reduced to the amines VII upon treatment with a mixture $NiCl_2/NaBH_4$ (or other conventional reagents). The amines VII also may be used for the next step without further purification, and upon treatment with 2-phenylacetyl isothiocyanates afford phenylacetylthioureas VIII bearing the amido-substituents such as the ones shown in the scheme A.

Scheme A

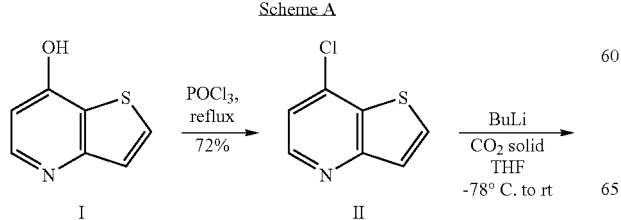

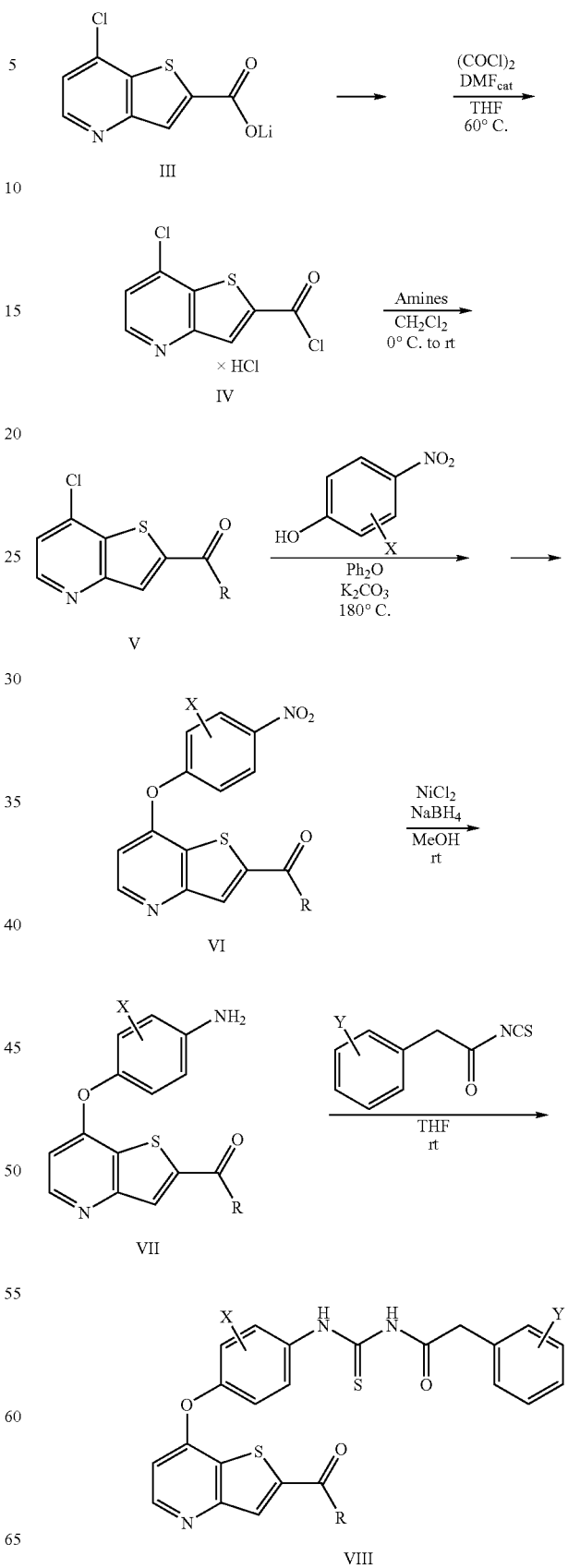

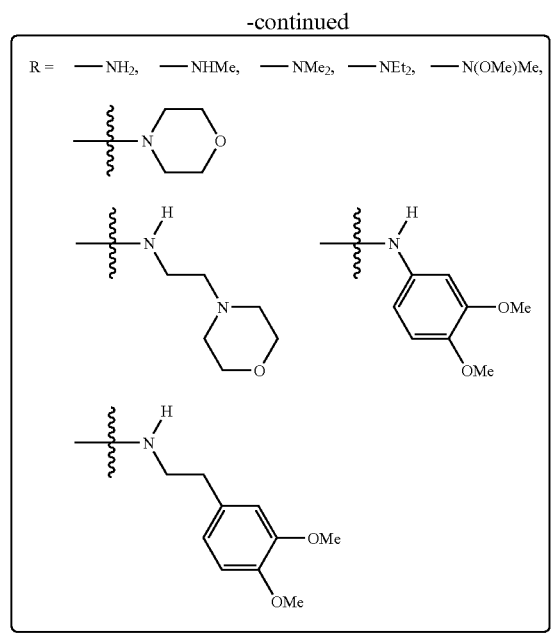

Substituents X and Y (up to three, same or different in each of the indicated benzene rings) are independently selected from halo, $C_1$-$C_6$ alkyl, $C_1$-$C_6$ alkoxy, cyano, nitro, hydroxy, amino, $C_1$-$C_6$ alkylamino Thieno[3,2-d]pyrimidine based compounds of formula A-0 may be prepared according to the procedures illustrated in the scheme B. Thus, thieno[3,2-d]pyrimidine-7-ol (IX) upon treatment with $POCl_3$ is converted to the chloride X. Treatment of this material with a strong base such as lithium tetramethylpiperidide (LiTMP) generated in situ followed by an addition of carbon dioxide affords the carboxylate XI which is used without purification in the next step, providing the acyl chloride XII (presumably as a hydrochloride salt) upon its reaction with oxalyl chloride. The acyl chloride XII reacting with different primary and secondary amines is converted to a variety of primary and secondary amides XIII which can further be derivatized via a substitution of the chlorine atom in the pyrimidine ring.

Thus, XIII reacting with substituted 4-nitrophenols in a high boiling point solvent, such as diphenyl ether in the presence of a base such as potassium carbonate, produce the nitro derivatives XIV which are then reduced to the amines XV upon treatment with a mixture $NiCl_2$/$NaBH_4$ (or other conventional reagents). The amines XV upon treatment with 2-phenylacetyl isothiocyanates afford the phenylacetylthioureas XVI bearing the amido-substituents such as the ones shown in the scheme B.

Scheme B

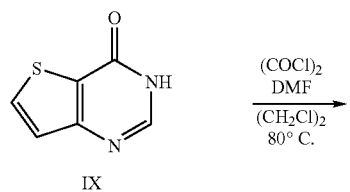

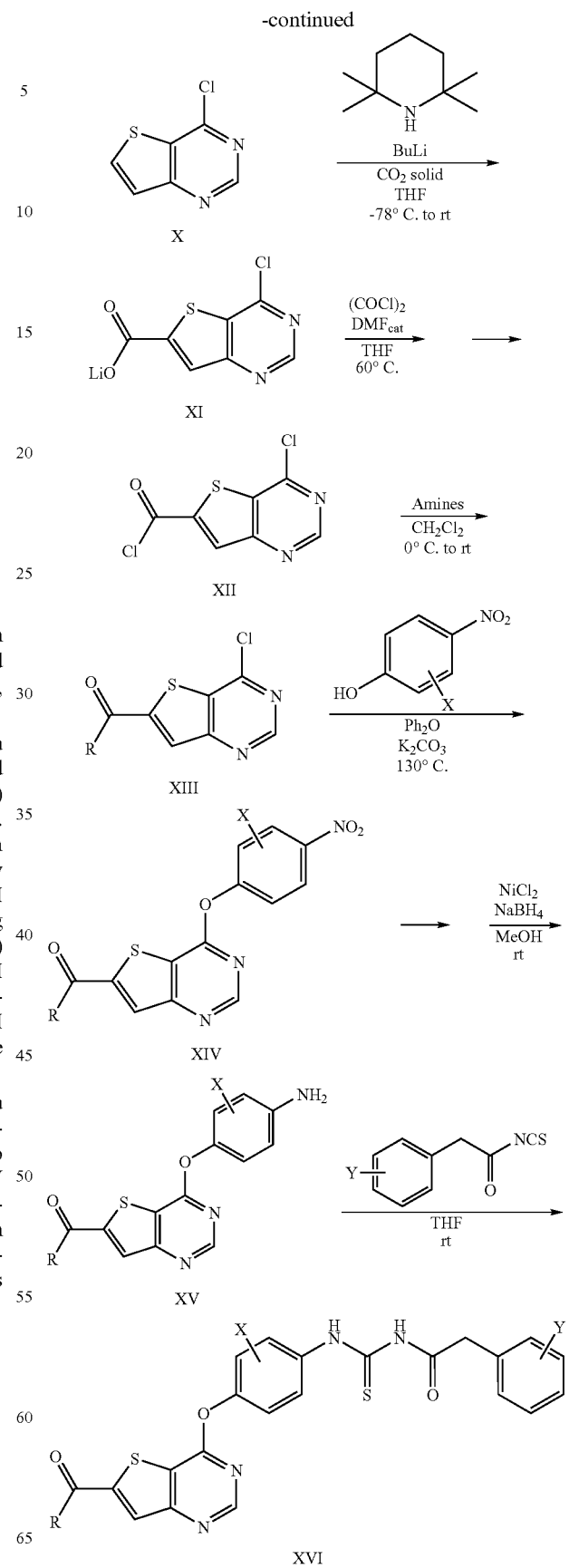

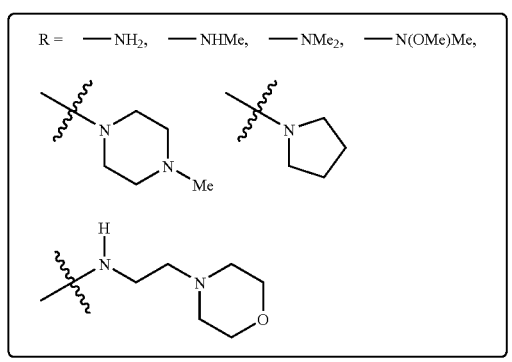

Substituents X and Y (up to three, same or different in each of the indicated benzene rings) are independently selected from halo, $C_1$-$C_6$ alkyl, $C_1$-$C_6$ alkoxy, cyano, nitro, hydroxy, amino, $C_1$-$C_6$ alkylamino Thieno[3,2-b]pyridine based phenylacetylureas of formula A-0 bearing heteroaryl substituents instead of the amido moieties may be prepared according to the procedures illustrated in the scheme C. Thus, treatment of the chloride II with a strong base such as n-BuLi followed by an addition of trimethyltin (or tributyltin) chloride affords the trimethylstannyl (or tributylstannyl) derivative XVII. This material reacting with different heteroaryl bromides in the presence of a Pd-catalyst (Stille coupling reaction or similar type reactions) produces heteroaryl-substituted thienopyridines XVIII which can further be derivatized via a substitution of the chlorine atom in the pyridine ring.

Scheme C

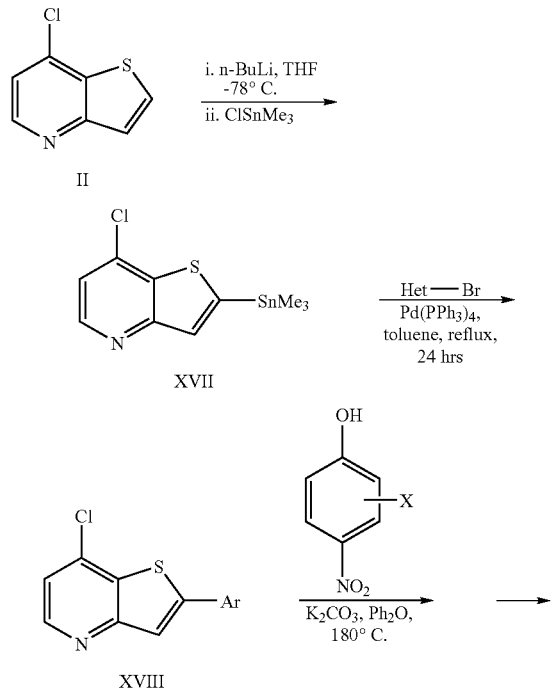

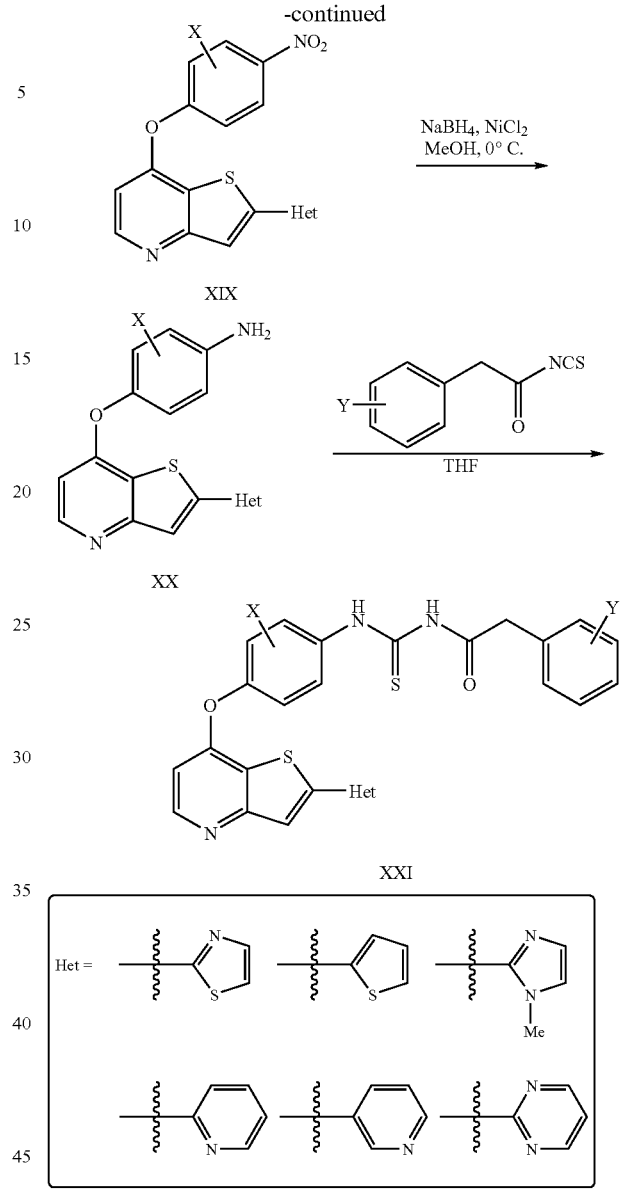

Substituents X and Y (up to three, same or different in each of the indicated benzene rings) are independently selected from halo, $C_1$-$C_6$ alkyl, $C_1$-$C_6$ alkoxy, cyano, nitro, hydroxy, amino, $C_1$-$C_6$ alkylamino Thus, XVIII reacting with substituted 4-nitrophenols in a high boiling point solvent, such as diphenyl ether in the presence of a base such as potassium carbonate, produced the nitro derivatives XIX which are then reduced to the amines XX upon treatment with a mixture $NiCl_2$/$NaBH_4$ (or other conventional reagents). The amines XX could be used for the next step without further purification, and upon treatment with 2-phenylacetyl isothiocyanates afford the phenylacetylthioureas XXI bearing the heteroaryl substituents such as the ones shown in the scheme C. Heteroaryls shown in the scheme B, in turn may bear additional substituents exemplified (but not limited to) alkyls, amines, alkylamino, aminoalkyls, alkoxyalkyls, hydroxyalkyls, alkylsulfonylalkyls, etc.—known in the art as solubilizing functionalities.

Scheme D

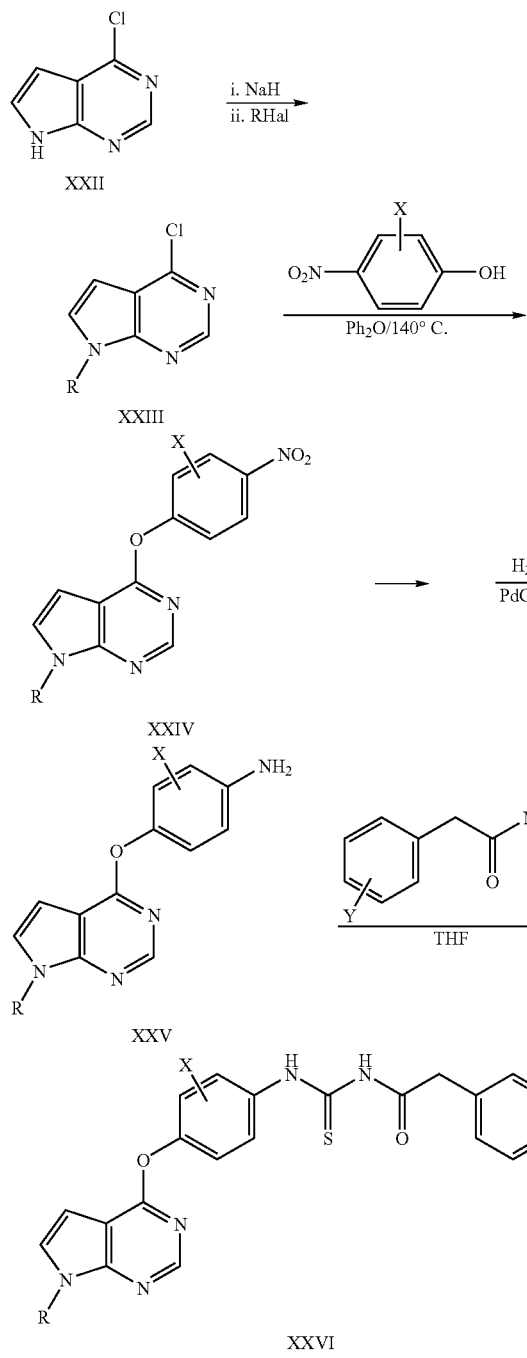

R = Me, Et, CH$_2$Ph

Substituents X and Y (up to three, same or different in each of the indicated benzene rings) are independently selected from halo, $C_1$-$C_6$ alkyl, $C_1$-$C_6$ alkoxy, cyano, nitro, hydroxy, amino, $C_1$-$C_6$ alkylamino Pyrrolo[2,3-d]pyrimidine based compounds of formula B-0 may be prepared according to the procedures illustrated in the scheme D. Treatment of the 4-chloro-7H-pyrrolo[2,3-d]pyrimidine (XXII) with an alkyl halide in the presence of a base such as sodium hydride affords the alkylated chlorides XXIII, which reacting with substituted 4-nitrophenols in a high boiling point solvent, such as diphenyl ether in the presence of a base such as cesium carbonate, produced the nitro derivatives XXIV reduced to the amines XXV upon hydrogenation (or treatment with conventional reducing agents). The amines XXV reacting with 2-phenylacetyl isothiocyanates afford the phenylacetylthioureas XXVI bearing the alkyl substituents such as the ones shown in the scheme D.

Scheme E

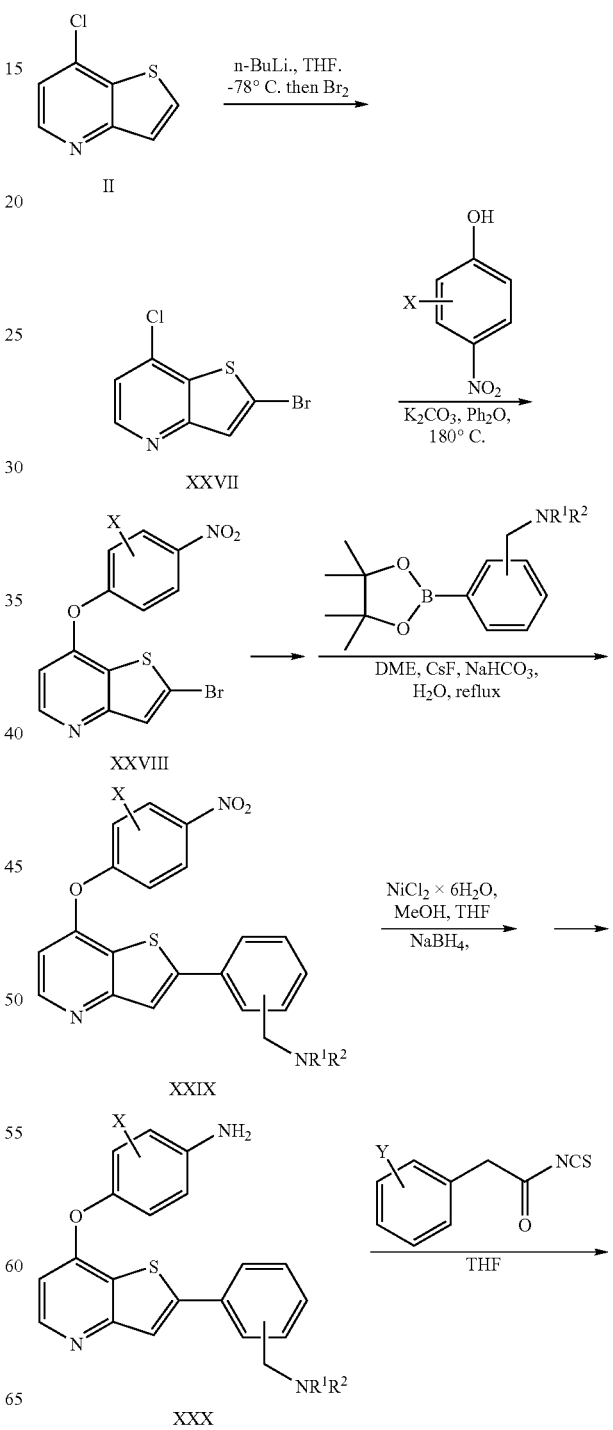

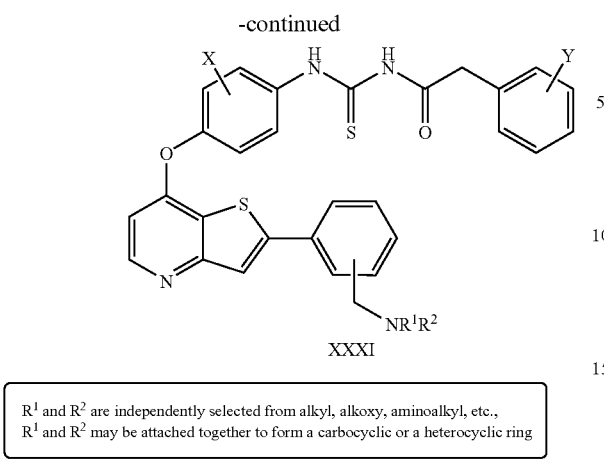

XXXI

R[1] and R[2] are independently selected from alkyl, alkoxy, aminoalkyl, etc.,
R[1] and R[2] may be attached together to form a carbocyclic or a heterocyclic ring Substituents X and Y (up to three, same or different in each of the indicated benzene rings) are independently selected from halo, $C_1$-$C_6$alkyl, $C_1$-$C_6$alkoxy, cyano, nitro, hydroxy, amino, $C_1$-$C_6$alkylamino Thieno[3,2-b]pyridine based phenylacetylureas of formula A-0 bearing aryl substituents may be prepared according to the procedures illustrated in the scheme E. Thus vhloride II upon lithiation and subsequent bromination is converted to the bromide XXVII that reacting with substituted 4-nitrophenols produces more elaborated compound XXVIII. This material can be used for Suzuki type (and like) reactions with a variety of aryl boronic acids (or boronates), in particular with the ones functionalized with basic groups, thus providing compounds XXIX. Reduction of XXIX with a mixture $NiCl_2$/$NaBH_4$ (or other conventional reagents) affords amines XXX. The latter upon treatment with 2-phenylacetyl isothiocyanates afford the phenylacetylthioureas XXXI bearing aryl substituents such as the ones shown in the scheme E.

Scheme F

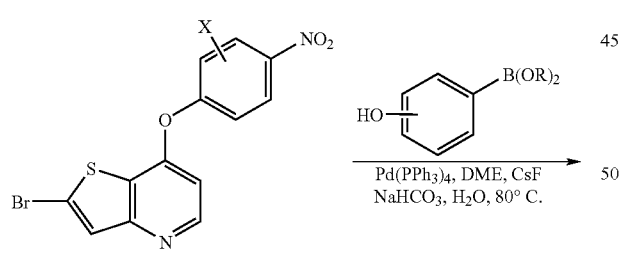

XXVIII

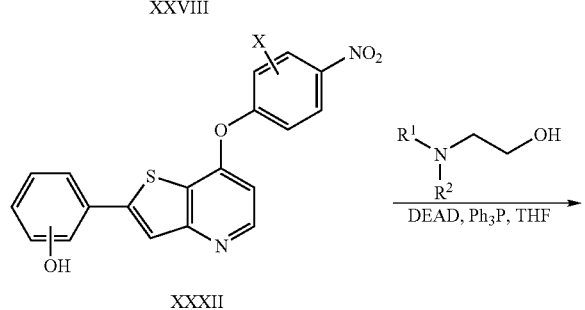

XXXII

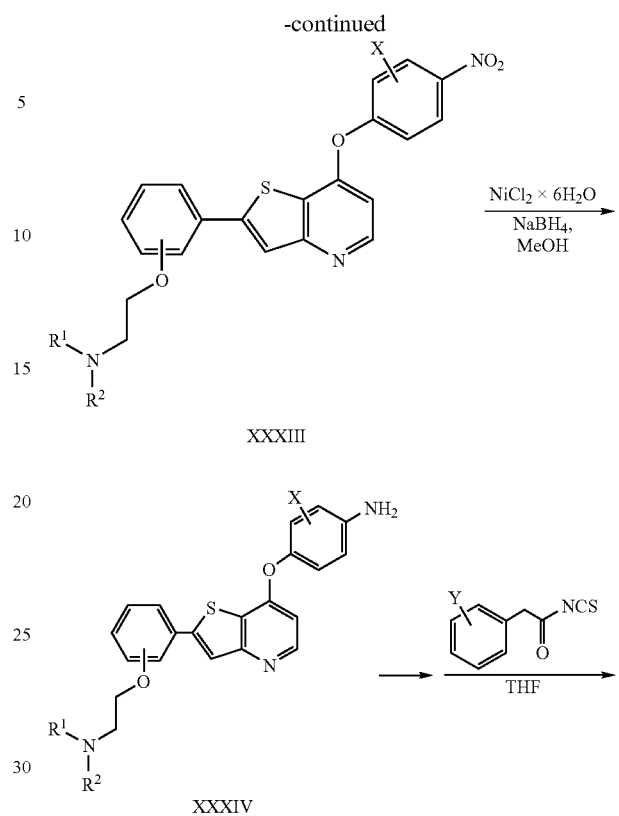

XXXIII

XXXIV

XXXV

R[1] and R[2] are independently selected from alkyl, alkoxy, aminoalkyl, etc.,
R[1] and R[2] may be attached together to form a carbocyclic or a heterocyclic ring Substituents X and Y (up to three, same or different in each of the indicated benzene rings) are independently selected from halo, $C_1$-$C_6$alkyl, $C_1$-$C_6$alkoxy, cyano, nitro, hydroxy, amino, $C_1$-$C_6$alkylamino Bromides XXVIII also can be used for Suzuki type (and like) reactions with a variety of hydroxyphenyl boronic acids (boronates), to form phenolic compounds XXXII. These phenols reacting with different alcohols (Mitsunobu reaction), in particular functionalized with basic groups, provide compounds XXXIII. Reduction of XXXIII with a mixture $NiCl_2$/$NaBH_4$ (or other conventional reagents) affords amines XXXIV which upon treatment with 2-phenylacetyl isothiocyanates afford the phenylacetylthioureas XXXV bearing the aryl substituents such as the ones shown in the scheme F.

II. SPECIFIC EXAMPLES

Scheme 1

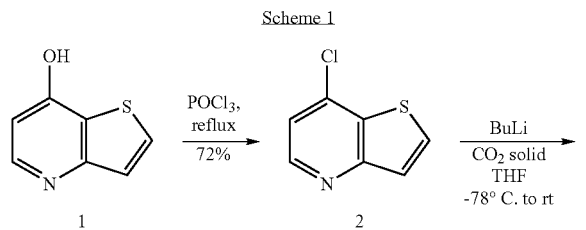

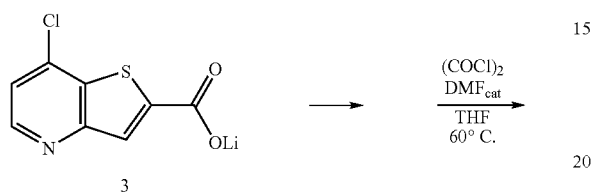

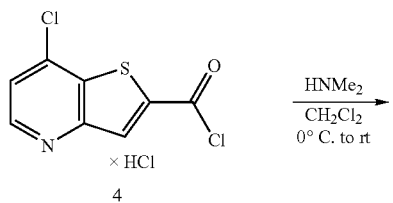

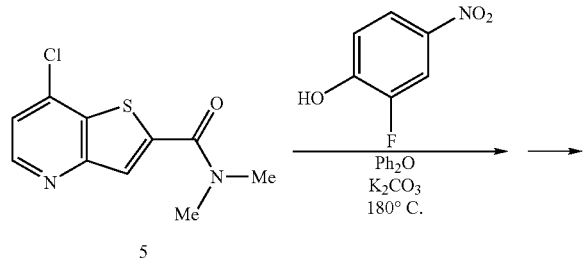

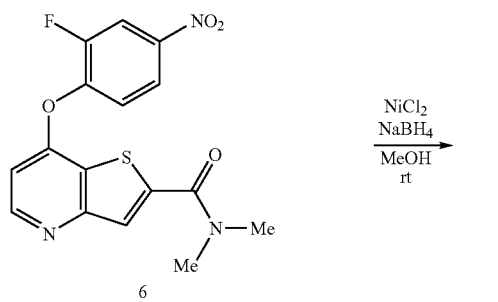

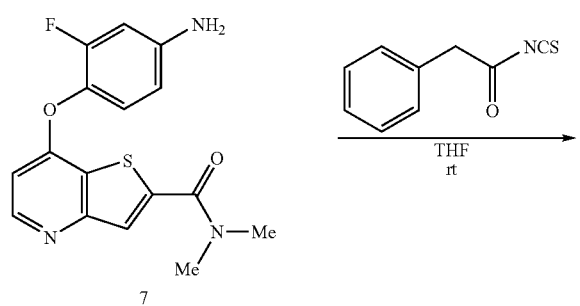

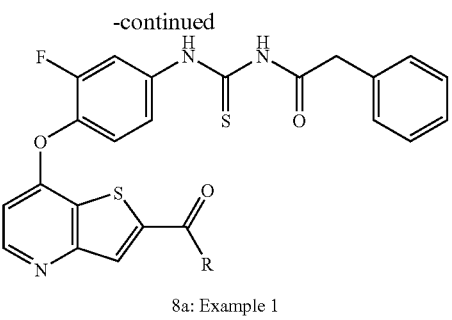

8a: Example 1

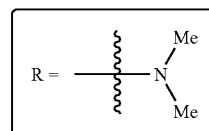

Example 1

1-(4-(2-(Dimethylcarbamoyl)thieno[3,2-b]pyridin-7-yloxy)-3-fluorophenyl)-3-(2-phenylacetyl)thiourea (8a)

Step 1: 7-Chlorothieno[3,2-b]pyridine (2)

A stirred suspension of thieno[3,2-b]pyridin-7-ol (1, 5.0 g, 33.1 mmol) in POCl$_3$ (15 mL) was heated to 105° C. in an oil bath for 4 hrs. The resultant solution was cooled to room temperature and the POCl$_3$ was removed under reduced pressure. The residue was cooled in an ice/water bath and cold water was added. The water was made basic with concentrated NH$_4$OH solution and extracted with EtOAc. The organic extract was dried over anhydrous sodium sulfate and concentrated to produce an oil which was purified by column chromatography (eluent EtOAc-hexane, 1:4) to afford the title compound as a brown solid (4.5 g, 72% yield). $^1$H NMR (400 MHz, CDCl$_3$) δ (ppm): 8.60 (d, J=4.9 Hz, 1H), 7.80 (d, J=5.5 Hz, 1H), 7.60 (d, J=5.5 Hz, 1H), 7.30 (d, J=4.9 Hz, 1H).

Steps 2-4: 7-Chloro-N,N-dimethylthieno[3,2-b]pyridine-2-carboxamide (5)

To a stirred solution of 2 (3.0 g, 17.8 mmol) in dry THF (60 mL) at −78° C. was added n-BuLi (7.8 mL, 19.6 mmol, 2.5 M solution in hexanes) and the resultant suspension was stirred for 15 minutes. Solid carbon dioxide (excess) was added and the mixture was allowed to warm to room temperature over a period of 1 hour. The solvent was removed under reduced pressure and the resultant lithium carboxylate 3 was used without further purification (3.88 g, quantitative).

To a stirred suspension of 3 (3.5 g, 15.9 mmol) in dry DCM (50 mL) was added (COCl)$_2$ (3.96 g, 31.2 mmol) and dry DMF (1 drop). The reaction mixture was heated to reflux for 2 hrs. The solvents were evaporated to produce 4 (presumably as an HCl salt) which was used directly in the next step.

Acyl chloride 4 (2.42 g, 10.5 mmol) was suspended in dry DCM (105 mL) at 0° C. and Me$_2$NH (15.7 mL, 2M solution in THF, 31.4 mmol) was added and the reaction mixture was stirred overnight. The solvent was removed and the residue was dissolved in EtOAc and washed with water. The organic phase was collected and dried over anhydrous sodium sulfate then filtered and concentrated under reduced pressure to produce a residue, which was purified by column chromatography (eluent EtOAc-hexane, 9:1) to afford 5 as a yellow solid (1.65 g, 45% yield). $^1$H NMR (400 MHz, CDCl$_3$) δ (ppm): 8.62 (d, J=4.8 Hz, 1H), 7.76 (s, 1H), 7.37 (d, J=4.8 Hz, 1H), 3.35-3.25 (m, 3H), 3.25-3.20 (m, 3H).

Step 5: 7-(2-Fluoro-4-nitrophenoxy)-N,N-dimethylthieno[3,2-b]pyridine-2-carboxamide (6)

A mixture of 5 (1.65 g, 6.85 mmol), potassium carbonate (5.68 g, 41.1 mmol) and 2-fluoro-4-nitrophenol (1.65 g, 10.3 mmol) were heated to 170° C. in diphenyl ether (20 mL) for 5 hrs. The mixture was cooled to room temperature, diluted with EtOAc and washed with water. The organic phase was collected, dried over anhydrous sodium sulfate and the solvents were removed under reduced pressure. The residue was purified by column chromatography (eluents EtOAc-hexane 9:1, then MeOH-EtOAc 1:4) to afford 6 as a yellow solid (1.02 g, 41% yield).

$^1$H NMR (400 MHz, DMSO-d$_6$) δ (ppm): 8.64 (d, J=5.3 Hz, 1H), 8.46 (dd, J=2.8 and 10.3 Hz, 1H), 8.20 (ddd, J=1.3 and 2.6 and 9.0 Hz, 1H), 7.98 (s, 1H), 7.73 (dd, J=8.3 Hz, 1H), 6.99 (dd, J=0.9 and 4.8 Hz, 1H), 3.25-3.30 (m, 3H), 3.02-3.11 (m, 3H).

Steps 6-7: 1-(4-(2-(Dimethylcarbamoyl)thieno[3,2-b]pyridin-7-yloxy)-3-fluorophenyl)-3-(2-phenylacetyl)thiourea (8a)

To a solution of 6 (190 mg, 0.55 mmol) in MeOH (10 mL) at 0° C. was added NiCl$_2$×6H$_2$O (241 mg, 1.02 mmol) and NaBH$_4$ (81.4 mg, 2.2 mmol). The reaction mixture was stirred for 1 hr, concentrated to dryness and the resultant solid was dissolved in 1 M HCl. The aqueous solution was then made basic with concentrated NH$_4$OH solution and extracted with EtOAc. The organic phase was collected, dried over anhydrous sodium sulfate and filtered. The solvent was evaporated under reduced pressure and the resultant solid was triturated with diethyl ether to afford 7 as a white solid that was used immediately in the next step.

To a suspension of 7 (465.8 mg, 1.41 mmol) in THF (20 mL) was added benzyl isothiocyanate (374 mg, 2.12 mmol) and the reaction mixture was stirred for 1 hr, concentrated under reduced pressure and the resultant residue was purified by column chromatography (eluent EtOAc-MeOH 19:1) to afford a yellow solid which was triturated with Et$_2$O to afford 8a as an off-white solid (534 mg, 75% yield). $^1$H NMR (400 MHz, DMSO-d$_6$) δ (ppm): 12.47 (s, 1H), 11.78 (s, 1H), 8.57 (d, J=4.2 Hz, 1H), 8.05-7.95 (m, 1H), 7.93 (s, 1H), 7.52 (s, 2H), 7.33 (d, J=3.9 Hz, 1H), 7.28-7.23 (m, 1H), 6.72 (d, J=5.3 Hz, 1H), 3.83 (s, 2H), 3.26 (s broad, 3H), 3.05 (s broad, 3H).

Examples 2-11

Examples 2-11 (compounds 8b-k) were prepared using the same procedures as described for the compound 8a, example 1 (scheme 1). Characterization of 8b-k is provided in table 1.

TABLE 1

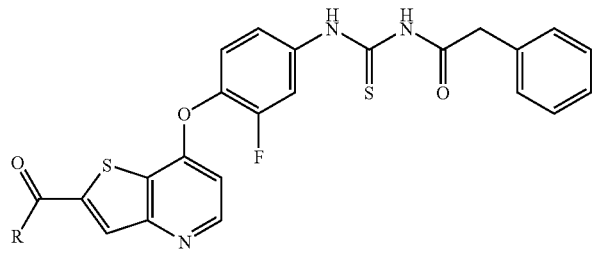

8b-k: Examples 2-11

Characterization of compounds 8b-k (examples 2-11)

| Cpd | Ex | R | Name | Characterization |
|---|---|---|---|---|
| 8b | 2 | ~NH-CH$_2$CH$_2$-morpholine | 1-(4-(2-(2-morpholinoethylcarbamoyl)thieno[3,2-b]pyridin-7-yloxy)-3-fluorophenyl)-3-(2-phenylacetyl)thiourea | $^1$H NMR (400 MHz, DMSO-d$_6$). δ.ppm: 12.52 (s, 1H), 11.85 (s, 1H), 8.96 (t, J = 5.3 Hz, 1H), 8.62 (d, J = 5.5 Hz, 1H), 8.28 (s, 1H), 8.06 (d, J = 10.9 Hz, 1H), 7.57 (d, J = 6.5 Hz, 2H), 7.38-7.30 (m, 5H), 6.77 (d, J = 5.2 Hz, 1H), 3.86 (s, 2H), 3.61 (t, J=4.4 Hz, 4H), 3.46 (q, J = 6.6 Hz, 2H), 3.39-3.36 (m, 6H). |
| 8c | 3 | ~N(CH$_2$CH$_2$)-morpholine | 1-(4-(2-(morpholinoethylcarbamoyl)thieno[3,2-b]pyridin-7-yloxy)-3-fluorophenyl)-3-(2-phenylacetyl)thiourea | $^1$H NMR (400 MHz, DMSO-d$_6$). δ.ppm: 12.52 (s, 1H), 8.72 (s, 1H), 8.54 (d, J = 6.1 Hz, 1H), 8.0-7.98 (m, 2H), 7.38-7.26 (m, 7H), 6.73 (d, J = 5.7 Hz, 1H), 3.72 (s, 8H), 2.02 (s, 2H). |

TABLE 1-continued

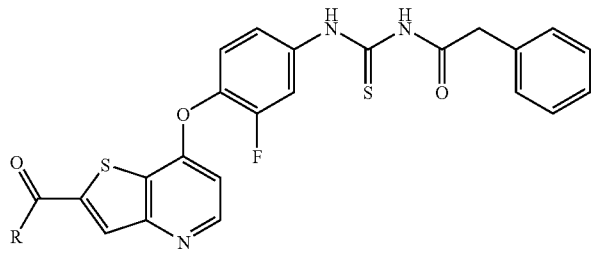

8b-k: Examples 2-11

Characterization of compounds 8b-k (examples 2-11)

| Cpd | Ex | R | Name | Characterization |
|---|---|---|---|---|
| 8d | 4 | NH-(3,4-dimethoxyphenyl) | 1-(4-(2-(3,4-dimethoxyphenylcarbamoyl)thieno[3,2-b]pyridin-7-yloxy)-3-fluorophenyl)-3-(2-phenylacetyl)thiourea | $^1$H NMR (400 MHz, DMSO-$d_6$). δ.ppm: 10.64 (s, 1H), 8.61 (d, J = 5.4 Hz, 1H), 8.51 (s, 1H), 8.03 (d, J = 12.7 Hz, 1H), 7.92 (s, 1H), 7.54 (m, 2H), 7.44 (d, J = 2.4 Hz, 1H), 7.29 (m, 7H), 6.96 (d, J = 8.8 Hz, 1H), 6.76 (d, J = 6.1 Hz, 1H), 3.82 (s, 2H), 3.76 (d, J = 8.3 Hz, 6H). |
| 8e | 5 | N(H)(Me) | 1-(4-(2-(methylcarbamoyl)thieno[3,2-b]pyridin-7-yloxy)-3-fluorophenyl)-3-(2-phenylacetyl)thiourea | $^1$H NMR (400 MHz, DMSO-$d_6$). δ.ppm: 12.47 (s, 1H), 11.80 (s, 1H), 8.92 (s, 1H), 8.55 (d, J = 3.7 Hz, 1H), 8.18 (s, 1H), 8.01 (d,.J = 11.9 Hz, 1H), 7.52 (s, 2H), 7.32 (s, 4H), 7.25 (s, 1H), 6.71 (d, J = 4.9 Hz, 1H), 3.81 (s, 2H), 2.83 (d, J = 3.3 Hz, 3H). |
| 8f | 6 | NH-CH2CH2-(3,4-dimethoxyphenyl) | 1-(4-(2-(3,4-dimethoxyphenethylcarbamoyl)thieno[3,2-b]pyridin-7-yloxy)-3-fluorophenyl)-3-(2-phenylacetyl)thiourea | $^1$H NMR (400 MHz, DMSO-$d_6$). δ.ppm: 12.47 (s, 1H), 11.81 (s, 1H), 9.03 (t, J = 5.7 Hz, 1H), 8.56 (d, J = 5.5 Hz, 1H), 8.22 (s, 1H), 8.02 (d, J = 11.4 Hz, 1H), 7.53 (s, 2H), 7.33 (m, 4H), 7.27 (m, 1H), 6.84 (m, 2H), 6.73 (m, 2H), 3.82 (s, 2H), 3.70 (d, J = 4.5 Hz, 6H), 3.50 (q, J = 6.6 Hz, 2H), 2.80 (t, J = 7.0 Hz, 2H). |
| 8g | 7 | N(Et)(Et) | 1-(4-(2-(diethylcarbamoyl)thieno[3,2-b]pyridin-7-yloxy)-3-fluorophenyl)-3-(2-phenylacetyl)thiourea | $^1$H NMR (400 MHz, DMSO-$d_6$). δ.ppm: 12.58 (s, 1H), 8.71 (s, 1H), 8.59 (s, 1H), 8.05-7.92 (m, 2H), 7.40 (m, 4H), 7.33 (m, 3H), 6.71 (s, 1H), 3.80 (s, 2H), 3.59 (q, J = 7.2 Hz, 4H), 1.29 (m, 6H). |
| 8h | 8 | NH-(4-isopropylphenyl) | 1-(4-(2-(4-isopropylphenylcarbamoyl)thieno[3,2-b]pyridin-7-yloxy)-3-fluorophenyl)-3-(2-phenylacetyl)thiourea | $^1$H NMR (400 MHz, DMSO-$d_6$). δ. ppm: 12.48 (s, 1H), 11.81 (s, 1H), 10.56 (s, 1H), 8.61 (d J = 5.4 Hz, 1H), 8.53 (s, 1H), 8.03 (d, J = 12.3 Hz, 2), 7.66 (d, J = 8.4 Hz, 2H), 7.54 (m, 2H), 7.33 (m, 4H), 7.23 (m, 3H), 6.75 (d, J = 5.3 Hz, 1H), 3.82 (s, 2H), 2.87 (m, 1H), 1.20 (d, J = 6.8 Hz, 6H). |

TABLE 1-continued

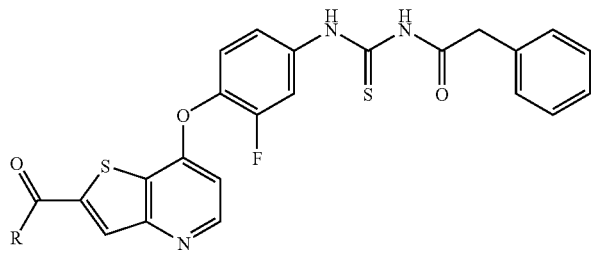

8b-k: Examples 2-11

Characterization of compounds 8b-k (examples 2-11)

| Cpd | Ex | R | Name | Characterization |
|---|---|---|---|---|
| 8i | 9 | (NH, NH) | 1-(4-(2-carbamoylthieno[3,2-b]pyridin-7-yloxy)-3-fluorophenyl)-3-(2-phenylacetyl)thiourea | $^1$H NMR (400 MHz, DMSO-$d_6$). δ. ppm: 12.48 (s, 1H), 11.81 (s, 1H), 8.56 (dd, J = 0.6 Hz and 5.5 Hz, 1H), 8.40 (s, 1H), 8.25 (d, J = 0.8 Hz, 1H), 8.01 (d, J = 13.3 Hz, 1H), 7.86 (s, 1H), 7.33 (m, 4H), 7.25 (m, 1H), 6.72 (d, J = 5.3 Hz, 1H), 3.82 (s, 2H). |
| 8j | 10 | (N(OMe)Me) | 1-(4-(2-(N-methoxy-N-methylcarbamoyl)thieno[3,2-b]pyridin-7-yloxy)-3-fluorophenyl)-3-(2-phenylacetyl)thiourea | $^1$H NMR (400 MHz, DMSO-$d_6$). δ. ppm: 12.51 (s, 1H), 11.85 (s, 1H), 8.63 (d, J = 5.3 Hz, 1H), 8.22 (s, 1H), 8.04 (d, J = 13.1 Hz, 1H), 7.57 (m, 2H) 7.36 (m, 4H), 7.30 (m, 1H), 6.77 (d, J = 5.3 Hz, 1H), 3.87 (s, 3H), 3.85 (s, 3H), 3.39 (s, 3H). |
| 8k | 11 | (NH-CH(Me)-C(O)OMe) | Methyl 2-(1-(4-(2-(carbamoyl)thieno[3,2-b]pyridin-7-yloxy)-3-fluorophenyl)-3-(2-phenylacetyl)thioureido)propanoate | $^1$H NMR (400 MHz, DMSO-$d_6$). δ ppm: 12.48 (s, 1H), 11.80 (s, 1H), 9.28 (d, J = 6.9 Hz, 1H), 8.59 (d, J = 5.3 Hz, 1H), 8.38 (s, 1H), 8.02 (d, J = 12.9 Hz, 1H), 7.53 (m, 2H), 7.33 (m, 4H), 7.28 (m, 1H), 6.75 (d, J = 5.3 Hz, 1H), 4.49 (m, 1H), 3.82 (s, 2H), 3.66 (s, 3H), 1.44 (d, J = 7.4 Hz, 3H). |

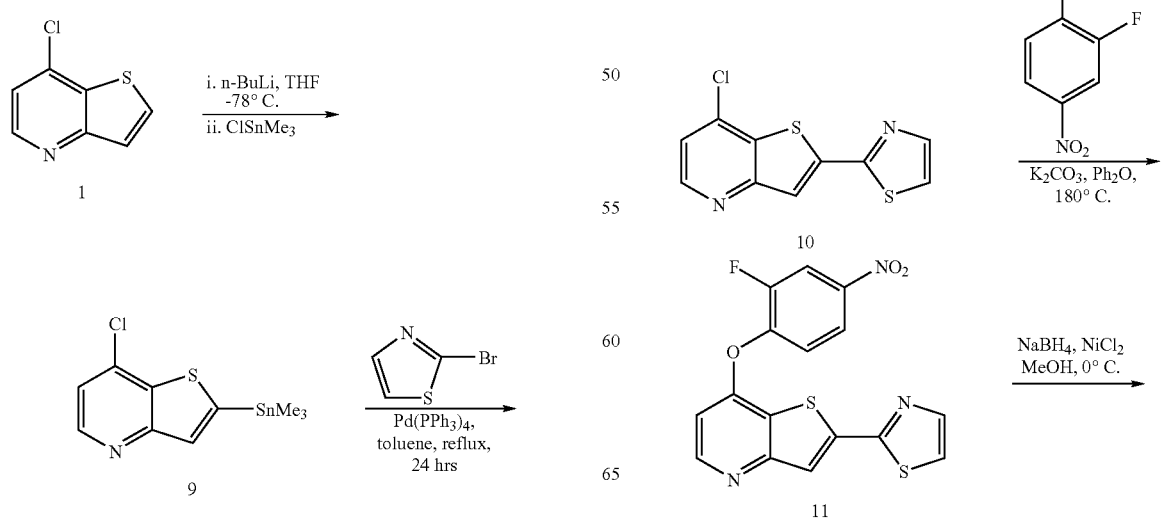

Scheme 2

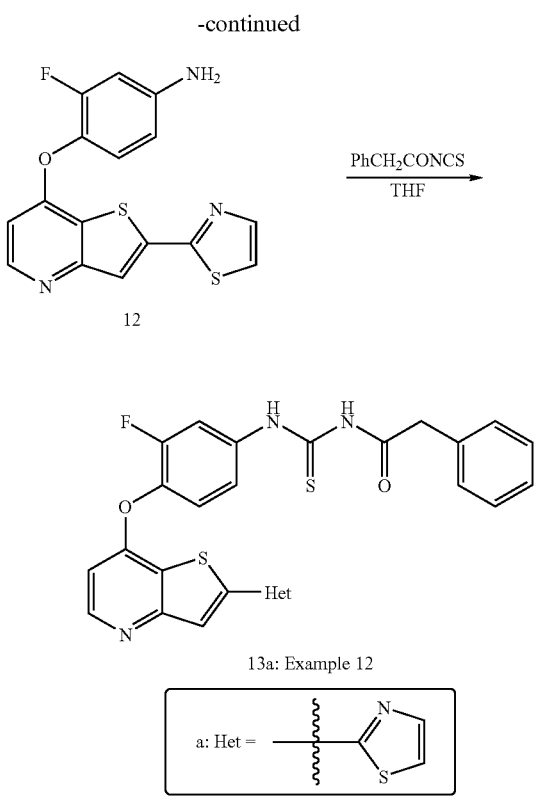

Example 12

1-(4-(2-(Thiazol-2-yl)thieno[3,2-b]pyridin-7-yloxy)-3-fluorophenyl)-3-(2-phenylacetyl)thiourea (13a)

Step 1:
7-Chloro-2-(trimethylstannyl)thieno[3,2-b]pyridine

To a solution of 2 (1.0 g, 5.9 mmol) in dry THF (60 mL) at −78° C. was added n-BuLi (2.36 mL, 5.9 mmol, 2.5 M solution in hexanes) and the resultant brown precipitate was stirred for 10 min. Trimethytin chloride (1.18 g, 5.9 mmol) in dry THF (10 mL) was added slowly and the mixture was allowed to stir at −78° C. for 2 hrs, quenched with methanol at −78° C. and the solvents were removed under reduced pressure. The residue was dissolved in EtOAc and washed with water; the organic phase was collected, dried over anhydrous sodium sulfate and filtered. The EtOAc was evaporated under reduced pressure and the resultant oil was purified by column chromatography (eluent EtOAc-hexane 1:4) to afford 9 (1.2 g, 63% yield) as a brown solid. $^1$H NMR (400 MHz, CDCl$_3$) δ ppm: 8.21 (d, J=5.1 Hz, 1H), 7.36 (s, 1H), 6.91 (m, 1H), 0.16 (s, 9H).

Step 2:
7-Chloro-2-(thiazol-2-yl)thieno[3,2-b]pyridine (10)

To a solution of 9 (175 mg, 0.53 mmol) and 2-bromothiazole (94 mg, 0.58 mmol) in dry toluene (6 mL) was added Pd(PPh$_3$)$_4$ (62 mg, 0.053 mmol) and the reaction mixture was refluxed overnight, cooled to room temperature and the solvents were removed under reduced pressure. The resultant solid was triturated with hexane/Et$_2$O and then purified by column chromatography (eluent EtOAc-hexane 1:1) to give 10 as a white solid (75 mg, 56% yield). $^1$H NMR (400 MHz, DMSO-d$_6$) δ ppm: 8.65 (d, J=5.1 Hz), 8.2 (s, 1H), 7.97 (s, 2H), 7.61 (d, J=5.1 Hz).

Step 3: 7-(2-Fluoro-4-nitrophenoxy)-2-(thiazol-2-yl)thieno[3,2-b]pyridine (11)

To a suspension of 10 (194 mg, 0.77 mmol) in Ph$_2$O (10 mL) was added 2-fluoro-4-nitrophenol (240 mg, 1.53 mmol) and potassium carbonate (425 mg, 3.08 mmol) and the reaction mixture was heated at 180° C. for 4 hrs. The reaction mixture was cooled to room temperature and diluted with EtOAc. The resultant solution was washed with water and the organic layer was collected, dried over anhydrous sodium sulfate and filtered. The solvents were removed under reduced pressure; the residue was dissolved in DCM, and purified by column chromatography (eluent EtOAc-hexane 4:1) to afford 11 (190 mg, 66% yield) as a yellow solid. $^1$H NMR (400 MHz, DMSO-d$_6$) δ ppm: 8.61 (d, J=5.5 Hz, 1H), 8.46 (dd, J=2.74 and 10.37 Hz), 8.24 (s, 1H), 8.20-8.10 (m, 1H), 7.95 (s, 2H), 7.73 (t, J=8 Hz, 1H), 6.98 (d, J=5.3 Hz, 1H).

Steps 4-5. 1-(4-(2-(Thiazol-2-yl)thieno[3,2-b]pyridin-7-yloxy)-3-fluorophenyl)-3-(2-phenylacetyl)thiourea (13a)

To a suspension of 11 (190 mg, 0.55 mmol) in MeOH (10 mL) at 0° C. was added NiCl$_2$.6H$_2$O (241 mg, 1.02 mmol) and NaBH$_4$ (81.4 mg, 2.2 mmol). The reaction mixture was allowed to stir for 1 hr, concentrated to dryness and the resultant solid was dissolved in 1 M HCl. The aqueous solution was then made basic with concentrated ammonium hydroxide solution whereupon 12 precipitated as a grey solid, which was collected by filtration and used crude in the next step.

To a suspension of the amine 12 (152 mg, 0.44 mmol) in THF (10 mL) was added benzyl isothiocyanate (118 mg, 0.66 mmol) and the reaction mixture was stirred for 1 hr, concentrated under reduced pressure and purified by column chromatography (eluents EtOAc-hexane 3:1, then EtOAc) to afford a yellow solid. Trituration of this material with Et$_2$O/hexane gave 13a (100 mg, 43% yield) as a white solid. $^1$H NMR (400 MHz, DMSO-d$_6$) δ ppm: 12.48 (s, 1H), 11.81 (s, 1H), 8.55 (d, J=5.5 Hz, 1H), 8.19 (s, 1H), 8.00 (d, J=13.3 Hz, 1H), 7.95 (d, J=3.1 Hz, 1H), 7.94 (d, J=3.1 Hz, 1H), 7.53 (m, 2H), 7.33 (m, 3H), 7.25 (m, 2H), 6.72 (d, J=5.5 Hz, 1H), 3.82 (s, 2H).

Example 13

Examples 13-19 (compounds 13b-h) were prepared using the same procedures as described for the compound 13a (example 12, scheme 2). Characterization of compounds 13b-h (examples 13-19) is provided in table 2.

TABLE 2

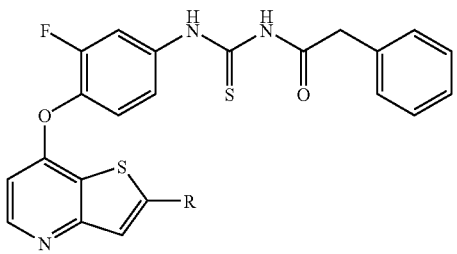

13b-h: examples 13-19

Characterization of compounds 13b-h (examples 13-19)

| Cpd | Ex | R | Name | Characterization |
|---|---|---|---|---|
| 13b | 13 | 2-pyridyl | 1-(4-(2-(Pyridin-2-yl)thieno[3,2-b]pyridin-7-yloxy)-3-fluorophenyl)-3-(2-phenylacetyl)thiourea | $^1$H NMR (400 MHz, DMSO-$d_6$). δ ppm: 12.47 (s, 1H), 11.81 (s, 1H), 8.61 (d, J = 2.9 Hz, 1H), 8.51 (d, J = 5.5 Hz, 1H), 8.36 (s, 1H), 8.26 (d, J = 8.0 Hz, 1H), 8.0 (d, J = 17 Hz, 1H), 7.93 (dt, J = 1.76 and 7.82 Hz, 1H), 7.51 (m, 2H), 7.32 (m, 4H), 7.26 (m, 1H), 6.65 (d, J = 5.5 Hz, 1H), 3.82 (s, 2H). MS (m/z) 515.2 (M + H) |
| 13c | 14 | pyrimidin-2-yl | N-(3-Fluoro-4-(2-(pyrimidin-2-yl)thieno[3,2-b]pyridin-7-yloxy)phenylcarbamothioyl)-2-phenylacetamide | $^1$H NMR (400 MHz, DMSO-$d_6$). δ ppm; 12.51 (s, 1H), 11.82 (s, 1H), 8.95 (m, 2H), 8.59 (m, 1H), 8.34 (s, 1H), 8.04 (m, 1H), 7.55 (m, 3H), 7.34 (m, 4H), 7.28 (m, 1H), 6.75 (m, 1H), 3.82 (s, 2H). MS (m/z) 516.2 (M + H) |
| 13d | 15 | 1-methyl-1H-imidazol-2-yl | N-(3-Fluoro-4-(2-(1-methyl-1H-imidazol-2-yl)thieno[3,2-b]pyridin-7-yloxy)phenylcarbamothioyl)-2-phenylacetamide | $^1$H NMR (400 MHz, DMSO-$d_6$). δ ppm; 12.48 (s, 1H), 11.84 (s, 1H), 8.50 (m, 1H), 8.1 (s, 1H), 8.04 (d, J = 12.1 Hz, 1H), 7.63 (s, 1H), 7.56 (m, 2H), 7.39 (s, 1H), 7.33 (m, 4H), 7.27 (m, 1H), 7.19 (m, 1H), 6.77 (d, J = 5.7 Hz, 1H). MS (m/z) 518.2 (M + H) |
| 13e | 16 | thiophen-2-yl | N-(3-Fluoro-4-(2-(thiophen-2-yl)thieno[3,2-b]pyridin-7-yloxy)phenylcarbamothioyl)-2-phenylacetamide | $^1$H NMR (400 MHz, DMSO-$d_6$). δ ppm: 12.48 (s, 1H), 11.84 (s, 1H), 8.50 (m, 1H), 8.04 (m, 1H), 7.79 (s, 1H), 7.73 (s, 1H), 7.63 (m, 2H), 7.39 (s, 4H), 7.27 (m, 1H), 7.19 (m, 1H), 6.65 (m, 1H), 5.74 (m, 1H), 3.81 (s, 2H). MS (m/z) 520.0 (M + H) |
| 13f | 17 | 1,3,4-thiadiazol-2-yl | N-(4-(2-(1,3,4-Thiadiazol-2-yl)thieno[3,2-b]pyridin-7-yloxy)-3-fluorophenylcarbamothioyl)-2-phenylacetamide | $^1$H NMR (400 Mhz, DMSO-$d_6$). δ ppm; 12.47 (s, 1H), 11.82 (s, 1H), 8.57 (d, J = 5.5 Hz, 1H), 8.16 (s, 1H), 8.0 (d, J = 13 Hz, 1H), 7.56 (m, 1H), 7.36 (m, 4H), 7.26 (m, 2H), 6.71 (d, J = 5.3 Hz, 1H), 3.82 (s, 2H). MS (m/z) 522 (M + H) |
| 13g | 18 | pyridin-3-yl | N-(3-fluoro-4-(2-(pyridin-3-yl)thieno[3,2-b]pyridin-7-yl)-yloxy)phenylcarbamothioyl)-2-phenylacetamide | $^1$H NMR (400 MHz, DMSO-$d_6$) δ ppm; 12.49 (s, 1H), 11.85 (s, 1H), 9.12 (dd, J = 0.8 and 2.3 Hz), 8.63 (dd, J = 1.6 and 4,7 Hz, 1H), 8.55 (d, J = 5.5 Hz, 1H), 8.27 (m, 1H), 8.23 (s, 1H), 8.0 (d, J = 13.1 Hz, 1H), 7.54 (m, 3H), 7.32 (m, 4H), 7.26 (m, 2H), 6.69 (dd, J = 0.9 and 5.5 Hz, 1H), 3.81 (s, 2H). MS (m/z) 515.2 (M + H) |

TABLE 2-continued
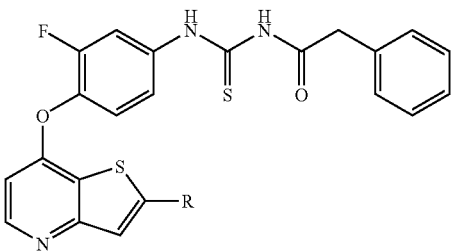
13b-h: examples 13-19
Characterization of compounds 13b-h (examples 13-19)
| Cpd | Ex | R | Name | Characterization |
|---|---|---|---|---|
| 13h | 19 | (morpholinothiazolyl group) | N-(3-fluoro-4-(2-(2-morpholinothiazol-5-yl)thieno[3,2-b]pyridin-7-yloxy)phenylcarbamothioyl)-2-phenylacetamide | $^1$H NMR (400 MHz, DMSO-$d_6$). δ ppm: 12.45 (s, 1H), 11.81 (s, 1H), 8.44 (dd, J = 1.2, 5.48 Hz, 1H), 7.98 (d, J = 12 Hz, 1H), 7.74 (s, 1H), 7.50 (s, 3H), 7.33 (m, 4H), 7.27 (m, 2H), 6.59 (d, J = 5.5 Hz, 1H), 3.82 (s, 2H), 3.72 (t, J = 4.7 Hz, 4H), 3.47 (t, J = 4.9 Hz, 4H). MS (m/z) 606.2 (M + H) |
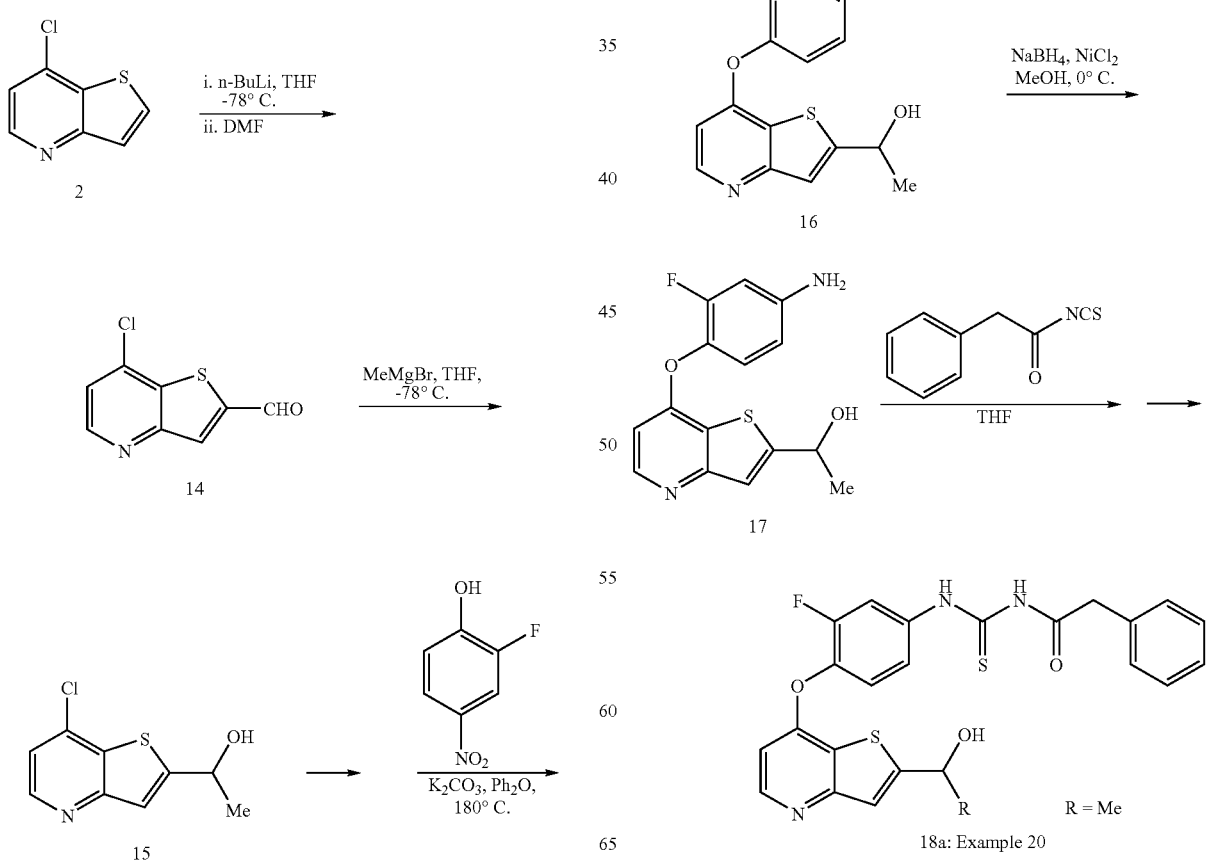

Example 20

1-(4-(2-(1-Hydroxyethyl)thieno[3,2-b]pyridin-7-yloxy)-3-fluorophenyl)-3-(2-phenylacetyl)thiourea (18a)

Step 1.
7-Chlorothieno[3,2-b]pyridine-2-carbaldehyde (14)

To a solution of 2 (200 mg, 1.18 mmol) in dry THF (10 mL) at −78° C. was added n-BuLi (0.57 mL, 1.42 mmol, 2.5 M solution in hexanes) and the resultant suspension was stirred for 20 min. Dry DMF (0.5 mL, excess) was added and the reaction mixture was stirred for an additional 2 hrs. The reaction mixture was quenched with methanol at −78° C. and water was added. The mixture was extracted with EtOAc and the organic extracts were combined, dried over anhydrous sodium sulfate and filtered. The solvent was removed under reduced pressure and the resultant yellow solid was triturated with hexane to afford 14 (250 mg, 100% yield) as a pale yellow solid. $^1$H NMR (400 MHz, DMSO-d$_6$) δ ppm: 10.2 (s, 1H), 8.78 (d, J=5.1 Hz, 1H), 8.61 (s, 1H), 7.78 (d, J=5.1 Hz, 1 H).

Steps 2-3. 1-(7-(2-Fluoro-4-nitrophenoxy)thieno[3,2-b]pyridin-2-yl)ethanol (16)

To a solution of 14 (200 mg, 1 mmol) in dry THF (5 mL) at −78° C. was added methylmagnesium bromide (0.51 mL, 1 mmol, 2 M solution in dibutyl ether) and the reaction mixture was stirred at −78° C. for 1 hr. The reaction was quenched with water and extracted with EtOAc. The organic phase was dried over anhydrous sodium sulfate and evaporated. The resultant solid was washed with hexane to give 15 as a white solid (177 mg, 83% yield), which was used crude in the next step.

To a suspension of 15 (170 mg, 0.79 mmol) in Ph$_2$O (10 mL) was added 2-fluoro-4-nitrophenol (250 mg, 1.58 mmol) and potassium carbonate (436 mg, 3.16 mmol) and the reaction mixture was heated at 180° C. for 4 hrs, cooled to room temperature and diluted with EtOAc. The solution was washed with water and the organic layer was collected, dried over anhydrous sodium sulfate and filtered. The solvents were removed under reduced pressure. The residue was dissolved in DCM, and purified by column chromatography (eluent EtOAc-hexane, 4:1) to afford 16 (125 mg, 47% yield) as a yellow solid. $^1$H NMR (400 MHz, DMSO-d6) δ ppm: 8.52 (dd, J=0.8 and 5.5 Hz, 1H), 8.44 (dd, J=2.5 and 10.2 Hz, 1H), 8.15 (d, J=10.2 Hz, 1H), 7.63 (t, J=8.2 Hz, 1H), 7.41 (s, 1H), 6.86 (d, J=5.3 Hz, 1H), 5.96 (dd, J=0.4 Hz and 4.9 Hz), 5.09 (m, 1H), 1.49 (d, J=6.5 Hz, 3H).

Steps 4-5. 1-(4-(2-(1-Hydroxyethyl)thieno[3,2-b]pyridin-7-yloxy)-3-fluorophenyl)-3-(2-phenylacetyl)thiourea (18a)

To a suspension of 16 (129 mg, 0.39 mmol) in MeOH (5 mL) at 0° C. was added NiCl$_2$.6H$_2$O (183 mg, 0.77 mmol) and sodium borohydride (57 mg, 1.5 mmol). The reaction mixture was allowed to stir for 1 hr, concentrated to dryness and the resultant solid was dissolved in 1 M HCl. The aqueous solution was then made basic with concentrated ammonium hydroxide solution, extracted with EtOAc and the organic extract was dried over anhydrous sodium sulfate then filtered. The solvent was removed under reduced pressure to give 17 (110 mg, 94% yield) as brown oil, which was used immediately in the next step.

To an emulsion of 17 (110 mg, 0.36 mmol) in THF (10 mL) was added 2-phenylacetyl isothiocyanate (76 mg, 0.43 mmol) and the reaction mixture was stirred for 1 hr, concentrated and the residue was purified by column chromatography (eluents EtOAc-hexane 3:1, then EtOAc) to afford a yellow solid which upon trituration with diethyl ether/hexane gave 18a as an off-white solid (90 mg, 52% yield). $^1$H NMR (400 MHz, DMSO-d$_6$) δ ppm: 12.47 (s, 1H), 11.81 (s, 1H), 8.43 (d, J=5.5 Hz, 1H), 8.2 (s, 1H), 7.9 (d, J=12.3 Hz, 1H), 7.51-7.44 (m, 2H), 7.30 (d, J=0.9 Hz, 1H), 7.33-7.31 (m, 3H), 7.30-7.24 (m, 1H), 6.57 (d, J=5.3 Hz, 1H), 5.91 (d, J=4.9 Hz, 1H), 5.09 (m, 1H), 3.9 (s, 2H), 1.49 (d, J=6.3 Hz, 3H).

Example 21

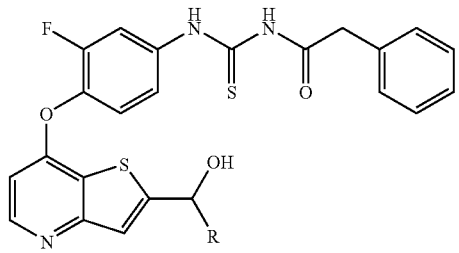

18 b: Example 21

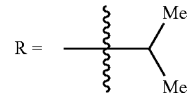

1-(4-(2-(1-Hydroxy-2-methylpropyl)thieno[3,2-b]pyridin-7-yloxy)-3-fluorophenyl)-3-(2-phenylacetyl)thiourea (18b)

Title compound was prepared using the same procedures as described for the compound 18a (example 20, scheme 3). $^1$H NMR (400 MHz, DMSO-d$_6$) δ 1 ppm: 12.46 (s, 1H), 11.80 (s, 1H), 8.43 (d, J=5.9 Hz, 1H), 7.98 (d, J=2.2 Hz, 1H), 7.52-7.45 (m, 2H), 7.35 (s, 1H), 7.32 (m, 3H), 7.28 (m, 1H), 6.55 (d, J=5.5 Hz, 1H), 5.91 (d, J=4.7 Hz, 1H), 4.70 (t, J=5.1 Hz, 1H), 3.8 (s, 2H), 1.95 (m, 1H), 0.9 (dd, J=0.7 and 10.2 Hz, 6H).

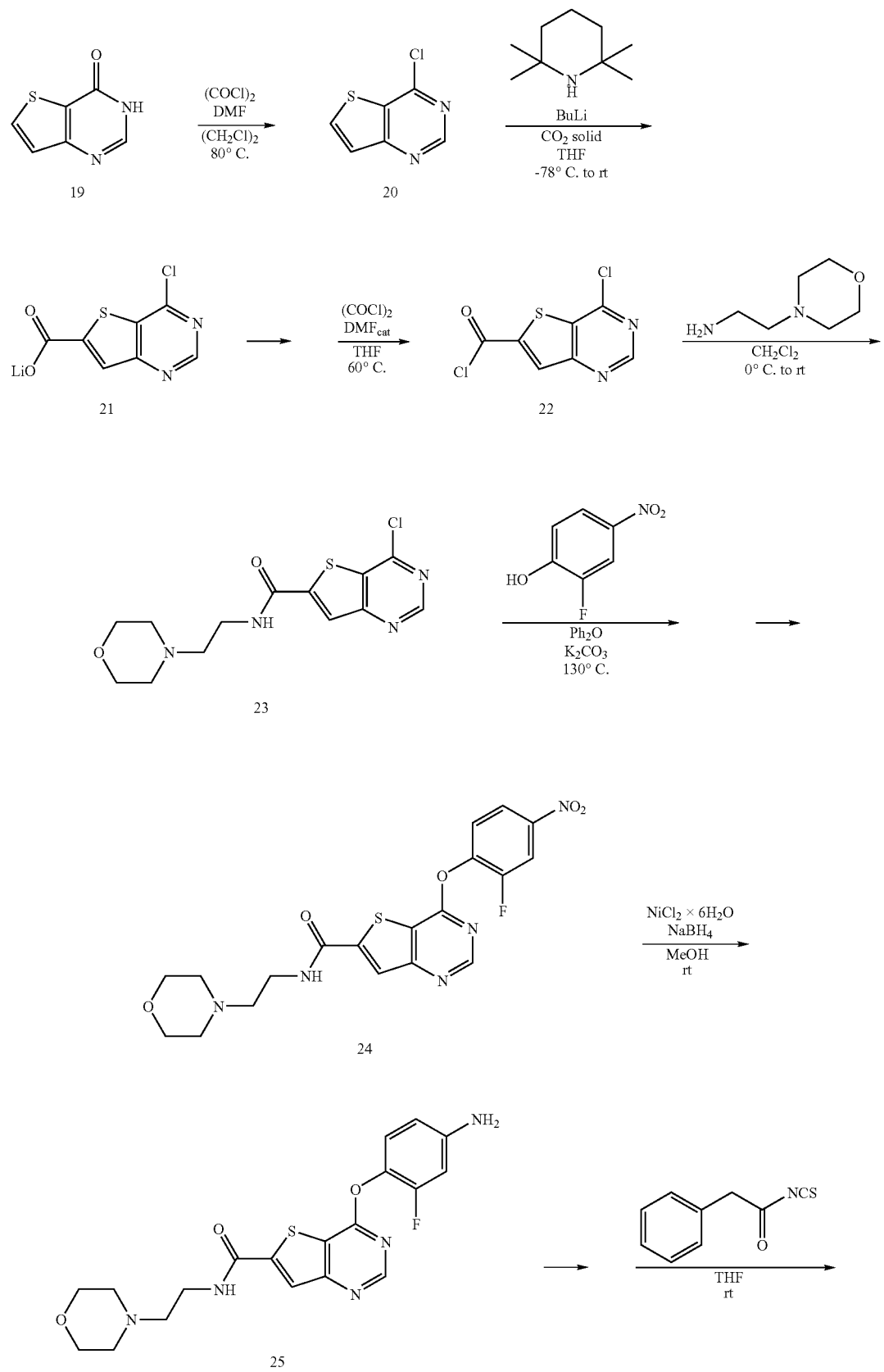

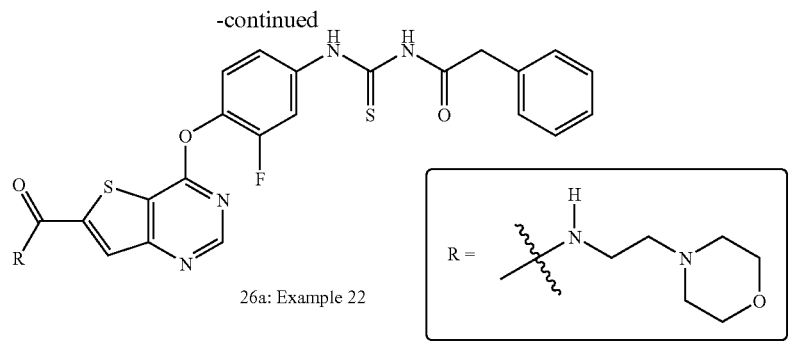

26a: Example 22

Example 22

1-(4-(6-(2-Morpholinoethylcarbamoyl)thieno[3,2-d]pyrimidin-4-yloxy)-3-fluorophenyl)-3-(2-phenylacetyl)thiourea (26a)

Step 1: 4-Chlorothieno[3,2-d]pyrimidine (20)

To a stirred solution of $(COCl)_2$ (7.33 mL, 84.11 mmol) in anhydrous $(CH_2Cl)_2$ (20 mL) at 0° C. under nitrogen was added DMF (4.47 mL, 57.18 mmol). After 20 min a solution of thieno[3,2-d]pyrimidin-4(3H)-one (19) (4 g, 26.28 mmol) in anhydrous $(CH_2Cl)_2$ (5 mL added drop wise to the reaction mixture which was stirred for 20 min at 0° C., warmed to room temperature over another 20 min, heated at 80° C. for 1.5 hours, and cooled to room temperature. Finally, the reaction mixture was poured into water and extracted with DCM. The extract was washed sequentially with water, brine, dried over $Na_2SO_4$, filtered and evaporated to afford the title compound 20 (4.36 g, 97% yield) as a yellow solid. $^1$H NMR (400 MHz, DMSO-$d_6$) δ(ppm): 9.02 (s, 1H), 8.59 (d, J=5.2 Hz, 1H), 7.75 (d, J=5.2 Hz, 1H).

Step 2: 4-Chlorothieno[3,2-d]pyrimidine-6-carbonyl chloride (22)

To a stirred solution of 2,2,6,6-tetramethylpiperidine (4.45 mL, 26.37 mmol) in anhydrous THF (50 mL) at 0° C. under nitrogen was added n-BuLi (10.55 mL, 26.37 mmol, 2.5 M in hexanes). The reaction mixture was stirred for 30 min, then a solution of 20 (3 g, 17.58 mmol) in anhydrous THF (10 mL) was added drop wise at −78° C. over 30 min followed by dry ice (10 g). The resultant suspension was warmed to the room temperature over 2 hours and filtered to afford the lithium carboxylate 21 as a yellow solid (4.5 g), which was used for the next step without further purification.

To a stirred solution of $(COCl)_2$ (2.95 mL, 33.82 mmol) in anhydrous DCM (30 mL) at 0° C. under nitrogen was added DMF (0.5 mL, 6.45 mmol). The reaction mixture was stirred for 20 min and treated with a solution of the carboxylate 21 (3.71 g, 16.89 mmol) in anhydrous DCM (5 mL) (drop wise addition at 0° C.), stirred for additional 10 min and heated at 60° C. for 3 hours, cooled to room temperature and concentrated under reduced pressure to afford the title compound 22 (3.90 g, 99% yield) as a yellow solid. $^1$H NMR (400 MHz, DMSO-$d_6$) δ(ppm): 9.02 (s, 1H), 8.59 (d, J=5.2 Hz, 1H), 7.75 (d, J=5.2 Hz, 1H).

Step 3: 4-Chloro-N-(2-morpholinoethyl)thieno[3,2-d]pyrimidine-6-carboxamide (23)

To a stirred solution of 22 (500 mg, 2.15 mmol) in anhydrous DCM (20 mL) at 0° C. under nitrogen was added 4-(2-aminoethyl)-morpholine (307 mg, 2.36 mmol). The reaction mixture was allowed to warm to the room temperature over 3 hours and was stirred for additional 14 hours, treated with saturated aqueous solution of $NHCO_3$ and extracted with DCM. The organic layer was dried over $Na_2SO_4$, filtered, and concentrated. The residues was purified by flash chromatography on silica gel (eluents MeOH—DCM, 5:95, then 1:9) to afford the title compound 23 (458 mg, 65% yield) as a white solid. $^1$H NMR (400 MHz, CDCl$_3$) δ(ppm): 9.13 (t, J=5.6 Hz, 1H), 9.08 (s, 1H), 8.32 (s, 1H), 3.60-3.54 (m, 4H), 3.44 (q, J=6.8 Hz, 2H), 2.54-2.48 (m, 2H), 2.46-2.40 (m, 4H).

Step 4: 4-(2-Fluoro-4-nitrophenoxy)-N-(2-morpholinoethyl)thieno[3,2-d]pyrimidine-6-carboxamide (24)

To a stirred solution of compound 23 (458 mg, 1.40 mmol) in $Ph_2O$ (6 mL) was added 2-fluoro-4-nitrophenol (242 mg, 1.54 mmol). The reaction mixture was heated at 120° C. for 2.5 hours, treated with $K_2CO_3$ (80 mg, 0.56 mmol) and heated at the same temperature for additional 18 hours. After cooling, the reaction mixture was purified by flash chromatography on a silica gel column (eluents EtOAc-hexane 5:95, 1:1, then MeOH-DCM, 5:95 and 1:9), to afford the title compound 24 (570 mg, 91% yield) as a yellow solid. $^1$H NMR (400 MHz, CDCl$_3$) δ(pm): 9.09 (t, J=5.6 Hz, 1H), 8.77 (s, 1H), 8.41 (dd, J=2.4 and 10.4 Hz, 1H), 8.30 (s, 1H), 8.22 (dd, J=2.4 and 8.8 Hz, 1H), 7.88 (t, J=8.8 Hz, 1H), 3.60-3.52 (m, 4H), 3.45 (q, J=6.8 Hz, 2H), 2.50 (q, J=6.8 Hz, 2H), 2.46-2.40 (m, 4H).

Step 5: 4-(4-Amino-2-fluorophenoxy)-N-(2-morpholinoethyl)thieno[3,2-d]pyrimidine-6-carboxamide (25)

To a stirred solution of 24 (1.30 g, 2.72 mmol) in anhydrous MeOH (15 mL) at room temperature under nitrogen were added $NiCl_2 \times 6H_2O$ (605 mg, 2.54 mmol) and $NaBH_4$ (192 mg, 5.08 mmol), respectively. The reaction mixture was stirred for 50 min, concentrated, cooled to 0° C., treated with HCl (10 mL, 1M) followed by addition of $NH_4OH$ (29%) (pH 9-10), and finally extracted with AcOEt. The organic extract was successively washed with water and brine, dried over $Na_2SO_4$, filtered, and concentrated to afford the title compound 25 (450 mg, 85% yield) as a yellow solid. $^1$H NMR (400 MHz, CDCl₃) δ(ppm): 9.04 (t, J=5.6 Hz, 1H), 8.73 (s, 1H), 8.23 (s, 1H), 7.07 (t, J=8.8 Hz, 1H), 6.48 (dd, J=2.4 and 13.2 Hz, 1H), 6.40 (dd, J=2.4 and 8.8 Hz, 1H), 5.47 (s, 2H), 3.62-3.52 (m, 4H), 3.44 (q, J=6.8 Hz, 2H), 2.56-2.48 (m, 2H), 2.46-2.40 (m, 4H).

Step 6: 1-(4-(6-(2-Morpholinoethylcarbamoyl)thieno[3,2-d]pyrimidin-4-yloxy)-3-fluorophenyl)-3-(2-phenylacetyl)thiourea (26a)

To a stirred solution of 25 (450 mg, 1.07 mmol) in anhydrous THF (10 mL) under nitrogen was slowly added benzyl isothiocyanate (0.5 mL). The reaction mixture was stirred for 18 hours and concentrated under reduced pressure. The residue was purified by flash chromatography on a silica gel column (eluent MeOH-DCM, 5:95→10:90) followed by reversed phase chromatography purification (column Phenomene X, C18, eluent H₂-MeOH, 50:50→5:95, 10 mL/min) to afford the title compound 26a (104 mg, 16% yield) as a white solid. ¹H NMR (400 MHz, DMSO-d₆) δ((ppm): 12.43 (s, 1H), 11.80(s, 1H), 9.07(t, J=5.6 hz, 1H), 8.76(s, 1H), 8.28(s, 1H), 7.93(dd, J=2.4 and 12.0 Hz, 1H), 7.54(t, J=8.8 Hz, 1H), 7.48(dd, J=1.2 and 8.8 Hz, 1H), 7.39-7.30(m, 4H), 7.30-7.20(m, 1H), 3.82(s, 2H), 3.60-3.54(m, 4H), 3.45(q, J=6.4 Hz, 2H), 2.50(m, 2H), 2.48-2.40(m, 4H).

Examples 23-27

Examples 23-27 (compounds 26b-e) were prepared using the same procedures as described for the compound 26a, example 22 (scheme 4). Characterization of compounds 26b-e (examples 23-27) is provided in table 3.

TABLE 3

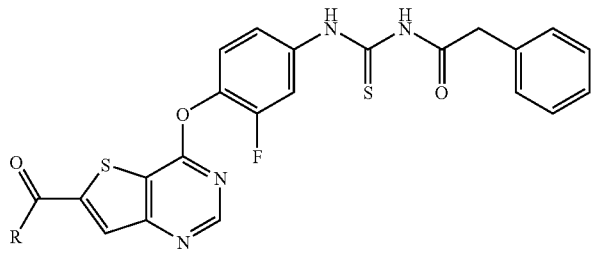

26b-e: Examples 23-27

Characterization of compounds 26b-e (examples 23-27)

| Cpd | Ex | R | Name | Characterization |
|---|---|---|---|---|
| 26b | 23 | —N(Me)Me | 1-(4-(6-(Dimethylcarbamoyl)thieno[3,2-d]pyrimidin 4-yloxy)-3-fluorophenyl)-3-(2-phenylacetyl)thiourea | ¹H NMR (400 MHz, DMSO-d₆) δ (ppm): 8.77 (s, 1H), 8.01 (s, 1H), 7.93 (dd, J = 2.4 and 12.4 Hz, 1H), 7.54 (t, J = 8.4 Hz, 1H), 7.50-7.44 (m, 1H), 7.38-7.30 (m, 4H), 7.30-7.23 (m, 1H), 3.82 (s, 2H), 3.24 (s, 3H), 3.07 (s, 3H). |
| 26c | 24 | —N-piperazinyl-N-Me | 1-(4-(6-(4-N-Methylpiperazylcarbamoyl)thieno[3,2-d]pyrimidin-4-yloxy)3-fluorophenyl)-3-(2-phenylacetyl)thiourea | ¹H NMR (400 MHz, DMSO-d₆) δ (ppm): 12.43 (s, 1H), 11.80 (s, 1H), 8.77 (s, 1H), 7.93 (s, 1H), 7.93 (dd, J = 2.0 and 12.0 Hz, 1H), 7.53 (t, J = 8.4 Hz, 1H), 7.48 (dd, J = 2.0 and 8.4 Hz, 1H), 7.38-7.30 (m, 4H), 7.30-7.24 (m, 1H), 3.82 (s, 2H), 3.74-3.62 (m, 4H), 2.48-2.36 (m, 4H), 2.25 (bs, 3H). |
| 26d | 25 | —N(H)Me | 1-(4-(6-(Methylcarbamoyl)thieno[3,2-d]pyrimidin-4-yloxy)-3-fluorophenyl)-3-(2-phenylacetyl)thiourea | ¹H NMR (400 MHz, DMSO-d₆) δ (ppm): 12.42 (s, 1H), 11.80 (s, 1H), 9.10 (q, J = 4.4 Hz, 1H), 8.76 (s, 1H), 8.23 (s, 1H), 7.92 (dd, J = 2.0 and 12.0 Hz, 1H), 7.54 (t, J = 8.8 Hz, 1H), 7.48 (dd, 2.0 and 8.8 Hz, 1H), 7.36-7.30 (m, 4H), 7.30-7.24 (m, 1H), 3.82 (s, 2H), 2.87 (d, J = 4.4 Hz, 1H). |
| 26e | 26 | —N(OMe)Me | 1-(4-(6-(N-Methoxy-N-methylcarbamoyl)thieno[3,2-d]pyrimidin-4-yloxy)-3-fluorophenyl)-3-(2-phenylacetyl)thiourea | ¹H NMR (400 MHz, DMSO-d₆) δ (ppm): 8.79 (s, 1H), 8.23 (s, 1H), 7.93 (dd, J = 2.0 and 11.6 Hz, 1H), 7.55 (t, J = 8.8 Hz, 1H), 7.48 (dd, J = 2.0 and 8.8 Hz, 1H), 7.36-7.30 (m, 4H), 7.30-7.24 (m, 1H), 3.87 (s, 3H), 3.82 (s, 2H), 3.39 (s, 3H). |

TABLE 3-continued

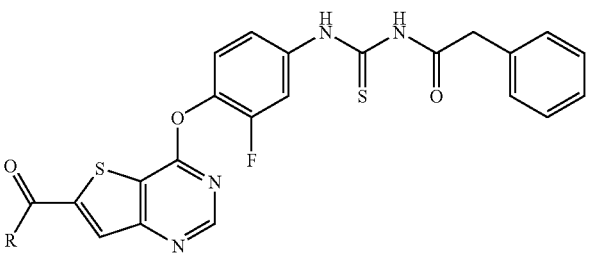

26b-e: Examples 23-27

Characterization of compounds 26b-e (examples 23-27)

| Cpd | Ex | R | Name | Characterization |
|---|---|---|---|---|
| 26f | 27 | ⁓N(H)–N(H)⁓ | 1-(4-(6-Carbamoylthieno[3,2-d]pyrimidin-4-yloxy)-3-fluorophenyl)-3-(2-phenylacetyl)thiourea | $^1$H NMR (400 MHz, DMSO-$d_6$) δ (ppm): 12.43 (s, 1H), 11.80 (s, 1H), 8.76 (s, 1H), 8.55 (bs, 1H), 8.29 (s, 1H), 8.07 (bs, 1H), 7.93 (dd, J = 2.0 and 12 Hz, 1H), 7.54 (t, J = 8.8 Hz, 1H), 7.48 (dd, J = 2.0 and 8.8 Hz, 1H), 7.36-7.30 (m, 4H), 7.30-7.23 (m, 1H), 3.82 (s, 2H). |

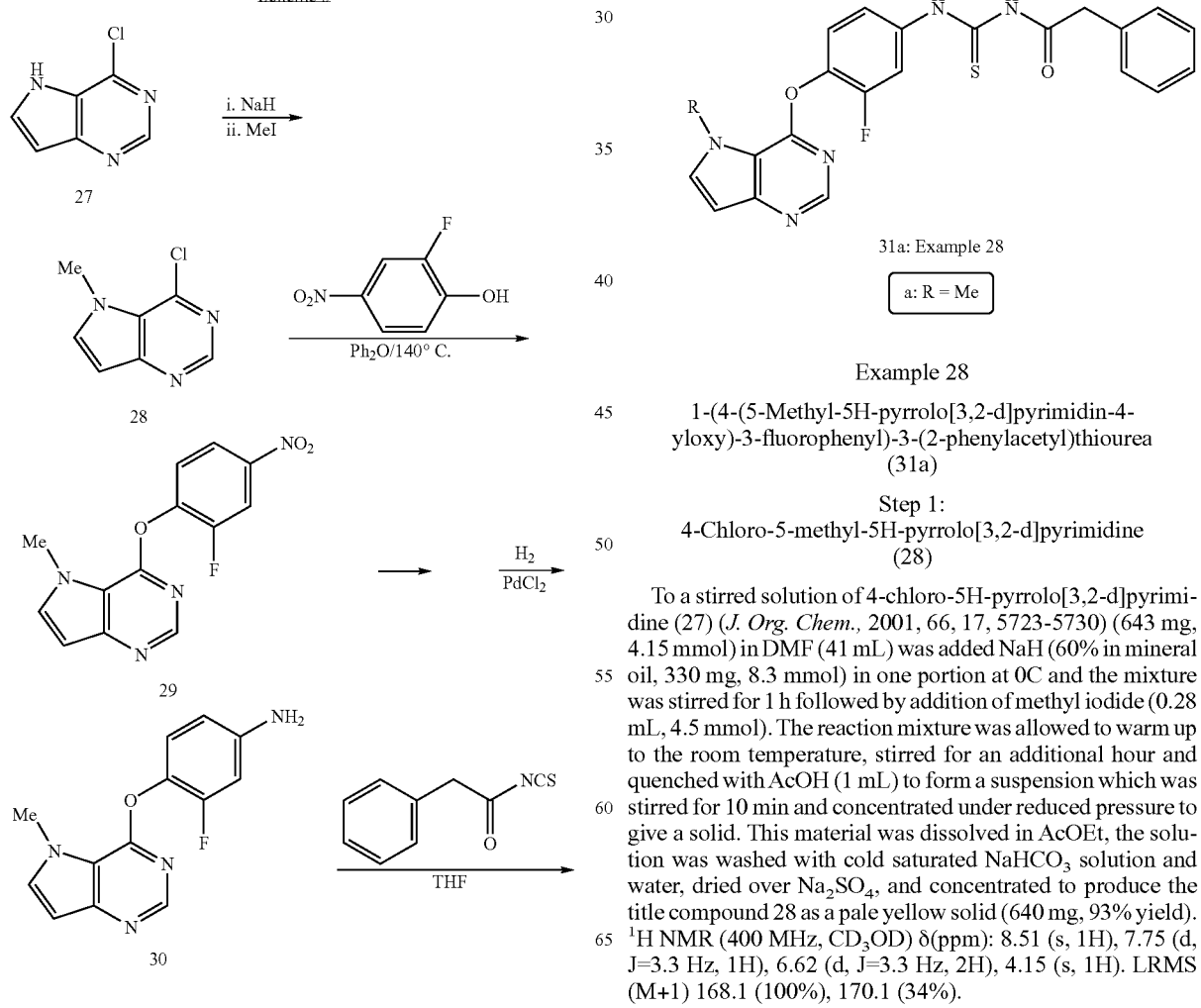

31a: Example 28 a: R = Me

Example 28

1-(4-(5-Methyl-5H-pyrrolo[3,2-d]pyrimidin-4-yloxy)-3-fluorophenyl)-3-(2-phenylacetyl)thiourea (31a)

Step 1:
4-Chloro-5-methyl-5H-pyrrolo[3,2-d]pyrimidine (28)

To a stirred solution of 4-chloro-5H-pyrrolo[3,2-d]pyrimidine (27) (*J. Org. Chem.*, 2001, 66, 17, 5723-5730) (643 mg, 4.15 mmol) in DMF (41 mL) was added NaH (60% in mineral oil, 330 mg, 8.3 mmol) in one portion at 0C and the mixture was stirred for 1 h followed by addition of methyl iodide (0.28 mL, 4.5 mmol). The reaction mixture was allowed to warm up to the room temperature, stirred for an additional hour and quenched with AcOH (1 mL) to form a suspension which was stirred for 10 min and concentrated under reduced pressure to give a solid. This material was dissolved in AcOEt, the solution was washed with cold saturated NaHCO$_3$ solution and water, dried over Na$_2$SO$_4$, and concentrated to produce the title compound 28 as a pale yellow solid (640 mg, 93% yield). $^1$H NMR (400 MHz, CD$_3$OD) δ(ppm): 8.51 (s, 1H), 7.75 (d, J=3.3 Hz, 1H), 6.62 (d, J=3.3 Hz, 2H), 4.15 (s, 1H). LRMS (M+1) 168.1 (100%), 170.1 (34%).

Step 2: 4-(2-Fluoro-4-nitrophenoxy)-5-methyl-5H-pyrrolo[3,2-d]pyrimidine (29)

A suspension of 4-chloro-5-methyl-5H-pyrrolo[3,2-d]pyrimidine (28) (300 mg, 1.79 mmol), 4-nitro-2-fluorophenol (422 mg, 2.69 mmol) and cesium carbonate (1.2 g, 3.58 mmol) in diphenyl ether (18 mL) was stirred overnight at 140° C. The reaction mixture was cooled to room temperature, concentrated under reduced pressure and the residue was triturated with $Et_2O$, filtered, and dried to afford the title compound 29 as a grey solid (258 mg, 49% yield). LRMS (M+1) 289.1 (100%).

Step 3: 4-(5-Methyl-5H-pyrrolo[3,2-d]pyrimidin-4-yloxy)-3-fluorobenzenamine (30)

To a solution of 4-(2-fluoro-4-nitrophenoxy)-5-methyl-5H-pyrrolo[3,2-d] pyrimidine (29) (253.6 mg, 0.879 mmol) in AcOH (3 mL) at 90° C. was added iron powder (245 mg, 4.4 mmol). The mixture was stirred vigorously for 10 min and filtered. The filtrate was concentrated under reduced pressure to produce a solid, which was dissolved in DCM. The resultant solution was washed with cold $NaHCO_3$ solution and water, dried over $Na_2SO_4$ and concentrated to provide a residue which was purified by column chromatography (eluent $MeOH—CH_2Cl_2$ 1:20) to afford the title compound 30 as a brown solid (120.6 mg, 53% yield). LRMS (M+1) 240.1 (100%).

Step 4: 1-(4-(5-Methyl-5H-pyrrolo[3,2-d]pyrimidin-4-yloxy)-3-fluorophenyl)-3-(2-phenylacetyl)thiourea (31a)

To a solution of 4-(5-methyl-5H-pyrrolo[3,2-d]pyrimidin-4-yloxy)-3-fluorobenzenamine (30) (120.8 mg, 0.5 mmol) and benzyl isothiocyanate (0.1 mL, 0.55 mmol) in THF (5 mL) was stirred 2 h at room temperature, concentrated under reduced pressure and the residue was subjected to a column chromatography on silica gel, (eluent EtOAc-hexane 1:1) to afford the title compound 31a as a white solid (97.6 mg, 45%). $^1$H NMR (400 MHz, DMSO-$d_6$) δ (ppm): 12.42 (s, 1H), 11.79 (s,1H), 8.28 (d, J=0.6 Hz, 1H), 7.88 (dd, J=2.3 Hz, J=12.1 Hz, 1H), 7.81 (d, J=3.1 Hz, 1H), 7.50 (t, J=8.4 Hz, 1H), 7.44 (dd, J=2.1 Hz, J=8.8 Hz, 1H), 7.33 (m, 4H), 7.28 (m, 1H), 6.65 (dd, J=0.6 Hz, J=2.9 Hz, 1H), 4.10 (s, 3H), 3.83 (s, 2H). LRMS (M+1) 436.1 (100%).

Example 29

1-(4-(5-Ethyl-5H-pyrrolo[3,2-d]pyrimidin-4-yloxy)-3-fluorophenyl)-3-(2-phenylacetyl)thiourea (31b)

Title compound 31b was obtained according to the scheme 5 using procedures similar to the ones described for example 28 but using ethyl iodide (instead of methyl iodide) in the step 1. Characterization of 31b is provided in table 4.

Example 30

1-(4-(5-Benzyl-5H-pyrrolo[3,2-d]pyrimidin-4-yloxy)-3-fluorophenyl)-3-(2-phenylacetyl)thiourea (31c)

Title compound 31c was obtained according to the scheme 5 using procedures similar to the ones described for the example 28 but using benzyl bromide (instead of methyl iodide) in the step 1. Characterization of 31c is provided in table 4.

TABLE 4

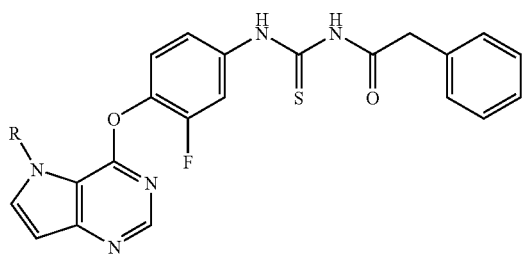

31b-c: Examples 29-30
Characterization of 31b-c (examples 29-30)

| Cpd | Ex | R | Name | Characterization |
|---|---|---|---|---|
| 31b | 29 | Et | 1-(4-(5-Ethyl-5H-1H), pyrrolo[3,2-d]pyrimidin-4-yloxy)-3-fluorophenyl)-3-(2-phenylacetyl)thiourea | $^1$H NMR (400 MHz, DMSO-$d_6$) δ (ppm): 12.4 (br, 1H), 11.8 (br, 8.3 (s, 1H), 7.90-7.85 (m, 2H), 7.54-7.41 (m, 2H), 7.40 (m, 4H), 7.29 (m, 1H), 6.63 (d, J = 3.1 Hz, 1H), 4.46 (q, J = 7.0 Hz, J =14.3 Hz, 2H), 3.83 (s, 2H), 1.46 (t, J = 7.0 Hz, 3H). LRMS (M + 1) 450.2 (100%). |
| 31c | 30 | —$CH_2Ph$ | 1-(4-(5-Benzyl-5H-pyrrolo[3,2-d]pyrimidin-4-yloxy)-3-fluorophenyl)-3-(2-phenylacetyl)thiourea | $^1$H NMR (400 MHz, DMSO-$d_6$) δ (ppm): 12.34 (s, 1H), 11.79 (s, 1H), 8.3 (s, 1H), 8.04 (d, J = 3.1 Hz, 1H), 7.8 (dd, J = 2.3 Hz, J = 7.8 Hz, 1H), 7.4 (m, 1H), 7.35-7.76 (m, 11H), 6.7 (d, 3.1 Hz, 1H), 5.66 (s, 2H), 3.82 (s, 2H). LRMS (M + 1) 512.3 (100%). |

Scheme 6

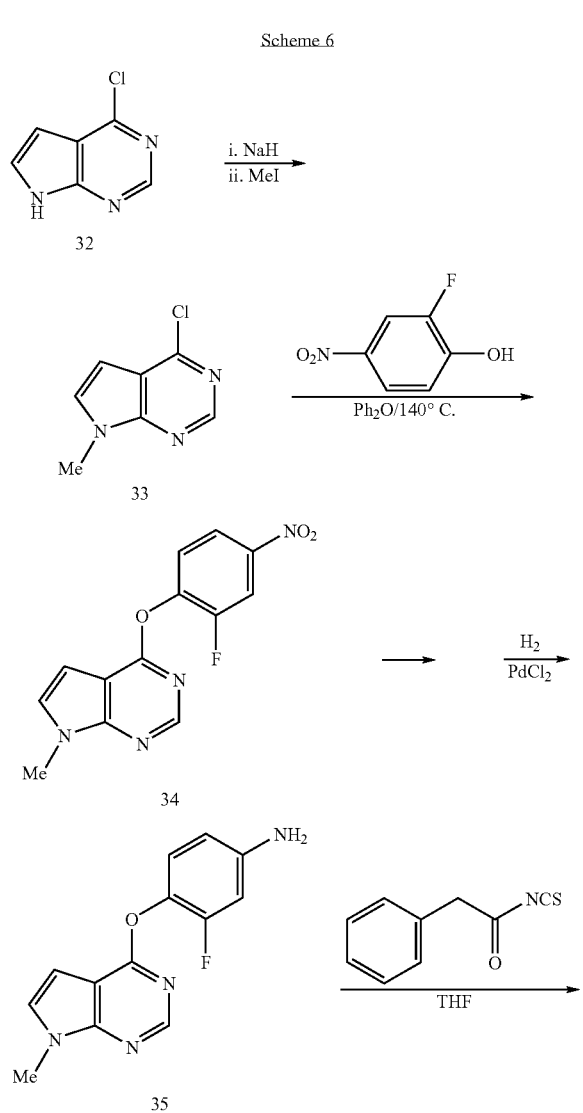

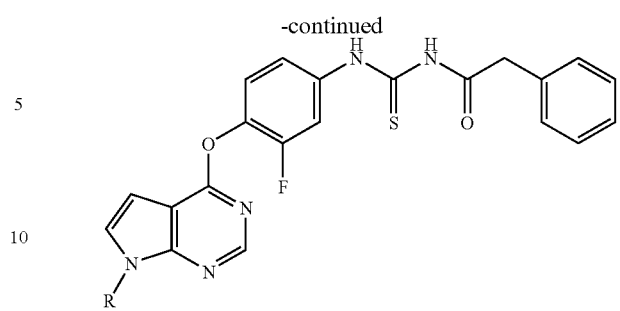

36a: Example 31 a: R = Me

Example 31

1-(4-(7-Methyl-7H-pyrrolo[2,3-d]pyrimidin-4-yloxy)-3-fluorophenyl)-3-(2-phenylacetyl)thiourea (36a)

Title compound 36a (scheme 6) was obtained according to the procedures similar to the ones described for the example 28 (scheme 5) but using as a starting material 4-chloro-7H-pyrrolo[2,3-d]pyrimidine 32 (instead of chloride 27). Characterization of 36a is provided in table 5.

Example 32

1-(4-(7-Ethyl-7H-pyrrolo[2,3-d]pyrimidin-4-yloxy)-3-fluorophenyl)-3-(2-phenylacetyl)thiourea (36b)

Title compound 36b was obtained according to the scheme 6 using the procedures similar to the ones described for the example 31 but using ethyl iodide (instead of methyl iodide) in the step 1. Characterization of 36b is provided in table 5.

Example 33

1-(4-(7-Benzyl-7H-pyrrolo[2,3-d]pyrimidin-4-yloxy)-3-fluorophenyl)-3-(2-phenylacetyl)thiourea (36c)

Title compound 36c was obtained according to the scheme 6 using the procedures similar to the ones described for the example 31 but using benzyl bromide (instead of methyl iodide) in the step 1. Characterization of 36c is provided in table 5.

TABLE 5

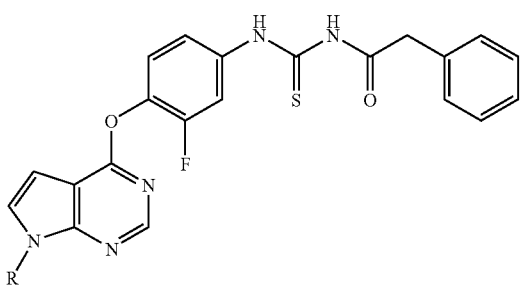

36a-c: Examples 31-33
Characterization of 36a-c (examples 31-33)

| Cpd | Ex | R | Name | Characterization |
|---|---|---|---|---|
| 36a | 31 | Me | 1-(4-(7-Methyl-7H-pyrrolo[2,3-d]pyrimidin-4-yloxy)-3-fluorophenyl)-3- | $^1$NMR (400 MHz, DMSO-$d_6$) δ (ppm): 12.43 (s, 1H), 11.79 (s, 1H), 8.34 (s, 1H), 7.87 (dd, J = 1.8 Hz, |

TABLE 5-continued

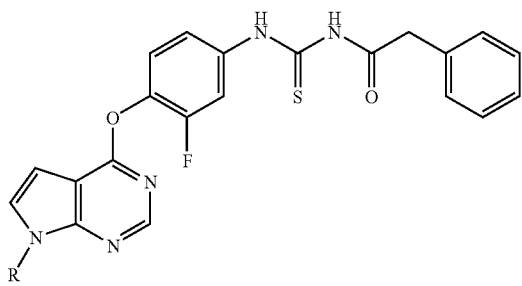

36a-c: Examples 31-33
Characterization of 36a-c (examples 31-33)

| Cpd | Ex | R | Name | Characterization |
|---|---|---|---|---|
| | | | (2-phenyl acetyl)thiourea | J = 13.1 Hz, 1H), 7.55 (d, J = 3.5 Hz, 1H), 7.44 (m, 2H), 7.33 (m, 4H), 7.27 (m, 1H), 6.62 (d, J = 3.5 Hz, 1H), 3.83 (m, 5H). LRMS (M + 1) 436.1 (100%). |
| 36b | 32 | Et | 1-(4-(7-Ethyl-7H-pyrrolo[2,3-d]pyrimidin-4-yloxy)-3-fluorophenyl)-3-(2-phenyl acetyl)thiourea | $^1$NMR (400 MHz, DMSO-$d_6$) δ (ppm): 12.41 (br, 1H), 11.78 (br, 1H), 8.32 (s, 1H), 7.87 (m, 1H), 7.63 (d, J = 3.5, Hz, 1H), 7.43 (in, 2H), 7.33 (m, 4H), 7.27 (m, 1H), 6.63 (d, J = 3.5 Hz, 1H), 4.29 (q, J = 7.2 Hz, J = 14.5 Hz, 2H), 3.82 (s, 2H), 1.40 (t, J = 7.2 Hz, 3H). LRMS (M +1) 450.2 (100%). |
| 36c | 33 | —CH$_2$Ph | 1-(4-(7-Benzyl-7H-pyrrolo[2,3-d]pyrimidin-4-yloxy)-3-fluorophenyl)-3-(2-phenyl acetyl)thiourea | $^1$H NMR (400 MHz, DMSO-$d_6$) δ (ppm): 12.41 (s, 1H), 11.79 (s, 1H), 8.35 (s, 1H), 7.87 (m, 1H), 7.68 (d, J = 3.5 Hz, 1H), 7.44 (m, 2H), 7.35-7.23 (m, 10H), 6.68 (d, 3.5 Hz, 1H), 5.48 (s, 2H), 3.82 (s, 2H). LRMS (M + 1) 512.3 (100%). |

Scheme 7

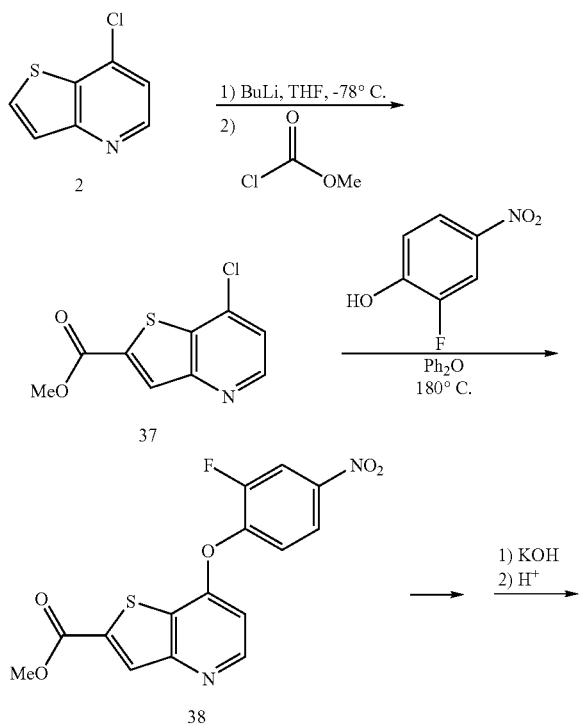

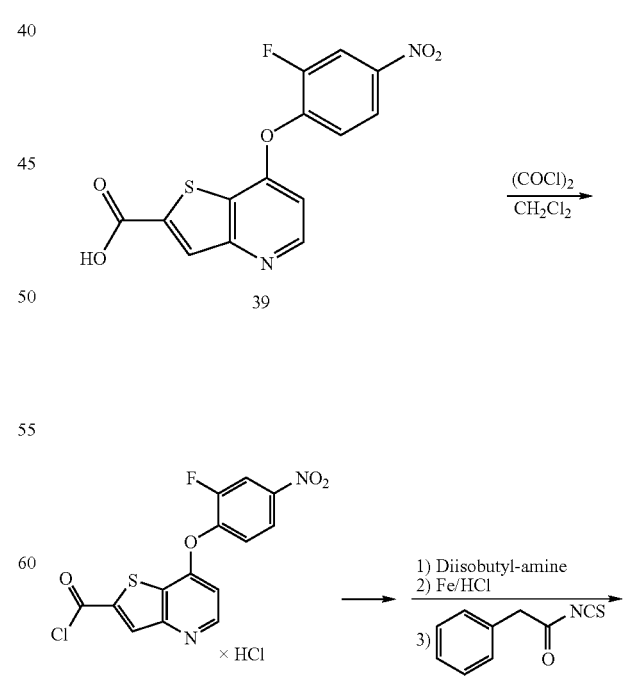

-continued

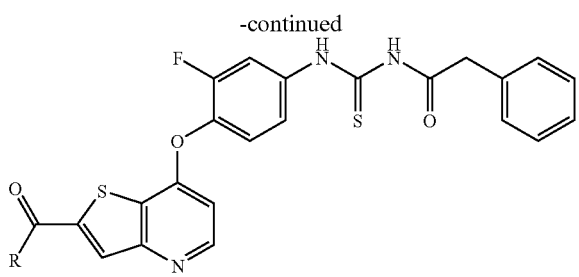

8I: Example 34

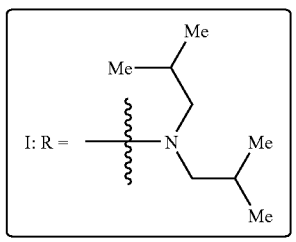

Example 34

7-(2-Fluoro-4-(3-(2-phenylacetyl)thioureido)phenoxy)-N,N-diisobutylthieno[3,2-b]pyridine-2-carboxamide (81)

Step 1: Methyl 7-chlorothieno[3,2-b]pyridine-2-carboxylate (37)

To a stirred solution of 2 (7.0 g, 41.3 mmol) in anhydrous THF (100 mL) at −78° C. under a nitrogen atmosphere was added n-BuLi (24.7 mL, 2.5 M in hexanes, 61.8 mmol). After 1 hour, methyl chloroformate (9.6 ml, 124 mmol) was added and the reaction mixture was stirred for an extra hour at the same temperature, quenched with excess methanol and allowed to warm to room temperature. The solvent was then evaporated and the residue was purified by flash chromatography using hexane—AcOEt (70:30) as an eluent. The product from the column was re-crystallized from ethyl acetate to afford title compound 37 (4.3g, 46% yield) as a white solid. $^1$H NMR (400 MHz, DMSO-$d_6$) δ(ppm): 8.75 (dd, J=0.8 and 4.8 Hz, 1H), 8.26 (d, J=0.8 Hz, 1H), 7.74 (dd, J=0.8 and 5.2 Hz, 1H), 3.93 (s, 3H).

Step 2: Methyl 7-(2-fluoro-4-nitrophenoxy)thieno[3,2-b]pyridine-2-carboxylate (38)

A mixture of 37 (4.0 g, 17.6 mmol), 2-fluoro-4-nitrophenol (5.5 g, 35.0 mmol) and $K_2CO_3$ (12.1 g, 87.5 mmol) in $Ph_2O$ was heated at 180° C. for 5 hours. The mixture was cooled to room temperature, diluted with EtOAc and washed with water. The organic phase was collected, dried over anhydrous sodium sulfate and the solvents were removed under reduced pressure. The residue was purified by flash chromatography using hexane—AcOEt (70:30) as an eluent. The product from the column was re-crystallized from a mixture of ethyl acetate-hexanes to afford 38 (3.6 g, 59% yield) as a white solid. $^1$H NMR (400 MHz, DMSO-$d_6$) δ(ppm): 8.69 (d, J=5.2 Hz, 1H), 8.47 (dd, J=2.4 and 10.0 Hz, 1H), 8.27 (s, 1H), 7.77 (dd, J=8.0 and 9.2 Hz, 1H), 7.06 (dd, J=0.8 and 5.2 Hz, 1H), 3.93 (s, 3H).

Step 3: 7-(2-Fluoro-4-nitrophenoxy)thieno[3,2-b]pyridine-2-carboxylic acid (39)

To a stirred solution of 38 (2.5 g, 7.18 mmol) in THF (50 ml) was added KOH (14.3 ml, 1.0 N in $H_2O$, 14.3 mmol). After 4 hours the reaction mixture was concentrated and the resultant residue was dissolved in $H_2O$ (50 ml). The aqueous layer was then washed with ethyl acetate and acidified with 1N HCl (pH=1). The precipitate that formed upon acidification was collected by filtration, washed with water and dried under high vacuum to afford title compound 39 (2.3 g, 96% yield) as a white solid. $^1$H NMR (400 MHz, DMSO-$d_6$) δ(pm): 8.68 (d, J=5.2 Hz, 1H), 8.47 (dd, J=2.8 and 10.4 Hz, 1H), 8.20 (m, 1H), 8.17 (s, 1H), 7.76 (dd, J=8.0 and 8.8 Hz, 1H), 7.04 (d, J=5.2 Hz, 1H).

Step 4: 7-(2-Fluoro-4-nitrophenoxy)thieno[3,2-b]pyridine-2-carbonyl chloride (40)

To a solution of 39 (2.0 g, 5.98 mmol) in anhydrous $CH_2Cl_2$ (30 ml) under an atmosphere of nitrogen, was added oxalyl chloride (2.6 ml, 29.8 mmol). After stirring for 2 hours the solvent was evaporated, anhydrous toluene (10 mL) was added and the resultant mixture was evaporated (procedure of addition of toluene followed by evaporation was performed twice) to afford title compound 40 (2.2 g, 94% yield) as a white solid. The product was used without further purification and characterization and was assumed to be the mono-HCl salt.

Step 5: 7-(2-Fluoro-4-(3-(2-phenylacetyl)thioureido) phenoxy)-N,N-diisobutylthieno[3,2-b]pyridine-2-carboxamide (81)

To a solution of 40 (150 mg, 0.385 mmol) and TEA (107 μl, 0.771 mmol) in anhydrous $CH_2Cl_2$ under an atmosphere of nitrogen was added diisobutylamine (67 μL, 0.385 mmol). After stirring for 1 hour, methanol (2 mL) was added followed by iron powder (150 mg) and HCl (conc., 0.4 mL). The reaction mixture was stirred for additional 2 hours and then partitioned between ethyl acetate (20 mL) and a mixture of $H_2O$ (20 mL) and $NH_4OH$ (2 mL). Organic phase was collected, washed with brine, dried over anhydrous $MgSO_4$, filtered and evaporated. The residue was treated with 2-phenylacetyl isothiocyanate (102 mg, 0.58 mmol) in THF (2 mL), the resultant mixture was allowed to stand for 2 hours at ambient temperature, quenched with methanol (5.0 mL), loaded onto 5 ml of silica gel and purified by flash chromatography using hexane—AcOEt (70:30) as an eluent, to afford compound 81 (41 mg, 18%) as a white solid. $^1$H NMR (400 MHz, $CD_3OD$) δ (ppm): 8.54 (d, J=5.6 Hz, 1H), 8.08 (dd, J=2.0 and 12.0 Hz, 1H), 7.69 (s, 1H), 7.38-7.49 (m, 2H), 7.28 - 7.35 (m, 5H), 6.77 (dd, J=1.2 and 5.6 Hz, 1H), 3.77 (s, 2H), 3.46 (bs, 4H), 2.18 (bs, 1H), 2.02 (bs, 1H), 1.02 (bs, 6H), 0.87 (bs, 6H). LRMS (M+1):592.7 (calcd), 593.3 (found).

TABLE 6

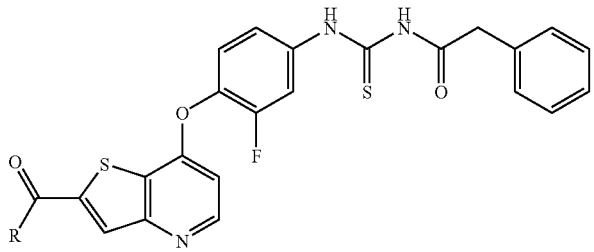

8m-y: Examples 35-47

Characterization of compounds 8m-y (examples 35-47)

| Cmp | Ex | R | Name | Characterization |
|---|---|---|---|---|
| 8m | 35 | Me-N(CH2-furan)- | 7-[2-Fluoro-4-(3-phenylacetyl-thioureido)-phenoxy]-thieno[3,2-b]pyridine-2-carboxylic acid furan-2-ylmethyl-methyl-amide | $^1$H NMR (400 MHz, DMSO-d$_6$) δ (ppm): 12.49 (s, 1H), 11.82 (s, 1H), 8.59 (d, J = 5.6 Hz, 1H), 7.92-8.05 (m, 2H), 7.67 (bs, 1H), 7.54 (m, 2H), 7.25-7.37 (m, 5H), 6.75 (d, J = 0.8, 5.2 Hz, 1H), 6.46 (s, 2H), 4.74 (bs, 2H), 3.83 (s, 2H), 3.27 (bs, 1.5H), 2.99 (bs, 1.5 H). LRMS (M + 1):574.6 (cald), 575.2 (found). |
| 8n | 36 | (iPr)2N-CH2CH2-NH- | 7-[2-Fluoro-4-(3-phenylacetyl-thioureido)-phenoxy]-thieno[3,2-b]pyridine-2-carboxylic acid (2-diisopropylamino-ethyl)-amide, formate salt | 12.45 (s, 1H), 11.78 (s, 1H), 8.92 (t, J = 5.6 Hz, 1H), 8.53 (d, J = 5.6 Hz, 1H), 8.16 (s, 1H), 8.12 (s, 1H), 7.99 (m, 1H), 7.50 (m, 2H), 7.21-7.30 (m, 5H), 6.69 (d, J = 5.2 Hz, 1H), 3.79 (s, 2H), 3.22 (m, 2H), 2.97 (m, 2H), 2.55 (t, J = 7.6 Hz, 2H), 0.964 (d, J = 6.4 Hz, 12H). LRMS (M + 1) .607.8 (calcd.), 608.3 (found). |
| 8o | 37 | pyrrolidin-1-yl | 1-{3-Fluoro-4-[2-(pyrrolidine-1-carbonyl)-thieno[3,2-b]pyridin-7-yloxy]-phenyl}-3-phenylacetyl-thiourea | $^1$H NMR (400 MHz, DMSO-d$_6$) δ (ppm): 12.48 (s, 1H), 11.82 (s, 1H), 8.58 (d, J = 5.3 Hz, 1H), 8.03 (m, 2H), 8.00 (s, 1H), 7.53 (m, 2H), 7.33 (m, 4H), 7.28 (m, 1H), 6.73 (d, J = 5.3 Hz, 1H), 3 86 (t, J = 6.4 Hz, 2H), 3.83 (s, 2H), 3.53 (t, J = 6.84 Hz, 2H), 1.95-1.86 (m, 4H). LRMS (M + 1). 534. 6 (calcd.), 535.2 (found). |
| 8p | 38 | (R)-3-hydroxypyrrolidin-1-yl | (R)-N-(3-Fluoro-4-(2-(3-hydroxypyrrolidine-1-carbonyl)thieno[3,2-bg]pyridin-7-yloxy)phenylcar-bamothioyl)-2-phenylacetamide | $^1$H NMR (400 MHz, DMSO-d$_6$) δ (ppm): 12.48 (s, 1H), 11.81 (s, 1H), 8.59 (d, J=5.6 Hz, 1H), 8.04 (m, 2H), 7.54 (m, 2H), 7.22-7.34 (m, 5H), 6.74 (d, J=5.2 Hz, 1H), 5.07 (bs, 1H), 4.36 (bd, J=19.6 Hz, 1H), 3.99 (m, 1H), 3.82 (s, 2H), 3.38-3.68 (m, 3H), 1.80-2.06 (m, 2H). MS (m/z): 551.1 (M + H) (found). |
| 8q | 39 | (S)-3-hydroxypyrrolidin-1-yl | (S)-N-(3-Fluoro-4-(2-(3-hydroxypyrrolidine-1-carbonyl)thieno[3,2-b]pyridin-7-yloxy) phenylcarbamothioyl)-2-phenylacetamide | $^1$H NMR (DMSO-d$_6$) δ (ppm): 12.51 (s, 1H), 11.84 (s, 1H), 8.62 (d. 1H, J=5.3 Hz), 8.08-8.01 (m, 2H), 7.56-7.52 (m, 2H), 7.36-7.31 (m, 4H), 7.28-7.24 (m, 1H), 6.77 (d, 1H, J=5.7 Hz), 4.38-4.32 (m, 1H), 4.00-3.92 (m, 1H), 3.81 (s, 2H), 3.67-3.55 (m, 4H), 2.06-1.83 (m, 2H). MS (m/z): 551.1 (M + H) (found). |

TABLE 6-continued 8m-y: Examples 35-47

Characterization of compounds 8m-y (examples 35-47)

| Cmp | Ex | R | Name | Characterization |
|---|---|---|---|---|
| 8r | 40 | (pyrrolidine-2-carboxamide group) | (S)-1-(7-(2-Fluoro-4-(3-(2-phenylacetyl)thioureido)phenoxy)thieno[3,2-b]pyridine-2-carbonyl)pyrrolidine-2-carboxamide | LRMS (M + 1) 577.6 (calcd.), 578.3 (found). |
| 8s | 41 | (N-cyclopropyl-N-(2-cyanoethyl) group) | 7-[2-Fluoro-4-(3-phenylacetyl-thioureido)-phenoxy]-thieno[3,2-b]pyridine-2-carboxylic acid (2-cyano-ethyl)-cyclopropyl-amide | LRMS (M + 1): 573.7 (calcd.), 574.2 (found). |
| 8t | 42 | (2-dimethylaminoethylamino group) | 7-[2-Fluoro-4-(3-phenylacetyl-thioureido)-phenoxy]-thieno[3,2-b]pyridine-2-carboxylic acid (2-dimethylamino-ethyl)-amide, formate salt | LRMS (M + 1): 551.7 (cald), 552.2 (found) |
| 8u | 43 | (bis-(2-methoxyethyl)amino group) | 7-[2-Fluoro-4-(3-phenylacetyl-thioreido)-phenoxy]-thieno[3,2-b]pyridine-2-carboxylic acid bis-(2-methoxy-ethyl)-amide | LRMS (M + 1): 596.7 (cald), 597.3 (found). |
| 8v | 44 | (benzylamino group) | 7-[2-Fluoro-4-(3-phenylacetyl-thioureido)-phenoxy]-thieno[3,2-b]pyridine-2-carboxylic acid benzylamide | LRMS (M + 1): 570.7 (calcd), 571.3 (found). |
| 8w | 45 | (N-phenyl-N-(2-cyanoethyl) group) | 7-[2-Fluoro-4-(3-phenylacetyl-thioureido)-phenoxy]-thieno[3,2-b]pyridine-2-carboxylic acid (2-cyano-ethyl)-phenyl-amide | LRMS (M + 1): 609.7 (calcd.), 610.2 found. |
| 8x | 46 | (leucinamide group) | (R)-N-(1-amino-4-methyl-1-oxopentan-2-yl)-7-(2-fluoro-4-(3-(2-phenylacetyl)thioureido)phenoxy)thieno[3,2-b]pyridine-2-carboxamide | LRMS (M + 1): 593.6 (calcd), 594.2 (found). |

TABLE 6-continued

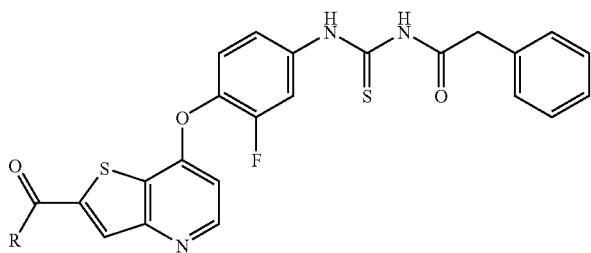

8m-y: Examples 35-47

Characterization of compounds 8m-y (examples 35-47)

| Cmp | Ex | R | Name | Characterization |
|---|---|---|---|---|
| 8y | 47 | Me, pyrazole structure | 7-[2-Fluoro-4-(3-phenylacetyl-thioureido)-phenoxy]-thieno[3,2-b]pyridine-2-carboxylic acid (2,5-dimethyl-2H-pyrazol-3-yl)-amide | LRMS (M + 1): 574.6 (calcd), 575.2 (found) |

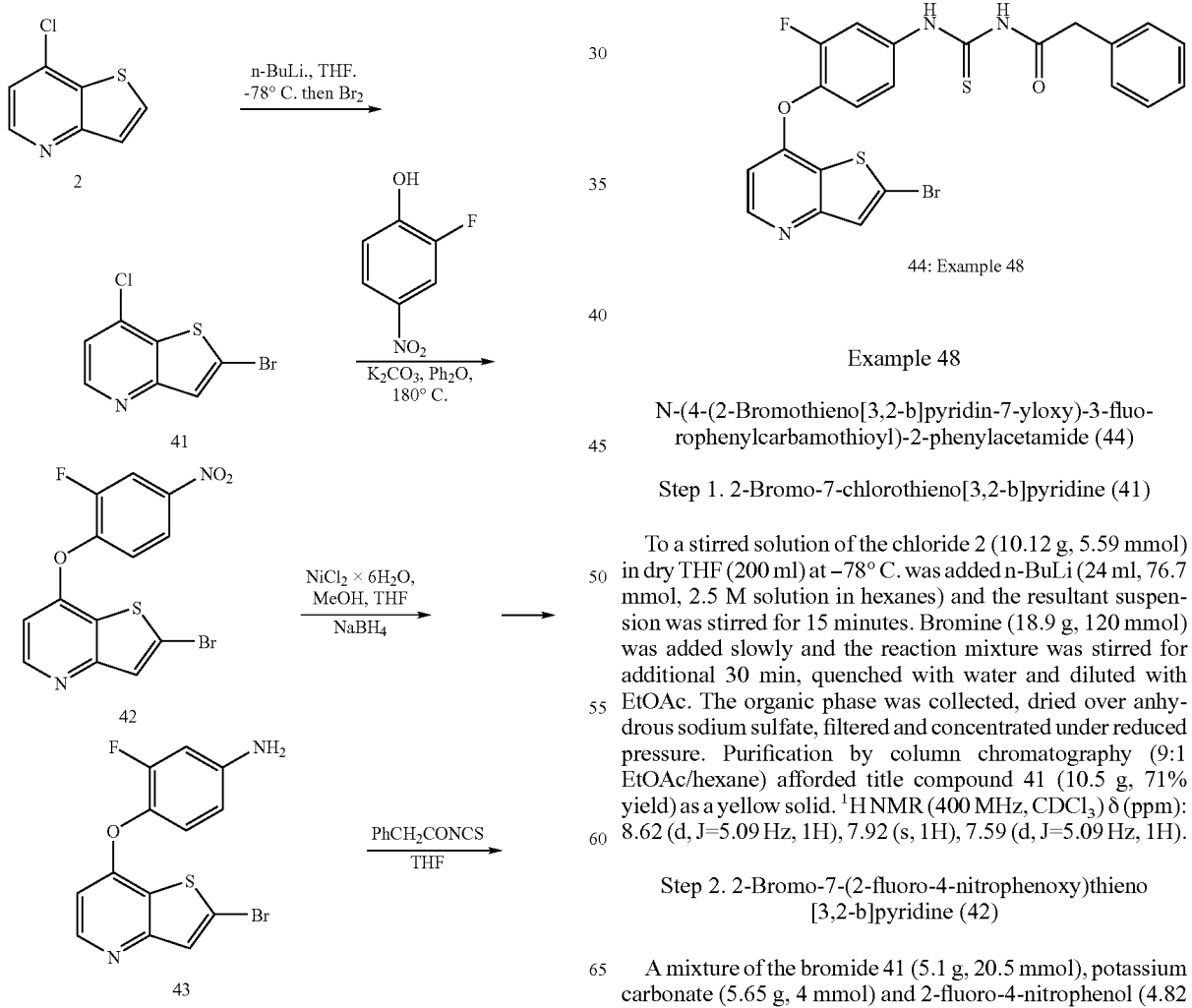

Example 48

N-(4-(2-Bromothieno[3,2-b]pyridin-7-yloxy)-3-fluorophenylcarbamothioyl)-2-phenylacetamide (44)

Step 1. 2-Bromo-7-chlorothieno[3,2-b]pyridine (41)

To a stirred solution of the chloride 2 (10.12 g, 5.59 mmol) in dry THF (200 ml) at −78° C. was added n-BuLi (24 ml, 76.7 mmol, 2.5 M solution in hexanes) and the resultant suspension was stirred for 15 minutes. Bromine (18.9 g, 120 mmol) was added slowly and the reaction mixture was stirred for additional 30 min, quenched with water and diluted with EtOAc. The organic phase was collected, dried over anhydrous sodium sulfate, filtered and concentrated under reduced pressure. Purification by column chromatography (9:1 EtOAc/hexane) afforded title compound 41 (10.5 g, 71% yield) as a yellow solid. $^1$H NMR (400 MHz, CDCl$_3$) δ (ppm): 8.62 (d, J=5.09 Hz, 1H), 7.92 (s, 1H), 7.59 (d, J=5.09 Hz, 1H).

Step 2. 2-Bromo-7-(2-fluoro-4-nitrophenoxy)thieno[3,2-b]pyridine (42)

A mixture of the bromide 41 (5.1 g, 20.5 mmol), potassium carbonate (5.65 g, 4 mmol) and 2-fluoro-4-nitrophenol (4.82 g, 30.7 mmol) was heated at 190° C. in diphenyl ether (25 ml)

for 3 hrs. After cooling to room temperature it was diluted with DCM and filtered. The filtrate was concentrated under reduced pressure and the residue was purified by column chromatography (eluent EtOAc:hexane, 3:1) to afford title compound 42 as a yellow solid (5.4 g, 71% yield). $^1$H NMR (400 MHz, DMSO-$d_6$) δ (ppm): 8.55 (d, J=5.28 Hz, 1H), 8.46 (dd, J=2.5 and 10.4 Hz, 1H), 8.19 (d, J=8.8 Hz, 1H), 7.87 (s, 1H), 7.72 (t, J=8.4 Hz), 6.99 (d, J=5.47 Hz, 1H).

Steps 3-4. 1-(4-(2-Bromothieno[3,2-b]pyridin-7-yloxy)-3-fluorophenyl)-3-(2-phenylacetyl)thiourea (44)

To a solution of the nitro compound 42 (100 mg, 0.27 mmol) in THF (2 ml) and water (0.5 ml) was added SnCl$_2$2H$_2$O (76.99 mg, 1.5 eq, 0.41 mmol) and the reaction mixture was refluxed for 3 hrs, cooled to room temperature, diluted with EtOAc and washed with conc. ammonium hydroxide solution. EtOAc-extract was collected and the aqueous fractions were combined and washed with DCM. DCM extract was combined with the AcOEt-extract, the mixture was dried over sodium sulfate, filtered and evaporated to form the amine 43 (92 mg, 100%), which was used without any further purification.

To a solution of the amine 43 (92 mg, 0.27 mmol) in THF (10 ml) was added benzyl isothiocyanate (72 mg, 1.5 eq, 0.407 mmol). The reaction mixture was stirred for 1 hr at room temperature, concentrated under reduced pressure and the residue was purifed by column chromatograpy (7:3 hexane:EtOAc to 1:1 MeOH:EtOAc) to afford the title compound 44 as a white solid (28 mg, 20% yield). $^1$H NMR (400 MHz, DMSO-$d_6$) δ (ppm): 12.48 (s, 1H), 11.81 (s, 1H), 8.55-8.52 (m, 1H), 8.01 (d, J=11.9 Hz, 1H), 7.85 (s, 1H), 7.55-7.49 (m, 2H), 7.45-7.19 (m, 5H), 6.73 (d, J=5.7 Hz, 1H), 3.82 (s, 2H). MS (m/z): 518.2/520.2 (M+H).

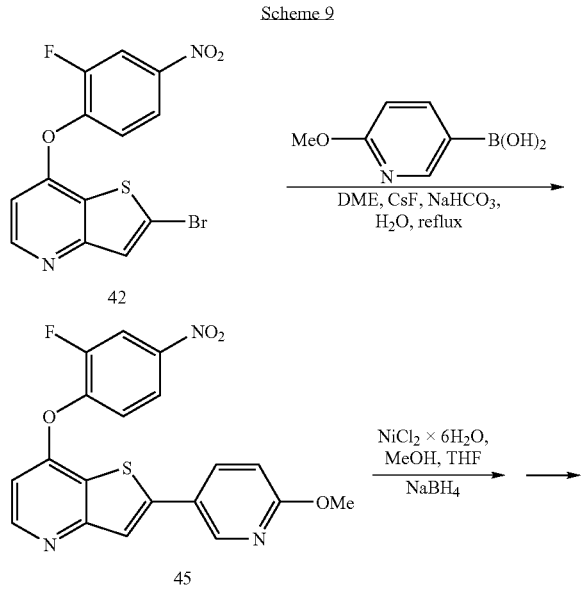

Scheme 9

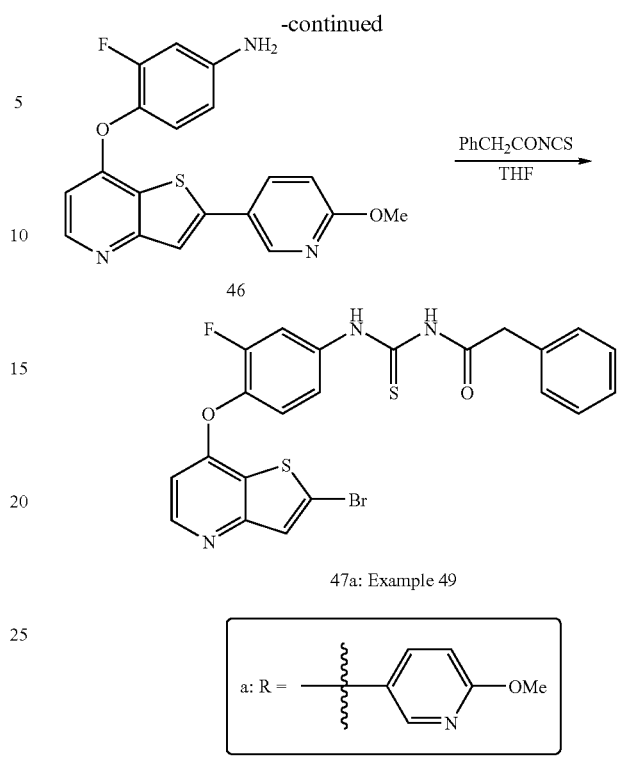

Example 49

N-(3-Fluoro-4-(2-(6-methoxypyridin-3-yl)thieno[3,2-b]pyridin-7-yloxy)phenylcarbamothioyl)-2-phenylacetamide (47a)

Step 1. 7-(2-Fluoro-4-nitrophenoxy)-2-(6-methoxypyridin-3-yl)thieno[3,2-b]pyridine (45)

A mixture of the nitro compound 42 (500 mg, 1.36 mmol), 6-methoxypyridin-3-ylboronic acid (312 mg, 2.04 mmol) and CsF (620 mg, 4.08 mmol) were suspended in DME (12 ml) and NaHCO$_3$ (342 mg, 4.08 mmol), dissolved in the minimum amount of water, was added. The mixture was de-aerated by bubbling N$_2$ through the solution for 10 min, heated at 80° C. for 3 hrs and concentrated to dryness. The formed residue was dissolved in DCM and washed with water. The DCM was collected, dried over sodium sulfate, filtered and the DCM was removed by evaporation. The resultant solid was triturated with Et$_2$O to afford the title compound 45 (176 mg, 32% yield), which was used without further purification. $^1$H NMR (400 MHz, DMSO-$d_6$) δ (ppm): 8.71 (m, 1H), 8.56 (m 1H), 8.46 (m, 1H), 8.22 (m, 2H), 8.01 (s, 1H), 7.72 (t, J=8.6 Hz, 1H), 6.99 (d, J=5.47 Hz, 1H), 6.90 (m, 1H), 3.97 (s, 3H).

Step 2. N-(3-Fluoro-4-(2-(6-methoxypyridin-3-yl)thieno[3,2-b]pyridin-7-yloxy)phenylcarbamothioyl)-2-phenylacetamide (47a)

To a solution of 45 (176 mg, 0.44 mmol) in MeOH (10 ml) and THF (10 ml) at 0° C. was added NiCl$_2$×6H$_2$O (210 mg, 0.89 mmol) and NaBH$_4$ (65 mg, 1.76 mmol). The reaction mixture was stirred for 1 hr, concentrated to dryness and the resultant solid was dissolved in 1 M HCl. The acidic solution was then made basic with aqueous ammonium hydroxide and extracted with EtOAc. The organic phase was collected, dried over anhydrous sodium sulfate and filtered. The filtrate was evaporated under reduced pressure and the residue was triturated with Et$_2$O to afford the amine 46 as a white solid which was used immediately in the next step.

To a suspension of the amine 46 (162 mg, 0.44 mmol) in THF (7 ml) was added 2-phenylacetyl isothiocyanate (117 mg, 0.66 mmol). The reaction mixture was stirred for 1 hr, concentrated under reduced pressure and the residue was purified by column chromatography (eluent EtOAc-MeOH, 95:5); a solid was obtained which was triturated with Et$_2$O to afford title compound 47a (80 mg, 33% yield). $^1$H NMR (400 MHz, DMSO-d$_6$) δ (ppm): 12.50 (s, 1H), 11.85 (s, 1H), 8.70 (s, 1H), 8.68 (d, J=6.07 Hz, 1H), 8.28 (m, 1H), 8.10 (s, 2H), 7.59 (s, 2H), 7.34-7.27 (m, 5H), 7.01 (d, J=8.61 Hz, 1H), 6.93 (d, J=5.7 Hz, 1H), 3.93 (s, 3H), 3.83 (s, 2H).

Examples 50-54

Examples 50-54 (compounds 47b-f) were prepared similarly to the compound 47a (example 49) according to the scheme 9.

TABLE 7

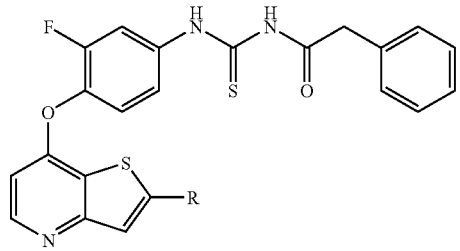

47b-f: Examples 50-54

Characterization of compounds 47b-f (examples 50-54)

| Cpd | Ex | R | Name | Characterization |
|---|---|---|---|---|
| 47b | 50 | 5-(6-fluoropyridin-3-yl) | N-(3-Fluoro-4-(2-(6-fluoropyridin-3-yl)thieno[3,2-b]pyridin-7-yloxy)phenylcarbamothioyl)-2-phenylacetamide | $^1$H NMR (400 MHz, DMSO-d$_6$) δ ppm): 12.46 (s, 1H), 11.82 (s, 1H), 8.79 (m, 1H), 8.55 (d, J=5.48 Hz, 1H), 8.50 (m, 1H), 8.19 (s, 1H), 8.02 (d, J=13 Hz, 1H), 7.53 (m, 1H), 7.37-7.26 (m, 6H), 6.68 (m, 1H), 6.68 (m, 1H), 3.82 (s, 2H). |
| 47c | 51 | pyrimidin-5-yl | N-(3-Fluoro-4-(2-(pyrimidin-5-yl)-thieno[3,2-b]pyridin-7-yloxy)phenylcarbamothioyl)-2-phenylacetamide dihydochloride. | H NMR (400 MHz, DMSO-d6) δ ppm): 12.48 (s, 1H), 11.83 (s, 1H), 9.2 (bs, 3H) 8.63 (m, 1H), 8.34 (s, 1H), 8.03 (d, J=11 Hz, 1H), 7.55 (m, 2H), 7.30 (m, 6H), 6.68 (m, 1H), 3.82 (s, 2H). |
| 47d | 52 | 1-methyl-1H-pyrrol-2-yl | N-(3-Fluoro-4-(2-(1-methyl-1H-pyrrol-2-yl)thieno[3,2-b]pyridin-7-yloxy)phenylcarbamothioyl)-2-phenylacetamide | $^1$H NMR (400 MHz, DMSO-d6) δ (ppm): 8.46 (d, J=5.9 Hz, 1H), 8.04 (m, 1H), 7.59 (s, 1H), 7.51 (m, 2H), 7.3-7.2 (m, 6H), 7.01 (s, 1H) 6.58 (d, J=5.9 Hz, 1H), 6.53 (m, 1H), 6.10 (m, 1H), 3.87 (s, 3H), 3.81 (s, 2H). |
| 47e | 53 | furan-3-yl | N-(3-Fluoro-4-(2-(furan-3-yl)thieno[3,2-b]pyridin-7-yloxy)-phenylcarbamothioyl)-2-phenylacetamide | 1H NMR (DMSO) δ (ppm): 12.49 (s, 1H), 11.84 (s, 1H), 8.49 (d, J=5.5 Hz, 1H), 8.36 (s, 1H), 8.00 (d, J=11.3 Hz, 1H), 7.85-7.83 (m, 1H), 7.82 (s, 1H), 7.52-7.51 (m, 2H), 7.34-7.33 (m, 4H), 7.28-7.26 (m, 1H), 7.09 (brs, 1H), 6.62 (d, J=5.3 Hz, 1H), 3.82 (s, 2H), MS (m/z) 504.0 (M + H) |
| 47f | 54 | 4-methylthiophen-3-yl | 1-(3-Fluoro-4-(2-(4-methylthiophen-3-yl)thieno[3,2-b]pyridin-7-yloxy)-phenyl)-3-(2-phenylacetyl)thiourea | $^1$H NMR (DMSO) δ (ppm): 12.49 (s, 1H), 11.84 (s, 1H), 8.52 (d, J=5.5 Hz, 1H), 8.01 (d, J=5.6 Hz, 1H), 7.94 (d, J=2.7 Hz, 1H), 7.70 (s, 1H), 7.54-7.52 (m, 2H), 7.41-7.40 (m, 1H), 7.35-7.34 (m, 3H), 7.33 (s, 1H), 7.27 (m, 1H), 6.64 (dd, J=4.7 Hz, 1H), 3.82 (s, 2H), 2.43 (s, 3H), MS (m/z) 534.0 (M + H). |

Scheme 10

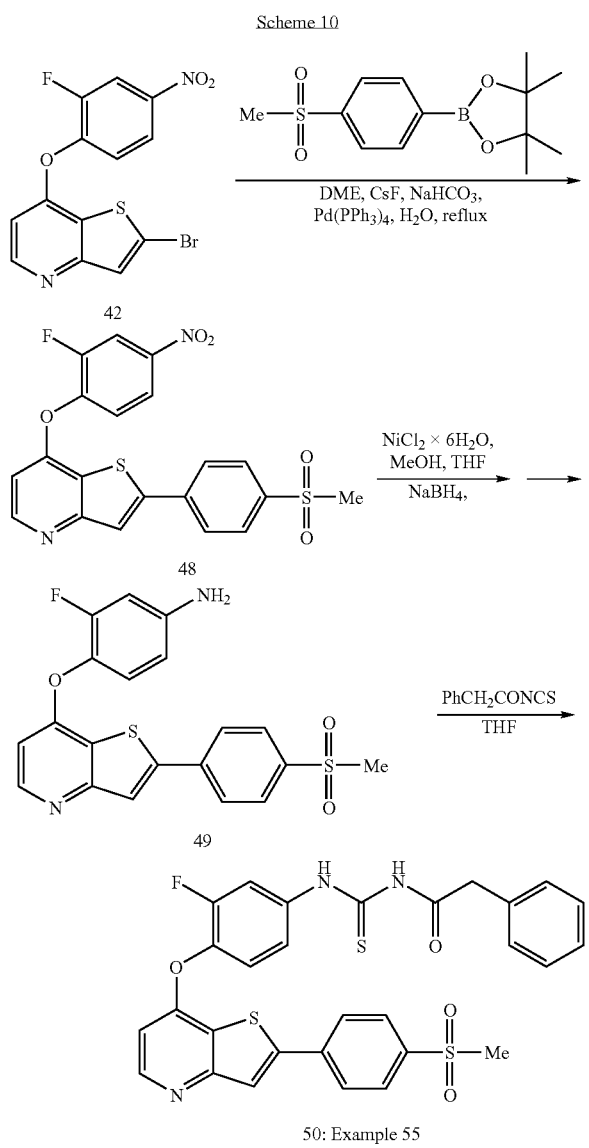

50: Example 55

Example 55

N-(3-Fluoro-4-(2-(4-(methylsulfonyl)phenyl)thieno[3,2-b]pyridin-7-yloxy) phenylcarbamothioyl)-2-phenylacetamide (50)

Step 1. 7-(2-Fluoro-4-nitrophenoxy)-2-(4-(methylsulfonyl)phenyl)thieno[3,2-b]pyridine (48)

To a solution of 42 (461 mg, 1.3 mmol, scheme 8) in DME (4 mL) was added 4,4,5,5-tetramethyl-2-(4-(methylsulfonyl)phenyl)-1,3,2-dioxaborolane (500 mg, 2.5 mmol), CsF (391 mg, 3.8 mmol), Pd(PPh$_3$)$_4$ (72 mg, 63 μmol) and NaHCO$_3$ (315 mg, 3.8 mmol) pre-dissolved in H$_2$O (1 ml). The reaction mixture was purged with nitrogen and refluxed for 2 hours. The DME was removed under reduced pressure and the aqueous layer was extracted with EtOAc. The extract was dried over sodium sulphate, filtered and evaporated to form a residue which was purified by column chromatography (eluent EtOAc/hexane, 1:1) to afford the title compound 48 (97 mg, 18% yield) as a white solid. $^1$HNMR (DMSO) δ (ppm): 8.63 (d, J=1.2 Hz, 1H), 8.49 (d-d, J=2.7 Hz, 1H), 8.33 (s, 1H), 8.22-8.19 (m, 2H), 8.16 (s, 2H), 8.02 (d, J=8.6 Hz, 2H), 7.75 (t, J=8.0 Hz, 1H), 7.77-7.58 (m, 2H), 7.58-7.50 (m, 2H), 6.97 (d, J=5.5 Hz, 1H), 3.33 (s, 3H), MS (m/z): 444.8 (M+H).

Step 2. 3-Fluoro-4-(2-(4-(methylsulfonyl)phenyl)thieno[3,2-b]pyridin-7-yloxy)benzenamine (49)

Nitro compound 48 (97 mg, 2 mmol) was dissolved in a mixture of THF (7 mL) and MeOH (15 mL); NiCl$_2$.×6H$_2$O (130 mg, 0.5 mmol) was added and the solution was cooled to 0° C. To the cooled mixture NaBH$_4$ (42 mg, 1.1 mmol) was added portion wise. The reaction was stirred for 20 min and quenched with 2 M HCl. The solvents were removed under reduced pressure and the residue was treated with concentrated ammonium hydroxide solution (pH 10) and extracted with EtOAc. The organic extract was dried over anhydrous sodium sulfate, filtered and evaporated. The residue was purified by column chromatography (eluent EtOAc) to afford the title compound 49 (46.7 mg, 51% yield) as a white solid. $^1$H NMR (DMSO) δ (ppm): 8.52 (d, J=5.5 Hz, 1H), 8.25 (s, 1H), 8.15 (d, J=8.4 Hz, 2H), 8.03 (d, J=8.4 Hz, 2H), 7.63-7.58 (m, 2H), 7.56-7.52 (m, 2H), 7.13 (t, J=8.6 Hz, 1H), 6.61 (d, J=2.2 Hz, 1H), 6.56 (dd, J=10 Hz, 1H), 6.46 (dd, J=5.7 Hz, 1H), 5.57 (s, 2H), 3.29 (s, 3H), MS (m/z): 414.8 (M+H).

Step 3. N-(3-Fluoro-4-(2-(4-(methylsulfonyl)phenyl)thieno[3,2-b]pyridin-7-yloxy)phenylcarbamothioyl)-2-phenylacetamide (50)

To a solution of 49 (46.7 mg, 0.1 mmol) in dry THF (5 mL), 2-phenylacetyl isothiocyanate (40 mg, 0.2 mmol) was added and the reaction was allowed to stir for 30 minutes. The THF was removed under reduced pressure and the resultant product was purified by column chromatography on silica gel, eluent hexane/EtOAc (1:1), to afford the title compound 50 (35.4 mg, 53% yield). $^1$HNMR (DMSO) δ (ppm): 12.49 (s, 1H), 1 1.85 (s, 1H), 8.57 (d, J=5.5 Hz, 1H), 8.30 (s, 1H), 8.17 (d, J=8.4Hz, 2H), 8.02 (d, J=8.4 Hz, 2H), 7.63-7.52 (m, 5H), 7.34 (d, J=4.1 Hz, 2H), 6.71 (d, J=5.3 Hz, 1H), 3.82 (brs, 2H), 3.27 9s, 3H) MS (m/z) 592.0 (M$^+$).

Scheme 11

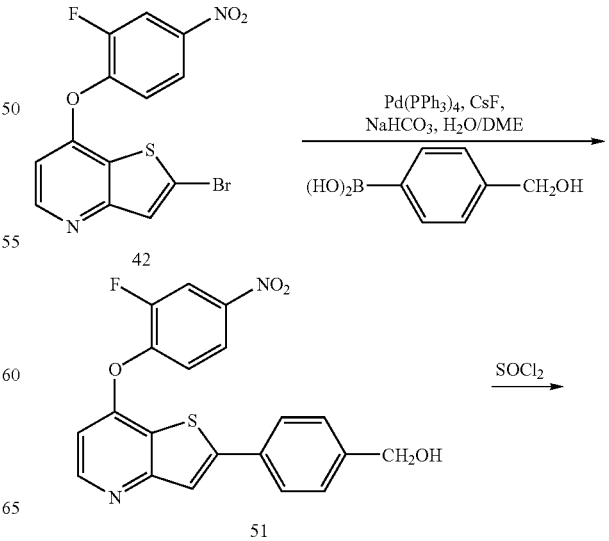

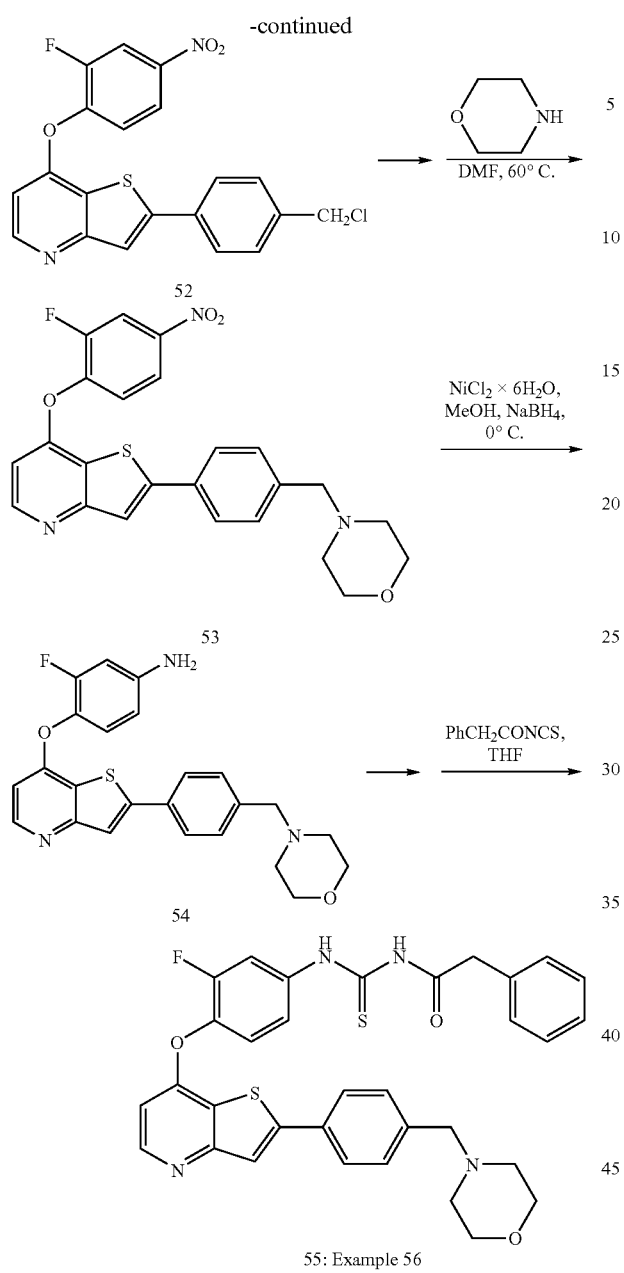

washed with water, dried over anhydrous sodium sulfate, filtered and evaporated. The resultant solid residue was triturated with Et₂O to afford the title compound 51 as a white solid (880 mg, 82% yield). MS (m/z): 397.1 (M+H).

Step 2. 2-(4-(Chloromethyl)phenyl)-7-(2-fluoro-4-nitrophenoxy)thieno[3,2-b]pyridine (52)

The alcohol 51 (880 mg, 2.22 mmol) was suspended in SOCl₂ (10 ml) and the reaction mixture was refluxed for 1 hour, cooled and carefully poured onto ice/water. A precipitate was formed which was collected by filtration, washed with additional cold water and dried under vacuum to afford the title compound 52 (919 mg, 100% yield), which was used without additional purification. MS (m/z): 415.1(100%) (M+H), 417.1 (36%) (M+H).

Step 3. 7-(2-Fluoro-4-nitrophenoxy)-2-(4-(morpholinomethyl)phenyl)thieno[3,2-b]pyridine (53)

To a suspension of 52 (823 mg, 1.82 mmol) in DMF (10 ml) was added morpholine (317 mg, 3.65 mmol) and the reaction mixture was heated for 4 hours at 60° C., the solvent was removed under reduced pressure and the residual solid was triturated with EtOAc and collected by filtration. It was further washed with EtOAc until no color was observed in the filtrate, to form the title compound 53 (800 mg, 94% yield), which was used without additional purification. ¹HNMR (DMSO) δ (ppm): 8.57 (d, J=4.7 Hz, 1H), 8.46 (dd, J=2.7 and 10.4 Hz, 1H), 8.18 (m, 1H), 8.07 (s, 1H), 7.83 (d, J=12.2 Hz, 1H), 7.71 (t, J=8.02 Hz, 1H), 7.42 (d, J=8.2 Hz, 1H), 6.91 (d, J=5.3 Hz, 1H), 3.56 (m, 4H), 3.51 (m, 2H), 3.33 (m, 2H), 2.50 (m, 2H).

Step 4. 1-(3-Fluoro-4-(2-(4-(morpholinomethyl)phenyl)thieno[3,2-b]pyridin-7-yloxy)phenyl)-3-(2-phenylacetyl)thiourea (55)

To a solution of 53 (1.1 g, 2.37 mmol) in MeOH (20 mL) and THF (20 mL) at 0° C. was added NiCl₂×6H₂O (1.12 g, 4.73 mmol) and NaBH₄ (350 mg, 9.48 mmol). The reaction mixture was allowed to stir for 1 hr, solvents were removed under reduced pressure and the resultant solid residue was dissolved in 1 M HCl. This solution was made basic with concentrated aqueous ammonium hydroxide and extracted with EtOAc. The organic phase was collected, dried over anhydrous sodium sulfate and filtered. The filtrate was evaporated under reduced pressure and the resultant solid was triturated with Et₂O to afford the amine 54 as a white solid (1.02 g, 100% yield), which was used in the next step without further purification.

To a suspension of the amine 54 (1.02 g, 2.34 mmol) in THF (10 mL) was added 2-phenylacetyl isothiocyanate (622 mg, 3.52 mmol) and the reaction mixture was stirred for 1 hr at room temperature, concentrated under reduced pressure and purified by column chromatograpy (eluent EtOAc: MeOH, 95:5) to afford title compound 55 as a yellow powder (288 mg, 12% yield). ¹H NMR (400 MHz, DMSO-d₆) δ (ppm): 12.48 (s, 1H), 11.84 (s, 1H), 8.63 (m, 1H), 8.18 (s, 1H), 8.01 (d, J=7.8 Hz, 2H), 7.75 (m, 2H), 7.57 (s, 2H), 7.33 (m, 4H), 6.80 (d, J=11.7 Hz, 2H), 3.83 (s, 5H), 3.37 (d, J=11.7 Hz, 2H), 3.12 (m, 2H). MS (m/z) 613.3 (M+H).

Example 56

1-(3-Fluoro-4-(2-(4-(morpholinomethyl)phenyl)thieno[3,2-b]pyridin-7-yloxy)phenyl)-3-(2-phenylacetyl)thiourea (55)

Step 1. (4-(7-(2-Fluoro-4-nitrophenoxy)thieno[3,2-b]pyridin-2-yl)phenyl)methanol (51)

To a solution of 42 (1.0 g, 2.71 mmol) in dry DME (20 ml) was added 4-(hydroxymethyl)phenylboronic acid (823 mg, 5.4 mmol), NaHCO₃ (682 mg, 8.13 mmol), CsF (820 mg, 5.4 mmol) and water (10 mL) and the reaction mixture was refluxed under nitrogen for 2 hrs. After cooling to room temperature the DME was removed under reduced pressure, the residue was dissolved in EtOAc and the organic solution was

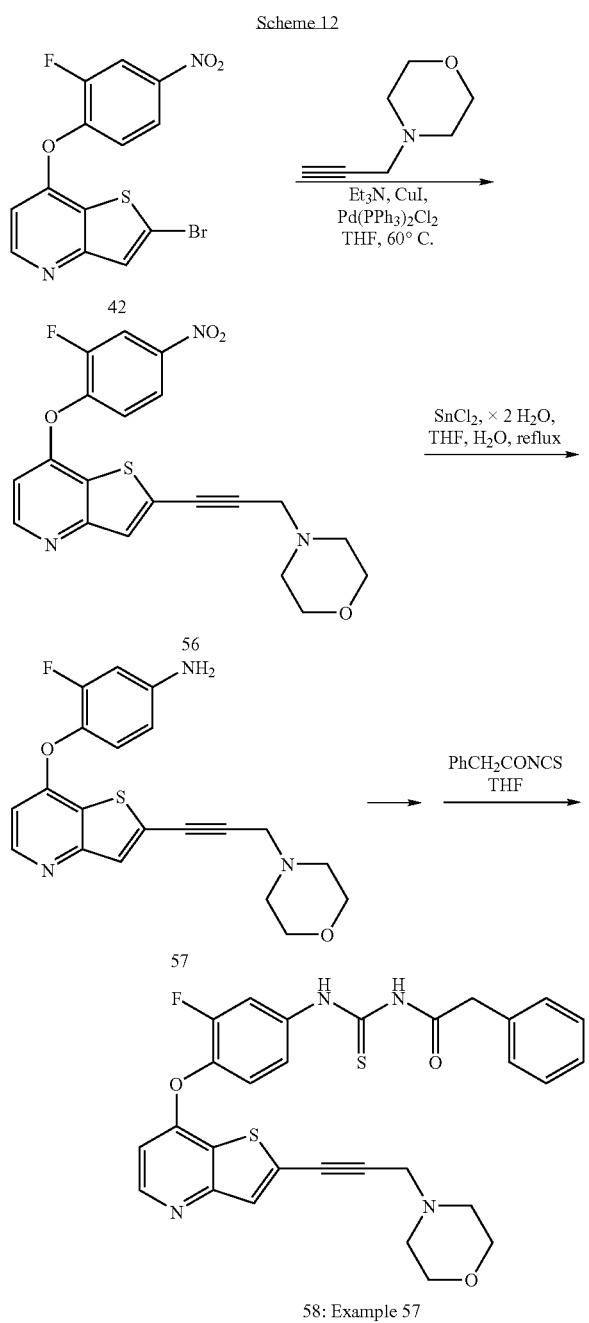

mmol) and Pd(PPh$_3$)$_2$Cl$_2$ (5.3 mg, 7.56 μmol). The reaction mixture was degassed with nitrogen and refluxed for 2 hrs, cooled to room temperature and adsorbed onto silica. Purification by column chromatography (eluent EtOAc) afforded the title compound 56 as a beige solid (88 mg, 79%). MS (m/z): 397.1 (M+H).

Steps 2-3. 1-(3-Fluoro-4-(2-(3-morpholinoprop-1-ynyl)thieno[3,2-b]pyridin-7-yloxy)phenyl)-3-(2-phenylacetyl)thiourea (58)

To a solution of the nitro compound 56 (300 mg, 0.724 mmol) in THF (10 mL) and NH$_4$Cl (6 mL) was added SnCl$_2$× 2H$_2$O (489 mg, 2.17 mmol) and the reaction mixture was refluxed for 3 hrs. After cooling the mixture was diluted with EtOAc and washed with concentrated aqueous ammonium hydroxide. EtOAc phase was separated and the aqueous phase was extracted with DCM. Both EtOAc phase and DCM extract were combined, dried over anhydrous sodium sulfate and filtered. The filtrate was evaporated to dryness to afford the amine 57 (277 mg, 100% yield), which was used without further purification.

To a solution of the amine 57 (270 mg, 0.74 mmol) in THF (10 mL) was added 2-phenylacetyl isothiocyanate (188 mg, 1.06 mmol) and the reaction mixture was stirred for 1 hr, concentrated under reduced pressure and purified by column chromatography (eluent EtOAc) to afford title compound 58 (37 mg, 10% yield) as a white solid. $^1$H NMR (400 MHz, DMSO-d$_6$) δ (ppm): 12.47 (s, 1H), 11.82 (s, 1H), 8.55 (d, J=5.3 Hz, 1H), 8.01 (d, J=13.2 Hz, 1H), 7.79 (s, 1H), 7.52 (s, 1H), 7.33 (m, 4H), 7.28 (m, 1H), 6.72 (d, J=5.3 Hz, 1H), 3.82 (s, 2H), 3.64 (s, 2H), 3.61 (m, 5H), 2.51 (m, 4H). MS (m/z): 561.3 (M+H).

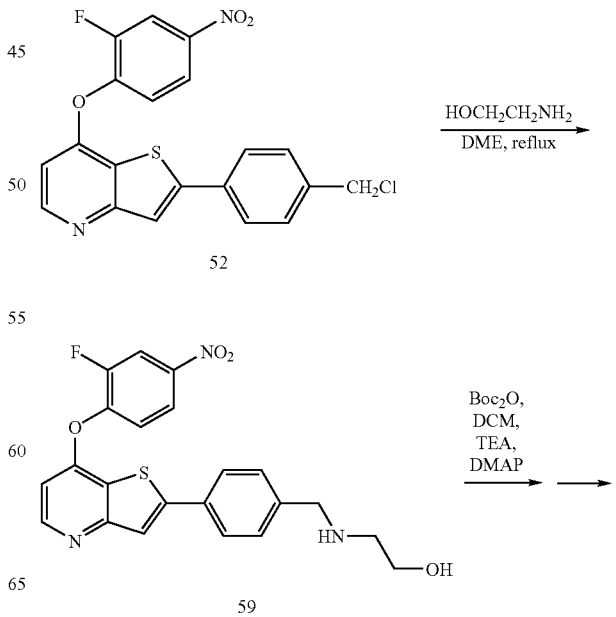

Example 57

1-(3-Fluoro-4-(2-(3-morpholinoprop-1-ynyl)thieno [3,2-b]pyridin-7-yloxy)phenyl)-3-(2-phenylacetyl) thiourea (58)

Step 1. 7-(2-Fluoro-4-nitrophenoxy)-2-(3-morpholinoprop-1-ynyl)thieno[3,2-b]pyridine (56)

To a solution of bromide 42 (100 mg, 0.27 mmol) in THF (5 ml) was added 4-(prop-2-ynyl)morpholine (68 mg, 0.54 mmol) [H-W. Tsou, et. al. *J. Med. Chem.*, 2001, 44, 2719-2734], triethylamine (68 mg, 0.67 mmol), CuI (5 mg, 0.03

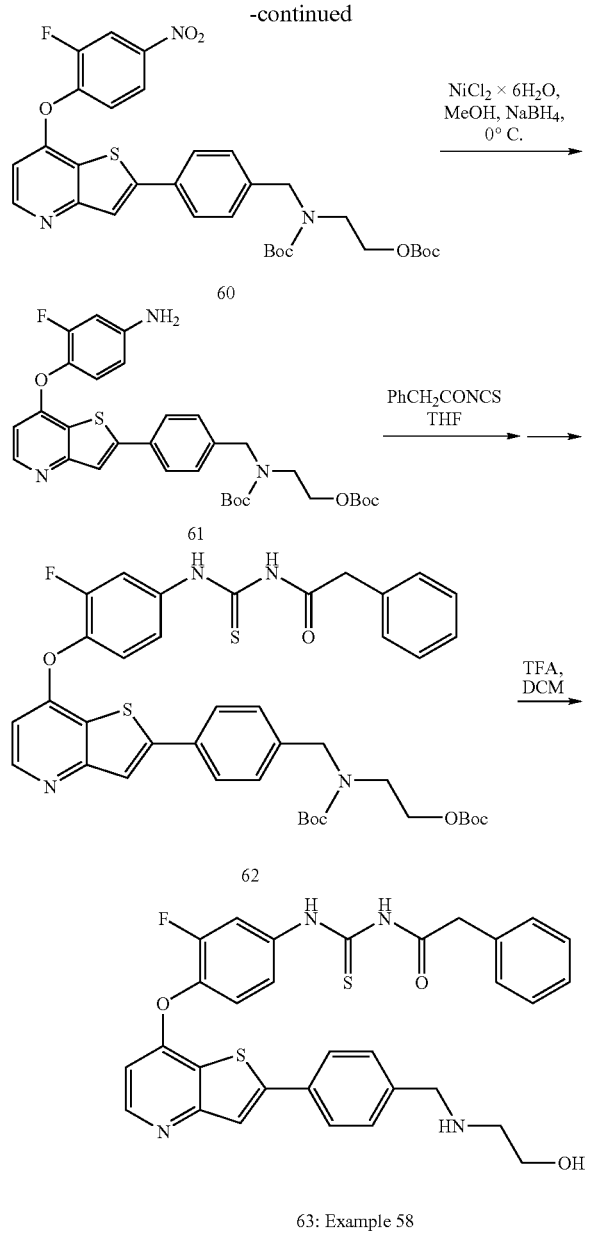

10.4 Hz, 1H), 8.21 (m, 1H), 8.17 (s, 1H), 7.83 (d, J=8.0 Hz, 1H), 7.71 (t, J=8.6 Hz, 1H), 7.44 (d, J=8.0 Hz, 1H), 6.91 (d, J=5.5 Hz, 1H), 4.48 (t, J=5.5 Hz, 1H), 3.75 (s, 2H), 3.45 (q, J=5.6 Hz, 2H), 3.33 (m, 1H), 3.15 (d, J=5.1 Hz, 2H), 2.56 (t, J=5.7 Hz, 2H).

Step 2. Carbonic acid 2-(tert-butoxycarbonyl-{4-[7-(2-fluoro-4-nitro-phenoxy)-thieno[3,2-b]pyridin-2-yl]-benzyl}-amino)-ethyl ester tert-butyl ester (60)

To a solution of 59 (200 mg, 0.45 mmol) in DCM (7 mL) at room temperature was added triethylamine (188 mg, 1.82 mmol), DMAP (cat) and $Boc_2O$ (355 mg, 1.82 mmol). The reaction mixture was stirred at room temperature overnight, the DCM was removed under reduced pressure and the residue was dissolved in EtOAc, washed sequentially with dilute HCl solution, saturated $NaHCO_3$ and brine, dried over anhydrous sodium sulfate and filtered. The filtrate was evaporated and the residue was purified by column chromatography (eluent EtOAc:hexane, 3:7) to afford title compound 60 (200 mg, 69% yield) as a yellow oil. $^1H$ NMR (DMSO) δ (ppm): 8.58 (d, J=5.3 Hz, 1H), 8.47 (dd, J=2.7 and 10.3 Hz, 1H), 8.21 (m, 1H), 8.09 (s, 1H), 7.87 (m, 2H), 7.72 (t, J=8.4 Hz, 1H), 7.33 (d, J=8.2 Hz, 2H), 6.91 (d, J=5.3 Hz, 1H), 4.44 (s, 2H), 4.07 (t, J=5.5 Hz, 2H), 3.40 (m, 2H), 1.36 (m, 18H).

Steps 3-4. Carbonic acid 2-[tert-butoxycarbonyl-(4-{7-[2-fluoro-4-(3-phenylacetyl-thioureido)-phenoxy]-thieno[3,2-b]pyridin-2-yl}-benzyl)-amino]-ethyl ester tert-butyl ester (62)

To a solution of 60 (500 mg, 1.1 mmol) in MeOH (10 mL) at 0° C. was added $NiCl_2 \times 6H_2O$ (148 mg, 0.63 mmol) and $NaBH_4$ (46 mg, 1.24 mmol). The reaction mixture was allowed to stir for 1 hr, concentrated to dryness and the resultant solid was dissolved in 1 M HCl. The acidic solution was then made basic with concentrated ammonium hydroxide solution and extracted with EtOAc. The organic phase was collected, dried over anhydrous sodium sulfate and filtered. The filtrate was evaporated under reduced pressure and the resultant solid was triturated with $Et_2O$ to afford the crude amine 61 as a white solid (190 mg, 100% yield), which was used for the next step without characterization and additional purification.

To a suspension of the amine 61 (190 g, 0.31 mmol) in THF (7 mL) was added 2-phenylacetyl isothiocyanate (118 mg, 0.62 mmol) and the reaction mixture was stirred for 1 hr at room temperature, concentrated under reduced pressure and purified by column chromatography (eluent EtOAc-MeOH, 6:4) to afford title compound 62 as a yellow powder (190 mg, 77% yield). $^1H$ NMR (400 MHz, DMSO-$d_6$) δ (ppm): 12.48 (s, 1H), 11.83 (s, 1H), 8.51 (s, 1H), 8.04 (s, 1H), 8.01 (d, J=11.7 Hz, 1H), 7.86 (d, J=7.7 Hz, 2H), 7.52 (m, 2H), 7.34 (m, 6H), 7.32 (m, 1H), 6.64 (d, J=5.5 Hz, 1H), 4.43 (s, 2H), 4.07 (t, J=5.3 Hz, 2H), 3.81 (s, 2H), 3.44 (m, 2H), 1.37 (m, 18H).

Step 5. 1-(3-Fluoro-4-(2-(4-((2-hydroxyethylamino) methyl)phenyl)thieno[3,2-b]pyridin-7-yloxy)phenyl)-3-(2-phenylacetyl)thiourea (63)

To a solution of 62 in DCM (190 mg, 0.24 mmol) was added TFA (excess) at room temperature and the reaction mixture was stirred for 3 hrs, evaporated under reduced pressure and the residual solid was triturated with $Et_2O$ to afford the title compound 63 as the di-TFA salt (100 mg, 51% yield). $^1H$ NMR (400 MHz, DMSO-$d_6$) δ (ppm): 12.49 (s, 1H), 11.84

Example 58

2-((4-(7-(2-Fluoro-4-nitrophenoxy)thieno[3,2-b]pyridin-2-yl)phenyl)methylamino) ethanol (63)

Step 1. 2-{4-[7-(2-Fluoro-4-nitro-phenoxy)-thieno[3,2-b]pyridin-2-yl]-benzylamino}-ethanol (59)

To a suspension of the chloride 52 (500 mg, 1.1 mmol) in DME (10 mL) was added ethanolamine (336 mg, 5.5 mmol). The reaction mixture refluxed for 2 hrs, the solvent was removed under reduced pressure; the residue was dissolved in EtOAc and washed with water. The organic phase was collected, dried over sodium sulfate, filtered and evaporated. The remaining solid was triturated with $Et_2O$ to afford the title compound 59 as a yellow solid (200 mg, 41% yield). $^1H$ NMR (DMSO) δ (ppm): 8.57 (d, J=5.5 Hz, 1H), 8.47 (dd, J=2.7 and (s, 1H), 8.89 (s, 1H), 8.53 (d, J=5.1 Hz, 1H), 8.14 (s, 1H), 8.01 (m, 1H), 7.62 (dd, J=2.5 and 7.7 Hz, 2H), 7.54 (d, J=2.7 Hz, 2H), 7.33 (m, 4H), 7.28 (m, 1H), 6.67 (d, J=5.5 Hz, 1H), 4.64 (m, 1H), 4.30 (m, 1H), 4.22 (t, J=5.3 Hz, 2H), 3.82 (s, 2H), 3.63 (t, J=5.3 Hz, 2H), 2.98 (m, 1H). MS (m/z) 587.0 (M+H).

Scheme 14

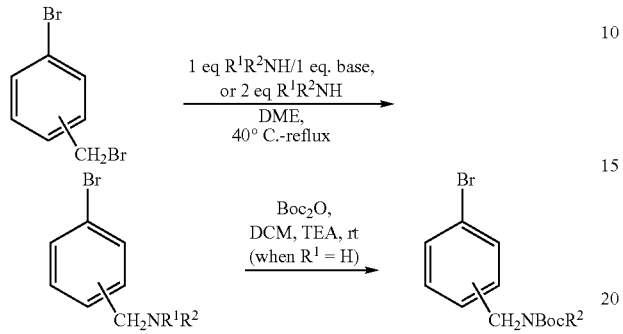

Substituted aryl bromides (compounds 64–71)
N-(3-Bromobenzyl)-2-methoxyethanamine (64)

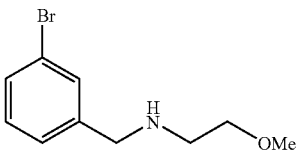

64

To a solution of 2-methoxyethanamine (900 mg, 12 mmol) in DME (15 mL) was added 3-bromobenzylbromide (2.5 g, 10 mmol) and the reaction mixutre was stirred at 40° C. (scheme 14). After 30 minutes, Et$_3$N (1.01 g, 10 mmol) was added and the reaction was allowed to stir for another 10 minutes, filtered and the filtrate was concentrated to afford bromide 64 as a colorless oil (2.0 g, 80% yield). MS (m/z): 244.1/246.1 (M+H). tert-Butyl 3-bromobenzyl(2-methoxyethyl)carbamate (65)

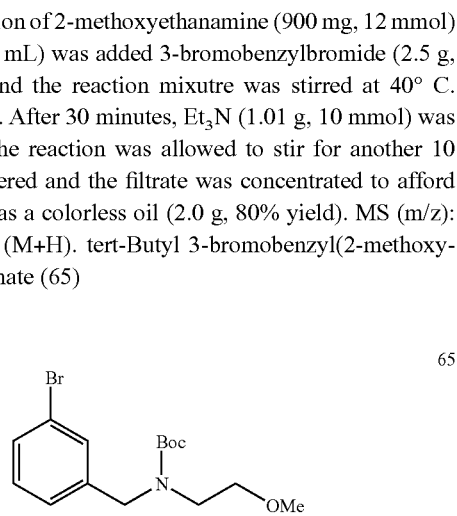

65

To a solution of compound 64 (997 mg, 4 mmol) in CH$_2$Cl$_2$ (12 mL), di-tert-butylcarbonate (1.8 g, 8 mmol) was added and the reaction mixture was stirred for 3 hrs (scheme 14). DMAP (cat.) was added to the solution and the reaction mixture was allowed to stir for additional 76 hours. Solvent was removed under reduced pressure and the crude product was purified by column chromatography, eluent EtOAc/hexane (1:10) to afford the title compound 65 (778 mg, 56% yield) as a colorless oil. MS (m/z): 368.1/370.1 (M+Na).

TABLE 8

Aryl bromides 66-70 prepared according to the scheme 14

| Cpd | Aryl bromide | Chemical name | Characterization MS (m/z) | Amine reagent used to obtain the aryl bromides |
|---|---|---|---|---|
| 66 | [structure: 3-Br-C6H4-CH2-N(Boc)-CH2CH2-morpholine] | tert-Butyl 3-bromobenzyl(2-morpholinoethyl)carbamate | 399.1/401.1 (M + H) | [structure: morpholine-CH2CH2-NH2] |
| 67 | [structure: 4-Br-C6H4-CH2-N(Boc)-CH2CH2-OMe] | tert-Butyl 4-bromobenzyl(2-methoxyethyl)carbamate | 344.1/346.1 (M + H) | H$_2$N-CH2CH2-OMe |
| 68 | [structure: 2-Br-C6H4-CH2-N(Boc)-CH2CH2-OMe] | tert-Butyl 2-bromobenzyl(2-methoxyethyl)carbamate | 365.9/367.9 (M + Na) | H$_2$N-CH2CH2-OMe |

TABLE 8-continued

Aryl bromides 66-70 prepared according to the scheme 14

| Cpd | Aryl bromide | Chemical name | Characterization MS (m/z) | Amine reagent used to obtain the aryl bromides |
|---|---|---|---|---|
| 69 | 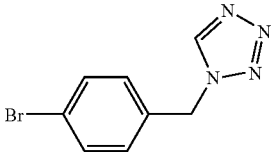 | 1-(4-Bromobenzyl)-1H-tetrazole | 238.9/240.9 (M + H) | 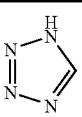 |
| 70 | 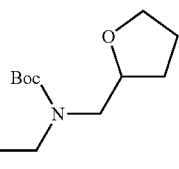 | tert-Butyl 4-bromobenzyl((tetrahydrofuran-2-yl)methyl)carbamate | 370.1/372.1 (M + H) | 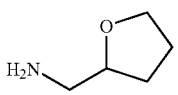 | bis-tert-Butyl 2-(3-bromobenzylamino)ethyl(methyl)carbamate (71)

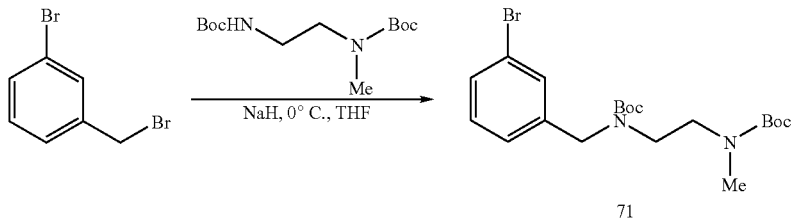

To a solution of tert-butyl 2-tert-butyloxycarbonylaminoethyl(methyl)carbamate (600 mg, 2.2 mmol) in dry THF (5 mL) at 0° C., was added NaH (91 mg, 3.8 mmol) and the reaction was stired for 30 minutes. 3-Bromobenzylbromide was added and the reaction was refluxed for 3 hours, cooled to room temperature and poured into MeOH. Solvents were removed under reduced pressure and the product was partitioned between EtOAc and water. Organic phase was collected and dried over anhydrous sodium sulphate, filtered and evaporated. The crude product was purified by column chromatography on silica gel, eluent EtOAc/hexane (1:5), to afford the title compound 71 (672 mg, 80% yield) as a colourless oil. MS (m/z): 343.0/345.0 (M-Boc).

Scheme 15

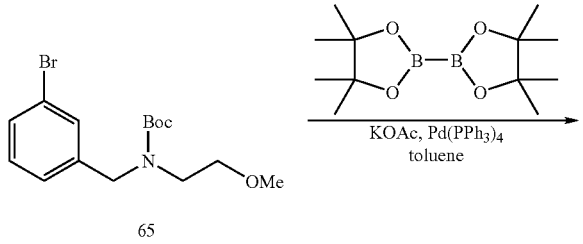

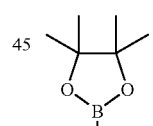

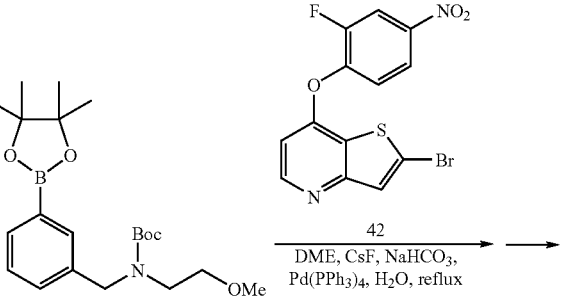

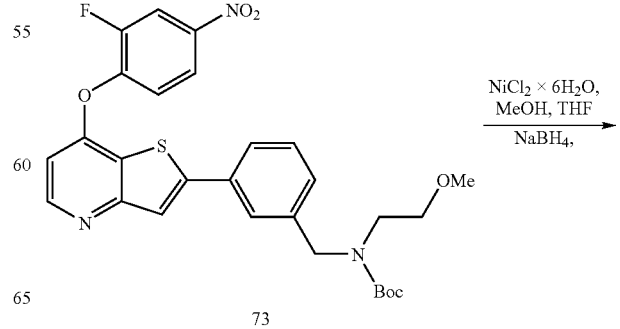

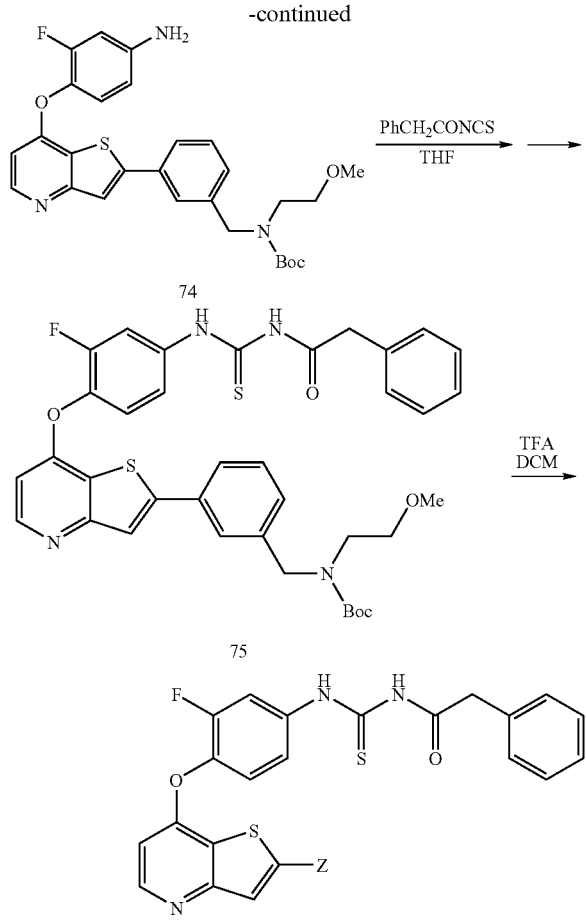

Example 59

N-(3-Fluoro-4-(2-(3-((2-methoxyethylamino)methyl)phenyl)thieno[3,2-b]pyridin-7-yloxy)phenylcarbamothioyl)-2-phenylacetamide (76a)

Step 1. tert-Butyl 2-methoxyethyl(3-(pinacolatoborolan-2-yl)benzyl)carbamate (72)

To a solution of bromide 65 (778 mg, 2.3 mmol), in dry toluene (12 mL), was added the bis(pinacolato)diboron (872 mg, 3.4 mmol), KOAc (677 mg, 6.9 mmol) and Pd(PPh$_3$)$_4$ (80 mg, 69 μmol). The reaction mixture was purged with nitrogen, refluxed for 2 hours and was allowed to cool to room temperature. The solvent was removed under reduced pressure and the residue was partitioned between DCM and water (30 mL/30 mL). The organic phase was collected and dried over anhydrous sodium sulphate, filtered and evaporated. The remained solid was purified by column chromatography, eluent EtOAc/hexane (1:10) to afford title compound 72 (577 mg, 64% yield) as a colorless oil. $^1$H NMR (DMSO) δ (ppm): 7.54-7.52 (m, 2H), 7.33-7.31 (m, 2H), 4.39 (s, 2H), 3.40-3.35 (m, 2H), 3.33-3.25 (m, 2H), 3.20 (s, 3H), 1.43-1.32 (m, 9H), 1.28 (s, 12H).

Step 2. tert-Butyl 3-(7-(2-fluoro-4-nitrophenoxy)thieno{3,2-b}pyridine-2-yl)benzyl(2-methoxyethyl)carbamate (73)

To a solution of the bromo-nitro compound 42 (272 mg, 0.7 mmol) in DME (4 mL), was added pinacolate 72 (578 mg, 1.5 mmol), CsF (226 mg, 2.2 mmol), Pd(PPh$_3$)$_4$ (43 mg, 37 μmol) and NaHCO$_3$ (186 mg, 2.2 mmol) pre-dissolved in water (2 mL). The reaction mixture was purged with nitrogen, refluxed for 1 hour, cooled to room temperature and the solvent was removed under reduced pressure. The residue was extracted with EtOAc, the extract was dried over anhydrous sodium sulfate, filtered and concentrated to produce a brown oil which was purified by chromatography on silica gel, eluent EtOAc, to afford the title compound 73 (347 mg, 85% yield) as a white solid. $^1$H NMR (DMSO) δ (ppm): 8.60 (d, J=5.3 Hz, 1H), 8.47 (d-d, J=7.6 Hz, 1H), 8.19 (d, J=6.5 Hz, 1H), 8.07 (s, 1H), 7.80 (d, J=7.8 Hz, 1H), 7.73-7.69 (m, 2H), 7.48 (t, J=7.8 Hz, 1H), 7.30 (d, J=7.4 Hz, 1H), 6.95 (d, J=5.5 Hz, 1H), 4.48 (s, 2H), 3.21 (s,3H), 2.50 (q, J=2.2 Hz, 4H), 1.44-1.33 (m, 9H), MS (m/z): 554.0 (M+H).

Step 3. tert-Butyl 3-(7-(4-amino-2-fluorophenoxy)thieno[3,2-b]pyridin-2-yl)benzyl(2-methoxyethyl)carbamate (74)

To a solution of 73 (347 mg, 0.6 mmol) in THF (4 mL) and MeOH (2 mL), NiCl$_2$ (372 mg, 1.6 mmol) was added and the solution was cooled to 0° C. NaBH$_4$ (95 mg, 2.5 mmol) was added portion wise. After 20 minutes, the reaction was treated with 2 M HCl and solvents were removed under reduced pressure. The concentrated mixture was basified to pH 10 with ammonium hydroxide solution and the mixture was extracted with EtOAc, the extract was dried over anhydrous sodium sulfate, filtered and evaporated. The residue was purified by silica gel column chromatography, eluent EtOAc, to afford the title compound 74 (235 mg, 72% yield) as a white solid. $^1$H NMR (DMSO) δ (ppm): 8.47 (d, J=5.6 Hz, 1H), 7.97 (s, 1H), 7.77 (d, J=7.2 Hz, 1H), 7.70 (s, 1H), 7.48 (t, J=7.6 Hz, 1H), 6.56-6.51 (m, 2H), 6.44 (dd, J=6.3 Hz, 1H), 5.54 (s, 2H), 4.84 (s, 2H), 3.43 (s, 2H), 3.23 (s, 3H), 2.50 (q, J=2.2 Hz, 4h), 1.46-1.35 (m, 9H).

Step 4. tert-Butyl 3-(7-(2-fluoro-4-(3-(2-phenylacetyl)thioureido)phenoxy)thieno[3,2-b]pyridin-2-yl)benzyl(2-methoxyethyl)carbamate (75)

To a solution of 74 (235 mg, 0.5 mmol) in dry THF (5 mL), 2-phenylacetyl isothiocyanate (159 mg, 0.9 mmol) was added and the reaction was allowed to stir for 30 min. The solvent was removed under reduced pressure and the resulting product was purified by chromatography on silica gel using EtOAc/hexane (1:1) as eluting system to give the desired product (440 mg, 90%) as a white solid. $^1$H NMR (DMSO) δ (ppm): 8.52 (d, J=5.3 Hz, 1H), 8.01 (t, J=6.5 Hz, 2H), 7.79 (d, J=7.4 Hz, 1H), 7.70 (s, 1H), 7.53-7.52 (m, 2H), 7.47 (t, J=7.6 Hz, 1H), 7.34 (d, J=4.5 Hz, 4H), 7.30-7.24 (m, 2H), 6.67 (d, J=5.3 Hz, 1H), 4.49 (s, 2H), 3.83 (s, 2H), 3.42 (s, 2H), 3.22 (s, 3H), 2.50 (q, J=2.2 Hz, 4H), 1.45-1.33 (m, 9H).

Step 5. N-(3-Fluoro-4-(2-(3-((2-methoxyethylamino)methyl)phenyl)thieno[3,2-b]pyridin-7-yloxy)phenylcarbamothioyl)-2-phenylacetamide (76a)

To a solution of 75 (440 mg, 0.6 mmol) in DCM (10 mL), TFA (145 μL, 1.9 mmol) was added and the reaction was stirred for 12 hours, concentrated under reduced pressure, and the residue was purified by silica gel column chromatography, eluent MeOH/EtOAc (1:10), to afford the title compound 76a (227 mg, 63% yield) as a light yellow solid. $^1$H NMR (DMSO) δ (ppm): 8.54 (d, J=5.5 Hz, 1H), 8.07 (s, 1H), 8.02-8.0 (m, 2H), 7.93 (d-t, J=2.0 Hz, 1H), 7.55-7.53 (m, 4H), 7.34-7.32 (m, 4H), 7.29-7.26 (m, 1H), 6.68 (d, J=5.3 Hz, 1H), 4.19 (s, 2H), 3.81 (s, 1H), 3.57 (t, J=4.9 Hz, 2H), 3.33 (s, 2H), 3.29 (s, 3H), 3.08 (t, J=4.9 hz, 2H), 2.84 (q, J=2.2 Hz, 4H).

Examples 60-65

Compounds 76b-g (examples 60-65) were synthesized similarly to the compound 76a (example 59) according to the schemes 14-15, starting from bromides 66-69 and 71. Characterization of 76b-g is provided in Table 8a.

TABLE 8a

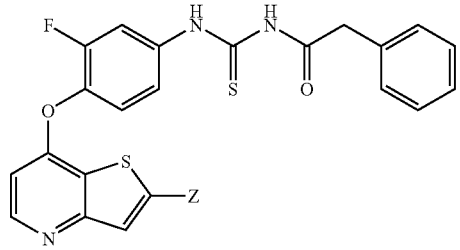

76b-g: Examples 60-65

Characterization of compounds 76b-g (examples 60-65)

| Cpd | Ex | Z | Chemical name | Characterization |
|---|---|---|---|---|
| 76b | 60 | 2-position benzyl with NH-CH2CH2-OMe | 1-(3-Fluoro-4-(2-(2-((2-methoxyethylamino)methyl)phenyl)thieno[3,2-b]pyridin-7-yloxy)phenyl)-3-(2-phenylacetyl)thiourea | $^1$H NMR (400MHz, DMSO-d$_6$) δ ppm): 12.50 (s, 1H), 11.83 (s, 1H), 8.57 (d, J=5.5 Hz, 1H), 8.03-8.00 (m, 1H), 7.76-7.74 (m, 2H), 7.61-7.50 (m, 5H), 7.36-7.25 (m, 5H), 6.70 (d, J=5.3 Hz, 1H), 4.32 (s, 2H), 3.81 (s, 2H), 3.52 (t, J=5.1 Hz, 2H), 3.16 (s, 3H), 3.08 (t, J=4.7 Hz, 2H), MS (m/z): 601.0 (M + H). |
| 76c | 61 | 3-position benzyl with HN-CH2CH2-morpholine | 1-(3-Fluoro-4-(2-(3-((2-morpholinoethylamino)methyl)phenyl)thieno[3,2-b]pyridin-7-yloxy)phenyl)-3-(2-phenylacetyl)thiourea | $^1$H NMR (400 MHz, DMSO-d6) δ (ppm): 12.49 (s, 1H), 11.85 (s, 1H), 8.56 (d, J=5.1 Hz, 1H), 8.09-7.98 (m, 5H), 7.61-7.55 (m, 5H), 7.33 (s, 1H), 7.27 (brs, 2H), 6.70 (d, J=5.1 Hz, 1H), 4.30 (brs, 2H), 3.82 (brs, 2H), 3.73 (brs, 4H), MS (m/z) 656.2 (M + H). |
| 76d | 62 | 4-position benzyl with MeHN-CH2CH2-NH | N-(3-Fluoro-4-(2-(4-((2-(methylamino)ethylamino)methyl)phenyl)thieno[3,2-b]pyridin-7-yloxy)phenylcarbamothioyl)-2-phenylacetamide | 1H NMR (DMSO): 12.49 (s, 1H), 11.84 (s, 1H), 8.51 (d, J=5.5 Hz), 8.04-7.99 (m, 2H), 7.87 (d, J=7.6 Hz, 2H), 7.54-7.53 (m, 2H), 7.34-7.33 (m, 5H), 7.29-7.22 (m, 2H), 6.64 (d, J=5.5 Hz, 1H), 4.42-4.39 (m, 2H), 3.82 (s, 2H), 3.29 (brs, 2H), 3.23 (brs, 3H), 2.78-2.76 (m, 2H), MS: calcd 599.74, found 800.1 (M + H). |

TABLE 8a-continued

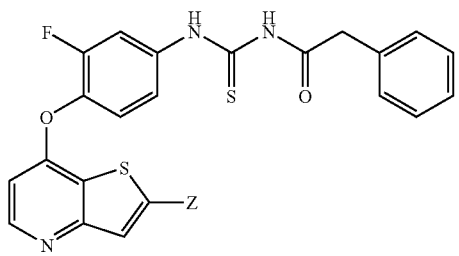

76b-g: Examples 60-65

Characterization of compounds 76b-g (examples 60-65)

| Cpd | Ex | Z | Chemical name | Characterization |
|---|---|---|---|---|
| 76e | 63 | (4-((2-methoxyethylamino)methyl)phenyl) | 1-(3-Fluoro-4-(2-(4-((2-methoxyethylamino)methyl)phenyl)thieno-[3,2-b]pyridin-7-yloxy)phenyl)-3-(2-phenylacetyl)thiourea | $^1$H NMR (400 MHz, DMSO-$d_6$) δ ppm): 12.48 (s, 1H), 11.83 (s, 1H), 9.02 (s, 2H), 8.54 (d, J=5.5 Hz, 1H), 8.13 (s, 1H), 8.02 (d, J=13.3 Hz, 1H), 7.97 (d, J=8.2 Hz, 2H), 7.53 (m, 2H), 7.33 (m, 4H), 7.28 (m, 2H), 6.67 (d, J=5.5 Hz, 1H), 4.22 (m, 2H), 3.83 (s, 2H), 3.59 (t, J=4.9 Hz, 2H), 3.31 (s, 3H), 3.12 (m, 2H), MS (m/z): 601.2 (M + H). |
| 76f | 64 | (3-((2-(methylamino)ethylamino)methyl)phenyl) | 1-(3-Fluoro-4-(2-(3-((2-(methylamino)ethylamino)methyl)phenyl)-thieno[3,2-b]pyridin-7-yloxy)phenyl)-3-(2-phenylacetyl)thiourea | $^1$H NMR (DMSO) δ (ppm): 12.49 (s, 1H), 11.85 (s, 1H), 8.55 (d, J=5.09 Hz, 1H), 8.08 (s, 1H), 8.04 (brs, 1H), 8.00-7.97 (m, 2H), 7.62-7.53 (m, 4H), 7.36-7.32 (m, 4H), 7.29-7.26 (m, 1H), 6.69 (d, J=5.5 Hz, 1H), 4.31 (brs, 2H), 3.82 (s, 2H), 3.31-3.27 (m, 4H), 2.63 (s, 3H), MS (m/z) 600.2 (M + H). |
| 76g | 65 | (4-((1H-Tetrazol-1-yl)methyl)phenyl) | 1-(4-(2-(4-((1H-Tetrazol-1-yl)methyl)phenyl)-thieno[3,2-b]pyridin-7-yloxy)-3-fluorophenyl)-3-(2-phenylacetyl)thiourea | $^1$H NMR (DMSO) δ (ppm): 12.46 (s, 1H), 11.82 (s, 1H), 9.54 (s, 1H), 8.51 (dd, J=1.1 and 5.09 Hz, 1H), 8.1 (s, 1H), 7.96 (d, J=23.3 Hz, 1H), 7.90 (d, J=6.7 Hz, 2H), 7.53 (m, 2H), 7.43 (d, J=8.6 Hz, 2H), 7.32 (m, 4H), 7.26 (m, 1H), 6.65 (d, J=5.5 Hz, 1H), 5.78 (s, 2H), 3.82 (s, 2H). MS (m/z) 596.1 (M + H). |

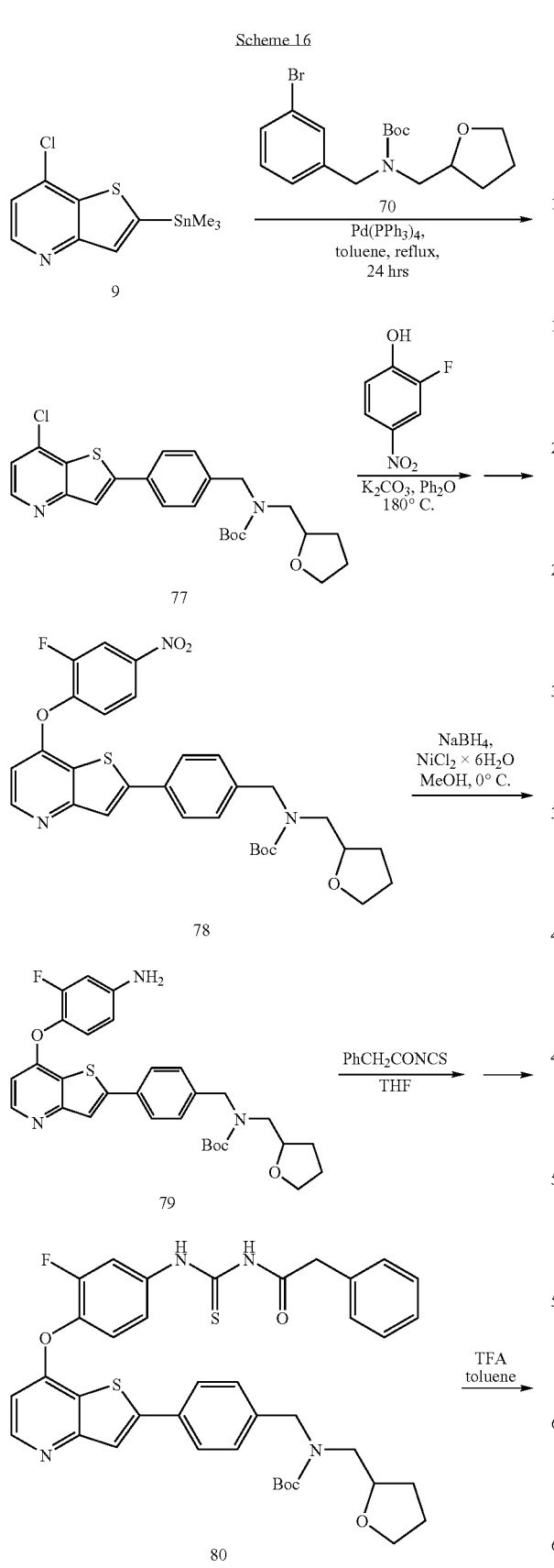
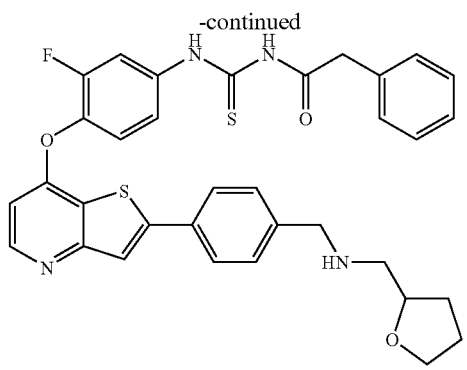

Example 66

1-(3-Fluoro-4-(2-(4-(((tetrahydrofuran-2-yl)methylamino)methyl)phenyl)thieno[3,2-b]pyridin-7-yloxy)phenyl)-3-(2-phenylacetyl)thiourea (81)

Step 1. tert-Butyl(4-(7-chlorothieno[3,2-b]pyridin-2-yl)phenyl)methyl((tetrahydrofuran-2-yl) methyl)carbamate (77)

To a solution of the trimethyltin compound 9 (1.4 g, 3.06 mmol) (scheme 2) and bromide 70 (2.25 g, 6.11 mmol) (scheme 14, Table 8) in dry toluene (50 ml) was added Pd(PPh$_3$)$_4$ (176 mg, 0.153 mmol). The reaction mixture was refluxed overnight, cooled to room temperature and the solvents were removed under reduced pressure. The resultant solid was triturated with hexane/ether and then purified by column chromatography, eluents EtOAc/Hexane 1:9, then EtOAc:hexane 4:6, to afford title compound 77 as a white solid (1.2 g, 86% yield). MS (m/z): 459.2/461.2 (M+H).

Step 2. tert-Butyl (4-(7-(2-fluoro-4-nitrophenoxy)thieno[3,2-b]pyridin-2-yl)phenyl)methyl((tetrahydrofuran-2-yl)methyl)carbamate (78)

To a solution of 77 (1.0 g, 2.18 mmol) in Ph$_2$O (10 ml) was added 2-fluoro-4-nitrophenol (856 mg, 5.45 mmol) and potassium carbonate (904 mg, 6.55 mmol). The reaction mixture was heated at 180° C. for 4 hrs, cooled to room temperature, diluted with DCM, filtered and concentrated. The residue was purified by column chromatography, eluent EtOAc:hexane 8:2, to afford title compound 78 (250 mg, 20% yield). MS (m/z): 580.3 (M+H).

Steps 3-4. tert-Butyl (4-(7-(2-Fluoro-4-(3-(2-phenylacetyl)thioureido)phenoxy)thieno[3,2-b]pyridin-2-yl)phenyl)methyl((tetrahydrofuran-2-yl)methyl)carbamate (80)

To a solution of 78 (250 mg, 0.431 mmol) in MeOH (10 mL) at 0° C. was added NiCl$_2$×6H$_2$O (205 mg, 0.86 mmol) and NaBH$_4$ (64 mg, 1.72 mmol). The reaction mixture was allowed to stir for 1 hr, concentrated to dryness and the resultant solid was dissolved in 2 M HCl. This solution was then made basic with concentrated aqueous ammonium hydroxide and extracted with DCM. The DCM extract was dried over anhydrous sodium sulfate, filtered and evaporated to form the amine 79 (236 mg, 100% yield), which was used without characterization and further purification.

To a solution of the amine 79 (236 mg, 0.43 mmol) in THF (10 mL) was added 2-phenylacetyl isothiocyanate (114 mg, 6.44 mmol). The reaction mixture was stirred for 1 hr, concentrated and the residue was purified by column chromatograpy, eluent—gradient from EtOAc:hexane 1:1 to EtOAc, to afford title compound 80 (200 mg, 64% yield) as a white solid. MS (m/z): 725.5 (M+H).

Step 5.1-(3-Fluoro-4-(2-(4-(((tetrahydrofuran-2-yl) methylamino)methyl)phenyl)thieno[3,2-b]pyridin-7-yloxy)phenyl)-3-(2-phenylacetyl)thiourea (81)

To a solution of 80 (200 mg, 0.28 mmol) in toluene (5 mL), TFA (excess) was added. The reaction mixture was allowed to stir overnight, the solvent was removed under reduced pressure and the remained solid was triturated with diethyl ether to afford title compound 81 as the di-TFA salt (130 mg, 57% yield). $^1$H NMR (DMSO) δ (ppm): 12.47 (s, 1H), 11.83 (s, 1H), 9.06 (s, 2H), 8.53 (dd, J=2.0 and 5.5 Hz, 1H), 8.13 (s, 1H), 8.0 (d, J=12.1 Hz, 1H), 7.97 (d, J=8.7 Hz, 2H), 7.63 (d, J=8.2 Hz, 2H), 7.53 (m, 2H), 7.32 (m, 4H), 7.27 (m, 1H), 6.68 (d, J=5.8 Hz, 1H), 4.23 (m, 1H), 3.82 (s, 2H), 3.78 (m, 1H), 3.71 (m, 1H), 3.11 (m, 1H), 2.95 (m, 1H), 2.0 (m, 1H), 1.98 (m, 2H), 1.56 (m, 1H). MS (m/z) 627.3 (M+H).

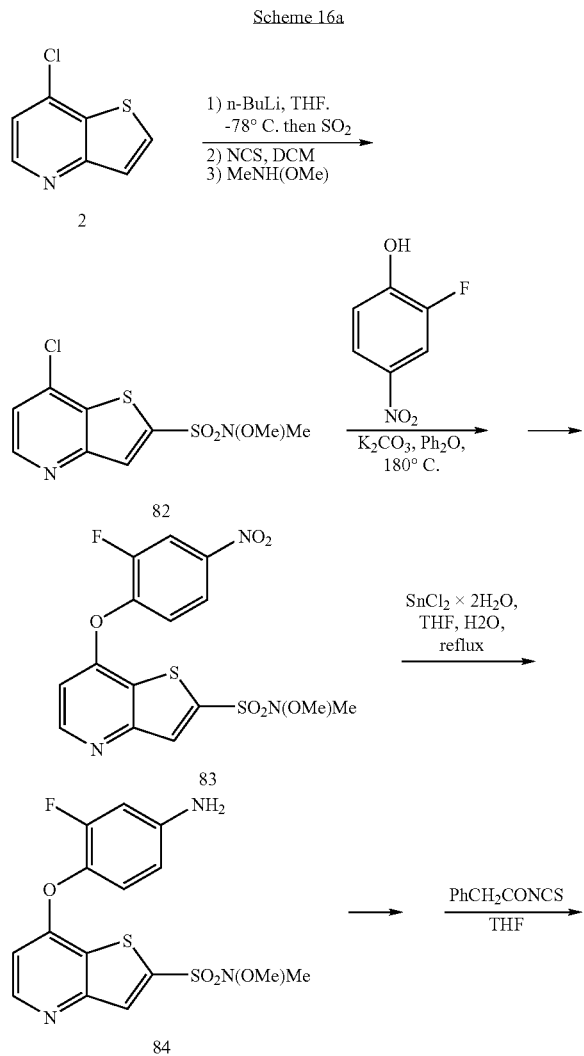

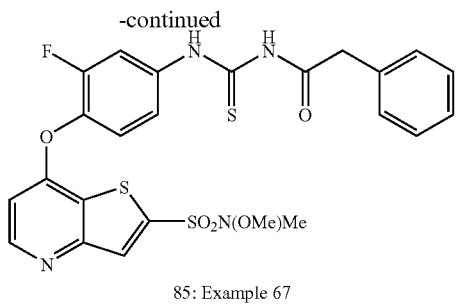

85: Example 67

Example 67

7-[2-Fluoro-4-(3-phenylacetyl-thioureido)-phenoxy]-thieno[3,2-b]pyridine-2-sulfonic acid methoxy-methyl-amide (85)

Step 1. 7-Chloro-N-methoxy-N-methylthieno[3,2-b] pyridine-2-sulfonamide (82)

To a solution of chloride 2 (scheme 1) (700 mg, 4.14 mmol) in THF (20 ml) was added n-BuLi (2 ml, 4.97 mmol, 2.5 M solution in hexanes) at −78° C. and the reaction mixture was stirred for 20 mins. SO$_2$-gas was passed over the surface of the solution for 3 hrs at the same temperature, then for an additional hr at 0° C. The reaction mixture was evaporated. DCM (20 ml) and NCS (605 mg, 4.55 mmol) were added and the reaction mixture was stirred at room temperature for 1.5 hrs, filtered through a celite pad and concentrated to produce a pink solid. The solid was dissolved in acetone (20 ml); MeNH (OMe) hydrochloride (608 mg, 6.21 mmol) and triethylamine (627 mg, 6.21 mmol) were added and the reaction mixture was stirred at room temperature overnight. The solvent was removed under reduced pressure and the residue was dissolved in EtOAc. The EtOAc solution was washed with water, dried over anhydrous sodium sulfate, filtered and evaporated. The residue was purified by column chromatography (eluent EtOAc:hexane, 1:1) to afford the title compound 82 (485 mg, 40% yield) as a pink solid. MS (m/z) 561.1 (M+H).

Step 2. 7-(2-Fluoro-4-nitrophenoxy)-N-methoxy-N-methylthieno[3,2-b]pyridine-2-sulfonamide (83)

A mixture of 82 (400 mg, 1.37 mmol), 2-fluoro-4-nitrophenol (321 mg, 2.05 mmol) and K$_2$CO$_3$ (756 mg, 5.48 mmol) were heated to 190° C. in diphenyl ether (55 ml) for 3 hrs. The mixture was cooled to room temperature, diluted with DCM and filtered. The filtrate was concentrated and purified by column chromatography (eluent EtOAc:hexane, 1:1) to afford title compound 83 (225 mg, 40% yield). MS (m/z) 414.0 (M+H).

Steps 3-4. 7-[2-Fluoro-4-(3-phenylacetyl-thioureido)-phenoxy]-thieno[3,2-b]pyridine-2-sulfonic acid methoxy-methyl-amide (85)

To a solution of the nitro compound 83 (225 mg, 0.54 mmol) in THF (5 ml) and water (2 ml) was added SnCl$_2$× 2H$_2$O (742 mg, 3.3 mmol). The reaction mixture was refluxed for 3 hrs, diluted with EtOAc and washed with aqueous ammonium hydroxide. The washings were combined and extracted with DCM. Both EtOAc- and DCM- phases were combined, dried over anhydrous sodium sulfate, filtered and evaporated to produce the amine 84 (168 mg, 81% yield), which was used without characterization and further purification.

To a solution of the amine 84 (225 mg, 0.59 mmol) in THF (8 ml) was added phenyl-acetyl isothiocyanate (208 mg, 1.18 mmol). The reaction mixture was stirred for 1 hr, concentrated under reduced pressure and purified by column chromatography (eluent EtOAc) to afford 85 (323 mg, 98% yield) as a white solid. $^1$H NMR (400 MHz, DMSO-$d_6$) δ (ppm): 12.52 (s, 1H), 11.86 (s, 1H), 8.74 (d, J=5.3 Hz, 1H), 8.33 (s, 1H), 8.07 (d, J=13.5 Hz, 1H), 7.61 (m, 2H), 7.36 (m, 4H), 7.29 (m, 1H), 3.86 (s, 3H), 3.84 (s, 2H), 2.96 (s, 3H), MS (m/z): 561.3 (M+H).

Example 68

7-[2-Fluoro-4-(3-phenylacetyl-thioureido)-phenoxy]-thieno[3,2-b]pyridine-2-sulfonic acid amide (86)

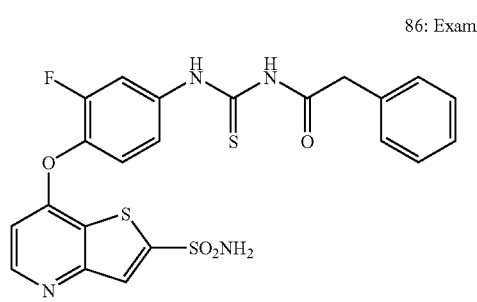

86: Example 68

Title compound 86 was obtained following the procedures described for the compound 85 (example 67, scheme 16) but substituting in the first step O-methyl hydroxylamine for ammonia. $^1$H NMR (400 MHz, DMSO-$d_6$) δ (ppm): 13.82 (s, 1H), 13.15 (s, 1H), 9.98 (m, 1H), 9.4-9.2 (m, 4H), 8.87 (s, 2H), 8.64 (m, 5H), 8.15 (s, 1H), 3.82 (s, 2H). MS (m/z): 517.3 (M+H).

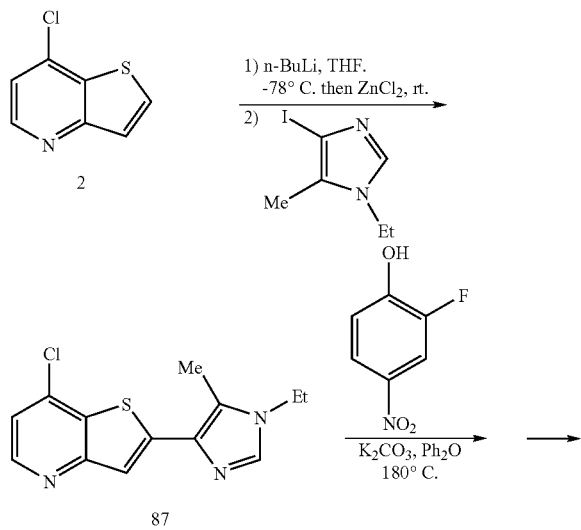

Scheme 17

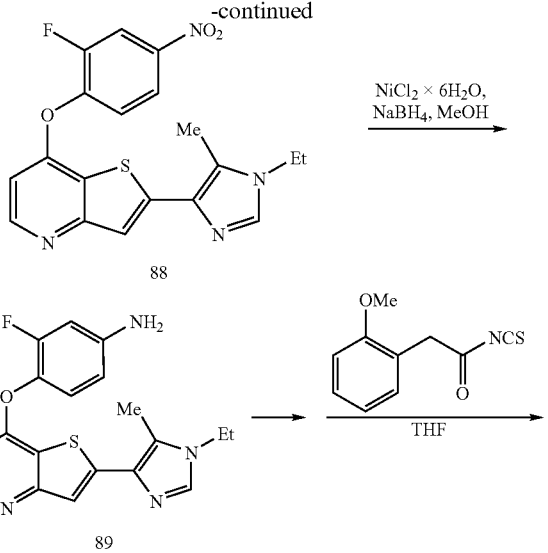

Example 69

1-(4-(2-(1-Ethyl-5-methyl-1H-imidazol-4-yl)thieno[3,2-b]pyridin-7-yloxy)-3-fluorophenyl-3-(2-(2-methoxyphenyl)acetyl)thiourea (90)

Step 1. 7-Chloro-2-(1-ethyl-5-methyl-1H-imidazol-4-yl)-thieno[3,2-b]pyridine (87)

To a solution of 2 (1.14 g, 6.76 mmol) in THF (60 ml) was added, at −78° C., n-BuLi (3.38 ml, 2.5 M soln in hexanes) and the reaction mixture was stirred at the same temperature for 10 min. A solution of ZnCl$_2$ (16.9 ml, 2.5 ml, 0.5M in THF) was added and the reaction mixture was warmed to room temperature. Then a solution of 1-ethyl-4-iodo-5-methyl-1H-imidazole (800 mg, 3.38 mmol) (Pyne, S. G and Cliff, M. D. Synthesis 1994, 681) and Pd(PPh$_3$)$_4$ (390 mg, 0.34 mmol) in THF (15 ml) were added and the reaction mixture was refluxed for 3 hrs, cooled to room temperature, quenched with conc. ammonium hydroxide solution and made neutral with concentrated aqueous HCl. The neutral solution was extracted with EtOAc, the extract was collected, dried over anhydrous sodium sulfate, and filtered. The filtrate was evaporated and the residue was purified by column chromatography (eluent MeOH:EtOAc, 1:9) to afford the title compound 87 (1.1 g, 100% yield) as a brown oil. MS (m/z) 278.0/280.0 (M+H).

Step 2. 2-(1-Ethyl-5-methyl-1H-imidazol-4-yl)-7-(2-fluoro-4-nitro-phenoxy)-thieno[3,2-b]pyridine (88)

A suspension of 87 (650 mg, 2.35 mmol), potassium carbonate (970 mg, 7.04 mmol) and 2-fluoro-4-nitrophenol (738 mg, 4.7 mmol) were heated at 190° C. in diphenyl ether (15 ml) for 3 hrs. The mixture was cooled to room temperature, diluted with DCM and filtered. The filtrate was concentrated and the residue was purified by column chromatography (eluents EtOAc, then MeOH:EtOAc, 1:9) to afford title compound 88 (600 mg, 64%) as a yellow solid. MS (m/z) 399.0 (M+H).

Steps 3-4. 1-(4-(2-(1-Ethyl-5-methyl-1H-imidazol-4-yl)thieno[3,2-b]pyridin-7-yloxy)-3-fluorophenyl)-3-(2-(2-methoxyphenyl)acetyl)thiourea (90)

To a solution of 88 (200 mg, 0.5 mmol) in MeOH (8 ml) and THF (2 ml) at 0° C. was added NiCl$_2$×6H$_2$O (237 mg, 1 mmol) and NaBH$_4$ (74 mg, 2 mmol). The reaction mixture was allowed to stir for 1 hr, concentrated to dryness and the resultant solid was dissolved in 1 M HCl. The acidic solution was then made basic with concentrated aqueous ammonium hydroxide and extracted with EtOAc. The organic phase was collected, dried over anhydrous sodium sulfate and filtered. The solvent was evaporated under reduced pressure and the residue was triturated with EtOAc to afford the crude amine 89 (184 mg, 100% yield) which was used immediately in the next step [without characterization].

To a solution of the amine 89 (180 mg, 0.49 mmol) in THF (10 ml) was added (2-methoxy-phenyl)-acetyl isothiocyanate (200 mg, 0.98 mmol). The reaction mixture was stirred for 10 min, concentrated and the residue was purified by column chromatography (eluents EtOAc, then to MeOH-EtOAc, 1:9), to afford title compound 90 (84 mg, 30% yield) as yellow solid. $^1$H NMR (400 MHz, DMSO-d$_6$) δ (ppm) 12.56 (s, 1H), 11.73 (s, 1H), 8.43 (d, J=5.5 Hz, 1H), 8.04 (d, J=12.3 Hz, 1H), 7.71 (s, 1H), 7.51 (m, 4H), 7.25 (m, 2H), 6.97 (d, J=8.2 Hz, 1H), 6.92 (t, J=7.2 Hz, 1H), 6.97 (d, J=8.2 Hz, 1H), 6.92 (t, J=7.2 Hz, 1H), 6.56 (d, J=5.5 Hz, 1H), 4.0 (q, J=3.2 Hz, 2H), 3.80 (s, 2H), 3.77 (s, 3H), 2.47 (s, 3H), 1.31 (t, J=3.2 Hz, 2H). MS (m/z) 576.1 (M+H).

Scheme 18

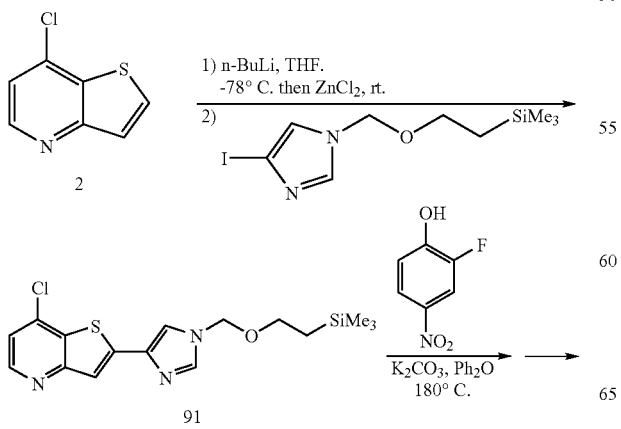
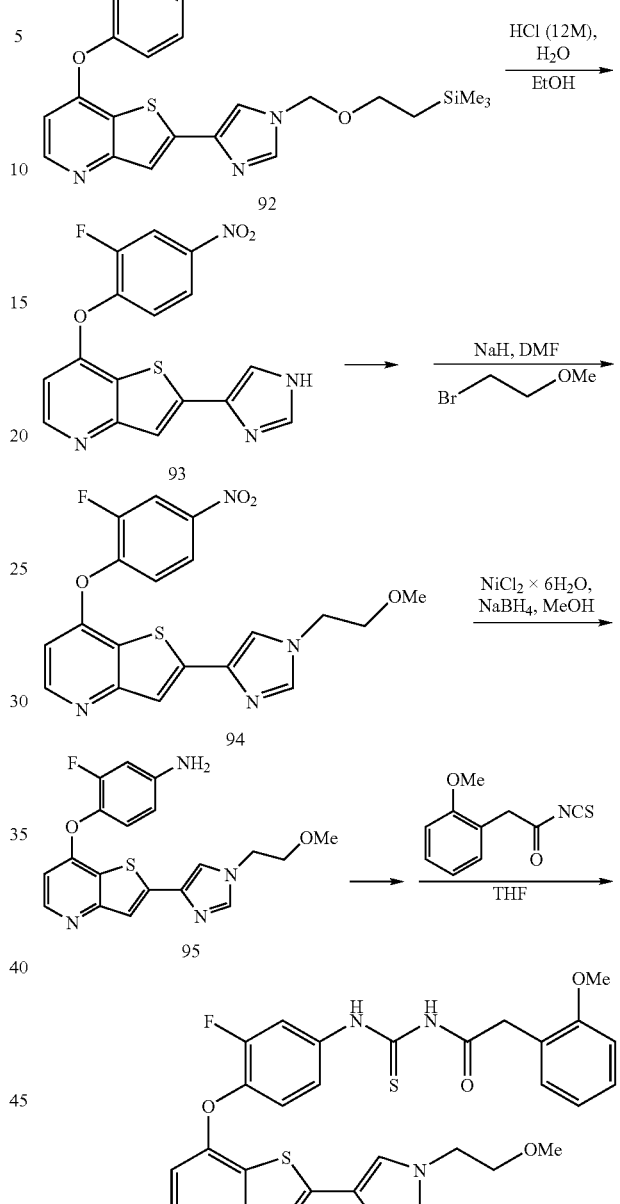

96: Example 70

Example 70

N-(3-Fluoro-4-(2-(1-(2-methoxyethyl)-1H-imidazol-4-yl)thieno[3,2-b]pyridin-7-yloxy)phenylcarbamothioyl)-2-(2-methoxyphenyl)acetamide (96)

Step 1. 7-Chloro-2-(1-((2-(trimethylsilyl)ethoxy)methyl)-1H-imidazol-4-yl)thieno[3,2-b]pyridine (91)

To a solution of 2 (9.4 g, 56.0 mmol) in THF (150 ml) at −78° C. was added n-BuLi (28 ml, 70.0 mmol, 2.5 M soln in hexanes) and the reaction mixture was stirred at −78° C. for 45 mins. A solution of ZnCl$_2$ (140 ml, 70.0 mmol, 0.5M in THF) was added and the reaction mixture was warmed to room temperature. To the warmed mixture a solution of 4-iodo-1-(2-trimethylsilanyl-ethoxymethyl)-1H-imidazole [Carl J. Lovey et al, *Tetrahedron Lett.*, 2004, 45(28), 5529-5532] (9.0 g, 28.0 mmol) and Pd(PPh$_3$)$_4$ (2.5 g, 2.1 mmol) in THF added. The reaction mixture was heated to reflux for 3 hrs, cooled to room temperature, quenched with aqueous ammonium hydroxide and made neutral with aqueous HCl. The neutral solution was extracted with EtOAc, the organic phase was collected, dried over anhydrous sodium sulfate and filtered. The filtrate was evaporated under reduced pressure and the residue was purified by column chromatography (eluent MeOH-EtOAc, 1:20) to afford the title compound 91 (7.5 g, 73% yield) as a brown oil. MS (m/z) 366.0/368.0 (M+H).

Step 2. 7-(2-Fluoro-4-nitrophenoxy)-2-(1-((2-(trimethylsilyl)ethoxy)methyl)-1H-imidazol-4-yl)thieno[3,2-b]pyridine (92)

A suspension of 91 (4.2 g, 11.5 mmol), potassium carbonate (7.95 g, 57.5 mmol) and 2-fluoro-4-nitrophenol (4.97 g, 31.6 mmol) was heated at 190° C. in diphenyl ether (15 ml) for 4.5 hrs, cooled to room temperature, diluted with DCM and filtered. The filtrate was concentrated under reduced pressure and purified by column chromatography (eluents hexane and acetone/hexane, 45:55) to afford title compound 92 (3.4 mg, 61% yield) as a yellow solid MS (m/z) 487.0 (M+H).

Step 3. 7-(2-Fluoro-4-nitrophenoxy)-2-(1H-imidazol-4-yl)thieno[3,2-b]pyridine (93)

To a suspension of 92 (3.3 g, 6.8 mmol) in EtOH (8 ml) was added concentrated HCl (7 ml) and distilled water (4 ml). The mixture was heated at 80-90° C. for 2.5 h, cooled to room temperature and concentrated under reduced pressure. The remaining residue was subjected to azeotropic distillation with EtOH followed by neutralization with saturated aqueous NaHCO$_3$. The solid that precipitated was filtered and washed with water, and the filtrate was extracted with EtOAc. The solid and EtOAc extract were combined, evaporated under reduced pressure and the residue was collected and dried to afford the title compound 93 (2.4 g, 100% yield) as a yellow solid. MS (m/z) 357.0 (M+H).

Step 4. 7-(2-Fluoro-4-nitrophenoxy)-2-(1-(2-methoxyethyl)-1H-imidazol-4-yl)thieno[3,2-b]pyridine (94)

To a solution of 93 (300 mg, 0.84 mmol) in dry DMF (3 ml) at 0° C. was added NaH (40 mg, 60% dispersion in oil, 1.0 mmol). The mixture was allowed to warm to room temperature over 0.5 h then re-cooled to 0° C. Bromoethylmethyl ether (123 mg, 0.88 mmol) was added and mixture was allowed to warm to room temperature over 20 hours, concentrated and partitioned between EtOAc and water. The EtOAc phase was dried over anhydrous Na$_2$SO$_4$, filtered, concentrated and purified by column chromatography (eluents hexane and acetone/hexane 75:25) to afford the title compound 94 (126 mg, 36% yield) as a pale yellow solid. MS (m/z) 415.1.0 (M+H).

Step 5. 3-Fluoro-4-(2-(1-(2-methoxyethyl)-1H-imidazol-4-yl)thieno[3,2-b]pyridin-7-yloxy)benzenamine (95)

Following the procedure described above for compound 89 (scheme 17) but replacing the nitro compound 88 with the nitro compound 94, title compound 95 was obtained as a beige solid (23 mg, 100% yield). MS (m/z) 385.2 (M+H).

Step 6. N-(3-Fluoro-4-(2-(1-(2-methoxyethyl)-1H-imidazol-4-yl)thieno[3,2-b]pyridin-7-yloxy)phenylcarbamothioyl)-2-(2-methoxyphenyl)acetamide (96)

Following the procedure described above for the compound 90 (scheme 17) but replacing the amine 89 with the amine 95 and using 2-(2-methoxyphenyl)acetyl isothiocyanate instead of 2-phenylacetyl isothiocyanate, title compound 96 was obtained as a beige solid (6 mg, 17% yield). $^1$H NMR (400 MHz, DMSO-d$_6$) δ (ppm) 12.57 (1H, s), 11.77 (1H, s), 8.53 (1H, d, J=5.48 Hz), 8.08 (1H, d, J=12.03 Hz), 8.02 (1H, s), 7.91 (1H, s), 7.76 (1H, s), 7.59-7.52 (2H, m), 7.28-7.21 (2H, m), 6.98 (1H, d, J=8.22 Hz), 6.91 (1H, d, J=7.44 Hz), 6.71 (1H, d, J=5.67 Hz), 4.21 (2H, t, J=4.89 Hz), 3.80 (2H, s), 3.77 (3H, s), 3.65 (2H, t, J=4.89 Hz), 3.26 (3H, s). MS (m/z) 592.1 (M+H).

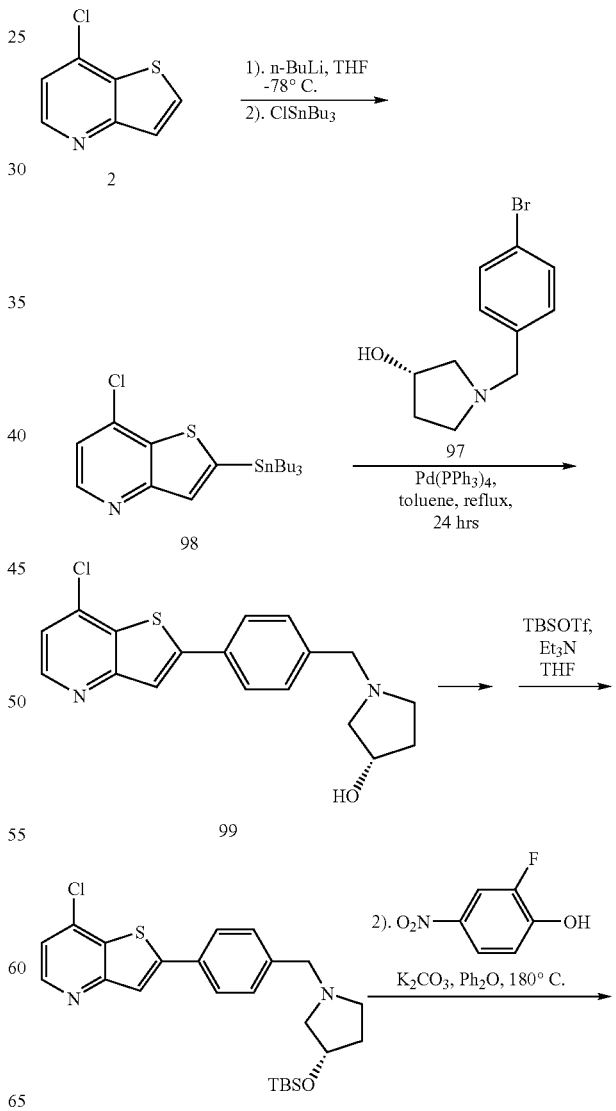

Scheme 19

117

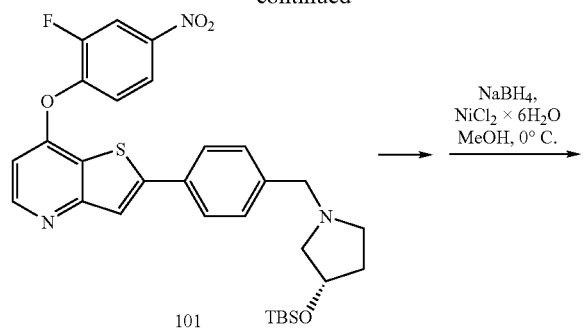

101

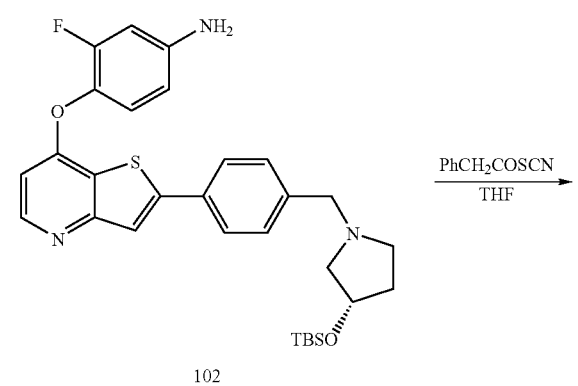

102

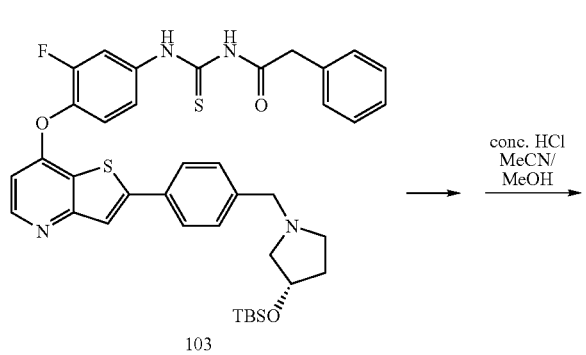

103

104: Example 71

NaBH₄,
NiCl₂ × 6H₂O
MeOH, 0° C.

PhCH₂COSCN
THF conc. HCl
MeCN/
MeOH

118

Example 71

(S)—N-(3-Fluoro-4-(2-(4-(((3-hydroxypyrrolidin-1-yl)methyl)phenyl)thieno[3,2-b]pyridin-7-yloxy)phenylcarbamothioyl)-2-phenylacetamide (104)

Step 1. (S)-1-(4-Bromobenzyl)pyrrolidin-3-ol (97)

Title compound 97 was obtained, according to the scheme 14 by reacting (S)-pyrrolidin-3-ol with 3-bromobenzylbromide, as a white solid (1.3 g 63% yield). LRMS 256.1/258.1 (M+1).

Step 2.
7-Chloro-2-(tributylstannyl)thieno[3,2-b]pyridine (98)

To a solution of the chloride 2 (18.72 g, 110 mmol) in THF (200 mL) at −78° C. n-BuLi (51 mL, 127 mmol) was added and the reaction mixture was stirred for about 30 minutes. The tributylchlorostannane (25.4 mL, 93 mmol) was added and the mixture was stirred at −78° C. for another 60 minutes, quenched with water [at the same temperature] and allowed to warm up to room temperature. The warmed mixture was extracted with EtOAc, the extract was dried over anhydrous sodium sulfate, filtered and evaporated under reduced pressure. The residue was purified by flash chromatography, eluents EtOAc-hexane (15:85), then EtOAc-hexane (25:75) to afford title compound 98 (30.2 g, 77% yield) as a yellow oil. LRMS (M+1) 459.1 (100%).

Step 3. (S)-1-(4-(7-Chlorothieno[3,2-b]pyridin-2-yl)benzyl)pyrrolidin-3-ol (99)

To a solution of 98 (2.44 g, 5.30 mmol) and bromide 97 (1.3 g, 5.07 mmol) in dry toluene (30 mL) was added Pd(PPh₃)₄ (290 mg, 0.25 mmol). The reaction mixture was heated to reflux for 1.5 h, cooled to room temperature and the solvent was removed under reduced pressure. The resultant solid was purified by column chromatography, eluents EtOAc-Hexane (1:1) then MeOH/EtOAc (20:80), to afford title compound 99 (1.24 g, 71% yield) as a white solid. MS (m/z): 345.1/347.1 (M+H).

Step 4. (S)-2-(4-((3-(tert-Butyldimethylsilyloxy)pyrrolidin-1-yl)methyl)phenyl)-7-chlorothieno[3,2-b]pyridine (100)

To a suspension of 99 (0.5 g, 1.45 mmol) in dry THF (7 ml) at 0° C. was added TBDMSOTf (0.5 ml, 2.2 mmol) and the reaction mixture was stirred for 20 min. Et₃N (0.61 ml, 4.4 mmol) was added and mixture was stirred at the same conditions for another hour, quenched by the addition of water (~2 ml) and concentrated to dryness. The remained solid was partitioned between EtOAc and water. Organic phase was collected, washed with brine, dried over anhydrous Na₂SO₄ and concentrated. The residue was purified by column chromatography, eluents EtOAc/hexane (1:1) then MeOH/EtOAc (5:95) to afford title compound 100 (637 mg, 96% yield) as a white solid. MS (m/z): 459.2/461.2 (M+H).

Step 5. (S)-2-(4-((3-(tert-Butyldimethylsilyloxy) pyrrolidin-1-yl)methyl)phenyl)-7-(2-fluoro-4-nitrophenoxy)thieno[3,2-b]pyridine (101)

To a solution of 100 (250.0 mg, 0.54 mmol) in Ph$_2$O (4 ml) was added 2-fluoro-4-nitrophenol (171 mg, 1.1 mmol) and potassium carbonate (304 mg, 2.2 mmol). The reaction mixture was heated to 195° C. for 3 hrs, cooled to room temperature, diluted with DCM, filtered and concentrated. The residue was purified by column chromatography, eluents EtOAc, then MeOH/EtOAc (20-80), to afford title compound 101 (94 mg, 30% yield) as a white solid. MS (m/z): 580.3 (M+H).

Step 6. (S)—N-(4-(2-(4-((3-(tert-Butyldimethylsilyloxy)pyrrolidin-1-yl)methyl)phenyl)thieno[3,2-b]pyridin-7-yloxy)-3-fluorophenylcarbamothioyl)-2-phenylacetamide (103)

To a solution of the nitro compound 101 (90 mg, 0.16 mmol) in MeOH (4 ml) at 0° C. was added NiCl$_2$×6H$_2$O (74 mg, 0.31 mmol) and NaBH$_4$ (23 mg, 0.62 mmol). The reaction mixture was allowed to stir for 1 hr, concentrated to dryness and the resultant solid was dissolved in 2 M HCl. The acidic solution was then made basic with aqueous ammonium hydroxide solution and extracted with EtOAc. The organic extract was dried over anhydrous sodium sulfate, filtered and evaporated to form the amine 102 (80 mg, 95% yiled), which was used without further purification and characterization.

To a solution of the amine 102 (80 mg, 0.15 mmol) in THF (2 mL) was added 2-phenylacetyl isothiocyanate (64 mg, 0.36 mmol).The reaction mixture was stirred for 1 hr, concentrated and the residue was purified by column chromatography, eluents EtOAc:hexane (1:1), then EtOAc, to afford title compound 103 (34 mg, 30% yield) as a white solid. MS (m/z): 727.5 (M+H).

Step 7. (S)—N-(3-fluoro-4-(2-(4-((3-hydroxypyrrolidin-1-yl)methyl)phenyl)thieno[3,2-b]pyridin-7-yloxy)phenylcarbamothioyl)-2-phenylacetamide (104)

To a solution of 103 (34 mg, 0.047 mmol) in CH$_3$CN/MeOH (0.5 mL/2.0 mL), concentrated HCl (8 drops) was added and the reaction was allowed to stir 2 h. The solvents were removed under reduced pressure and the resultant solid was triturated with diethyl ether followed by purification by Gilson HPLC preparative system, column Aquasil C18 (25% MeOH in water to 100% MeOH), to afford title compound 104 (2.5 mg, 9% yield), as a white solid. $^1$H NMR (DMSO) δ (ppm): 11.82 (1H, s), 8.51 (1H, d, J=5.28 Hz), 8.23 (1H, s), 8.02-7.98 (2H, m), 7.82 (2H, d, J=7.83 Hz), 7.52 (2H, br), 7.41 (2H, d, J=7.83 Hz), 7.33-7.25 (5H, m), 6.64 (1H, d, J=5.09 Hz), 4.20 (1H, br), 3.83 (2H, s), 3.38 (2H, s), 2.34-2.32 (2H, m), 2.03-1.96 (2H, m), 1.56 (2H, br). MS (m/z) 613.3 (M+H).

Example 72

(S)-1-(4-(7-(2-Fluoro-4-(3-(2-phenylacetyl)thioureido)phenoxy)thieno[3,2-b]pyridin-2-yl)benzyl)pyrrolidine-2-carboxylic acid (106)

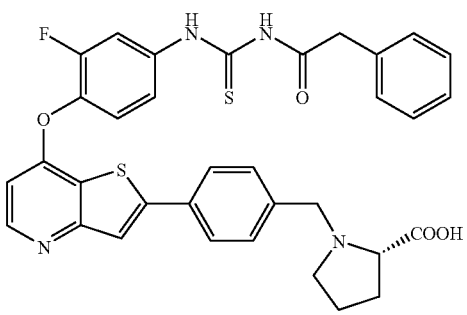

106: Example 72

Step 1. (S)-tert-Butyl1-(4-bromobenzyl)pyrrolidine-2-carboxylate (105)

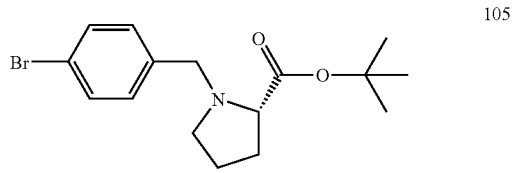

Title compound 105 was obtained, according to the scheme 14 by reacting (S)-tert-butyl pyrrolidine-2-carboxylate with 3-bromobenzylbromide, as a white solid (1.62 g, 94% yield). LRMS 340.1/342.1 (M+1).

(S)-1-(4-(7-(2-Fluoro-4-(3-(2-phenylacetyl)thioureido)phenoxy)thieno[3,2-b]pyridin-2-yl)benzyl)pyrrolidine-2-carboxylic acid (106)

Title compound 106 was obtained following the procedures similar to the ones described above for the synthesis of compound 104 (example 71, scheme 19), replacing bromide 97 with the bromide 105 in the second step, skipping the step 4 (TBS-protection) and using in the last step TFA/DCM mixture for tert-butyl ester de-protection. $^1$H NMR (400 MHz, DMSO-d$_6$): δ12.47 (1H, s), 11.82 (1H, s), 8.53 (1H, br), 8.13 (1H, s), 8.01 (1H, d, J=12.91 Hz), 7.96 (2H, d, J=7.02 Hz), 7.60 (2H, d, J=7.63 Hz), 7.54 (2H, br), 7.34-7.27 (5H, m), 6.67 (1H, d, J=5.09 Hz), 4.40 (1H, br), 4.23 (1H, br), 3.83 (2H, s), 3.38 (2H, s), 2.38 (1H, br), 2.00 (2H, br), 1.85 (1H, br). MS (m/z) 641.3 (M+H).

Examples 73-82 (Compounds 13i-13r)

Following the procedures described above for the synthesis of compound 13a (example 12, scheme 2) but substituting trimethyltin chloride in the step 1 for tributyltin chloride and 2-bromothiazole in the step 2 for heteroaryl bromides shown in the Table 9, title compounds 13i-13r were synthesized. Characterization of compounds 13i-13r (examples 73-82) is provided in the Table 10.

TABLE 9

Heteroaryl bromides used in the synthesis of compounds 13i-13r (examples 73-82)

| Heteroaryl bromide | Preparation |
|---|---|

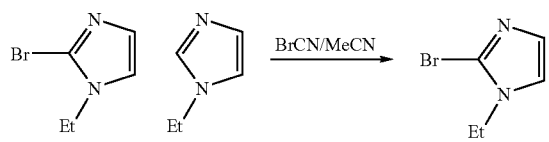

McCullum, P., et al., Aust. J. Chem. 52(3), 1999, 159-166

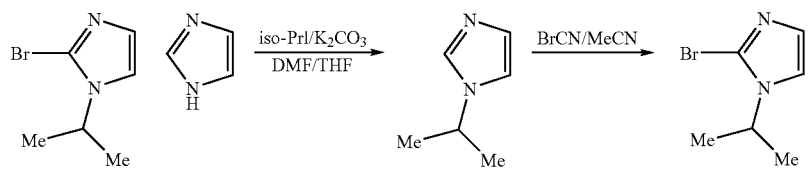

McCullum, P., et al., Aust. J. Chem. 52(3), 1999, 159-166

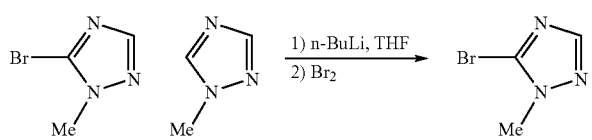

Borai, M. El et al. Pol. J. Chem. 55, 1981, 1659

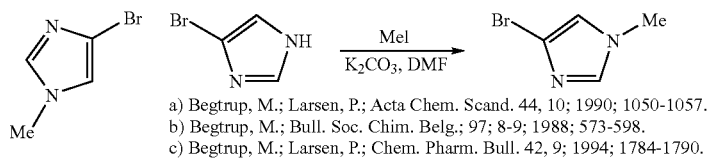

a) Begtrup, M.; Larsen, P.; Acta Chem. Scand. 44, 10; 1990; 1050-1057.
b) Begtrup, M.; Bull. Soc. Chim. Belg.; 97; 8-9; 1988; 573-598.
c) Begtrup, M.; Larsen, P.; Chem. Pharm. Bull. 42, 9; 1994; 1784-1790.

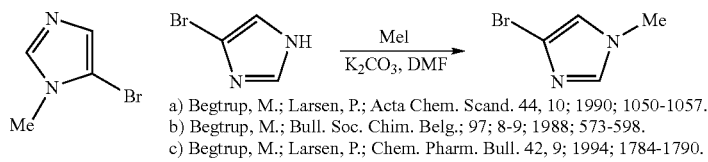

a) Begtrup, M.; Larsen, P.; Acta Chem. Scand. 44, 10; 1990; 1050-1057.
b) Begtrup, M.; Bull. Soc. Chim. Belg.; 97; 8-9; 1988; 573-598.
c) Begtrup, M.; Larsen, P.; Chem. Pharm. Bull. 42, 9; 1994; 1784-1790.

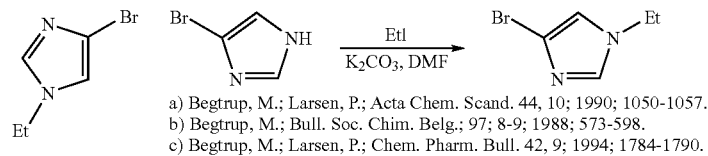

a) Begtrup, M.; Larsen, P.; Acta Chem. Scand. 44, 10; 1990; 1050-1057.
b) Begtrup, M.; Bull. Soc. Chim. Belg.; 97; 8-9; 1988; 573-598.
c) Begtrup, M.; Larsen, P.; Chem. Pharm. Bull. 42, 9; 1994; 1784-1790.

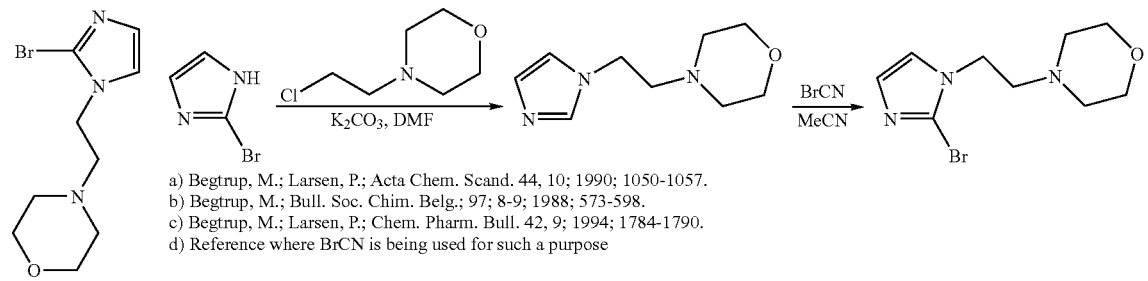

a) Begtrup, M.; Larsen, P.; Acta Chem. Scand. 44, 10; 1990; 1050-1057.
b) Begtrup, M.; Bull. Soc. Chim. Belg.; 97; 8-9; 1988; 573-598.
c) Begtrup, M.; Larsen, P.; Chem. Pharm. Bull. 42, 9; 1994; 1784-1790.
d) Reference where BrCN is being used for such a purpose TABLE 9-continued Heteroaryl bromides used in the synthesis of compounds 13i-13r (examples 73-82)

| Heteroaryl bromide | Preparation |
|---|---|
| (4-bromo-1-(2-morpholinoethyl)-1H-pyrazole) | (from 4-bromo-1H-pyrazole + 4-(2-chloroethyl)morpholine, $K_2CO_3$, DMF)<br>a) Begtrup, M.; Larsen, P.; Acta Chem. Scand. 44, 10; 1990; 1050-1057.<br>b) Begtrup, M.; Bull. Soc. Chim. Belg.; 97; 8-9; 1988; 573-598.<br>c) Begtrup, M.; Larsen, P.; Chem. Pharm. Bull. 42, 9; 1994; 1784-1790. |
| 4-bromo-1-ethyl-1H-pyrazole | (from 4-bromo-1H-pyrazole + EtI, $K_2CO_3$, DMF)<br>a) Begtrup, M.; Larsen, P.; Acta Chem. Scand. 44, 10; 1990; 1050-1057.<br>b) Begtrup, M.; Bull. Soc. Chim. Belg.; 97; 8-9; 1988; 573-598.<br>c) Begtrup, M.; Larsen, P.; Chem. Pharm. Bull. 42, 9; 1994; 1784-1790. |
| 4-bromo-1-methyl-1H-pyrazole | A commercial product |
| 4-chloro-6-morpholinopyrimidine | A commercial product |

TABLE 10

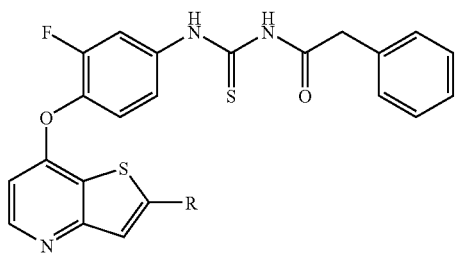

13i–13r: Examples 73–82

Characterization of compounds 13i-13r (examples 73-82)

| Cpd | Ex | R | Name | Characterization |
|---|---|---|---|---|
| 13i | 73 | (1-Ethyl-1H-imidazol-2-yl) | N-(4-(2-(1-Ethyl-1H-imidazol-2-yl)thieno[3,2-b]pyridin-7-yloxy)-3-fluorophenyl-carbamothioyl)-2-phenylacetamide | $^1$H NMR (400 MHz, DMSO-$d_6$) δ ppm 12.48(1H, s), 11.81(1H, s), 8.52(1H, d, J=5.09Hz), 8.02(1H, d, J=12.13Hz), 7.82(1H, s), 7.53-7.46(3H, m), 7.34-7.28(5H, m), 7.06(1H, s), 6.68(1H, d, J=5.48Hz), 4.37(2H, q, J=6.85Hz), 3.83(2H, s), 1.43(3H, t, J=7.24Hz) MS(m/z) 532.3(M+H) |

TABLE 10-continued

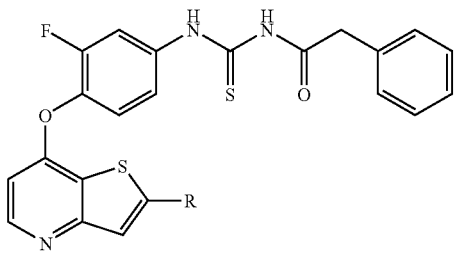

13i–13r: Examples 73–82

Characterization of compounds 13i-13r (examples 73-82)

| Cpd | Ex | R | Name | Characterization |
|---|---|---|---|---|
| 13j | 74 | (imidazole with N-CH(Me)₂ isopropyl) | N-(3-Fluoro-4-(2-(1-isopropyl-1H-imidazol-2-yl)thieno[3,2-b]pyridin-7-yloxy)phenyl-carbamothioyl)-2-phenylacetamide | $^1$H nmr (400 MHz, DMSO-d$_6$) δ ppm 12.48(1H, s), 11.82(1H, s), 8.53(1H, d, J=5.38Hz), 8.02(1H, d, J=12.13Hz), 7.81(1H, s), 7.60(1H, s), 7.53(2H, d, J=5.28Hz), 7.34-7.26(5H, m), 7.09(1H, s), 6.68(1H, d, J=5.28Hz), 4.98(1H, quintet, J=6.46Hz), 3.83(2H, s), 1.49(6H, d, J=6.46Hz) MS(m/z) 546.3(M+H) |
| 13k | 75 | (4-methyl-triazole) | N-(3-Fluoro-4-(2-(4-methyl-4H-1,2,4-triazol-3-yl)thieno[3,2-b]pyridin-7-yloxy)phenyl-carbamothioyl)-2-phenylacetamide | $^1$H nmr (400 MHz, DMSO-d$_6$) δ ppm 12.45(1H, s), 11.78(1H, s), 8.56(1H, d, J=5.28Hz), 8.16(1H, s), 8.02(s, 1H), 7.98(1H, s), 7.52(2H, s), 7.30-7.21(5H, m), 6.72(1H, d, J=5.09), 4.16(3H, s), 3.78(2H, s). MS(m/z) 519.2(M+H) |
| 13l | 76 | (1-methyl-imidazol-4-yl) | N-(3-Fluoro-4-(2-(1-methyl-1H-imidazol-4-yl)thieno[3,2-b]pyridin-7-yloxy)phenyl-carbamothioyl)-2-phenylacetamide | $^1$H nmr (400 MHz, DMSO-d$_6$) δ ppm 44(1H, d, J=5.67Hz), 8.01(1H, d, J=12.13Hz), 7.85(1H, s), 7.71(1H, s), 7.68(1H, s), 7.51-7.50(2H, m), 7.33-7.27(5H, m), 6.57(1H, d, J=5.48Hz), 3.83(2H, s), 3.72(3H, s). MS(m/z) 518.2(M+H) |
| 13m | 77 | (1-ethyl-imidazol-4-yl) | N-(4-(2-(1-Ethyl-1H-imidazol-4-yl)thieno[3,2-b]pyridin-7-yloxy)-3-fluorophenyl-carbamothioyl)-2-phenylacetamide | $^1$H nmr (400 MHz, DMSO-d$_6$) δ ppm 12.50(1H, s), 11.84(1H, s), 8.56(1H, d, J=5.87Hz), 8.14(1H, s), 8.11-8.04(2H, m), 7.78(1H, s), 7.57-7.56(2H, m), 7.35-7.56(5H, m), 6.76(1H, d, J=5.48Hz), 4.10(2H, q, J=7.24Hz), 3.84(2H, s), 1.44(3H, t, J=7.24Hz). MS(m/z) 532.2(M+H) |
| 13n | 78 | (imidazole with morpholinoethyl) | N-(3-Fluoro-4-(2-(1-(2-morpholinoethyl)-1H-imidazol-2-yl)thieno[3,2-b]pyridin-7-yloxy)phenyl-carbamothioyl)-2-phenylacetamide | $^1$H nmr (400 MHz, DMSO-d$_6$) δ ppm 12.49(1H, s), 11.82(1H, s), 8.52(1H, d, J=5.09Hz), 8.02(1H, d, J=11.93Hz), 7.90(1H, s), 7.54-7.48(3H, m), 7.33-7.24(5H, m), 7.06(1H, s), 6.69(1H, d, J=4.90Hz), 4.44(2H, s), 3.83(2H, s), 3.55-3.51(4H, m), 2.71(2H, s), 2.50(2H, s). MS(m/z) 617.3(M+H) |

TABLE 10-continued

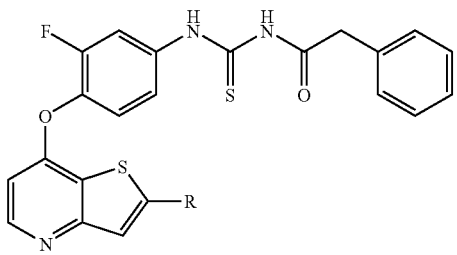

13i–13r: Examples 73–82

Characterization of compounds 13i-13r (examples 73-82)

| Cpd | Ex | R | Name | Characterization |
|---|---|---|---|---|
| 13o | 79 | (1-(2-morpholinoethyl)-1H-pyrazol-4-yl) | N-(3-Fluoro-4-(2-(1-(2-morpholinoethyl)-1H-pyrazol-4-yl)thieno[3,2-b]pyridin-7-yloxy)phenyl-carbamothioyl)-2-phenylacetamide | $^1$H NMR (DMSO) δ (ppm): 12.46(1H, s), 11.81(1H, s), 8.45(1H, d, J=5.48Hz), 8.33(1H, s), 8.01-7.99(2H, m), 7.69(1H, s), 7.51-7.49(2H, m), 7.34-7.24(5H, m), 6.59(1H, d, J=5.48Hz), 4.26(2H, t, J=6.46Hz), 3.82(2H, s), 3.54(4H, t, J=4.40Hz), 2.74(2H, t, J=6.46Hz), 2.42(4H, br). MS(m/z) 617.3 (M+H). |
| 13p | 80 | (1-Ethyl-1H-pyrazol-4-yl) | N-(4-(2-(1-Ethyl-1H-pyrazol-4-yl)thieno[3,2-b]pyridin-7-yloxy)-3-fluorophenyl-carbamothioyl)-2-phenylacetamide | $^1$H NMR (400 MHz, DMSO-d$_6$) δ ppm: 12.49(s, 1H), 11.84(s, 1H), 8.47(d, J=5.6Hz, 1H), 8.36(s, 1H), 8.02-7.99(m, 2H), 7.70(s, 1H), 7.58-7.51(m, 2H), 7.39-7.32(m, 4H), 7.31-7.25(m, 1H), 6.60(d, J=5.6Hz, 1H), 4.18(q, J=7.2Hz, 2H), 3.83(s, 2H), 1.41(t, J=7.2Hz, 3H). |
| 13q | 81 | (1-methyl-1H-pyrazol-4-yl) | N-(3-Fluoro-4-(2-(1-methyl-1H-pyrazol-4-yl)thieno[3,2-b]pyridin-7-yloxy)phenyl-carbamothioyl)-2-phenylacetamide | $^1$H NMR (400 MHz, DMSO-d$_6$) δ ppm: 12.50(s, 1H), 11.85(s, 1H), 8.47(d, J=5.6Hz, 1H), 8.31(s, 1H), 8.02(d, J=12.0Hz, 1H), 7.99(s, 1H), 7.70(s, 1H), 7.55-7.52(m, 2H), 7.38-7.32(m, 4H), 7.31-7.28(m, 1H), 6.60(d, J=5.6Hz, 1H), 3.89(s, 3H), 3.83(s, 2H). |
| 13r | 82 | (6-morpholinopyrimidin-4-yl) | N-(3-Fluoro-4-(2-(6-morpholinopyrimidin-4-yl)thieno[3,2-b]pyridin-7-yloxy)phenyl-carbamothioyl)-2-phenylacetamide | $^1$H NMR (400 MHz, DMSO-d$_6$) δ ppm: 12.48(s, 1H), 11.82(s, 1H), 8.60(s, 1H), 8.56(d, J=5.6Hz, 1H), 8.55(s, 1H), 8.03(d, J=12.0Hz, 1H), 7.66(s, 1H), 7.58-7.52(m, 2H), 7.37-7.31(m, 4H), 7.31-7.24(m, 1H), 6.70(d, J=5.6Hz, 1H), 3.82(s, 2H), 3.78-3.68(m, 8H). |

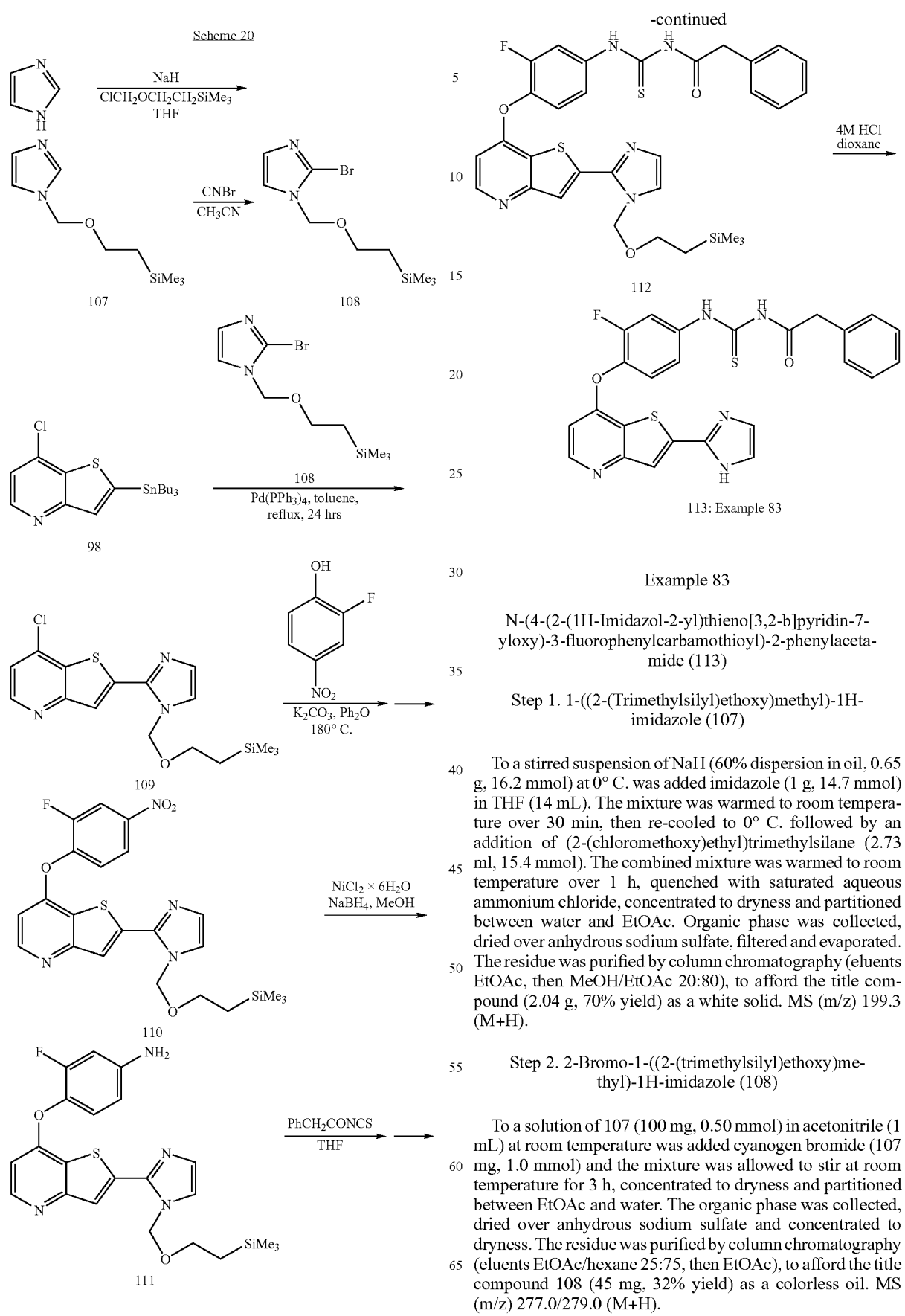

Example 83

N-(4-(2-(1H-Imidazol-2-yl)thieno[3,2-b]pyridin-7-yloxy)-3-fluorophenylcarbamothioyl)-2-phenylacetamide (113)

Step 1. 1-((2-(Trimethylsilyl)ethoxy)methyl)-1H-imidazole (107)

To a stirred suspension of NaH (60% dispersion in oil, 0.65 g, 16.2 mmol) at 0° C. was added imidazole (1 g, 14.7 mmol) in THF (14 mL). The mixture was warmed to room temperature over 30 min, then re-cooled to 0° C. followed by an addition of (2-(chloromethoxy)ethyl)trimethylsilane (2.73 ml, 15.4 mmol). The combined mixture was warmed to room temperature over 1 h, quenched with saturated aqueous ammonium chloride, concentrated to dryness and partitioned between water and EtOAc. Organic phase was collected, dried over anhydrous sodium sulfate, filtered and evaporated. The residue was purified by column chromatography (eluents EtOAc, then MeOH/EtOAc 20:80), to afford the title compound (2.04 g, 70% yield) as a white solid. MS (m/z) 199.3 (M+H).

Step 2. 2-Bromo-1-((2-(trimethylsilyl)ethoxy)methyl)-1H-imidazole (108)

To a solution of 107 (100 mg, 0.50 mmol) in acetonitrile (1 mL) at room temperature was added cyanogen bromide (107 mg, 1.0 mmol) and the mixture was allowed to stir at room temperature for 3 h, concentrated to dryness and partitioned between EtOAc and water. The organic phase was collected, dried over anhydrous sodium sulfate and concentrated to dryness. The residue was purified by column chromatography (eluents EtOAc/hexane 25:75, then EtOAc), to afford the title compound 108 (45 mg, 32% yield) as a colorless oil. MS (m/z) 277.0/279.0 (M+H).

Step 3. 7-Chloro-2-(1-((2-(trimethylsilyl)ethoxy) methyl)-1H-imidazol-2-yl)thieno[3,2-b]pyridine (109)

Starting from the compound 98 (scheme 19) and following the procedure described above for the synthesis of compound 10 (example 12, scheme 2) but substituting 2-bromothiazole in the step 2 for the bromide 108, title compound 109 was obtained as a white solid (22 mg, 41% yield). MS (m/z) 366.1/368.1 (M+H).

Step 4. 7-(2-Fluoro-4-nitrophenoxy)-2-(1-((2-(trimethylsilyl)ethoxy)methyl)-1H-imidazol-2-yl)thieno[3,2-b]pyridine (110)

Following the procedure described above for the synthesis of compound 11 (example 12, step 3, scheme 2) but substituting compound 10 for compound 109, title compound 110 was obtained as a yellow solid (104 mg, 50% yield). MS (m/z) 487.3 (M+H).

Steps 5-6. N-(3-Fluoro-4-(2-(1-((2-(trimethylsilyl)ethoxy)methyl)-1H-imidazol-2-yl)thieno[3,2-b]pyridin-7-yloxy)phenylcarbamothioyl)-2-phenylacetamide (112)

Following the procedure described above for the synthesis of compound 13a (example 12, steps 4-5, scheme 2) but substituting compound 11 for compound 110 and using intermediate amine 111 (instead of amine 12), title compound 112 was obtained as a beige solid (48 mg, 33% yield). MS (m/z) 634.3 (M+H).

Step 7. N-(4-(2-(1H-Imidazol-2-yl)thieno[3,2-b]pyridin-7-yloxy)-3-fluorophenylcarbamothioyl)-2-phenylacetamide (113)

A solution of 112 (21 mg, 0.033 mmol) in 4N HCl in dioxane (3.5 mL) was allowed to stir at 55° C. for 1 h. The mixture was then cooled and solvent was removed under reduced pressure. The resultant gum was triturated with ether several times to form a solid material that was dried under high vacuum to afford the product 113 as a beige solid (5 mg, 28% yield). $^1$H NMR (400 MHz, DMSO-$d_6$) δ ppm 12.50 (1H, s), 11.84 (1H, s), 8.66 (1H, d, J=5.67 Hz), 8.39 (1H, s), 8.06 (1H, d, J=12.72 Hz), 7.68 (2H, s), 7.59-7.58 (2H, m), 7.36-7.30 (5H, m), 6.86 (1H, d, J=5.48 Hz), 3.83 (2H, s). MS (m/z) 504.1 (M+H).

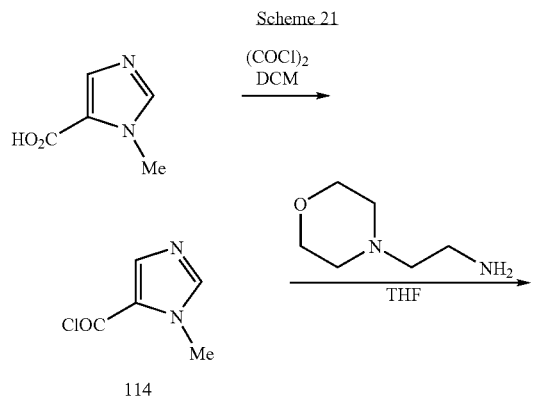

Scheme 21

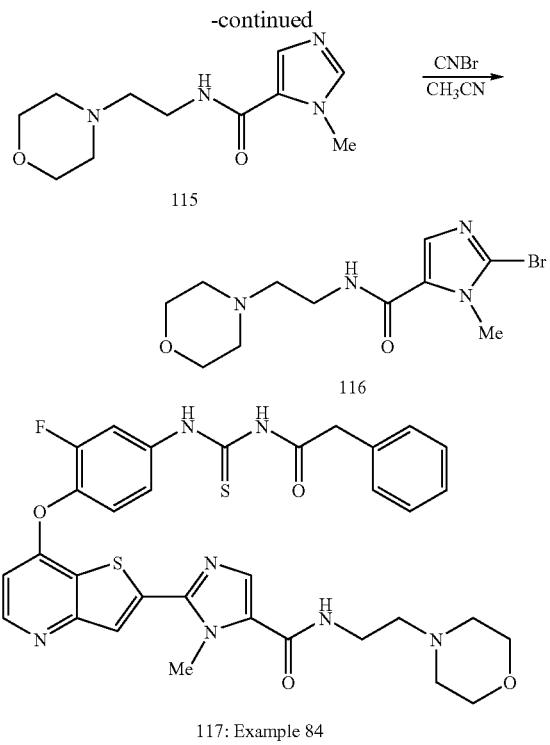

Example 84

2-(7-(2-Fluoro-4-(3-(2-phenylacetyl)thioureido)phenoxy)thieno[3,2-b]pyridin-2-yl)-1-methyl-N-(2-morpholinoethyl)-1H-imidazole-5-carboxamide (117)

Step 1. 1-Methyl-N-(2-morpholinoethyl)-1H-imidazole-5-carboxamide (115)

To a suspension of 1-methyl-1H-imidazole-5-carboxylic acid (0.92 g, 7.3 mmol) [Rapoport, H., et al.; *Synthesis* 1988; 767.1] in dichloromethane (10 ml), was added oxalyl chloride (2.6 ml, 29.2 mmol) and the reaction mixture was heated to reflux for 1 h, cooled, concentrated to dryness to form acid chloride 114 (1.05 g, 100%) which was used without characterization and further purification.

To a suspension of the acid chloride 114 (1.05 g, 7.3 mmol) in THF (10 mL) was added 2-morpholinoethanamine (2.38 g, 18.5 mmol). The mixture was stirred at room temperature for 1 h, concentrated to dryness and the residue was purified by column chromatography (eluent chloroform/MeOH/ammonium hydroxide, 100:2:0.5), to afford the title compound 115 (551 mg, 32% yield) as a white solid. MS (m/z) 239.1 (M+H).

Step 2. 2-Bromo-1-methyl-N-(2-morpholinoethyl)-1H-imidazole-5-carboxamide (116)

To a solution of 115 (550 mg, 2.31 mmol) in acetonitrile (5 mL) was added cyanogen bromide (489 mg, 4.6 mmol). The reaction flask was covered with aluminum foil and the mixture was allowed to stir at room temperature for 18 h. The solvent was removed under reduced pressure and the residue was purified by column chromatography (eluents 100% EtOAc to 30% MeOH/EtOAc), to afford title compound 116 as a beige solid (230 mg, 31%). MS (m/z) 317.1/319.1 (M+H).

Step 3. 2-(7-(2-Fluoro-4-(3-(2-phenylacetyl)thioureido)phenoxy)thieno[3,2-b]pyridin-2-yl)-1-methyl-N-(2-morpholinoethyl)-1H-imidazole-5-carboxamide (117)

Following the procedures described above for the synthesis of compound 13a (example 12, scheme 2) but substituting trimethyltin chloride in the step 1 for tributyltin chloride and 2-bromothiazole in the step 2 for the bromide 116, title compound 117 was synthesized. $^1$H NMR (400 MHz, DMSO-$d_6$) δ ppm 8.55 (1H, d, J=5.28 Hz), 8.47 (1H, br), 8.04 (1H, s), 7.97 (1H, d, J=12.52 Hz), 7.67 (1H, s), 7.49 (2H, br), 7.33-7.32 (4H, m), 7.26 (1H, m), 6.70 (1H, d, J=5.09 Hz), 4.18 (3H, s), 3.84 (2H, s), 3.57 (4H, br), 2.47-2.33 (8H, m). MS (m/z) 674.3 (M+H).

Scheme 22

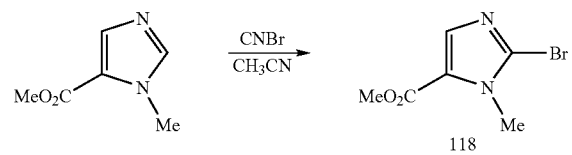

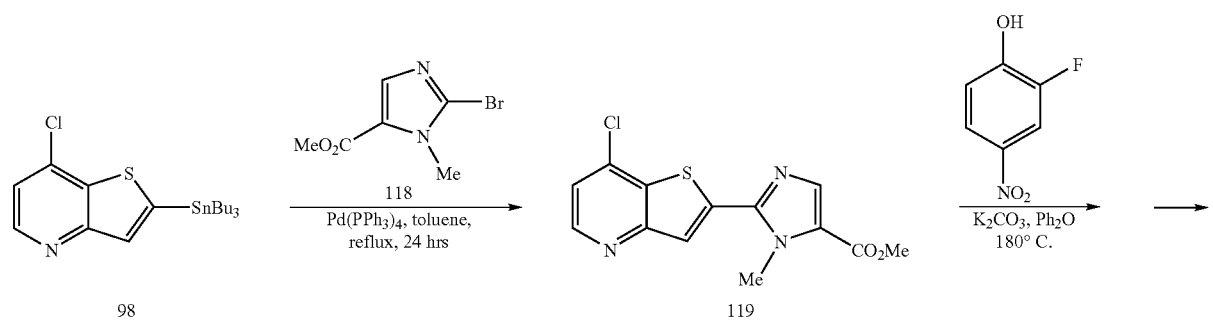

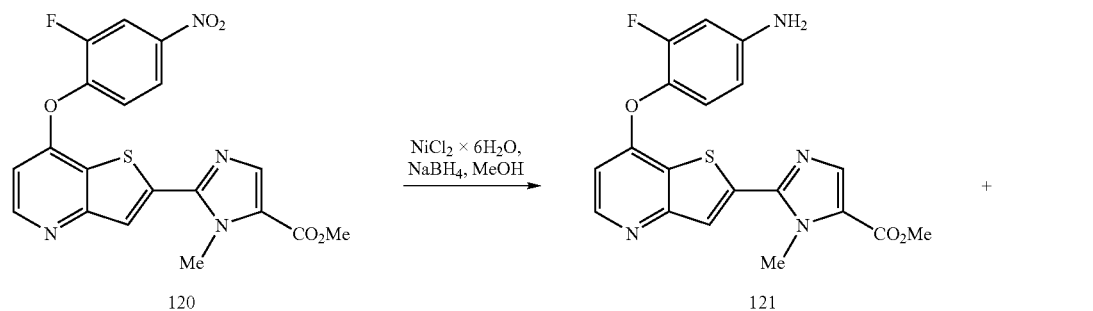

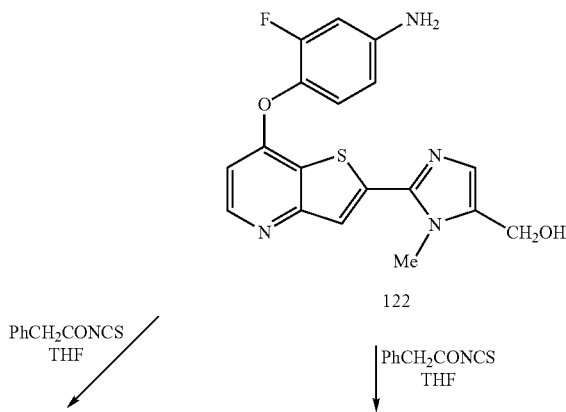

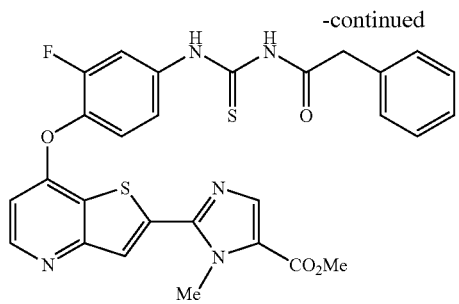

123: Example 85

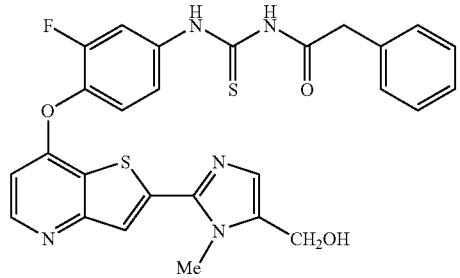

124: Example 86

Examples 85 and 86

Methyl 2-(7-(2-fluoro-4-(3-(2-phenylacetyl)thioureido)phenoxy)thieno[3,2-b]pyridin-2-yl)-1-methyl-1H-imidazole-5-carboxylate (123), and N-(3-Fluoro-4-(2-(5-(hydroxymethyl)-1-methyl-1H-imidazol-2-yl)thieno[3,2-b]pyridin-7-yloxy)phenylcarbamothioyl)-2-phenylacetamide (124)

Step 1. Methyl 2-bromo-1-methyl-1H-imidazole-5-carboxylate (118)

Following the procedure described above for the compound 116 (scheme 21) but replacing compound 115 with methyl 1-methyl-1H-imidazole-5-carboxylate, title compound 118 was obtained as a beige solid (373 mg, 49% yield). MS (m/z) 219.1/221.1 (M+H).

Step 2. Methyl 2-(7-chlorothieno[3,2-b]pyridin-2-yl)-1-methyl-1H-imidazole-5-carboxylate (119)

Starting from the compound 98 (scheme 19) and following the procedure described above for the synthesis of compound 10 (example 12, scheme 2) but substituting 2-bromothiazole in the step 2 for the bromide 118, title compound 119 was obtained as a white solid (580 mg, 100% yield). MS (m/z) 308.1/310.0 (M+H).

Step 3. Methyl 2-(7-(2-fluoro-4-nitrophenoxy)thieno[3,2-b]pyridin-2-yl)-1-methyl-1H-imidazole-5-carboxylate (120)

Following the procedure described above for the synthesis of compound 11 (example 12, step 3, scheme 2) but substituting compound 10 for compound 119, title compound 120 was obtained as a yellow solid (254 mg, 31% yield). MS (m/z) 429.1 (M+H).

Step 4. Methyl 2-(7-(4-amino-2-fluorophenoxy)thieno[3,2-b]pyridin-2-yl)-1-methyl-1H-imidazole-5-carboxylate (121) and (2-(7-(4-amino-2-fluorophenoxy)thieno[3,2-b]pyridin-2-yl)-1-methyl-1H-imidazol-5-yl)methanol (122)

Following the procedure described above for the synthesis of compound 12 (example 12, step 4, scheme 2) but substituting compound 11 for compound 120, title compounds 121 and 122 were obtained as white solids (39 mg, 21% yield and 56 mg, 32% yield). MS (m/z) 399.1 (M+H) and MS (m/z) 371.1 (M+H) respectively.

Step 5. Methyl 2-(7-(2-fluoro-4-(3-(2-phenylacetyl)thioureido)phenoxy)thieno[3,2-b]pyridin-2-yl)-1-methyl-1H-imidazole-5-carboxylate (123)

Following the procedure described above for the synthesis of compound 13a (example 12, step 3, scheme 2) but substituting compound 12 for compound 121, title compound 123 was obtained as a beige solid (35 mg, 63% yield). $^1$H NMR (400 MHz,DMSO-$d_6$) δ ppm 12.48 (1H, s), 11.82 (1H, s), 8.58 (1H, dd, 5.48, 0.98 Hz), 8.13 (1H, d, J=0.98 Hz), 8.03 (1H, d, J=12.52 Hz), 7.81 (1H, d, J=1.17 Hz), 7.55-7.54 (2H, m), 7.36-7.31 (4H, m) 7.27 (1H, m), 6.74 (1H, d, J=5.48 Hz), 4.21 (3H, s), 3.83 (3H, s), 3.83 (2H, s). MS (m/z) 576.2 (M+H).

Step 5a. N-(3-Fluoro-4-(2-(5-(hydroxymethyl)-1-methyl-1H-imidazol-2-yl)thieno[3,2-b]pyridin-7-yloxy)phenylcarbamothioyl)-2-phenylacetamide (124)

Following the procedure described above for the synthesis of compound 13a (example 12, step 3, scheme 2) but substituting compound 12 for compound 122, title compound 124 was obtained as a beige solid (32 mg, 39% yield). $^1$H NMR (400 MHz,DMSO-$d_6$) δ ppm 12.48 (1H, s), 11.82 (1H, s), 8.58 (1H, dd, 5.48, 0.98 Hz), 8.13 (1H, d, J=0.98 Hz), 8.03 (1H, d, J=12.52 Hz), 7.81 (1H, d, J=1.17 Hz), 7.55-7.54 (2H, m), 7.36-7.31 (4H, m), 7.27 (1H, m), 6.74 (1H, d, J=5.48 Hz), 4.21 (3H, s), 3.83 (3H, s), 3.83 (2H, s). MS (m/z) 576.2 (M+H).

Scheme 23

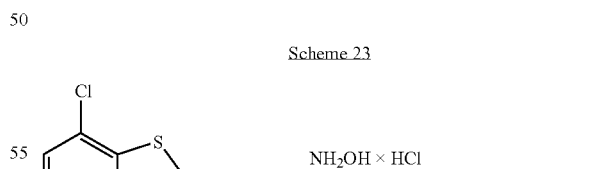

14

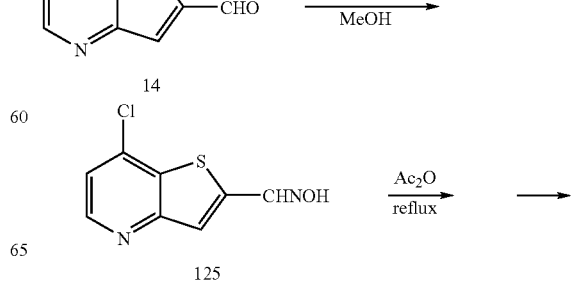

125

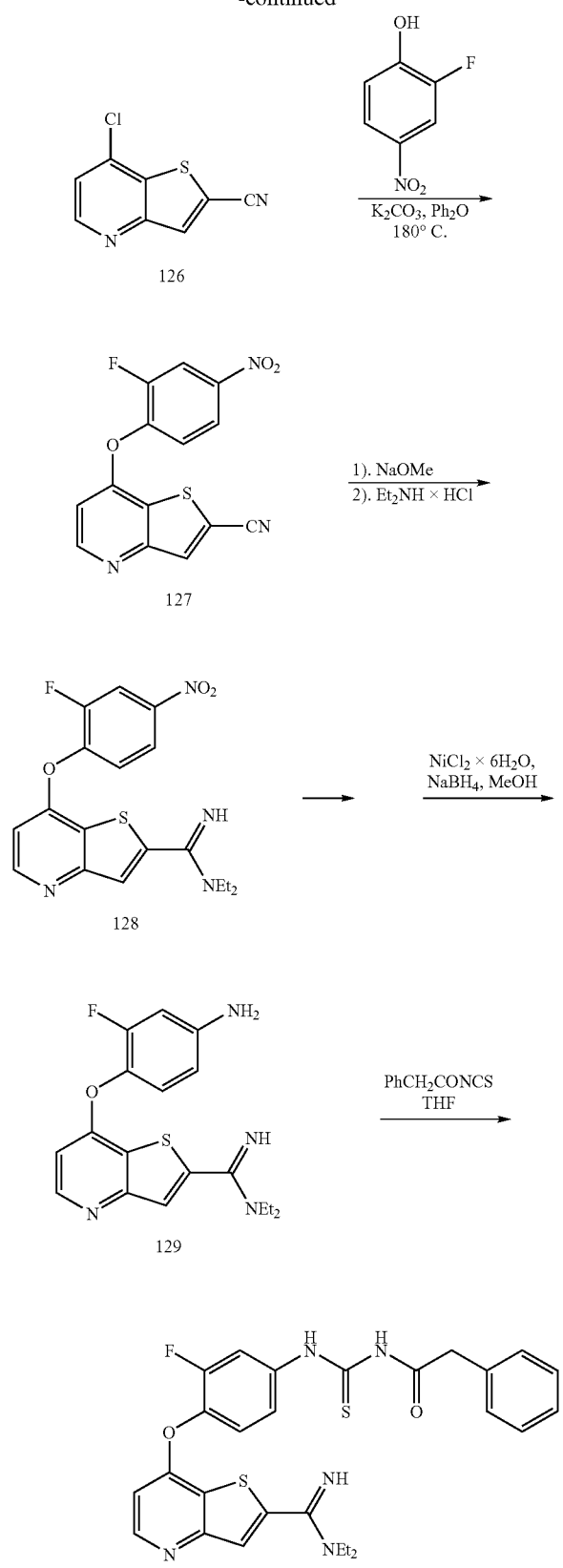

138

Example 87

N-(4-(2-(N,N-Diethylcarbamimidoyl)thieno[3,2-b]pyridin-7-yloxy)-3-fluorophenylcarbamothioyl)-2-phenylacetamide (130)

Step 1.
7-Chlorothieno[3,2-b]pyridine-2-carbaldehyde oxime (125)

To a solution of aldehyde 14 (scheme 3) in MeOH was added NH$_2$OH×HCl (227 mg, 3.26 mmol) in water (0.5 mL) and the mixture was stirred at room temperature for 0.5 h. The solvents were removed by under reduced pressure and the residue was partitioned between EtOAc and water. The organic phase was dried over anhydrous sodium sulfate, filtered and evaporated to dryness to afford the title compound 125 (458 mg, 85% yield) as a white solid. MS (m/z) 213.1/215.1 (M+H).

Step 2. 7-Chlorothieno[3,2-b]pyridine-2-carbonitrile (126)

A solution of the oxime 125 (100 mg, 0.47 mmol) in acetic anhydride (2 ml) was set to reflux for 3 h and then at 90° C. for 48 h. The acetic anhydride was removed under reduced pressure and the residue was partitioned between a cold aqueous K$_2$CO$_3$ solution and EtOAc. The organic phase was dried over anhydrous sodium sulfate, concentrated to dryness and remained solid was purified by column chromatography, eluents 25% EtOAc/hexane (25:75), then 100% EtOAc, to afford the title compound 126 (65 mg, 71% yield). MS (m/z) 195.1/197.1 (M+H).

Step 3. 7-(2-Fluoro-4-nitrophenoxy)thieno[3,2-b]pyridine-2-carbonitrile (127)

Following the procedure described above for the synthesis of compound 11 (example 12, step 3, scheme 2) but substituting compound 10 for compound 126, title compound 127 was obtained as a yellow solid (114 mg, 60% yield). MS (m/z) 316.0 (M+H).

Step 4. N,N-Diethyl-7-(2-fluoro-4-nitrophenoxy)thieno[3,2-b]pyridine-2-carboximidamide (128)

To a solution of nitrile 127 (116 mg, 0.37 mmol) in MeOH (3 mL) was added NaOMe (25% in MeOH, 0.09 ml, 0.39 mmol) and the mixture was allowed to stir at room temperature for 18 h. Subsequently, Et$_2$NH×HCl (1.01 g, 9.25 mmol) was added and the mixture was heated to reflux for 12 h., cooled to room temperature and the solvent was removed under reduced pressure. The residue was partitioned between EtOAc and saturated aqueous ammonium chloride, the organic phase was dried over anhydrous sodium sulfate, filtered and concentrated to dryness. The remained solid was purified by column chromatography (eluents EtOAc then CHCl$_3$/MeOH/NH$_4$OH 44:5:0.5), to afford the title compound 128 (30 mg, 21% yield) as a white solid. MS (m/z) 389.2 (M+H).

Steps 4-5. N-(4-(2-(N,N-Diethylcarbamimidoyl)thieno[3,2-b]pyridin-7-yloxy)-3-fluorophenylcarbamothioyl)-2-phenylacetamide (130)

Following the procedure described above for the synthesis of compound 13a (example 12, steps 4-5, scheme 2) but substituting compound 11 for compound 128 and using intermediate amine 129 (instead of amine 12), title compound 130 was obtained as a beige solid (5 mg, 13% yield). $^1$H NMR (DMSO) δ (ppm): 8.58 (1H, d, J=5.48 Hz), 8.29 (1H, s), 8.02 (1H, d, J=11.35 Hz), 7.81 (1H, d, J=2.54 Hz), 7.53 (2H, br), 7.34-7.33 (5H, m), 6.74 (1H, d, J=5.28 Hz), 3.83 (2H, s), 3.40 (4H, q, J=6.91 Hz), 1.16 (6H, t, J=6.95 Hz). MS (m/z) 536.2 (M+H).

Scheme 24

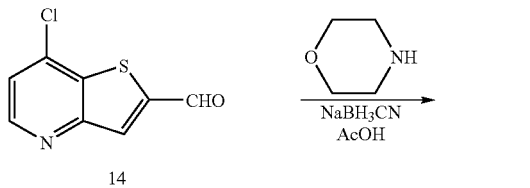

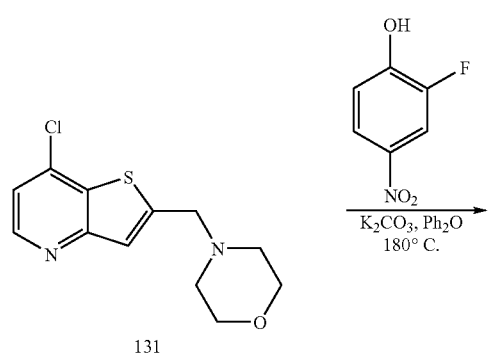

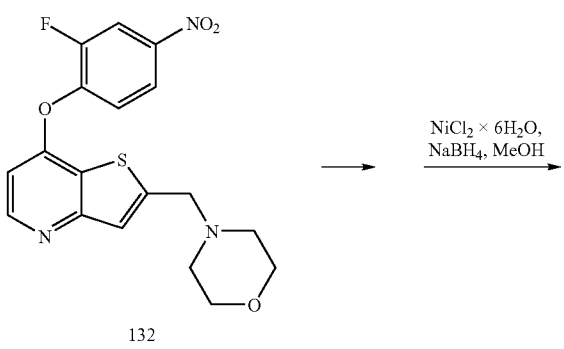

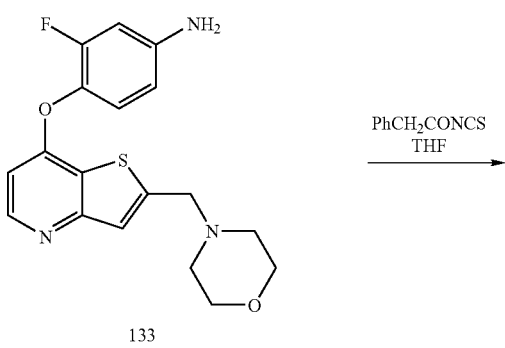

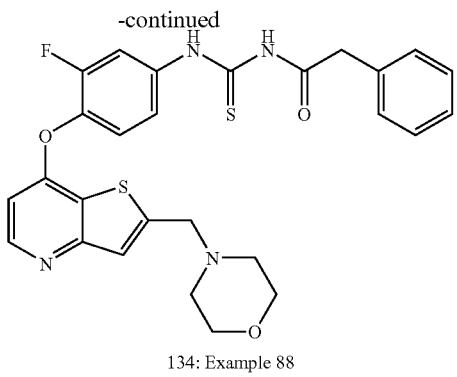

134: Example 88

Example 88

N-(3-Fluoro-4-(2-(morpholinomethyl)thieno[3,2-b]pyridin-7-yloxy)phenylcarbamothioyl)-2-phenylacetamide (134)

Step 1. 4-((7-Chlorothieno[3,2-b]pyridin-2-yl)methyl)morpholine (131)

To a solution of aldehyde 14 (scheme 3) (316 mg, 1.6 mmol) and morpholine (0.15 ml, 1.52 mmol) in MeOH (20 mL) was added acetic acid (0.88 ml, 15 mmol), followed by sodium cyanoborohydride (105 mg, 1.67 mmol). The resultant mixture was allowed to stir for 18 h, quenched with saturated aqueous potassium carbonate solution (5 mL), evaporated under reduced pressure and the residue was partitioned between EtOAc and water. The organic phase was dried over anhydrous sodium sulfate, concentrated to dryness and the remained solid was purified by column chromatography, eluents EtOAc/hexane (30:70), then MeOH/EtOAc (1:99), to afford the title compound 131 (120 mg, 29% yield). MS (m/z) 269.0/271.0 (M+H).

Step 2. 4-((7-(2-Fluoro-4-nitrophenoxy)thieno[3,2-b]pyridin-2-yl)methyl)morpholine (132)

Following the procedure described above for the synthesis of compound 11 (example 12, step 3, scheme 2) but substituting compound 10 for compound 131, title compound 132 was obtained as a yellow solid (110 mg, 69% yield). MS (m/z) 390.1 (M+H).

Steps 3-4. N-(3-Fluoro-4-(2-(morpholinomethyl)thieno[3,2-b]pyridin-7-yloxy)phenylcarbamothioyl)-2-phenylacetamide (134)

Following the procedure described above for the synthesis of compound 13a (example 12, steps 4-5, scheme 2) but substituting compound 11 for compound 132 and using intermediate amine 133 (instead of amine 12), title compound 134 was obtained as a white solid (38 mg, 27% yield). $^1$H NMR (DMSO) δ (ppm): 12.89 (1H, s), 12.24 (1H, s), 8.87 (1H, d, J=4.71 Hz), 8.42 (1H, d, J=12.13 Hz), 7.95-7.88 (3H, m), 7.76-7.68 (5H, m), 7.00 (1H, d, J=5.28 Hz), 4.26-4.25 (4H, m), 4.02 (4H, br), 3.76 (2H, s), 2.90 (2H, s). MS (m/z) 537.2 (M+H).

Examples 89-92

(S)-tert-Butyl1-(7-(2-fluoro-4-(3-(2-phenylacetyl)thioureido)phenoxy)thieno[3,2-b]pyridine-2-carbonyl)pyrrolidine-2-carboxylate (135a), (R)-tert-Butyl3-((7-(2-fluoro-4-(3-(2-phenylacetyl)thioureido)phenoxy)thieno[3,2-b]pyridine-2-carboxamido)methyl)pyrrolidine-1-carboxylate (135b), (R)—N-(4-(2-(3-(Dimethylamino)pyrrolidine-1-carbonyl)thieno[3,2-b]pyridin-7-yloxy)-3-fluorophenylcarbamothioyl)-2-phenylacetamide (135c), and N-(3-Fluoro-4-(2-(piperidine-1-carbonyl)thieno[3,2-b]pyridin-7-yloxy)phenylcarbamothioyl)-2-phenylacetamide (135d)

Compounds 135a-d (examples 89-92) were obtained following the procedures described above for the synthesis of compound 8a (example 1, scheme 1). Characterization of 135a-d is provided in Table 11.

TABLE 11

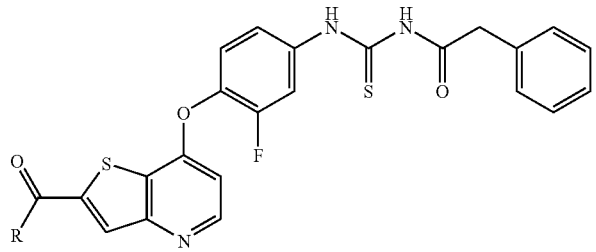

135 a–d: Examples 89–92

Characterization of compounds 135a-d (examples 89-92)

| Cpd | Ex | R | Name | Characterization |
|---|---|---|---|---|
| 135a | 89 | | (S)-tert-Butyl 1-(7-(2-fluoro-4-(3-(2-phenylacetyl)thioureido)phenoxy)thieno[3,2-b]pyridine-2-carbonyl)pyrrolidine-2-carboxylate | 1H NMR (400 MHz, DMSO-d6) δ ppm: 12.48(s, 1H), 11.82(s, 1H), 8.61(d, J=5.6Hz, 0.7H), 8.58(d, J=5.6Hz, 0.3H), 8.10(s, 0.7H), 8.03(bd, J=12.0Hz, 1H), 7.86(s, 0.3H), 7.57-7.51(m, 2H), 7.47-7.20(m, 5H), 6.77(d, J=5.6Hz, 0.7H), 6.75(d, J=5.6Hz, 0.3H), 5.02-4.97(m, 0.3H), 4.20(dd, J=3.2 and 8.4Hz, 0.7H), 3.97(t, J=6.8Hz, 1.4H), 3.82(s, 1.4H), 3.80(t, J=6.8Hz, 0.6H), 3.55(s, 0.6H), 2.3-1.10(m, 5H), 1.41(s, 6.3H), 1.19(s, 2.7H). |
| 135b | 90 | | (R)-tert-Butyl 3-((7-(2-fluoro-4-(3-(2-phenylacetyl)thioureido)phenoxy)thieno[3,2-b]pyridine-2-carboxamido)methyl)pyrrolidine-1-carboxylate | 1H NMR (400 MHz, DMSO-d6) δ ppm: 12.48(s, 1H), 11.81(s, 1H), 9.05-8.90(m, 1H), 8.58(d, J=5.6Hz, 1H), 8.32-8.22(m, 1H), 8.02(d, J=11.6Hz, 1H), 7.56-7.52(m, 2H), 7.36-7.30(m, 4H), 7.30-7.24(m, 1H), 6.73(d, J=5.6Hz, 1H), 4.00-3.90(m, 1H), 3.82(s, 2H), 3.54-3.20(m, 4H), 1.91-1.74(m, 4H), 1.39(bs, 9H). |
| 135c | 91 | | (R)-N-(4-(2-(3-(Dimethylamino)pyrrolidine-1-carbonyl)thieno[3,2-b]pyridin-7-yloxy)-3-fluoro-phenylcarbamothioyl)-2-phenylacetamide | 1H NMR (400 MHzCDCl3) δ ppm: 12.54(s, 1H), 8.80(s, 1H), 8.54(d, 1H, J=5.5Hz), 8.14(s, 1H), 7.96(dd, 1H, J=11.4/2.1Hz), 7.52-7.26(m, 6H), 6.63(d, 1H, J=5.5Hz), 4.35-3.52(m, 5H), 3.80(s, 2H), 2.79(s, 6H), 2.70-2.40(m, 2H). |
| 135d | 92 | | N-(3-Fluoro-4-(2-(piperidine-1-carbonyl)thieno[3,2-b]pyridin-7-yloxy)phenylcarbamothioyl)-2-phenylacetamide | LRMS(M+1) 549.3(100%), 550.3(32%). |

Example 93

N-(3-Fluoro-4-(2-(piperidine-1-carbonyl)thieno[3,2-b]pyridin-7-yloxy)phenylcarbamothioyl)-2-phenylacetamide hydrochloride (136a)

N-(3-Fluoro-4-(2-(piperidine-1-carbonyl)thieno[3,2-b]pyridin-7-yloxy)phenylcarbamothioyl)-2-phenylacetamide (135d, example 92) (686 mg, 1.25 mmol) was solubilized in THF (2 mL); dichloromethane (4 mL) and 1M hydrogen chloride in ether (1.5 mL, 1.5 mmol) were successfully added. The reaction mixture was stirred for 1 hour, the solvents were partially evaporated under reduced pressure to form a precipitate, which was collected by filtration, to afford the title compound 136a (380 mg, 65% yield) as a light-yellow solid. Characterization of this material is provided in Table 12.

Example 94

N-(3-Fluoro-4-(2-(pyrrolidine-1-carbonyl)thieno[3,2-b]pyridin-7-yloxy)phenylcarbamothioyl)-2-phenylacetamide hydrochloride (136b)

Following the procedure described above for the synthesis of compound 136a (example 93) but substituting compound 135d (example 92, table 11) for the compound 8o (example 37, table 6), title compound 136b was obtained. Characterization of this material is provided in Table 12.

Example 95

(S)-1-(7-(2-Fluoro-4-(3-(2-phenylacetyl)thioureido)phenoxy)thieno[3,2-b]pyridine-2-carbonyl)pyrrolidine-2-carboxylic acid hydrochloride (136c)

Following the procedure described above for the synthesis of compound 136a (Example 93) but substituting compound 135d (example 92, table 11) for the compound 135a (Example 89, Table 11), title compound 136c was obtained. Characterization of this material is provided in Table 12.

Example 96

N-(4-(2-(Azepane-1-carbonyl)thieno[3,2-b]pyridin-7-yloxy)-3-fluorophenylcarbamothioyl)-2-phenylacetamide hydrochloride (136d)

Title compound 136d was obtained following the procedures described above for the synthesis of compound 136a (example 93, table 12). Characterization of 136d is provided in Table 12.

TABLE 12

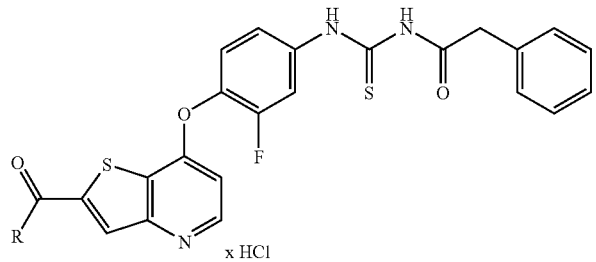

136 a–d: Examples 93–96

Characterization of compounds 136a-d (examples 93-96)

| Cpd | Ex | R | Name | Characterization |
|---|---|---|---|---|
| 136a | 93 | piperidin-1-yl | N-(3-Fluoro-4-(2-(piperidine-1-carbonyl)thieno[3,2-b]pyridin-7-yloxy)phenylcarbamothioyl)-2-phenylacetamide hydrochloride | 1H NMR (400 MHz DMSO-d6) δ ppm: 12.49(s, 1H), 11.83(s, 1H), 8.65(d, 1H, J=5.7Hz), 8.05(d, 1H, J=11.3Hz), 7.82(s, 1H), 7.56-7.55(m, 2H), 7.34-7.26(m, 5H), 6.84(d, 1H, J=5.7Hz), 3.83(s, 2H), 3.61-3.58(m, 4H), 1.65-1.09(m, 6H). |
| 136b | 94 | pyrrolidin-1-yl | N-(3-Fluoro-4-(2-(pyrrolidine-1-carbonyl)thieno[3,2-b]pyridin-7-yloxy)phenylcarbamothioyl)-2-phenylacetamide hydrochloride | 1H NMR (400 MHz, DMSO-d6) δ ppm: 12.49(s, 1H), 11.82(s, 1H), 8.64(d, J=5.6Hz, 1H), 8.08-8.01(m, 1H), 8.05(s, 1H), 7.58-7.53(m, 1H), 7.36-7.31(m, 4H), 7.30-7.24(m, 1H), 6.82(d, J=5.6Hz, 1H), 3.85(t, J=6.4Hz, 2H), 3.82(s, 2H), 3.54(t, J=6.4Hz, 2H), 1.97(quin, J=6.4Hz, 2H), 1.89(quin, J=6.4Hz, 2H). |

TABLE 12-continued

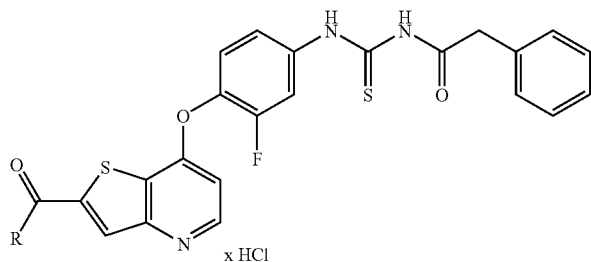

136 a–d: Examples 93–96

Characterization of compounds 136a-d (examples 93-96)

| Cpd | Ex | R | Name | Characterization |
|---|---|---|---|---|
| 136c | 95 | (pyrrolidine-2-carboxylic acid, HO₂C) | (S)-1-(7-(2-Fluoro-4-(3-(2-phenylacetyl)thioureido)phenoxy)thieno[3,2-b]pyridine-2-carbonyl)pyrrolidine-2-carboxylic acid hydrochloride | 1H NMR (400 MHz, DMSO-d6) δ ppm: 12.49(s, 1H), 11.82(s, 1H), 8.67(d, J=5.6Hz, 0.7H), 8.63(d, J=5.6Hz, 0.3H), 8.12(s, 0.7H), 8.05(d, J=21.0Hz, 1H), 7.88(s, 0.3H), 7.58-7.54(m, 2H), 7.37-7.10(m, 4H), 7.30-7.24(m, 1H), 6.85(d, J=5.6Hz, 0.7H), 6.81(d, J=5.6Hz, 0.3H), 5.03-4.99(m, 0.3H), 4.48(dd, J=4.4 and 8.0Hz, 0.7H), 3.98(t, J=7.2Hz, 1.4H), 3.82(s, 2H), 3.68-3.60(m, 0.6H), 2.32-2.25(m, 1H), 2.08-1.90(m, 3H). |
| 136d | 96 | (azepane) | N-(4-(2-(Azepane-1-carbonyl)thieno[3,2-b]pyridin-7-yloxy)-3-fluorophenylcarbamothioyl)-2-phenylacetamide hydrochloride | 1H NMR (400 MHzDMSO-d6) δ ppm: 12.49(s, 1H), 11.83(s, 1H), 8.64(d, 1H, J=5.7Hz), 8.04(d, 1H, J=11.5Hz), 7.85(s, 1H), 7.56-7.55(m, 2H), 7.34-7.26(m, 5H), 6.81(d, 1H, J=5.5Hz), 3.83(s, 2H), 3.67-3.56(m, 4H), 1.76-1.57(m, 8H). |

Scheme 25

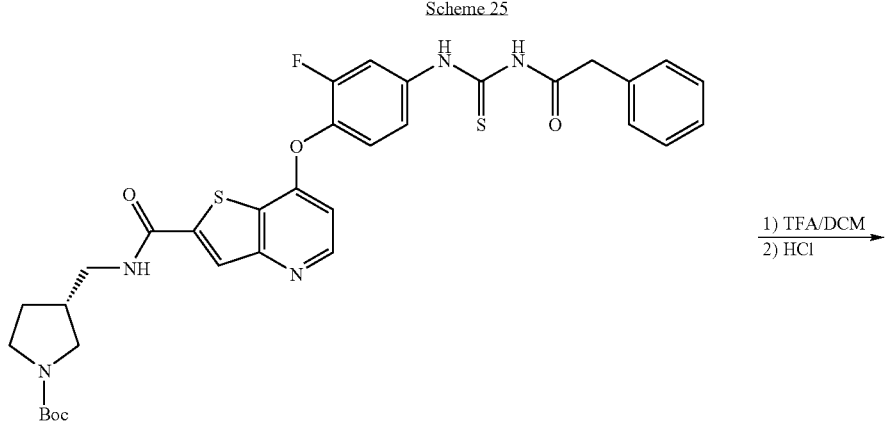

1) TFA/DCM
2) HCl

135b

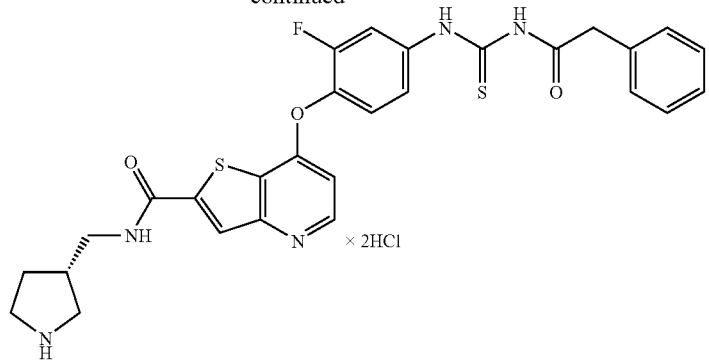

137a: Example 97

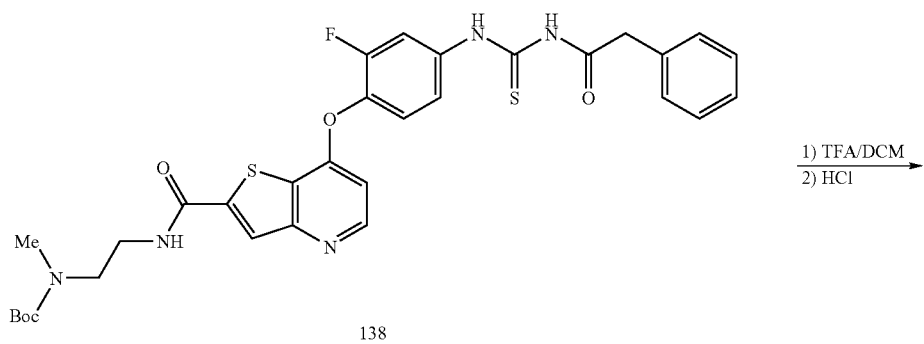

138

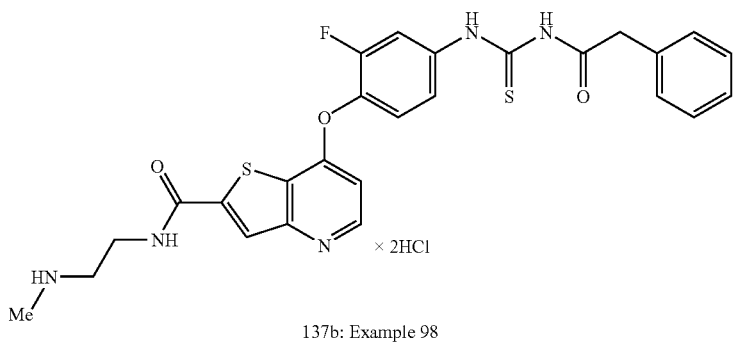

137b: Example 98

Example 97

(S)-7-(2-Fluoro-4-(3-(2-phenylacetyl)thioureido) phenoxy)-N-(pyrrolidin-3-ylmethyl)thieno[3,2-b] pyridine-2-carboxamide hydrochloride (137a)

To a solution of 135b (table 11) (16 mg, 0.028 mmol) in $CH_2Cl_2$ (15 mL) was added TFA (1 mL). The reaction mixture was stirred at room temperature until the reaction is complete, then the reaction mixture was quenched with saturated aqueous sodium bicarbonate solution a extracted with DCM. The extract was concentrated, the residue was dissolved in DCM (15 mL) and hydrogen chloride (0.5M in ether, 46 μL, 0.046 mmol) was added. The reaction mixture was stirred for one hour, the solvents were partially evaporated under reduced pressure to form a precipitate, which was collected by filtration, to afford the title compound 137a (10 mg, 87% yield) as a white solid. $^1$H NMR (400 MHz, DMSO-$d_6$) δ ppm: 12.48(s, 1H), 11.82(s, 1H), 9.49-9.43(m, 1H), 9.24(bs, 1H), 8.74(bs, 1H), 8.62(d, J=5.6 Hz, 1H), 8.38(s, 1H), 8.03(d, J=12.0 Hz, 1H), 7.58-7.5(m, 2H), 7.3-7.30(m, 4H), 7.30-7.24(m, 1H), 6.79(d, J=5.6 Hz, 1H), 3.80-3.54(m, 3H), 3.30-3.20(m, 1H), 3.20-3.10(m, 1H), 2.12-2.02(m, 1H), 2.00-1.95(m, 2H), 1.74-1.63(m, 1H).

Example 98

7-(2-fluoro-4-(3-(2-phenylacetyl)thioureido)phenoxy)-N-(2-(methylamino)ethyl) thieno[3,2-b]pyridine-2-carboxamide hydrochloride (137b)

Steps 1-7. tert-Butyl 2-(7-(2-fluoro-4-(3-(2-phenylacetyl)thioureido)phenoxy)thieno[3,2b]pyridine-2-carboxamido)ethyl(methyl)carbamate (138)

Following the procedures described above for the synthesis of compound 8a (Example 1, scheme 1) but replacing dimethyl amine with tert-butyl 2-aminoethyl(methyl)carbamate, title compound 138 was obtained (13%). LRMS (M+1) 638.2 (100%).

Step 8. 7-(2-Fluoro-4-(3-(2-phenylacetyl)thioureido)phenoxy)-N-(2-(methylamino)ethyl) thieno[3,2-b]pyridine-2-carboxamide hydrochloride (137b)

Following the procedure described above for the synthesis of 137a but replacing compound 135b with compound 138, title compound 137b was obtained as an HCl salt in 65% yield. $^1$H NMR (400 MHz, DMSO-$d_6$) δ ppm: 12.49(s, 1H), 11.83(s, 1H), 9.39(t, J=5.2 Hz, 1H), 8.80(bs, 1H), 8.62(d, J=5.6 Hz, 1H), 8.39(s, 1H), 8.04(d, J=11.6 Hz, 1H), 7.97(bs, 1H), 7.58-7.50(m, 2H), 7.37-7.31(m, 4H), 7.31-7.24(m, 1H), 6.80(d, J=5.6 Hz, 1H), 3.78-3.71(m, 0.5H), 3.61(q, J=6.0 Hz, 1H), 3.21-3.24(m, 0.5H), 3.18-3.04(m, 2H), 2.60(t, J=4.8 Hz, 2H).

Scheme 26

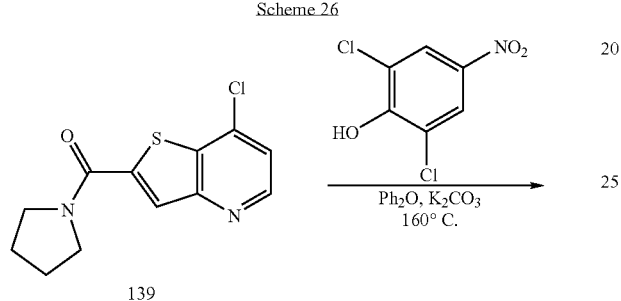

139

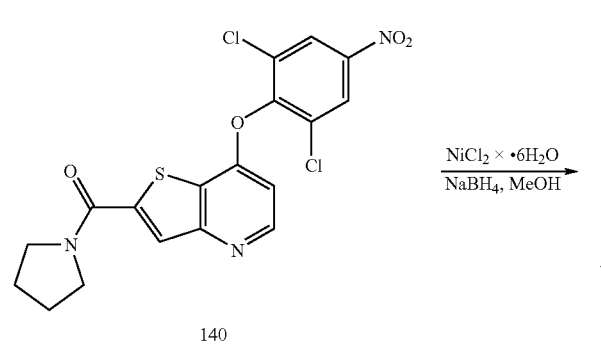

140

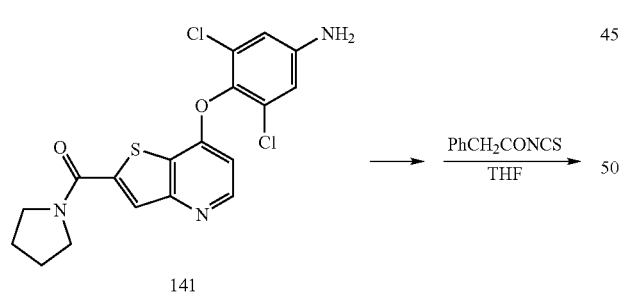

141

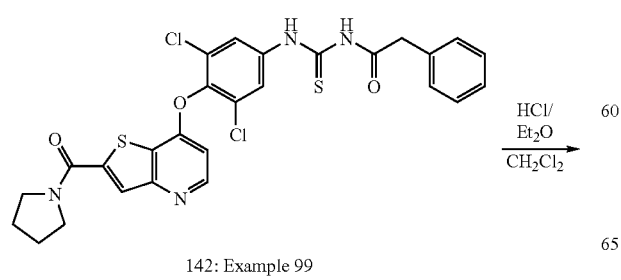

142: Example 99

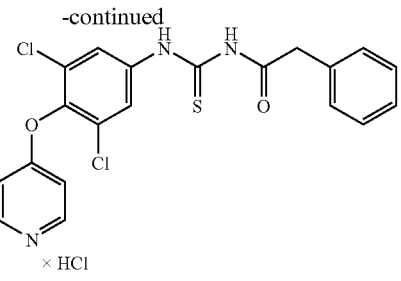

143: Example 100

Examples 99 and 100

N-(3,5-Dichloro-4-(2-(pyrrolidine-1-carbonyl)thieno[3,2-b]pyridin-7-yloxy)phenylcarbamothioyl)-2-phenylacetamide (142) and 7-(2,6-dichloro-4-(3-(2-phenylacetyl)thioureido)phenoxy)-2-(pyrrolidine-1-carbonyl)thieno[3,2-b]pyridin-4-ium chloride (143)

Steps 1-4. (7-Chlorothieno[3,2-b]pyridin-2-yl)(pyrrolidin-1-yl)methanone (139)

Following the procedures described above for the synthesis of compound 5 (scheme 1, example 1) but replacing dimethyl amine in the step 4 for pyrrolidine, title compound 139 was obtained. LRMS (M+1) 267.1 (100%).

Step 5. (7-(2,6-Dichloro-4-nitrophenoxy)thieno[3,2-b]pyridin-2-yl)(pyrrolidin-1-yl)methanone (140)

Starting from the compound 139 and following the procedure described above for the synthesis of compound 6 (scheme 1, example 1) but replacing 2-fluoro-4-nitrophenol with 2,6-dichloro-4-nitrophenol, title compound 140 was obtained in 69% yield. LRMS (M+1) 438.0 (100%), 439.1 (20%), 440.1 (70%).

Steps 6-7. N-(3,5-Dichloro-4-(2-(pyrrolidine-1-carbonyl)thieno[3,2-b]pyridin-7-yloxy)phenylcarbamothioyl)-2-phenylacetamide (142)

Starting from the nitro compound 140 and following the procedures described above for the synthesis of 8a (steps 6-7, scheme 1, example 1) title compound 142 was obtained in 49% yield. LRMS (M+1) 585.3 (100%), 586.2 (34%), 587.3 (72%).

7-(2,6-Dichloro-4-(3-(2-phenylacetyl)thioureido)phenoxy)-2-(pyrrolidine-1-carbonyl)thieno[3,2-b]pyridin-4-ium chloride (143)

Following the procedure described above for the synthesis of compound 136a (Table 12, Example 93) but replacing compound 135d with compound 142, title compound 143 was obtained in 42% yield. Characterization of 143 is provided in the Table 13.

Examples 101 and 102

N-(3-Chloro-4-(2-(pyrrolidine-1-carbonyl)thieno[3,2-b]pyridin-7-yloxy)phenylcarbamothioyl)-2-phenylacetamide hydrochloride (144) and N-(3-Methyl-4-(2-(pyrrolidine-1-carbonyl)thieno[3,2-b]pyridin-7-yloxy)phenylcarbamothioyl)-2-phenylacetamide hydrochloride (145)

Compounds 144-145 (examples 101-102) were obtained following the procedures described above for the synthesis of compound 143 (example 100). Characterization of compounds 144-145 is provided in the Table 13.

Examples 103 and 104

2-Phenyl-N-(4-(2-(pyrrolidine-1-carbonyl)thieno[3,2-b]pyridin-7-yloxy)phenylcarbamothioyl)acetamide (146) and N-(3-(Dimethylamino)-4-(2-(pyrrolidine-1-carbonyl)thieno[3,2-b]pyridin-7-yloxy)phenylcarbamothioyl)-2-phenylacetamide (147)

Compounds 146-147 (Examples 103-104) were obtained following the procedures described above for the synthesis of compound 142 (Example 99). Characterization of compounds 145-147 is provided in the Table 13.

TABLE 13

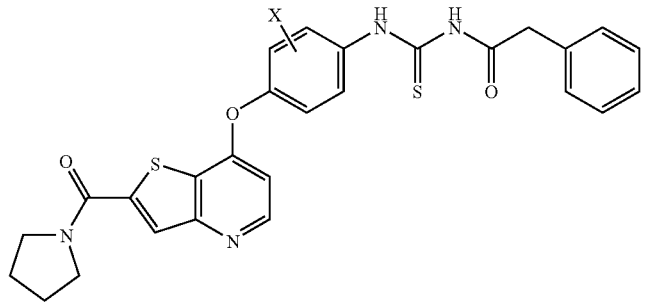

143–147: Examples 100–104

Characterization of compounds 143-146 (examples 99-103)

| Cpd | Ex | Ar | Name | Characterization |
|---|---|---|---|---|
| 143 | 100 | (3,5-dichlorophenyl) | N-(3,5-Dichloro-4-(2-(pyrrolidine-1-carbonyl)thieno[3,2-b]pyridin-7-yloxy)phenylcarbamothioyl)-2-phenylacetamide hydrochloride | $^1$H NMR (400 MHz, DMSO-$d_6$) δ ppm: 12.44(s, 1H), 11.91(s, 1H), 8.61(d, 1H, J=5.5Hz), 8.10(s, 2H), 8.06(s, 1H), 7.34-7.27(m, 5H), 6.68(d, 1H, J=5.5Hz), 3.88-3.83(m, 4H), 3.70-3.40(m, 2H), 1.99-1.18(m, 4H). |
| 144 | 101 | (3-chlorophenyl) | N-(3-Chloro-4-(2-(pyrrolidine-1-carbonyl)thieno[3,2-b]pyridin-7-yloxy)phenylcarbamothioyl)-2-phenylacetamide hydrochloride | $^1$H NMR (400 MHz, DMSO-$d_6$) δ ppm: 12.43(s, 1H), 11.83(s, 1H), 8.65(d, 1H, J=5.7Hz), 8.14(d, 1H, J=2.3Hz), 8.06(s, 1H), 7.70(dd, 1H, J=8.8/2.5Hz), 7.55(d, 1H, J=8.8Hz), 7.34-7.26(m, 5H), 6.74(d, 1H, J=5.7Hz), 3.87-3.83(m, 4H), 3.56-3.53(m, 2H), 1.99-1.88(m, 4H). |
| 145 | 102 | (3-methylphenyl) | N-(3-Methyl-4-(2-(pyrrolidine-1-carbonyl)thieno[3,2-b]pyridin-7-yloxy)phenylcarbamothioyl)-2-phenylacetamide hydrochloride | $^1$H NMR (400 MHz, DMSO-$d_6$) δ ppm: 12.43(s, 1H), 11.74(s, 1H), 8.62(d, 1H, J=5.7Hz), 8.04(s, 1H), 7.69-7.65(m, 2H), 7.43-7.26(m, 6H), 6.67(d, 1H, J=5.7Hz), 3.87-3.82(m, 4H), 3.67-3.38(m, 2H), 2.13(s, 3H), 1.99-1.18(m, 4H). |

TABLE 13-continued

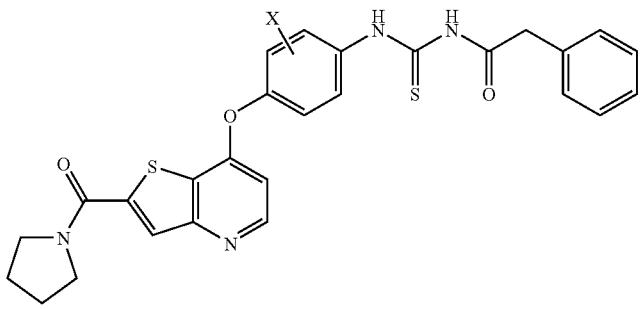

143–147: Examples 100–104

Characterization of compounds 143-146 (examples 99-103)

| Cpd | Ex | Ar | Name | Characterization |
|---|---|---|---|---|
| 146 | 103 | | 2-Phenyl-N-(4-(2-(pyrrolidine-1-carbonyl)thieno[3,2-b]pyridin-7-yloxy)phenylcarbamothioyl)acetamide | $^1$H NMR (400 MHz, DMSO-$d_6$) δ ppm: 12.41(s, 1H), 11.75(s, 1H), 8.68(d, J=5.6Hz, 1H), 8.06(s, 1H), 7.77(d, J=8.8Hz, 2H), 7.36(d, J=8.8Hz, 2H), 7.34-7.31(m, 4H), 7.30-7.24(m, 1H), 6.85(d, J=5.6Hz, 1H), 3.84(t, J=6.4Hz, 2H), 3.82(s, 2H), 3.54(t, J=6.4Hz, 2H), 1.97(quin, J=6.4Hz, 2H), 1.89(quin, J=6.4Hz, 2H). |
| 147 | 104 | | N-(3-(Dimethylamino)-4-(2-(pyrrolidine-1-carbonyl)thieno[3,2-b]pyridin-7-yloxy)phenylcarbamothioyl)-2-phenylacetamide | $^1$H NMR (400 MHz, CDCl$_3$) δ ppm: 8.48(d, 1H, J=6.1Hz), 8.27(s, 1H), 7.56(m, 8H), 6.67(m, 1H), 3.91(t, 2H, J=6.8Hz), 3.78(s, 2H), 3.74(t, 2H, J=6.8Hz), 2.73(s, 6H), 2.19-2.01(m, 4H). |

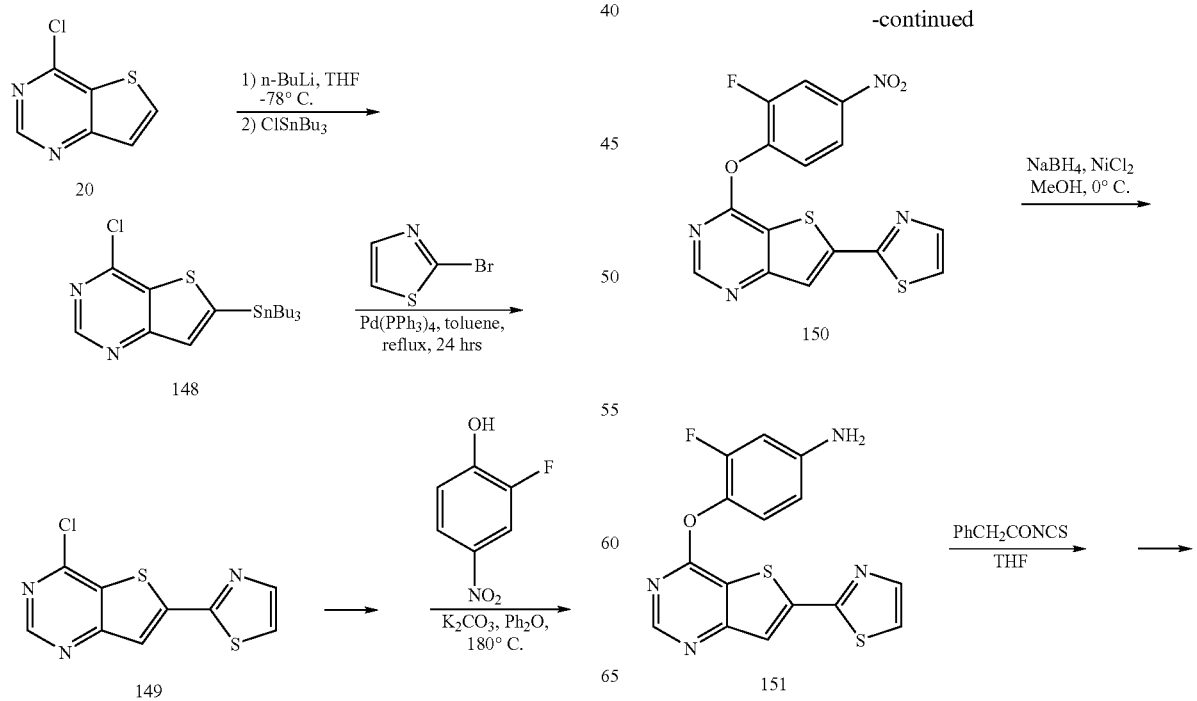

Scheme 27

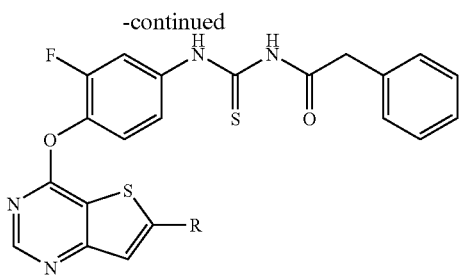

152a: Example 105

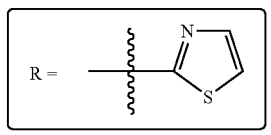

Example 105

N-(3-Fluoro-4-(6-(thiazol-2-yl)thieno[3,2-d]pyrimidin-4-yloxy)phenylcarbamothioyl)-2-phenylacetamide (152a)

Step 1. 4-Chloro-6-(tributylstannyl)thieno[3,2-d]pyrimidine (148)

Starting from 4-chloro-thieno[3,2-d]pyrimidine (20, scheme 4) and following the procedure described above for the synthesis of tributyltin compound 98 (scheme 19), title compound 148 was obtained in 79% yield. LRMS (M+1) 461.1 (100%).

Step 2. 4-Chloro-6-(thiazol-2-yl)thieno[3,2-d]pyrimidine (149)

Starting from the tributyltin compound 148 and following the procedure described above for the synthesis of compound 10 (scheme 2, example 12), title compound 149 was obtained in 81% yield. LRMS (M+1) 254.0 (100%).

Step 3. 4-(2-Fluoro-4-nitrophenoxy)-6-(thiazol-2-yl)thieno[3,2-d]pyrimidine (150)

Starting from the bis-aryl compound 149 and following the procedure described above for the synthesis of compound 11 (scheme 2, example 12) title compound 150 was obtained in 65% yield. LRMS (M+1) 375.0 (100%).

Steps 4-5. N-(3-Fluoro-4-(6-(thiazol-2-yl)thieno[3,2-d]pyrimidin-4-yloxy)phenylcarbamothioyl)-2-phenylacetamide (152a)

Starting from the nitro compound 150, following the procedure described above for the synthesis of compound 13a (via the intermediate amine 12, scheme 2, example 12), title compound 152a was obtained [via intermediate 3-fluoro-4-(6-(thiazol-2-yl)thieno[3,2-d]pyrimidin-4-yloxy)benzenamine (151)] in 7% yield. Characterization of 152a is provided in the Table 14.

Examples 106-108

N-(3-Fluoro-4-(6-(pyridin-2-yl)thieno[3,2-d]pyrimidin-4-yloxy)phenylcarbamothioyl)-2-phenylacetamide (152b), N-(3-Fluoro-4-(6-(thiophen-2-yl)thieno[3,2-d]pyrimidin-4-yloxy)phenylcarbamothioyl)-2-phenylacetamide (152c), and N-(3-Fluoro-4-(6-(thiophen-2-yl)thieno[3,2-d]pyrimidin-4-yloxy)phenylcarbamothioyl)-2-phenylacetamide (152d)

Compounds 152b-d (Examples 106-108) were synthesized according to the Scheme 27, similarly to the compound 152a (Example 105). Characterization of 152b-d is provided in the Table 14.

TABLE 14

| | | Characterization of Compounds 152a-d (Examples 105-108) | | |
|---|---|---|---|---|
| Cpd | Ex | R | Name | Characterization |
| 152a | 105 | thiazol-2-yl | N-(3-Fluoro-4-(6-(thiazol-2-yl)thieno[3,2-d]pyrimidin-4-yloxy)phenylcarbamothioyl)-2-phenylacetamide | $^1$H NMR (400 MHz, DMSO-$d_6$) δ ppm: 8.75(s, 1H), 8.32(s, 1H), 8.05(d, J=3.2Hz, 1H), 8.03(d, J=3.2Hz, 1H), 7.96-7.88(m, 1H), 7.58-7.50(m, 1H), 7.50-7.43(m, 1H), 7.36-7.30(m, 4H), 7.30-7.23(m, 1H), 3.83(s, 2H). |
| 152b | 106 | pyridin-2-yl | N-(3-Fluoro-4-(6-(pyridin-2-yl)thieno[3,2-d]pyrimidin-4-yloxy)phenylcarbamothioyl)-2-phenylacetamide | $^1$H NMR (400 MHz, DMSO-$d_6$) δ ppm: 12.44(s, 1H), 11.80(s, 1H), 8.73(s, 1H), 8.70-8.64(m, 1H), 8.47(s, 1H), 8.38(m, J=8.0Hz, 1H), 8.00(td, J=2.0 and 8.0Hz, 1H), 7.92(dd, J=2.0 and 12.0Hz, 1H), 7.55(t, J=8.8Hz, 1H), 7.53-7.46(m, 2H), 7.36-7.31(m, 4H), 7.30-7.24(m, 1H), 3.82(s, 2H). |

TABLE 14-continued

Characterization of Compounds 152a-d (Examples 105-108)

| Cpd | Ex | R | Name | Characterization |
|---|---|---|---|---|
| 152c | 107 |  | N-(3-Fluoro-4-(6-(thiophen-2-yl)thieno[3,2-d]pyrimidin-4-yloxy)phenylcarbamothioyl)-2-phenylacetamide | $^1$H NMR (400 MHz, DMSO-d$_6$) δ ppm: 12.42(s, 1H), 11.80(s, 1H), 8.69(s, 1H), 7.92(dd, J=2.4 and 10.4Hz, 1H), 7.91(s, 1H), 7.82(dd, J=1.2 and 4.8Hz, 1H), 7.79(dd, J=1.2 and 3.6Hz, 1H), 7.54(t, J=8.8Hz, 1H), 7.47(dd, J=2.4 and 8.8Hz, 1H), 7.36-7.30(m, 4H), 7.30-7.25(m, 1H), 7.24(dd, J=3.6 and 4.8Hz, 1H), 3.82(s, 2H). |
| 152d | 108 |  | N-(3-Fluoro-4-(6-(pyrimidin-2-yl)thieno[3,2-d]pyrimidin-4-yloxy)phenylcarbamothioyl)-2-phenylacetamide | $^1$H NMR (400 MHz, DMSO-d$_6$) δ ppm: 12.44(s, 1H), 11.80(s, 1H), 9.00(s, 1H), 8.98(s, 1H), 8.77(s, 1H), 8.37(s, 1H), 7.94(dd, J=2.4 and 12.0Hz), 7.61(t, J=5.2Hz, 1H), 7.57(t, J=8.8Hz, 1H), 7.49(dd, J=2.4 and 8.8Hz, 1H), 7.38-7.31(m, 4H), 7.30-7.25(m 1H), 3.83(s, 2H). |

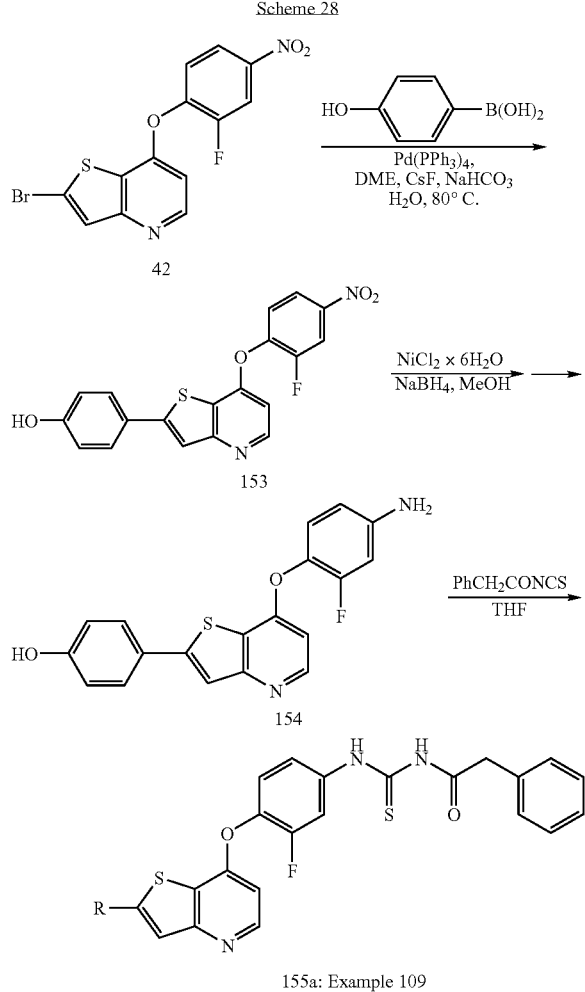

Scheme 28

155a: Example 109

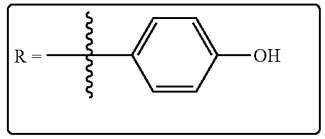

Example 109

N-(3-Fluoro-4-(2-(4-hydroxyphenyl)thieno[3,2-b]pyridin-7-yloxy)phenylcarbamothioyl)-2-phenylacetamide (155a)

Step 1. 4-(7-(2-Fluoro-4-nitrophenoxy)thieno[3,2-b]pyridin-2-yl)phenol (153)

To a solution of 2-bromo-7-(2-fluoro-4-nitrophenoxy)thieno[3,2-b]pyridine (42, scheme 8) (650 mg, 1.76 mmol) in ethylene glycol dimethyl ether (18 mL) were added 4-hydroxyphenylboronic acid (486 mg, 3.52 mmol), tetrakis-triphenylphosphine palladium(0) (203 mg, 0.18 mmol), cesium fluoride (802 mg, 5.28 mmol) and a solution of sodium bicarbonate (444 mg, 5.28 mmol) in water (1 mL). The reaction mixture was purged with nitrogen, heated at 80° C. for 4 hours, quenched with saturated aqueous ammonium chloride and extracted with EtOAc. The extract was washed with water and brine, dried over anhydrous magnesium sulfate, filtered and evaporated under reduced pressure. The residue was purified by trituration with methanol and ether to afford title compound 153 (418 mg, 62% yield) as a yellow solid. LRMS (M+1) 383.1 (100%).

Step 2. 4-(7-(4-Amino-2-fluorophenoxy)thieno[3,2-b]pyridin-2-yl)phenol (154)

Following the procedure described above for the synthesis of the amine 49 (scheme 10, example 55) but substituting nitro compound 48 for the nitro compound 153, title compound 154 was obtained in 99% yield (crude material, used in the next step without additional purification). LRMS (M+1) 353.1 (100%).

Step 3. N-(3-Fluoro-4-(2-(4-hydroxyphenyl)thieno[3,2-b]pyridin-7-yloxy)phenylcarbamothioyl)-2-phenylacetamide (155a)

Following the procedure described above for the synthesis of Compound 50 (Scheme 10, Example 55) but substituting amine 49 for the amine 154, title Compound 155a was obtained in 3% yield. Characterization of 155a is provided in the Table 14a.

Examples 110-118

N-(3-Fluoro-4-(2-(4-methoxyphenyl)thieno[3,2-b]pyridin-7-yloxy)phenylcarbamothioyl)-2-phenylacetamide (155b)

N-(3-Fluoro-4-(2-(3-methoxyphenyl)thieno[3,2-b]pyridin-7-yloxy)phenylcarbamothioyl)-2-phenylacetamide (155c)

N-(3-Fluoro-4-(2-(3-fluoro-4-methoxyphenyl)thieno[3,2-b]pyridin-7-yloxy)phenylcarbamothioyl)-2-phenylacetamide (155d)

N-(3-Fluoro-4-(2-(4-morpholinophenyl)thieno[3,2-b]pyridin-7-yloxy)phenylcarbamothioyl)-2-phenylacetamide (155e)

N-(3-Fluoro-4-(2-phenylthieno[3,2-b]pyridin-7-yloxy)phenylcarbamothioyl)-2-phenylacetamide (155f)

N-(3-Fluoro-4-(2-(2-morpholinopyrimidin-5-yl)thieno[3,2-b]pyridin-7-yloxy)phenylcarbamothioyl)-2-phenylacetamide (155 g)

N-(3-Fluoro-4-(2-(2-(2-morpholinoethoxy)pyrimidin-5-yl)thieno[3,2-b]pyridin-7-yloxy)phenylcarbamothioyl)-2-phenylacetamide (155h)

N-(3-Fluoro-4-(2-(2-methoxyphenyl)thieno[3,2-b]pyridin-7-yloxy)phenylcarbamothioyl)-2-phenylacetamide (155i) and N-(3-Fluoro-4-(2-(4-hydroxy-3-methoxyphenyl)thieno[3,2-b]pyridin-7-yloxy)phenylcarbamothioyl)-2-phenylacetamide (155j)

Compounds 155b-j (Examples 110-118) were prepared similarly to the Compound 155a (Example 109, Scheme 28). Characterization of 155b-j is provided in the Table 14a.

TABLE 14a

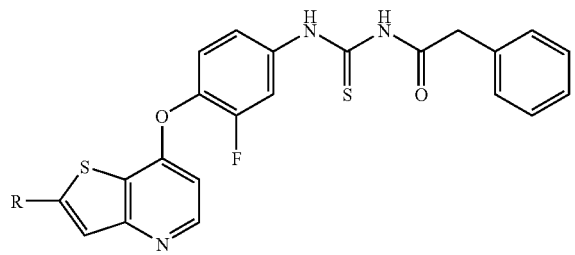

155a–j: Examples 109–118

Characterization of compounds 152a-j (examples 109-118)

| Cpd | Ex | R | Name | Characterization |
|---|---|---|---|---|
| 155a | 109 | 4-hydroxyphenyl | N-(3-Fluoro-4-(2-(4-hydroxyphenyl)thieno[3,2-b]pyridin-7-yloxy)phenylcarbamothioyl)-2-phenylacetamide | $^1$H NMR (400 MHz, DMSO-$d_6$) δ ppm: 12.46(s, 1H), 11.82(s, 1H), 9.95(s, 1H), 8.46(d, 1H, J=5.3Hz), 7.99(d, 1H, J=13.1Hz), 7.83(s, 1H), 7.70(d, 2H, J=13.1Hz), 7.52-7.51(m, 2H), 7.34-7.27(m, 5H), 6.86(d, 2H, J=8.6Hz), 6.59(d, 1H, J=5.5Hz), 3.83(s, 2H). |
| 155b | 110 | 4-methoxyphenyl | N-(3-Fluoro-4-(2-(4-methoxyphenyl)thieno[3,2-b]pyridin-7-yloxy)phenylcarbamothioyl)-2-phenylacetamide | $^1$H NMR (400 MHz, DMSO-$d_6$) δ ppm: 12.46(s, 1H), 11.82(s, 1H), 8.48(d, J=5.6Hz, 1H), 8.00(d, J=7.6Hz, 1H), 7.91(s, 1H), 7.81(d, J=8.8Hz, 2H), 7.66-7.60(m, 2H), 7.37-7.31(m, 4H), 7.31-7.24(m, 1H), 7.05(d, J=8.8Hz, 2H), 6.61(d, J=5.6Hz, 1H), 3.82(s, 3H). |
| 155c | 111 | 3-methoxyphenyl | N-(3-Fluoro-4-(2-(3-methoxyphenyl)thieno[3,2-b]pyridin-7-yloxy)phenylcarbamothioyl)-2-phenylacetamide | $^1$H NMR (400 MHz, DMSO-$d_6$) δ ppm: 12.46(s, 1H), 11.82(s, 1H), 8.52(d, J=5.6Hz, 1H), 8.10(s, 1H), 8.01(d, J=12.4Hz, 1H), 7.56-7.51(m, 2H), 7.46-7.37(m, 3H), 7.37-7.31(m, 4H), 7.31-7.24(m, 1H), 7.05-7.00(m, 1H), 6.65(d, J=5.6Hz, 1H), 3.85(s, 3H), 3.82(s, 2H). |

TABLE 14a-continued

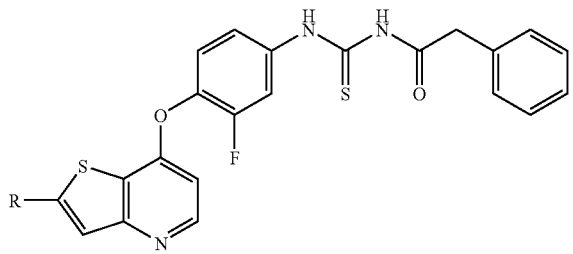

155a–j: Examples 109–118

Characterization of compounds 152a-j (examples 109-118)

| Cpd | Ex | R | Name | Characterization |
|---|---|---|---|---|
| 155d | 112 | (3-fluoro-4-methoxyphenyl) | N-(3-Fluoro-4-(2-(3-fluoro-4-methoxyphenyl)thieno[3,2-b]pyridin-7-yloxy)phenylcarbamothioyl)-2-phenylacetamide | $^1$H NMR (400 MHz, DMSO-d$_6$) δ ppm: 12.46(s, 1H), 11.82(s, H), 8.49(d, J=5.6Hz, 1H), 8.01(s, 1H), 8.2-7.76(m, 1H), 7.84(dd, J=2.4 and 12.0Hz, 1H), 7.66-7.61(m, 1H), 7.55-7.51(m, 2H), 7.38-7.10(m, 6H), 6.63(d, J=5.6Hz, 1H), 3.90(s, 3H), 3.82(s, 2H). |
| 155e | 113 | (4-morpholinophenyl) | N-(3-Fluoro-4-(2-(4-morpholinophenyl)thieno[3,2-b]pyridin-7-yloxy)phenylcarbamothioyl)-2-phenylacetamide | $^1$H NMR (400 MHz, DMSO-d$_6$) δ ppm: 12.49(s, 1H), 11.85(s, 1H), 8.63(d, J=5.6Hz, 1H), 8.03(d, J=11.6Hz, 1H), 7.89(s, 1H), 7.79(d, J=8.8Hz, 2H), 7.63-7.56(m, 2H), 7.36-7.31(m, 4H), 7.31-7.25(m, 1H), 7.05(d, J=8.8Hz, 2H), 6.87(d, J=5.6Hz, 1H), 3.83(s, 2H), 3.78-3.73(m, 4H), 3.30-3.24(m, 4H). |
| 155f | 114 | phenyl | N-(3-Fluoro-4-(2-phenylthieno[3,2-b]pyridin-7-yloxy)phenylcarbamothioyl)-2-phenylacetamide | $^1$H NMR (400 MHz, DMSO-d$_6$) δ ppm: 12.46(s, H), 11.82(s, 1H), 8.52(d, J=5.6Hz, 1H), 8.06(s, 1H), 8.01(d, J=12.4Hz, 1H), 7.88(d, J=6.8Hz, 2H), 7.58-7.41(m, 5H), 7.38-7.31(m, 4H), 7.31-7.24(m, 1H), 6.65(d, J=5.6Hz, 1H), 3.82(s, 2H). |
| 155g | 115 | (2-morpholinopyrimidin-5-yl) | N-(3-Fluoro-4-(2-(2-morpholinopyrimidin-5-yl)thieno[3,2-b]pyridin-7-yloxy)phenylcarbamothioyl)-2-phenylacetamide | $^1$H NMR (400 MHz, DMSO-d$_6$) δ ppm: 12.46(s, 1H), 11.82(s, 1H), 8.89(s, 2H), 8.49(d, J=5.6hz, 1H), 8.00(d, J=12.0Hz, 1H), 7.98(s, 1H), 7.56-7.51(m, 2H), 7.37-7.31(m, 4H), 7.31-7.24(m, 1H), 6.61(d, J=5.6Hz, 1H), 3.82(s, 2H), 3.82-3.76(m, 4H), 3.70-3.66(m, 4H). |

TABLE 14a-continued

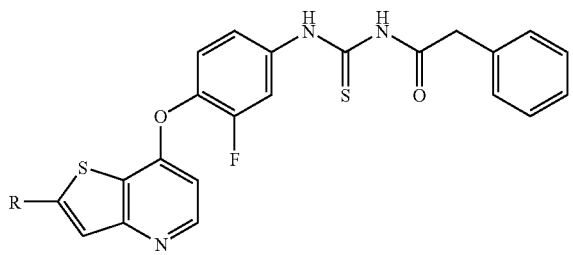

155a–j: Examples 109–118

Characterization of compounds 152a-j (examples 109-118)

| Cpd | Ex | R | Name | Characterization |
|---|---|---|---|---|
| 155h | 116 | [2-(2-morpholinoethoxy)pyrimidin-5-yl] | N-(3-Fluoro-4-(2-(2-(2-morpholinoethoxy)pyrimidin-5-yl)thieno[3,2-b]pyridin-7-yloxy)phenylcarbamothioyl)-2-phenylacetamide | $^1$H NMR (400 MHz, DMSO-$d_6$) δ ppm: 12.49(s, 1H), 11.85(s, 1H), 9.13(s, 2H), 8.56(d, J=5.6Hz, 1H), 8.18(s, 1H), 8.03(d, J=1.8Hz, 1H), 7.60-7.54(m, 2H), 7.39-7.32(m, 4H), 7.32-7.25(m, 1H), 6.68(d, J=5.6Hz, 1H), 4.50(t, J=5.6Hz, 2H), 3.83(s, 2H), 3.57(t, J=4.4Hz, 4H), 2.73(t, J=5.6Hz, 2H), 2.51-2.44(m, 4H). |
| 155i | 117 | 2-methoxyphenyl (MeO) | N-(3-Fluoro-4-(2-(2-methoxyphenyl)thieno[3,2-b]pyridin-7-yloxy)phenylcarbamothioyl)-2-phenylacetamide | $^1$H NMR (400 MHz, DMSO-$d_6$) δ ppm: 12.51(s, 1H), 11.84(s, 1H), 8.67(d, 1H, J=6.1Hz), 8.13(s, 1H), 8.08(d, 1H, J=13.1Hz), 8.02(dd, 1H, J=7.7/1.5Hz), 7.61-7.60(m, 2H), 7.50(td, 1H, J=7.8/1.7Hz), 7.35-7.32(m, 4H), 7.29-7.26(m, 2H), 7.13(td, 1H, J=7.6/1.1Hz), 6.88(d, 1H, J=6.1Hz), 4.00(s, 3H), 3.83(s, 2H). |
| 155j | 118 | 4-hydroxy-3-methoxyphenyl (OMe, OH) | N-(3-Fluoro-4-(2-(4-hydroxy-3-methoxyphenyl)thieno[3,2-b]pyridin-7-yloxy)phenylcarbamothioyl)-2-phenylacetamide | $^1$H NMR (400 MHz, DMSO-$d_6$) δ ppm: 12.49(s, 1H), 11.85(s, 1H), 9.57(s, 1H), 8.49(d, 1H, J=5.5Hz), 8.01(d, 1H, J=13.5Hz), 7.94(s, 1H), 7.54-7.53(m, 2H), 7.44(d, 1H, J=2.3Hz), 7.38-7.27(m, 6H), 6.88(d, 1H, J=8.2Hz), 6.61(d, 1H, J=4.9Hz), 3.89(s, 3H), 3.83(s, 2H). |

Scheme 29

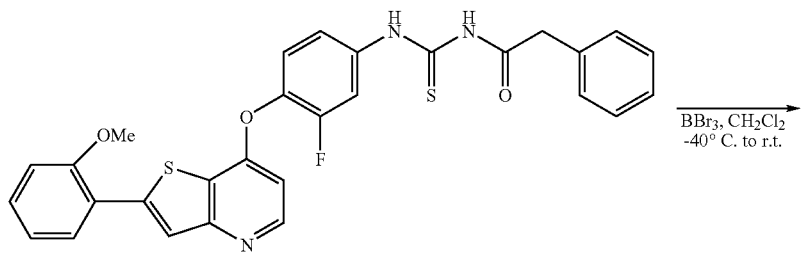

155I: Example 117

BBr$_3$, CH$_2$Cl$_2$
-40° C. to r.t.

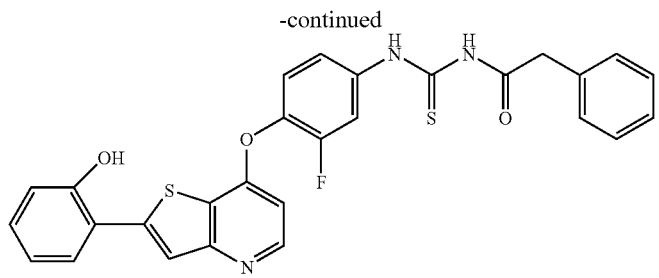

155k: Example 119

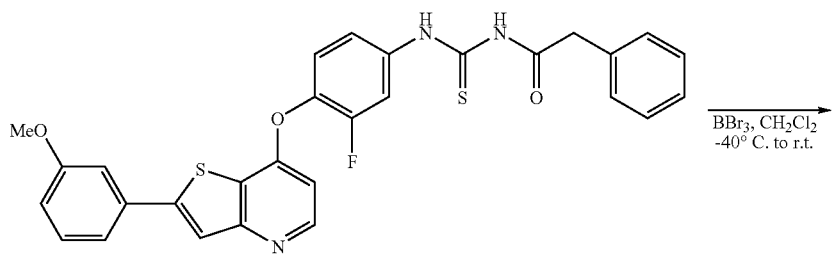

155c: Example 111

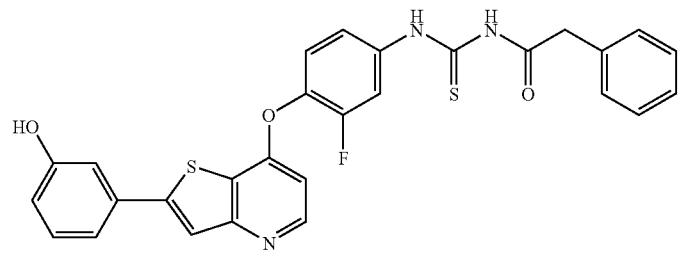

155l: Example 120

Example 119

N-(3-Fluoro-4-(2-(2-hydroxyphenyl)thieno[3,2-b]pyridin-7-yloxy)phenylcarbamothioyl)-2-phenylacetamide (155k)

To a cold (−40° C.) solution of the compound 155i (80 mg, 0.15 mmol) in DCM (3 mL) was added tribromoborane (1M in DCM, 0.60 mL, 0.60 mmol). The reaction mixture was stirred overnight at room temperature. Water and methanol were added and the mixture was stirred for additional 20 minutes. Organic phase was separated and the aqueous layer was extracted with EtOAc. Both organic phases were combined, washed with water and brine, dried over anhydrous magnesium sulfate, filtered and evaporated under reduced pressure. The residue was purified by flash chromatography (eluent MeOH-DCM, 2:98) then triturated with methanol, to afford the title compound 155k (6 mg, 7%yield), as a light yellow solid. $^1$H NMR (400 MHz, DMSO-$d_6$) δ ppm: 12.47 (d, 1H, J=0.4 Hz), 11.82 (s, 1H), 10.65 (s, 1H), 8.48 (d, 1H, J=5.5 Hz), 8.07 (s, 1H), 8.01 (d, 1H, J=11.5 Hz), 7.84 (d, 1H, J=7.8 Hz), 7.53-7.49 (m, 2H), 7.38-7.23 (m, 6H), 7.01 (d, 1H, J=8.2 Hz), 6.93 (t, 1H, J=7.4 Hz), 6.58 (d, 1H, J=5.5 Hz), 3.83 (s, 2H). LRMS (M+1) 530.2 (100%).

Example 120

N-(3-Fluoro-4-(2-(3-hydroxyphenyl)thieno[3,2-b]pyridin-7-yloxy)phenylcarbamothioyl)-2-phenylacetamide (155l)

Following the procedure described above for the synthesis of compound 155k (example 119, scheme 29) but substituting methoxy-compound 155i for the methoxy-compound 155c, title compound 155l was prepared in 62% yield. $^1$H NMR (400 MHz, DMSO-$d_6$) δ ppm: 12.49(s, 1H), 11.84(s, 1H), 8.68(d, J=5.6 Hz, 1H), 8.07(d, J=12.0 Hz, 1H), 7.99(s, 1H), 7.64-7.56(m, 2H), 7.38-7.24(m, 8H), 6.96-6.88(m, 2H), 3.83 (s, 2H).

Scheme 30
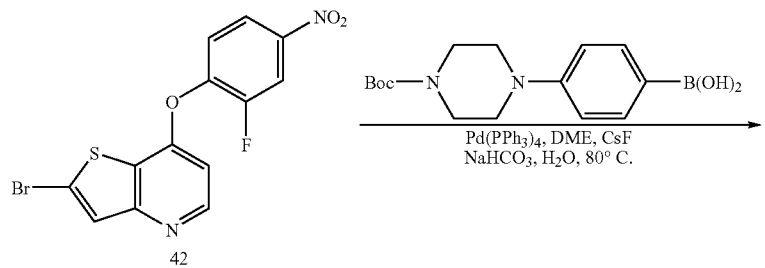
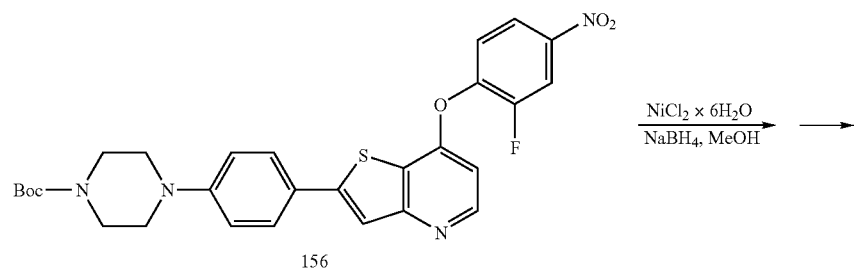
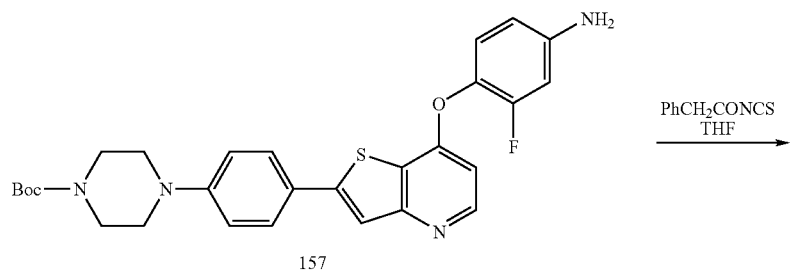
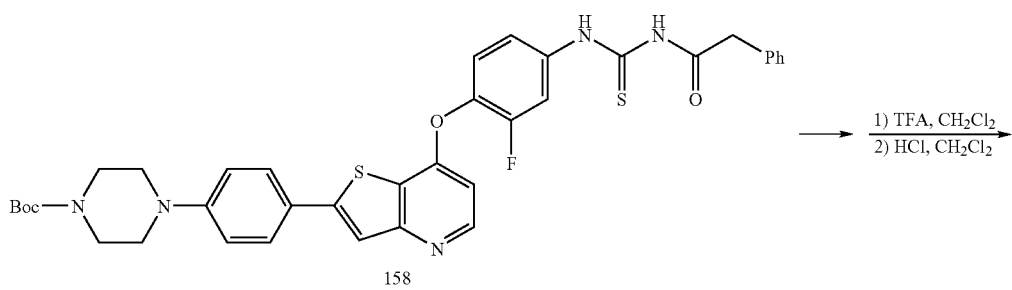
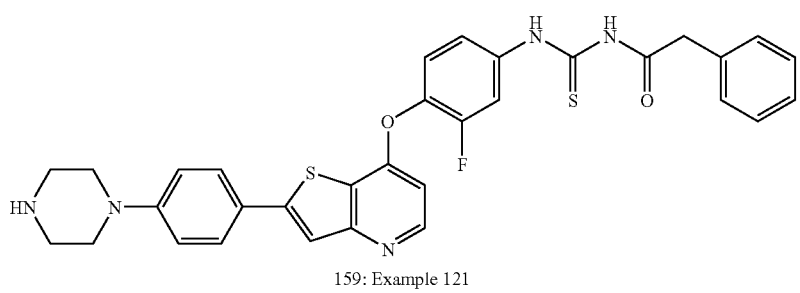

Example 121

N-(3-Fluoro-4-(2-(4-(piperazin-1-yl)phenyl)thieno[3,2-b]pyridin-7-yloxy)phenylcarbamothioyl)-2-phenylacetamide di-hydro chloride (159)

Step 1. tert-Butyl 4-(4-(7-(2-fluoro-4-nitrophenoxy)thieno[3,2-b]pyridin-2-yl)phenyl)piperazine-1-carboxylate (156)

Starting from the nitro-bromo compound 42, following the procedure described above for the synthesis of compound 48 (scheme 10, example 55) but substituting 4,4,5,5-tetramethyl-2-(4-(methylsulfonyl)phenyl)-1,3,2-dioxaborolane for 4-(4-(tert-butoxycarbonyl)piperazin-1-yl)phenylboronic acid, title compound 156 was obtained in 70% yield. LRMS (M+1) 550.6 (100%).

Step 2. tert-Butyl 4-(4-(7-(4-amino-2-fluorophenoxy)thieno[3,2-b]pyridin-2-yl)phenyl)piperazine-1-carboxylate (157)

Following the procedure described above for the synthesis of amine 49 (scheme 10, example 55) but substituting nitro compound 48 for the nitro compound 156, title compound 157 was obtained in 99% yield (crude material, used in the next step without additional purification). LRMS (M+1) 520.2 (100%).

Step 3. tert-Butyl 4-(4-(7-(2-fluoro-4-(3-(2-phenylacetyl)thioureido)phenoxy)thieno[3,2-b]pyridine-2-yl)phenyl)piperazine-1-carboxylate (158)

Following the procedure described above for the synthesis of compound 50 (scheme 10, example 55) but substituting amine 49 for the amine 157, title compound 158 was obtained in 41% yield. LRMS (M+1) 697.2 (100%).

Step 4. N-(3-Fluoro-4-(2-(4-(piperazin-1-yl)phenyl)thieno[3,2-b]pyridin-7-yloxy)phenylcarbamothioyl)-2-phenylacetamide di-hydrochloride (159)

Following the procedure described above for the synthesis of compound 137a (scheme 25, example 97) but substituting compound 135b for the compound 158, title compound 159 was obtained in 21% yield. $^1$H NMR (400 MHz, DMSO-$d_6$) δ ppm: 12.48(s, 1H), 11.84(s, 1H), 9.26(bs, 1H), 8.62(d, J=5.6 Hz, 1H), 8.05(d, J=12.0 Hz, 1H), 7.94(s, 1H), 7.81(d, J=8.8 Hz, 2H), 7.62-7.55(m, 2H), 7.37-7.31(m, 4H), 7.31-7.24(m, 1H), 7.10(d, J=8.8 Hz, 2H), 6.85(d, J=5.6 Hz, 1H), 3.83(s, 2H), 3.58-3.51(m, 4H), 3.26-3.18(m, 4H). LRMS (M+1) 597.2 (100%).

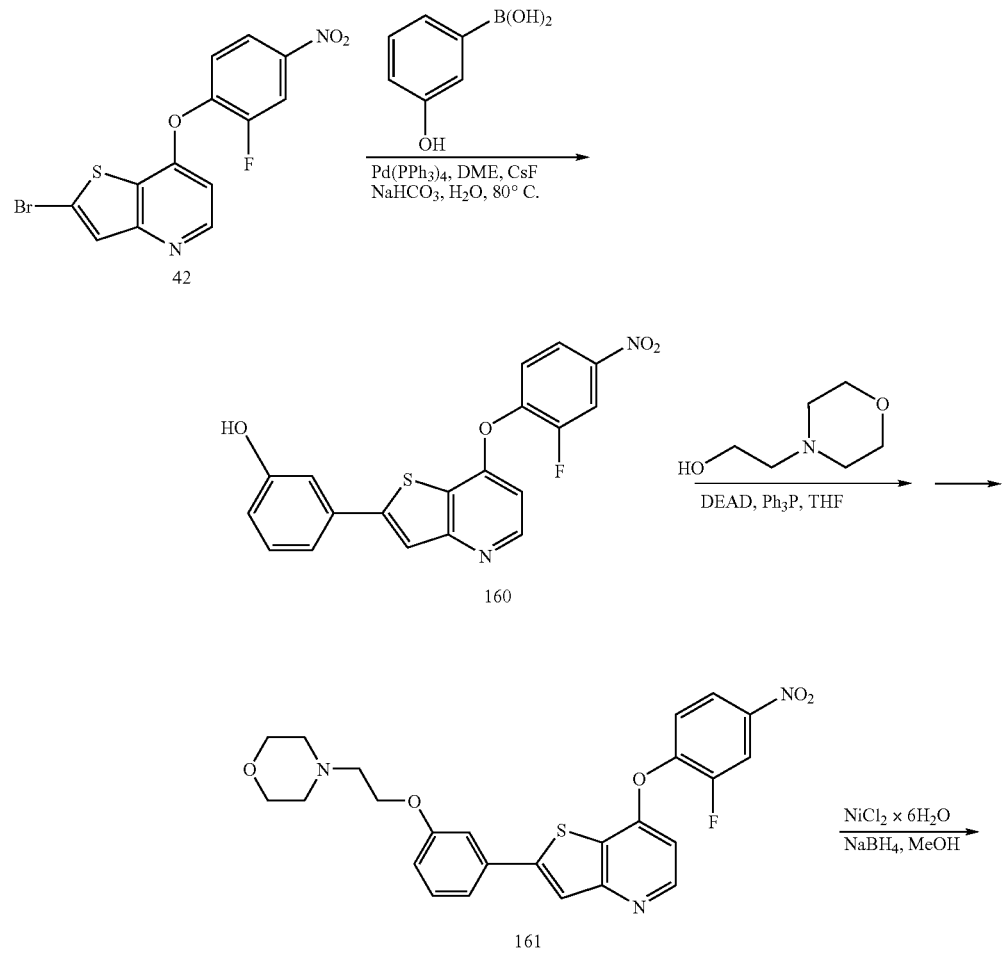

Scheme 31

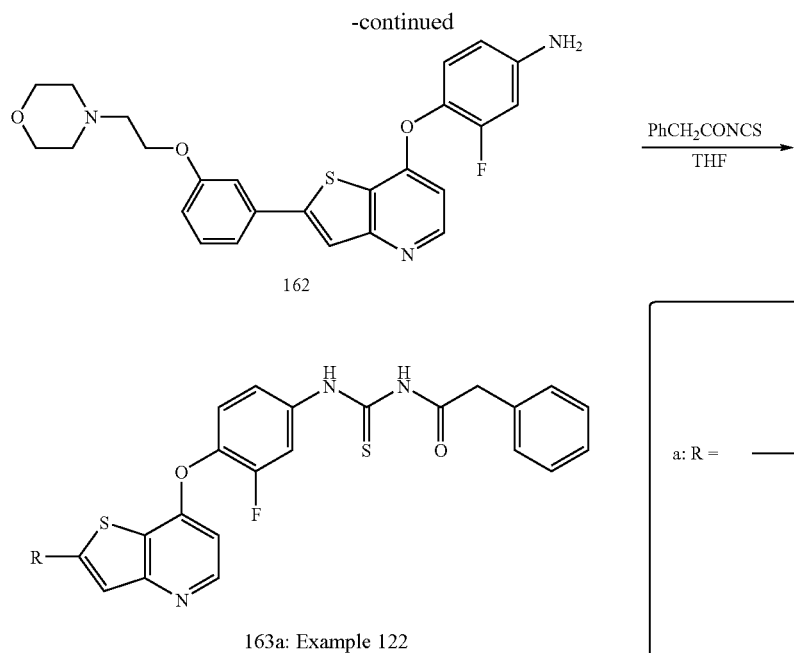

Example 122

N-(3-Fluoro-4-(2-(3-(2-morpholinoethoxy)phenyl)thieno[3,2-b]pyridin-7-yloxy)phenylcarbamothioyl)-2-phenylacetamide (163a)

Step 1. 3-(7-(2-Fluoro-4-nitrophenoxy)thieno[3,2-b]pyridin-2-yl)phenol (160)

Starting from the nitrobromo compound 42, following the procedure described above for the synthesis of compound 153 (scheme 28, example 109) but substituting 4-hydroxyphenylboronic acid for 3-hydroxyphenylboronic acid, title compound 160 was obtained in 66% yield as a gray solid. LRMS (M+1) 383.1 (100%).

Step 2. 4-(2-(3-(7-(2-Fluoro-4-nitrophenoxy)thieno[3,2-b]pyridin-2-yl)phenoxy)ethyl)morpholine (161)

Diethylazodicarboxylate (0.6 mL, 3.84 mmol) was added to the solution of 160 (1.05 g, 2.75 mmol), 2-morpholinoethanol (0.5 mL, 3.84 mmol) and triphenylphosphine (1.01 g, 3.84 mmol) in tetrahydrofuran (27 mL). The reaction mixture was stirred until its completion, quenched with saturated aqueous ammonium chloride and extracted with EtOAc. The organic phase was washed with water and brine, dried over anhydrous magnesium sulfate, filtered and evaporated under reduced pressure. The residue was purified by flash chromatography, eluent MeOH-DCM (2:98) to afford title compound 161 (906 mg, 66%yield) as a light-yellow solid. LRMS (M+1) 496.3 (100%).

Step 3. 3-Fluoro-4-(2-(3-(2-morpholinoethoxy)phenyl)thieno[3,2-b]pyridin-7-yloxy)benzenamine (162)

Following the procedure described above for the synthesis of amine 49 (scheme 10, example 55) but substituting nitro compound 48 for the nitro compound 161, title compound 162 was obtained in 91% yield (crude material, used in the next step without additional purification). LRMS (M+1) 466.2 (100%).

Step 4. N-(3-Fluoro-4-(2-(3-(2-morpholinoethoxy)phenyl)thieno[3,2-b]pyridin-7-yloxy)phenylcarbamothioyl)-2-phenylacetamide (163a)

Following the procedure described above for the synthesis of compound 50 (scheme 10, example 55) but substituting amine 49 for the amine 162, title compound 163a was obtained in 29% yield. Characterization of 163a is provided in the table 15.[LRMS (M+1) 643.3 (100%).

Examples 123-127

N-(3-Fluoro-4-(2-(4-(2-morpholinoethoxy)phenyl)thieno[3,2-b]pyridin-7-yloxy)phenylcarbamothioyl)-2-phenylacetamide (163b)

N-(3-Fluoro-4-(2-(4-(2-(piperidin-1-yl)ethoxy)phenyl)thieno[3,2-b]pyridin-7-yloxy)phenylcarbamothioyl)-2-phenylacetamide (163c)

N-(3-Fluoro-4-(2-(4-(2-(pyridin-2-yl)ethoxy)phenyl)thieno[3,2-b]pyridin-7-yloxy)phenylcarbamothioyl)-2-phenylacetamide hydrochloride (163d)

N-(3-Fluoro-4-(2-(4-(3-morpholinopropoxy)phenyl)thieno[3,2-b]pyridin-7-yloxy)phenylcarbamothioyl)-2-phenylacetamide (163e)

tert-Butyl 2-(4-(7-(2-fluoro-4-(3-(2-phenylacetyl)thioureido)phenoxy)thieno[3,2-b]pyridin-2-yl)phenoxy)ethyl(methyl)carbamate (163f)

Starting from the phenol 153 (scheme 28, example 109) and following the procedures described above for the synthesis of 163a (Scheme 31, Example 122) title compounds 163b-f were obtained. Characterization of 163b-f is provided in the Table 15.

Examples 128-129

N-(3-Fluoro-4-(2-(3-methoxy-4-(2-morpholinoethoxy)phenyl)thieno[3,2-b]pyridin-7-yloxy)phenylcarbamothioyl)-2-phenylacetamide (163g)

N-(3-Fluoro-4-(2-(2-(2-morpholinoethoxy)phenyl)thieno[3,2-b]pyridin-7-yloxy)phenylcarbamothioyl)-2-phenylacetamide hydrochloride (163h)

Following the procedures described above for the synthesis of 163a (Scheme 31, example 122) but replacing in the first step 3-hydroxyphenylboronic acid with 4-hydroxy-3-methoxyphenylboronic acid or 2-hydroxyphenylboronic acid, title compounds 163g-h were obtained. Characterization of 163g-h is provided in the table 15.

TABLE 15

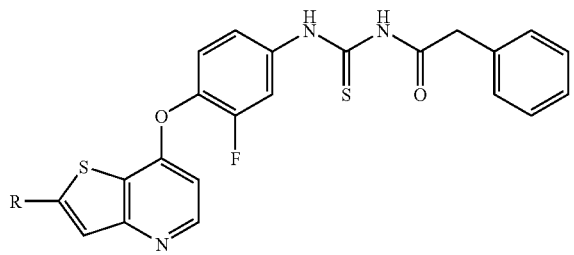

163a–h: Example 122–128

Characterization of compounds 163a-h (examples 122-128)

| Cpd | Ex | R | Name | Characterization |
|---|---|---|---|---|
| 163a | 122 | (3-morpholinoethoxyphenyl) | N-(3-Fluoro-4-(2-(3-(2-morpholinoethoxy)phenyl)thieno[3,2-b]pyridin-7-yloxy)phenylcarbamothioyl)-2-phenylacetamide | $^1$H NMR (400 MHz, DMSO-d$_6$) δ ppm: 12.47(s, 1H), 11.82(s, 1H), 8.52(d, 1H, J=5.5Hz), 8.12(s, 1H), 8.01(d, 1H, J=12.1Hz), 7.54-7.52(m, 2H), 7.45-7.26(m, 8H), 7.04-7.01(m, 1H), 6.65(d, 1H, J=5.3Hz), 4.20(t, 2H, J=5.8Hz), 3.83(s, 2H), 3.57(t, 4H, J=4.6Hz), 2.73(t, 2H,J=5.6Hz), 2.51-2.49(m, 4H). |
| 163b | 123 | (4-morpholinoethoxyphenyl) | N-(3-Fluoro-4-(2-(4-(2-morpholinoethoxy)phenyl)thieno[3,2-b]pyridin-7-yloxy)phenylcarbamothioyl)-2-phenylacetamide | $^1$H NMR (400 MHz, DMSO-d$_6$) δ ppm: 12.46(s, 1H), 11.82(s, 1H), 8.49(s, J=5.6Hz, 1H), 8.00(d, J=12.0Hz, 1H), 7.94(s, 1H), 7.90-7.78(m, 2H), 7.56-7.38(m, 2H), 7.39-7.22(m, 5H), 7.16-7.02(m, 2H), 6.62(d, J=5.6H, 1H), 4.34-3.90(m, 3H), 3.82(s, 2H), 3.76-2.40(m, 9H). |
| 163c | 124 | (4-(2-piperidin-1-yl)ethoxyphenyl) | N-(3-Fluoro-4-(2-(4-(2-(piperidin-1-yl)ethoxy)phenyl)thieno[3,2-b]pyridin-7-yloxy)phenylcarbamothioyl)-2-phenylacetamide | $^1$H NMR (400 MHz, DMSO-d$_6$) δ ppm: 8.52(bs, 1H), 8.38(d, J=5.6Hz, 1H), 8.0(dd, J=2.0 and 12.0Hz, 1H), 7.75(d, J=8.4Hz, 2H), 7.64(s, 1H), 7.44-7.40(m, 1H), 7.38-7.29(m, 5H), 7.29-7.24(m, 1H), 7.07(d, J=8.4Hz, 2H), 6.60(d, J=5.6Hz, 1H), 4.39-4.31(m, 2H), 3.75(s, 2H), 3.39-3.33(m, 2H), 3.20-3.05(m, 4H), 1.89-1.79(m, 4H), 1.70-1.60(m, 2H). |

TABLE 15-continued

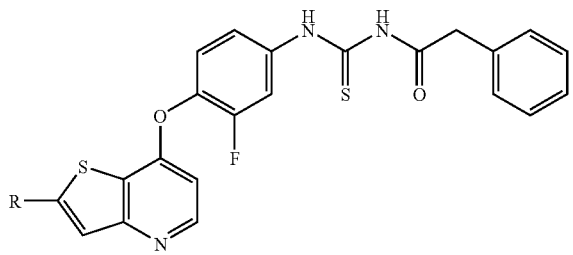

163a–h: Example 122–128

Characterization of compounds 163a-h (examples 122-128)

| Cpd | Ex | R | Name | Characterization |
|---|---|---|---|---|
| 163d | 125 | (4-(2-(pyridin-2-yl)ethoxy)phenyl) | N-(3-Fluoro-4-(2-(4-(2-(pyridin-2-yl)ethoxy)phenyl)thieno[3,2-b]pyridin-7-yloxy)phenylcarbamothioyl)-2-phenylacetamide hydrochloride | ¹H NMR (400 MHz, DMSO-d₆) δ ppm: 12.48(s, 1H), 11.84(s, 1H), 8.81(d, J=4.8Hz, 1H), 8.61(d, J=5.6Hz, 1H), 8.44(t, J=7.6Hz, 1H), 8.35-7.98(m, 2H), 7.97(s, 1H), 7.86(d, J=8.8Hz, 2H), 7.61-7.55(m, 2H), 7.38-7.31(m, 4H), 7.31-7.24(m, 1H), 7.07(d, J=8.8Hz, 2H), 6.82(d, J=5.6Hz, 1H), 4.51(t, J=6.0Hz, 2H), 3.83(s, 2H), 3.52(t, J=6.0Hz, 2H). |
| 163e | 126 | (4-(3-morpholinopropoxy)phenyl) | N-(3-Fluoro-4-(2-(4-(3-morpholinopropoxy)phenyl)thieno[3,2-b]pyridin-7-yloxy)phenylcarbamothioyl)-2-phenylacetamide | ¹H NMR (400 MHz, DMSO-d₆) δ ppm: 12.46(s, 1H), 11.82(s, 1H), 8.48(d, 1H, J=5.3Hz), 8.00(d, 1H, J=12.5Hz), 7.91(s, 1H), 7.80(d, 2H, J=8.8Hz), 7.53(m, 2H), 7.34-7.22(m, 5H), 7.04(d, 2H, J=8.6Hz), 6.61(d, 1H, J=5.7Hz), 4.10-4.07(m, 2H), 3.83(s, 2H), 3.59-3.55(m, 4H),2.50-2.41(m, 6H), 1.92(m, 2H) |
| 163f | 127 | (4-(2-(N-methyl-N-Boc-amino)ethoxy)phenyl) | tert-Butyl 2-(4-(7-(2-fluoro-4-(3-(2-phenylacetyl)thioureido)phenoxy)thieno[3,2-b]pyridin-2-yl)phenoxy)ethyl (methyl)carbamate | ¹H NMR (400 MHz, DMSO-d₆) δ ppm: 12.50(S, 1H), 11.85(s, 1H), 8.50(d, 1H, J=5.5Hz), 8.02(d, 1H, J=13.3Hz), 7.94(s, 1H), 7.83(d, 2H, J=8.8Hz), 7.55-7.54(m, 2H), 7.38-7.26(m, 5H), 7.08(d, 2H, J=8.8Hz), 6.63(d, 1H, J=5.3Hz), 4.17(br s, 2H), 3.83(s, 2H),3.56(m, 2H), 2.90-2.86(m, 3H), 1.40-1.36(m, 9H). |
| 163g | 128 | (3-methoxy-4-(2-morpholinoethoxy)phenyl) | N-(3-Fluoro-4-(2-(3-methoxy-4-(2-morpholinoethoxy)phenyl)thieno[3,2-b]pyridin-7-yloxy)phenylcarbamothioyl)-2-phenylacetamide | ¹H NMR (400 MHz, DMSO-d₆) δ ppm: 8.51(d, 1H, J=5.5Hz), 8.03-8.01(m, 2H), 7.55-7.53(m, 2H), 7.47(d, 1H, J=2.2Hz), 7.39-7.24(m, 6H), 7.10(d, 1H, J=8.6Hz), 6.63 (d, 1H, J=5.5Hz), 4.14(t, 2H, J=5.9Hz), 3.88(s, 3H), 3.83(s, 2H), 3.58(t, 4H, J=4.6Hz), 2.71(t, 2H, J=5.9Hz), 2.46-2.43(m, 4H). |
| 163h | 129 | (2-(2-morpholinoethoxy)phenyl) | N-(3-Fluoro-4-(2-(2-(2-morpholinoethoxy)phenyl)thieno[3,2-b]pyridin-7-yloxy)phenylcarbamothioyl)-2-phenylacetamide hydrochloride | 1H NMR (400 MHz, DMSO-d6) δ ppm: 12.50(s, 1H), 11.86(s, 1H), 11.66-11.50(br s, 1H), 8.79-8.76(m, 1H), 8.37(d, 1H, J=5.9Hz), 8.08(dd, 1H, J=11.3/2.0Hz), 7.93(dd, 1H, J=7.6/1.6Hz), 7.63-7.52(m, 3H), 7.35-7.16(m, 7H), 6.99(t, 1H, J=4.8Hz), 4.71(br s, 2H), 3.93-3.91(m, 2H), 3.84(s, 2H), 3.80-3.77(m, 4H), 3.53-3.50(m, 2H), 3.36-3.33(m, 2H). |

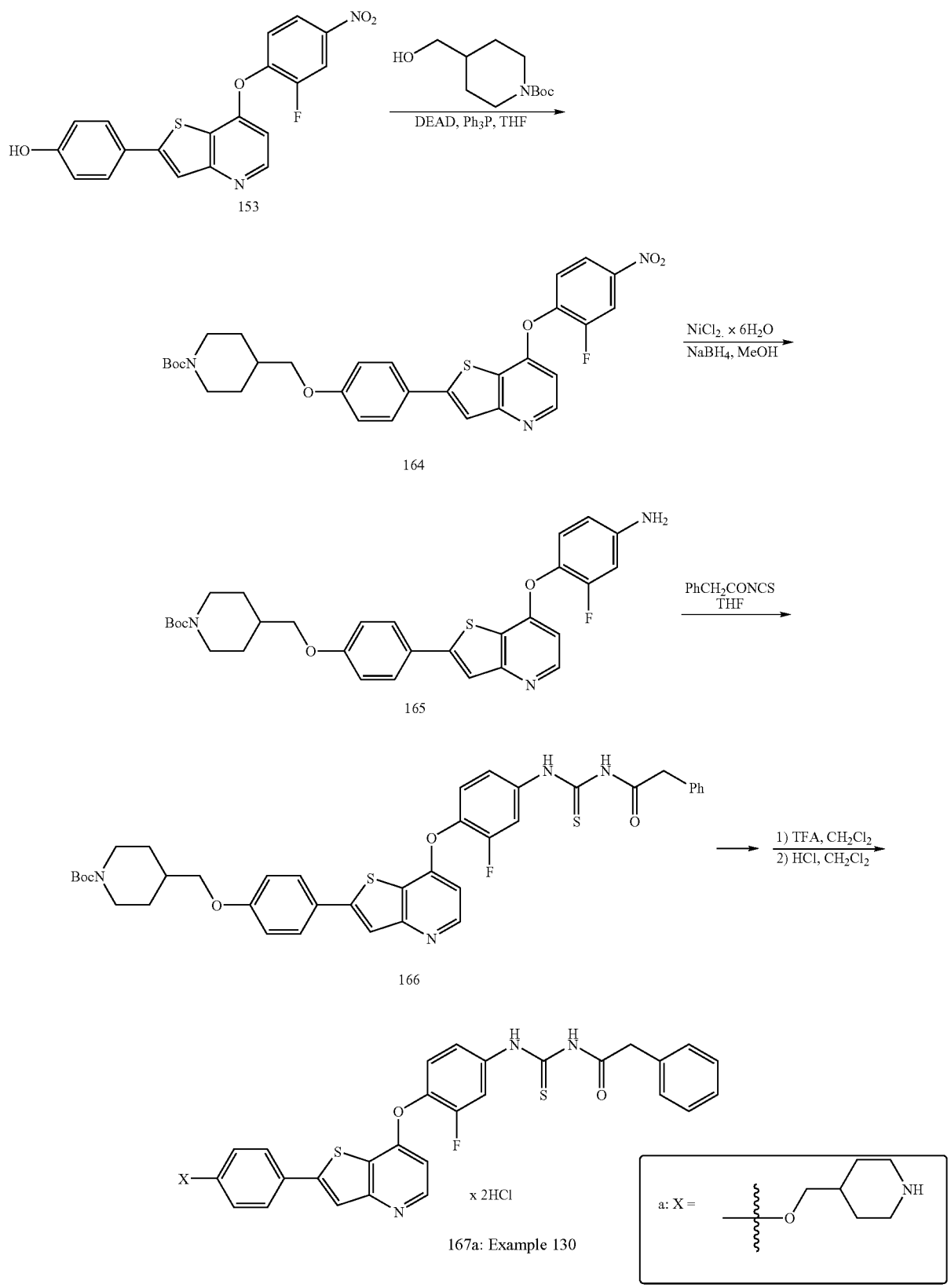

Example 130

N-(3-Fluoro-4-(2-(4-(piperidin-4-ylmethoxy)phenyl)thieno[3,2-b]pyridin-7-yloxy)phenylcarbamothioyl)-2-phenylacetamide (167a)

Step 1. tert-Butyl-4-((4-(7-(2-fluoro-4-nitrophenoxy)thieno[3,2-b]pyridin-2-yl)phenoxy)methyl)piperidine-1-carboxylate (164)

Starting from the compound 153 (shown in the scheme 28) and following the procedure described above for the synthesis of compound 161 (step 2, scheme 31, example 122), title compound 164 was obtained in 69% yield. LRMS (M+1) 579.2 (100%).

Step 2. tert-Butyl 4-((4-(7-(4-amino-2-fluorophenoxy)thieno[3,2-b]pyridin-2-yl)phenoxy)methyl)piperidine-1-carboxylate (165)

Following the procedure described above for the synthesis of amine 157 (scheme 30, example 121) but substituting nitro compound 156 for the nitro compound 164, title compound 165 was obtained in 99% yield (crude material, used in the next step without additional purification). LRMS (M+1) 549.2 (100%).

Step 3. tert-Butyl-4-((4-(7-(2-fluoro-4-(3-(2-phenylacetyl)thioureido)phenoxy)thieno[3,2-b]pyridin-2-yl)phenoxy)methyl)piperidine-1-carboxylate (166)

Following the procedure described above for the synthesis of compound 158 (scheme 30, example 121) but substituting amino compound 157 for the amino compound 165, title compound 166 was obtained in 31% yield. LRMS (M+1) 726.2 (100%).

Step 4. N-(3-Fluoro-4-(2-(4-(piperidin-4-ylmethoxy)phenyl)thieno[3,2-b]pyridin-7-yloxy)phenylcarbamothioyl)-2-phenylacetamide di-hydrochloride (167a)

Following the procedure described above for the synthesis of compound 159 (scheme 30, example 121) but substituting Boc-protected amino compound 158 for the Boc-protected amino compound 166, title compound 167a (presumably as a di-hydrochloride salt) was obtained in 15% yield. Characterization of 167a is provided in the table 16. LRMS (M+1) 626.2 (100%).

Example 131-132

(S)—N-(3-Fluoro-4-(2-(4-(pyrrolidin-2-ylmethoxy)phenyl)thieno[3,2-b]pyridin-7-yloxy)phenylcarbamothioyl)-2-phenylacetamide (167b) and N-(4-(2-(4-(4-Aminobutoxy)phenyl)thieno[3,2-b]pyridin-7-yloxy)-3-fluorophenylcarbamothioyl)-2-phenylacetamide (167c)

Following the procedures described above for the synthesis of 167a (scheme 32, example 130) but replacing in the first step tert-butyl 4-(hydroxymethyl)piperidine-1-carboxylate with (S)-tert-butyl2-(hydroxymethyl)pyrrolidine-1-carboxylate or tert-butyl 4-hydroxybutylcarbamate, title compounds 167b-c were obtained. Characterization of 167b-c is provided in the table 16.

TABLE 16

167a–c: Examples 130–132

Characterization of compounds 167a-c (examples 130-132)

| Cpd | Ex | X | Name | Characterization |
| --- | --- | --- | --- | --- |
| 167a | 130 | 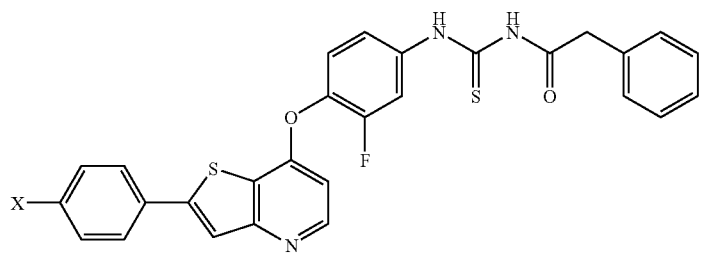 | N-(3-Fluoro-4-(2-(4-(piperidin-4-ylmethoxy)phenyl)thieno[3,2-b]pyridin-7-yloxy)phenylcarbamothioyl)-2-phenylacetamide di-hydrochloride | $^1$H NMR (400 MHz, DMSO-$d_6$) δ ppm: 8.41(d, J=5.6hz, 1H), 8.06(dd, J=3.2 and 12.4Hz, 1H), 7.75(d, J=8.8Hz, 2H), 7.65(s, 1H), 7.37-7.43(m, 1H), 7.39(d, J=8.4Hz, 1H), 7.37-7.33(m, 4H), 7.33-7.25(m, 1H), 7.04(d, J=8.8Hz, 2H), 6.64(d, J=5.6Hz, 1H), 3.98(d,J=5.6Hz, 2H), 3.76(s, 2H), 3.50-3.42(m, 2H), 3.12-3.01(m, 2H), 2.25-2.16(m, 1H), 2.162.06(m, 2H), 1.92-1.58(m, 2H). |

TABLE 16-continued

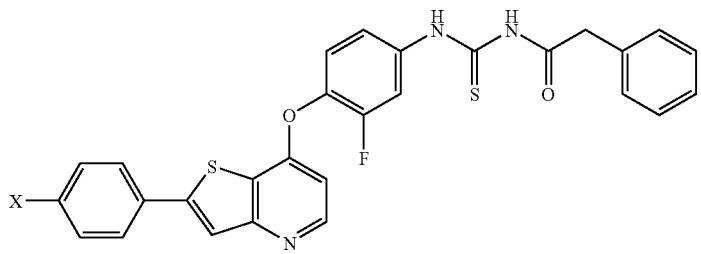

167a–c: Examples 130–132

Characterization of compounds 167a-c (examples 130-132)

| Cpd | Ex | X | Name | Characterization |
|---|---|---|---|---|
| 167b | 131 | ![pyrrolidinylmethoxy] | (S)-N-(3-Fluoro-4-(2-(4-(pyrrolidin-2-ylmethoxy)phenyl)thieno[3,2-b]pyridin-7-yloxy)phenylcarbamothioyl)-2-phenylacetamide di-hydrochloride | $^1$H NMR (400 MHz, DMSO-d$_6$) δ ppm: 12.46(s, 1H), 11.82(s, 1H), 8.49(d, J=5.6Hz, 1H), 8.04-7.88(m, 1H), 7.96(s, 1H), 7.86(d, J=8.8Hz, 1H), 7.56-7.51(m, 2H), 7.36-7.31(m, 4H), 7.31-7.24(m, 1H), 7.11(d, J=8.8Hz, 2H), 6.63(d, J=5.6Hz, 1H), 4.34(dd, J=4.4 and 10.8Hz, 1H), 4.20-4.12(m, 1H), 4.00-3.90(m, 1H), 3.82(s, 2H), 3.28-3.18(m, 2H), 2.20-2.10(m, 1H), 2.05-1.88(m, 2H), 1.82-1.70(m, 1H). |
| 167c | 132 | —O(CH$_2$)$_4$NH$_2$ | N-(4-(2-(4-(4-Aminobutoxy)phenyl)thieno[3,2-b]pyridin-7-yloxy)-3-fluorophenylcarbamothioyl)-2-phenylacetamide di-hydrochloride | $^1$H NMR (400 MHz, DMSO-d$_6$) δ ppm: 8.40(d, J=5.6Hz, 1H), 8.05(dd, J=3.2 and 12.0Hz, 1H), 7.75(d, J=8.8Hz, 2H), 7.64(s, H), 7.48-7.43(m, 1H), 7.39(d, J=8.8Hz, 1H), 7.37-7.31(m, 4H), 7.31-7.24(m, 1H), 7.03(d, J=8.8Hz, 2H), 6.64(d, j=5.6Hz, 1H), 4.11(t, J=5.6Hz, 2H), 3.76(s, 2H), 3.03(t, J=7.2Hz, 2H), 1.99-1.83(m, 4H). |

Scheme 33

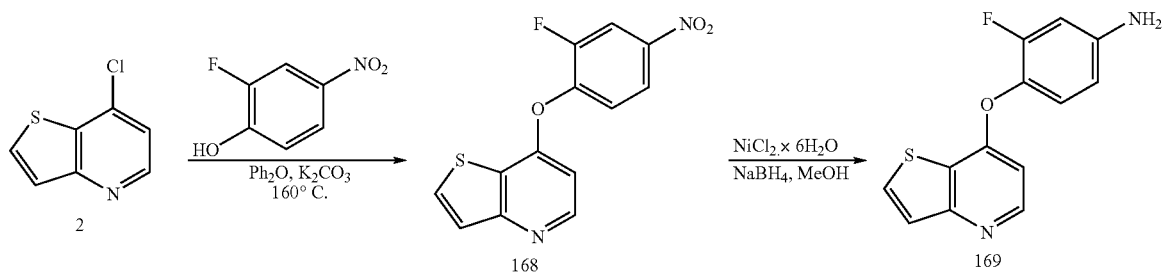

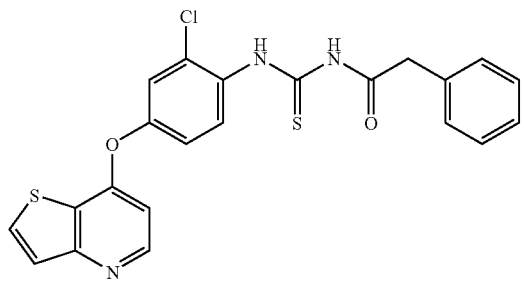

170b: Example 134

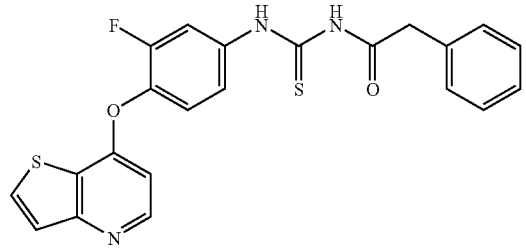

170a: Example 133

Example 133

N-(3-Fluoro-4-(thieno[3,2-b]pyridin-7-yloxy)phenyl-carbamothioyl)-2-phenylacetamide (170a)

Step 1.
7-(2-Fluoro-4-nitrophenoxy)thieno[3,2-b]pyridine (168)

Starting from the chloride 2 (scheme 1) and following the procedure described above for the synthesis of compound 6 (scheme 1, example 1), title compound 168 was obtained in 45% yield. LRMS (M+1) 290.3 (100%).

Step. 3-Fluoro-4-(thieno[3,2-b]pyridin-7-yloxy)benzenamine (169)

Starting from the nitro compound 168 and following the procedure described above for the synthesis of amine 49 (scheme 10, example 55), title compound 169 was obtained in 41% yield. LRMS (M+1) 260.3 (100%).

Step 3. N-(3-Fluoro-4-(thieno[3,2-b]pyridin-7-yloxy)phenylcarbamothioyl)-2-phenylacetamide (170a)

Starting from the amine 169 and following the procedure described above for the synthesis of compound 50 (scheme 10, example 55), title compound 170a was obtained in 29% yield. $^1$H NMR (400 MHz, DMSO-$d_6$) δ ppm: 12.46(s, 1H), 11.81(s, 1H), 8.52(d, J=5.2 Hz, 1H), 8.17(d, J=5.2 Hz, 1H), 8.01(dd, J=2.0 and 11.2 Hz, 1H), 7.60(d, J=5.2 Hz, 1H), 7.58-7.48(m, 2H), 7.36-7.30(m, 4H), 7.30-7.22(m, 1H), 6.64 (d, J=5.2 Hz, 1H), 3.82(s, 2H). LRMS (M+1) 437.5 (100%).

Example 134

N-(2-Chloro-4-(thieno[3,2-b]pyridin-7-yloxy)phenylcarbamothioyl)-2-phenylacetamide (170b)

Title compound 170b (example 134) was obtained according to the scheme 33 via a 3-step synthesis starting from the chloride 2 and replacing 2-fluoro-4-nitrophenol [in the step 1] with 3-chloro-4-nitrophenol. $^1$H NMR (400 MHz, DMSO-$d_6$) δ ppm: 12.36(s, 1H), 11.88(s, 1H), 8.55(d, J=5.6 Hz, 1H), 8.159d, J=5.6 Hz, 1H), 8.08(d, J=8.8 Hz, 1H), 7.61(d, J=2.8 Hz, 1H), 7.60(d, J=5.6 Hz, 1H), 7.36-7.30(m, 4H), 7.32(m, J=2.8 Hz, 1H), 7.30-7.24(m, 1H), 6.73(d, J=5.6 Hz, 1H), 3.84(s, 2H).

Scheme 34

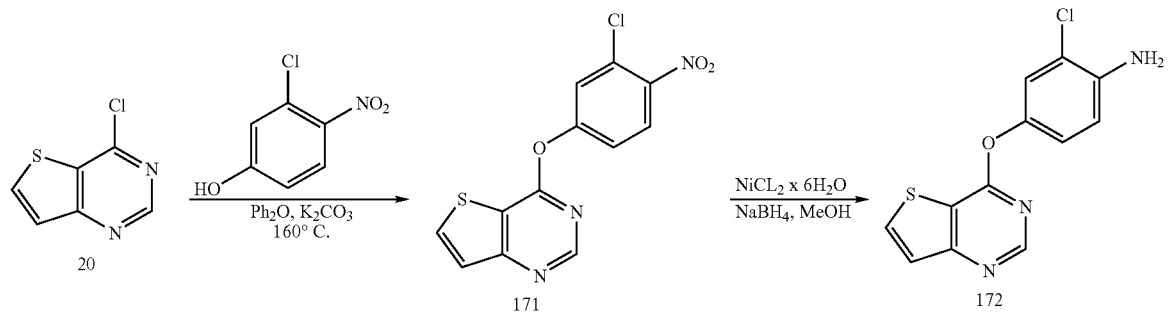

PhCH$_2$CONCS
THF

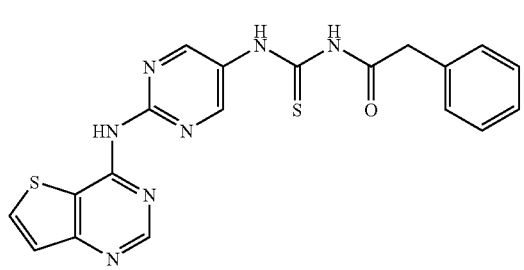

174: Example 136

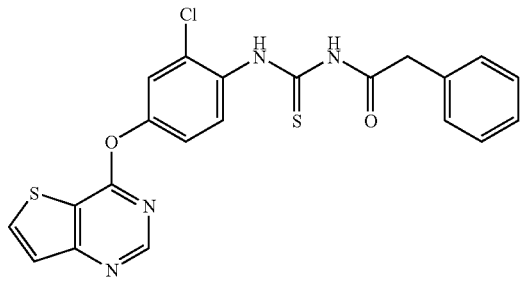

173: Example 135

Example 135

N-(2-Chloro-4-(thieno[3,2-d]pyrimidin-4-yloxy)phenylcarbamothioyl)-2-phenylacetamide (173)

Step 1. 4-(3-Chloro-4-nitrophenoxy)thieno[3,2-d]pyrimidine (171)

Starting from the chloride 20 (scheme 4) and following the procedure described above for the synthesis of compound 24 (scheme 4, example 22) remplacing 2-fluoro-4-nitrophenol with 3-chloro-4-nitrophenol, title compound 171 was obtained in 72% yield. LRMS (M+1) 307.7 (100%).

Step 2. 2-Chloro-4-(thieno[3,2-d]pyrimidin-4-yloxy)benzenamine (172)

Starting from the nitro compound 171 and following the procedure described above for the synthesis of amine 25 (scheme 4, example 22), title compound 172 was obtained in 80% yield. LRMS (M+1) 277.7 (100%).

Step 3. N-(2-Chloro-4-(thieno[3,2-d]pyrimidin-4-yloxy)phenylcarbamothioyl)-2-phenylacetamide (173)

Starting from the amine 172 and following the procedure described above for the synthesis of compound 26a (scheme 4, example 22), title compound 173 was obtained in 9% yield. $^1$H NMR (400 MHz, DMSO-d$_6$) δ ppm: 12.35(s, 1H), 11.89 (s, 1H), 8.72(s, 1H), 8.48(d, J=5.6 Hz, 1H), 8.04(d, J=8.8 Hz, 1H), 7.69(d, J=2.8 Hz, 1H), 7.68(d, J=5.6 Hz, 1H), 7.40(dd, J=2.8 and 8.8 Hz, 1H), 7.36-7.30(m, 4H), 7.30-7.24(m, 1H), 3.84(s, 2H). LRMS (M+1) (100%).

Example 136

2-Phenyl-N-(2-(thieno[3,2-d]pyrimidin-4-ylamino)pyrimidin-5-ylcarbamothioyl)acetamide (174)

Title compound 174 (example 136) was obtained according to the scheme 34 via a 3-step synthesis starting from the chloride 20 and replacing 3-chloro-4-nitrophenol [in the step 1] with 5-nitropyrimidin-2-amine. $^1$H NMR (400 MHz, DMSO-d$_6$) δ ppm: 11.85(bs, 2H), 10.91(bs, 1H), 8.71(s, 1H), 8.64(s, 2H), 8.63-8.61(m, 1H), 8.25(d, J=5.6 Hz, 1H), 7.45(d, J=5.6 Hz, 1H), 7.34-7.27(m, 4H), 7.27-7.21(m, 1H), 3.79(s, 2H).

Scheme 35

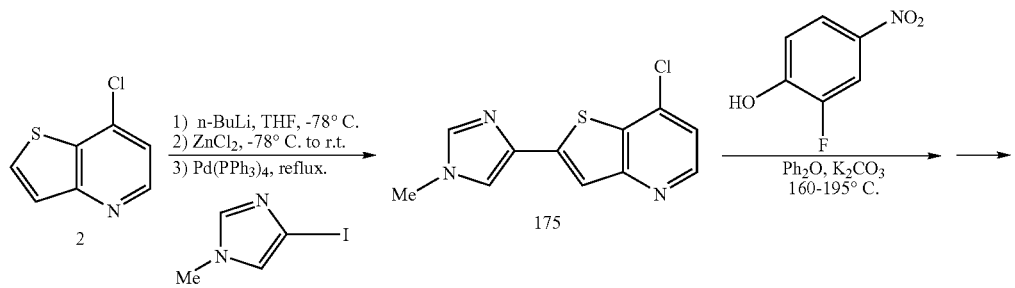

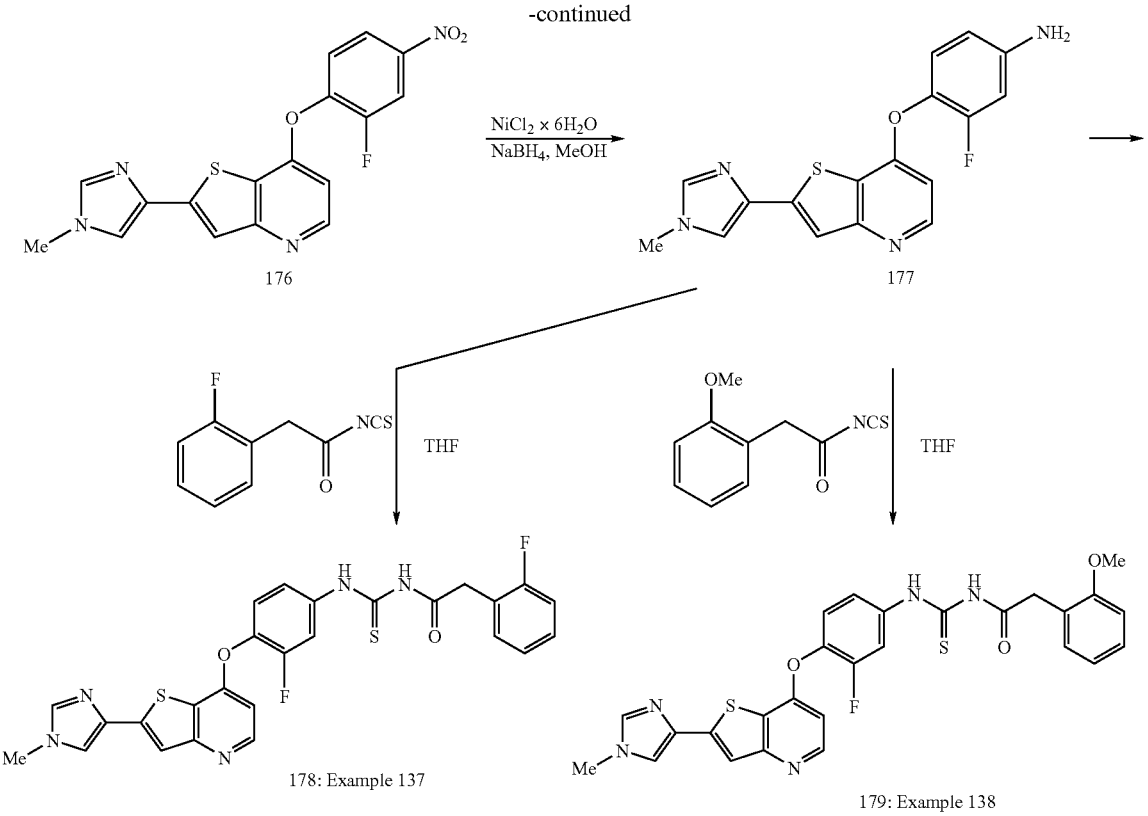

178: Example 137

179: Example 138

Example 137

N-(3-Fluoro-4-(2-(1-methyl-1H-imidazol-4-yl)thieno[3,2-b]pyridin-7-yloxy)phenylcarbamothioyl)-2-(2-fluorophenyl)acetamide (178)

Step 1. 7-Chloro-2-(1-methyl-1H-imidazol-4-yl)thieno[3,2-b]pyridine (175)

To a solution of chloride 2 (scheme 1) (2.45 g, 14.4 mmol) in THF (48 mL) at −78° C. was slowly added n-BuLi (2.5M in hexane, 7.2 mL, 18.0 mmol). The reaction mixture was stirred for one hour [at −78° C.] followed by slow addition of ZnCl (0.5M in THF, 36 mL, 18.0 mmol). In a few minutes the reaction mixture was allowed to warm to room temperature and stirred for one hour.

A solution of 4-iodo-1-methyl-1H-imidazole (1.50 g, 7.2 mmol) [*Tet. Lett.* 2004, 45, 5529] in THF (5 mL) and the tetrakis(triphenylphosphine) palladium (0) (0.83 g, 0.72 mmol) were added to the reaction mixture which was heated to reflux for 1 hour, cooled to room temperature, diluted with aqueous ammonium hydroxide and, finally neutralized with a 1N HCl solution. The acidic solution was extracted with DCM, the extract was washed with water and brine, dried over anhydrous magnesium sulfate, filtered and evaporated under reduced pressure. The residue was purified by flash chromatography (eluents DCM, then DCM-MeOH, 97:3) to afford title compound 175 (1.45 g, 81% yield) as a yellow solid. LRMS (M+1) 263.9 (100%), 265.9 (33%).

Step 2. 7-(2-Fluoro-4-nitrophenoxy)-2-(1-methyl-1H-imidazol-4-yl)thieno[3,2-b]pyridine (176)

Starting from the chloride 175 and following the procedure described above for the synthesis of compound 11 (scheme 2, example 12), title compound 176 was obtained in 47% yield. LRMS (M+1) 371.0 (100%).

Step 3. 3-Fluoro-4-(2-(1-methyl-1H-imidazol-4-yl)thieno[3,2-b]pyridin-7-yloxy)benzenamine (177)

Starting from the nitro compound 176 and following the procedure described above for the synthesis of amine 49 (scheme 10, example 55), title compound 177 was obtained in 74% yield. LRMS (M+1) 341.0 (100%).

Step 4. N-(3-Fluoro-4-(2-(1-methyl-1H-imidazol-4-yl)thieno[3,2-b]pyridin-7-yloxy)phenylcarbamothioyl)-2-(2-fluorophenyl)acetamide (178)

Starting from the amine 177, following the procedure described above for the synthesis of compound 50 (scheme 10, example 55) but replacing 2-phenylacetyl isothiocyanate with 2-(2-fluorophenyl)acetyl isothiocyanate, title compound 178 was obtained in 24% yield. $^1$H NMR (400 MHz, DMSO-$d_6$) δ ppm: 12.44 (s, 1H), 11.88 (s, 1H), 8.46 (d, 1H, J=5.5 Hz), 8.34 (dd, 1H, J=12.3/2.2 Hz), 7.87 (d, 1H, J=1.2 Hz), 7.72 (d, 1H, J=1.2 Hz), 7.69 (s, 1H), 7.57-7.49 (m, 2H), 7.43-7.31 (m, 2H), 7.23-7.15 (m, 2H), 6.59 (d, 1H, J=5.5 Hz), 3.94 (s, 2H), 3.73 (s, 3H). LRMS (M+1) 536.1 (100%).

Example 138

N-(3-Fluoro-4-(2-(1-methyl-1H-imidazol-4-yl)thieno[3,2-b]pyridin-7-yloxy)phenylcarbamothioyl)-2-(2-methoxyphenyl)acetamide (179)

Starting from the amine 177, following the procedure described above for the synthesis of compound 50 (scheme 10, example 55) but replacing 2-phenylacetyl isothiocyanate with 2-(2-methoxyphenyl)acetyl isothiocyanate, title compound 179 was obtained in 52% yield. $^1$H NMR (400 MHz, DMSO-$d_6$) δ ppm: 12.58 (s, 1H), 11.75 (s, 1H), 8.46 (d, 1H, J=5.5 Hz), 8.72 (dd, 1H, J=12.3/2.2 Hz), 7.86 (d, 1H, J=1.2 Hz), 7.72 (d, 1H, J=0.8 Hz), 7.70 (s, 1H), 7.57-7.49 (m, 2H), 7.30-7.23 (m, 2H), 7.00 (d, 1H, J=7.8 Hz), 6.92 dt, 1H, J=7.3/0.9 Hz), 6.58 (d, 1H, J=5.1 Hz), 3.82 (s, 2H), 3.79 (s, 3H), 3.72 (s, 3H).

Scheme 36

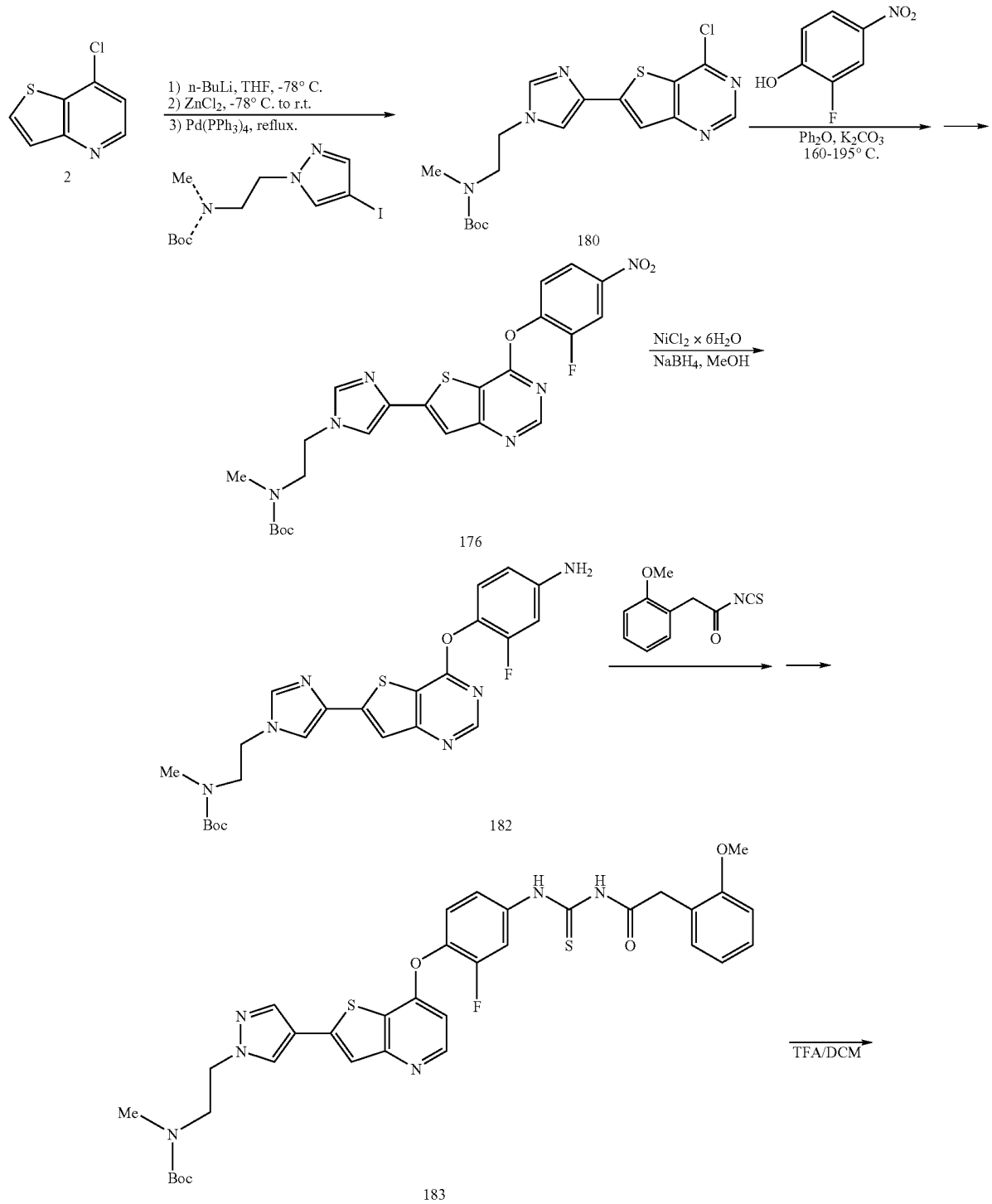

-continued

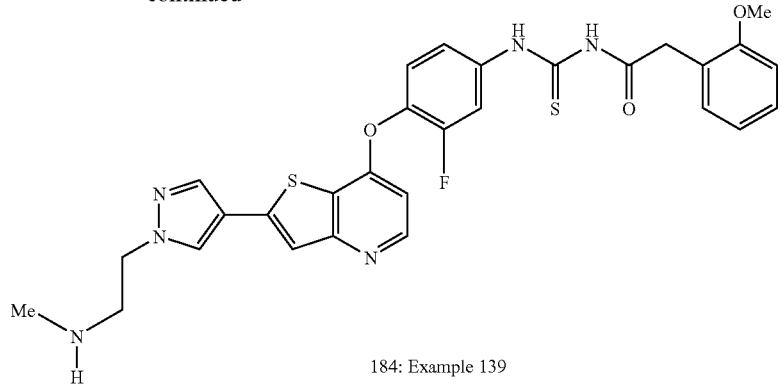

184: Example 139

Example 139

N-(3-Fluoro-4-(2-(1-(2-(methylamino)ethyl)-1H-pyrazol-4-yl)thieno[3,2-b]pyridin-7-yloxy)phenyl-carbamothioyl)-2-(2-methoxyphenyl)acetamide (184)

Step 1. tert-Butyl 2-(4-(7-chlorothieno[3,2-b]pyridin-2-yl)-1H-pyrazol-1-yl)ethyl(methyl)carbamate (180)

Starting from the chloride 2 and following the procedure described above for the synthesis of 175 (scheme 35, example 138), but replacing 4-iodo-1-methyl-1H-imidazole with tert-butyl 2-(4-iodo-1H-pyrazol-1-yl)ethyl(methyl)carbamate, title compound 180 was obtained in 75% yield. LRMS (M+1) 393.1 (100%).

Step 2. tert-Butyl 2-(4-(7-(2-Fluoro-4-nitrophenoxy)thieno[3,2-b]pyridin-2-yl)-1H-pyrazol-1-yl)ethyl(methyl)carbamate (181)

Starting from the chloride 180 and following the procedure described above for the synthesis of compound 11 (scheme 2, example 12), title compound 181 was obtained in 37% yield. LRMS (M+1) 514.1 (100%).

Step 3. tert-Butyl 2-(4-(7-(4-amino-2-fluorophenoxy)thieno[3,2-b]pyridin-2-yl)-1H-pyrazol-1yl)ethyl(methyl)carbamate (182)

Starting from the nitro compound 181 and following the procedure described above for the synthesis of amine 49 (scheme 10, example 55), title compound 182 was obtained in 22% yield. LRMS (M+1) 484.2 (100%).

Step 4. tert-Butyl 2-(4-(7-(2-fluoro-4-(3-(2-(2-methoxyphenyl)acetyl)thioureido)phenoxy)thieno[3,2-b]pyridin-2-yl)-1H-pyrazol-1-yl)ethyl(methyl)carbamate (183)

Starting from the amine 182, following the procedure described above for the synthesis of compound 50 (scheme 10, example 55) but replacing 2-phenylacetyl isothiocyanate with 2-(2-methoxyphenyl)acetyl isothiocyanate, title compound 183 was obtained in 90% yield. LRMS (M+1) 691.2 (100%).

Step 5. N-(3-Fluoro-4-(2-(1-(2-(methylamino)ethyl)-1H-pyrazol-4-yl)thieno[3,2-b]pyridin-7-yloxy)phenylcarbamothioyl)-2-(2-methoxyphenyl)acetamide (184)

Starting from the compound 183 and following the procedure described above for the synthesis of compound 159 (scheme 30, step 4, example 121), title compound 184 was obtained in 66% yield. $^1$H NMR (400 MHz, DMSO-d$_6$) δ ppm: 8.45(d, J=5.6 Hz, 1H), 8.33(s, 1H), 8.00(s, 1H), 7.85-7.75(m, 1H), 7.69(s, 1H), 7.39(t, J=8.4 Hz, 1 H), 7.35-7.28 (m, 1H), 7.28-7.22(m, 1H), 7.22(d, J=7.6 Hz, 1H), 6.97(d, J=8.4 Hz, 1H), 6.89(t, J=7.6 Hz, 1H), 6.57(d, J=5.6 Hz, 1H), 4.19(t, J=6.4 Hz, 2H), 3.82(s, 2H), 3.77(s, 3H), 2.88(t, J=6.4 Hz, 2H), 2.28(s, 3H).

Example 140

N-(3-Fluoro-4-(2-(1-(2-morpholinoethyl)-1H-imidazol-4-yl)thieno[3,2-b]pyridin-7-yloxy)phenylcarbamothioyl)-2-(2-methoxyphenyl)acetamide (185)

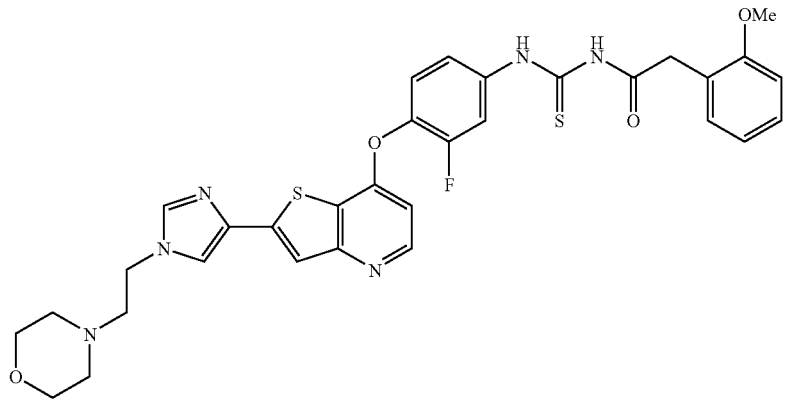

185: Example 140

Title compound 185 (example 140) was obtained following the procedures described above for compound 183 [according to the scheme 36] via a 4-step synthesis starting from chloride 2 and replacing tert-butyl 2-(4-iodo-1H-pyrazol-1-yl)ethyl(methyl)carbamate [in the step 1] with 4-(2-(4-iodo-1H-imidazol-1-yl)ethyl)morpholine [*Tet. Lett.* 2004, 45, 5529]. $^1$H NMR (400 MHz, DMSO-$d_6$) δ ppm: 12.56(s, 1H), 11.75(s, 1H), 8.55(d, J=5.6 Hz, 1H), 8.50 -8.20(m, 1H), 7.93 (d, J=1.2 Hz, 1H), 7.78(s, 1H), 7.60-7.55(m, 2H), 7.35(d, J=1.2 Hz, 1H), 7.32-7.25(m, 1H), 7.23(dd, J=1.6 and 7.2 Hz, 1H), 7.00(d, J=7.6 Hz, 1H), 6.92(td, J=0.8 and 7.6 Hz, 1H), 6.69(d, J=5.6 Hz, 1H), 4.35(t, J=6.0 Hz, 2H), 3.81(s, 2H), 3.78(s, 3H), 3.48(t, J=4.4 Hz, 4H), 2.59(t, J=6.0 Hz, 2H), 2.35(t, J=4.4 Hz, 4H).

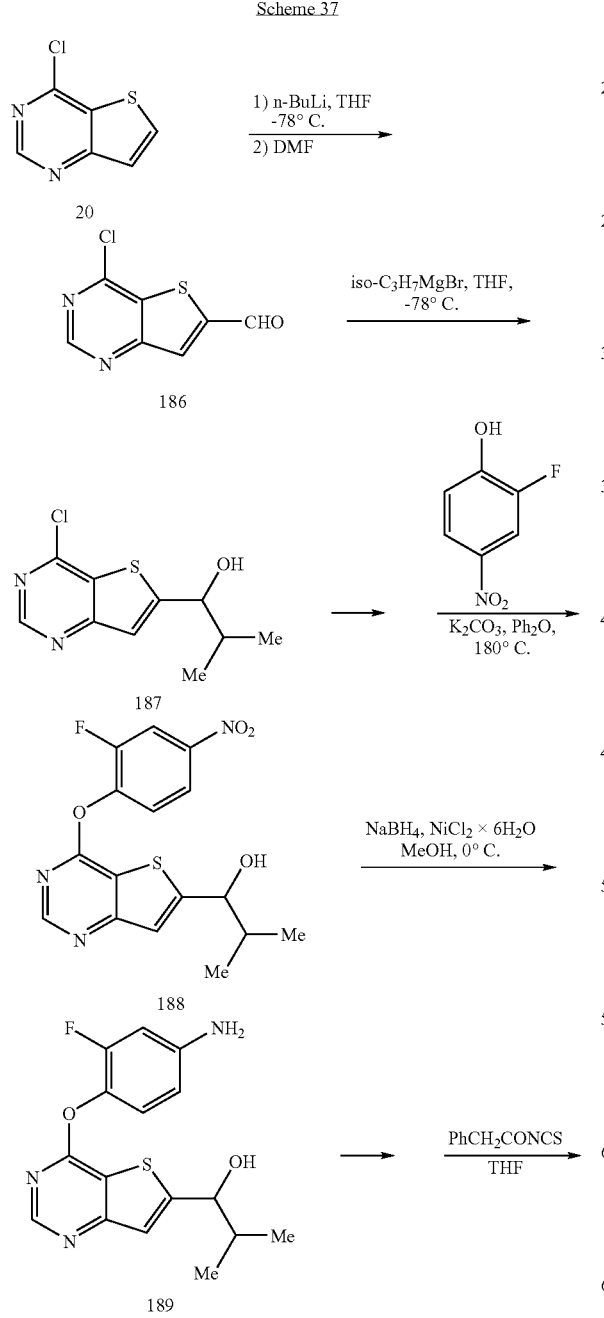

Scheme 37

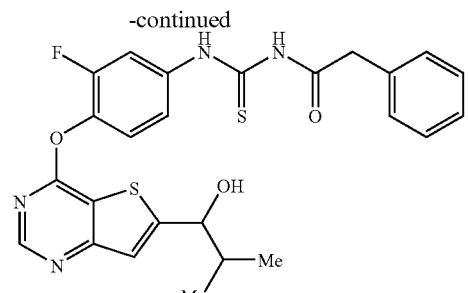

190: Example 141

Example 141

N-(3-Fluoro-4-(6-(1-hydroxy-2-methylpropyl)thieno[3,2-d]pyrimidin-4-yloxy)phenylcarbamothioyl)-2-phenylacetamide (190)

Step 1.
4-Chloro-thieno[3,2-d]pyrimidine-6-carbaldehyde (186)

Starting from 4-chloro-thieno[3,2-d]pyrimidine (20, scheme 4) and following procedure described above for the synthesis of aldehyde 14 (scheme 3, step 1, example 20), title compound 186 was obtained in 84% yield. LRMS (M+1) 199.0 (100%).

Steps 2-3.1-[4-(2-Fluoro-4-nitro-phenoxy)-thieno[3,2-d]pyrimidin-6-yl]-ethanol (188)

Starting from the aldehyde 186 and following procedures described above for the synthesis of nitro compound 16 (scheme 3, steps 2-3, example 20), title compound 188 was obtained [via the intermediate alcohol 187], in 25% yield. LRMS (M+1) 336.0 (100%).

Steps 3-4. N-(3-Fluoro-4-(6-(1-hydroxy-2-methylpropyl)thieno[3,2-d]pyrimidin-4-yloxy)phenylcarbamothioyl)-2-phenylacetamide (190)

Starting from the nitro compound 188 and following procedures described above for the synthesis of compound 18a (scheme 3, steps 4-5, example 20), title compound 190 was obtained [via the intermediate amino alcohol 189], in 24% yield. $^1$H NMR (400 MHz, DMSO-$d_6$) δ ppm: 12.42(s, 1H), 11.80(s, 1H), 8.64(s, 1H), 7.90(dd, J=2.0 and 12.0 Hz, 1H), 7.52(t, J=H), 7.528.4 Hz, 1H), 7.48(d, J=0.8 Hz, 1H), 7.46 (dd, J=2.0 and 8.4 Hz, 1H), 7.36-7.31(m, 4H), 7.31-7.24(m, 1H), 6.15(d, 4.8 Hz, 1H), 4.82(td, J=0.8 and 5.2 Hz, 1H), 3.82(s, 1.98(m, 1H), 0.93(d, J=6.8 Hz, 3H), 0.90(d, J=6.8 Hz, 3H).

Examples 142-148

N-(3-Fluoro-4-(6-(pyrrolidine-1-carbonyl)thieno[3,2-d]pyrimidin-4-yloxy)phenylcarbamothioyl)-2-phenylacetamide (26f)

N-(4-(2-(Azetidine-1-carbonyl)thieno[3,2-b]pyridine-7-yloxy)-3-fluorophenylcarbamothioyl)-2-phenylacetamide hydrochloride (26 g)

1-(4-(6-(N-Ethyl-N-methylcarbamoyl)thieno[3,2-d]pyrimidin-4-yloxy)-3-fluorophenyl)-3-(2-phenylacetyl)thiourea (26h)

N,N-Diethyl-4-(2-fluoro-4-(3-(2-phenylacetyl)thioureido)phenoxy)thieno[3,2-d]pyrimidine-6-carboxamide (26i)

(R)—N-(3-Fluoro-4-(6-(2-(hydroxymethyl)pyrrolidine-1-carbonyl)thieno[3,2-d]pyrimidin-4-yloxy)phenylcarbamothioyl)-2-phenylacetamide (26j)

(S)—N-(4-(6-(3-(tert-Butyldimethylsilyloxy)pyrrolidine-1-carbonyl)thieno[3,2-d]pyrimidin-4-yloxy)-3-fluorophenylcarbamothioyl)-2-phenylacetamide (26k)

tert-Butyl 1-(4-(2-fluoro-4-(3-(2-phenylacetyl)thioureido)phenoxy)thieno[3,2-d]pyrimidine-6-carbonyl)pyrrolidin-3-ylcarbamate (26l)

Compounds 26f-l (examples 142-148) were obtained by following the procedures described above for the compound 26a (example 22, scheme 4). Characterization of 26f-l is provided in the table 17.

TABLE 17

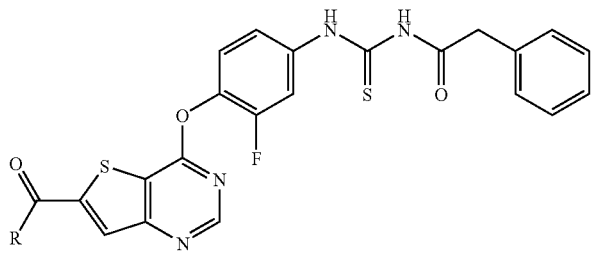

26f-l: Examples 142–148

Characterization of compounds 26f-l (examples 142-148)

| Cpd | Ex | R | Name | Characterization |
|---|---|---|---|---|
| 26f | 142 | pyrrolidin-1-yl | N-(3-Fluoro-4-(6-(pyrrolidine-1-carbonyl)thieno[3,2-d]pyrimidin-4-yloxy)phenylcarbamothioyl)-2-phenylacetamide | $^1$H NMR (400 MHz, DMSO-$d_6$) δ (ppm): 12.42(s, 1H), 11.79(s, 1H), 8.77(s, 1H), 8.11(s, 1H), 7.92(dd, J = 2.0 and 11.6Hz, 1H), 7.54(t, J = 8.4Hz, 1H), 7.47(dd, J = 2.0 and 8.4Hz, 1H), 7.36-7.31(m, 4H), 7.30-7.32(m, 1H), 3.85(t, J = 6.4Hz, 2H), 3.82(s, 2H), 3.55(t, J = 6.4Hz, 2H), 1.96(quin, J = 6.4Hz, 2H), 1.89(quin, J = 6.4Hz, 2H). |
| 26g | 143 | azetidin-1-yl | N-(4-(2-(Azetidine-1-carbonyl)thieno[3,2-b]pyridine-7-yloxy)-3-fluorophenylcarbamothioyl)-2-phenylacetamide hydrochloride | $^1$H NMR (400 MHz, DMSO-$d_6$) δ (ppm): 12.48(s, 1H), 11.82(s, 1H), 8.64(d, J = 5.6Hz, 1H), 8.03(db, J = 12.8Hz, 1H), 7.91(s, 1H), 7.58-7.52(m, 2H), 7.37-7.31(m, 4H), 7.30-7.24(m, 1H), 6.82(d, J = 5.6Hz, 1H), 4.62(t, J = 7.2Hz, 2H), 4.11(t, J=7.2Hz, 2H), 3.82(s, 2H), 2.35(quin, J = 7.2Hz, 2H). |
| 26h | 144 | N(Me)(Et) | 1-(4-(6-(N-Ethyl-N-methylcarbamoyl)thieno[3,2-d]pyrimidin-4-yloxy)-3-fluorophenyl)-3-(2-phenylacetyl)thiourea | $^1$H NMR (400 MHz, DMSO-$d_6$) δ (ppm): 12.44(s, 1H), 11.81(s, 1H), 8.77(s, 1H), 8.03(s, 1/2H), 7.93(dd, 1H, J = 11.9/2.3Hz), 7.89(s, 1/2H), 7.54(t, 1H, J = 8.5Hz), 7.48(dd, 1H, J = 8.8/2.2Hz), 7.38-7.32(m, 4H), 7.30-7.25(m, 1H), 3.82(s, 2H), 3.52(m, 2H), 3.23(s, 3/2H), 3.04(s, 3/2H), 1.19(m, 3H). |
| 26i | 145 | N(Et)(Et) | N,N-Diethyl-4-(2-fluoro-4-(3-(2-phenylacetyl)thioureido)phenoxy)thieno[3,2-d]pyrimidine-6-carboxamide | $^1$H NMR (400 MHz, DMSO-$d_6$) δ (ppm): 12.44(s, 1H), 11.80(s, 1H), 8.77(s, 1/3H), 8.77(s, 2/3H), 7.93(dd, 1H, J = 2.2/11.9Hz), 7.89(s, 1/3H), 7.89(s, 2/3H), 7.54(t, 1H, J = 8.5Hz), 7.48(dd, 1H, J = 1.8/8.3Hz), 7.34-7.33(m, 4H), 7.29-7.26(m, 1H), 3.83(s, 2H), 3.53-3.48(m, 4H), 1.21(m, 6H). |
| 26j | 146 | (R)-2-(hydroxymethyl)pyrrolidin-1-yl | ®-N-(3-Fluoro-4-(6-(2-(hydroxymethyl)pyrrolidine-1-carbonyl)thieno[3,2-d]pyrimidin-4-yloxy)phenylcarbamothioyl)-2-phenylacetamide | $^1$H NMR (400 MHz, DMSO-$d_6$) δ (ppm): 12.41(s, 1H); 11.80(s, 1H); 8.77(s, 1H); 8.08(s, 1H); 7.92(d, J = 11.6Hz, 1H); 7.54(t, J = 8.8Hz, 1H); 7.49-7.45(m, 1H); 7.34-7.26(m, 5H); 4.84(t, J = 4.4Hz, 1H); 4.23-4.19(m, 1H); 3.91-3.78(m, 2H); 3.82(s, 2H); 3.62-3.51(m, 2H); 2.07-1.87(m, 4H). |

TABLE 17-continued

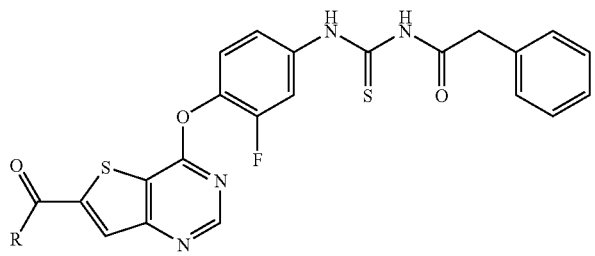

26f-l: Examples 142–148

Characterization of compounds 26f-l (examples 142-148)

| Cpd | Ex | R | Name | Characterization |
|---|---|---|---|---|
| 26k | 147 | (pyrrolidine with OTBS) | (S)-N-(4-(6-(3-(tert-Butyldimethylsilyloxy)pyrrolidine-1-carbonyl)thieno[3,2-d]pyrimidin-4-yloxy)-3-fluorophenylcarbamothioyl)-2-phenylacetamide | $^1$H NMR (400 MHz, CDCl$_3$) δ (ppm): 12.5(s, 1H), 8.79(s, 1H), 8.66(d, 1H, J = 0.4Hz), 8.03-7.91(m, 2H), 7.52-7.21(m, 6H), 4.60-4.52(m, 1H), 4.07-3.67(m, 4H), 2.13-1.97(m, 2H), 1.28-1.26(m, 2H), 0.93-0.89(m, 9H), 0.14-0.09(m, 6H). |
| 26l | 148 | (pyrrolidine with NHBoc) | tert-Butyl 1-(4-(2-fluoro-4-(3-(2-phenylacetyl)thioureido)phenoxy)thieno[3,2-d]pyrimidine-6-carbonyl)pyrrolidin-3-ylcarbamate | 1H NMR (400 MHz, DMSO-d6) δ (ppm): 8.77(s, 1H), 8.09(s, 0.5H), 8.05(s, 0.5H), 7.96-7.93(m, 0.5H), 7.93-7.90(m, 0.5H), 7.58-7.50(m, 1H), 7.50-7.46(m, 1H), 7.38-7.31(nm, 4H), 7.31-7.24(m, 1H), 3.82(s, 2H), 4.15-1.20(m, 7H). |

Scheme 38

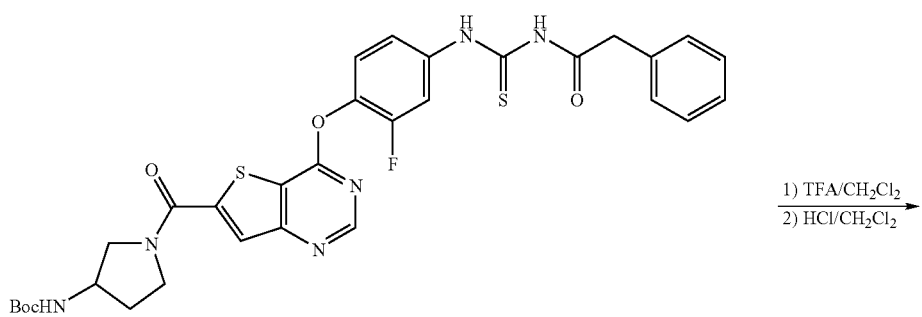

26l: Example 148

1) TFA/CH$_2$Cl$_2$
2) HCl/CH$_2$Cl$_2$

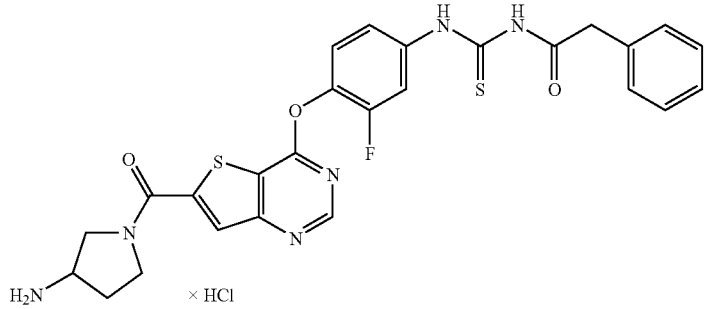

191: Example 149

Example 149

N-(4-(6-(3-Aminopyrrolidine-1-carbonyl)thieno[3,2-d]pyrimidin-4-yloxy)-3-fluorophenylcarbamothioyl)-2-phenylacetamide hydrochloride(191)

Following the procedure described above for the synthesis of compound 159 (scheme 30, example 121) but substituting Boc-protected amino compound 158 for the Boc-protected amino compound 261, title compound 191 was obtained in 40% yield. $^1$H NMR (400 MHz, DMSO-$d_6$) δ (ppm): 8.77(s, 1H), 8.12(s, 0.5H), 8.06(s, 0.5H), 7.92(dd, J=2.4 and 12.0 Hz, 1H), 7.54(t, J=8.4 Hz, 1H), 7.48(dd, J=2.4 and 8.4 Hz, 1H), 7.36-7.31(m, 4H), 7.30-7.25(m, 1H), 4.2-3.80(m, 1H), 3.08 (s, 2H), 3.80-3.50(m, 4H), 2.10-1.98(m, 1H), 1.82-1.64(m, 1H). LRMS (M+1) 550.6 (100%).

Scheme 39

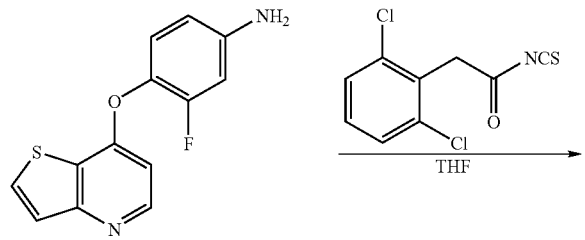

169

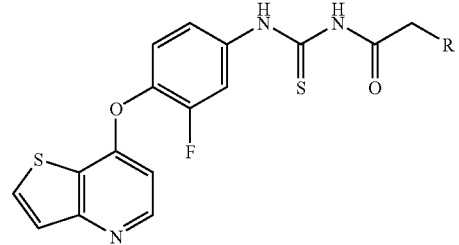

192a: Example 150

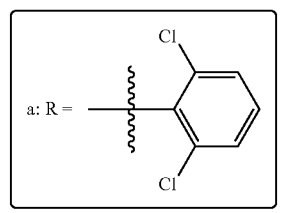

Example 150

2-(2,6-Dichlorophenyl)-N-(3-fluoro-4-(thieno[3,2-b]pyridin-7-yloxy)phenylcarbamothioyl)acetamide (192a)

Starting from the amine 169 (scheme 33), following the procedures described above for the synthesis of compound 170a (example 133) but replacing 2-phenylacetyl isothiocyanate with 2-(2,6-dichlorophenyl)acetyl isothiocyanate, title compound 192a was obtained in 7% yield. Characterization of 192a is provided in table 18.

Example 151

N-(3-Fluoro-4-(thieno[3,2-b]pyridin-7-yloxy)phenylcarbamothioyl)-2-(thiophen-2-yl)acetamide (192b)

Starting from the amine 169 (scheme 33), following the procedures described above for the synthesis of compound 170a (example 133) but replacing 2-phenylacetyl isothiocyanate with 2-(thiophen-2-yl)acetyl isothiocyanate, title compound 192b was obtained in 9% yield. Characterization of 192b is provided in table 18.

Example 152

2-(2,6-Difluorophenyl)-N-(3-fluoro-4-(thieno[3,2-b]pyridin-7-yloxy)phenylcarbamothioyl)acetamide (192c)

Starting from the amine 169 (scheme 33), following the procedures described above for the synthesis of compound 170a (example 133) but replacing 2-phenylacetyl isothiocyanate with 2-(2,6-difluorophenyl)acetyl isothiocyanate, title compound 192c was obtained in 23% yield. Characterization of 192c is provided in table 18.

Example 153

N-(3-Fluoro-4-(thieno[3,2-b]pyridin-7-yloxy)phenylcarbamothioyl) 1-phenylcyclopropanecarboxamide (192d)

Starting from the amine 169 (scheme 33), following the procedures described above for the synthesis of compound 170a (example 133) but replacing 2-phenylacetyl isothiocyanate with 1-phenylcyclopropanecarbonyl isothiocyanate, title compound 192d was obtained in 41% yield. Characterization of 192d is provided in table 18.

Example 154

N-(3-Fluoro-4-(thieno[3,2-b]pyridin-7-yloxy)phenyl-carbamothioyl)-2-phenylpropanamide (192e)

Starting from the amine 169 (scheme 33), following the procedures described above for the synthesis of compound 170a (example 133) but replacing 2-phenylacetyl isothiocyanate with 3-methyl-2-phenylbutanoyl isothiocyanate, title compound 192e was obtained in 49% yield. Characterization of 192e is provided in table 18.

Example 155

N-(3-Fluoro-4-(thieno[3,2-b]pyridin-7-yloxy)phenyl-carbamothioyl)-3-phenylpropanamide (192f)

Starting from the amine 169 (scheme 33), following the procedures described above for the synthesis of compound 170a (example 133) but replacing 2-phenylacetyl isothiocyanate with 3-phenylpropanoyl isothiocyanate, title compound 192f was obtained in 59% yield. Characterization of 192f is provided in table 18.

TABLE 18

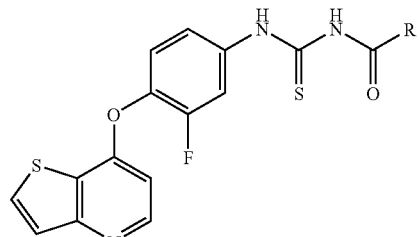

192a–f: Examples 150–155

Characterization of compounds 192a-f (examples 150-155)

| Cpd | Ex | R | Name | Characterization |
|---|---|---|---|---|
| 192a | 150 | 2,6-dichlorobenzyl | 2-(2,6-Dichlorophenyl)-N-(3-fluoro-4-(thieno[3,2-b]pyridin-7-yloxy)phenylcarbamothioyl)acetamide | $^1$H NMR (400 MHz, DMSO-$d_6$) δ(ppm): 12.27(s, 1H), 12.01(s, 1H), 8.52(d, J = 5.6Hz, 1H), 8.35-8.00(m, J = 12.0Hz, 1H), 7.59(d, J = 5.6Hz, 1H), 7.58-7.47(m, 4H), 7.36(t, J = 8.0Hz, 1H), 6.64(d, J = 5.6Hz, 1H), 4.21(s, 2H). |
| 192b | 151 | thiophen-2-ylmethyl | N-(3-Fluoro-4-(thieno[3,2-b]pyridin-7-yloxy)phenylcarbamothioyl)-2-(thiophen-2-yl)acetamide | $^1$H NMR (400 MHz, DMSO-$d_6$) δ(ppm): 12.37(s, 1H), 11.80(s, 1H), 8.52(d, J = 5.6Hz, 1H), 8.17(d, J = 5.6Hz, 1H), 7.98(d, J = 12.4Hz, 1H), 7.60(d, J = 5.6Hz, 1H), 7.54-7.46(m, 2H), 7.42(dd, J = 1.6 and 5.2Hz, H), 7.20-6.97(m, 2H), 6.64(d, J = 5.6Hz, 1H), 4.07(s, 2H). |
| 192c | 152 | 2,6-difluorobenzyl | 2-(2,6-Difluorophenyl)-N-(3-fluoro-4-(thieno[3,2-b]pyridin-7-yloxy)phenylcarbamothioyl)acetamide | $^1$H NMR (400 MHz, DMSO-$d_6$) δ(ppm): 12.28(s, H), 11.93(s, 1H), 8.52(d, J = 5.6Hz, H), 8.17(d, J = 5.6Hz, 1H), 8.03-7.98(m, 1H), 7.60(d, J = 5.6Hz, 1H), 7.57-7.48(m, 2H), 7.46-7.37(m, 1H), 7.12(t, J = 7.6Hz, 2H), 6.65(d, J = 5.6Hz, 1H), 3.96(s, 2H). |
| 192d | 153 | 1-phenylcyclopropyl | N-(3-Fluoro-4-(thieno[3,2-b]pyridin-7-yloxy)phenylcarbamothioyl)-1-phenylcyclopropane carboxamide | $^1$H NMR (DMSO) δ (ppm): 12.31(1H, s), 9.26(1H, s), 8.52(1H, d, J = 5.28Hz), 8.17(1H, d, J = 5.28Hz), 7.96(1H, d, J = 11.93Hz), 7.60(1H, d, J = 5.28Hz), 7.52-7.31(7H, m), 6.64(1H, d, J = 5.09Hz), 1.62(2H, brd, J = 1.96Hz), 1.33(2H, brd, J = 2.35Hz). MS (m/z) 464.2(M+H). |

TABLE 18-continued

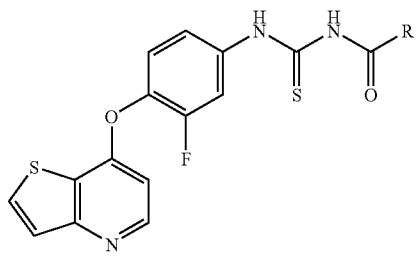

192a–f: Examples 150–155

Characterization of compounds 192a-f (examples 150-155)

| Cpd | Ex | R | Name | Characterization |
|---|---|---|---|---|
| 192e | 154 | Me, phenyl (CH(Me)Ph) | N-(3-Fluoro-4-(thieno[3,2-b]pyridin-7-yloxy)phenylcarbamothioyl)-2-phenylpropanamide | $^1$H NMR (400 MHz, DMSO-$d_6$) δ ppm 12.50(1H, s), 11.77(1H, s), 8.52(1H, d, J = 5.28Hz), 8.16(1H, d, J = 5.48Hz), 8.00(1H, d, J=11.74), 7.60(1H, d, J = 5.48Hz), 7.55-7.48(2H, m), 7.41-7.33(5H, m), 6.63(d, J = 5.48Hz), 4.10(1H, q, J = 6.85Hz), 1.44(3H, d, J = 6.85Hz). MS (m/z) 452.1(M+H) |
| 192f | 155 | CH$_2$CH$_2$Ph | N-(3-Fluoro-4-(thieno[3,2-b]pyridin-7-yloxy)phenylcarbamothioyl)-3-phenylpropanamide | $^1$H NMR (400 MHz, DMSO-$d_6$) δ ppm 12.58(2, 1H), 11.62(s, 1H), 8.53(1H, d, J = 5.48Hz), 8.17(1H, d, J = 5.28Hz), 8.03(1H, d, J = 11.35Hz), 7.60(1H, d, J = 5.48Hz), 7.53-7.52(2H, br), 7.31-7.21(5H, m), 6.66(1H, d, J = 5.28Hz), 2.92-2.87(2H, m), 2.83-2.79(2H, m). MS(m/z) 452.1(M+H) |

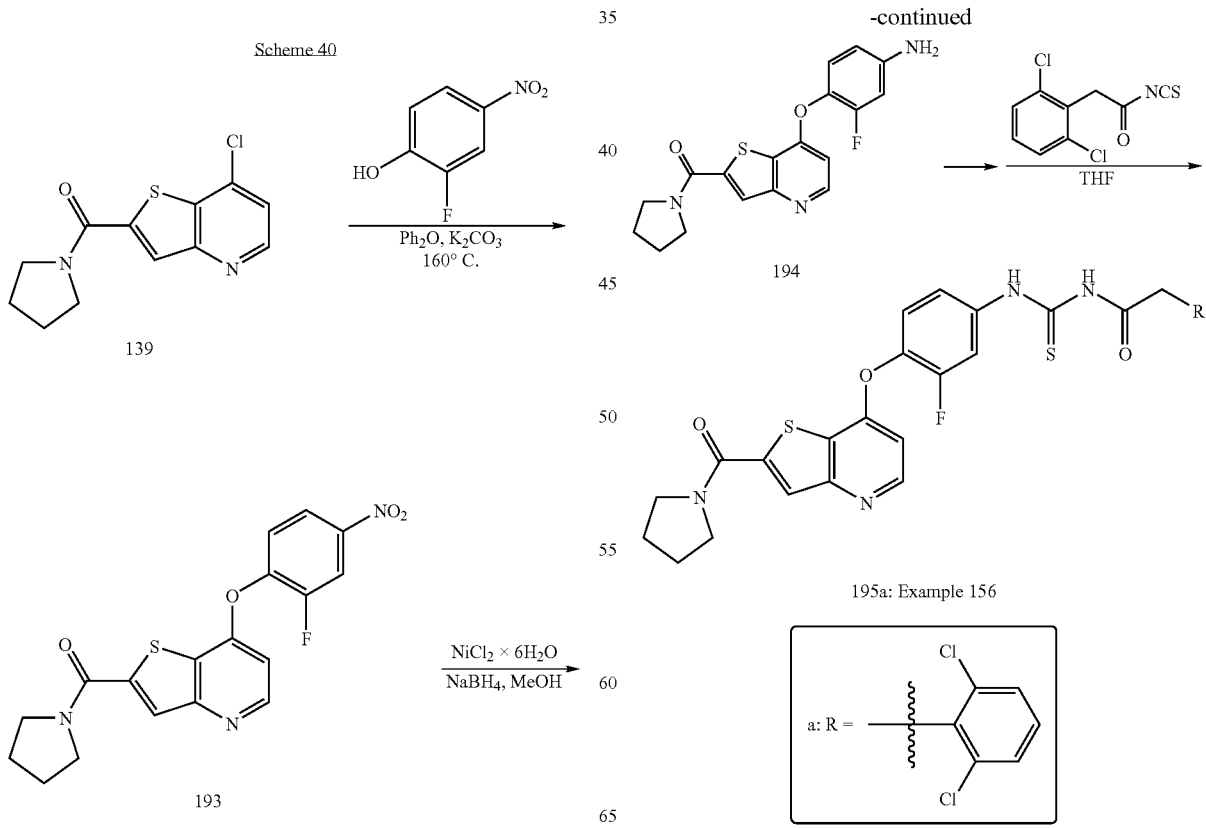

Scheme 40

195a: Example 156

Example 156

2-(2,6-Dichlorophenyl)-N-(3-fluoro-4-(2-(pyrrolidine-1-carbonyl)thieno[3,2-b]pyridin-7-yloxy)phenylcarbamothioyl)acetamide (195a)

Step 1. (7-(2-Fluoro-4-nitrophenoxy)thieno[3,2-b]pyridin-2-yl)(pyrrolidin-1-yl)methanone (193)

Starting from (7-chlorothieno[3,2-b]pyridin-2-yl)(pyrrolidin-1-yl)methanone (139, scheme 26) and following the procedure described above for the synthesis of compound 6 (scheme 1, example 1), title compound 193 was obtained in (93% yield). LRMS (M+1) 387.4 (100%).

Step 2. (7-(4-Amino-2-fluorophenoxy)thieno[3,2-b]pyridin-2-yl)(pyrrolidin-1-yl)methanone (194)

Starting from the nitro compound 183 and following the procedures described above for the synthesis of amine 7, (scheme 1, example 1) title compound 194 was obtained in 92% yield. LRMS (M+1) 357.4 (100%).

Step 3. 2-(2,6-Dichlorophenyl)-N-(3-fluoro-4-(2-(pyrrolidine-1-carbonyl)thieno[3,2-b]pyridin-7-yloxy)phenylcarbamothioyl)acetamide (195a)

Starting from the amine 194 and following the procedure described above for the synthesis of compounds 50 (scheme 10), 170a (scheme 33) or 192a-f (scheme 39), title compound 195a was obtained in 70% yield. Characterization of 195a is provided in table 19.

Examples 157-181 (compounds 195b-q)

Compounds 195b-q (examples 157-181) were obtained starting from the amine 194, following the procedure described above for the synthesis of compound 195a and replacing 2-(2,6-difluorophenyl)acetyl isothiocyanate with an appropriately substituted homologue. Characterization of 195b-q is provided in the table 19.

TABLE 19

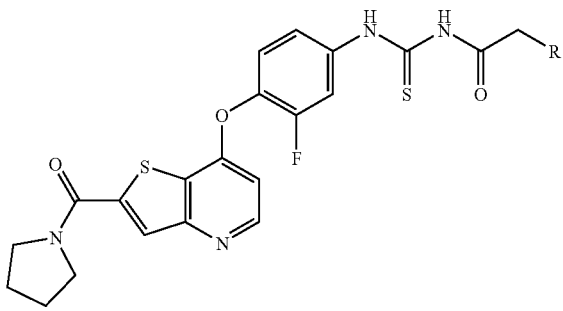

195a–q: Examples 156–181

Characterization of compounds 195a–q (examples 156–181)

| Cpd | Ex | R | Name | Characterization |
|---|---|---|---|---|
| 195a | 156 | 2,6-dichlorophenyl | 2-(2,6-Dichlorophenyl)-N-(3-fluoro-4-(2-(pyrrolidine-1-carbonyl)thieno[3,2-b]pyridin-7-yloxy)phenylcarbamothioyl)acetamide hydrochloride | $^1$H NMR (400MHz, DMSO-d$_6$) δ (ppm): 12.29(s, 1H), 12.02(s, 1H), 8.63(d, J = 5.6Hz, 1H), 8.08–8.02(m, 1H), 8.04(s, 1H), 7.62(m, 4H), 7.36(dd, J = 7.2 and 8.4Hz, 1H), 6.80(d, J = 5.6Hz, 1H), 4.21(s, 2H), 3.85(t, J = 6.4Hz, 2H), 3.54(t, J = 6.4Hz, 2H), 1.97(quint, J = 6.4Hz, 2H), 1.88(quint, J = 6.4Hz, 2H). |
| 195b | 157 | 2,6-difluorophenyl | 2-(2,6-Difluorophenyl)-N-(3-fluoro-4-(2-(pyrrolidine-1-carbonyl)thieno[3,2-b]pyridin-7-yloxy)phenylcarbamothioyl)acetamide hydrochloride | $^1$H NMR (400MHz, DMSO-d$_6$) δ (ppm): 12.29(s, 1H), 11.94(s, 1H), 8.63(d, J = 5.6Hz, 1H), 8.07–8.01(m, 1H), 8.05(s, 1H), 7.60–7.51(m, 2H), 7.46–7.37(m, 1H), 7.18–709(m, 2H), 6.80(d, J = 5.6Hz, 1H), 3.97(s, 2H), 3.85(t, J = 6.4Hz, 2H), 3.54(t, J = 6.4Hz, 2H), 1.97(quin, J = 6.4Hz, 2H), 1.89(quin, J = 6.4Hz, 2H). |
| 195c | 158 | cyclohexyl | 2-Cyclohexyl-N-(3-fluoro-4-(2-(pyrrolidine-1-carbonyl)thieno[3,2-b]pyridin-7-yloxy)phenylcarbamothioyl)acetamide hydrochloride | $^1$H NMR (400MHz, DMSO-d$_6$) δ (ppm): 12.67(s, 1H), 11.55(s, 1H), 8.65(d, J = 5.6Hz, 1H), 8.12–8.06(m, 1H), 8.06(s, 1H), 7.60–7.53(m, 2H), 6.82(d, J = 5.6Hz, 1H), 3.86(t, J = 6.4Hz, 2H), 3.54(t, J = 6.4Hz, 2H), 2.37(d, J = 6.8Hz, 2H), 1.97(quin, J = 6.4Hz, 2H), 1.89(quin, J = 6.4Hz, 2H), 1.71–1.58(m, 6H), 1.30–1.08(m, 3H), 1.07–0.92(m, 2H). |

TABLE 19-continued

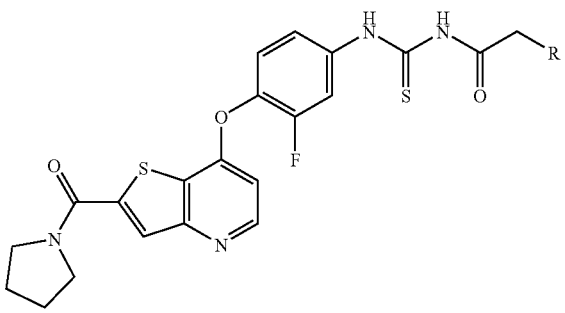

195a–q: Examples 156–181

Characterization of compounds 195a–q (examples 156–181)

| Cpd | Ex | R | Name | Characterization |
|---|---|---|---|---|
| 195d | 159 | 4-methoxyphenyl | N-(3-Fluoro-4-(2-(pyrrolidine-1-carbonyl)thieno[3,2-b]pyridin-7-yloxy) phenylcarbamothioyl)-2-(4-methoxyphenyl) acetamide hydrochloride | $^1$H NMR (400MHz, DMSO-d$_6$) δ (ppm): 12.50(s, 1H), 11.77(s, 1H), 8.64(d, J = 5.6Hz, 1H), 8.07–8.01(m, 1H), 8.05(s, H), 7.58–7.53(m, 2H), 7.28–7.22(m, 2H), 6.94–6.88(m, 2H), 6.81(d, J = 5.6Hz, 1H), 3.85(t, J = 6.4Hz, 2H), 3.73(s, 2H), 3.73(s, 3H), 3.54(t, J = 6.4Hz, 2H), 1.97(quin, J = 6.4Hz, 2H0, 1.89(quin, J = 6.4Hz, 2H). |
| 195e | 160 | 3-chlorophenyl | 2-(3-Chlorophenyl)-N-(3-fluoro-4-(2-(pyrrolidine-1-carbonyl)thieno[3,2-b]pyridin-7-yloxy) phenylcarbamothioyl) acetamide hydrochloride | $^1$H NMR (400MHz, DMSO-d$_6$) δ (ppm): 12.42(s, 1H), 11.83(s, 1H), 8.65(d, J = 5.6Hz, 1H), 8.07–8.01(m, 1H), 8.05(s, 1H), 7.59–7.52(m, 2H), 7.44–7.26(m, 4H), 6.82(d, J = 5.6Hz, 1H), 3.86(s, 2H), 3.85(t, J = 6.4Hz, 2H), 3.54(t, J = 6.4Hz, 2H), 1.97(quin, J = 6.4Hz, 2H), 1.89(quin, J = 6.4Hz, 2H). |
| 195f | 161 | thiophen-2-yl | N-(3-Fluoro-4-(2-(pyrrolidine-1-carbonyl)thieno[3,2-b]pyridin-7-yloxy) phenylcarbamothioyl)-2-(thiophen-2-yl) acetamide hydrochloride | $^1$H NMR (400MHz, DMSO-d$_6$) δ (ppm): 12.39(s, 1H), 11.82(s, 1H), 8.65(d, J = 5.6Hz, 1H), 8.08–8.00(m, 1H), 8.05(s, 1H), 7.60–.7.55(m, 2H), 7.46–7.42(m, 1H), 7.04–6.98(m, 2H), 6.83(d, J = 5.6Hz, 1H), 4.06(s, 2H), 3.85(t, J '6.4Hz, 2H), 3.54(t, J '6.4Hz, 2H), 1.98(quin, J = 6.4Hz, 2H), 1.89(quin, J = 6.4Hz, 2H). |
| 195g | 162 | 2-chloro-6-fluorophenyl | 2-(2-Chloro-6-fluorophenyl)-N-(3-fluoro-4-(2-(pyrrolidine-1-carbonyl)thieno[3,2-b]pyridin-7-yloxy) phenylcarbamothioyl) acetamide hydrochloride | $^1$H NMR (400MHz, DMSO-d$_6$) δ (ppm): 12.30(s, 1H), 11.99(s, 1H), 8.63(d, J = 5.6Hz, 1H), 8.08–8.01(m, 1H), 8.05(s, 1H), 7.60–7.51(m, 2H), 7.44–7.36(m, 2H), 7.30–7.24(m, 1H), 6.80(d, J = 5.6Hz, 1H), 4.07(s, 2H), 3.85(t, J = 6.4Hz, 2H), 3.54(t, J = 6.4Hz, 2H), 1.95(quin, J = 6.4Hz, 2H), 1.89(quin, J = 6.4Hz, 2H). |
| 195h | 163 | adamantan-1-yl | 1-(2-Adamantan-1-yl-acetyl)-3-{3-fluoro-4-[2-(pyrrolidine-1-carbonyl)-thieno[3,2-b]pyridin-7-yloxy]-phenyl}-thiourea | $^1$H NMR (400MHz, DMSO-d$_6$) δ (ppm): 12.75(s, 1H), 11.45(s, 1H), 8.67(d, J = 5.6Hz, 1H), 8.12(d, J = 12.4Hz, 1H), 8.06(s, 1H), 7.62–7.53(m, 2H), 6.86(d, J = 5.6Hz, 1H), 3.85(t, J = 6.4Hz, 2H), 3.54(t, J = 6.4Hz, 2H), 2.26(s, 2H), 2.02–1.92(m, 5H), 1.89(quin, J =6.4Hz, 2H), 1.70–1.57(m, 12H). |

TABLE 19-continued

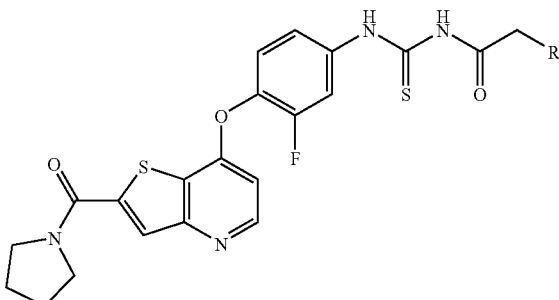

195a–q: Examples 156–181

Characterization of compounds 195a–q (examples 156–181)

| Cpd | Ex | R | Name | Characterization |
|---|---|---|---|---|
| 195i | 164 | cyclopentyl | 2-Cyclopentyl-N-(3-fluoro-4-(2-(pyrrolidine-1-carbonyl)thieno[3,2-b]pyridin-7-yloxy)phenylcarbamothioyl) acetamide hydrochloride | $^1$H NMR (400MHz, DMSO-$d_6$) δ (ppm): 12.66(s, 1H), 11.55(s, 1H), 8.65(d, J = 5.6Hz, 1H), 8.10–8.03(m, 2H), 7.59–7.54(m, 2H), 6.82(d, J = 5.6Hz, 1H), 3.86(t, J = 6.4Hz, 2H), 3.54(t, J = 6.4Hz, 2H), 2.20(quin, J = 7.6Hz, 1H), 1.97(quin, J = 6.4Hz, 2H), 1.89(quin, J = 6.4Hz, 2H), 1.83–1.71(m, 2H), 1.68–1.47(m, 4H), 1.26–1.12(m, 2H). |
| 195j | 165 | 3,4,5-trimethoxyphenyl | N-(3-Fluoro-4-(2-(pyrrolidine-1-carbonyl)thieno[3,2-b]pyridin-7-yloxy) phenylcarbamothioyl)-2-(3,4,5-trimethoxyphenyl) acetamide hydrochloride | $^1$NMR (400MHz, DMSO-$d_6$) δ (ppm): 12.49(s, 1H), 11.76(s, 1H), 8.60(d, J = 5.6Hz, 1H), 8.07–8.01(m, 2H), 7.58–7.54(m, 2H), 6.77(d, J = 5.6Hz, 1H), 6.65(s, 2H), 3.86(t, J = 6.4Hz, 2H), 3.76(s, 6H), 3.74(s, 2H), 3.63(s, 3H), 3.54(t, J = 6.4Hz, 2H), 1.97(quin, J = 6.4Hz, 2H), 1.89(quin, J = 6.4Hz, 2). |
| 195k | 166 | 4-(CO$_2$Me)phenyl | Methyl 4-(2-(3-(3-fluoro-4-(2-(pyrrolidine-1-carbonyl)thieno[3,2-b]pyridin-7-yloxy)phenyl)thioureido)-2-oxoethyl)benzoate hydrochloride | $^1$H NMR (400MHz, DMSO-$d_6$) δ (ppm): 12.41(s, 1H), 11.86(s, 1H), 8.60(d, J = 5.6Hz, 1H), 8.04(s, 1H), 8.04–8.00(m, 1H), 7.93(d, J = 8.0Hz, 2H), 7.58–7.50(m, 2H), 7.47(d, J =8.0Hz, 2H), 6.76(d, J '5.6Hz, 1H), 3.94(s, 2H), 3.86(t, J '6.4Hz, 2H), 3.84(s, H), 3.54(t, J = 6.4Hz, 2H), 1.97(quin, J = 6.4Hz, 2H), 1.89(quin, J = 64Hz, 2H). |
| 195l | 167 | (R)-2,2-dimethyl-1,3-dioxolan-4-yl | (R)-2-(2,2-Dimethyl-5-oxo-1,3-dioxolan-4-yl)-N-(3-fluoro-4-(2-(pyrrolidine-1-carbonyl)thieno[3,2-b]pyridin-7-yloxy)phenylcarbamoyl) ethanethioamide hydrochloride | $^1$H NMR (400MHz, DMSO-$d_6$) δ (ppm): 12.32(s, 1H), 11.73(s, 1H), 8.64(d, J = 5.6Hz, 1H), 8.05(s, 1H), 8.04–8.00(m, 1H), 7.60–7.54(m, 2H), 6.81(d, J = 5.6Hz, 1H), 4.93(t, J = 4.4Hz, 1H), 3.86(t, J = 6.4Hz, 2H), 3.54(t, J =6.4Hz, 2H), 3.16(dd, J = 4.4 and 16.8Hz, 1H), 2.99(dd, J = 5.0 and 16.8Hz, 1H), 1.97(quin, J = 6.4Hz, 2H), 1.89(quin, J = 6.4Hz, 2H). |
| 195m | 168 | 2-fluorophenyl | N-(3-Fluoro-4-(2-(pyrrolidine-1-carbonyl)thieno[3,2-b]pyridin-7-yloxy) phenylcarbamothioyl)-2-(2-fluorophenyl) acetamide hydrochloride | $^1$H NMR (400MHz, DMSO-$d_6$) δ (ppm): 12.42(s, 1H), 11.88(s, 1H), 8.67(d, J = 5.6Hz, 1H), 8.08–8.02(m, 1H), 8.06(s, H), 7.60–7.52(m, 2H), 7.43–7.30(m, 2H), 7.24–7.16(m, 2H), 6.85(d, J=5.6Hz, 1H), 3.989s, 2H), 3.85(t, J=6.4Hz, 2H), 3.54(t, J = 6.4Hz, 2H), 1.97(quin, J = 6.4Hz, 2H), 1.89(quin, J = 6.4Hz, 2H). |

TABLE 19-continued

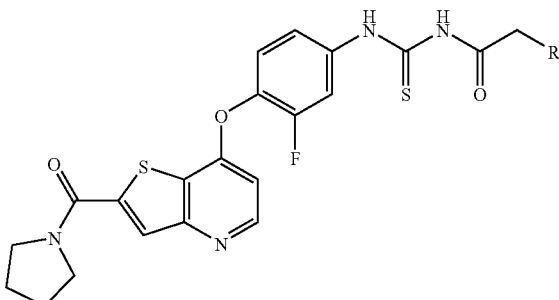

195a–q: Examples 156–181

Characterization of compounds 195a–q (examples 156–181)

| Cpd | Ex | R | Name | Characterization |
|---|---|---|---|---|
| 195n | 169 | (tetrahydro-2H-pyran-4-yl) | N-(3-Fluoro-4-(2-(pyrrolidine-1-carbonyl)thieno[3,2-b]pyridin-7-yloxy) phenylcarbamothioyl)-2-(tetrahydro-2H-pyran-4-yl)acetamide hydrochloride | $^1$H NMR (400MHz, DMSO-$d_6$) δ (ppm): 12.63(s, 1H), 11.59(s, 1H), 8.66(d, J = 5.2Hz, 1H), 8.11–8.02(m, 1H), 8.06(s, 1H), 7.60–7.54(m, 2H), 6.84(d, J = 5.2Hz, 1H), 3.85(t, J = 6.8Hz, 2H), 3.85–3.79(m, 2H), 3.54(t, J = 6.8Hz, 2H), 3.30(t, J = 12.0Hz, 2H), 2.43(d, J = 6.8Hz, 2H), 2.20–1.95(m, 1H), 1.97(quin, J = 6.8Hz, 2H), 1.89(quin, J = 6.8Hz, 2H), 1.61(d, J = 12.8Hz, 2H), 1.25(qd, J = 4.0 and 12.0Hz, 2H). |
| 195o | 179 | 2-MeO-phenyl | N-(3-Fluoro-4-(2-(pyrrolidine-1-carbonyl)thieno[3,2-b]pyridin-7-yloxy) phenylcarbamothioyl)-2-(2-methoxyphenyl) acetamide hydrochloride | $^1$H NMR (400MHz, DMSO-$d_6$) δ (ppm): 12.55(s, 1H), 11.73(s, 1H), 8.63(d, J = 5.6Hz, 1H), 8.10–8.04(m, 2H), 7.60–7.51(m, 2H), 7.26(td, J = 1.6 and 8.0Hz, 1H), 7.21(dd, J =1.6 and 7.6Hz, 1H), 6.99(d, J '8.0Hz, H), 6.90(ts, J '1.2 and 7.6Hz, 1H), 6.80(d, J '5.6Hz, 1H), 3.86(t, J = 6.4Hz, 2H), 3.81(s, 2H), 3.78(s, 3H), 3.54(t, J = 6.4Hz, 2H), 1.97(quin, J = 6.4Hz, 2H), 1.89(quin, J = 6.4Hz, 2H). |
| 195p | 180 | 2,5-dimethoxyphenyl | 2-(2,5-Dimethoxyphenyl)-N-(3-fluoro-4-(2-(pyrrolidine-1-carbonyl)thieno[3,2-b]pyridin-7-yloxy) phenylcarbamothioyl) acetamide hydrochloride | $^1$H NMR (400MHz, DMSO-$d_6$) δ (ppm): 12.53(s, 1H), 11.71(s, 1H), 6.64(d, J = 5.6Hz, 1H)< 8.10–8.04(m, 1H), 8.05(s, 1H), 7.60–7.52(m, 2H), 6.93–6.78(m, 4H), 3.85(t, J = 6.4Hz, 2H), 3.78(s, 2H), 3.72(s, 3H), 3.69(s, 3H), 3.54(t, J = 6.4Hz, 2H), 1.97(quin, J = 6.4Hz, 2H), 1.89(quin, J = 6.4Hz, 2H). |
| 195q | 181 | 3,4-dimethoxyphenyl | 2-(3,4-Dimethoxyphenyl)-N-(3-fluoro-4-(2-(pyrrolidine-1-carbonyl)thieno[3,2-b]pyridin-7-yloxy) phenylcarbamothioyl) acetamide hydrochloride | $^1$H NMR (400MHz, DMSO-$d_6$) δ (ppm): 12.51(s, 1H), 11.76(s, 1H), 8.69(d, J = 5.6Hz, 1H), 8.08–8.02(m, 1H), 8.07(s, 1H), 7.61–7.54(m, 2H), 6.98–6.82(m, 4H), 3.85(t, J = 6.4Hz, 2H), 3.78–3.70(m, 8H), 3.54(t, J = 6.4Hz, 2H), 1.97(quin, J = 6.4Hz, 2H), 1.89(quin, J = 6.4Hz, 2H). |

Scheme 41

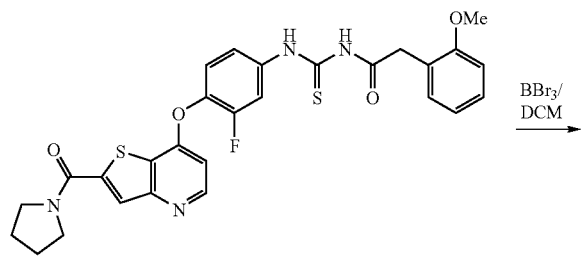

195o: Example 179

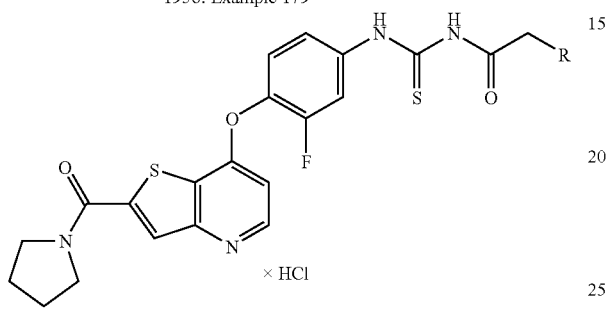

196a: Example 182

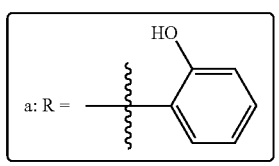

a: R =

Example 182

N-(3-Fluoro-4-(2-(pyrrolidine-1-carbonyl)thieno[3,2-b]pyridin-7-yloxy)phenylcarbamothioyl)-2-(2-hydroxyphenyl)acetamide hydrochloride (196a)

Starting from the compound 195o and following the procedure described above for the synthesis of compound 155k (scheme 29, example 119), title compound 196a was obtained in 62% yield. Characterization of 196a is provided in table 20.

Example 183

2-(2,5-Dihydroxyphenyl)-N-(3-fluoro-4-(2-(pyrrolidine-1-carbonyl)thieno[3,2-b]pyridin-7-yloxy)phenylcarbamothioyl)acetamide hydrochloride (196b)

Starting from the compound 195p and following the procedure described above for the synthesis of 196a, title compound 196b was obtained in 83% yield. Characterization of 196b is provided in table 20.

Example 184

2-(3,4-Dihydroxyphenyl)-N-(3-fluoro-4-(2-(pyrrolidine-1-carbonyl)thieno[3,2-b]pyridin-7-yloxy)phenylcarbamothioyl)acetamide (196c)

Starting from the compound 195q and following the procedure described above for the synthesis of 196a, title compound 196c was obtained in 25% yield. Characterization of 196c is provided in table 20.

TABLE 20

Characterization of compounds 196a–c (examples 182–184)

| Cpd | Ex | R | Name | Characterization |
|---|---|---|---|---|
| 196a | 182 | (2-hydroxyphenyl) | N-(3-Fluoro-4-(2-(pyrrolidine-1-carbonyl)thieno[3,2-b]pyridin-7-yloxy)phenylcarbamothioyl)-2-(2-hydroxyphenyl)acetamide hydrochloride | $^1$H NMR (400MHz, DMSO-$d_6$) δ (ppm): 12.60(s, 1H), 11.67(s, 1H), 9.63(bs, 1H), 8.63(d, J = 5.6Hz, 1H), 8.09–8.00(m, H), 8.05(s, 1H), 7.60–7.50(m, 2H), 7.13(d, J = 7.6Hz, 1H), 7.08(t, J = 7.6Hz, 1H), 6.83–6.77(m, 2H), 6.74(t, J = 7.6Hz, 1H), 3.85(t, J = 6.4Hz, 2H), 3.76(s, 2H), 3.54(t, J = 6.4Hz, 12H), 1.97(quin, J = 6.4Hz, 2H), 1.89(quin, J = 6.4Hz, 2H). |
| 196b | 183 | (2,5-dihydroxyphenyl) | 2-(2,5-Dihydroxyphenyl)-N-(3-fluoro-4-(2-(pyrrolidine-1-carbonyl)thieno[3,2-b]pyridin-7-yloxy)phenylcarbamothioyl)acetamide hydrochloride | $^1$H NMR (400MHz, DMSO-$d_6$) δ (ppm): 12.59(s, 1H), 11.59(s, 1H), 8.60(d, J = 5.6Hz, 1H), 8.08–8.03(m, 1H), 8.04(s, 1H), 7.58–7.52(m, 2H), 6.77(d, J = 5.6Hz, 1H), 6.60(d, J = 8.4Hz, 1H), 6.57(d, J = 2.8Hz, 1H), 6.49(dd, J = 2.8 and 8.4Hz, 1H), 3.86(t, J = 6.4Hz, 2H), 3.54(t, j=6.54Hz, 2H), 1.97(quin, J = 6.4Hz, 2H), 1.89(quin, J = 6.4Hz, 2H). |
| 196c | 184 | (3,4-dihydroxyphenyl) | 2-(3,4-Dihydroxyphenyl)-N-(3-fluoro-4-(2-(pyrrolidine-1-carbonyl)thieno[3,2-b]pyridin-7-yloxy)phenylcarbamothioyl)acetamide | $^1$H NMR (400MHz, DMSO-$d_6$) δ (ppm): 8.53(d, J = 5.6Hz, 1H), 8.07(dd, J = 2.4 and 12.0Hz, 1H), 7.94(s, 1H), 7.50–7.44(m, 1H), 7.40(t, J = 8.4Hz, 1H), 6.82–6.71(m, 3H), 6.65(dd, J = 2.4 and 8.4Hz, 1H), 3.92(t, J = 6.4Hz, 2H), 3.67(t, J = 6.4Hz, 1H), 3.59(s, 2H), 2.09(quin, J = 6.4Hz, 2H), 2.02(quin, J = 6.4Hz, 2H). |

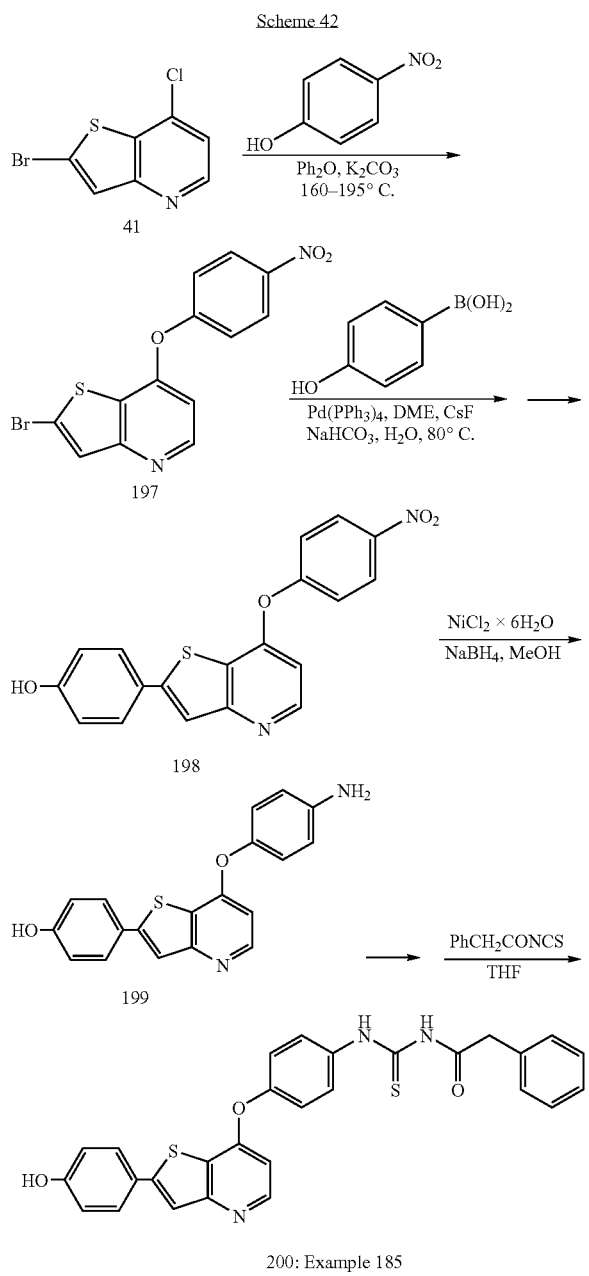

Example 185

N-(4-(2-(4-Hydroxyphenyl)thieno[3,2-b]pyridin-7-yloxy)phenylcarbamothioyl)-2-phenylacetamide (200)

Step 1.
2-Bromo-7-(4-nitrophenoxy)thieno[3,2-b]pyridine (197)

Starting from the compound 41 (scheme 8) and following the procedure described above for the synthesis of compound 42 (scheme 8) but replacing 2-fluoro-4-nitrophenol for 4-nitrophenol, title compound 197 was obtained in 48% yield. LRMS (M+1) 350.9 (100%). 352.9 (100%).

Step 2. 4-(7-(4-Nitrophenoxy)thieno[3,2-b]pyridin-2-yl)phenol (198)

Starting from the compound 197 and following the procedure described above for the synthesis of compound 153 (scheme 28), title compound 198 was obtained in 81% yield. LRMS (M+1) 365.0 (100%).

Step 3. 4-(7-(4-Aminophenoxy)thieno[3,2-b]pyridin-2-yl)phenol (199)

Starting from the compound 198 and following the procedure described above for the synthesis of compound 154 (scheme 28), title compound 199 was obtained in 83% yield. LRMS (M+1) 335.0 (100%).

Step 4. N-(4-(2-(4-Hydroxyphenyl)thieno[3,2-b]pyridin-7-yloxy)phenylcarbamothioyl)-2-phenylacetamide (200)

Starting from the compound 199 and following the procedure described above for the compound 155a (scheme 28, example 109), title compound 200 was obtained in 3% yield. $^1$H NMR (400 MHz, DMSO-$d_6$) δ ppm: 12.38 (s, 1H), 11.74 (s, 1H), 9.94 (s, 1H), 8.46 (d, 1H, J=5.3 Hz), 7.81 (s, 1H), 7.72 (d, 2H, J=9.0 Hz), 7.69 (dd, 2H, J=6.7/1.8 Hz), 7.34-7.27 (m, 7H), 6.86 (dd, 2H, J=6.7/1.8 Hz), 6.61 (d, 1H, J=5.5 Hz), 3.82 (s, 2H). LRMS (M+1) 512.1 (100%).

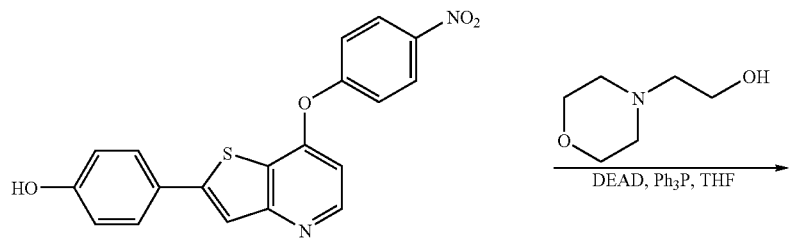

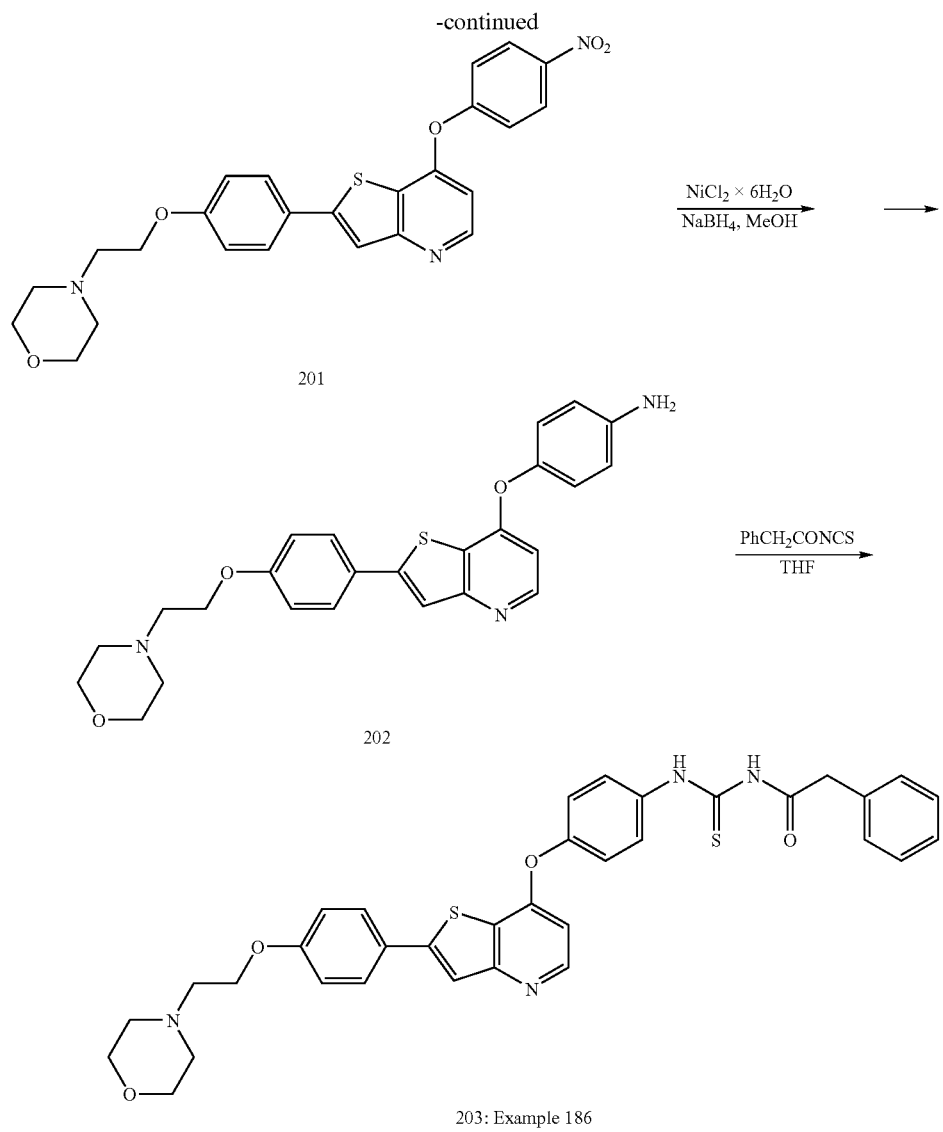

Example 186

N-(4-(2-(4-(2-Morpholinoethoxy)phenyl)thieno[3,2-b]pyridin-7-yloxy)phenylcarbamothioyl)-2-phenylacetamide (203)

Step 1. 4-(2-(4-(7-(4-Nitrophenoxy)thieno[3,2-b]pyridin-2-yl)phenoxy)ethyl)morpholine (201)

Starting from the compound 198 (scheme 42) and following the procedure described above for the compound 161 (scheme 31), title compound 201 was obtained in 69% yield. LRMS (M+1) 478.1 (100%).

Step 2. 4-(2-(4-(2-Morpholinoethoxy)phenyl)thieno[3,2-b]pyridin-7-yloxy)benzenamine (202)

Starting from the compound 201 and following the procedure described above for the compound 162 (scheme 31), title compound 202 was obtained in 69% yield. LRMS (M+1) 448.2 (100%).

Step 3. N-(4-(2-(4-(2-Morpholinoethoxy)phenyl) thieno[3,2-b]pyridin-7-yloxy)phenylcarbamothioyl)-2-phenylacetamide (203)

Starting from the compound 202 and following the procedure described above for the compound 163a (scheme 31), title compound 203 was obtained in 30% yield. $^1$H NMR (400 MHz, DMSO-$d_6$) δ ppm: 12.38 (s, 1H), 11.73 (s, 1H), 8.47 (d, 1H, J=5.5 Hz), 7.90 (s, 1H), 1H), 7.79 (s, 2H, J=9.0), 7.36 (d, 2H, J=9.0 Hz), 7.43-7.27 (m, 7H), 7.05 (d, 2H, J=9.0 Hz), 6.63 (d, 1H, J=5.3 Hz), 4.15 (t, 2H, J=5.6 Hz), 3.82 (s, 2H), 3.58 (t, 4H, J=4.6 Hz), 2.71 (t, 2H, J=5.7 Hz), 2.51-2.46 (m, 4H). LRMS (M+1) 625.2 (100%).

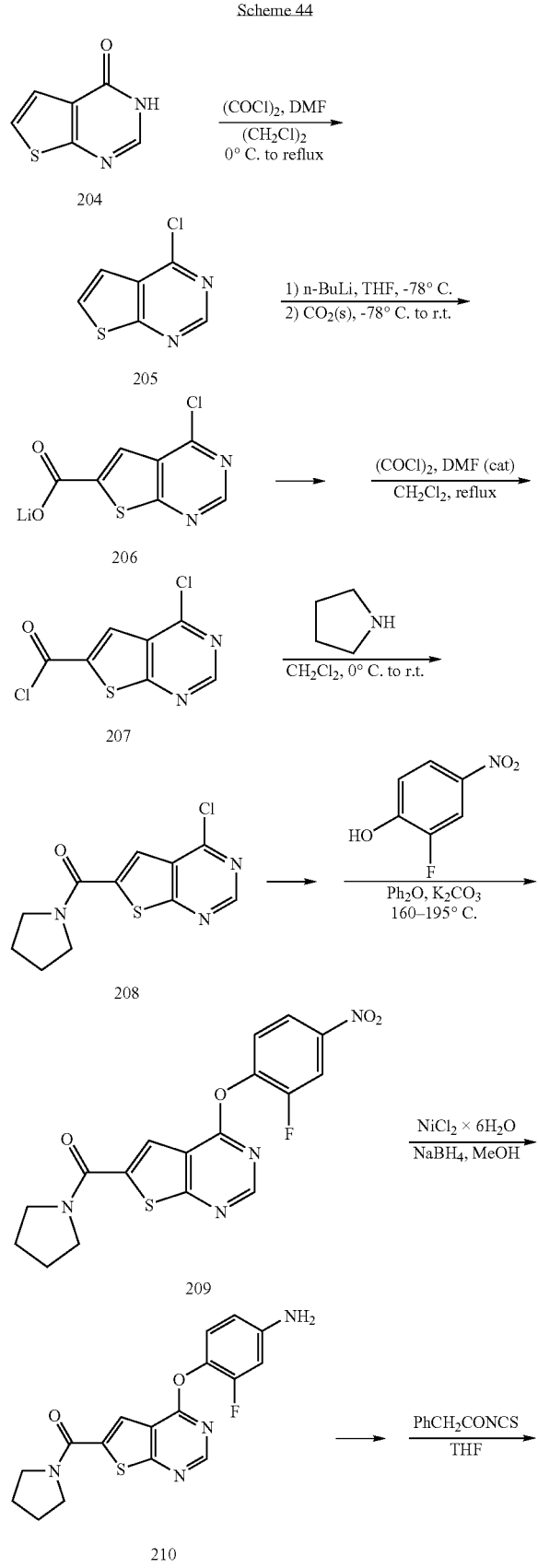
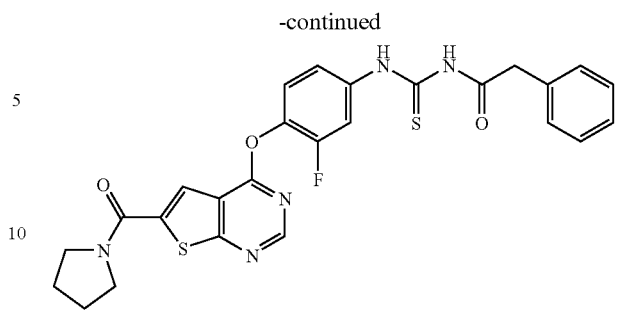

Example 187

N-(3-fluoro-4-(6-(pyrrolidine-1-carbonyl)thieno[2,3-d]pyrimidin-4-yloxy)phenylcarbamothioyl)-2-phenylacetamide (211)

Step 1. 4-Chlorothieno[2,3-d]pyrimidine (205)

Starting from thieno[2,3-d]pyrimidin-4(3H)-one (204) [*J. Med. Chem.,* 1999, 42, 26, 5437-5447, *Bull. Soc. Chim. Fr.,* 1975, 587-591] and following the procedure described above for the synthesis of compound 20 (scheme 4, example 22), title compound 205 was obtained in 93% yield. LRMS (M+1) 169.1 (100%), 171.1 (32%).

Steps 2-4. (4-Chlorothieno[2,3-d]pyrimidin-6-yl)(pyrrolidin-1-yl)methanone (208)

Starting from the compound 205 and following the procedures described above for the synthesis of amide 5 (scheme 1, steps 2-4, example 1), title compound 208 was obtained [via intermediates 206 and 207], in 76% yield as dark-brown oil (crude material, was used for the next step without additional purification). LRMS (M+1) 268.2 (100%).

Step 5. (4-(2-Fluoro-4-nitrophenoxy)thieno[2,3-d]pyrimidin-6-yl)(pyrrolidin-1-yl)methanone (209)

Starting from the compound 208 and following the procedures described above for the synthesis of nitro compound 6 (scheme 1, step 5, example 1), title compound 209 was obtained in 24% yield. LRMS (M+1) 389.1 (100%).

Step 6. (4-(4-Amino-2-fluorophenoxy)thieno[2,3-d]pyrimidin-6-yl)(pyrrolidin-1-yl)methanone (210)

Starting from the compound 209 and following the procedures described above for the synthesis of amine 7 (scheme 1, step 6, example 1), crude title compound 210 was obtained. It was purified by flash chromatography, eluents DCM followed by DCM-MeOH-Et$_3$N (97.75:2:0.25), to afford title compound 210 in 54% yield as a yellow solid. LRMS (M+1) 359.1 (100%).

Step 7. N-(3-Fluoro-4-(6-(pyrrolidine-1-carbonyl)thieno[2,3-d]pyrimidin-4-yloxy)phenylcarbamothioyl)-2-phenylacetamide (211)

Starting from the compound 210 and following the procedures described above for the synthesis of compound 8a (scheme 1, step 7, example 1), crude title compound 211 was obtained. It was purified by flash chromatography, eluents DCM and DCM-MeOH-Et$_3$N (97.75:2:0.25) followed by trituration with a mixture of MeOH-EtOAc, to afford title compound 211 in 17% yield as a yellow solid. $^1$H NMR (400 MHz, DMSO-d$_6$) δ (ppm): 12.43 (s, 1H), 11.80 (s, 1H), 8.70 (s, 1H), 8.06 (s, 1H), 7.93 (d, 1H, J=11.7/2.3 Hz), 7.53-7.47 (m, 2H), 7.34-7.26 (m, 5H), 3.90 (t, 2H, J=6.7 Hz), 3.83 (s, 2H), 3.55 (t, 2H, J=6.7 Hz), 1.99-1.85 (m, 4H). LRMS (M+1) 536.2 (100%).

Example 188

2-Phenyl-N-(4-(thieno [3,2-b]pyridin-7-yloxy)phenylcarbamothioyl)acetamide (170c)

Step 1. 7-(4-Nitrophenoxy)thieno[3,2-b]pyridine (212)

Staring from the chloride 2, following the procedure described above for the synthesis of compound 6 (scheme 1, example 1) but substituting 2-fluoro-4-nitrophenol for 4-nitrophenol, title compound 212 was obtained in 89% yield. MS (m/z) 273.0 (M+H).

Scheme 45

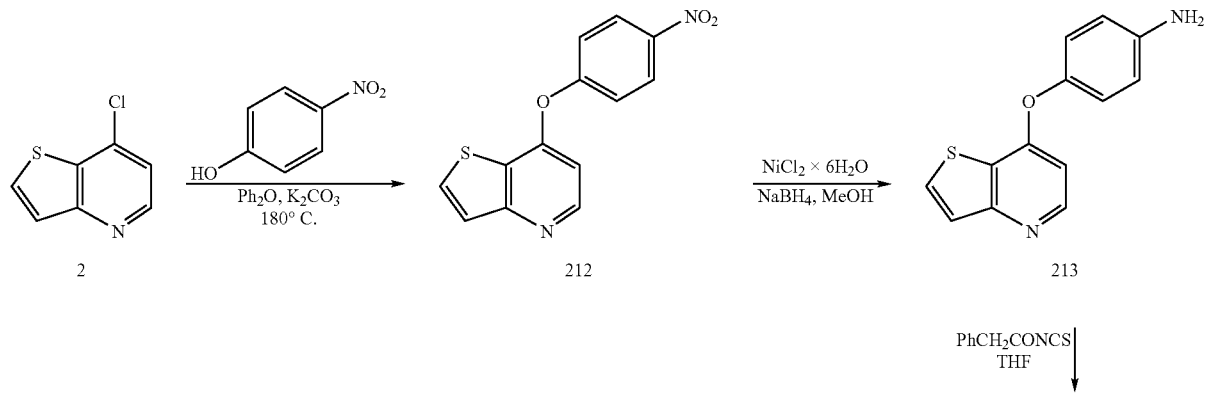

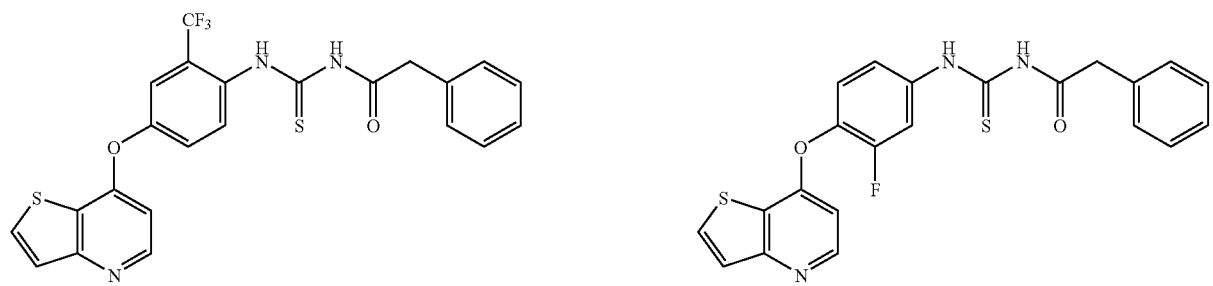

170d: Example 189

170c: Example 188

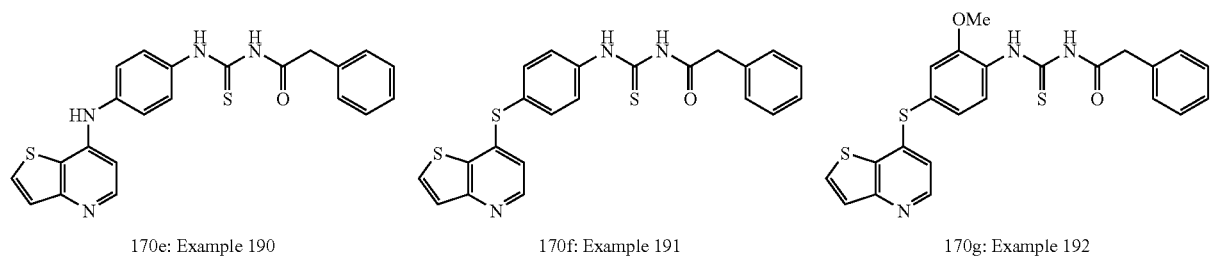

170e: Example 190

170f: Example 191

170g: Example 192

223

Step 2.
4-(Thieno[3,2-b]pyridin-7-yloxy)benzenamine (213)

Staring from the nitro compound 212, following the procedure described above for the synthesis of amine 49 (scheme 10, example 55), title compound 213 was obtained in 90% yield. MS (m/z) 243.1 (M+H).

Step 3. 2-Phenyl-N-(4-(thieno[3,2-b]pyridin-7-yloxy)phenylcarbamothioyl)acetamide (170c)

Staring from the amine 213, following the procedure described above for the synthesis of compound 50 (scheme 10, example 55), title compound 170c was obtained in 34% yield. $^1$H NMR (400 MHz,DMSO-d$_6$) δ ppm 12.35 (1H, s), 11.69 (1H, s), 8.47 (1H, d, J=5.28 Hz), 8.10 (1H, d, J=5.28 Hz), 7.70 (1H, s), 7.68 (1H, s), 7.54 (1H, d, J=5.28 Hz), 7.30-7.22 (7H, m), 6.61 (1H, d, J=5.28 Hz), 3.78 (2H, s). MS (m/z) 420.0 (M+H).

Example 189

2-Phenyl-N-(4-(thieno[3,2-b]pyridin-7-yloxy)-2-(trifluoromethyl)phenylcarbamothioyl)acetamide (170d)

Title compound 170d was obtained according to the scheme 45 via a three-step synthesis starting from the chloride 2 and replacing 4-nitrophenol [in the first step] with 4-nitro-3-(trifluoromethyl)phenol. $^1$H NMR (400 MHz, DMSO-d$_6$) δ (ppm): 12.29 (s, 1H), 11.99 (s, 1H), 8.56 (d, J=5.3 Hz, 1H), 8.17 (d, J=5.3 Hz, 1H), 7.84 (d, J=8.6 Hz, 1H), 7.74 (d, J=2.7 Hz, 1H), 7.63 (m, 2H), 7.34 (m, 4H), 7.26 (m, 2H), 6.75 (d, J=5.3 Hz, 1H), 3.85 (s, 1H). MS (m/z): 488.3 (M+H).

Example 190

2-Phenyl-N-(4-(thieno[3,2-b]pyridin-7-ylamino)phenylcarbamothioyl)acetamide (170e)

Title compound 170e was obtained according to the scheme 45 via a three-step synthesis starting from the chloride 2 and replacing 4-nitrophenol [in the first step] with 4-nitrobenzenamine.
$^1$H NMR (400 MHz, DMSO-d$_6$) δ (ppm) 12.39 (s, 1H), 11.72 (s, 1H), 8.97 (s, 1H), 8.35 (d, J=5.1 Hz, 1H), 8.03 (d, J=5.5 Hz, 1H), 7.64 (d, J=8.4 Hz, 2H), 7.49 (d, J=5.3 Hz, 1H), 7.38 (m, 4H), 7.32 (d, J=8.4 Hz, 3H), 6.94 (d, J=5.5 Hz, 1H), 3.87 (s, 1H). MS (m/z): 419.2 (M+H).

Example 191

2-Phenyl-N-(4-(thieno[3,2-b]pyridin-7-ylthio)phenylcarbamothioyl)acetamide (170f)

Title compound 170f was obtained according to the scheme 45 via a three-step synthesis starting from the chloride 2 and replacing 4-nitrophenol [in the first step] with 4-nitrobenzenethiol.

224

$^1$H NMR (400 MHz,DMSO-d$_6$) δ ppm 12.65 (1H, s), 11.91 (1H, s), 8.62 (1H, d, J=4.70 Hz), 8.28 (1H, d, J=5.28 Hz), 8.01-7.90 (2H, m), 7.79-7.68 (5H, m), 7.23 (1H, m), 3.95 (2H, m). MS (m/z) 436.0 (M+H)

Example 192

N-(2-Methoxy-4-(thieno[3,2-b]pyridin-7-yloxy)phenylcarbamothioyl)-2-phenylacetamide (170 g)

Title compound 170 g was obtained according to the scheme 45 via a three-step synthesis starting from the chloride 2 and replacing 4-nitrophenol [in the first step] with 3-methoxy-4-nitrophenol [Hodgson, C., *J. Chem. Soc.*, 1929, 2778). $^1$H NMR (DMSO) δ (ppm): 12.70 (1H, s), 11.71 (1H, s), 8.63 (1H, d, J=8.80 Hz), 8.51 (1H, d, J=5.28 Hz), 8.14 (1H, d, J=5.48 Hz), 7.50 (1H, dd, J=5.48, 0.78 Hz), 7.36-7.25 (5H, m), 7.13 (1H, d, J=2.54 Hz), 6.89 (1H, dd, J=8.80, 2.54 Hz), 6.69 (1H, d, J=5.48 Hz), 3.82 (5H, s). MS (m/z) 449.55 (M+H).

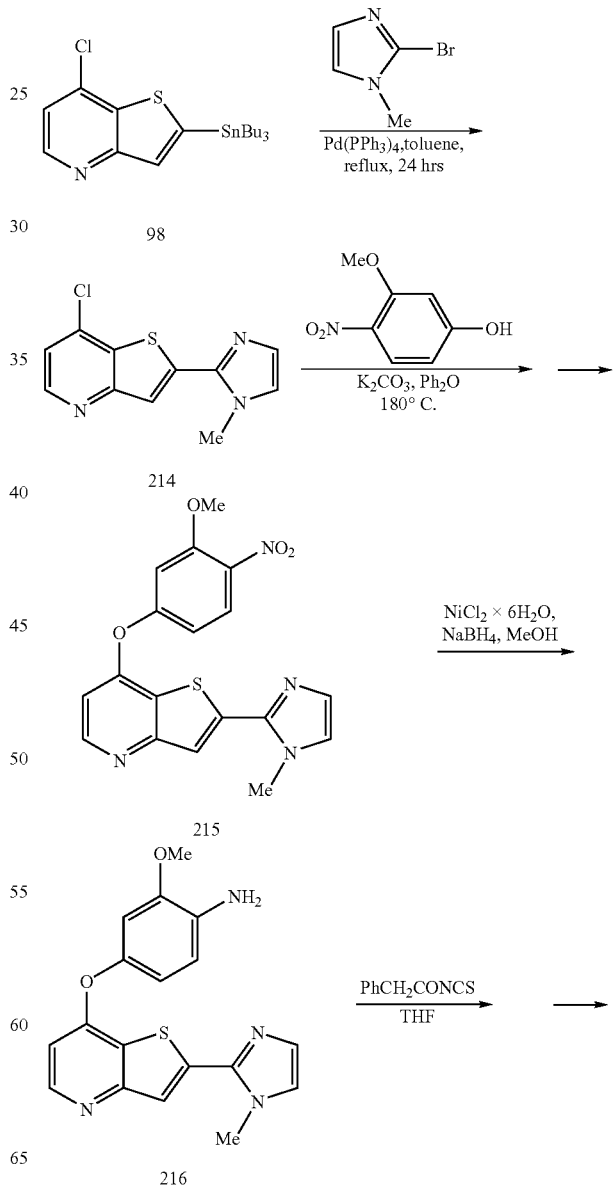

Scheme 46

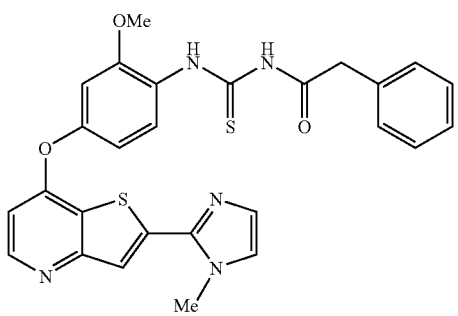

217: Example 193

Example 193

N-(2-Methoxy-4-(2-(1-methyl-1H-imidazol-2-yl)thieno[3,2-b]pyridin-7-yloxy)phenylcarbamothioyl)-2-phenylacetamide (217)

Step 1. 7-Chloro-2-(1-methyl-1H-imidazol-2-yl)thieno[3,2-b]pyridine (214)

Starting from tributyltin compound 98 (scheme 19) and following the procedure described above for the synthesis of compound 10 (scheme 2, step 2, example 12) but replacing 2-bromothiazole with 2-bromo-1-methyl-1H-imidazole, title compound 214 was obtained in 95% yield. MS (m/z) 250.1 (100%), 252.1 (37%), (M+H).

Step 2. 7-(3-Methoxy-4-nitrophenoxy)-2-(1-methyl-1H-imidazol-2-yl)thieno[3,2-b]pyridine (215)

Starting from compound 214, following the procedure described above for the synthesis of compound 11 (scheme 2, step 3, example 12) but replacing 2-fluoro-4-nitrophenol with 3-methoxy-4-nitrophenol [Hodgson, C., *J. Chem. Soc.,* 1929, 2778], title compound 215 was obtained in 9% yield. MS (m/z) 383.1 (M+H).

Step 3. 2-Methoxy-4-(2-(1-methyl-1H-imidazol-2-yl)thieno[3,2-b]pyridin-7-yloxy)benzenamine (216)

Starting from compound 215 and following the procedure described above for the synthesis of compound 12 (scheme 2, step 4, example 12), title compound 216 was obtained in 100% yield. MS (m/z) 353.1 (M+H).

Step 4. N-(2-Methoxy-4-(2-(1-methyl-1H-imidazol-2-yl)thieno[3,2-b]pyridin-7-yloxy)phenylcarbamothioyl)-2-phenylacetamide (217)

Starting from compound 216 and following the procedure described above for the synthesis of compound 13a (scheme 2, step 5, example 12), title compound 217 was obtained in 48% yield. $^1$H NMR (400 MHz, DMSO-$d_6$) δ ppm. 12.07 (1H, s), 11.59 (1H, s), 8.45 (1H, d, J=5.48 Hz), 7.91 (1H, d, J=8.80 Hz), 7.85 (1H, s), 7.41 (1H, s), 7.24-6.98 (8H, m), 6.66 (1H, d, J=5.67 Hz), 3.99 (3H, s), 3.78 (3H, s), 3.59 (2H, s). MS (m/z) 530.2 (M+H).

Scheme 47

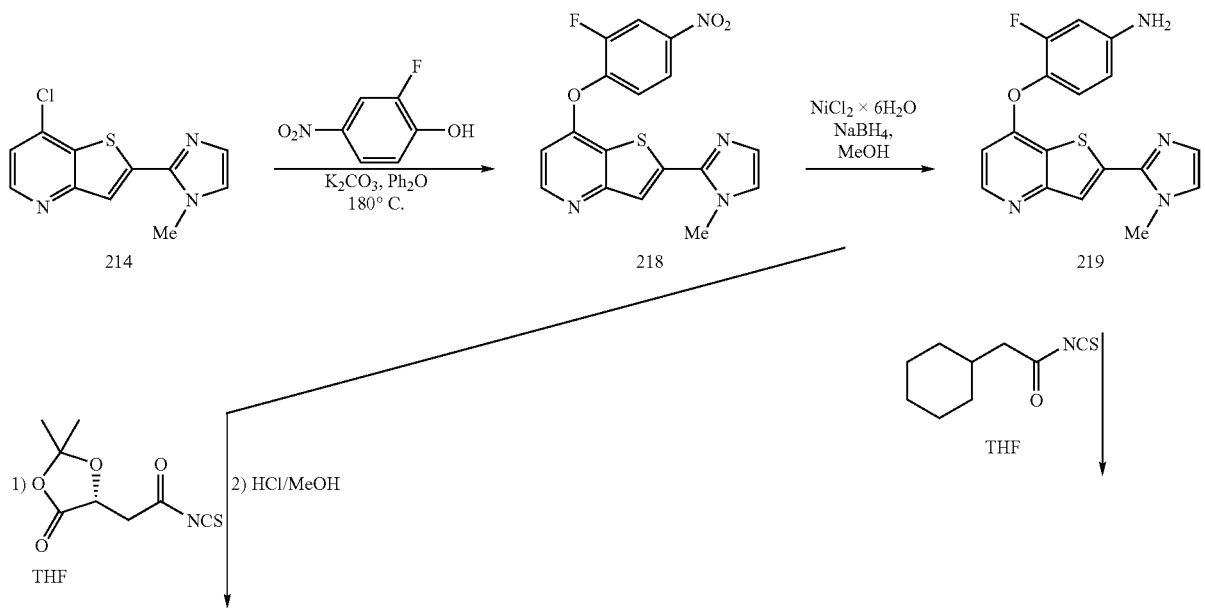

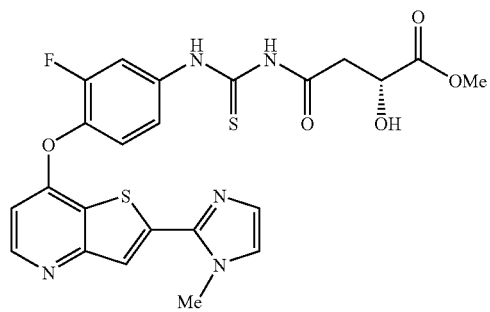

220f: Example 199

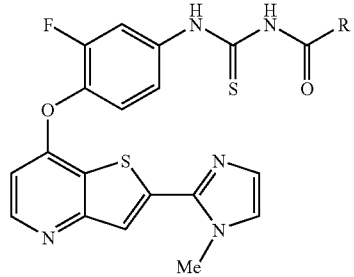

220a: Example 194

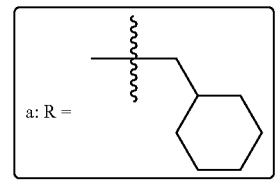

a: R =

Example 194

2-Cyclohexyl-N-(3-fluoro-4-(2-(1-methyl-1H-imidazol-2-yl)thieno[3,2-b]pyridin-7-yloxy)phenylcarbamothioyl)acetamide (220a)

Step 1. 7-(2-Fluoro-4-nitrophenoxy)-2-(1-methyl-1H-imidazol-2-yl)thieno[3,2-b]pyridine (218)

Starting from compound 214 (scheme 46) and following the procedure described above for the synthesis of compound 11 (scheme 2, step 3, example 12), title compound 218 was obtained in 45% yield. MS (m/z) 371.1 (M+H).

Step 2. 3-Fluoro-4-(2-(1-methyl-1H-imidazol-2-yl)thieno[3,2-b]pyridin-7-yloxy)benzenamine (219)

Starting from compound 218 and following the procedure described above for the synthesis of compound 12 (scheme 2, step 4, example 12), title compound 219 was obtained in 86% yield. MS (m/z) 341.1 (M+H).

Step 3: 2-Cyclohexyl-N-(3-fluoro-4-(2-(1-methyl-1H-imidazol-2-yl)thieno[3,2-b]pyridin-7-yloxy)phenylcarbamothioyl)acetamide (220a)

To a suspension of 219 (50 mg, 0.145 mmol) in THF (1.5 mL) was added 2-cyclohexylacetyl isothiocyanate (40 mg, 0.22 mmol) [P. A. S. Smith and R. O. Kan. *J. Org. Chem.*, 1964, 2261] and the reaction mixture was stirred for 3 hours transferred onto a flash chromatography column and eluted with EtOAc-MeOH mixture (19:1), to afford title compound 220a (27.5 mg, 31% yield) as a light yellow solid. Characterization of 220a is provided in the table 21.

Example 195

2-Cyclopentyl-N-(3-fluoro-4-(2-(1-methyl-1H-imidazol-2-yl)thieno[3,2-b]pyridin-7-yloxy)phenylcarbamothioyl)acetamide (220b)

Title compound 220b was obtained similarly to the compound 220a from the amine 219 and 2-cyclopentylacetyl isothiocyanate [P. A. S. Smith and R. O. Kan. *J. Org. Chem.* 1964, 2261] in 47% yield. Characterization of 220b is provided in the table 21.

Example 196

N-(3-Fluoro-4-(2-(1-methyl-1H-imidazol-2-yl)thieno[3,2-b]pyridin-7-yloxy)phenylcarbamothioyl)-2-(2-oxopyrrolidin-1-yl)acetamide (220c)

Title compound 220c was obtained similarly to the compound 220a from the amine 219 and 2-(2-oxopyrrolidin-1-yl)acetyl isothiocyanate [prepared according to the reference P. A. S. Smith and R. O. Kan. *J. Org. Chem.* 1964, 2261] in 18% yield. Characterization of 220c is provided in the table 21.

Example 197

N-(3-Fluoro-4-(2-(1-methyl-1H-imidazol-2-yl)thieno[3,2-b]pyridin-7-yloxy)phenylcarbamothioyl)-2-(tetrahydro-2H-pyran-4-yl)acetamide (220d)

Title compound 220d was obtained similarly to the compound 220a from the amine 219 and 2-(tetrahydro-2H-pyran-4-yl)acetyl isothiocyanate [prepared according to the reference P. A. S. Smith and R. O. Kan. *J. Org. Chem.* 1964, 2261] in 15% yield. Characterization of 220d is provided in the table 21.

Example 198

N-(3-Fluoro-4-(2-(1-methyl-1H-imidazol-2-yl)thieno[3,2-b]pyridin-7-yloxy)phenylcarbamothioyl)acetamide (220e)

Title compound 220f was obtained similarly to the compound 220a from the amine 219 and acetyl isothiocyanate in 28% yield. Characterization of 220f is provided in the table 21.

Example 199

(R)-Methyl 4-(3-(3-fluoro-4-(2-(1-methyl-1H-imidazol-2-yl)thieno[3,2-b]pyridin-7-yloxy)phenyl)thioureido)-2-hydroxy-4-oxobutanoate (220f)

To a suspension of 219 (60 mg, 0.186 mmol) in THF (1.9 mL) was added (R)-2-(2,2-dimethyl-5-oxo-1,3-dioxolan-4-yl)acetyl isothiocyanate (60 mg, 0.28 mmol) [P. A. S. Smith and R. O. Kan. *J. Org. Chem.* 1964, 2261]. The reaction mixture was stirred for 3 hours, concentrated, purified by flash chromatography, eluent EtOAc-MeOH (19:1), to produce a solid material (29.5 mg) which was dissolved in MeOH, treated with HCl (1N in Et$_2$O, 0.1 mL) and the mixture was stirred for 10 min at room temperature. The solution was concentrated, and the residue was purified by preparative HPLC (Aquasil C18 column, gradient: 30% MeOH to 95% MeOH in water, 45 min), to afford title compound 220f (15 mg, 13% yield) as a white solid. Characterization of 220f is provided in the table 21.

TABLE 21

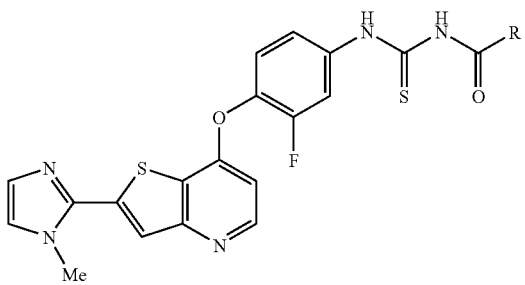

220a–f: Examples 194–199

Characterization of compounds 220a–f (examples 194–199)

| Cpd | Ex | R | Name | Characterization |
|---|---|---|---|---|
| 220a | 194 | (cyclohexylmethyl) | 2-Cyclohexyl-N-(3-fluoro-4-(2-(1-methyl-1H-imidazol-2-yl)thieno[3,2-b]pyridin-7-yloxy)phenylcarbamothioyl)acetamide | $^1$HNMR: (DMSO-d$_6$) δ (ppm): 12.68(s, 1H), 11.57(s, 1H), 8.72(d, 5.5Hz, 1H), 8.40(s, 1H), 8.1(m, 1H), 7.88(m, 1H), 7.75(s, 1H), 7.61(m, 2H), 6.90(d, J=5.5Hz, 1H), 4.05(s, 3H), 2.37(d, J=6.8Hz, H), 1.79–1.60(m, 6H), 1.28–1.12(m, 3H), 1.02–0.94(m, 2H). MS(m/z): 524.3(M+1). |
| 220b | 195 | (cyclopentylmethyl) | 2-Cyclopentyl-N-(3-fluoro-4-(2-(1-methyl-1H-imidazol-2-yl)thieno[3,2-b]pyridin-7-yloxy)phenylcarbamothioyl)acetamide | $^1$H NMR (DMSO-d$_6$) δ (ppm): 12.66(s, 1H), 11.55(s, 1H), 8.5(m, 1H), 8.06(d, J = 12.5Hz, 1H), 7.9(s, 1H), 7.55(m, 2H), 7.41(s, 1H), 7.05(s, 1H), 6.69(m, 1H), 4.0(s, 3H), 2.5(m, 2H), 2.2(m, 1H), 1.78(m, 2H), 1.61–1.52(m, 4H), 1.18(m, 2H). MS(m/z): 510.2(M+1) |
| 220c | 196 | (2-oxopyrrolidin-1-ylmethyl) | N-(3-Fluoro-4-(2-(1-methyl-1H-imidazol-2-yl)thieno[3,2-b]pyridin-7-yloxy)phenylcarbamothioyl)-2-(2-oxopyrrolidin-1-yl)acetamide | $^1$H NMR (DMSO-d$_6$) δ (ppm): 8.52(d, J=5.4Hz, 1H), 7.98(m, 1H), 7.89(m, 1H), 7.46(m, 2H), 7.40(s, 1H), 7.04(m, 1H), 6.68(d, J = 5.3Hz, 1H), 4.18(s, 2H), 3.99(s, 3H), 3.37(m, 2H), 2.27(m, 2H), 2.0(m, 2H). MS(m/z): 525.3(M+1). |
| 220d | 197 | (tetrahydro-2H-pyran-4-ylmethyl) | N-(3-Fluoro-4-(2-(1-methyl-1H-imidazol-2-yl)thieno[3,2-b]pyridin-7-yloxy)phenylcarbamothioyl)-2-(tetrahydro-2H-pyran-4-yl)acetamide | $^1$H NMR (DMSO-d$_6$) δ (ppm): 8.53(d, J = 5.3Hz, 1H), 8.03(d, J = 12.5Hz, 1H), 7.89(s, 1H), 7.52(m, 2H), 7.41(m, 1H), 7.04(m, 1H), 6.69(d, J = 5.4Hz, 1H), 3.99(s, 3H), 3.82(m, 2H), 3.59(m, 1H), 3.3(m, 2H), 2.43(m, 2H), 1.76(m, 2H), 1.25(m, 2H). MS(m/z): 526.2(M+1). |
| 220e | 198 | CH$_3$ | N-(3-Fluoro-4-(2-(1-methyl-1H-imidazol-2-yl)thieno[3,2-b]pyridin-7-yloxy)phenylcarbamothioyl)acetamide | $^1$H NMR (DMSO-d$_6$) δ (ppm): 12.55(br, 1H), 11.52(br, 1H), 8.53(m, 1H), 8.03(m, 1H), 7.90(s, 1H), 7.52(m, 2H), 7.41(s, 1H), 7.04(s, 1H), 6.69(m, 1H), 4.00(s, 3H), 2.18(s, 2H). MS(m/z): 442.1(M+1). |

TABLE 21-continued

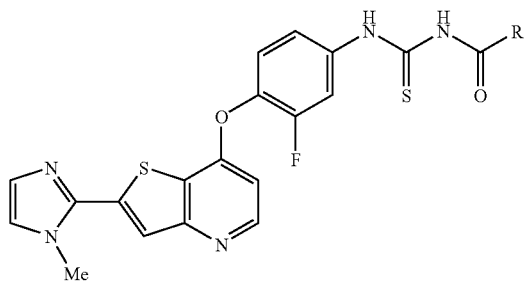

220a–f: Examples 194–199

Characterization of compounds 220a–f (examples 194–199)

| Cpd | Ex | R | Name | Characterization |
|---|---|---|---|---|
| 220f | 199 | (structure: methyl group with CH2-C(=O)-OMe and OH, R-configuration) | (R)-Methyl 4-(3-(3-fluoro-4-(2-(1-methyl-1H-imidazol-2-yl)thieno[3,2-b]pyridin-7-yloxy)phenyl)thioureido)-2-hydroxy-4-oxobutanoate | $^1$H NMR (DMSO-$d_6$) δ (ppm): 8.55(d, J=5.5Hz, 1H), 8.04(m, 1H), 7.92(s, 1H), 7.55(m, 2H), 7.43(d, J = 1Hz, 1H), 7.06(d, J=1Hz, 1H), 6.70(dd, J=5.5Hz, J=1Hz, 1H), 4.48(dd, J '5.2Hz, J '7.2Hz, 1H), 4.0(s, 3H), 3.67(s, 3H), 2.92(dd, J=5.2Hz, J '15.5Hz, 1H), 2.86(dd, J = 7.4Hz, J=15.5Hz, 1H). MS(m/z): 530.2(M+1) |

Scheme 48

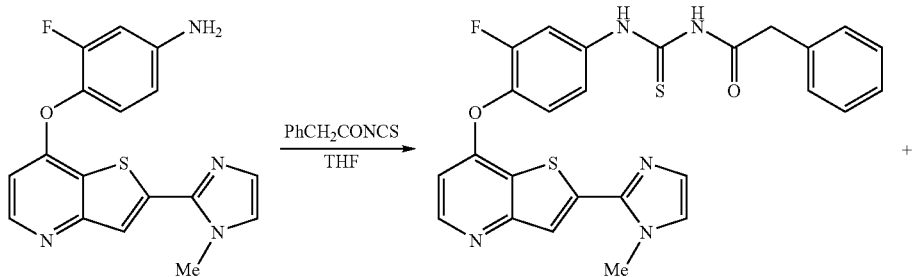

219 → 13d: Example 15

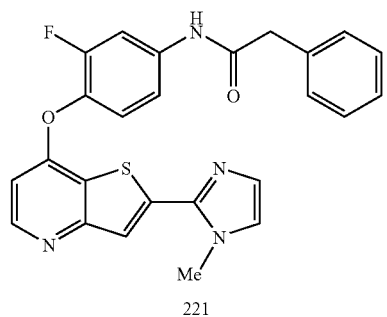

221

1) NaH/DMF
2) MeI
3) HCl (6N)

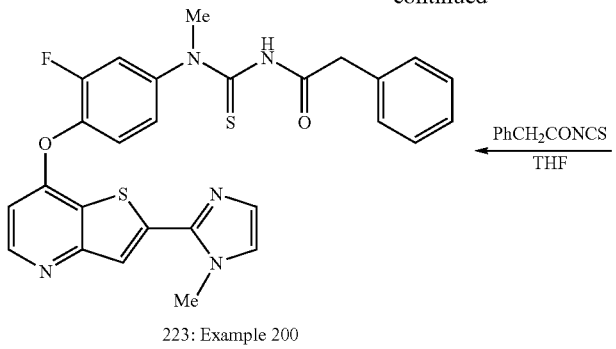

223: Example 200

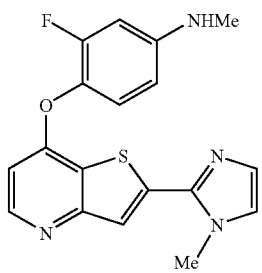

222

Example 200

N-((3-Fluoro-4-(2-(1-methyl-1H-imidazol-2-yl)thieno[3,2-b]pyridin-7-yloxy)phenyl)(methyl)carbamothioyl)-2-phenylacetamide (223)

Step 1: N-(3-Fluoro-4-(2-(1-methyl-1H-imidazol-2-yl)thieno[3,2-b]pyridin-7-yloxy)phenylcarbamothioyl)-2-phenylacetamide (13d) and N-(3-fluoro-4-(2-(1-methyl-1H-imidazol-2-yl)thieno[3,2-b]pyridin-7-yloxy)phenyl)-2-phenylacetamide (221)

To a suspension of 219 (400 mg, 1.18 mmol) in THF (12 mL) was added 2-2-phenylacetyl isothiocyanate (312 mg, 1.76 mmol) [P. A. S. Smith and R. O. Kan. *J. Org. Chem.* 1964, 2261], the reaction mixture was stirred for 3 hours, transferred onto a flash chromatography column and eluted with EtOAc/MeOH mixture (98:2), to afford title compounds 13d (example 15, 254 mg, 42% yield) and 221 (96 mg, 17% yield).

Characterization of 13d (example 15) is provided in the table 2. Compound 221 is characterized by its mass-spectrum: MS (m/z): 459.1 (M+1).

Step 2. 3-Fluoro-N-methyl-4-(2-(1-methyl-1H-imidazol-2-yl)thieno[3,2-b]pyridin-7-yloxy)benzenamine (222)

To a solution of 221 (274.8 mg, 0.6 mmol) in DMF (6 mL) NaH (60% in mineral oil, 36 mg, 0.9 mmol) was added in one portion at 0° C. and the reaction mixture was stirred for 1 h, followed by addition of MeI (0.037 mL, 0.6 mmol). The reaction mixture was allowed to warm up to room temperature, stirred overnight, diluted with EtOAc, washed with water, dried over anhydrous $Na_2SO_4$ and concentrated under reduced pressure. The residue was treated with 6N HCl (3 mL), and heated at 100° C. for 3 h, cooled to room temperature and partitioned between water and DCM. Aqueous phase was collected, basified with 1N NaOH to pH 11 and extracted with EtOAc. The extract was dried over anhydrous $Na_2SO_4$ and concentrated. The residue was purified by flash chromatography (eluent EtOAc/MeOH, 9:1) to afford title compound 222 (102 mg, 46% yiled) as a syrup. MS (m/z): 355.1 (M+1).

Step 3: N-((3-Fluoro-4-(2-(1-methyl-1H-imidazol-2-yl)thieno[3,2-b]pyridin-7-yloxy)phenyl)(methyl)carbamothioyl)-2-phenylacetamide (223)

To a suspension of the 222 (102 mg, 2.88 mmol) in THF (3 ml) was added 2-phenylacetyl isothiocyanate (51 mg, 0.288 mmol). The reaction mixture was stirred for 1 hr, transferred onto a chromatography column and eluted with a mixture EtOAc/MeOH (19: 1) to afford title compound 223 (30 mg, 20% yield) as a white solid. $^1$HNMR: (DMSO-$d_6$) δ (ppm): 10.88 (s, 1H), 8.51 (d, J=5.3 Hz, 1H), 7.91 (s, 1H), 7.41-7.18 (m, 6H), 7.04 (m, 4H), 6.5 (d, J=5.3 Hz, 1H), 4.0 (s, 3H), 3.6 (s, 2H), 3.43 (s, 3H). MS (m/z): 532.3 (M+1).

Scheme 49

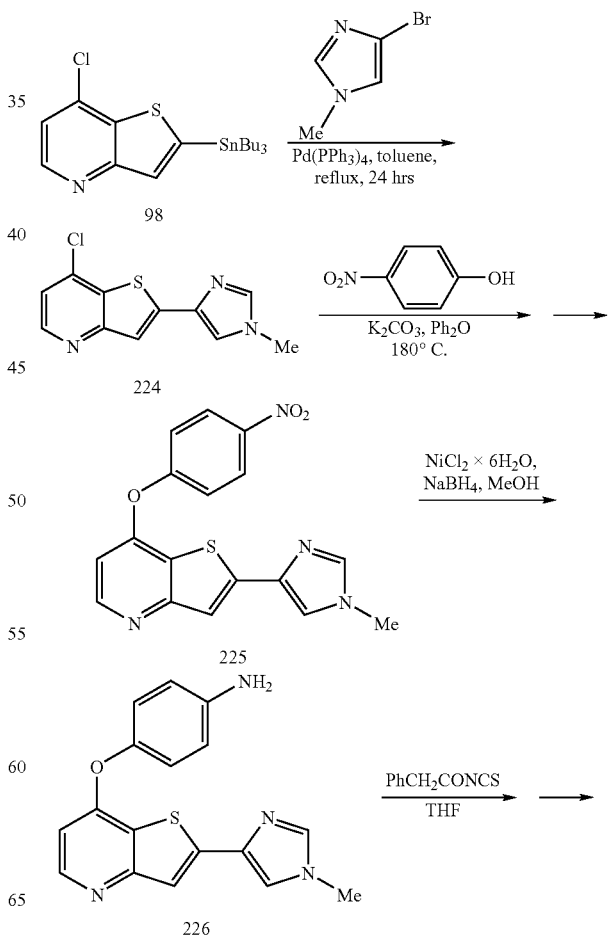

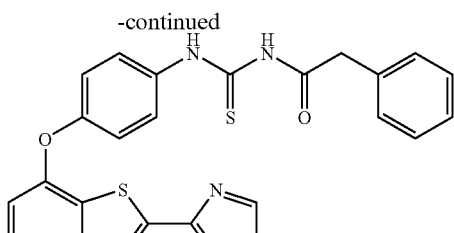

227: Example 201

Example 201

N-(4-(2-(1-Methyl-1H-imidazol-4-yl)thieno[3,2-b] pyridin-7-yloxy)phenylcarbamothioyl)-2-phenylacetamide (227)

Step 1: 7-Chloro-2-(1-methyl-1H-imidazol-4-yl) thieno[3,2-b]pyridine (224)

Starting from the compound 98 (scheme 19), following the procedure described above for the synthesis of compound 10 (scheme 2, step 2, example 12) but replacing 2-bromothiazole with 4-bromo-1-methyl-1H-imidazole, title compound 224 was obtained in 29% yield. MS (m/z): 250.1 (100%), 252.1 (37%) (M+1).

Step 2: 2-(1-Methyl-1H-imidazol-4-yl)-7-(4-nitrophenoxy)thieno[3,2-b]pyridine (225)

A mixture of 224 (950 mg, 3.81 mmol), 4-nitrophenol (795 mg, 5.72 mmol), $K_2CO_3$ (1.05 g, 7.62 mmol) and $Ph_2O$ (5 mL) was stirred at 190° C. for 2 h in a sealed tube, cooled and treated with additional amount of 4-nitrophenol (795 mg, 5.72 mmol). The mixture was stirred for another hour at the same conditions, cooled to room temperature and diluted with DCM. The DCM solution was extracted with 2N HCl; the aqueous phase was collected, basified with concentrated ammonium hydroxide solution (pH~11) and extracted with EtOAc. The extract was dried over anhydrous $Na_2SO_4$ and concentrated under reduced pressure to afford 225 (860 mg, 64% yield) as an orange solid. MS (m/z): 353.1(M+1).

Step 3: 4-(2-(1-Methyl-1H-imidazol-4-yl)thieno[3,2-b]pyridin-7-yloxy)benzenamine (226)

To a solution of 225 (860 mg, 2.44 mmol) and $NiCl_2 \times 6H_2O$ (1.16 mg, 4.88 mmol) in MeOH/THF (49/81 mL) $NaBH_4$ (278 mg, 7.32 mmol) was carefully added. The reaction mixture was stirred for 10 min, concentrated under reduced pressure and the residue was suspended in 10% HCl. The suspension was basified with concentrated $NH_4OH$ solution (pH~11) and extracted with EtOAc.

The extract was dried over anhydrous $Na_2SO_4$ and concentrated under reduced pressure to produce a solid material. The aqueous phase (a suspension) was filtered; the precipitate was collected, washed with MeOH and dried under reduced pressure.

Both precipitate and the solid obtained from the organic phase, were combined to afford title compound 226 (947.4 mg, crude) as a brown solid that was used in the next step without further purification. MS (m/z): 323.1 (M+1).

Step 4: N-(4-(2-(1-Methyl-1H-imidazol-4-yl)thieno[3,2-b]pyridin-7-yloxy)phenylcarbamothioyl)-2-phenylacetamide (227)

To a suspension of the 226 (385 mg, ~0.99 mmol) in THF (10 mL) was added 2-phenylacetyl isothiocyanate (263 mg, 1.49 mmol). The reaction mixture was stirred for 1 hr, transferred onto a chromatography column and eluted with EtOAc/MeOH (9:1) producing a solid material which was re-crystallized from MeCN to afford title compound 227 (74.3 mg, 15% yield) as a white solid. $^1$HNMR: (DMSO-$d_6$) d(ppm): 12.39 (s, 1H), 11.73 (s, 1H), 8.43 (d, J=5.3 Hz, 1H), 7.84 (s, 1H), 7.72 (m, 3H), 7.66 (s, 1H), 7.34-7.27 (m, 7H), 6.69 (d, J=5.3 Hz, 1H), 3.82 (s, 2H), 3.72 (s, 3H). MS (m/z): 500.1 (M+1).

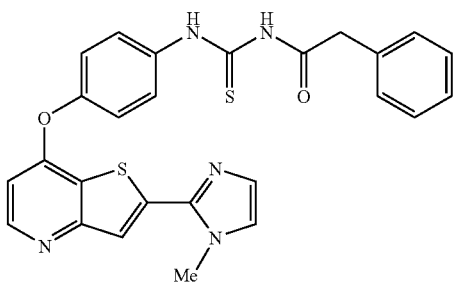

228: Example 202

Example 202

N-(4-(2-(1-Methyl-1H-imidazol-2-yl)thieno[3,2-b] pyridin-7-yloxy)phenylcarbamothioyl)-2-phenylacetamide (228)

Title compound 228 was obtained starting from the compound 214 (scheme 46) and following the procedures described above for the synthesis of compound 227 (scheme 49, example 201). $^1$H NMR (DMSO-$d_6$) δ (ppm): 12.42 (s, 1H), 11.77 (s, 1H), 8.74 (m, 1H), 8.37 (m, 1H), 7.87-7.78 (m, 1H), 7.70 (m, 1H), 7.42-7.20 (m, 7H), 6.90 (m, 1H), 4.05 (d, J=1 Hz, 3H), 3.83 (s, 2H). MS (m/z): 500.3.

Scheme 50

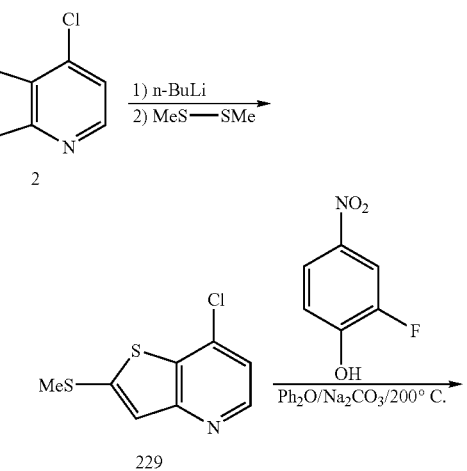

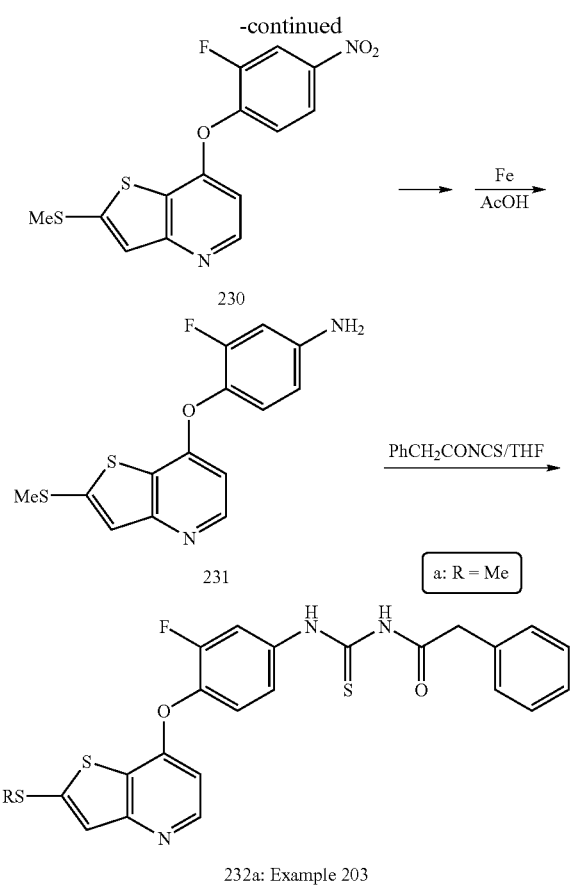

232a: Example 203

Example 203

1-(4-(2-(Methylthio)thieno[3,2-b]pyridin-7-yloxy)-3-fluorophenyl)-3-(2-phenylacetyl)thioure (232a)

Step 1:
7-Chloro-2-(methylthio)thieno[3,2-b]pyridine (229)

To a solution of 2 (200 mg, 1.18 mmol) in dry THF (11 ml) at −78° C. was added n-BuLi (0.57 mL, 2.5M solution on hexane, 1.41 mmol) and the resultant brown precipitate was stirred for 10 minutes. Methyl disulfide (0.16 ml, 1.77 mmol) was added slowly, the mixture was stirred at −78° C. for 3 hours and partitioned between DCM and water. Organic phase was separated, dried over anhydrous $Na_2SO_4$, filtered and concentrated under reduced pressure to afford title compound 229 (0.240 g, 94% yield, crude) as a yellow solid. MS (m/z): 216.1 (100%), 218.1 (39%) (M+1).

Step 2: 7-(2-Fluoro-4-nitrophenoxy)-2-(methylthio)thieno[3,2-b]pyridine (230)

To a suspension of 229 (100 mg, 0.463 mmol) in diphenyl ether (4 mL), was added 2-fluoro-4-nitrophenol (109 mg, 0.695 mmol) and sodium carbonate (147 mg, 1.39 mmol). The reaction mixture was heated atr 200° C. overnight, cooled to room temperature, loaded onto a flash chromatography column and eluted with EtOAc/hexane (1:1) to afford title compound 230 (0.135 mg, 86% yield) as a yellow solid. MS (m/z): 337.0 (M+1).

Step 3: 4-(2-(Methylthio)thieno[3,2-b]pyridin-7-yloxy)-3-fluorobenzenamine (231)

To as solution of 230 (84 mg, 0.250 mmol) in acetic acid (5 mL) at 100° C., was added iron powder (0.069 g, 1.249 mmol). The reaction mixture was allowed to stir for 5 minutes, filtered through a celite pad and concentrated under reduced pressure. The residue was purified by column chromatography, eluent DCM/MeOH (50:1), to afford title compound 231 (61 mg, 80% yield) as yellow oil. MS (m/z): 307.1 (M+1).

Step 4:1-(4-(2-(Methylthio)thieno[3,2-b]pyridin-7-yloxy)-3-fluorophenyl)-3-(2-phenylacetyl)thiourea (232a)

To a suspension of 231 (61 mg) in THF (2 mL) was added 2-phenylacetyl isothiocyanate (42 mg, 0,199 mmol). The reaction mixture was stirred for 3 hours, concentrated under reduced pressure and the residue was purified by column chromatography, eluent EtOAc/hexane (35:65), to produce yellow oil. Purification of this material by preparative HPLC (column C-18 Aquasil, gradient: 60% MeOH to 95% MeOH) afforded title compound 232a (25 mg, 26% yield) as a cream solid. Characterization of 232a is provided in the table 22.

Example 204

1-(4-(2-(Butylthio)thieno[3,2-b]pyridin-7-yloxy)-3-fluorophenyl)-3-(2-phenylacetyl)thiourea (232b)

Starting from the compound 2, following procedures described above for the synthesis of compound 232a (example 203, scheme 50) but replacing methyl disulfide with n-butyl disulfide in the step 1, title compound 232b was synthesized. Characterization of 232b is provided in the table 22.

Example 205

1-(4-(2-(Benzylthio)thieno[3,2-b]pyridin-7-yloxy)-3-fluorophenyl)-3-(2-phenylacetyl)thiourea (232c)

Starting from the compound 2, following procedures described above for the synthesis of compound 232a (example 203, scheme 50) but replacing methyl disulfide with benzyl disulfide in the step 1, title compound 232c was synthesized. Characterization of 232c is provided in the table 22.

Example 206

1-(4-(2-(Pyridin-2-ylthio)thieno[3,2-b]pyridin-7-yloxy)-3-fluorophenyl)-3-(2-phenylacetyl)thiourea (232d)

Starting from the compound 2, following procedures described above for the synthesis of compound 232a (example 203, scheme 50) but replacing methyl disulfide with 2-pyridyl disulfide in the step 1, title compound 232d was synthesized. Characterization of 232d is provided in the table 22.

TABLE 22

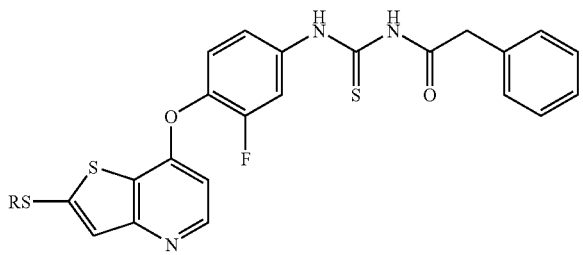

232a–d: Examples 203–206

Characterization of compounds 232a–d (examples 203–206)

| Cpd | Ex | R | Name | Characterization |
|---|---|---|---|---|
| 232a | 203 | Me | 1-(4-(2-(Methylthio) thieno[3,2-b] pyridin-7-yloxy)-3- fluorophenyl)-3- (2-phenylacetyl) thiourea | $^1$HNMR: (DMSO-d6) δ (ppm): 12.46(s, 1H), 11.81(s, 1H), 8.45(s, 1H), 7.99(d, J = 12.5, 1H), 7.51(s, 1H), 7.50(s, 1H), 7.46(s, 1H), 7.34–7.30(m, 2H), 7.30–7.27(m, 3H), 6.61(d, J = 5.5Hz, 1H), 3.82(s, 2H), 2.71(s, 3H). MS(m/z): 484.1. |
| 232b | 204 | n-Bu | 1-(4-(2-(Butylthio) thieno[3,2-b] pyridin-7-yloxy)-3- fluorophenyl)-3-(2- phenylacetyl)thiourea | $^1$H NMR (DMSO-d$_6$) δ (ppm): 12.46(s, 1H), 11.81(s, 1H), 8.46(d, J = 5.5Hz, 1H), 7.98(d, J = 12.44Hz, 1H), 7.54(s, 1H), 7.53–7.47(m, 2H), 7.35–7.31(m, 4H), 7.31–7.24(m, 1H), 6.60(d, J = 5.5Hz, 1H), 3.82(s, 2H), 3.13(t, J = 7.24Hz, 2H), 1.64(q, J = 7.43Hz, 2H), 1.42(sextuplet, J = 7.43Hz, 2H), 0.90(t, J = 7.24Hz, 3H). MS(m/z): 526.2 |
| 232c | 205 | (benzyl) | 1-(4-(2-(Benzylthio) thieno[3,2-b]pyridin- 7-yloxy)-3- fluorophenyl)-3-(2- phenylacetyl)thiourea | $^1$H NMR (DMSO-d$_6$) δ (ppm): 12.46(s, 1H), 11.81(s, 1H), 8.44(d, J=5.5Hz, 1H), 7.98(d, J = 11.83Hz, 1H), 7.52–7.45(m, 3H), 7.38–7.22(m, 10H), 6.60(d, J=5.5Hz, 1H), 4.39(s, 2H), 3.82(s, 2H). MS(m/z): 560.2 |
| 232d | 206 | (pyridin-2-ylmethyl) | 1-(4-(2-(Pyridin-2- ylthio)thieno[3,2- b]pyridin-7-yloxy)- 3-fluorophenyl)-3- (2-phenylacetyl) thiourea | $^1$H NMR (DMSO-d6) δ (ppm): 8.55(d, J = 5.3Hz, 1H), 8.45(d, J=3.91Hz, 1H), 8.00–7.95(m, 2H), 7.74(td, J=7.83Hz; 1.76Hz, 1H), 7.50(s, 2H), 7.35–7.23(m, 8H), 6.70(d, J=5.3Hz, 1H), 3.82(s, 2H), 1.23(s, 1H). MS(m/z): 547.2 |

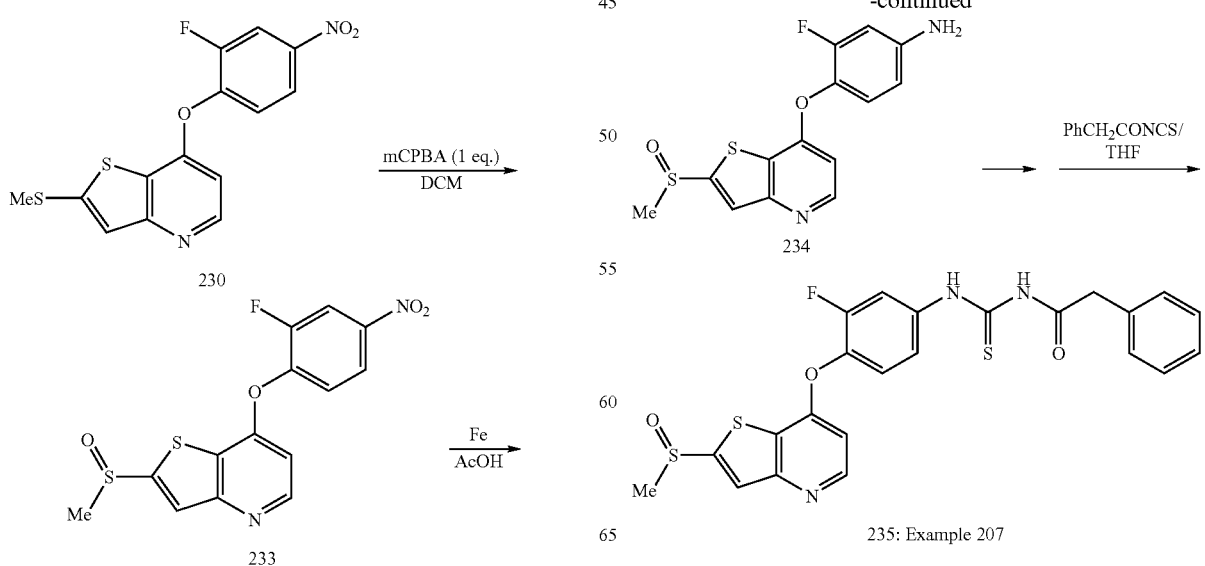

Scheme 51

Example 207

1-(4-(2-(Methylsulfinyl)thieno[3,2-b]pyridin-7-yloxy)-3-fluorophenyl)-3-(2-phenylacetyl)thiourea (207)

Step 1: 7-(2-Fluoro-4-nitrophenoxy)-2-(methylsulfinyl)thieno[3,2-b]pyridine (233)

To a solution of 230 (400 mg, 1.189 mmol, scheme 50) in DCM (12 mL) at 0° C. was added m-CPBA (77%, 272 mg, 1.189 mmol). The reaction mixture was stirred at 0° C. for 30 minutes, water was added and the phases were separated. The organic phase was collected, washed with a 1% sodium hydroxide solution, dried over anhydrous $Na_2SO_4$ and concentrated under reduced pressure. The residue was purified by column chromatography, eluent DCM/MeOH (20:1), to afford title compound 233 (414 mg, 90% yield, crude), which was used in the next step without further purification. MS (m/z): 353.0 (M+1).

Step 2: 4-(2-(Methylsulfinyl)thieno[3,2-b]pyridin-7-yloxy)-3-fluorobenzenamine (234)

To as solution of 233 (400 mg, 1.135 mmol) in acetic acid (10 mL) at 100° C., was added iron powder (317 mg, 5.675 mmol). The reaction mixture was stirred for 5 minutes, filtered through a celite pad and concentrated under reduced pressure. The residue was purified by column chromatography, eluent EtOAc/hexane (4:1), to afford title compound 234 (0.285 g, 69% yield) as a yellow solid. MS (m/z): 323.0 (M+1).

Step 3: 1-(4-(2-(Methylsulfinyl)thieno[3,2-b]pyridin-7-yloxy)-3-fluorophenyl)-3-(2-phenylacetyl)thiourea (235)

To a suspension of 234 (280 mg, 0.868 mmol) in THF (8 mL) was added 2-phenyl acetyl isothiocyanate (185 mg, 1.04 mmol). The reaction mixture was stirred for 3 hours, concentrated; the solid residue washed with $Et_2O$ and dried, to afford title compound 235 (229 mg, 53% yield) as a white-rose solid. $^1$HNMR: (DMSO-d6) δ (ppm):12.41(s,1H), 11.75(s,1H), 8.54(d, J=5.3 Hz, 1H), 7.98 (s, 1H), 7.96(d, J=13.5 Hz, 1H), 7.48(d, J=5.0 Hz, 2H), 7.30-7.26(m, 2H), 7.26-7.18(m, 3H), 6.69(d, J=5.5 Hz, 1H), 3.25(s, 2H), 2.98(s, 3H). MS (m/z): 500.1 (M+1).

Scheme 52

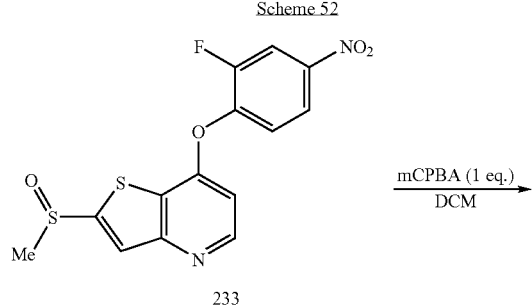

233

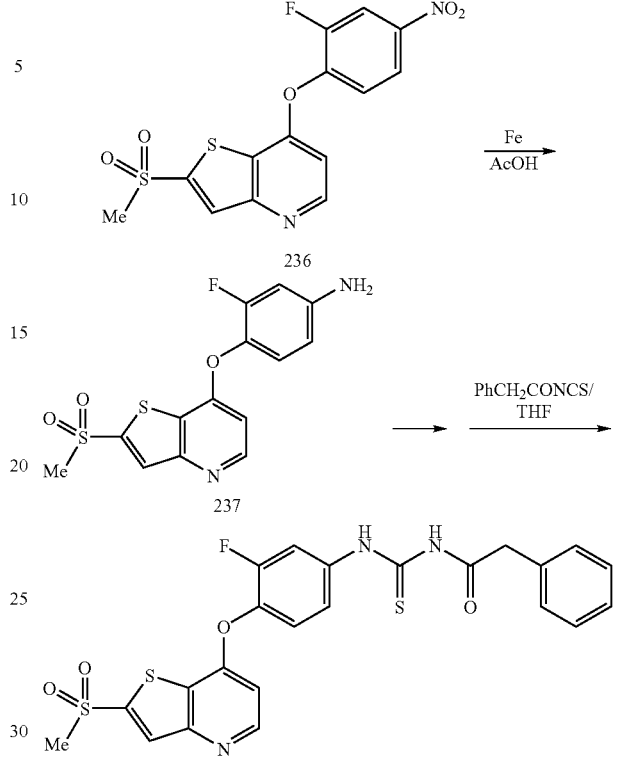

238: Example 208

Example 208

1-(4-(2-(Methylsulfonyl)thieno[3,2-b]pyridin-7-yloxy)-3-fluorophenyl)-3-(2-phenylacetyl)thiourea (238)

Step 1: 7-(2-Fluoro-4-nitrophenoxy)-2-(methylsulfonyl)thieno[3,2-b]pyridine (236)

To a solution of 233 (50 mg, 0.142 mmol) in DCM (2 mL), was added mCPBA (77%, 33 mg, 0.142 mmol) at 0° C. The mixture was stirred at 0° C. for 1 hour, water was added and the phases were separated. The organic layer was collected, washed with a 1% sodium hydroxide solution, dried over anhydrous $Na_2SO_4$ and concentrated under reduced pressure to afford title compound 236 (46 mg, 88% yield, crude) as a yellow solid which was used in the next step without additional purification. MS (m/z): 369.0 (M+1).

Step 2: 4-(2-(Methylsulfonyl)thieno[3,2-b]pyridin-7-yloxy)-3-fluorobenzenamine (237)

To a solution of 236 (45 mg, 0.122 mmol) in acetic acid (4 mL) at 100° C., was added iron powder (34 mg, 0.611 mmol). The reaction mixture was stirred for 5 minutes, filtered through a celite pad and concentrated under reduced pressure to afford title compound 237 (20 mg, 48% yield, crude) as a yellow oil that was used in the next step without further purification.

MS (m/z): 339.0 (M+1).

Step 3. 1-(4-(2-(Methylsulfonyl)thieno[3,2-b]pyridin-7-yloxy)-3-fluorophenyl)-3-(2-phenylacetyl)thiourea (238)

To a suspension of 237 (20 mg, 0.059 mmol) in THF (10 mL) was added 2-phenylacetyl isothiocyanate (26 mg, 0.146 mmol). The reaction mixture was stirred for 2 hours, concentrated under reduced pressure and the residue was purified by column chromatography, eluent EtOAc/MeOH (19:1), to afford a solid material that was dissolved in a minimum MeOH and precipitated with hexane to afford title compound 238 (9.6 mg, 31%) as a white solid.

$^1$HNMR: (DMSO-$d_6$) δ (ppm):12.48(s,1H), 11.81(s,1H), 8.69(d,J=5.5 Hz, 1H), 8.36(s,1H), 8.03(d, J=12.13 Hz, 1H), 7.55(s,2H), 7.36-7.30(m, 2H), 7.30-7.24(m, 3H), 6.86(d, J=5.5 Hz,1H), 3.83(s,2H), 3.54(s,3H). MS (m/z): 516.2.

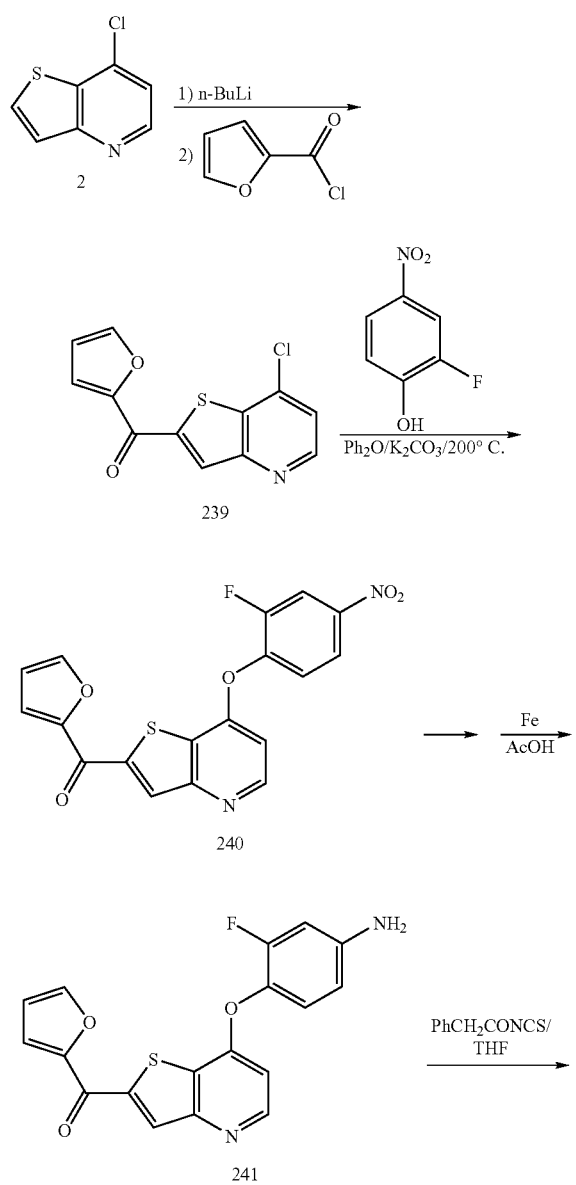

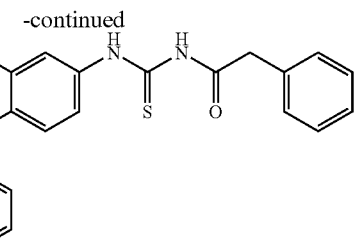

242a: Example 209

Example 209

N-(3-Fluoro-4-(2-(furan-2-carbonyl)thieno[3,2-b]pyridin-7-yloxy)phenylcarbamothioyl)-2-phenylacetamide (242)

Step 1: (7-Chlorothieno[3,2-b]pyridin-2-yl)(furan-2-yl)methanone (239)

To a solution of 2 (100 mg, 0.589 mmol) in THF (6 mL) at −78° C., was added n-BuLi (2.5 M in hexane, 0.259 mL, 8,84 mmol) and the reaction mixture was stirred 15 minutes. 2-Furoyl chloride (0.087 mL, 0.884 mmol) was added drop wise; the mixture was stirred for additional 2 hours and partitioned between DCM and water. The organic layer was separated, dried over anhydrous $Na_2SO_4$ and concentrated under reduced pressure to afford title compound 239 (35 mg, 23% yield, crude) as a yellow solid, that was used in the next step without additional purification. MS (m/z): 264.0 (100%), 266.0 (40%) (M+1).

Step 2: (7-(2-Fluoro-4-nitrobenzyl)thieno[3,2-b]pyridin-2-yl)(furan-2-yl)methanone (240)

To a suspension of 239 (35 mg, 0.133 mmol) in $Ph_2O$ (2 mL) was added 2-fluoro-4-nitrophenol (42 mg, 0.265 mmol) and $K_2CO_3$ (73 mg, 0.530 mmol). The reaction mixture was heated at 180° C. in a sealed flask for 60 hrs, cooled down to room temperature, loaded onto a flash chromatography column and eluted with EtOAc/hexane mixture (1:1), to afford title compound 240 (20 mg 39% yield) as a yellow solid. MS (m/z): 385.1 (M+1).

Step 3: (7-(4-Amino-2-fluorobenzyl)thieno[3,2-b]pyridin-2-yl)(furan-2-yl)methanone (241)

To as solution of 240 (20 mg, 0.052 mmol) in acetic acid (2 mL) at 100° C., was added iron powder (15 mg, 0.260 mmol). The reaction mixture was stirred for 3 minutes, filtered through a celite pad and concentrated under reduced pressure. The residue was purified by flash chromatography, eluent EtOAc/hexane (3:7) to afford title compound 241 (3.3 mg, 18% yield) as a yellow solid. MS (m/z): 355.1 (M+1).

Step 4: N-(3-Fluoro-4-(2-(furan-2-carbonyl)thieno[3,2-b]pyridin-7-yloxy)phenylcarbamothioyl)-2-phenylacetamide (242)

To a solution of 241 (3.3 mg, 0.0093 mmol) in THF (1 mL) was added 2-phenylacetyl isothiocyanate (2 mg, 0.011 mmol). The reaction mixture was stirred for 3 hours, concentrated under reduced pressure and purified by column chromatography, eluent EtOAc/hexane (20:80), followed by precipitation from a mixture acetone/hexane. Thus, title compound 242 was obtained (2.2 mg, 44% yield) as a yellow solid. ¹HNMR: 1HNMR: (DMSO-d6) δ (ppm):12.49(s, 1H), 11.82(s, 1H), 8.67(d, J=5.5 Hz, 1H), 8.63(s, 1H), 8.22(s, 1H), 8.03(d, J=13.1 Hz, 1H), 7.79(d, J=3.7 Hz, 1H), 7.60-7.55(m, 2H), 7.55-7.25(m,5H), 6.89-6.87(m, 1H), 6.83(d, J=5.5 Hz, 1H), 3.82(s, 2H). MS (m/z): 532.1 (M+1).

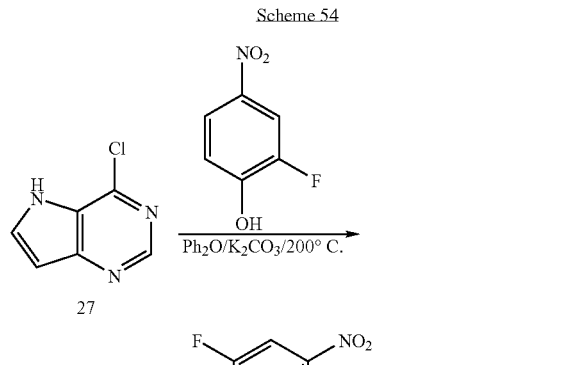

Example 210

N-(3-Fluoro-4-(5-(methoxymethyl)-5H-pyrrolo[3,2-d]pyrimidin-4-yloxy)phenylcarbamothioyl)-2-phenylacetamide (246)

Step 1. 4-(2-Fluoro-4-nitrophenoxy)-5H-pyrrolo[3,2-d]pyrimidine (243)

To a suspension of 27 (0,400 g, 2,60 mmol) [G. B. Evans, R. H. Furneaux, et. al *J. Org. Chem.*, 2001, 66, 17, 5723-57301] in diphenylether (25 ml) was added 2-fluoro-4-nitrophenol (614 mg, 3.90 mmol) and HCl (2N in Et₂O) (0.19 ml, 3.90 mmol). The reaction mixture was heated at 120° C. for 4 hours, cooled to room temperature and concentrated under reduced pressure, to afford title compound 243 (610 mg, 86% yield) as a black solid. MS (m/z): 274.1 (M+1).

Step 2: 4-(2-Fluoro-4-nitrophenoxy)-5-(methoxymethyl)-5H-pyrrolo[3,2-d]pyrimidine (244)

To a suspension of 243 (150 mg, 0.547 mmol in DMF (6 mL) was added NaH (66 mg, 1.64 mmol). and the reaction mixture was stirred at 0° C. for 1 hour. Chloromethyl methyl ester (132 mg, 1.641 mmol) was added drop wise and the mixture was stirred at room temperature over night. MeOH (2 mL) was added and the mixture was stirred for an additional hour and partitioned between EtOAc and water. The organic phase was collected, dried over anhydrous sodium sulfate and concentrated under reduced pressure to afford title compound 244 (86 mg, 49% yield, crude) as an orange solid. MS (m/z): 319.1 (M+1).

Step 3: 3-Fluoro-4-(5-(methoxymethyl)-5H-pyrrolo[3,2-d]pyrimidin-4-yloxy)benzenamine (245)

To as solution of 244 (85 mg, 0.267 mmol) in acetic acid (8 mL) at 100° C., was added iron powder (75 mg, 1.34 mmol). The reaction mixture was stirred for 5 minutes, filtered through Celite® pad and concentrated to dryness; the residue was purified by flash chromatography, eluent DCM/MeOH (30:1) to afford title compound 245 (18 mg, 23% yield) as an orange solid. MS (m/z): 289.1 (M+1).

Step 4: N-(3-Fluoro-4-(5-(methoxymethyl)-5H-pyrrolo[3,2-d]pyrimidin-4-yloxy)phenylcarbamothioyl)-2-phenylacetamide (246)

To a suspension of 245 (18 mg, 0.062 mmol) in THF (1 mL) was added 2-phenylacetyl isothiocyanate (12 mg, 0.069 mmol). The reaction mixture was stirred for 3 hours, concentrated under reduced pressure and the residue was purified by flash chromatography, eluent hexane/EtOAc (3:2) followed by recrystallization (MeCN/water), and preparative HPLC (Aquasil C-18, gradiend: 60% MeOH to 95% MeOH in water), to afford title compound 246 (9.2 mg, 33% yield) as a white solid. ¹HNMR: (CD₃OD) δ (ppm): 8.35(s, 1H), 8.03 (d, J=12.4 Hz, 1H), 7.96(d, J=3.13 Hz, 1H), 7.44-7.26(m, 6H), 6.69 (d, J=3.13 Hz, 1H), 5.29 (quintuplet, J=6.65 Hz, 1H), 3.75(s, 2H), 3.60 (d, J=10.96 Hz, 3H), 1.63(d, J=6.65 Hz, 6H). MS (m/z): 464.16 (M+1).

247

Scheme 55

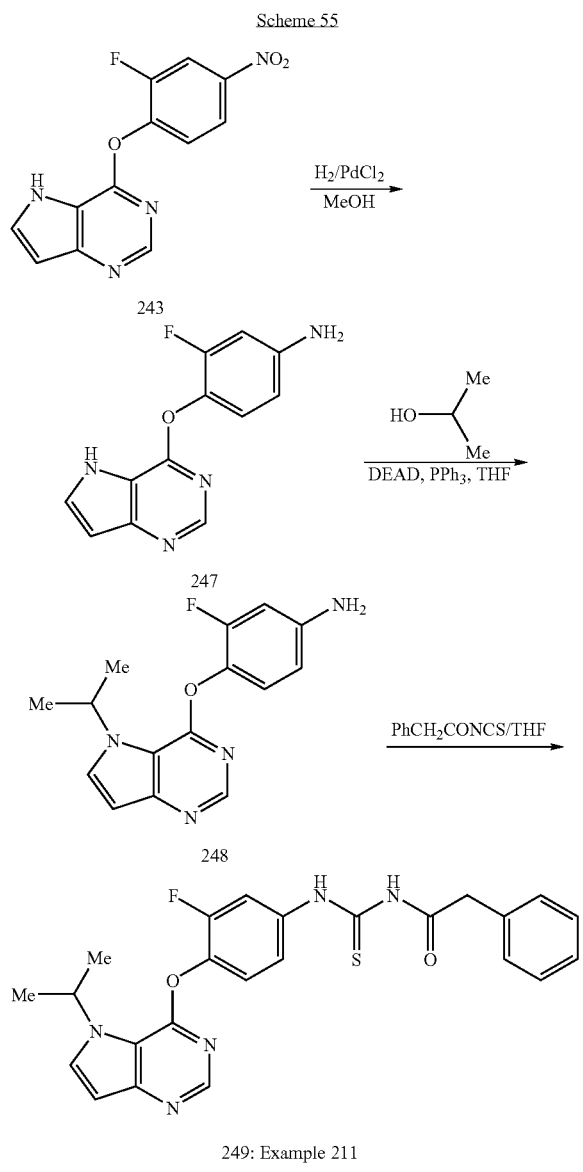

249: Example 211

Example 211

N-(3-Fluoro-4-(5-isopropyl-5H-pyrrolo[3,2-d]pyrimidin-4-yloxy)phenylcarbamothioyl)-2-phenylacetamide (249)

Step 1: 4-(5H-Pyrrolo[3,2-d]pyrimidin-4-yloxy)-3-fluorobenzenamine (247)

A solution of 243 (263 mg, 0.966 mmol, scheme 54) in MeOH (10 mL) and PdCl₂ (1.8 mg, 0.01 mmol) was stirred in the atmosphere of hydrogen for 60 hrs. The reaction mixture was filtered and the filtrate was concentrated under reduced pressure. Water was added to the residue and the aqueous solution was extracted with DCM. The extract was dried over anhydrous Na₂SO₄ and concentrated under reduced pressure, to afford title compound 247 (170 mg, 72% yield, crude) as a gray solid. MS (m/z): 243.08 (M+1).

248

Step 2: 3-Fluoro-4-(5-isopropyl-5H-pyrrolo[3,2-d]pyrimidin-4-yloxy)benzenamine (248)

To a suspension of 247 (80 mg, 0.327 mmol) in THF (4 mL), was added PPh₃ (258 mg, 0.983 mmol), DEAD (0.155 ml, 0.983 mmol) and isopropanol (0.075 ml, 0.983 mmol), and the reaction mixture was allowed to stir for 48 hours. 3N HCl solution (1.0 mL) was added and the mixture was extracted with DCM. Aqueous phase was collected, neutralized with NaOH 10% (pH ~11) and extracted with DCM. The organic phase was collected, dried over anhydrous sodium sulfate and concentrated under reduced pressure. The residue was purified twice by column chromatography: eluents EtOAc/hexane (3:7) and MeOH/DCM (1:20), to afford title compound 248 (19 mg, 31% yield) as yellow solid. MS (m/z): 287.1 (M+1).

Step 3: N-(3-Fluoro-4-(5-isopropyl-5H-pyrrolo[3,2-d]pyrimidin-4-yloxy)phenylcarbamothioyl)-2-phenylacetamide (249)

To a suspension of 248 (10 mg, 0.035 mmol) in THF (1 mL) was added 2-phenylacetyl isothiocyanate (0.007 mL, 0.038 mmol). The reaction mixture was stirred for 3 hours, concentrated under reduced pressure and the residue was purified by flash chromatography, eluent EtOAc/hexane (1:1) and preparative HPLC (C-18 Aquasyl column, gradient: 60% to 95% MeOH in water, 45 min), to afford title compound 249 (4 mg, 26% yield) as a white solid. ¹HNMR: (CD₃OD) δ (ppm): 8.35(s, 1H), 8.03 (d, J=12.4 Hz, 1H), 7.96(d, J=3.13 Hz, 1H), 7.44-7.26(m, 6H), 6.69 (d, J=3.13 Hz, 1 H), 5.29 (quintuplet, J=6.65 Hz, 1H), 3.75(s, 2H), 3.60 (d, J=10.96 Hz, 3H), 1.63 (d, J=6.65 Hz, 6H). MS (m/z): 464.2 (M+1).

Scheme 56

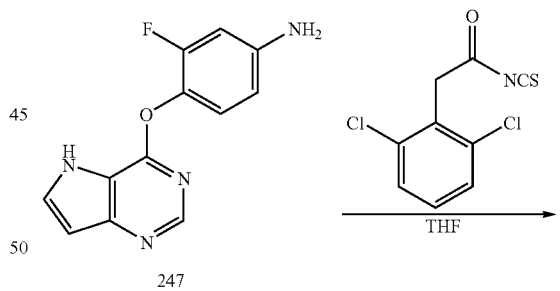

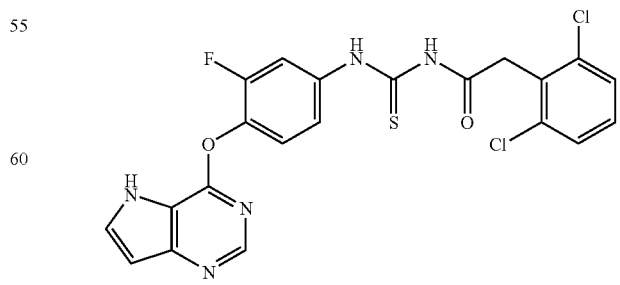

250: Example 212

Example 212

N-(4-(5H-Pyrrolo [3,2-d]pyrimidin-4-yloxy)-3-fluorophenylcarbamothioyl)-2-(2,6-dichlorophenyl)acetamide (250)

Step 1: N-(4-(5H-pyrrolo[3,2-d]pyrimidin-4-yloxy)-3-fluorophenylcarbamothioyl)-2-(2,6-dichlorophenyl)acetamide (250)

To a solution of 247 (200 mg, 0.819 mmol, scheme 55) in THF (8.2 mL) 2-(2,6-dichlorophenyl)acetyl isothiocyanate (302 mg, 1.33 mmol) was added. The mixture was stirred for 1 h at room temperature, transferred onto a flash chromatography column and eluted with EtOAc/hexane (1:1). The solid material obtained was triturated with diethyl ether, filtered and dried under reduced pressure, to afford title compound 250 (200 mg, 0.408, 50% yield) as a light brown solid. $^1$HNMR: (DMSO-$d_6$) δ (ppm) 12.69 (s, 1H), 12.26 (s, 1H), 12.04 (s, 1H), 7.94 (m, 2H), 7.53 (m, 4H), 7.39 (m, 1H), 6.72 (m, 1H), 4.22 (s, 2H). MS (m/z): 490.1 (100%, 492.1 (77%) (M+1).

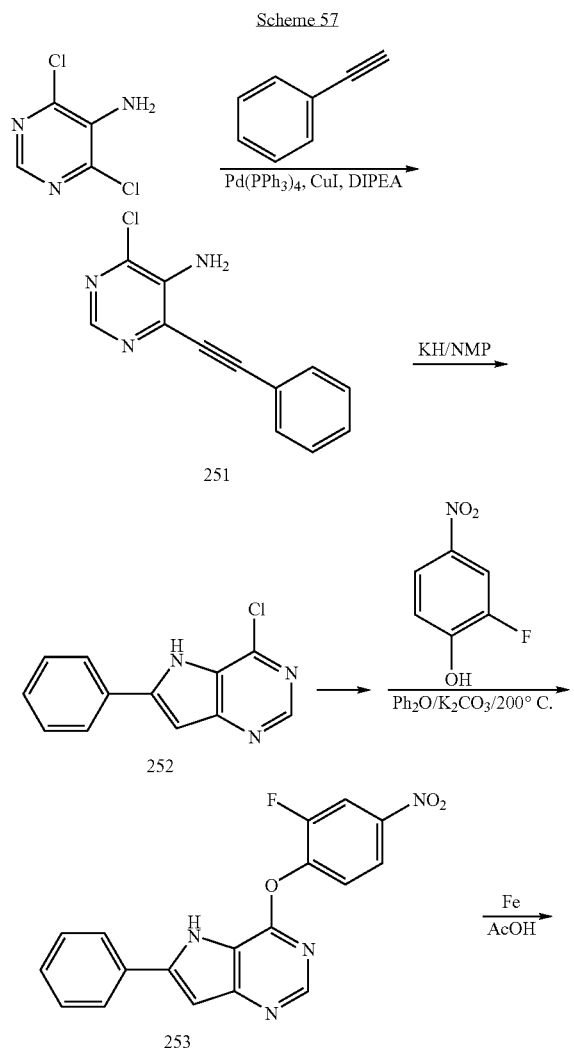

Scheme 57

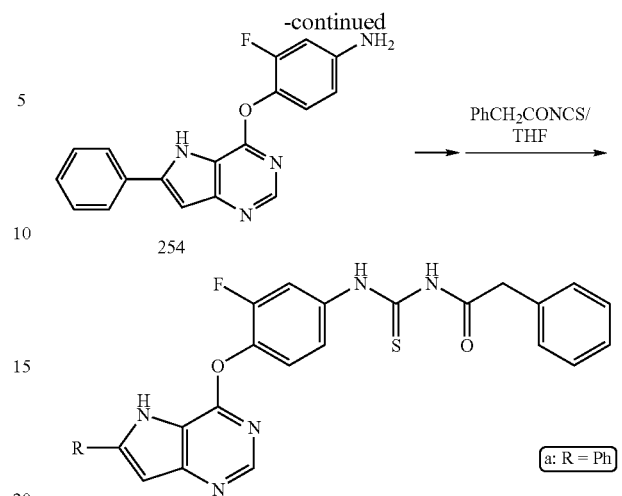

255a: Example 213

Example 213

N-(3-Fluoro-4-(6-phenyl-5H-pyrrolo[3,2-d]pyrimidin-4-yloxy)phenylcarbamothioyl)-2-phenylacetamide (255a)

Step 1: 4-Chloro-6-(phenylethynyl)pyrimidin-5-amine (251)

Ethynylbenzene (0.092 mL, 0.92 mmol) was added to a solution of 4,6-dichloropyrimidin-5-amine (100 mg, 0.61 mmol), Pd(PPh$_3$)$_4$ (140 mg, 0.12 mmol), CuI (116 mg, 0.61 mmol) and DIPEA (0.5 mL, 3.05 mmol) in DME (6.1 mL). The reaction mixture was stirred in the dark over night at room temperature, diluted with DCM, washed sequentially with dilute aqueous citric acid and water, dried over anhydrous Na$_2$SO$_4$ and concentrated under reduce pressure. The residue was purified by flash chromatography, eluent EtOAc/hexane (1:3), to afford title compound 251 (30.8 mg, 22% yield) as a yellow solid. MS (m/z): 230.1 (100.0%), 232.1 (33%) (M+1).

Step 2: 4-Chloro-6-phenyl-5H-pyrrolo[3,2-d]pyrimidine (252)

To a solution of 251 (30.8 mg, 0.134 mmol) in NMP (1.4 mL) a suspension of KH in mineral oil (35%, 31 mL, 0.268 mmol) was added in one portion. The mixture was stirred at room temperature overnight and partitioned between EtOAc and water. The organic phase was collected, dried over anhydrous Na$_2$SO$_4$ and concentrated. The residue was purified by flash chromatography, eluent EtOAc/hexane (1:2) to afford title compound affording 252 (22.7 mg, 74% yield). MS (m/z): 230.1 (100%) 232.1 (33%) (M+1).

Step 3: 4-(2-Fluoro-4-nitrophenoxy)-6-phenyl-5H-pyrrolo[3,2-d]pyrimidine (253)

A mixture of 252 (47.9 mg, 0.21 mmol), 4-nitrophenol (50 mg, 0.32 mmol), K$_2$CO$_3$ (58 mg, 0.42 mmol) and Ph$_2$O (4 mL) was stirred at 190° C. overnight in a sealed tube. The mixture was cooled down, more 4-nitrophenol (50 mg, 0.32 mmol) was added and the mixture was stirred at 190° C. for additional 8 h. It was cooled again, transferred onto a chromatography column and eluted sequentially with EtOAc/hexane (1:10) and EtOAc/hexane (1:3), to afford title compound 253 (71.4 mg, 97% yield) as a white foam. MS (m/z): 351.1 (M+1).

Step 4: 3-Fluoro-4-(6-phenyl-5H-pyrrolo[3,2-d]pyrimidin-4-yloxy)benzenamine (254)

To a solution of 253 (71.4 mg, 0.21 mmol) in acetic acid (2.1 mL) at 100° C., was added iron powder (59 mg, 1.05 mmol). The reaction mixture was stired for 5 minutes, filtered through a Celite® pad and concentrated under reduced pressure. The residue was purified by column chromatography, eluent EtOAc/hexane (2:1), to afford title compound 254 (27.9 mg, 40% yield). MS (m/z): 321.1 (M+1).

Step 5: N-(3-Fluoro-4-(6-phenyl-5H-pyrrolo[3,2-d]pyrimidin-4-yloxy)phenylcarbamothioyl)-2-phenylacetamide (255a)

To a suspension of the 254 (26.8 mg, 0.84 mmol) in THF (1.6 ml) was added 2-phenylacetyl isothiocyanate (23 mg, 0.13 mmol). The mixture was stirred for 1 hr transferred onto a chromatography column and eluted sequentially with EtOAc/MeOH (9:1) and EtOAc/hexane (1:1), to afford title compound 255a (30 mg, 72% yield) as a white solid.

$^1$HNMR: (DMSO-$d_6$) δ (ppm):12.65 (s, 1H), 12.43 (s, 1H), 11.79 (s, 1H), 8.31 (s, 1H), 8.06 (d, J=7.6 Hz, 2H), 7.91 (m, 1H), 7.52 (m, 4H), 7.43 (m, 1H), 7.34, (m, 4H), 7.27 (m, 1H), 7.18 (m, 1H), 3.83 (s, 2H). MS (m/z): 498.2 (M+1).

Example 214

N-(3-Fluoro-4-(6-(pyridin-2-yl)-5H-pyrrolo[3,2-d]pyrimidin-4-yloxy)phenylcarbamothioyl)-2-phenylacetamide (255b)

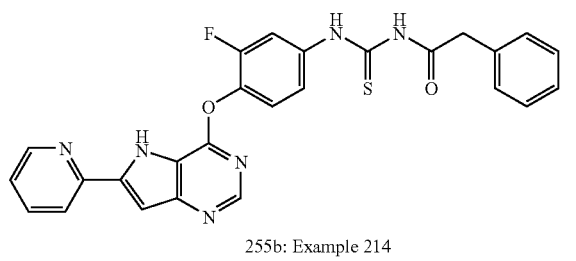

255b: Example 214

Following the procedures described above for the synthesis of compound 255a (example 213, scheme 57) but replacing ethynylbenzene in the step 1 with 2-ethynylpyridine, title compound 255b was obtained. $^1$H NMR (DMSO-$d_6$) δ (ppm): 12.85 (br, 1H), 12.65 (br, 1H), 11.75 (br, 1H), 8.71 (m, 1H), 8.33 (s, 1H), 8.21 (d, J=8 Hz, 1H), 7.96 (m, 1H), 7.89 (m, 1H), 7.52-7.42 (m, 3H), 7.34-7.32 (m, 5H), 7.28 (m, 1H), 3.83 (s, 2H). MS (m/z): 499.2 (M+1).

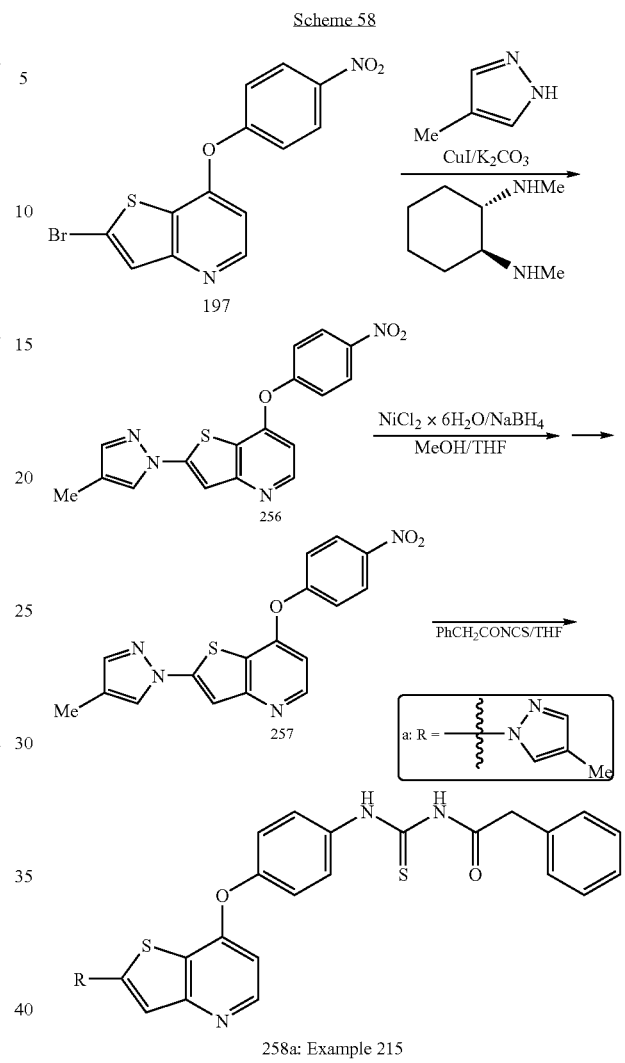

258a: Example 215

Example 215

N-(4-(2-(4-Methyl-1H-pyrazol-1-yl)thieno[3,2-b]pyridin-7-yloxy)phenylcarbamothioyl)-2-phenylacetamide (258a)

Step 1: 2-(4-Methyl-1H-pyrazol-1-yl)-7-(4-nitrophenoxy)thieno[3,2-b]pyridine (256)

A mixture of 197 (300 mg, 0.86 mmol, scheme 42), 4-methyl-1H-pyrazole (69 mg, 0.86 mmol), CuI (16.4 mg, 0.086 mmol), trans-N$^1$,N$^2$-dimethylcyclohexane-1,2-diamine (24.4 mg, 0.172 mmol) [J. C. Antilla, A. Klapars, et. al. *JACS*, 2002, 124, 11684-1688] and K$_2$CO$_3$ (238 mg, 1.72 mmol) in toluene (1.7 mL) was stirred at room temperature in an atmosphere of nitrogen nitrogen overnight, diluted with EtOAc (100 mL), filtered through a Celite® pad, and concentrated under reduced pressure. The residue was purified by flash chromatography with gradient elution with EtOAc/hexane (1:1) to EtOAc/hexane (2:1) to afford title compound 256 (88.8 mg, 37% yield) as a white solid. MS (m/z): 352.06 (M+1).

Step 2: 4-(2-(4-Methyl-1H-pyrazol-1-yl)thieno[3,2-b]pyridin-7-yloxy)benzenamine (257)

To a solution of 256 (168.4 mg, 0.478 mmol) and NiCl$_{2\times}$6H$_2$O (226 mg, 0.956 mmol) in MeOH/THF (10/10 mL) NaBH$_4$ (72 mg, 1.92 mmol) was carefully added. The reaction mixture was stirred for 10 min, concentrated to dryness and the resultant solid was suspended in 10% HCl. The aqueous solution was basified (pH ~11) with concentrated aqueous NH$_4$OH and extracted with EtOAc. The organic extract was collected, dried over anhydrous Na$_2$SO$_4$ and concentrated under reduced pressure, to afford title compound 257 (134.6.mg, 87% yield) as a white solid. MS (m/z): 322.09 (M+1).

Step 3: N-(4-(2-(4-Methyl-1H-pyrazol-1-yl)thieno[3,2-b]pyridin-7-yloxy)phenylcarbamothioyl)-2-phenylacetamide (258a)

To a suspension of the 257 (134.6 mg, 0.418 mmol) in THF (4.2 mL) was added 2-phenylacetyl isothiocyanate (111 mg, 0.627 mmol). The reaction mixture was stirred for 1 hr at room temperature, transferred onto a chromatography column and eluted wit a gradient of gradient EtOAc/hexane, 1:1 to 2:1, to provide a beige solid which was triturated with diethyl ether to afford title compound 258a (31 mg, 15% yield) as a white solid. Characterization of 258a is provided in the table 23.

Example 216

N-(4-(2-(1H-Pyrazol-1-yl)thieno[3,2-b]pyridin-7-yloxy)phenylcarbamothioyl)-2-phenylacetamide (258b)

Following the procedures described above for the synthesis of compound 258a (example 215, scheme 58) but replacing 4-methyl-1H-pyrazole in the step 1 with 1H-pyrazole, title compound 258b was obtained. Characterization of 258b is provided in the table 23.

Example 217

N-(4-(2-(3,5-Dimethyl-1H-pyrazol-1-yl)thieno[3,2-b]pyridin-7-yloxy)phenylcarbamothioyl)-2-phenylacetamide (258c)

Following the procedures described above for the synthesis of compound 258a (example 215, scheme 58) but replacing 4-methyl-1H-pyrazole in the step 1 with 3,5-dimethyl-1H-pyrazole, title compound 258c was obtained. Characterization of 258c is provided in the table 23.

TABLE 23

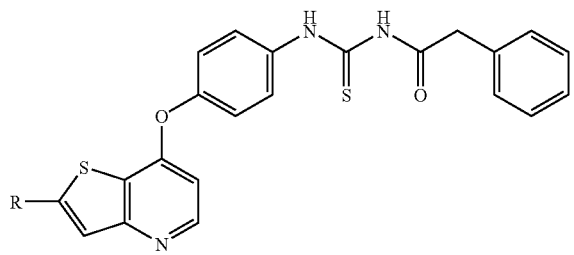

258a–c: Examples 215–217

Characterization of compounds 258a–c (examples 215–217)

| Cpd | Ex | R | Name | Characterization |
|---|---|---|---|---|
| 258a | 215 | (4-methyl-pyrazol-1-yl) | N-(4-(2-(4-Methyl-1H-pyrazol-1-yl)thieno[3,2-b]pyridin-7-yloxy)phenylcarbamothioyl)-2-phenylacetamide | $^1$HNMR: (DMSO-d$_6$) δ (ppm): 12.42(br, 1H), 11.76(br, 1H), 8.5(m, 2H), 7.75(m, 2H), 7.65(s, 2H), 7.32(m, 7H), 6.65(m, 1H), 3.83(s, 2H), 2.12(s, 3H). MS(m/z): 500.0(M+1). |
| 258b | 216 | (pyrazol-1-yl) | N-(4-(2-(1H-Pyrazol-1-yl)thieno[3,2-b]pyridin-7-yloxy)phenylcarbamothioyl)-2-phenylacetamide | $^1$H NMR (DMSO-d$_6$) δ (ppm): 12.4(s, 1H), 11.73(s, 1H), 8.74(d, J = 2.5Hz, 1H), 8.45(d, J = 5.7Hz, 1H), 7.87(s, 1H), 7.81(m, 1H), 7.74(d, J = 8.8Hz, 1H), 7.34–7.31(m, 7H), 6.66(m, 2H), 3.82(s, 2H). MS(m/z): 486.1 |
| 258c | 217 | (3,5-dimethyl-pyrazol-1-yl) | N-(4-(2-(3,5-Dimethyl-1H-pyrazol-1-yl)thieno[3,2-b]pyridin-7-yloxy)phenylcarbamothioyl)-2-phenylacetamide | $^1$H NMR (DMSO-d$_6$) δ (ppm): 12.44(s, 1H), 11.77(s, 1H), 8.6(d, J = 5.8, 1H), 7.78(m, 2H), 7.49(s, 1H), 7.38–7.28(m, 7H), 6.80(d, J = 5.8Hz, 2H), 6.27(s, 1H), 3.83(s, 2H), 2.59(s, 3H), 2.21(s, 3H). MS(m/z): 514.1 |

Scheme 59

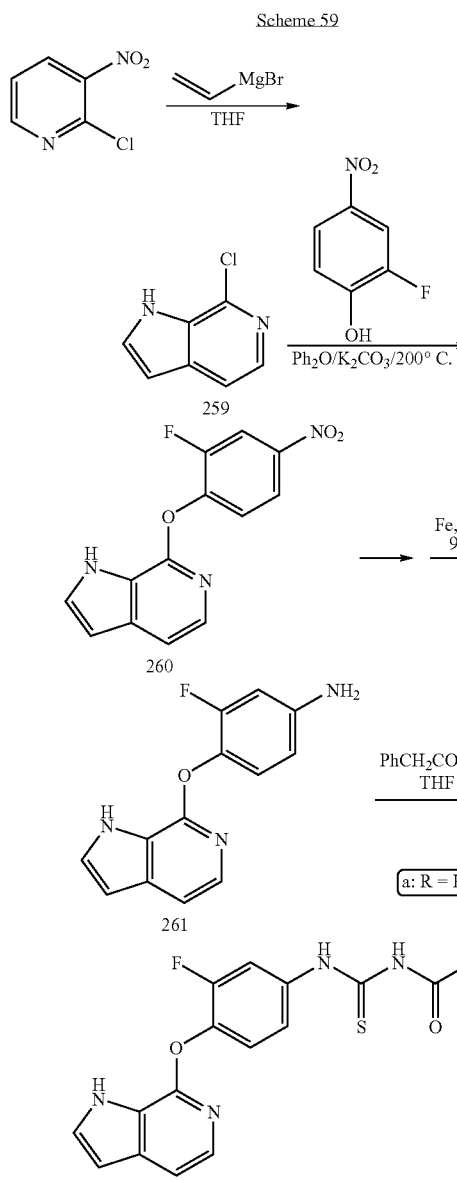

262a: Example 218

Example 218

N-(4-(1H-Pyrrolo[2,3-c]pyridin-7-yloxy)-3-fluorophenylcarbamothioyl)-2-phenylacetamide (262a)

Step 1. 7-Chloro-1H-pyrrolo[2,3-c]pyridine (259)

To a solution of 2-chloro-3-nitropyridine (5 g, 31.5 mmol)) in THF (200 mL) at −78° C., was added vinylmagnesium bromide (100 mL, 1.0M in THF) The reaction mixture was stirred at −20° C. for 8 hours, quenched with NH₄Cl solution (20%, 150 mL), extracted with EtOAc, dried over anhydrous Na₂SO₄ and concentrated. The residue was purified by flash chromatography, eluent EtOAc/hexane (1:5), to afford the title compound 259 (1.23 g, 26% yield) as a white solid [Z. Zhang, et al., *J. Org. Chem.*, 2002, 67, 2345-23471]. MS (m/z): 153.1 (M+H) (found).

Step 2. 7-(2-Fluoro-4-nitrophenoxy)-1H-pyrrolo[2,3-c]pyridine (260)

A mixture of 259 (420mg, 2.76 mmol), 2-fluoro-4-nitrophenol (651 mg, 4.14 mmol) and K₂CO₃ (1.14 g, 8.28 mmol) in Ph₂O (15 mL) was heated at 200° C. for 6 hours, cooled to room temperature and partitioned between EtOAc and water. Organic phase was collected, dried and concentrated. The residue was purified by flash column chromatography with gradient elution from hexane to hexane/EtOAc (3:1), to afford the title compound 260 (333 mg, 44% yield) as a yellowish solid. MS (m/z): 274.1(M+H) (found).

Step 3. 4-(1H-Pyrrolo[2,3-c]pyridin-7-yloxy)-3-fluorobenzenamine (261)

To a solution of 259(250mg, 1.64mmol) in DMF (16 mL) at 0° C., was added NaH 197 mg, 4.92 mmol), 60% in mineral oil), and the mixture was stirred for 30 min, followed by addition of MeI (112 μL, 1.80 mmol.) The reaction mixture was vigorously stirred at room temperature for 2 h before acetic acid )1 ml was added. Solvents were removed under reduced pressure, the residue was partitioned between water and EtOAc. Organic phase was collected, dried over anhydrous Na₂SO₄ and concentrated., The residue was purified by flash column chromatography, eluent EtOAc/hexane (1:1), to afford the title compound 263 (200 mg, 92% yield) as an off-white solid, MS (m/z): 167.1 (M+H)(found).

Step 4. N-(4-(1H-Pyrrolo[2,3-c]pyridin-7-yloxy)-3-fluorophenylcarbamothioyl)-2-phenylacetamide (262a)

A mixture of 261 (44 mg, 0.18 mmol) and 2-phenylacetyl isothiocyanate (36 □L, 0.19 mmol) in THF (2 mL) was stirred at room temperature for 2 hours, and concentrated. The residue was purified by flash column chromatography, eluent EtOAc/hexane (1:1), to afford the title compound 262a (30 mg, 40%) as an off-white solid. ¹H NMR (DMSO-d₆) δ (ppm): 12.41(s, 1H), 12.07(s, 1H), 11.77(s, 1H), 7.84(dd, 1H, J=10.95 Hz, J₂=2.0 Hz), 7.58(t, 1H), J₁=J₂=2.7 Hz), 7.51(d, 1H, J=5.7 Hz), 7.43-7.39(m, 2H), 7.37-7.33(m, 4H), 7.31-7.26(m, 2H), 6.55(dd, 1H, J₁=1.76 Hz, J₂=2.9 Hz), 3.84(s, 2H), MS (m/z): 421.1(M+H) (found).

Scheme 60

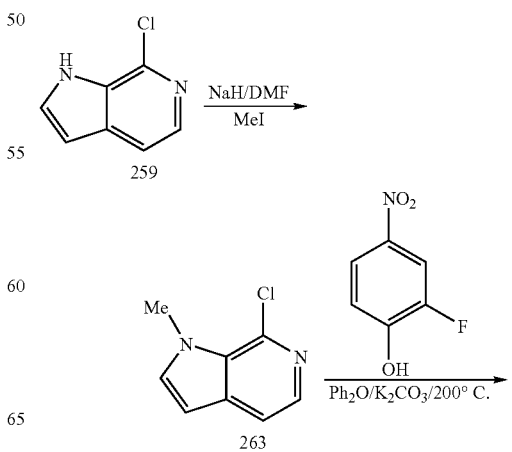

-continued

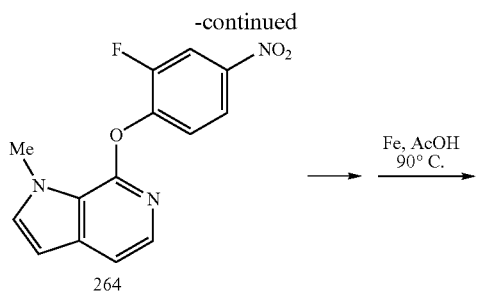

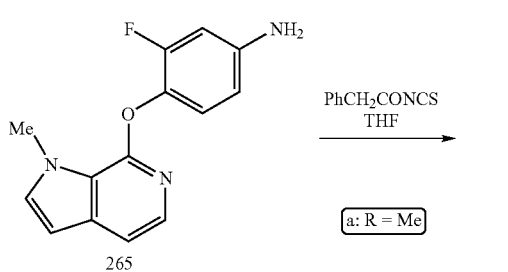

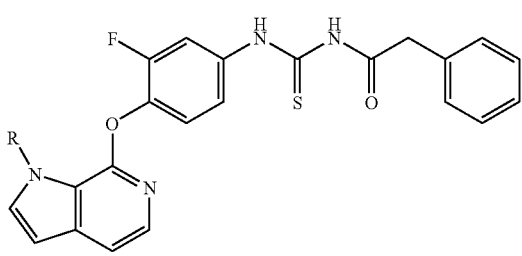

262b: Example 219

Example 219

N-(3-Fluoro-4-(1-methyl-1H-pyrrolo[2,3-c]pyridin-7-yloxy)phenylcarbamothioyl)-2-phenylacetamide (262b)

Step 1. 7-Chloro-1-methyl-1H-pyrrolo[2,3-c]pyridine (263)

To a solution of 259 (250mg, 1.64 mmol) in DMF (16 mL) at 0° C. was added NaH (197 mg, 4.92 mmol, 60% in mineral oil), and the mixture was stirred for 30 min, followed by addition of MeI (112 □L, 1.80 mmol). The reaction mixture was stirred at room temperature for 2 h before acetic acid (1 mL) was added. Solvents were removed under reduced pressure, the residue was partitioned between water and EtOAc. Organic phase was collected, dried over anhydrous $Na_2SO_4$ and concentrated. The residue was purified by flash column chromatography, eluent EtOAc/hexane (1:1), to afford the title compound 263 (200 mg, 92% yield) as an off-white solid. MS (m/z): 167.1(M+H) (found).

Step 2. 7-(2-Fluoro-4-nitrophenoxy)-1-methyl-1H-pyrrolo[2,3-c]pyridine (264)

Starting from the compound 263 and following the procedure described above for the synthesis of nitro compound 260 (scheme 59, step 2, example 218), title compound 264 was obtained in 91% yield as a yellow solid. MS (m/z): 288.1(M+H) (found).

Step 3.-Fluoro-4-(1-methyl-1H-pyrrolo[2,3-c]pyridin-7-yloxy)benzenamine(265)

Starting from the compound 264 and following the procedure described above for the synthesis of amine 261 (scheme 59, step 3, example 218), title compound 265 was obtained in 89% yield as an off-white solid. MS (m/z): 258.1(M+H) (found).

Step 4. N-(3-Fluoro-4-(1-methyl-1H-pyrrolo[2,3-c]pyridin-7-yloxy)phenylcarbamothioyl)-2-phenylacetamide (262b)

Starting from the compound 265 and following the procedure described above for the synthesis of compound 262a (scheme 59, step 4, example 218), title compound 262b was obtained in 87% yield as an off-white solid. $^1$H NMR (DMSO-$d_6$) δ (ppm): 12.40(s, 1H), 11.78(s, 1H), 7.83(dd, 1H, $J_1$=10.95 Hz, $J_2$=1.9 Hz), 7.56(d, 1H, 2.7 Hz), 7.49(d, 1H, J=5.5 Hz), 7.43-7.39(m, 2H), 7.37-7.33(m, 4H), 7.31-7.26 (m, 2H), 6.52(d,1H, $J_2$=2.9 Hz), 4.11(s, 3H), 3.84(s, 2H), MS (m/z): 435.1(M+H) (found).

Example 220

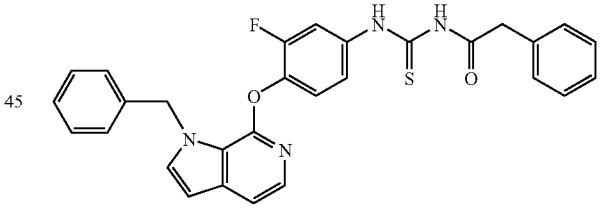

262c: Example 220

N-(4-(1-Benzyl-1H-pyrrolo[2,3-c]pyridin-7-yloxy)-3-fluorophenylcarbamothioyl)-2-phenylacetamide (262c)

Starting from the compound 259 and following the procedures described above for the synthesis of compound 262b (scheme 60, step 4, example 219) but using benzyl bromide in step 1 instead of methyl iodide, title compound 262c was obtained. $^1$H NMR (DMSO-$d_6$) δ (ppm): 12.36 (s, 1H), 11.76 (s, 1H), 7.78(m, 1H,), 7.58(t, 1H, $J_1$=$J_2$=2.7 Hz), 7.50(d, 1H, J=5.7 Hz), 7.34(m, 5H), 7.30-7.221(m, 5H), 7.15(dd, 1H, $J_1$=8.1 Hz, $J_2$=0.4 Hz), 7.10(t, 1H), 6.60(d, 1H, J=2.9 Hz), 5.68(s, 2H), 3.82(s, 2H). MS (m/z): 511.2(M+H) (found).

Scheme 61

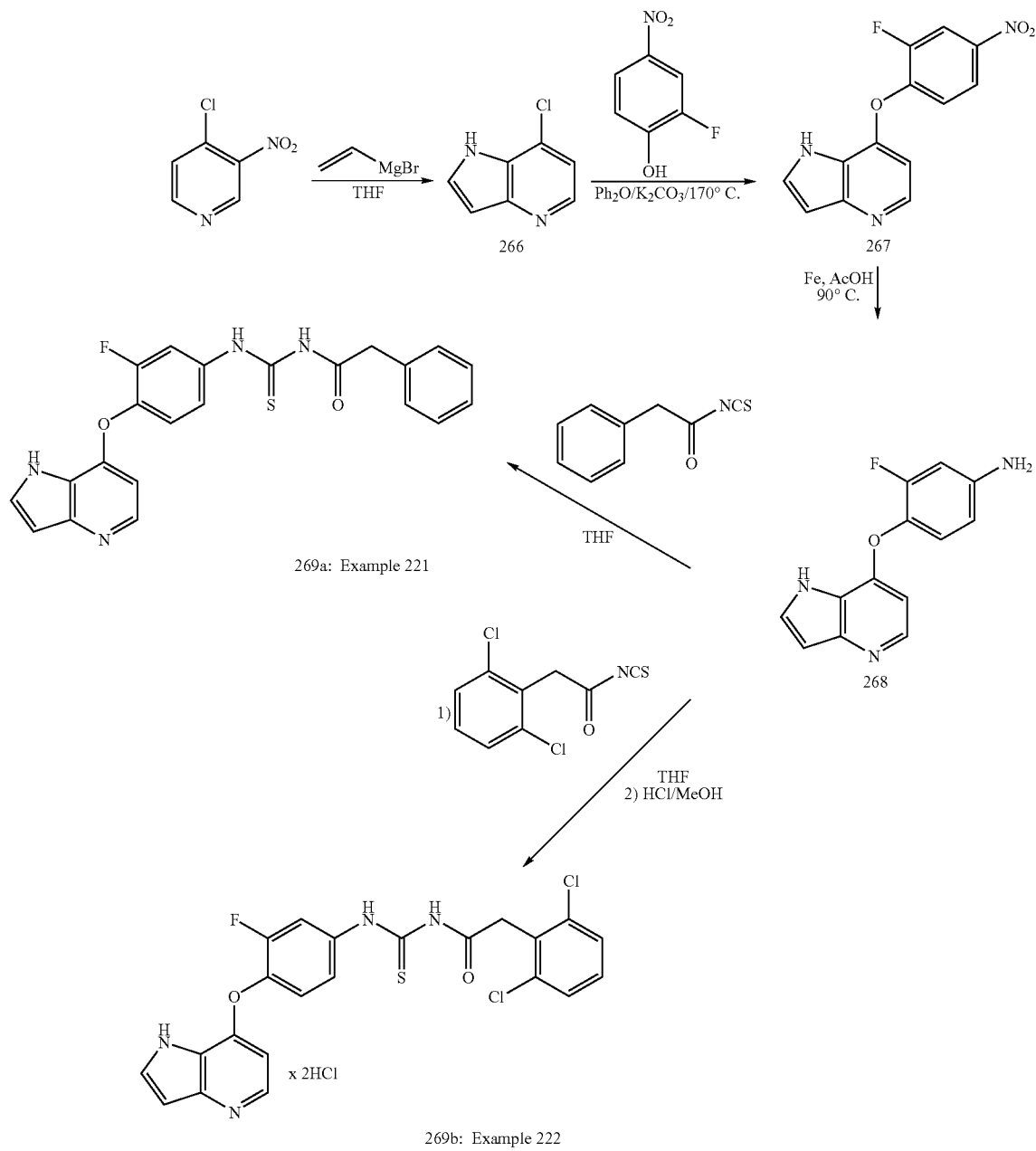

Example 221

N-(4-(1H-Pyrrolo[3,2-b]pyridin-7-yloxy)-3-fluorophenylcarbamothioyl)-2-phenyl acetamide (269a)

Step 1. 7-Chloro-1H-pyrrolo[3,2-b]pyridine (266)

To a solution of 2-chloro-3-nitropyridine (2.0 g, 12.6 mmol) [C. Almansa, et al., *J. Med. Chem.*, 2001, 44, 350-3611] in THF (80 mL) at −78° C., was added vinylmagnesium bromide (80 mL, 1.0M in THF), and the reaction mixture was stirred at −20° C. for 8 hours, quenched with NH₄Cl solution (20%, 100 mL), extracted with EtOAc, dried over anhydrous Na₂SO₄ and concentrated. The residue was purified by flash column chromatography, eluent EtOAc/Hexane (1:1), to afford the title compound 266 (240 mg, 11%) as yellow crystals. MS (m/z): 153.1 (M+H) (found).

Step 2. 7-(2-Fluoro-4-nitrophenoxy)-1H-pyrrolo[3,2-b]pyridine(267)

A mixture of 266 (180 mg, 1.18 mmol), 2-fluoro-4-nitrophenol (558 mg, 3.55 mmol) and K₂CO₃(981 mg, 7.10 mmol) in Ph₂O(4 mL) was heated at 170° C. for 8 hours, cooled to room temperature and partitioned between EtOAc and water. Organic phase was collected, dried over anhydrous Na₂SO₄ and concentrated. The residue was purified by flash column chromatography with gradient elution of hexane, to hexane/ EtOAc (1:1), to afford the title compound 267 (84 mg, 26% yield) as a yellowish solid. MS (m/z): 274.1 (M+H) (found).

Step 3. 4-(1H-Pyrrolo[3,2-b]pyridin-7-yloxy)-3-fluorobenzenamine (268)

To a solution of 267 (35 mg, 0.13 mmol) in AcOH (1 mL) at 90° C., was added iron powder (36 mg, 0.65 mmol). The reaction mixture was stirred vigorously for 10 min, cooled, filtered through a Celite pad and concentrated. The residue was partitioned between DCM and NaHCO$_3$ saturated solution. Phases were separated; the aqueous phase was neutralized with AcOH and extracted with DCM. Primary organic phase and the extract were combined and concentrated to give the title compound 268 (31 mg, 99%) as an off-white solid. MS (m/z): 244.1(M+H) (found).

Step 4. N-(4-(1H-Pyrrolo[3,2-b]pyridin-7-yloxy)-3-fluorophenylcarbamothioyl)-2-phenyl acetamide (269a)

A mixture of 268 (20 mg, 0.08 mmol) and 2-phenylacetyl isothiocyanate (16 µL, 0.08 mmol) in THF (1 mL) was stirred at room temperature for 2 hours and concentrated. The residue was purified by flash column chromatography (eluent EtOAc) followed by preparative HPLC (column Aqusil C18, gradient elution with 60-95% MeOH in water, 45 min) to afford the title compound 269a (13 mg, 40% yield) as an off-white solid. $^1$H NMR (CD$_3$OD) δ (ppm): 8.41(s, 1H), 8.16(d. 1H, J=5.6 Hz), 8.02(dd, 1H, J$_1$=2.3 Hz, J$_2$=12.2 Hz), 7.62(d, 1H, J=3.3 Hz), 7.44(m, 1H), 7.37-7.33(m, 4H) 7.31-7.26(m, 1H), 6.65(d, 1H, J=3.1 Hz), 6.52(d, 1H, J=5.7 Hz), 3.76(s, 2H), MS (m/z): 421.1(M+H) (found).

Example 222

N-(4-(1H-Pyrrolo[3,2-b]pyridin-7-yloxy)-3-fluorophenylcarbamothioyl)-2-(2,6-dichlorophenyl)acetamide dihydrochloride (269b)

Starting from the compound 268 and following the procedure described above for the synthesis of compound 269a (example 221) but replacing 2-phenylacethyl isothiocyanate with 2-(2,6-dichlorophenyl)acetyl isothiocyanate, a white solid was obtained. This material was dissolved in MeOH and treated with HCl (1 mL, 1.0M in ether). Solvents were removed under the reduced pressure and the residue was lyophilized, to afford the title compound 269b (48% yield) as a yellowish solid. $^1$H NMR (DMSO-d$_6$) δ (ppm): 13.29(s, 1H), 12.32(s, 1H), 12.05(s, 1H), 8.52(d, 1H,), 8.14(m, 2H), 7.64(m, 2H), 7.51(d, 1H), 7.37(dd, 1H), 6.86(m, 1H), 6.81 (dd, 1H), 4.22(s, 2H), MS (m/z): 489.1(M+H) (found).

Scheme 62

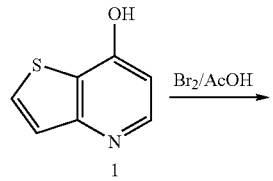

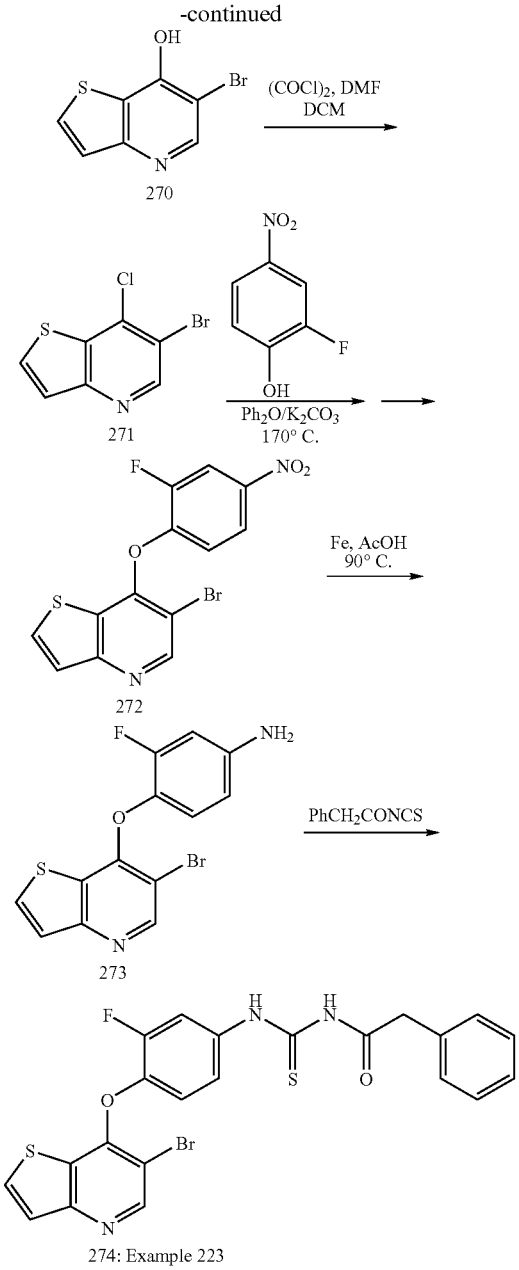

274: Example 223

Example 223

N-(4-(6-Bromothieno[3,2-b]pyridin-7-yloxy)-3-fluorophenylcarbamothioyl)-2-phenylacetamide (274)

Step 1. 6-Bromothieno[3,2-b]pyridin-7-ol (270)

To a solution of thieno[3,2-b]pyridin-7-ol (1, 2.55 g, 16.87 mmol) in acetic acid (50 mL) was added bromine(1.7 mL, 32.72 mmol). The mixture was heated at 110° C. for 1 h, cooled and the resultant precipitate was separated by filtration, to afford the title compound 270 (4.47 g, crude) as a dark brown powder, which was used in next step without further purification. M/S (m/z): 231.9(M+H) (found).

Step 2. 6-Bromo-7-chlorothieno[3,2-b]pyridine (271)

DMF (0.72 mL) was added slowly to a solution of $(COCl)_2$ in DCE at 0° C. and the mixture was stirred for 30 min, followed by addition of 270 (crude from above). The combined mixture was stirred for 10 min at the same conditions and was heated to reflux for 3 h. After cooling the mixture was concentrated and partitioned between DCM and water. Organic phase was collected and dried over anhydrous $Na_2SO_4$, filtered and concentrated. The residue was purified by flash column chromatography (eluent EtOAc), to afford the title compound 271 (0.66 g, 70% yield based on compound 1) as a yellowish solid. MS (m/z): 249.0(M+H) (found).

Step 3. 6-Bromo-7-(2-fluoro-4-nitrophenoxy)thieno[3,2-b]pyridine (272)

Starting from the compound 271 and following the procedure described above for the synthesis of compound 260 (scheme 59, example 218, step 2), title compound 272 was obtained in 61% yield as an off-white solid. MS (m/z): 368.9 (M+H).

Step 4. 4-(6-Bromothieno[3,2-b]pyridin-7-yloxy)-3-fluorobenzenamine (273)

Starting from the compound 272 and following the procedure described above for the synthesis of compound 261 (scheme 59, example 218, step 3), title compound 273 was obtained in 92% yield as a light brown solid. MS (m/z): 340.0(M+H).

Step 5. N-(4-(6-Bromothieno[3,2-b]pyridin-7-yloxy)-3-fluorophenylcarbamothioyl)-2-phenylacetamide (274)

Starting from the compound 273 and following the procedure described above for the synthesis of compound 262a (scheme 59, example 218, step 4), title compound 274 was obtained in 99% yield as a white solid. $^1$H NMR (DMSO-$d_6$) δ (ppm):12.44(s, 1H), 11.79(s, 1H), 8.82(s, 1H), 8.03(d, 1H), 7.99(dd, 1H), 7.54(d, 1H), 7.41(dd, 1H), 7.32-7.24(m, 6H), 3.80(s, 2H). MS (m/z):517.0 (M+H) (found).

Scheme 63

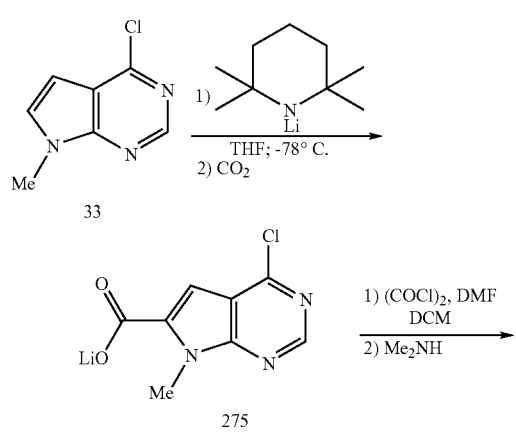

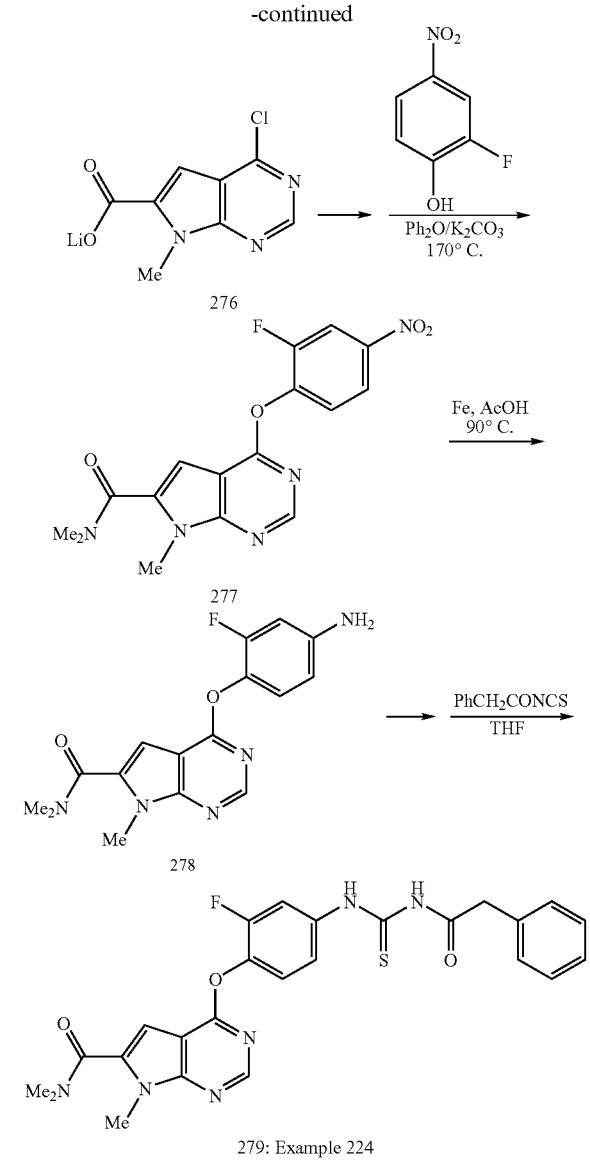

279: Example 224

Example 224

4-(2-Fluoro-4-(3-(2-phenylacetyl)thioureido)phenoxy)-N,N,7-trimethyl-7H-pyrrolo[2,3-d]pyrimidine-6-carboxamide (279)

Step 1. Lithium 4-chloro-7-methyl-7H-pyrrolo[2,3-d]pyrimidine-6-carboxylate (275)

To a solution of 2,2,6,6-tetramethylpiperidine (92 µL, 0.54 mmol) in THF (4 mL) at −10° C., n-BuLi (338 µL, 1.6M in hexane, 0.54 mmol) was added drop wise and the reaction mixture was stirred at −10° C. for 10 min. Compound 33 (60 mg, 0.36 mmol) [G. B. Evans et al. *J. Org. Chem.*, 2001, 66, 17, 5723-5730 and shown in the scheme 6] was added drop wise maintaining the temperature below −70° C. over a period of 15 min. Dried $CO_2$-gas was bubbled through the reaction mixture and stirred at room temperature overnight. The precipitate thus formed was collected by filtration and dried to afford the title compound 275 (78mg, 100% yield) as a yellow solid. MS (m/z): 209.9 (RCOOH, M−H) (found).

Step 2. 4-Chloro-N,N,7-trimethyl-7H-pyrrolo[2,3-d]pyrimidine-6-carboxamide (276)

A reaction mixture containing carboxylate 275 (78 mg, 0.36 mmo), oxalyl chloride (63 uL, 0.72 mmol), and a drop of DMF in DCM was stirred for 2 h. Solvents were removed under reduced pressure and the residue was re-dissolved in DCM (4 mL). To this solution Me$_2$NH (360 μL, 0.72 mmol, 2M in THF) in THF was added and the mixture was stirred at room temperature for 4 h. The solvent was removed under reduced pressure and the residue was purified by flash column chromatography (eluent EtOAc) to afford the title compound 276 (50 mg, 58% yield) as a yellowish solid. MS (m/z): 239.1(M+H) (found).

Step 3. 4-(2-Fluoro-4-nitrophenoxy)-N,N,7-trimethyl-7H-pyrrolo[2,3-d]pyrimidine-6-carboxamide (277)

Starting from the compound 276 and following the procedure described above for the synthesis of compound 260 (scheme 59, example 218, step 2) title compound 277 was obtained in 77% yield as an off-white solid. MS (m/z): 360.1 (M+H) (found).

Step 4. 4-(4-Amino-2-fluorophenoxy)-N,N,7-trimethyl-7H-pyrrolo[2,3-d]pyrimidine-6-carboxamide (278)

Starting from the compound 277 and following the procedure described above for the synthesis of compound 261 (scheme 59, example 218, step 3) title compound 278 was obtained in 72% yield as an off-white solid. MS (m/z): 330.1 (M+H) (found).

Step 5. 4-(2-Fluoro-4-(3-(2-phenylacetyl)thioureido)phenoxy)-N,N,7-trimethyl-7H-pyrrolo[2,3-d]pyrimidine-6-carboxamide (279)

Starting from the compound 278 and following the procedure described above for the synthesis of compound 262a (scheme 59, example 218, step 4) title compound 279 was obtained in 98% yield as an off-white solid. 1H NMR (DMSO-d6) δ (ppm): 12.45(s, 1H), 11.81(s, 1H), 8.43(s, 1H), 7.89(m, 1H), 7.46(m, 2H), 7.34(m, 4H), 7.28(m, 1H), 6.93(m, 1H), 4.03(s, 3H), 3.82(s, 2H), 3.81(s, 3H), 3.14(s, 3H), 3.06(s, 3H). MS (m/z): 507.1(M+H)(found).

Scheme 64

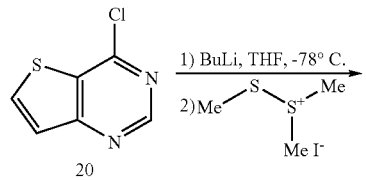

20

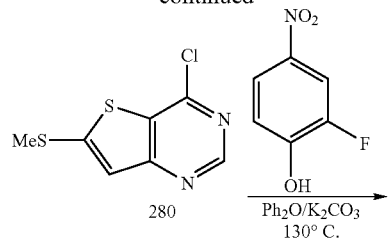

280

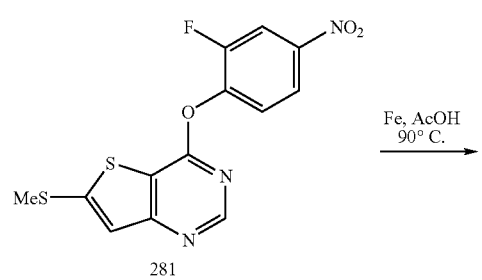

281

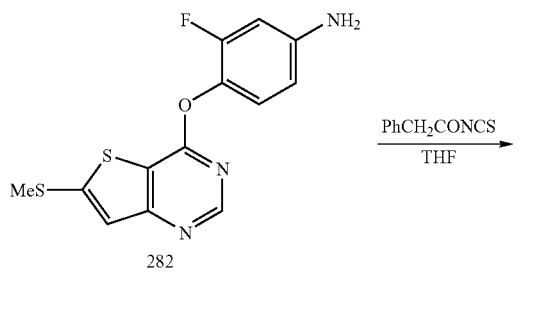

282

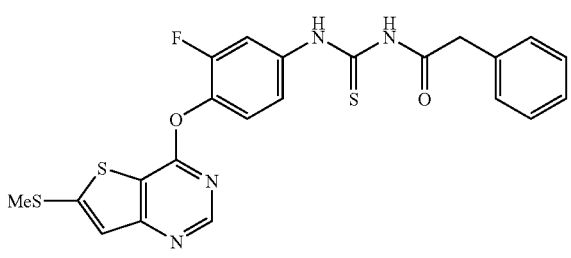

283: Example 225

Example 225

N-(3-Fluoro-4-(6-(methylthio)thieno[3,2-d]pyrimidin-4-yloxy)phenylcarbamothioyl)-2-phenylacetamide (283)

Step 1. 4-chloro-6-(methylthio)thieno[3,2-d]pyrimidine (280)

To a solution of 20 (shown in the scheme 4) (200 mg, 1.18 mmol) in THF (11 mL) was added n-BuLi (566 μL, 1.42 mmol, 2.5M in THF) very slowly at −78° C. and the mixture was stirred for 15 min at the same conditions. A solutions of dimethyl disulfide (160 uL, 1.77 mmol) and MeI (110 μL, 1.77 mmol) in THF (1 mL) was added drop wise. The reaction mixture was stirred for 2 h at −78° C., quenched with saturated aqueus $NH_4Cl$ solution, and extracted with DCM. The extract was dried over anhydrous $Na_2SO_4$ and concentrated to afford the title compound 280 (210 mg, 82% yield) as a yellowish solid. MS (m/z): 217.0(M+H) (found).

Step 2. 4-(2-Fluoro-4-nitrophenoxy)-6-(methylthio) thieno[3,2-d]pyrimidine (281)

A mixture of 280 (210 mg, 0.97 mmol), 2-fluoro-4-nitrophenol (278 mg, 1.77 mmol) and $K_2CO_3$ (560 mg, 3.54 mmol) in $Ph_2O$ (10 mL) was heated at 130° C. 60 hours, cooled to room temperature and partitioned between EtOAc and water. Organic phase was collected, dried over anhydrous $Na_2SO_4$, filtered, concentrated and purified by flash column chromatography with a gradient elution (hexane to hexane/EtOAc, 1:1) to afford the title compound 281 (288 mg, 88% yield) as a yellowish solid. MS (m/z): 338.1(M+H) (found).

Step 3. 3-Fluoro-4-(6-(methylthio)thieno[3,2-d]pyrimidin-4-yloxy)benzenamine (282)

To a solution of 281 (288 mg, 0.94 mmol) in AcOH (25 mL) at 90° C., was added iron powder (238 mg, 4.25 mmol), and the reaction mixture was stirred vigorously at 90° C. for 10 min, cooled, filtered through a Celite pad and concentrated. The residue was purified by flash column chromatography (eluent EtOAc) to afford the title compound 282 (248 mg, 95%) as an off-white solid. MS (m/z): 308.1(M+H) (found).

Step 4. N-(3-Fluoro-4-(6-(methylthio)thieno[3,2-d] pyrimidin-4-yloxy)phenylcarbamothioyl)-2-phenylacetamide (283)

A mixture of 282 (248mg, 0.80 mmol) and 2-phenylacetyl isothiocyanate (214 mg, 1.20 mmol) in THF (8 mL) was stirred for 2 hours, and concentrated. The residue was purified by flash column chromatography, eluent EtOAc/hexane (3:7), to afford title compound 283 (200 mg, 52% yield) as an off-white solid. $^1$H NMR (DMSO-$d_6$) δ (ppm): 12.42(s, 1H), 11.80(s, 1H), 8.63(s, 1H), 7.85(d, 1H), 7.54-7.44 (m, 3H), 7.35 (m, 4H), 7.30(m, 1H), 3.81(s, 2H), MS (m/z): 485.1 (M+H) (found).

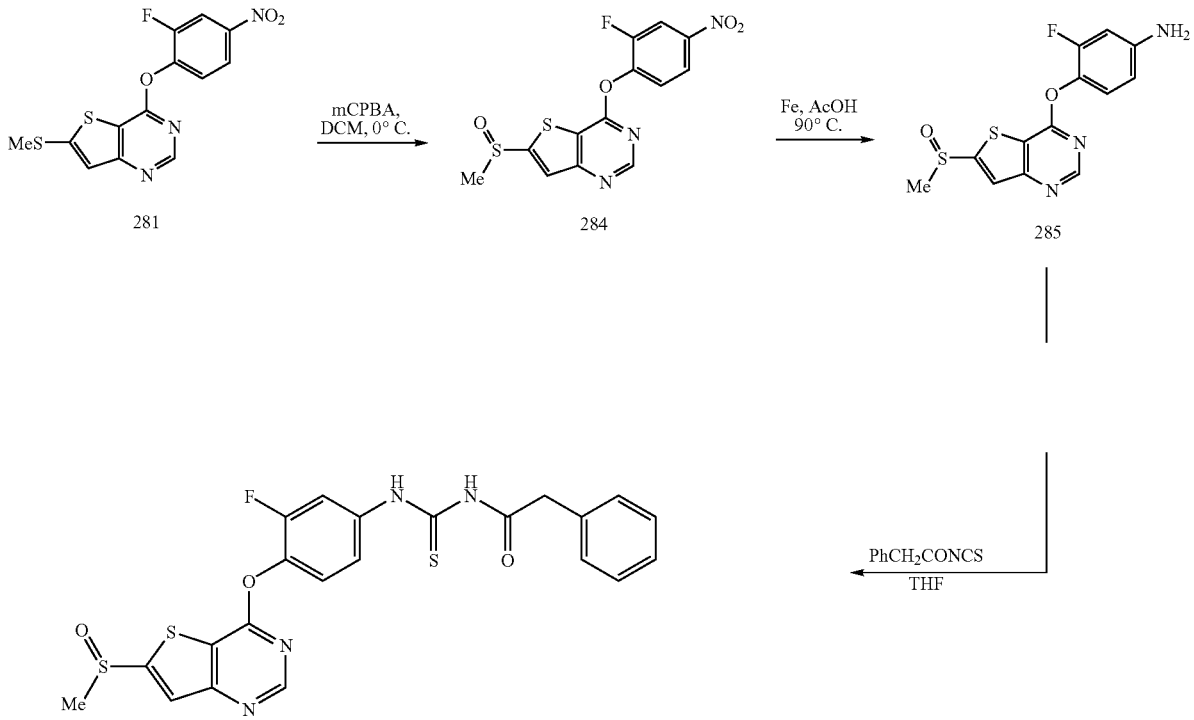

286: Example 226

Example 226

N-(3-Fluoro-4-(6-(methylsulfinyl)thieno[3,2-d]pyrimidin-4-yloxy)phenyl carbamothioyl)-2-phenylacetamide (286)

Step 1. 4-(2-Fluoro-4-nitrophenoxy)-6-(methylsulfinyl)thieno[3,2-d]pyrimidine (284)

A mixture of 281 (1.1 g, 3.2 mmol) and m-CPBA (77%, 890 mg, 12.8 mmol) in DCM at 0° C. was stirred for 2 hours, diluted with DCM, washed with ice water, $NaHCO_3$ solution and water again; dried and concentrated to give the title compound 284 (1.15 g, quantitative) as a yellowish solid. MS (m/z): 354.0(M+H) (found).

Step 2. 4-(2-Fluoro-4-nitrophenoxy)-6-(methylsulfinyl)thieno[3,2-d]pyrimidine (285)

Starting from the compound 284 and following the procedure described above for the synthesis of compound 282 (scheme 64, step 3, example 225), title compound 285 was obtained in 34% yield as an off-white solid. MS (m/z): 324.0 (M+H) (found).

Step 3. N-(3-Fluoro-4-(6-(methylsulfinyl)thieno[3,2-d]pyrimidin-4-yloxy)phenyl carbamothioyl)-2-phenylacetamide (286)

Starting from the compound 285 and following the procedure described above for the synthesis of compound 283 (scheme 64, step 4, example 225), title compound 286 was obtained in 36% yield as an off-white solid. $^1$H NMR (DMSO-$d_6$) δ (ppm): 12.45(s, 1H), 11.83(s, 1H), 8.80(s, 1H), 8.13(s, 1H), 7.93(dd, 1H, $J_1$=2.3 Hz, $J_2$=10.9 Hz), 7.55 (t, 1H, J=8.6 Hz), 7.48 (m, 1H), 7.34-7.31(m, 4H), 7.28-7.25(m, 1H), 3.81(s, 2H), 3.08(s, 3H). MS (m/z): 501.0(M+H) (found).

Scheme 66

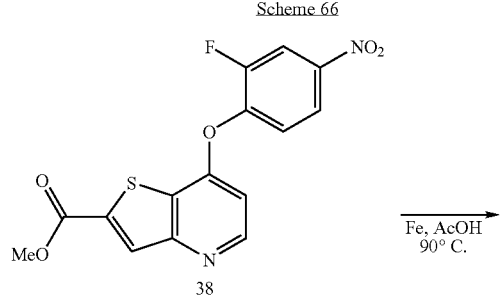

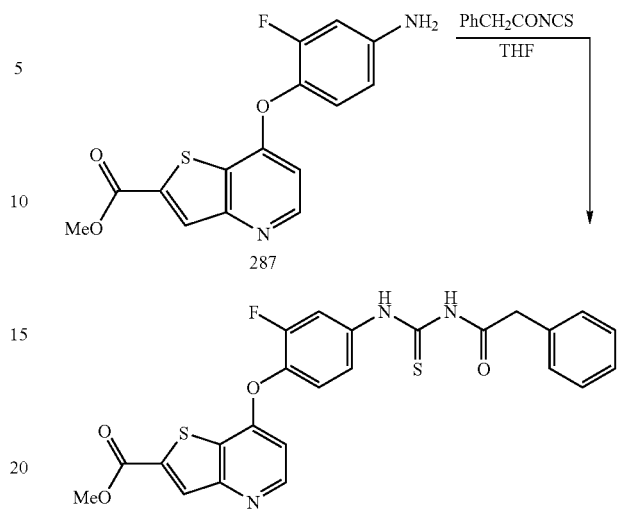

288: Example 227

Example 227

Methyl 7-(2-fluoro-4-(3-(2-phenylacetyl)thioureido) phenoxy)thieno[3,2-b]pyridine-2-carboxylate hydrochloride (288)

Step 1. Methyl 7-(4-amino-2-fluorophenoxy)thieno[3,2-b]pyridine-2-carboxylate (287)

Starting from the nitro compound 38 (shown in the scheme 7) and following the procedure described above for the synthesis of compound 261 (scheme 59, step 3, example 218), title compound 287 was obtained in 86% yield as an off-white solid. MS (m/z):319.0 (M+H) (found).

Step 2. Methyl 7-(2-fluoro-4-(3-(2-phenylacetyl)thioureido)phenoxy)thieno[3,2-b]pyridine-2-carboxylate hydrochloride (288)

Starting from the amine 287, following the procedure described above for the synthesis of compound 269b (scheme 561, example 222) and replacing 2-(2,6-dichlorophenyl) acetyl isothiocyanate with 2-phenylacetyl isothiocyanate, title compound 288 was obtained in 72% yield as a yellowish solid. $^1$H NMR (d-DMSO) δ (ppm): 12.51(s, 1H), 11.84(s, 1H), 8.64(dd, 1H, $J_1$=5.1 Hz, $J_2$=0.4 Hz), 8.24(s, 1H, J=0.4 Hz), 8.02(dd, 1H, $J_1$=1.8 Hz, $J_2$=13.4 Hz), 7.56-7.54(m, 2H), 7.36-7.31(m, 1H), 7.28-7.25(m, 1H), 6.81 (d, 1H, J=5.5 Hz), 3.91 (s, 3H), 3.81 (s, 2H). MS (m/z):496.3 (M+H) (found).

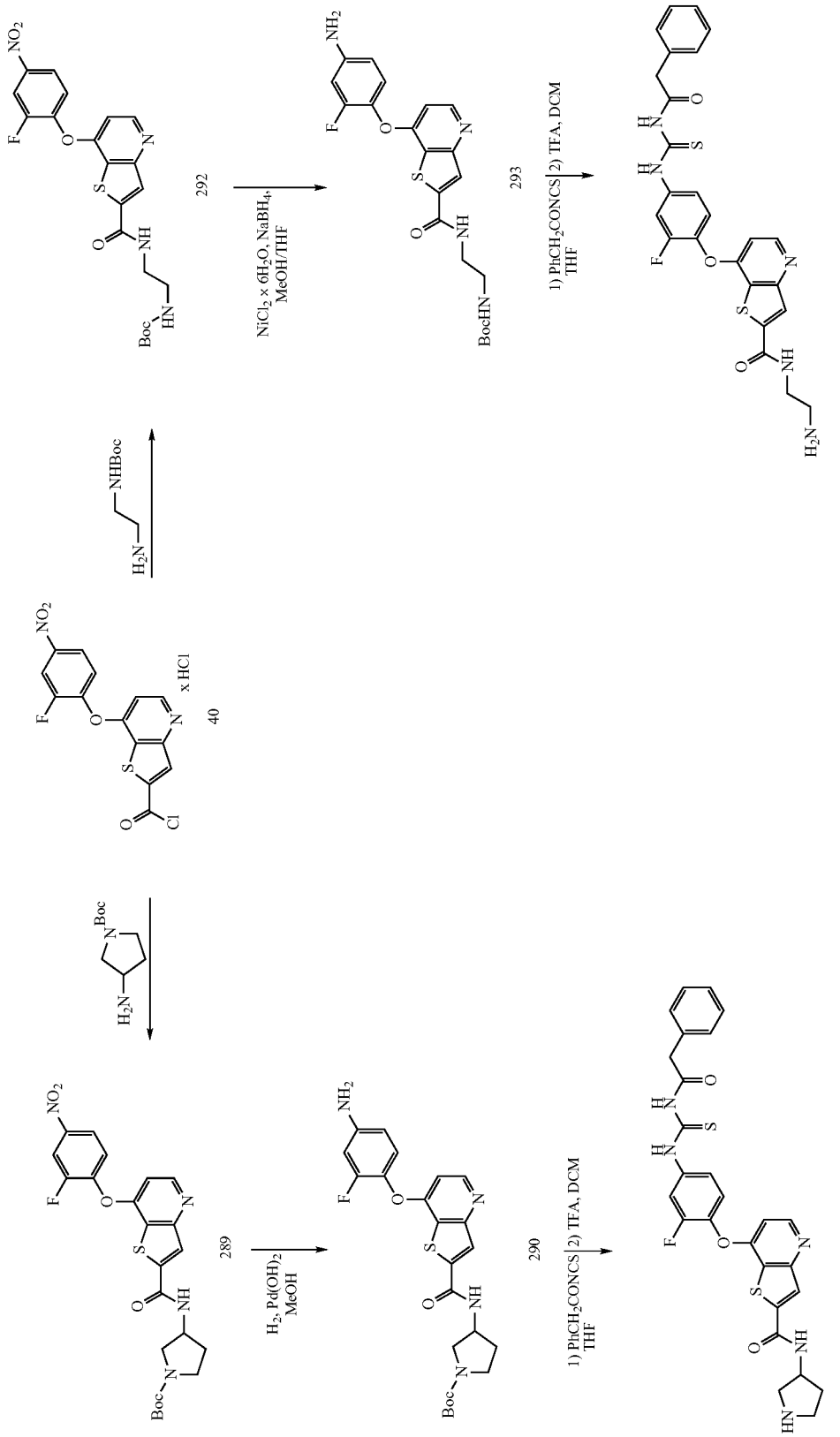

Example 228

7-(2-Fluoro-4-(3-(2-phenylacetyl)thioureido)phenoxy)-N-(pyrrolidin-3-yl)thieno[3,2-b]pyridine-2-carboxamide (291)

Step 1. tert-Butyl 3-(7-(2-fluoro-4-nitrophenoxy)thieno[3,2-b]pyridine-2-carboxamido)pyrrolidine-1-carboxylate (289)

A solution of 40 (shown in the scheme 7, 600 mg, 1.54 mmol), tert-butyl 3-aminopyrrolidine-1-carboxylate (369 mg, 2.0 mmol) in DCM (15 mL) was stirred overnight at room temperature. The solvent was removed under reduced pressure and the residue was purified by flash column chromatography, eluents EtOAc and EtOAc/MeOH (10:1), to afford the title compound 289 (160mg, 20%) as an off-white solid. MS (m/z): 503.3 (M+H) (found).

Step 2. tert-Butyl 3-(7-(4-amino-2-fluorophenoxy)thieno[3,2-b]pyridine-2-carboxamido)pyrrolidine-1-carboxylate (290)

A mixture of 289 (90 mg, 0.18 mmol) and Pd(OH)$_2$ in MeOH (2 mL) was hydrogenated at 1 atm for 1 h. The catalyst was filtered off and the filtrate was concentrated to afford the title compound 290 (60 mg, 70% yield) as a yellowish solid. MS (m/z): 473.2 (M+H) (found).

Step 3. 7-(2-Fluoro-4-(3-(2-phenylacetyl)thioureido)phenoxy)-N-(pyrrolidin-3-yl)thieno[3,2-b]pyridine-2-carboxamide (291)

A solution of 290 (40 mg, 0.084 mmol) and 2-phenylacetyl isothiocyanate (22 mg, 0.126 mmol) in THF (2 mL) was stirred for 30 min. The solvent was removed under reduced pressure and the residue was purified by flash column chromatography (eluent EtOAc), to afford a solid material, which was dissolved in a mixture of TFA/DCM (0.5 mL/0.5 mL) and stirred at room temperature for 2 h. Solvents were removed under reduced pressure and the residue was purified by preparative HPLC (Aqusil C18, gradient eluent, 60-95% MeOH in water, 45 min) to afford the title compound 291 (8 mg, 80% yield) as an off-white solid. $^1$H NMR (d-DMSO) δ (ppm): 9.27(d, 1H), 8.57(d, 1H), 8.37(s, 1H), 8.30(s, 1H), 8.01(d, 1H), 7.53(m, 2H), 7.33-7.31(m, 4H), 7.29-7.25(m, 1H), 6.74 (d, 1H), 4.46(m, 1H), 3.82(s, 2H), 3.11-3.03(m, 2H), 2.18-2.09(m, 2H), 1.93-1.89(m, 2H). MS (m/z): 550.2(M+H) (found).

Example 229

N-(2-Aminoethyl)-7-(2-fluoro-4-(3-(2-phenylacetyl)thioureido)phenoxy)thieno[3,2-b]pyridine-2-carboxamide (294)

Step 1. tert-Butyl 2-(7-(2-fluoro-4-nitrophenoxy)thieno[3,2-b]pyridine-2-carboxamido)ethylcarbamate (292)

A solution of 40 (shown in the scheme 7, 100 mg, 0.26 mmol), N-Boc-N-methylethylenediamine hydrochloride (50 mg, 0.26 mmol) and Et$_3$N (36 μL, 0.52 mmol) in DCM (2 mL) was stirred for 4 h at room temperature and diluted with EtOAc (10 mL). The combined mixture was washed with brine and phases were separated. The aqueous phase was extracted with EtOAc, and the extract was combined with the organic phase, dried over anhydrous Na$_2$SO$_4$ and concentrated to afford title compound 292 (119 mg, 96%, crude) as yellowish solid. MS (m/z): 477.1 (M+H) (found).

Step 2. tert-Butyl 2-(7-(4-amino-2-fluorophenoxy)thieno[3,2-b]pyridine-2-carboxamido)ethylcarbamate (293)

To a solution of 292 (80mg, 0.17 mmol) in MeOH/THF (1.7 mL/1.7 mL) at 0° C., was added NiCl$_{2\times6}$H$_2$O (85 mg, 0.35 mmol), followed by addition of NaBH$_4$ (26 mg, 0.68 mmol), portion wise. The reaction mixture was stirred for 15 min, treated with 2N aqueous HCl (2 mL), filtered; the filtrate was neutralized with aqueous NH$_4$OH to pH 7 and partitioned between EtOAc and water. Organic phase was collected, dried over anhydrous Na$_2$SO$_4$ and concentrated. The residue (75 mg, quantitative yield, crude) was used directly in next step without further purification. MS (m/z): 447.1(M+H) (found).

Step 3. N-(2-Aminoethyl)-7-(2-fluoro-4-(3-(2-phenylacetyl)thioureido)phenoxy)thieno[3,2-b]pyridine-2-carboxamide (294)

Following the procedure described above for the synthesis of compound 291 (example 228), title compound was obtained in 3% yield as an off-white solid. $^1$H NMR (d-DMSO) δ (ppm): 9.00(d, 1H), 8.50(m, 1H), 8.30(m, 1H), 8.20(d, 1H), 7.92(d, 1H), 7.44(m, 2H), 7.26-7.25(m, 3H), 7.21-7.18(m, 1H), 6.66(d, 1H), 3.75(s, 2H), 3.30-3.20(m, 6H). MS (m/z): 524.3(M+H).

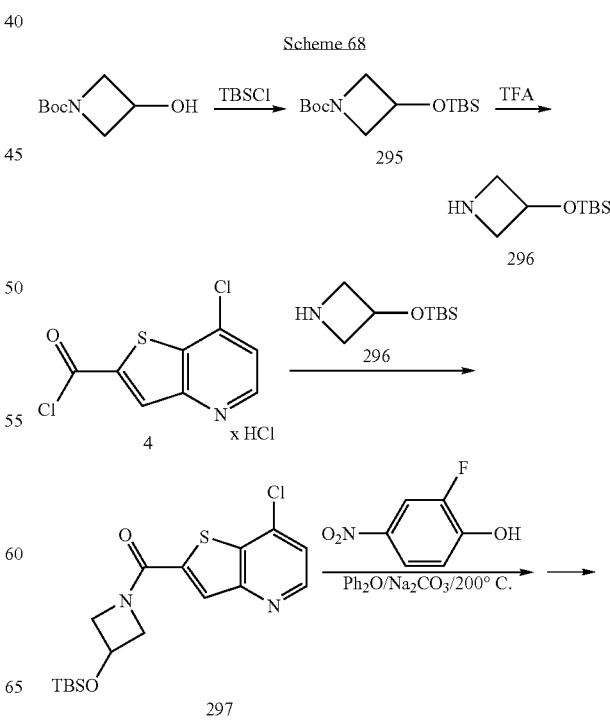

Scheme 68

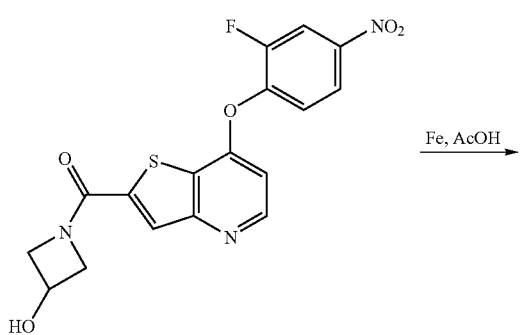

298

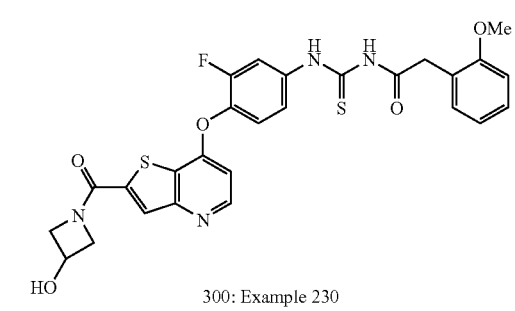

299

300: Example 230

Example 230

N-(3-Fluoro-4-(2-(3-hydroxyazetidine-1-carbonyl)
thieno[3,2-b]pyridin-7-yloxy)phenylcarbamothioyl)-
2-(2-methoxyphenyl)acetamide (300)

Step 1. tert-Butyl 3-(tert-butyldimethylsilyloxy)aze-
tidine-1-carboxylate (295)

A solution of tert-butyl 3-hydroxyazetidine-1-carboxylate (1 g, 5.77 mmol), TBSCl (6.35 mmol, 956 mg) in DCM (11.5 mL), was stirred for 72 hrs at room temperature. The solvent was removed under reduced pressure, EtOAc was added to the residue, and the solid material was removed by filtration. The filtrate was concentrated under reduced pressure and the residue was purified by flash chromatography with gradient elution wit EtOAc/hexane (9:1) to EtOAc/hexane (1:1), to afford title compound 295 (1.25 g, 75% yield) as a syrup. MS (m/z): 310.1 (M+23).

Step 2: 3-(tert-Butyldimethylsilyloxy)azetidine (296)

A mixture of 295 (200 mg, 0.696 mol), DCM (1 mL) and TFA (1 mL) was stirred for 1 h at room temperature, concentrated under reduced pressure; NaOH (1 M, 15 mL) was added to the residue and the suspension was extracted with DCM, the extract was dried (anhydrous $Na_2SO_4$) and concentrated, to afford title compound 296 (90.4 mg, 69% yield) as a syrup. MS (m/z): 188.1 (M+1).

Step 3: (3-(tert-Butyldimethylsilyloxy)azetidin-1-yl)
(7-chlorothieno[3,2-b]pyridin-2-yl)methanone (297)

Starting from the acyl chloride 4 (scheme 1), replacing dimethyl amine with the amine 296 and following the procedure described for the synthesis of amide 5 (scheme 1 as well), title compound 297 was obtained in 64% yield as a syrup. MS (m/z): 383.0 (M+1).

Step 4: (7-(2-Fluoro-4-nitrophenoxy)thieno[3,2-b]
pyridin-2-yl)(3-hydroxyazetidin-1-yl)methanone
(298)

Starting from the amide 297 and following the procedure described above for the synthesis of compound 230 (scheme 50, example 203), title compound 298 was obtained in 39% yield as a syrup. MS (m/z): 389.05 (M+1).

Step 5: (7-(4-Amino-2-fluorophenoxy)thieno[3,2-b]
pyridin-2-yl)(3-hydroxyazetidin-1-yl)methanone
(299)

Starting from the nitro compound 298 and following the procedure described above for the synthesis of the amine 231 (scheme 50, example 203), title compound 299 was obtained in 83% yield. MS (m/z): 359.07 (M+1).

Step 6: N-(3-Fluoro-4-(2-(3-hydroxyazetidine-1-
carbonyl)thieno[3,2-b]pyridin-7-yloxy)phenylcar-
bamothioyl)-2-(2-methoxyphenyl)acetamide (300)

Starting from the amine 299, following the procedure described above for the synthesis of compound 232a (scheme 50, example 203) but replacing 2-phenylacetyl isothiocyanate with (2-methoxy-phenyl)-acetyl isothiocyanate andtitle compound 300 was obtained in 39% yield as a creamy solid. $^1$HNMR: ($CD_3OD$) δ (ppm): 12.58 (s, 1H), 11.77 (s, 1H), 8.62 (m, 1H), 8.09 (d, J=12.3 Hz, 1H), 7.95 (s, 1H), 7.56 (m, 2H), 7.26 (m, 2H), 7.00 (m, 1H), 6.92 (m, 1H), 6.77 (m, 1H), 6.50 (d, J=5.9 Hz, 1H), 4.81 (m, 1H), 4.59 (m, 1H), 4.35 (m, 2H), 3.87-3.78 (m, 6H). MS (m/z): 567.0 (M+1).

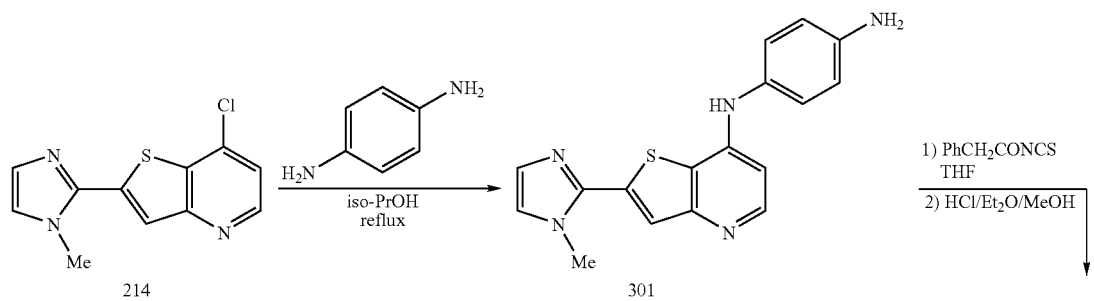

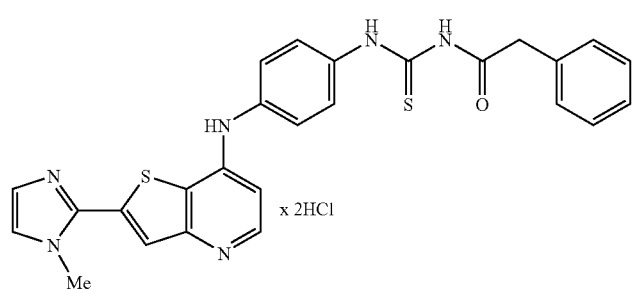

Example 231

N-(4-(2-(1-methyl-1H-imidazol-2-yl)thieno[3,2-b]pyridin-7-ylamino)phenyl carbamothioyl)-2-phenylacetamide (302)

Step 1. $N^1$-(2-(1-Methyl-1H-imidazol-2-yl)thieno[3,2-b]pyridin-7-yl)benzene-1,4-diamine (301)

A mixture of 214 (500 mg, 2.0 mmol, scheme 46) and benzene-1,4-diamine (500 mg, 4.62 mmol) in iso-PrOH (15 mL) was refluxed overnight, cooled to room temperature and filtered. The solid was collected, washed with iso-PrOH/H$_2$O mixture, to afford the title compound 301 (300 mg, 44% yield) as a yellowish solid. MS (m/z): 322.1(M+H) (found).

Step 2. N-(4-(2-(1-Methyl-1H-imidazol-2-yl)thieno[3,2-b]pyridin-7-ylamino)phenyl carbamothioyl)-2-phenylacetamide (302)

Starting from the compound 301, following the procedures described above for the synthesis of compound 269b (scheme 61, example 222) but replacing 2-(2,6-dichlorophenyl)acetyl isothiocyanate with 2-phenylacetyl isothiocyanate, title compound 302 was obtained in 12% yield, as a yellow solid. $^1$H NMR (d-DMSO) δ (ppm): 12.47(s, 1H), 11.76(s, 1H), 10.83(s, 1H), 8.41(d, 1H, J=6.9 Hz), 7.84(s, 1H), 7.80(s, 1H), 7.78(s, 1H), 7.55(s, 1H), 7.46(s, 1H), 7.43(s, 1H), 7.32(m, 4H), 7.28-7.20(m, 1H), 7.20(s, 1H), 6.94(d, 1H, J=6.8 Hz), 3.98(s, 3H), 3.81(s, 2H). MS (m/z): 499.1(M+H) (found).

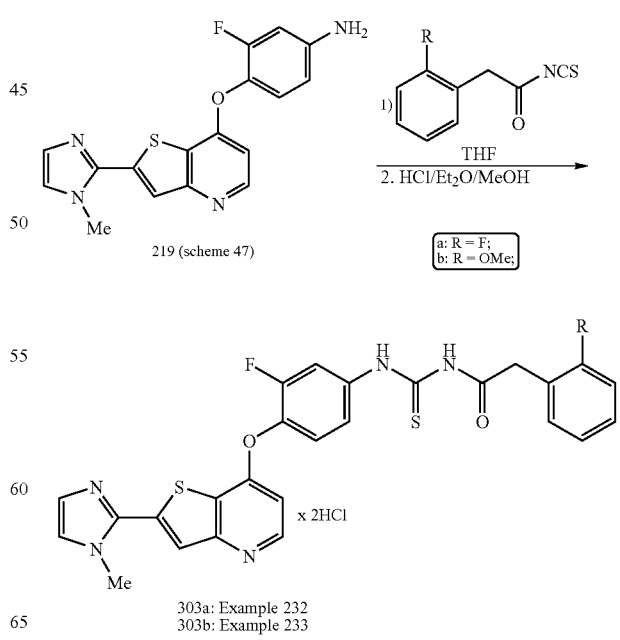

Example 232

N-(3-Fluoro-4-(2-(1-methyl-1H-imidazol-2-yl)thieno[3,2-b]pyridin-7-yloxy)phenyl carbamothioyl)-2-(2-fluorophenyl)acetamide di-hydrochloride (303a)

A mixture of aniline 219 (100 mg, 0.29 mmol, scheme 47) and 2-(2-fluorophenyl)acetyl isothiocyanate (115 mg, 0.58 mmol) in THF (3 mL) was stirred for 1 hour, loaded directly onto a column containing silica gel and eluted sequentially with EtOAc and EtOAc/MeOH (100:1), to produce a white solid. This material was suspended in MeOH (5 mL) and HCl (1.0M in ether, 1 mL) was added to form a clear solution that was evaporated to dryness. The residue was washed with ether, suspended in $H_2O$, and lyophilized to afford the title compound (80 mg, 45% yield) as a yellowish solid. $^1$H-NMR (DMSO-$d_6$) δ (ppm): 12.42(s, 1H), 11.88(s, 1H), 8.65(d. 1H, J=5.5 Hz), 8.20(s, 1H), 8.05(d, 1H, J=1.7 Hz), 7.74(s, 1H), 7.58-7.55(m, 3H) 7.39-7.32(m, 2H), 7.21-7.16(m, 2H), 6.82 (d, 1H, J=5.5 Hz), 4.02(s, 3H), 3.93(s, 2H), MS (m/z): 536.2 (M+H) (found).

Example 233

N-(3-Fluoro-4-(2-(1-methyl-1H-imidazol-2-yl)thieno[3,2-b]pyridin-7-yloxy)phenylcarbamothioyl)-2-(2-methoxyphenyl)acetamide di-hydrochloride (303b)

Starting from the compound 219, following the procedure described above for the synthesis of 303a (example 232) but replacing 2-(2-fluorophenyl)acetyl isothiocyanate with 2-(2-methoxyphenyl)acetyl isothiocyanate, title compound 303b was obtained in 44% as an off-white solid. $^1$H NMR (d-DMSO) δ (ppm): 12.55 (s, 1H), 11.73(s, 1H), 8.62(m, 1H), 8.09(m, 1H), 7.65(s, 1H), 7.57(m, 1H), 7.43(s, 1H), 7.27-7.20 (m, 1H), 6.98(d, 1H, J=8.2 Hz), 6.90(dt, 1H, $J_1$=1.0 Hz, $J_2$=7.4 Hz), 6.79(m, 1H), 4.02(s, 3H), 3.81(s, 2H), 3.77(s, 3H). MS (m/z): 548.3(M+H) (found).

Example 234

2-(2-Fluorophenyl)-N-(4-(2-(1-methyl-1H-imidazol-2-yl)thieno[3,2-b]pyridin-7-yloxy)phenylcarbamothioyl)acetamide dihydrochloride (304)

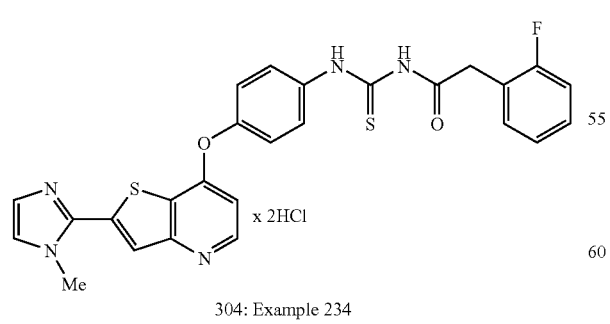

304: Example 234

Starting from the compound 214 (scheme 46) and following the procedures described above for the synthesis of compound 228 (example 202) and 303a (example 232), title compound 234 was obtained in 31% yield as an off-white solid. H NMR (d-DMSO) δ (ppm): 12.34(s, 1H), 11.81(s, 1H), 8.68 (m, 1H,), 8.24(s, 1H), 7.79(m, 3H), 7.62(s, 1H), 7.40-7.13(m, 6H), 6.86(d, 1H), 4.02(s, 3H), 3.93(s, 2H). MS (m/z): 518.1 (M+H) (found).

SCHEME 71

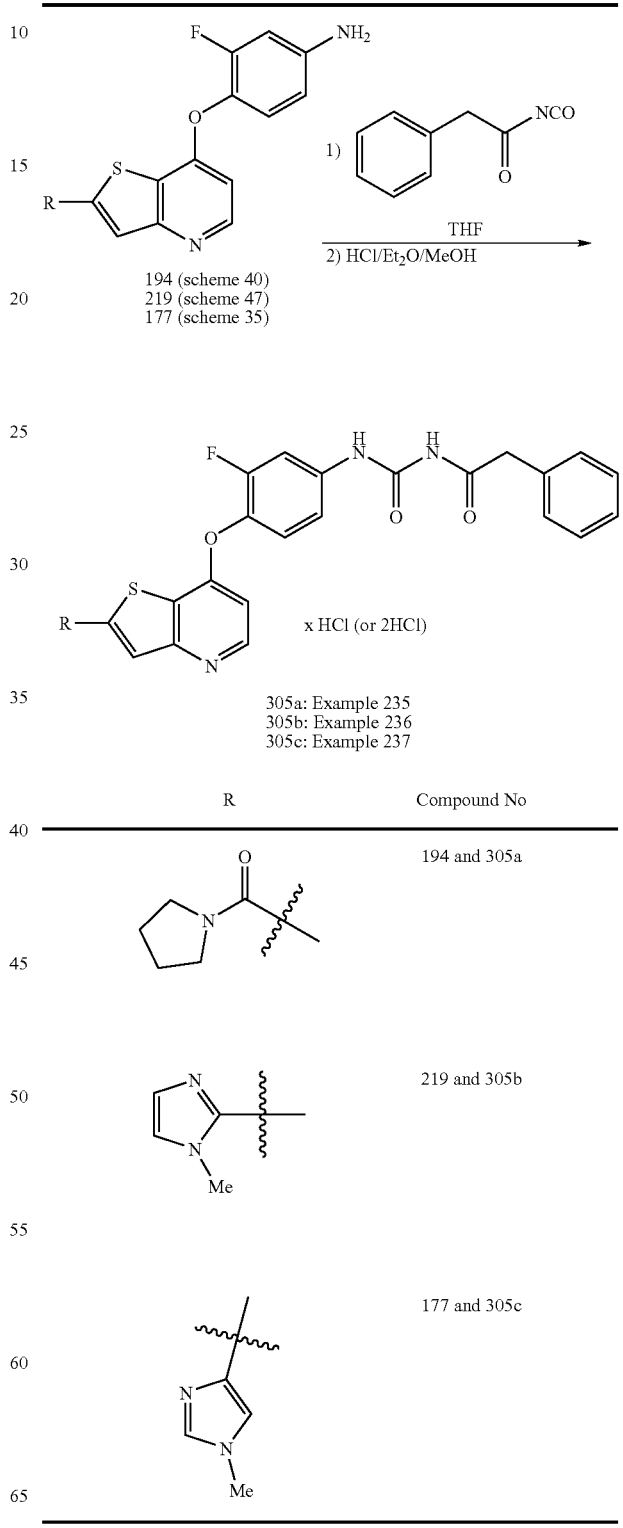

Examples 235

N-(3-Fluoro-4-(2-(pyrrolidine-1-carbonyl)thieno[3,2-b]pyridin-7-yloxy)phenyl carbamoyl)-2-phenylacetamide hydrochloride (305a)

A mixture of 194 (93 mg, 0.26 mmol, scheme 40) and 2-phenylacetyl isocyanate (83 mg, 0.62 mmoL) [J. Hill et al. *JACS*, 62: 1940; 1595] was stirred for 1 h at room temperature, loaded directly onto a flash chromatography column and eluted with EtOAc. A white solid was obtained, which was suspended in MeOH and treated with HCl (1 mL, 1.0M in Et$_2$O) to form a clear solution. The solution was concentrated to form a precipitate which was collected by filtration, to afford the title compound 305a (48 mg, 33% yield) as a white solid. $^1$H NMR (d-DMSO) δ (ppm): 11.05(s, 1H), 10.62(s, 1H), 8.57(d, 1H), 8.02(s, 1H), 7.81(d, 1H), 7.48-7.43(m, 2H), 7.33-7.25(m, 5H), 6.74(d, 1H), 3.85(t, 2H), 3.78(s, 2H), 3.51 (t, 2H), 1.98-1.86(m, 2H). MS (m/z): 519.2(M+H) (found).

Example 236

N-(3-Fluoro-4-(2-(1-methyl-1H-imidazol-2-yl)thieno[3,2-b]pyridin-7-yloxy)phenyl carbamoyl)-2-phenylacetamide dihydrochloride (305b)

Starting from the compound 219 (scheme 47) and following the procedure described above for the synthesis of compound 305a, title compound 305b was obtained in 15% yield as a white solid. $^1$H NMR (d-DMSO) δ (ppm): 11.07(s, 1H), 10.66(s, 1H), 8.67(d, 1H, J=5.5 Hz), 8.27(s, 1H), 7.85-7.80 (m, 2H), 7.65(s, 1H), 7.51(t, 1H, J=8.6 Hz), 7.46(d, 1H), 7.34-7.28(m, 5H), 6.85(d, 1H, J=5.3 Hz), 4.03(s, 3H), 3.74(s, 2H). MS (m/z): 502.2(M+H) (found).

Example 237

N-(3-Fluoro-4-(2-(1-methyl-1H-imidazol-4-yl)thieno[3,2-b]pyridin-7-yloxy)phenyl carbamoyl)-2-phenylacetamide dihydrochloride (305c)

Starting from the compound 177 (scheme 35) and following the procedure described above for the synthesis of compound 305a, title compound 305c was obtained in 54% yield as a white solid. $^1$H NMR (d-DMSO) δ (ppm): 11.08(s, 1H), 10.67(s, 1H), 8.66 (d, 1H, J=6.2 Hz), 8.26(s, 1H), 8.21(s, 1H), 7.93(s, 1H), 7.85(dd, 1H, J$_1$=12.9 Hz, J$_2$=2.5 Hz), 7.53(t, 1H, J=8.8 Hz), 7.65(s, 1H), 7.48-7.45(m, 1H), 7.35-7.30(m, 4H), 7.28-7.24(m, 1H), 6.94(d, 1H, J=6.1 Hz), 3.79(s, 3H), 3.75(s, 2H). MS (m/z): 502.1(M+H) (found).

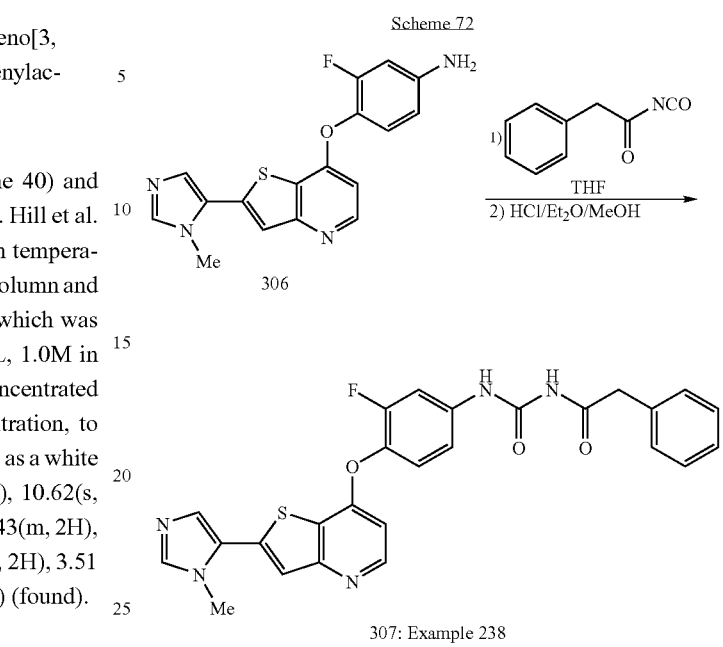

Scheme 72

307: Example 238

Example 238

N-(3-Fluoro-4-(2-(1-methyl-1H-imidazol-5-yl)thieno[3,2-b]pyridin-7-yloxy)phenyl carbamoyl)-2-phenylacetamide (307)

3-Fluoro-4-[2-(1-methyl-1H-imidazol-5-yl)-thieno[3,2-b]pyridin-7-yloxy]-phenylamine (306)

Starting from the compound 98 (scheme 19) and following the procedures described above for the synthesis of compound 12 (scheme 2, steps 1-4) but replacing 2-bromothiazole at the Stille coupling stage with 5-bromo-1-methyl-1H-imidazole (Table 9), title compound 306 was obtained. MS (m/z): 341.0M+H) (found).

N-(3-Fluoro-4-(2-(1-methyl-1H-imidazol-5-yl)thieno[3,2-b]pyridin-7-yloxy)phenyl carbamoyl)-2-phenylacetamide (307)

A mixture of 306 (99mg, 0.29 mmol) and 2-phenylacetyl isocyanate (97 mg, 0.60 mmoL) [A. J. Hill, et al. *JACS*, 62, 1940; 1595] was stirred for 1 h at room temperature, loaded directly onto a flash chromatography column and gradient eluted with EtOAc, to MeOH/EtOAc (10:90) to afford the title compound 307 (42% yield) as a white solid. $^1$H NMR (d-DMSO) δ (ppm): 11.11(s, 1H), 10.68(s, 1H, J=5.5 Hz), 8.49(d), 7.85(s, 1H), 7.82(dd, 1H, J$_1$=12.9 Hz, J$_2$=2.4Hz), 7.76(s, 1H), 7.43(m, 2H), 7.40(s, 1H), 7.32(m, 4H), 7.28(m, 1H), 6.61(d, 1H, J=5.5 Hz), 3.89(s, 3H), 3.74(s, 2H). MS (m/z):502.4 (M+H) (found).

Scheme 73

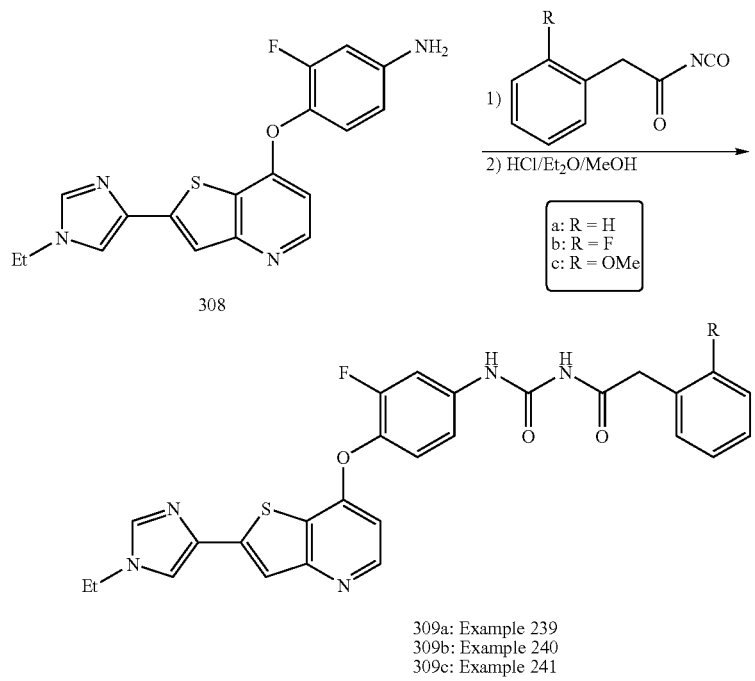

309a: Example 239
309b: Example 240
309c: Example 241

Example 239

N-(4-(2-(1-Ethyl-1H-imidazol-4-yl)thieno[3,2-b]pyridin-7-yloxy)-3-fluorophenyl carbamoyl)-2-phenylacetamide (309a)

4-[2-(1-Ethyl-1H-imidazol-4-yl)-thieno[3,2-b]pyridin-7-yloxy]-3-fluoro-phenylamine (308)

Starting from the compound 98 (scheme 19) and following the procedures described above for the synthesis of compound 12 (scheme 2, steps 1-4) but replacing 2-bromothiazole at the Stille coupling stage with 4-bromo-1-ethyl-1H-imidazole (Table 9), title compound 308 was obtained. MS (m/z): 355.1 (M+H) (found).

N-(4-(2-(1-Ethyl-1H-imidazol-4-yl)thieno[3,2-b]pyridin-7-yloxy)-3-fluorophenyl carbamoyl)-2-phenylacetamide (309a)

A mixture of 308 (300 mg, 0.85 mmol) and 2-phenylacetyl isocyanate (164 mg, 1.02 mmoL) [Arthur J. Hill, et al. *JACS*, 62: 1940; 1595] was stirred for 1 h at room temperature, loaded directly onto a flash chromatography column and gradient eluted with EtOAc, to MeOH/EtOAc (20:80) to afford the title compound 309a (45% yield) as a white solid. $^1$H NMR (d-DMSO) δ (ppm): 11.07(s, 1H), 10.63(s, 1H), 8.41(d, 1H, J=5.5 Hz), 7.94(d, 1H, J=1.4 Hz), 7.80(dd, 1H, $J_1$=13.1 Hz, $J_2$=2.4 Hz), 7.77(d, 1H, J=1.1 Hz), 7.65(s, 1H), 7.46-7.39 (m, 2H), 7.35-7.19(m, 4H), 7.28-7.24(m, 1H), 6.54(dd, 1H, $J_1$=5.5 Hz, $J_2$=0.8 Hz), 4.03(q, 2H), 3.73(s, 2H), 1.38(t, 3H). MS (m/z): 516.1(M+H) (found).

Example 240

N-(4-(2-(1-Ethyl-1H-imidazol-4-yl)thieno[3,2-b]pyridin-7-yloxy)-3-fluorophenyl carbamoyl)-2-(2-fluorophenyl)acetamide (309b)

A mixture of 308 (320 mg, 0.90 mmol) and (2-fluorophenyl)-acetyl isocyanate (600 mg, 3.35 mmoL) [A. J. Hill, et al. *JACS*, 62; 1940; 1595] was stirred for 1 h at room temperature, loaded directly onto a flash chromatography column and gradient eluted with EtOAc, to MeOH/EtOAc(20:80), to afford the title compound 309b in 42% yield as a white solid. $^1$H NMR (d-DMSO) δ (ppm): 11.10(s, 1H), 10.58(s, 1H), 8.42(d, 1H, J=5.5 Hz), 7.94(d, 1H, J=1.1 Hz), 7.82-7.77(m, 2H), 7.65(s, 1H), 7.45-7.30(m, 4H), 7.19-7.16(m, 2H), 6.54 (dd, 1H, $J_1$=0.7 Hz, $J_2$=5.4 Hz), 4.04(q, 2H), 3.83(s, 2H), 1.38(t, 3H). MS (m/z): 534.1(M+H) (found).

Example 241

N-(4-(2-(1-Ethyl-1H-imidazol-4-yl)thieno[3,2-b]pyridin-7-yloxy)-3-fluorophenyl carbamoyl)-2-(2-methoxyphenyl)acetamide (309c)

A mixture of 308 (370 mg, 1.05 mmol) and (2-methoxyphenyl)-acetyl isocyanate (240 mg, 1.25 mmoL) [A. J. Hill, et al. *JACS*, 62; 1940; 1595] was stirred for 1 h at room temperature, loaded directly onto a flash chromatography column and eluted with EtOAc, to afford the title compound 309c in 42% yield as a white solid. $^1$H NMR (d-DMSO) δ (ppm): 10.98(s, 1H), 10.69(s, 1H), 8.41(d, 1H, J=5.3 Hz), 7.94(d, 1H, J=1.2 Hz), 7.81(dd, 1H, $J_1$=13.1 Hz, $J_2$=2.4 Hz), 7.77(d, 1H, J=0.9 Hz), 7.65(s, 1H), 7.45-7.40(m, 2H), 7.26-7.19(m, 2H), 6.97(d, 1H, J=8.0 Hz), 6.89(dt, 1H, $J_1$=0.8 Hz, $J_2$=8.2 Hz), 6.54(d, 1H, J=5.5 Hz), 4.04(q, 2H), 3.75(s, 3H), 3.70(s, 2H), 1.38(t, 3H). MS (m/z): 546.1(M+H) (found).

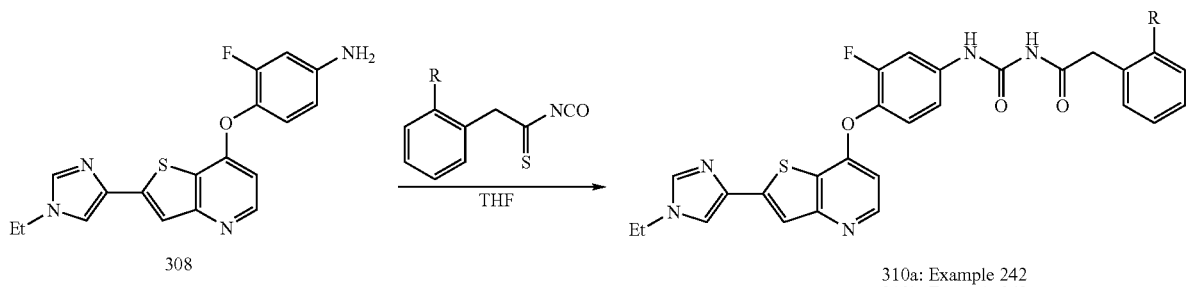

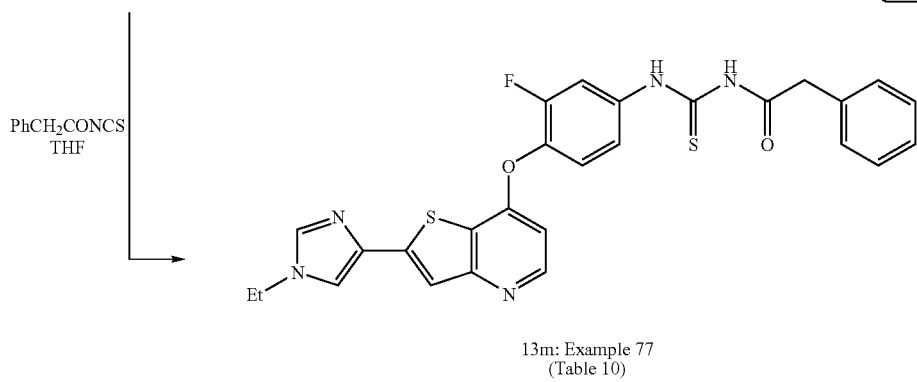

13m: Example 77
(Table 10)

Example 242

1-{4-[2-(1-Ethyl-1H-imidazol-4-yl)-thieno[3,2-b]pyridin-7-yloxy]-3-fluoro-phenyl}-3-[2-(2-fluorophenyl)-acetyl]-thiourea (310a)

To a suspension of the 308 (385 mg, 0.99 mmol) in THF (10 mL) was added 2-(2-fluorophenyl)acetyl isothiocyanate (263 mg, 1.49 mmol) and the reaction mixture was stirred for 1 hr, transferred onto a flash chromatography column and eluted with EtOAc/MeOH 19:1, to afford title compound 310a (366.9 mg, 67% yield) as a creamy solid. $^1$HNMR: (DMSO-$d_6$) δ (ppm): 12.42 (s, 1H), 11.87 (s, 1H), 8.44 (d, J=5.5 Hz, 1H), 8.02 (d, J=11.5 Hz, 1H), 7.95 (s, 1H), 7.78 (s, 1H), 7.67 (s, 1H), 7.52 (m, 2H), 7.42 (m, 2H), 7.25 (m, 2H), 7.06 (d, J=5.5 Hz, 1H), 4.04 (q, J=7.3 Hz, 2H), 3.92 (s, 2H), 7.4 (t, J=7.3 Hz, 3H). MS (m/z): 550.0 (M+1).

Example 243

1-{4-[2-(1-Ethyl-1H-imidazol-4-yl)-thieno[3,2-b]pyridin-7-yloxy]-3-fluoro-phenyl}-3-[2-(2-methoxyphenyl)acetyl]-thiourea (310b)

Starting from the compound 308, following the procedure described above for the synthesis of 310a but replacing 2-(2-fluorophenyl)acetyl isothiocyanate with (2-methoxy-phenyl)-acetyl isothiocyanate, title compound 310b was obtained in 82% yield. $^1$H NMR (DMSO-$d_6$) δ (ppm): 12,57 (s, 1H), 11.76 (s, 1H), 8.45 (d, J=5.5 Hz, 1H), 8.07 (m, 1H), 7.96 (d, J=1 Hz, 1H), 7.79 (d, J=1 Hz, 1H), 7.69 (s, 1H), 7.6 (m, 2H), 7.26 (m, 2H), 7.0 (d, J=7.4 Hz, 1H), 6.92 (m, 1H), 6.59 (d, J=5.5 Hz, 1H), 4.06 (q, J=7.5 Hz, 2H), 3.82 (s, 2H), 3.79 (s, 3H), 1.4 (t, J=7.4 Hz, 3H). MS (m/z): 562.0 (M+1).

Example 244

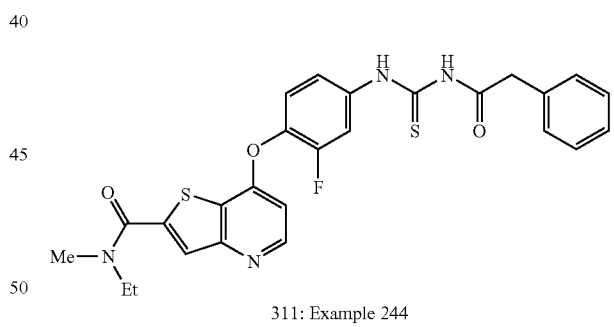

311: Example 244

N-Ethyl-7-(2-fluoro-4-(3-(2-phenylacetyl)thioureido)phenoxy)-N-methylthieno[3,2-b]pyridine-2-carboxamide (311)

Title compound 311 was obtained by following the procedures described above for the synthesis of compound 8a (scheme 1, example 1) but replacing dimethylamine in the step 4 with N-methylethanamine. $^1$H NMR (400 MHz, DMSO-d6) (ppm) 12.49 (s, 1H), 11.82 (s, 1H), 8.64 (d, J=5.48 Hz, 1H), 8.03 (d, J=12.7 Hz, 1H) 7.85 (m, 1H), 7.54 (m, 2H), 7.32 (m, 4H), 7.24 (m, 1H), 6.82 (d, J=5.3 Hz, 1H), 3.83 (s, 2H), 3.53 (m, 2H), 3.38 (m, 2H), 3.05 (s, 1H), 1.10 m, 3H). MS (calcd.) 522.1, found 523.2 (M+H).

Example 245

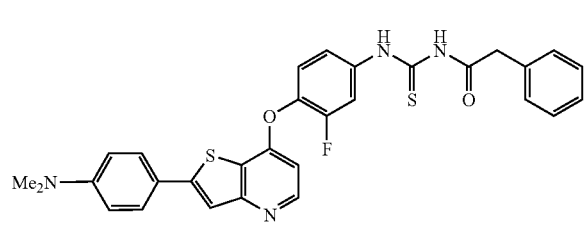

312: Example 245

N-(4-(2-(4-(Dimethylamino)phenyl)thieno[3,2-b]pyridin-7-yloxy)-3-fluorophenylcarbamothioyl)-2-phenylacetamide (312)

Title compound 312 was obtained by following the procedures described above for the synthesis of compound 50 (scheme 10, example 55) but replacing 4,4,5,5-tetramethyl-2-(4-(methylsulfonyl)phenyl)-1,3,2-dioxaborolane in the first step with 4-(dimethylamino)phenylboronic acid. $^1$H NMR (DMSO): 12.48 (1H, s), 11,83 (1H, s), 8.44 (1H, d, J=5.48 Hz), 7.99 (1H, d, J=12.91 Hz), 7.77 (1H, s), 7.68 (2H, d, J=8.41 Hz), 7.51 (2H, br), 7.33-7.28 (5H, m), 6.77 (2H, d, J=8.22 Hz), 6.56 (1H, d, J=4.89 Hz), 3.81 (2H, s), 2.96 (6H, s).

MS: calcd: 556.7, found: 556.9 (M+H).

Example 246

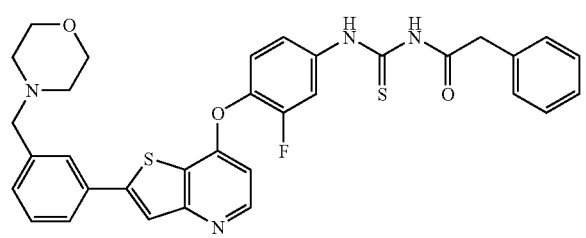

313: Example 246

N-(3-Fluoro-4-(2-(3-(morpholinomethyl)phenyl)thieno[3,2-b]pyridin-7-yloxy)phenylcarbamothioyl)-2-phenylacetamide (313)

Title compound 313 was obtained by following the procedures described above for the synthesis of compound 75 (scheme 15) but starting from 4-(3-bromobenzyl)morpholine instead of tert-butyl 3-bromobenzyl(2-methoxyethyl)carbamate (65). $^1$H NMR (DMSO): 12.49 (1H, s), 11.84 (1H, s), 8.52 (1H, d, J=5.48 Hz), 8.05 (1H, s), 8.01 (1H, d, J=12.72Hz), 7.79-7.78 (2H, m), 7.53 (2H, br), 7.46 (1H, t, J=7.63 Hz), 7.39 (1H, d, J=7.63 Hz), 7.34-7.26 (5H, m), 6.66 (1H, d, J=5.28 Hz), 3.82 (2H, s), 3.57 (4H, br), 3.32 (2H, s), 2.38 (4H, br). MS: calcd: 612.7, found: 613.3 (M+1).

Example 247

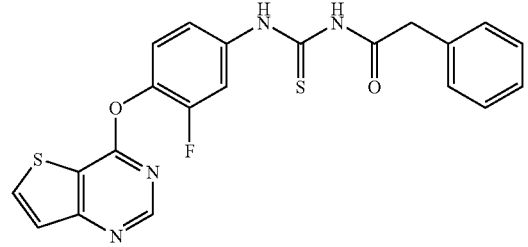

341: Example 247

N-(3-Fluoro-4-(thieno[3,2-d]pyrimidin-4-yloxy)phenylcarbamothioyl)-2-phenylacetamide (314)

Title compound 314 was obtained by following the procedures described above for the synthesis of compound 173 (scheme 34, example 135) but replacing 3-chloro-4-nitrophenol in the step 1 with 2-fluoro-4-nitrophenol. $^1$HNMR (DMSO-d$_6$) δ (ppm): 12.42 (bs, 1H), 11.79 (bs, 1H), 8.71 (s, 1H), 8.51 (d, J=5.2 Hz, 1H), 7.91 (dd, J=2.4 and 12.0 Hz, 1H), 7.70 (d, J=5.2 Hz, 1H), 7.53 (dd, J=8.4 Hz, 1H), 7.47 (dd, J=2.4 and 8.4 Hz, 1H), 7.38-7.30 (m, 4H), 7.30-7.27 (m, 1H), 3.82 (s, 2H). LRMS: 438.1(calc) 439.1 (found).

Example 248

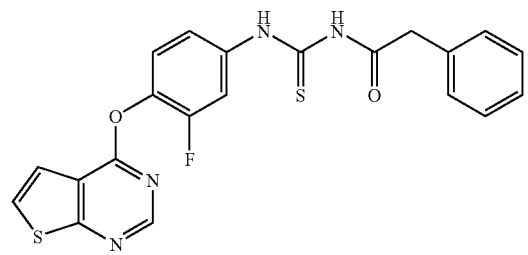

315: Example 248

N-(3-Fluoro-4-(thieno[2,3-d]pyrimidin-4-yloxy)phenylcarbamothioyl)-2-phenylacetamide (315)

Title compound 315 was obtained starting from the compound 205 (scheme 44) and following the procedures described above for the synthesis of compound 314. $^1$HNMR (DMSO-d$_6$) δ (ppm): 12.42 (s, 1H), 11.80 (s, 1H), 8.63 (s, 1H), 8.01 (d, J=5.6 Hz, 1H), 7.91 (dd, J=2.0 and 12.0 Hz, 1H), 7.70 (d, J=5.6 Hz, 1H), 7.50 (t, J=8.4 Hz, 1H), 7.46 (dd, J=2.4 and 8.4 Hz, 1H), 7.36-7.30 (m, 4H), 7.30-7.24 (m, 1H), 3.82 (s, 2H). LRMS: 438.4 (calc) 439.3 (found).

Example 249

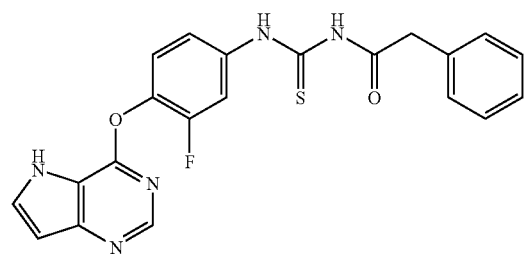

316: Example 249

N-(4-(5H-Pyrrolo[3,2-d]pyrimidin-4-yloxy)-3 -fluorophenylcarbamothioyl)-2-phenylacetamide (316)

Title compound 316 was obtained by following the procedures described above for the synthesis of compound 31 a (scheme 5, example 28) but skipping N-methylation step.

$^1$HNMR (DMSO-d$_6$) δ (ppm): 12.41(s, 1H), 8.32 (s, 1H), 7.91 (d, J=10 Hz, 1H), 7.48 (s, 1H), 7.56-7.42 (m, 2H), 7.39-7.32 (m , 4H), 7.30-7.22 (m, 1H), 6.66 (s, 1H), 3.83 (s, 2H). LRMS: 421.1 (calc) 422.1 (found).

Assay Examples

Assay Example 1

Inhibition of c-met and VEGF Activity

The following protocols were used to assay the compounds of the invention.

In Vitro Receptor Tyrosine Kinase Assays (c-Met/HGF Receptor and VEGF Receptor KDR)

These tests measure the ability of compounds to inhibit the enzymatic activity of recombinant human c-Met/HGF receptor and VEGF receptor enzymatic activity.

A 1.3-kb cDNA corresponding to the intracellular domain of c-Met or c-Met IC (Genbank accession number NP000236-1 amino acid 1078 to 1337) was cloned into the BamHI/XhoI sites of the pBlueBacHis2A vector (Invitrogen) for the production of a histidine-tagged version of that enzyme. This construct was used to generate recombinant baculovirus using the Bac-N-Blue™ system according to the manucfacturer's instructions (Invitrogen)

The c-Met IC protein was expressed in Hi-5 cells (*Trichoplusia Ni*) upon infection with recombinant baculovirus construct. Briefly, Hi-5 cells grown in suspension and maintained in serum-free medium (Sf900 II supplemented with gentamycin) at a cell density of about 2×10$^6$ cells/ml were infected with the abovementioned viruses at a multiplicity of infection (MOI) of 0.2 during 72 hours at 27° C. with agitation at 120 rpm on a rotary shaker. Infected cells were harvested by centrifugation at 398 g for 15 min. Cell pellets were frozen at –80° C. until purification was performed.

All steps described in cell extraction and purification were performed at 4° C. Frozen Hi-5 cell pellets infected with the C-Met IC recombinant baculovirus were thawed and gently resuspended in Buffer A (20 mM Tris pH 8.0, 10% glycerol, 1 µg/ml pepstatin, 2 µg/ml Aprotinin and leupeptin, 50 µg/ml PMSF, 50 µg/ml TLCK and 10 µM E64, 0.5 mM DTT and 1 mM Levamisole) using 3 ml of buffer per gram of cells. The suspension was Dounce homogenized after which it was centrifuged at 22500 g, 30 min., 4° C. The supernatant (cell extract) was used as starting material for purification of c-Met IC.

The supernatant was loaded onto a QsepharoseFF column (Amersham Biosciences) equilibrated with Buffer B (20 mM Tris pH 8.0, 10% glycerol) supplemented with 0.05M NaCl. Following a ten column volume (CV) wash with equilibration buffer, bound proteins were eluted with a 5 CV salt linear gradient spanning from 0.05 to 1M NaCl in Buffer B. Typically, the conductivity of selected fractions ranked between 6.5 and 37 mS/cm. This Qsepharose eluate had an estimated NaCl concentration of 0.33M and was supplemented with a 5M NaCl solution in order to increase NaCl concentration at 0.5M and also with a 5M Imidazole (pH 8.0) solution to achieve a final imidazole concentration of 15 mM. This material was loaded onto a HisTrap affinity column (GE Healthcare) equilibrated with Buffer C (50 mM NaPO$_4$ pH 8.0, 0.5M NaCl, 10% glycerol) supplemented with 15 mM imidazole. After a 10 CV wash with equilibration buffer and an 8 CV wash with buffer C +40 mM imidazole, bound proteins were eluted with an 8 CV linear gradient (15 to 500 mM) of imidazole in buffer C. C-Met IC enriched fractions from this chromatography step were pooled based on SDS-PAGE analysis. This pool of enzyme underwent buffer exchange using PD-10 column (GE Healthcare) against buffer D (25 mM HEPES pH 7.5, 0.1M NaCl, 10% glycerol and 2 mM ☐-mercaptoethanol) Final C-Met IC protein preparations concentrations were about 0.5 mg/ml with purity approximating 80%. Purified c-Met IC protein stocks were supplemented with BSA at 1 mg/ml, aliquoted and frozen at –80° C. prior to use in enzymatic assay.

In the case of VEGF receptor KDR a 1.6-kb cDNA corresponding to the catalytic domain of VEGFR2 or KDR (Genbank accession number AF035121 amino acid 806 to 1356) was cloned into the Pst I site of the pDEST20 Gateway vector (Invitrogen) for the production of a GST-tagged version of that enzyme. This construct was used to generate recombinant baculovirus using the Bac-to-Bac™ system according to the manufacturer's instructions (Invitrogen).

The GST-VEGFR2$_{806-1356}$ protein was expressed in Sf9 cells (*Spodoptera frugiperda*) upon infection with recombinant baculovirus construct. Briefly, Sf9 cells grown in suspension and maintained in serum-free medium (Sf900 II supplemented with gentamycin) at a cell density of about 2×10$^6$ cells/ml were infected with the abovementioned viruses at a multiplicity of infection (MOI) of 0.1 during 72 hours at 27° C. with agitation at 120 rpm on a rotary shaker. Infected cells were harvested by centrifugation at 398 g for 15 min. Cell pellets were frozen at –80° C. until purification was performed.

All steps described in cell extraction and purification were performed at 4° C. Frozen Sf9 cell pellets infected with the GST-VEGFR2$_{806-1356}$ recombinant baculovirus were thawed and gently resuspended in Buffer A (PBS pH 7.3 supplemented with 1 µg/ml pepstatin, 2 µg/ml Aprotinin and leupeptin, 50 µg/ml PMSF, 50 µg/ml TLCK and 10 µM E64 and 0.5 mM DTT) using 3 ml of buffer per gram of cells. Suspension was Dounce homogenized and 1% Triton X-100 was added to the homogenate after which it was centrifuged at 22500 g, 30 min., 4° C. The supernatant (cell extract) was used as starting material for purification of GST-VEGFR2$_{806-1356}$.

The supernatant was loaded onto a GST-agarose column (Sigma) equilibrated with PBS pH 7.3. Following a four column volume (CV) wash with PBS pH 7.3+1% Triton X-100 and 4 CV wash with buffer B (50 mM Tris pH 8.0, 20% glycerol and 100 mM NaCl), bound proteins were step eluted with 5 CV of buffer B supplemented with 5 mM DTT and 15 mM glutathion.GST-VEGFR2$_{806-1356}$ enriched fractions from this chromatography step were pooled based on U.V. trace i.e. fractions with high O.D.$_{280}$. Final GST-VEGFR2$_{806-1356}$ protein preparations concentrations were about 0.7 mg/ml with purity approximating 70%. Purified GST-VEGFR2$_{806-1356}$ protein stocks were aliquoted and frozen at –80° C. prior to use in enzymatic assay.

Inhibition of c-Met/HGF receptor and VEGFR/KDR was measured in a DELFIA™ assay (Perkin Elmer). The substrate poly(Glu$_4$,Tyr) was immobilized onto black high-binding polystyrene 96-well plates. The coated plates were washed and stored at 4° C. During the assay, enzymes were pre-incubated with inhibitor and Mg-ATP on ice in polypropylene 96-well plates for 4 minutes, and then transferred to the coated plates. The subsequent kinase reaction took place at 30° C. for 10-30 minutes. ATP concentrations in the assay were 10 uM for C-Met (5× the $K_m$) and 0.6 uM for VEGFR/KDR (2× the $K_m$). Enzyme concentration was 25 nM (C-Met) or 5 nM (VEGFR/KDR). After incubation, the kinase reactions were quenched with EDTA and the plates were washed. Phosphorylated product was detected by incubation with Europium-labeled anti-phosphotyrosine MoAb. After washing the plates, bound MoAb was detected by time-resolved fluorescence in a Gemini SpectraMax reader (Molecular Devices). Compounds were evaluated over a range of concentrations and $IC_{50}$'s (concentration of compounds giving 50% inhibition of enzymatic activity) were determined.

C-Met Phosphorylation Cell-Based Assay

This test measures the ability of compounds to inhibit HGF stimulated auto-phosphorylation of the c-Met/HGF receptor itself in a whole cell system.

MNNGHOS cell line expressing TPR-MET fusion protein were purchased from ATCC. The TPR-MET is the product of a chromosomal translocation placing the TPR locus on chromosome 1 upstream of the MET gene on chromosome 7 encoding for it's cytoplasmic region catalytic domain. Dimerization of the $M_r$ 65,000 TPR-Met oncoprotein through a leucine zipper motif encoded by the TPR portion leads to constitutive activation of the met kinase. Constitutive autophosphorylation occurs on residues Tyr361/365/366 of TPR-Met. These residues are homologous to Tyr1230/1234/1235 of MET which become phosphorylated upon dimerization of the receptor upon HGF binding.

Inhibitor of c-Met formulated as 30 mM stocks in DMSO. For MNNGHOS treatments, cells, compounds were added to tissue culture media at indicated doses for 3 hours prior to cell lysis. Cells were lysed in ice-cold lysis buffer containing 50 mM HEPES (pH 7.5), 150 mM NaCl, 1.5 mM MgCl2, 10% glycerol, 1% Triton X-100, 1 mM 4-(2-Aminoethyl)benzenesulfonyl fluoride hydrochloride, 200 µM sodium orthovanadate, 1 mM sodium fluoride, 10 µg/ml of leupeptin, 10 µg/ml of aprotinin/ml, 1 ug/ml of pepstatin and 50 ug/ml Na-p-Tosyl-L-lysine chloromethyl ketone hydrochloride.

Lysate were separated on 5-20% PAGE-SDS and immunoblots were performed using Immobilon P polyvinylidene difluoride membranes (Amersham) according to the manufacturer's instructions for handling. The blots were washed in Tris-buffered saline with 0.1% Tween 20 detergent (TBST). Tyr361/365/366 of TPR-Met were detected with polyclonal rabbit antibodies against tyrosine phosphorylated Met (Biosource International) and secondary antibodies anti-rabbit -horseradish peroxidase (Sigma) by chemiluminescence assays (Amersham, ECL) were performed according to the manufacturer's instructions and followed by film exposure. Signal was quantitated by densitometry on Alpha-Imager. $IC_{50}$ values were defined as the dose required to obtain 50% inhibition of the maximal HGF stimulated phosphorylated c-Met levels.

In Vivo Solid Tumor Disease Model

This test measures the capacity of compounds to inhibit solid tumor growth.

Tumor xenografts were established in the flank of female athymic CD1 mice (Charles River Inc.), by subcutaneous injection of $1 \times 10^6$ U87, A431 or SKLMS cells/mouse. Once established, tumors were then serially passaged s.c. in nude mice hosts. Tumor fragments from these host animals were used in subsequent compound evaluation experiments. For compound evaluation experiments female nude mice weighing approximately 20 g were implanted s.c. by surgical implantation with tumor fragments of 30 mg from donor tumors. When the tumors were approximately 100 mm in size (~7-10 days following implantation), the animals were randomized a separated into treatment and control groups. Each group contained 6-8 tumor-bearing mice, each of which was ear-tagged and followed individually throughout the experiment.

Mice were weighed and tumor measurements are taken by calipers three times weekly, starting on Day 1. These tumor measurements were converted to tumor volume by the well-known formula $(L+W/4)^3 4/3\pi$. The experiment was terminated when the control tumors reached a size of approximately 1500 mm³. In this model, the change in mean tumor volume for a compound treated group/the change in mean tumor volume of the control group (non-treated or vehicle treated)×100 ($\Delta T/\Delta C$) was subtracted from 100 to give the percent tumor growth inhibition (%TGI) for each test compound. In addition to tumor volumes, body weight of animals were monitored twice weekly for up to 3 weeks.

The activities of a number of compounds according to the invention measured by various assays are displayed in the following table, Table 24. In the table, "a" indicates inhibitory activity at a concentration of less than 50 nanomolar; "b" indicates inhibitory activity at a concentration ≧50 but <250 nanomolar, "c" indicates inhibitory activity at ≧250 but <500 and "d" indicates inhibitory activity at a concentration of ≧500 nanomolar; and "e" indicates no activity as measured by that assay.

TABLE 24

| Example No | Compound No | C-Met (enz.) ($IC_{50}$, µM) | VEGF(enz.) ($IC_{50}$, µM) | C-Met cell-based Y1230-34-35 tpr-met inhibition ($IC_{50}$, µM) |
|---|---|---|---|---|
| 1 | 8a | b | a | a |
| 2 | 8b | b | a | b |
| 3 | 8c | b | c | b |
| 5 | 8e | b | b | b |
| 7 | 8g | b | c | b |
| 9 | 8i | b | b | c |
| 10 | 8j | b | b | b |
| 11 | 8k | b | d | b |
| 12 | 13a | b | a | a |
| 13 | 13b | b | a | a |
| 14 | 13c | b | b | b |
| 15 | 13d | b | a | a |
| 133 | 170a | b | b | b |
| 16 | 13e | b | a | c |
| 18 | 13g | b | b | b |
| 20 | 18a | b | d | e |
| 22 | 26a | b | b | a |
| 23 | 26b | b | a | b |
| 24 | 26c | b | c | d |
| 25 | 26d | b | b | e |
| 26 | 26e | b | b | e |
| 27 | 26f | b | b | e |
| 28 | 31a | b | d | e |
| 29 | 31b | c | d | e |
| 35 | 8m | b | b | a |
| 36 | 8n | b | d | b |
| 37 | 8o | b | a | a |
| 40 | 8r | b | a | b |
| 75 | 13k | b | a | a |
| 142 | 26f | b | a | a |
| 188 | 170c | c | d | d |
| 221 | 269a | a | d | d |

In the following table, Table 25, "a" indicates % TGI in the range of 75-100; "b" indicates % TGI in the range of 50-74; "c" indicates % TGI in the range of 25-49, and "d" indicates % TGI in the range of 0-24. Regiment of administration was once daily.

TABLE 25

| Ex (Cpd) | Dosage mg/kg (once daily) | Vehicle | Tumor type | Duration of experiment (days) | Route of administration | Tumor Growth Inhibition (%) |
|---|---|---|---|---|---|---|
| 1 (8a) | 30 | DMSO | A431 | 14 | IP | d |
|  | 30 | DMSO | A549 | 14 | IP | b |
|  | 100 | 5% DMSO - 1% Tween-80 in water | U87MG | 14 | PO | c |
|  | 15 | DMSO | MKN74 | 10 | IP | d |
|  | 30 | DMSO | MKN74 | 10 | IP | c |
|  | 15 | DMSO | U87MG | 10 | IP | c |
|  | 30 | DMSO | U87MG | 7 | IP | c |
|  | 30 | DMSO | A431 | 14 | IP | c |
|  | 30 | DMSO | U87MG | 14 | IP | c |
|  | 30 | DMSO | SKLMS40 | 14 | IP | b |
|  | 30 | DMSO | SW48 | 14 | IP | b |
|  | 30 | DMSO | U87MG | 14 | IP | a* |
|  | 30 | DMSO | HGT116 | 14 | IP | c |
| 7 (8g) | 30 | DMSO | SW48 | 14 | IP | c |
|  | 30 | DMSO | HCT116 | 14 | IP | b |
| 12 (13a) | 30 | DMSO | SW48 | 14 | IP | b |
|  | 30 | DMSO | U87MG | 14 | IP | b |
|  | 30 | DMSO | HST116 | 14 | IP | c |
|  | 30 | DMSO | SW48 | 14 | IP | d |
| 13 (13b) | 30 | DMSO | A431 | 7 | IP | b |
|  | 30 | DMSO | SW48 | 14 | IP | d |
|  | 30 | DMSO | U87MG | 14 | IP | a |
|  | 30 | DMSO | DU145 | 10 | IP | d |
|  | 30 | DMSO | SKLMS40 | 10 | IP | b |
| 37 (8o) | 15 | DMSO | DU145 | 10 | IP | d |
|  | 30 | DMSO | DU145 | 10 | IP | d |
|  | 30 | DMSO | A431 | 14 | IP | b |
|  | 30 | DMSO | A549 | 14 | IP | c |
|  | 15 | 50/50 DMSO: 40/60 PEG/0.2 N HCl in saline | U87MG | 10 | IV | b |
|  | 30 | 50/50 DMSO: 40/60 PEG/0.2 N HCl in saline | U87MG | 10 | IV | c |
| 15 (13d) | 30 | DMSO | DU145 | 10 | IP | b |
|  | 30 | DMSO | SKLMS40 | 10 | IP | b |
|  | 30 | DMSO | A431 | 14 | IP | b |
|  | 30 | DMSO | A549 | 14 | IP | b |
|  | 15 | DMSO | DU145 | 10 | IP | d |
|  | 30 | DMSO | DU145 | 10 | IP | d |
|  | 15 | 50/50 DMS0: 40/60 PEG/0.2 N HCl in saline | U87MG | 10 | IV | b |
|  | 30 | 50/50 DMS0: 40/60 PEG/0.2 N HCl in saline | U87MG | 10 | IV | b |
|  | 100 | 5% DMS0 - 1% Tween-80 in water | U87MG | 14 | PO | a |
|  | 30 | DMSO | U87MG | 14 | IP | b |
|  | 75 | 5% DMSO - 1% Tween-80 in water | A549 | 12 | PO | c |
|  | 50 | 5% DMSO - 1% Tween-80 in water | A549 | 11 | PO | c |
|  | 75 | 5% DMSO - 1% Tween-80 in water | A549 | 10 | PO | b |
|  | 15 | DMSO | MKN74 | 10 | IP | c |
|  | 30 | DMSO | MKN74 | 10 | IP | c |
|  | 15 | DMSO | U87MG | 10 | IP | b |
|  | 30 | DMSO | U87MG | 10 | IP | b |
|  | 15 | DMSO | HCT116 | 10 | IP | c |
|  | 30 | DMSO | HCT116 | 10 | IP | c |
| 75 (13k) | 15 | DMSO | DU145 | 10 | IP | c |
|  | 15 | DMSO | SKLMS40 | 10 | IP | b |
|  | 100 | 5% DMSO - 1% Tween-80 in water | U87MG | 14 | PO | b |
|  | 30 | DMSO | U87MG | 14 | IP | c |
|  | 75 | 5% DMSO - 1% Tween-80 in water | A549 | 12 | PO | b |
|  | 30 | DMSO | U87MG | 10 | IP | c |
|  | 15 | DMSO | U87MG | 10 | IP | d |
| 73 (13i) | 100 | 5% DMSO - 1% Tween-80 in water | U87MG | 14 | PO | c |
| 38 (8p) | 30 | DMSO | A431 | 14 | IP | c |
|  | 30 | DMSO | A549 | 14 | IP | c |
| 39 (8g) | 30 | DMSO | A549 | 14 | IP | b |
| 148 (26l) | 30 | DMSO | DU145 | 10 | IP | c |
|  | 30 | 50/50 DMSO: 40/60 PEG/0.2 N HCl in saline | U87MG | 10 | IP | c |
| 76 (13l) | 75 | 5% DMSO - 1% Tween-80 in water | A549 | 10 | PO | b |
|  | 75 | 5% DMSO - 1% Tween-80 in water | DU145 | 10 | PO | c |
|  | 30 | DMSO | A549 | 14 | IP | b |
|  | 75 | 5% DMSO - 1% Tween-80 in water | A549 | 14 | PO | c |
| 157 (195b) | 30 | DMSO | A341 | 14 | IP | c |
|  | 30 | DMSO | A549 | 14 | IP | c |
| 56 (55) | 30 | DMSO | A549 | 12 | IP | c |
| 63 (76c) | 30 | DMSO | A549 | 10 | IP | b |
|  | 30 | DMSO | DU145 | 10 | IP | c |

TABLE 25-continued

| Ex (Cpd) | Dosage mg/kg (once daily) | Vehicle | Tumor type | Duration of experiment (days) | Route of administration | Tumor Growth Inhibition (%) |
|---|---|---|---|---|---|---|
| 77 (13m) | 30 | DMSO | A549 | 10 | IP | b |
| | 75 | 5% DMSO - 1% Tween-80 in water | A549 | 10 | PO | b |
| | 75 | 5% DMSO - 1% Tween-80 in water | U87MG | 14 | PO | b |
| | 75 | 5% DMS0 - 1% Tween-80 in water | SKLMS40 | 6 | PO | d |
| 201 (227) | 30 | DMSO | A549 | 10 | IP | c |
| | 75 | 5% DMSO - 1% Tween-80 in water | A549 | 10 | PO | c |
| 81 (13q) | 75 | 5% DMSO - 1% Tween-80 in water | SKLMS40 | 14 | PO | c |
| 242 (310a) | 75 | 5% DMSO - 1% Tween-80 in water | U87MG | 14 | PO | a |
| | 75 | 5% DMSO - 1% Tween-80 in water | HCT116 | 14 | PO | b |
| 243 (310b) | 75 | 5% DMSO - 1% Tween-80 in water | U87MG | 14 | PO | b |
| | 75 | 5% DMSO - 1% Tween-80 in water | SKLMS40 | 11 | PO | b |
| 137 (178) | 75 | 0.5% CMC in acetate buffer (pH 4.0) | MDA-MB-231 | 14 | PO | b |
| 138 (179) | 75 | 0.5% CMC in acetate buffer (pH 4.0) | MDA-MB-231 | 14 | PO | b | a* - greater than 100% tumor growth inhibition (i.e., tumor shrinkage)

REFERENCES

1. Fan, T. P. D.; Jaggar, R.; Bicknell, R. Controlling the vasculature: angiogenesis, anti-angiogenesis, and vascular targetting of gene therapy. Trends Pharmacol. Sci. 1995, 16, 57-66.
2. Folkman, J. Angiogenesis in cancer, vascular, rheumtoid and other disease. Nat. Med. 1995, 1, 27-31.
3. Jakeman, L. B.; Armanini, M.; Phillips, H. S.; Ferrara, N. Developmental expression of binding sites and messenger ribonucleic acid for vascular endothelial growth factor suggests a role for this protein in vasculogenesis and angiogenesis. Endocrinology 1993, 133, 848-859.
4. Connolly, D. T.; Olander, J. V.; Heuvelman, D.; Nelson, R.; Monsell, R.; Siegel, N.; Haymore, B. L.; Leimgruber, R.; Feder, J. Human vascular permeability factor. Isolation from U937 cells. J. Biol. Chem. 1989, 264, 20017-20024.
5. Plowman, G. D.; Ullrich, A.; Shawver, L. K. Receptor tyrosine kinases as targets for drug intervention. Drug News Perspect. 1994, 7, 334-339.
6. Straw, L. M.; Shawver, L. K. Tyrosine kinases in disease: overview of kinase inhibitors as therapeutic agents and current drugs in clinical trials. Exp. Opin. Invest. Drugs 1998, 7, 553-573.
7. Shawver, L. K.; Lipson, K. E.; Fong, T. A. T.; McMahon, G.; Plowman, G. D.; Strawn, L. M. Receptor tyrosine kinases as targets for inhibition of angiogenesis. Drug Discov. Today 1997, 2, 50-63.
8. De Vries, C.; Escobedo, J. A.; Ueno, H.; Houck, K.; Ferrara, N.; Williams, L. T. The fms-like tyrosine kinase, a receptor for vascular endothelial growth factor. Science 1992, 255, 989-991.
9. Terman, B. I.; Dougher-Vermazen, M.; Carrion, M. E.; Dimitrov, D.; Armellino, D. C.; Gospodarowicz, D.; Bohlen, P. Identification of the KDR tyrosine kinase as a receptor for vascular endothelial cell growth factor. Biochem. Biophys. Res. Commun. 1992, 187, 1579-1586.
10. Plate K. H., Breier G., Weich H. A., Mennel H. D., Risau W. Vascular endothelial growth factor and glioma angiogenesis: coordinate induction of VEGF receptors, distribution of VEGF protein and possible in vivo regulatory mechanisms. Int. J. Cancer, 59: 520-529, 1994.
11. Fuh G., Li B., Crowley C., Cunningham B., Wells J. A. Requirements for binding and signaling of the kinase domain receptor for vascular endothelial growth factor. J. Biol. Chem., 273. 11197-11204, 1998.
12. Wheeler-Jones C., Abu-Ghazaleh R., Cospedal R., Houliston R. A., Martin J., Zachary I. Vascular endothelial growth factor stimulates prostacyclin production and activation of cytosolic phospholipase $A_2$ in endothelial cells via p42/p44 mitogen-activated protein kinase. FEBS Lett., 420: 28-32, 1997.
13. Kim K. J., Li B., Winer J., Armanini M., Gillett N., Phillips H. S., Ferrara N. Inhibition of vascular endothelial growth factor-induced angiogenesis suppresses tumour growth in vivo. Nature (Lond.), 362: 841-844, 1993.
14. Kanai T., Konno H., Tanaka T., Baba M., Matsumoto K., Nakamura S., Yukita A., Asano M., Suzuki H., Baba S. Anti-tumour and anti-metastatic effects of human-vascular-endothelial-growth-factor-neutralizing antibody on human colon and gastric carcinoma xenotransplanted orthotopically into nude mice. Int. J. Cancer, 77: 933-936, 1998.
15. Zhu Z., Rockwell P., Lu D., Kotanides H., Pytowski B., Hicklin D. J., Bohlen P., Witte L. Inhibition of vascular endothelial growth factor-induced receptor activation with anti-kinase insert domain-containing receptor single chain antibodies from a phage display library. Cancer Res., 58: 3209-3214, 1998.
16. Siemeister G., Schirner M., Reusch P., Barleon B., Marme D., Martiny-Baron G. An antagonistic vascular endothelial growth factor (VEGF) variant inhibits VEGF-stimulated receptor autophosphorylation and proliferation of human endothelial cells. Proc. Natl. Acad. Sci. USA, 95: 4625-4629, 1998.
17. Lin P., Sankar S., Shan S., Dewhirst M. W., Polverini P. J., Quinn T. Q., Peters K. G. Inhibition of tumour growth by targeting tumour endothelium using a soluble vascular endothelial growth factor receptor. Cell Growth Differ., 9: 49-58, 1998.
18. Cheng S-Y., Huang H-J. S., Nagane M., Ji X-D., Wang D., Shih C. C-Y., Arap W., Huang C-M., Cavenee W. K. Suppression of glioblastoma angiogenicity and tumorigenicity by inhibition of endogenous expression of vascular endothelial growth factor. Proc. Natl. Acad. Sci. USA, 93: 8502-8507, 1996.
19. Millauer B., Longhi M. P., Plate K. H., Shawver L. K., Risau W., Ullrich A., Strawn L. M. Dominant-negative inhibition of Flk-1 suppresses the growth of many tumour types in vivo. Cancer Res., 56: 1615-1620, 1996.
20. Pennacchietti S, Michieli P, Galluzzo M, Mazzone M, Giordano S, Comoglio P M. Hypoxia promotes invasive growth by transcriptional activation of the met protooncogene. Cancer Cell. 2003 April;3(4):347-61.
21. Camps J L, Chang S M, Hsu T C, et al Fibroblast-mediated acceleration of human epithelial tumor growth in vivo. Proc Natl Acad Sci USA, 87: 75-9, 1990.
22. Nakamura T, Matsumoto K, Kiritoshi A, Tano Y Induction of hepatocyte growth factor in fibroblasts by tumor-derived factors affects invasive growth of tumor cells: in vitro analysis of tumor-stromal interactions. Cancer Res, 57: 3305-13, 1997.
23. Nishimura K, Kitamura M, Takada S, et al Regulation of invasive potential of human prostate cancer cell lines by hepatocyte growth factor. Int J Urol, 5: 276-81, 1998.
24. Bae-Jump V, Segreti E M, Vandermolen D, Kauma S Hepatocyte growth factor (HGF) induces invasion of endometrial carcinoma cell lines in vitro. Gynecol Oncol, 73: 265-72, 1999.
25. Nakamura T, Nawa K, Ichihara A Partial purification and characterization of hepatocyte growth factor from serum of hepatectomized rats. Biochem Biophys Res Commun, 122. 1450-9, 1984.
26. Nakamura T, Nishizawa T, Hagiya M, et al Molecular cloning and expression of human hepatocyte growth factor. Nature, 342: 440-3, 1989.
27. Ebert M, Yokoyama M, Friess H, Buchler M W, Korc M Coexpression of the c-met proto-oncogene and hepatocyte growth factor in human pancreatic cancer. Cancer Res, 54: 5775-8, 1994.
28. Di Renzo M F, Narsimhan R P, Olivero M, et al Expression of the Met/HGF receptor in normal and neoplastic human tissues. Oncogene, 6: 1997-2003, 1991.
29. Di Renzo M F, Poulsom R, Olivero M, Comoglio P M, Lemoine N R Expression of the Met/hepatocyte growth factor receptor in human pancreatic cancer. Cancer Res, 55: 1129-38, 1995.
30. Delehedde M, Sergeant N, Lyon M, Rudland P S, Fernig D G Hepatocyte growth factor/scatter factor stimulates migration of rat mammary fibroblasts through both mitogen-activated protein kinase and phosphatidylinositol 3-kinase/Akt pathways. Eur J Biochem, 268: 4423-9, 2001.
31. Bardelli A, Basile M L, Audero E, et al Concomitant activation of pathways downstream of Grb2 and PI 3-kinase is required for MET-mediated metastasis. Oncogene, 18: 1139-46, 1999.
32. Saucier C, Khoury H, Lai K M, Peschard P, Dankort D, Naujokas M A, Holash J, Yancopoulos G D, Muller W J, Pawson T, Park M. The Shc adaptor protein is critical for VEGF induction by Met/HGF and ErbB2 receptors and for early onset of tumor angiogenesis. Proc Natl Acad Sci U S A. 2004 Feb. 24;101(8):2345-50.

What is claimed is:
1. A compound of the formula (A)

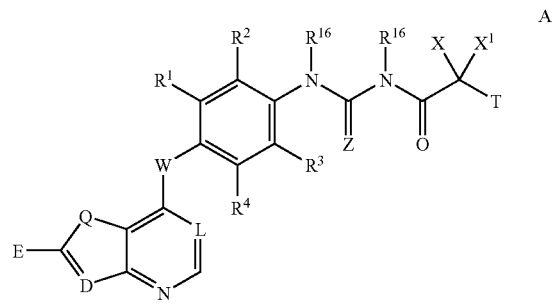

and pharmaceutically acceptable salts thereof, wherein
T is selected from the group consisting of arylalkyl, cycloalkyl, heterocyclyl, aryl and heteroaryl, wherein each of said arylalkyl, cycloalkyl, heterocyclyl, aryl and heteroaryl is optionally substituted with 1 to 3 independently selected $R^{20}$;
each $R^{20}$ is independently selected from the group consisting of —H, halogen, trihalomethyl, —CN, —NO$_2$, —NH$_2$, —OR$^{17}$, —OCF$_3$, —NR$^{17}$R$^{18}$, —S(O)$_{0-2}$R$^{17}$, —S(O)$_2$NR$^{17}$R$^{17}$, —C(O)OR$^{17}$, —C(O)NR$^{17}$R$^{17}$, —N(R$^{17}$)SO$_2$R$^{17}$, —N(R$^{17}$)C(O)R$^{17}$, —N(R$^{17}$)C(O)OR$^{17}$, —C(O)R$^{17}$, —C(O)SR$^{17}$, C$_1$-C$_4$ alkoxy, C$_1$-C$_4$ alkylthio, —O(CH$_2$)$_n$aryl, —O(CH$_2$)$_n$heteroaryl, —(CH$_2$)$_{0-5}$(aryl), —(CH$_2$)$_{0-5}$(heteroaryl), C$_1$-C$_6$ alkyl, C$_2$-C$_6$ alkenyl, C$_2$-C$_6$ alkynyl, —CH$_2$(CH$_2$)$_{0-4}$-T$^2$, an optionally substituted C$_{1-4}$ alkylcarbonyl, C$_{1-4}$ alkoxy, an amino optionally substituted by C$_{1-4}$ alkyl optionally substituted by C$_{1-4}$ alkoxy and a saturated or unsaturated three- to seven-membered carboxyclic or heterocyclic group, wherein T$^2$ is selected from the group consisting of —OH, —OMe, —OEt, —NH$_2$, —NHMe, —NMe$_2$, —NHEt and —NEt$_2$, and wherein the aryl, heteroaryl, C$_1$-C$_6$ alkyl, C$_2$-C$_6$ alkenyl, and C$_2$-C$_6$ alkynyl are optionally substituted;
W is selected from the group consisting of O, S, NH and NMe;
Z is selected from the group consisting of O, or S and NH;
X and $X^1$ are independently selected from the group consisting of H, C$_1$-C$_6$ alkyl, halo, cyano, or nitro, wherein C$_1$-C$_6$ alkyl is optionally substituted, or
X and $X^1$ taken together with the atom to which they are attached, form a C$_3$-C$_7$ cycloalkyl;
$R^1$, $R^2$, $R^3$ and $R^4$ independently represent hydrogen, halo, trihalomethyl, —CN, —NO$_2$, —OR$^{17}$, —NR$^{17}$R$^{18}$, —C(O)OR$^{17}$, —C(O)R$^{17}$, C$_1$-C$_4$ alkoxy, C$_1$C$_4$ alkylthio, C$_1$-C$_6$ alkyl, C$_2$-C$_6$ alkenyl or C$_2$-C$_6$ alkynyl, wherein C$_1$-C$_6$ alkyl, C$_2$-C$_6$ alkenyl and C$_2$-C$_6$ alkynyl are optionally substituted;
$R^{17}$ is selected from the group consisting of H and $R^{18}$;
$R^{18}$ is selected from the group consisting of a (C$_1$-C$_6$)alkyl, an aryl, a aryl(C$_1$-C$_6$)alkyl, a heterocyclyl and a heterocyclyl(C$_1$-C$_6$)alkyl, each of which is optionally substituted, or
$R^{17}$ and $R^{18}$, taken together with a common nitrogen to which they are attached, form an optionally substituted five- to seven-membered heterocyclyl, the optionally substituted five- to seven-membered heterocyclyl optionally containing at least one additional annular heteroatom selected from the group consisting of N, O, S and P;

$R^{16}$ is selected from the group consisting of —H, —CN, —(CH$_2$)$_{0-5}$(aryl), —(CH$_2$)$_{0-5}$(heteroaryl), C$_1$-C$_6$ alkyl, C$_2$-C$_6$ alkenyl, C$_2$-C$_6$ alkynyl, —CH$_2$(CH$_2$)$_{0-4}$-T$^2$, an optionally substituted C$_{1-4}$ alkylcarbonyl, and a saturated or unsaturated three- to seven-membered carboxyclic or heterocyclic group, wherein T$^2$ is selected from the group consisting of —OH, —OMe, —OEt, —NH$_2$, —NHMe, —NMe$_2$, —NHEt and —NEt$_2$, and wherein the aryl, heteroaryl, C$_1$-C$_6$ alkyl, C$_2$-C$_6$ alkenyl, and C$_2$-C$_6$ alkynyl are optionally substituted;

Q is S;

D is C-E, C—C$_1$-C$_6$ alkyl or CH, wherein the C$_1$-C$_6$ alkyl is optionally substituted by 1 to 5 independently selected R$^{38}$;

L is CR, wherein R is selected from the group consisting of —H, halo, —CN, C$_1$-C$_6$ alkyl, C$_2$-C$_6$ alkenyl, and C$_2$-C$_6$ alkynyl, wherein C$_1$-C$_6$ alkyl, C$_2$-C$_6$ alkenyl, and C$_2$-C$_6$ alkynyl are optionally substituted; and E is selected from the group consisting of E$^1$, E$^2$ and E$^3$, wherein E$^1$ is selected from the group consisting of C$_3$-C$_{10}$ cycloalkyl, —C(O)NR$^{42}$R$^{43}$, —NR$^{42}$R$^{43}$, —NR$^{42}$C(=O)R$^{43}$, —SO$_2$R$^{42}$, —SO$_2$NR$^{42}$R$^{43}$, —NR$^{37}$SO$_2$R$^{42}$, —C(=NR$^{42}$)NR$^{37}$R$^{43}$, —C(O)R$^{42}$, —CO$_2$R$^{42}$, —C(O)(heterocyclyl), —C(O)(C$_6$-C$_{10}$ aryl), —C(O)(heteroaryl), —Y—(C$_6$-C$_{10}$ aryl), —Y-(heteroaryl), —Y—(5-10 membered heterocyclic), —NR$^{6a}$ R$^{6b}$, —NR$^{6a}$SO$_2$R$^{6b}$, —NR$^{6a}$C(O)R$^{6b}$ —OC(O)R$^{6b}$, —OR$^{6a}$, —SR$^{6a}$, —S(O)R$^{6a}$, —SO$_2$R$^{6a}$, —SO$_2$NR$^{6a}$R$^{6b}$, —COR$^{6a}$, —CO$_2$R$^{6a}$, —CONR$^{6a}$R$^{6b}$, —(C$_1$-C$_4$)fluoroalkyl and —(C$_1$-C$_4$)fluoroalkoxy, —(CZ$^3$Z$^4$)$_a$CN, wherein n is an integer ranging from 0 to 6, and the aforementioned E$^1$ groups are substituted by 1 to 5 independently selected R$^{38}$, or E$^1$ is selected from a moiety selected from the group consisting of —(CZ$^3$Z$^4$)$_a$-aryl, —(CZ$^3$Z$^4$)$_a$-heterocycle, (C$_2$-C$_6$) alkynyl, —(CZ$^3$Z$^4$)$_a$—(C$_3$-C$_6$)cycloalkyl, —(CZ$^3$Z$^4$)$_a$—(C$_5$-C$_6$)cycloalkenyl and (C$_2$-C$_6$) alkenyl, which is substituted with 1 to 3 independently selected Y$^2$ groups, where a is 0, 1, 2, or 3, and wherein when a is 2 or 3, the CZ$^3$Z$^4$ units may be the same or different; wherein each R$^{38}$ is independently selected from cyano, nitro, azido, —OC(O)R$^{40}$, —OC(O)OR$^{40}$, —NR$^{36}$C(O)R$^{39}$, —NR$^{36}$R$^{39}$, —OH, —SO$_2$NR$^{36}$R$^{39}$, —(CH$_2$)$_j$(CH$_2$)$_i$NR$^{36}$R$^{39}$, —S(O)$_j$(C$_1$-C$_6$ alkyl), —(CH$_2$)$_j$NR$^{39}$(CH$_2$)$_i$NR$^{36}$R$^{39}$, —(CH$_2$)$_j$NR$^{39}$CH$_2$C(O)NR$^{36}$R$^{39}$, —(CH$_2$)$_j$NR$^{39}$(CH$_2$)$_j$NR$^{37}$C(O)R$^{40}$, —(CH$_2$)$_j$NR$^{39}$(CH$_2$)$_n$O(CH$_2$)$_i$OR$^{37}$ —(CH$_2$)$_i$NR$^{39}$(CH$_2$)$_i$S(O)$_j$(C$_1$-C$_6$ alkyl), —(CH$_2$)$_j$NR$^{39}$(CH$_2$)$_n$R$^{36}$, —SO$_2$(CH$_2$)$_n$(C$_6$-C$_{10}$ aryl), —SO$_2$(CH$_2$)$_n$(5-10 membered heterocyclyl), —(CH$_2$)$_n$NR$^{36}$R$^{39}$, —NR$^{37}$SO$_2$NR$^{36}$R$^{39}$, SO$_2$R$^{36}$ and C$_1$-C$_6$ alkylamino, wherein j is an integer ranging from 0 to 2, n is an integer ranging from 0 to 6, i is an integer ranging from 0 to 6, the —(CH$_2$)$_i$- and —(CH$_2$)$_n$- moieties of the foregoing R$^{38}$ groups optionally include a carbon-carbon double or triple bond where n is an integer between 2 and 6, and the alkyl, aryl, and heterocyclyl moieties of the foregoing R$^{38}$ groups are optionally substituted by one or more substituents independently selected from the group consisting of halo, cyano, nitro, trifluoromethyl, azido, —OH, —C(O)R$^{40}$, —C(O)OR$^{40}$, —OC(O)R$^{40}$, —OC(O)OR$^{40}$, —NR$^{36}$C(O)R$^{39}$, —C(O)NR$^{36}$R$^{39}$, —(CH$_2$)$_n$NR$^{36}$R$^{39}$, C$_1$-C$_6$ alkyl, C$_3$-C$_{10}$ cycloalkyl, —(CH$_2$)$_n$(C$_6$-C$_{10}$ aryl), —(CH$_2$)$_n$(5-10 membered heterocyclyl), —(CH$_2$)$_n$O(CH$_2$)$_i$OR$^{37}$, and —(CH$_2$)$_n$OR$^{37}$, wherein n is an integer ranging from 0 to 6 and i$^2$ is an integer ranging from 2 to 6;

each R$^{42}$ and R$^{43}$ is independently selected from the group consisting of C$_1$-C$_6$ alkyl, C$_1$-C$_6$ heteroalkyl, —Y—(C$_3$-C$_{10}$ cycloalkyl), —Y—(C$_6$-C$_{10}$ aryl), —Y—(C$_6$-C$_{10}$ heteroaryl), —Y—(5-10 membered heterocyclic), —Y—O—Y$^1$—OR$^{37}$, —Y$^1$—CO$_2$—R$^{37}$, and —Y—OR$^{37}$, wherein the alkyl, heteroalkyl, cycloalkyl, aryl, heteroaryl and heterocyclic moieties of the foregoing R$^{42}$ and R$^{43}$ groups are substituted by 1 or more substituents independently selected from R$^{44}$, wherein Y is a bond or is —(C(R$^{37}$)(H))$_{n}{}^2$, n$^2$ is an integer ranging from 1 to 6, and Y$^1$ is —(C(R$^{37}$)(H))$_n$, or R$^{42}$ and R$^{43}$ taken together with the nitrogen to which they are attached form a C$_5$-C$_9$ heterocyclyl ring or a heteroaryl ring, wherein said ring is substituted by 1 to 5 independently selected R$^{44}$ substituents, with the proviso that R$^{42}$ and R$^{43}$ are not both bonded to the nitrogen directly through an oxygen;

each R$^{44}$ is independently selected from the group consisting of cyano, nitro, azido, —OC(O)R$^{40}$, —OC(O)OR$^{40}$, —NR$^{36}$C(O)R$^{39}$, —NR$^{36}$R$^{39}$, —SO$_2$NR$^{36}$R$^{39}$, —SO$_2$R$^{36}$, —NR$^{36}$SO$_2$R$^{39}$, —NR$_{,}{}^{36}$SO$_2$NR$^{37}$R$^{41}$, —C$_1$-C$_6$ alkylamino, —(CH$_2$)$_i$O(CH$_2$)$_i{}^2$NR$^{36}$R$^{39}$, —S(O)$_j$(C$_1$-C$_6$ alkyl), —C(O)(CH$_2$)$_n$(C$_6$-C$_{10}$ aryl), —C(O)(CH$_2$)$_n$(5 to 10 membered heterocyclic), —(CH$_2$)$_j$NR$^{39}$(CH$_2$)$_i{}^2$NR$^{36}$R$^{39}$, —(CH$_2$)$_j$NR$^{39}$CH$_2$C(O)NR$^{36}$R$^{39}$, —(CH$_2$)$_j$NR$^{39}$(CH$^2$)$_i{}^2$NR$^{37}$C(O)R$^{40}$, —(CH$_2$)$_j$NR$^{39}$(CH$_2$)$_n$O(CH$_2$)$_i{}^2$OR$^{37}$, —(CH$_2$)$_j$NR$^{39}$ (CH$_2$)$_i{}^2$S(O)$_j$(C$_1$-C$_6$ alkyl), —(CH$_2$)$_j$NR$^{39}$(CH$_2$)$_n$R$^{36}$, —SO$_2$(CH$_2$)$_n$(C$_6$-C$_{10}$aryl), and —SO$_2$(CH$_2$)$_n$(5 to 10 membered heterocyclic) wherein, j is an integer from 0 to 2, n is an integer from 0 to 6 and i$^2$ is an integer ranging from 2 to 6, the —(CH$_2$)$_i{}^2$ and —(CH$_2$)$_n$ moieties of the foregoing R$^{44}$ groups optionally include a carbon-carbon double or triple bond wherein n is an integer from 2 to 6, and the alkyl, aryl and heterocyclic moieties of the foregoing R$^{44}$ groups are optionally substituted by 1 or more substituents independently selected from the group consisting of halo, cyano, nitro, trifluoromethyl, azido, —OH, —C(O)R$^{40}$, —C(O)OR$^{40}$, —OC(O)R$^{40}$, —OC(O)OR$^{40}$, —NR$^{36}$C(O)R$^{39}$, —C(O)NR$^{36}$R$^{39}$, —(CH$_2$)$_n$NR$^{36}$R$^{39}$, —SO$_2$R$^{36}$, —SO$_2$NR$^{36}$R$^{39}$, C$_1$-C$_6$ alkyl, C$_3$-C$_{10}$ cycloalkyl, —(CH$_2$)$_n$(C$_6$-C$_{10}$ aryl), —(CH$_2$)$_n$(5 to 10 membered heterocyclic), —(CH$_2$)$_n$O(CH$_2$)$_i{}^2$OR$^{37}$ and —(CH$_2$)$_n$OR$^{37}$, wherein n is an integer from 0 to 6 and i$^2$ is an integer from 2 to 6; and each R$^{40}$ is independently selected from H, C$_1$-C$_{10}$ alkyl, —(CH$_2$)$_n$(C$_6$-C$_{10}$ aryl), C$_3$-C$_{10}$ cycloalkyl, and —(CH$_2$)$_n$(5-10 membered heterocyclic), wherein n is an integer ranging from 0 to 6;

each R$^{36}$ and R$^{39}$ is independently selected from the group consisting of H, —OH, C$_1$-C$_6$ alkyl, C$_3$-C$_{10}$ cycloalkyl, —(CH$_2$)$_n$(C$_6$-C$_{10}$ aryl), —(CH$_2$)$_n$(5-1 0 membered heterocyclic), —(CH$_2$)$_n$O(CH$_2$)$_i$OR$^{37}$ and —(CH$_2$)$_n$O(CH$_2$)$_i{}^2$OR$^{37}$, wherein n is an integer ranging from 0 to 6 and i$^2$ is an integer ranging from 2 to 6, and the alkyl, aryl and heterocyclic moieties of the foregoing R$^{36}$ and R$^{39}$ groups are optionally substituted by one or more substituents independently selected from —OH, halo, cyano, nitro, trifluoromethyl, azido, —C(O)R$^{40}$, —C(O)OR$^{40}$, —OC(O)OR$^{40}$, —NR$^{37}$C(O)R$^{41}$, —C(O)NR$^{37}$R$^{41}$, —NR$^{37}$R$^{41}$, -C$_1$-C$_6$ alkyl, —(CH$_2$)$_n$ (C$_6$-C$_{10}$ aryl), —(CH$_2$)$_n$(5 to 10 membered heterocyclic), —(CH$_2$)$_n$O(CH$_2$)$_i{}^2$OR$^{37}$and —(CH$_2$)$_n$OR$^{37}$, wherein n is an integer ranging from 0 to 6 and i$^2$ is an integer ranging from 2 to 6, with the proviso that when $R^{36}$ and $R^{39}$ are both attached to the same nitrogen, then $R^{36}$ and $R^{39}$ are not both bonded to the nitrogen directly through an oxygen;

each $R^{37}$ and $R^{41}$ is independently selected from the group consisting of H, $OR^{36}$, $C_1$-$C_6$ alkyl and $C_3$-$C_{10}$ cycloalkyl;

each $R^{6a}$ and $R^{6b}$ is independently selected from the group consisting of hydrogen, —$(CZ^5Z^6)_u$—$(C_3$-$C_6)$cycloalkyl, —$(CZ^5Z^6)_u$—$(C_5$-$C_6)$cycloalkenyl, —$(CZ^5Z^6)_u$-aryl, —$(CZ^5Z^6)_u$-heteroaryl, —$(CZ^5Z^6)_u$-heterocycle, $(C_2$-$C_6)$alkenyl, and $(C_1$-$C_6)$alkyl, each of which is substituted with 1 to 3 independently selected $Y^3$ groups, where u is 0,1, 2, or 3, and wherein when u is 2 or 3, the $CZ^5Z^6$ units may be the same or different, or $R^6$a and $R^6$b taken together with adjacent atoms can form a heterocycle;

each $Z^3$, $Z^4$, $Z^5$ and $Z^6$ is independently selected from the group consisting of H, F and $(C_1$-$C_6)$alkyl, or each $Z^3$ and $Z^4$, or $Z^5$ and $Z^6$ are selected together to form a carbocycle, or two $Z^3$ groups on adjacent carbon atoms are selected together to optionally form a carbocycle;

each $Y^2$ is independently selected from the group consisting of nitro, tetrazolyl, guanidino, amidino, methylguanidino, azido, —$OC(O)NH_2$, —$OC(O)$ $NHZ^7$, —$OC(O)NZ^7Z^8$, —$NHC(O)Z^7$, —$NHC(O)NH_2$, —$NHC(O)NHZ^7$, —$NHC(O)NZ^7Z^8$, —$P(O)_3H_2$, —$P(O)_3(Z^7)_2$, —$S(O)_3H$, —$S(O)Z^7$, —$S(O)_2Z^7$, —$S(O)_3Z^7$, —OH, —$NH_2$, —$NHZ^7$, —$NZ^7Z^8$, —$C(=NH)NH_2$, —$C(=NOH)NH_2$, —N morpholino, )—$(CZ^9Z^{10})_rNH_2$,)—$(CZ^9Z^{10})_rNHZ^3$,— $(CZ^9Z^{10})_rNZ^7Z^8$,)—$X^6(CZ^9Z^{10})_r$—$(C_3$-$C_8)$cycloalkyl,)—$X^6(CZ^9Z^{10})_r$—$(C_5$-$C_8)$cycloalkenyl,)—$X^6$$(CZ^9Z^{10})_r$-aryl and —$X^6(CZ^9Z^{10})_r$-heterocycle, each $Y^3$ is independently selected from the group consisting of nitro, tetrazolyl, guanidino, amidino, methylguanidino, azido, —$OC(O)NH_2$, —$OC(O)NHZ^7$, —$OC(O)NZ^7Z^8$, —$NHC(O)Z^7$, —$NHC(O)NH_2$, —$NHC(O)NHZ^7$, —$NHC(O)NZ^7Z^8$, —$P(O)_3H_2$, —$P(0)_3(Z^7)_2$, —$S(O)_3H$, —$S(O)Z^7$, —$S(O)_2Z^7$, —$S(O)_3Z^7$, —OH, —$NH_2$, —$NHZ^7$, —$NZ^7Z^8$, —$C(=NH)NH_2$, —$C(=NOH)NH_2$, —N morpholino,)—$(CZ^9Z^{10})_rNH_2$,)—$(CZ^9Z^{10})_rNHZ^3$,— $(CZ^9Z^{10})_rNZ^7Z^8$,—$X^6(CZ^9Z^{10})_r$—$(C_3$-$C_8)$cycloalkyl, —$X(CZ^9Z^{10})_r(C_5$-$C_8)$cycloalkenyl,—$X^6(CZ^9Z^{10})_r$-aryl and —$X^6(CZ^9Z^{10})_r$-heterocycle, wherein r is 1, 2, 3 or 4;

$X^6$ is selected from the group consisting of S, NH, —C(O)—, —C(O)NH—, —C(O)O—, —S(O)—, —$S(O)_2$— and —$S(O)_3$—;

$Z^7$ and $Z^8$ are independently selected from the group consisting of an alkyl of 1 to 12 carbon atoms, an alkenyl of 2 to 12 carbon atoms, an alkynyl of 2 to 12 carbon atoms, a cycloalkyl of 3 to 8 carbon atoms, a cycloalkenyl of 5 to 8 carbon atoms, an aryl of 6 to 14 carbon atoms, a heterocycle of 5 to 14 ring atoms, an aralkyl of 7 to 15 carbon atoms, and a heteroaralkyl of 5 to 14 ring atoms, or $Z^7$ and $Z^8$ together may optionally form a heterocycle;

$Z^9$ and $Z^{10}$ are independently selected from the group consisting of H, F, a $(C_1$-$C_{12})$alkyl, a $(C_6$-$C_{14})$ aryl, a $(C_5$-$C_{14})$heteroaryl, a $(C_7$-$C_{15})$aralkyl and a $(C_5$-$C_{14})$heteroaralkyl, or $Z^9$ and $Z^{10}$ are taken together form a carbocycle, or two $Z^9$ groups on adjacent carbon atoms are taken together to form a carbocycle; or any two $Y^2$ or $Y^3$ groups attached to adjacent carbon atoms may be taken together to be —$O[C(Z^9)(Z^{10})]_rO$ or —$O[C(Z^9)(Z^{10})]_{r+1}$, or any two $Y^2$ or $Y^3$ groups attached to the same or adjacent carbon atoms may be selected together to form a carbocycle or heterocycle; and wherein any of the above-mentioned substituents comprising a $CH_3$ (methyl), $CH_2$ (methylene), or CH (methine) group which is not attached to a halogen, SO or $SO_2$ group or to a N, O or S atom optionally bears on said group a substituent selected from hydroxy, halogen, $(C_1$- $C_4)$ alkyl, $(C_1$-$C_4)$alkoxy and an —$N[(C_1$-$C_4)$alkyl]$[(C_1$-$C_4)$ alkyl];

$E^2$ is —C≡C-$(CR^{45}R^{45})_{n^2}$-$R^{46}$, $n^2$ is an integer ranging from 1 to 6;

$R^{45}$ is independently selected from the group consisting of H, a $(C_1$-$C_6)$alkyl and a $(C_3$- $C_8)$ cycloalkyl;

$R^{46}$ is selected from the group consisting of heterocyclyl, —$N(R^{47})$—$C(O)$—$N(R^{47})(R^{48})$, —$N(R^{47})$—$C(S)$—N $(R^{47})(R^{48})$,—$N(R^{47})$—$C(O)$—$OR^{48}$, —$N(R^{47})$—C (O)-$(CH_2)_n$—$R^{48}$, —$N(R^{47})$—$SO_2R^{47}$, —$(CH_2)_n$ $NR^{47}R^{48}$, —$(CH_2)_nSR^{49}$, —$(CH_2)_nS(O)R^{49}$, —$(CH_2)_n$ $S(O)_2R^{49}$, $OC(O)R^{49}$, $OC(O)OR^{49}$;

$R^{47}$ and $R^{48}$ are independently selected from the group consisting of H, $(C_1$-$C_6)$alkyl, $(C_3$-$C_8)$ cycloalkyl, heterocyclyl, —$(CH_2)_nNR^{50}R^{51}$, —$(CH_2)_nOR^{50}$, —$(CH_2)_n$ $C(O)R^{49}$, —$C(O)_2R^{49}$, $(CH_2)_sSR^{49}$, —$(CH_2)_nS(O)R^{49}$, —$(CH_2)_nS(O)_2R^{49}$, —$(CH_2)_sR^{49}$, —$(CH_2)_sCN$, aryl optionally substituted with one or more substituents selected from the group consisting of halo, —$CF_3$, $(C_1$-$C_6)$alkoxy, —$NO_2$, $(C_1$-$C_6)$alkyl, —CN, —$(CH_2)_nOR^{49}$, —$(CH_2)_n$heterocyclyl, —$(CH_2)_n$heteroaryl, —$SO_2R^{50}$ and —$(CH_2)_NNR^{50}R^{51}$, and heteroaryl optionally substituted with one or more substituents selected from the group consisting of halo, —$CF_3$, $(C_1$-$C_6)$alkoxy, —$NO_2$, $(C_1$-$C_6)$alkyl, —CN, —$(CH_2)_nOR^{49}$, —$(CH_2)_n$ heterocyclyl, —$(CH_2)_n$heteroaryl, —$SO_2R^{50}$ and —$(CH_2)_n$ $NR^{50}R^{51}$, or $R^{47}$ and $R^{48}$, together with the atom to which they are attached, form a 3-8 membered ring;

$R^{49}$ is selected from the group consisting of $(C_1$-$C_6)$alkyl, $(C_3$-$C_8)$cycloalkyl, heterocyclyl$(C_1$- $C_6)$ alkylene, aryl $(C_1$-$C_6)$alkylene wherein the aryl is optionally substituted with one or more substituents selected from the group consisting of halo, —$CF_3$, $(C_1$-$C_6)$alkoxy, —$NO_2$, $(C_1$-$C_6)$alkyl, —CN, —$SO_2R^{50}$ and —$(CH_2)_nNR^{50}R^{51}$, heteroaryl$(C_1$-$C_6)$alkylene wherein the heteroaryl is optionally substituted with one or more substituents selected from the group consisting of halo, —$CF_3$, $(C_1$-$C_6)$alkoxy, —$NO_2$, $(C_1$-$C_6)$alkyl, —CN, —$SO_2R^{50}$ and —$(CH_2)_nNR^{50}R^{51}$, aryl optionally substituted with one or more substituents selected from the group consisting of halo, —$CF_3$, $(C_1$-$C_6)$alkoxy, —$NO_2$, $(C_1$-$C_6)$alkyl, —CN, —$SO_2R^{50}$ and —$(CH_2)_n$ $NR^{50}R^{51}$, and heteroaryl optionally substituted with one or more substituents selected from the group consisting of halo, —$CF_3$, $(C_1$-$C_6)$alkoxy, —$NO_2$, $(C_1$-$C_6)$alkyl, —CN, —$SO_2R^{50}$ and —$(CH_2)_nNR^{50}R^{51}$;

$R^{50}$ and $R^{51}$ are independently selected from the group consisting of H, $(C_1$-$C_6)$alkyl, $(C_3$-$C_8)$ cycloalkyl and —$C(O)R^{45}$, or $R^{50}$ and $R^{51}$, together with the atom to which they are attached, form a 3-8 membered ring; and $E^3$ is the group defined by —$(Z_{11})$-$(Z^{12})_m$—$(Z^{13})_{m1}$, wherein $Z^{11}$ is heterocyclyl or heterocyclylene;

$Z^{12}$ is selected from the group consisting of OC(O) and OC(S);

$Z^{13}$ is selected from the group consisting of heterocyclyl, aralkyl, N(H)R$^{52}$, (C$_1$-C$_3$)alkyl, OR$^{52}$, halo, S(O)$_2$R$^{56}$, (C$_1$-C$_3$)hydroxyalkyl and (C$_1$-C$_3$)haloalkyl;

m is 0 or 1;

m1 is 0 or 1;

$R^{52}$ is selected from the group consisting of H, —(CH$_2$)$_q$S(O)$_2$R$^{54}$, R$^{55}$NR$^{53}$R$^{53}$, (C$_1$-C$_3$)alkyl, —(CH$_2$)$_q$OR$^{53}$, —C(O)R$^{54}$ and —C(O)OR$^{53}$;

q is 0, 1, 2, 3 or 4;

$R^{53}$ is (C$_1$-C$_3$)alkyl;

$R^{54}$ is (C$_1$-C$_3$)alkyl or N(H)R$^{53}$;

$R^{55}$ is (C$_1$-C$_6$) alkyl; and $R^{56}$ is selected from the group consisting of NH$_2$, (C$_1$-C$_3$) alkyl and OR$^{52}$.

2. The compound according to claim 1, wherein T is aryl or heteroaryl, wherein each of said aryl and heteroaryl is optionally substituted with 1 to 3 independently selected $R^{20}$.

3. The compound according to claim 1, wherein T is selected from the group consisting of arylalkyl, cycloalkyl and heterocyclyl, wherein each of said arylalkyl, cycloalkyl and heterocyclyl is optionally substituted with 1 to 3 independently selected $R^{20}$.

4. The compound according to claim 1, wherein W is O.

5. The compound according to claim 1, wherein Z is S or O.

6. The compound according to claim 1, wherein X and $X^1$ are both H.

7. The compound according to claim 1, wherein $R^1$ is H or halogen.

8. The compound according to claim 1, wherein $R^2$, $R^3$ and $R^4$ are each H.

9. The compound according to claim 1, wherein D is CH.

10. The compound according to claim 1, wherein R is H or halogen.

11. The compound according to claim 1, wherein E is selected from the group consisting of $E^1$ and $E^2$.

12. The compound according to claim 1, wherein E is $E^1$.

13. The compound according to claim 1, wherein E is $E^1$, wherein $E^1$ is selected from the group consisting of —C(O)NR$^{42}$R$^{43}$, —SO$_2$NR$^{42}$R$^{43}$, C(=NR$^{42}$)NR$^{37}$R$^{43}$, —CO$_2$R$^{42}$, —C(O)(heterocyclyl), —C(O)(heteroaryl), —Y—(C$_6$-C$_{10}$ membered heterocyclic), —SR$^{6a}$, —S(O)R$^{6a}$, —SO$_2$R$^{6a}$, wherein each of said $E^1$ are substituted with 1 to 5 independently selected $R^{38}$.

14. The compound according to claim 1, wherein $R^{38}$ is selected from the group consisting of —NR$^{36}$C(O)R$^{39}$, —NR$^{36}$R$^{39}$, —(CH$_2$)$_j$O(CH$_2$)$_i$NR$^{36}$R$^{39}$, —S(O)$_j$(C$_1$-C$_6$alkyl), —(CH$_2$)$_j$NR$^{39}$(CH$_2$)$_i$NR$^{36}$R$^{39}$, —(C$_2$)$_n$R$^{36}$, —(CH$_2$)$_n$NR$^{36}$R$^{39}$, wherein j is an integer ranging from 0 to 2, n is an integer ranging from 0 to 6, i is an integer ranging from 1 to 6, the —(CH$_2$)$_i$- and —(CH$_2$)$_n$-moieties of the foregoing $R^{38}$ groups optionally include a carbon-carbon double or triple bond where n is an integer between 2 and 6, and the alkyl, moieties of the foregoing $R^{38}$ groups are optionally substituted by one or more substituents independently selected from the group consisting of halo, cyano, nitro, trifluoromethyl, azido, —OH, —C(O)R$^4$, —C(O)OR$^{40}$, —OC(O)R$^{40}$, OC(O)OR$^{40}$, —NR$^{36}$C(O)R$^{39}$, —C(O)NR$^{36}$R$^{39}$, —(CH$_2$)$_n$NR$^{36}$R$^{39}$, C$_1$-C$_6$ alkyl, C$_3$-C$_{10}$ cycloalkyl, —(CH$_2$)$_n$(C$_6$-C$_{10}$ aryl), —(CH$_2$)$_n$(5-10 membered heterocyclyl), —(CH$_2$)$_n$O(CH$_2$)$_i$$^2$OR$^{37}$, and —(CH$_2$)$_n$0R$^{37}$, wherein n is an integer ranging from 0 to 6 and i$^2$ is an integer ranging from 2 to 6.

15. The compound according to claim 1, wherein each $R^{42}$ and $R^{43}$ independently selected from the group consisting of —Y—(C$_3$-C$_{10}$ cycloalkyl), —Y—(C$_6$-C$_{10}$ aryl), —Y—(C$_6$-C$_{10}$ heteroaryl) and —Y—(5 to 10 membered heterocyclic), wherein the cycloalkyl, aryl, heteroaryl and heterocyclic moieties of the foregoing $R^{42}$ and $R^{43}$ groups are substituted by 1 or more substituents independently selected from R44.

16. The compound according to claim 1, wherein one of $R^{42}$ and $R^{43}$ is —(C$_6$-C$_{10}$ heteroaryl) or —Y—(5 to 10 membered heterocyclic).

17. The compound according to claim 1, wherein Y is a bond.

18. The compound according to claim 1, wherein $R^{42}$ and $R^{43}$ taken together with the nitrogen to which they are attached form a C$_5$-C$_9$ heterocyclyl ring or a heteroaryl ring, wherein said ring is optionally substituted by 1 to 5 independently selected R$^{44}$ substituents, with the proviso that $R^{42}$ and $R^{43}$ are not both bonded to the nitrogen directly through an oxygen.

19. The compound according to claim 1, wherein each $R^{36}$ and $R^{39}$ is independently selected from the group consisting of H, C$_1$-C$_6$alkyl, —(CH$_2$)$_n$(5 to 10 membered heterocyclic) and —(CH$_2$)$_n$OR$^{37}$, wherein n is an integer ranging from 0 to 6 and i is an integer ranging from 2 to 6, with the proviso that when $R^{36}$ and $R^{39}$ are both attached to the same nitrogen, then $R^{36}$ and $R^{39}$ are not both bonded to the nitrogen directly through an oxygen.

20. The compound according to claim 1, wherein $R^{6a}$ is selected from the group consisting of —(CZ$^5$Z$^6$)$_u$-aryl, —(CZ$^5$Z$^6$)$_u$-heteroaryl and C$_1$-C$_6$alkyl, each of which is substituted with 1 to 3 independently selected Y$^3$ groups, wherein u is 0, 1, 2 or 3, and wherein when u is 2 or 3, the CZ$^5$Z$^6$ units may be the same or different.

21. The compound according to claim 1, wherein $Y^2$ is —OH.

22. The compound according to claim 1, wherein $E^2$ is —C≡C—(CR$^{45}$R$^{45}$)$_n$-$^{R46}$, wherein n is an integer ranging from 1 to 6.

23. The compound according to claim 1, represented by the formula A-0:

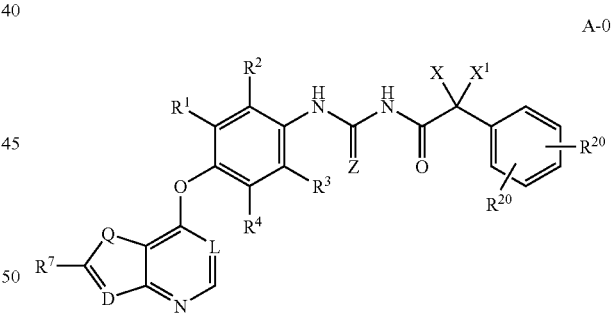

A-0 and pharmaceutically acceptable salts thereof, wherein Z is O or S;

X and $X^1$ are independently selected from the group consisting of H, C$_1$-C$_6$ alkyl, halo, cyano and nitro, wherein C$_1$-C$_6$ alkyl is optionally substituted;

$R^1$, $R^2$, $R^3$ and $R^4$ are independently selected from the group consisting of hydrogen, halo, trihalomethyl, —OR$^{17}$, C$_1$-C$_6$ alkyl, C$_2$-C$_6$ alkenyl or C$_2$-C$_6$ alkynyl, wherein C$_1$-C$_6$ alkyl, C$_2$-C$_6$ alkenyl and C$_2$-C$_6$ alkynyl are optionally substituted;

Q is S;

D is CH or C(C$_1$-C$_6$ alkyl), wherein the C$_1$-C$_6$ alkyl is optionally substituted by 1 to 5 independently selected $R^{38}$;

L is CR, wherein R is H, halo, —CN, $C_1$-$C_6$ alkyl, $C_2$-$C_6$ alkenyl, or $C_2$-$C_6$ alkynyl, wherein $C_1$-$C_6$ alkyl, $C_2$-$C_6$ alkenyl, and $C_2$-$C_6$ alkynyl are optionally substituted; and $R^7$ is —C(=O)$NR^9R^{10}$, —C(=O)($C_6$-$C_{10}$aryl), —C(=O)(heterocyclyl), —C(=O)(heteroaryl), —Y—($C_6$-$C_{10}$aryl), —Y—(5 to 10 membered heterocyclyl), —Y—(heteroaryl), —S-aryl, —S-$C_1$-$C_6$ alkyl, —SO-$C_1$-$C_6$ alkyl, —$SO_2$-$C_1$-$C_6$ alkyl, —$NR^9R^{10}$, —$SO_2NR^9R^{10}$ or $CO_2R^9$, wherein $C_1$-$C_6$ alkyl, aryl, heterocycle and heteroaryl are each independently substituted with 1 to 5 independently selected $R^{38}$;

$R^9$ and $R^{10}$ are independently selected from $C_1$-$C_6$ alkyl, —Y—($C_3$-$C_{10}$cycloalkyl), —Y—($C_6$-$C_{10}$aryl), —Y—(5 to 10 membered heterocyclyl), —Y—($C_6$-$C_{10}$heteroaryl), —Y—O—$Y^1$—O—$R^{11}$, —$Y^1$-$CO_2$-$R^{11}$, and $Y^1$—O—$R^{11}$, wherein $C_1$-$C_6$ alkyl, cycloalkyl, aryl, heterocycle, and heteroaryl are each substituted with 1 or more $R^{44}$, or $R^9$ and $R^{10}$ taken together with the nitrogen to which they are attached form a $C_5$-$C_9$ heterocyclyl ring or a heteroaryl ring, wherein said ring is substituted with 1 or more $R^{44}$;

Y is a bond or is —(C($R^{11}$)(H))$_t$—, wherein t is an integer from 1 to 6;

$Y^1$ is —(C($R^{11}$)(H))$_t$—, $R^{11}$ at each occurrence is independently H or $C_1$-$C_6$ alkyl, each $R^{20}$ is independently selected from the group consisting of hydrogen, halo, trihalomethyl, $OR^{17}$, $C_1$-$C_6$ alkyl, $C_2$-$C_6$ alkenyl or $C_2$-$C_6$ alkynyl, wherein $C_1$-$C_6$ alkyl, $C_2$-$C_6$ alkenyl and $C_2$-$C_6$ alkynyl are optionally substituted, and each $R^{17}$ is an independently selected $C_1$-$C_6$alkyl, wherein said $C_1$-$C_6$alkyl is optionally substituted.

24. The compound according to claim 23, wherein X and $X^1$ are both hydrogen.

25. The compound according to claim 23, wherein $R^1$ is fluorine.

26. The compound according to claim 23, wherein $R^{20}$ is —$OR^{17}$.

27. The compound according to claim 23, wherein L is CH.

28. The compound according to claim 23, wherein $R^7$ is —$CONR^9R^{10}$.

29. The compound according to claim 23, wherein $R^7$ is Y-Heteroaryl.

30. The compound according to claim 23, wherein Z is sulfur.

31. The compound according to claim 1, represented by the formula A-1:

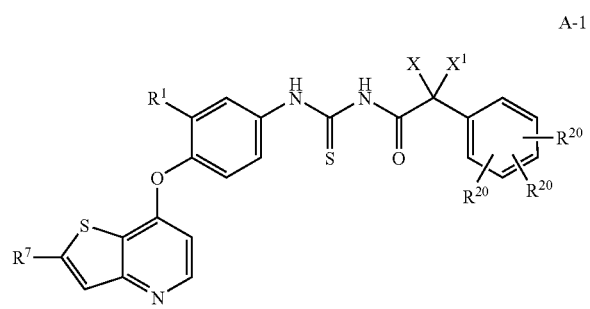

A-1 and pharmaceutically acceptable salts thereof, wherein $R^1$ is selected from the group consisting of hydrogen, halo, $C_1$-$C_6$ alkenyl or $C_2$-$C_6$ alkynyl, wherein $C_1$-$C_6$ alkyl, $C_2$-$C_6$ alkenyl and $C_2$-$C_6$ alkynyl are optionally substituted;

X and $X^1$ are independently selected from the group consisting of H and $C_1$-$C_6$ alkyl, wherein $C_1$-$C_6$ alkyl is optionally substituted, or X and $X^1$ taken together with the atom to which they are attached, form a $C_3$-$C_7$ cycloalkyl;

$R^7$ is C(=O)$NR^9R^{10}$, —C(=O)($C_6$-$C_{10}$aryl), —C(=O)(heterocyclyl), —C(=O)(heteroaryl), —Y—($C_6$-$C_{10}$aryl), —Y—(5 to 10 membered heterocyclyl), —Y—(heteroaryl), —$SR^{6a}$, —S-aryl, —S -(heteroaryl), —S—$C_1$-$C_6$ alkyl, —SO—$C_1$-$C_6$ alkyl, —$SO_2$—$C_1$-$C_6$ alkyl, —$NR^9R^{10}$, —$SO_2NR^9R^{10}$, $CO_2R^9$, —C≡C—($CR^{45}R^{45}$)$_{n-R^{46}}$ or —C(=$NR^{42}$)$NR^{37}R^{43}$, wherein n is an integer ranging from 0 to 6 and wherein $C_1$-$C_6$ alkyl, aryl, heterocycle and heteroaryl are each independently substituted with 1 to 5 independently selected $R^{38}$;

$R^9$ and $R^{10}$ are independently selected from $C_1$-$C_6$ alkyl, —Y—($C_3$-$C_{10}$cycloalkyl), —($C_1$-$C_6$ heteroalkyl), —Y—($C_6$-$C_{10}$aryl), —Y—(5 to 10 membered heterocyclyl), —Y—($C_6$-$C_{10}$heteroaryl), —Y—O—$Y^1$—O—$R^{11}$, —$Y^1$-$CO_2$—$^{11}$, and —Y—O—$R^{11}$, wherein said $C_1$-$C_6$ alkyl, heteroalkyl, cycloalkyl, aryl, heterocycle, and heteroaryl are each substituted with one or more independently selected $R^{44}$, or $R^9$ and $R^{10}$ taken together with the nitrogen to which they are attached form a $C_5$-$C_9$ heterocyclyl ring or a heteroaryl ring, wherein said ring is substituted with 1 to 5 independently selected $R^{44}$;

each $R^{20}$ is independently selected from the group consisting of H, halo, —$OR^{17}$ and —C(O)$OR^{17}$;

Y is a bond or is —(C($R^{11}$)(H))$_t$—, wherein t is an integer from 1 to 6;

$Y^1$ is —(C($R^{11}$)(H))$_t$—, and $R^{11}$ at each occurrence is independently H or $C_1$-$C_6$ alkyl.

32. The compound according to claim 31, wherein $R^1$ is fluorine.

33. The compound according to claim 31, wherein $R^7$ is selected from the group consisting of —C(=O)$NR^9R^{10}$, —Y—($C_6$-$C_{10}$ aryl), —Y—(heteroaryl) and —S—$C_1$-$C_6$ alkyl, wherein said —Y—(aryl), —Y-(heteroaryl) and —S—$C_1$-$C_6$ alkyl are substituted with 1 to 5 independently selected $R^{38}$.

34. The compound according to claim 31, wherein $R^7$ is —C(=O)$NR^9R^{10}$, substituted with one or more independently selected $R^{38}$.

35. The compound according to claim 31, wherein $R^7$ is —Y—($C_6$-$C_{10}$aryl), substituted with 1 to 5 independently selected $R^{38}$.

36. The compound according to claim 31, wherein $R^{38}$ is selected from the group consisting of —($CH_2$)$_j$$NR^{39}$($CH_2$)$_n$$R^{36}$, —($CH_2$)$_j$$NR^{39}$($CH_2$)$_2$$_i$$NR^{36}R^{39}$, and —($CH_2$)$_j$O($CH_2$)$_i$$NR^{36}R^{39}$, wherein n is an integer ranging from 0 to 6, j is an integer ranging from 0 to 2, and i is an integer ranging from 1 to 6.

37. The compound according to claim 31, wherein $R^9$ and $R^{10}$ are independently selected from the group consisting of $C_1$-$C_6$ alkyl, —$C_1$-$C_6$ heteroalkyl, —Y—($C_6$-$C_{10}$aryl), —Y-(5 to 10 membered heterocyclyl), —Y—($C_6$-$C_{10}$heteroaryl), and —Y—O—$R^{11}$, wherein a $C_1$-$C_6$ alkyl, $C_1$-$C_6$ heteroalkyl, aryl, heterocyclcyl and heteroaryl are each substituted with 1 or more independently selected $R^{44}$.

38. The compound according to claim 31, wherein $R^{36}$ is selected from the group consisting of H, $C_1$-$C_6$ alkyl, —$(CH_2)_nOR^{37}$ and —$(CH_2)_n$(5 to 10 membered heterocyclyl).

39. The compound according to claim 31, wherein each of $R^{37}$ and $R^{39}$ is independently H or $C_1$-$C_6$ alkyl.

40. The compound according to claim 31, wherein $R^{20}$ is selected from the group consisting of H, halogen, —$OR^{17}$ and —$C(O)OR^{17}$.

41. The compound according to claim 31, wherein $R^{17}$ is H or $C_1$-$C_6$ alkyl.

42. The compound according to claim 33, wherein $NR^9R^{10}$ is selected from the group consisting of:

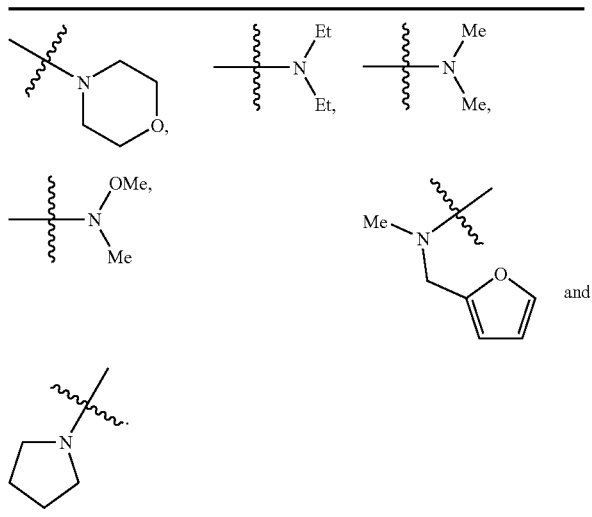

43. The compound according to claim 31, wherein X and $X^1$ are both H.

44. The compound according to claim 43, wherein $R^{17}$ is selected from the group consisting of H and $C_1$-$C_6$ alkyl.

45. The compound according to claim 1, represented by the formula A-4:

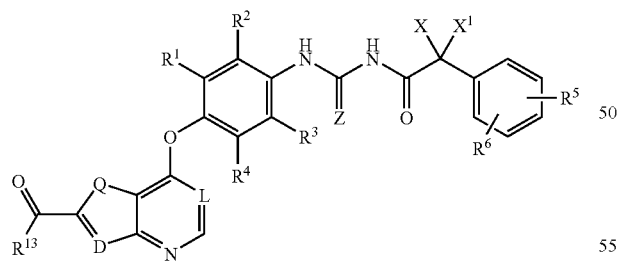

A-4 and pharmaceutically acceptable salts thereof, wherein

Z is O or S;

X and $X^1$ are independently selected from the group consisting of H, $C_1$-$C_6$ alkyl, halo, cyano and nitro, wherein $C_1$-$C_6$ alkyl is optionally substituted;

$R^1$, $R^2$, $R^3$, $R^4$, $R^5$ and $R^6$ are independently selected from the group consisting of hydrogen, halo, $C_1$-$C_6$ alkyl, $C_2$-$C_6$ alkenyl, $C_2$-$C_6$ alkynyl and $NR^{17}R^{18}$, wherein $C_1$-$C_6$ alkyl, $C_2$-$C_6$ alkenyl and $C_2$-$C_6$ alkynyl are optionally substituted;

$R^{17}$ and $R^{18}$ are independently $C_1$-$C_6$alkyl;

Q is S;

D is CH or $C(C_1$-$C_6$ alkyl), wherein the $C_1$-$C_6$ alkyl is optionally substituted by 1 to 5 independently selected $R^{38}$;

L is CR, wherein R is selected from the group consisting of H, halo, —CN, $C_1$-$C_6$ alkyl, $C_2$-$C_6$ alkenyl and $C_2$-$C_6$ alkynyl, wherein $C_1$-$C_6$ alkyl, $C_2$-$C_6$ alkenyl, and $C_2$-$C_6$ alkynyl are optionally substituted; and $R^{13}$ is heterocyclyl or heteroaryl, wherein heterocyclyl and heteroaryl are substituted with 1 to 5 independently selected $R^{38}$;

Y is a bond or is —$(C(R^{11})(H))_t$-, wherein t is an integer from 1 to 6; and $R^{11}$ at each occurrence is independently H or $C_1$-$C_6$ alkyl.

46. The compound according to claim 45, wherein X and $X^1$ are both hydrogen.

47. The compound according to claim 45, wherein $R^1$, $R^2$, $R^3$ and $R^4$ are independently H or halogen.

48. The compound according to claim 45, wherein $R^1$ is fluorine or chlorine.

49. The compound according to claim 45, wherein $R^2$, $R^3$, $R^5$, and $R^6$ are each hydrogen.

50. The compound according to claim 45, wherein $R^{11}$ is H.

51. The compound according to claim 45, wherein Z is sulfur.

52. The compound according to claim 45, wherein $R^{38}$ is $NR^{36}R^{39}$.

53. The compound according to claim 45, wherein $R^{40}$ is H or $C_1$-$C_{10}$ alkyl.

54. The compound according to claim 1, represented by the formula A-5.

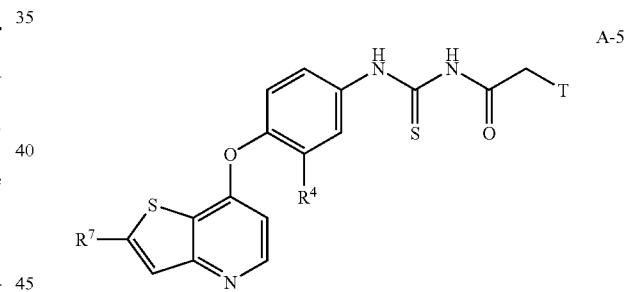

A-5 and pharmaceutically acceptable salts thereof, wherein $R^7$ is selected from the group consisting of —$C(O)NR^{42}R^{43}$, —Y—($C_6$-$C_{10}$aryl), —Y—(heteroaryl), —$C(O)$—($C_3$-$C_{10}$ cycloalkyl), —$C(O)$—(heterocyclyl), —$C(O)$—($C_6$-$C_{10}$ aryl) and —$C(O)$-heteroaryl), wherein the aforementioned $R^7$ groups are substituted with 1 to 5 independently selected $R^{38}$;

$R^4$ is selected from the group consisting of H and halogen; and

T is selected from the group consisting of cycloalkyl, heterocyclyl, aryl, heteroaryl and arylalkyl, each of which is optionally substituted with 1 to 3 independently selected $R^{20}$.

55. The compound according to claim 54, wherein $R^7$ is selected from the group consisting of $C(O)NR^{42}R^{43}$ and —Y—(heteroaryl), wherein —Y—(heteroaryl) is substituted with 1 to 5 independently selected $R^{38}$.

56. The compound according to claim 54, wherein $R^7$ is $C(O)NR^{42}R^{43}$ substituted with 1 to 5 independently selected $R^{38}$.

57. The compound according to claim 54, wherein $R^{42}$ and $R^{43}$ taken together with the nitrogen to which they are attached form a $C_5$-$C_9$ heterocyclyl ring, wherein said ring is substituted with 1 to 5 independently selected $R^{44}$ substituents, with the proviso that $R^{42}$ and $R^{43}$ are not both bonded to the nitrogen directly through and oxygen.

58. The compound according to claim 54, wherein $R^4$ is halogen.

59. The compound according to claim 1, represented by the formula A-6:

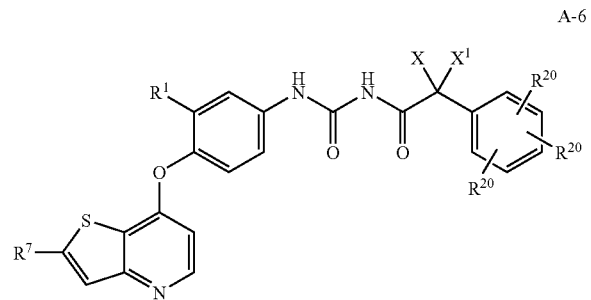

A-6 and pharmaceutically acceptable salts thereof, wherein
- $R^1$ is selected from the group consisting of hydrogen, halo, $C_1$-$C_6$ alkyl, $C_2$-$C_6$ alkenyl or $C_2$-$C_6$ alkynyl, wherein $C_1$-$C_6$ alkyl, $C_2$-$C_6$ alkenyl and $C_2$-$C_6$ alkynyl are optionally substituted;
- $R^7$ is selected from the group consisting of C(=O)NR$^9$R$^{10}$, —C(=O)(C$_6$-C$_{10}$aryl), —C(=O)(heterocyclyl), —C(=O)(heteroaryl), —Y—(C$_6$-C$_{10}$aryl), —Y—(5 to 10 membered heterocyclyl), —Y—(heteroaryl), —SR$^{6a}$, —S-aryl, —S—(heteroaryl), —S—C$_1$-C$_6$ alkyl, —SO—C$_1$-C$_6$ alkyl, —SO$_2$-C$_1$-C$_6$ alkyl, —NR$^9$R$^{10}$, —SO$_2$NR$^9$R$^{10}$CO$_2$R$^9$, —C≡C—(CR$^{45}$R$^{45}$)$_n$—R$^{46}$ and —C(=NR$^{42}$)NR$^{37}$R$^{43}$, wherein n is an integer ranging from 0 to 6 and wherein C$_1$-C$_6$ alkyl, aryl, heterocycle and heteroaryl are each independently substituted with 1 to 5 independently selected R$^{38}$;
- $R^9$ and $R^{10}$ are independently selected from the group consisting of C$_1$C$_6$ alkyl, —Y—(C$_3$-C$_{10}$cycloalkyl), —(C$_1$-C$_6$ heteroalkyl), —Y—(C$_6$-C$_{10}$aryl), —Y—(5 to 10 membered heterocyclyl), —Y—(C$_6$-C$_{10}$heteroaryl), —Y—O—Y$^1$—O—R$^{11}$, —Y$^1$—CO$_2$—R$^{11}$and —Y—O—R$^{11}$, wherein said C$_1$-C$_6$ alkyl, heteroalkyl, cycloalkyl, aryl, heterocycle, and heteroaryl are each substituted with one or more independently selected R$^{44}$, or
- $R^9$ and $R^{10}$ taken together with the nitrogen to which they are attached form a C$_5$-C$_9$ heterocyclyl ring or a heteroaryl ring, wherein said ring is substituted with 1 to 5 independently selected R$^{44}$;
- each R$^{20}$ is independently selected from the group consisting of H, halo, —OR$^{17}$ and —C(O)OR$^{17}$;
- Y is a bond or is —(C(R$^{11}$)(H))$_t$—, wherein t is an integer from 1 to 6;
- Y$^1$ is —(C(R$^{11}$)(H))$_t$—; and
- R$^{11}$ at each occurrence is independently H or C$_1$-C$_6$ alkyl.

60. The compound according to claim 59, wherein R$^7$ is selected from the group consisting of C(O)NR$^9$R$^{10}$ and —Y-(heteroaryl), wherein —Y—(heteroaryl) is substituted with 1 to 5 independently selected R$^{38}$.

61. The compound according to claim 59, wherein R$^9$ and R$^{10}$ taken together with the nitrogen to which they are attached form a $C_5$-$C_9$ heterocyclyl ring, wherein said ring is substituted with 1 to 5 independently selected R$^{44}$ substituents.

62. The compound according to claim 59, wherein R$^7$ is —Y—(heteroaryl), wherein said —Y—(heteroaryl) is substituted with 1 to 5 independently selected R$^{38}$.

63. The compound according to claim 59, wherein R$^1$ is fluorine.

64. The compound according to claim 59, wherein R$^{17}$ is selected from the group consisting of H and $C_1$-$C_6$ alkyl.

65. The compound according to claim 59, wherein R$^{37}$ is selected from the group consisting of H and $C_1$-$C_6$ alkyl.

66. The compound according to claim 59, wherein each R$^{20}$ is independently selected from the group consisting of H, halogen and —O—(C$_1$-C$_6$)alkyl.

67. A pharmaceutical composition comprising the compound according to claim 1 and a pharmaceutically acceptable carrier.

68. The compound according to claim 23, wherein R$^7$ is selected from the group consisting of

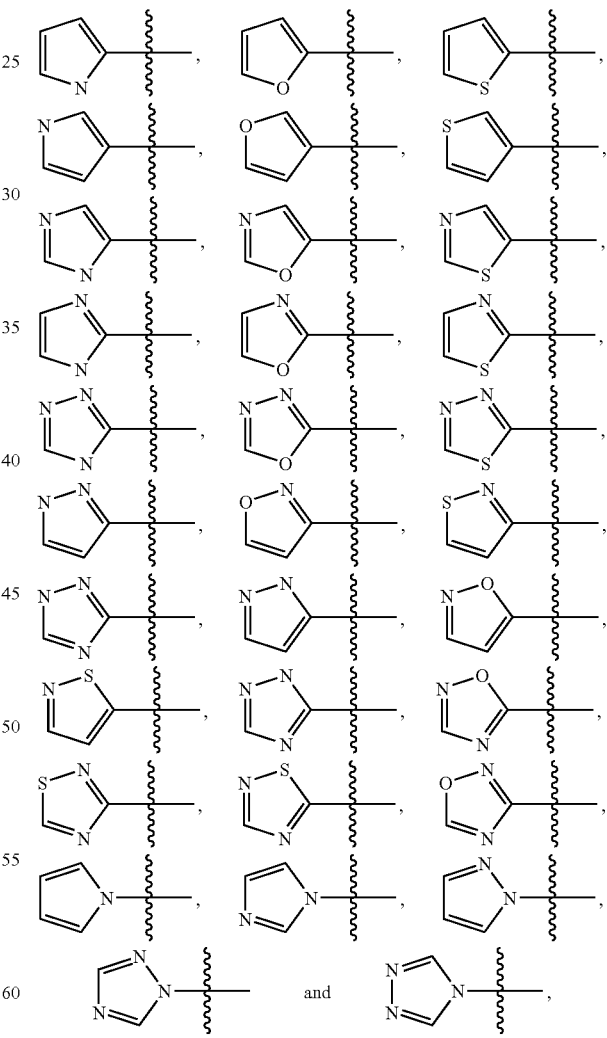

wherein the members of said group are optionally substituted by 1 to 3 independently selected R$^{38}$.

69. The compound according to claim 23, wherein R$^7$ is selected from the group consisting of

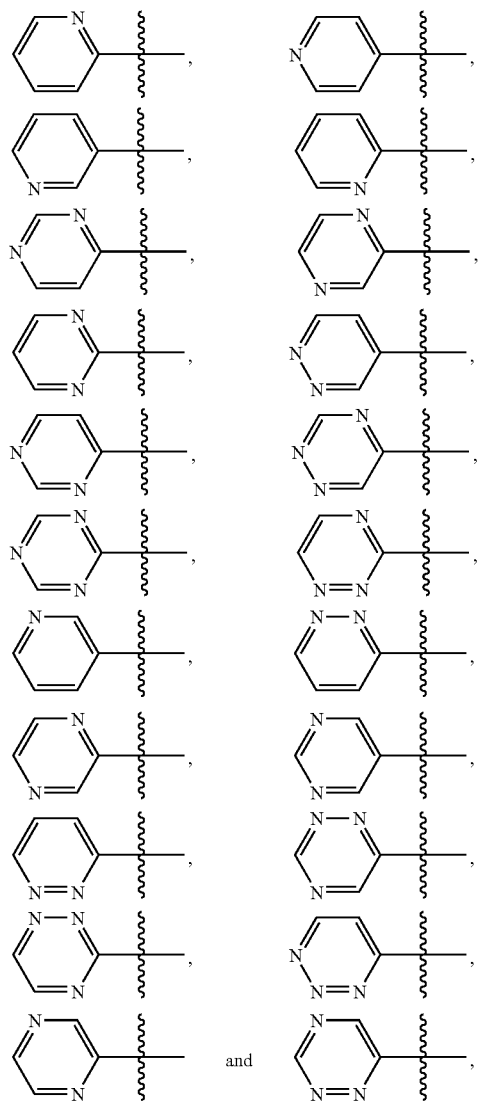

wherein the members of said group are optionally substituted with 1 to 3 independently selected $R^{38}$.

70. The compound according to claim 31, wherein $R^7$ is selected from the group consisting of

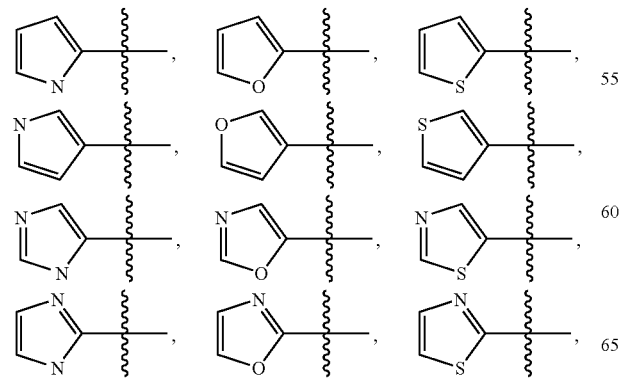

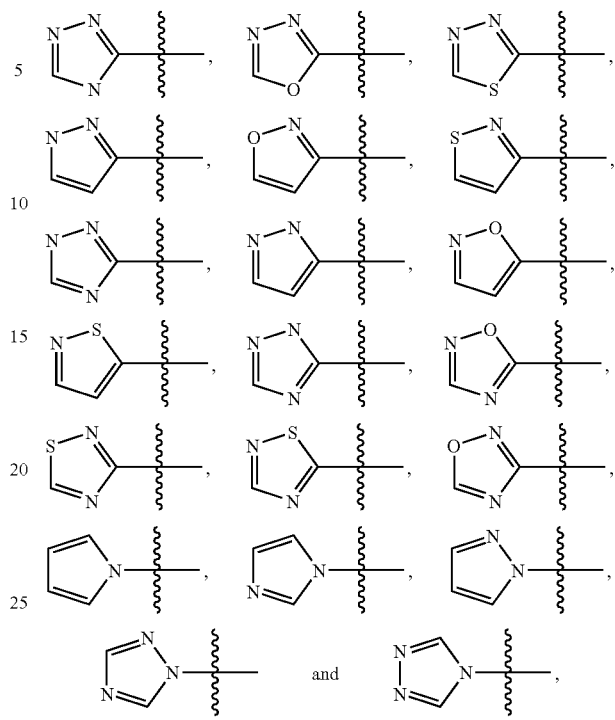

wherein the members of said group are optionally substituted by 1 to 3 independently selected $R^{38}$.

71. The compound according to claim 31, wherein $R^7$ is selected from the group consisting of

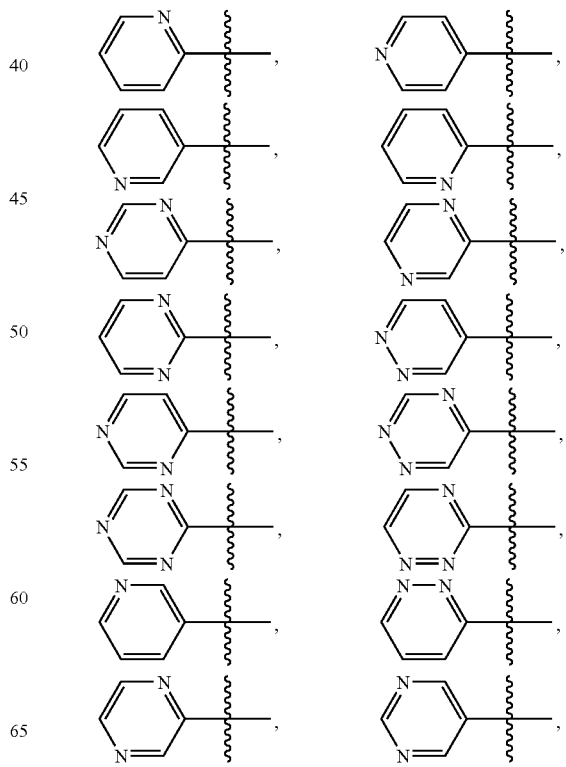

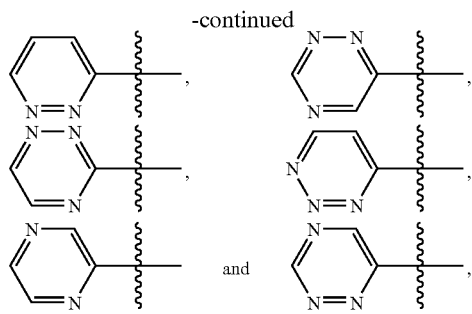

wherein the members of said group are optionally substituted with 1 to 3 independently selected $R^{38}$.

72. The compound according to claim 31, wherein $R^7$ is —Y—(heteroaryl), substituted with 1 to 5 independently selected $R^{38}$.

73. The compound according to claim 31, wherein X and $X^1$ are both H; $R^1$ is halogen, $R^7$ is —Y—(heteroaryl), substituted with 1 to 5 independently selected $R^{38}$; and $R^{38}$ is selected from the group consisting of —$(CH_2)_j NR^{39}$ $(CH_2)_n R^{36}$, —$(CH_2)_j NR^{39}(CH_2)_i NR^{36} R^{39}$, and —$(CH_2)_j O(CH_2)_i{}^2 NR^{36} R^{39}$, wherein n is an integer ranging from 0 to 6, j is an integer ranging from 0 to 2, and is an integer ranging from 1 to 6.

74. The compound according to claim 1, wherein
W is O;
Z is S or O;
X and $X^1$ are both H;
$R^1$ is H or halogen;
$R^2$, $R^3$ and $R^4$ are each H;
D is CH;
R is H or halogen;
E is $E^1$, wherein $E^1$ is selected from the group consisting of —$C(O)NR^{42} R^{43}$, —$SO_2 NR^{42} R^{43}$, $C(=NR^{42})NR^{37} R^{43}$, —$CO_2 R^{42}$, —C(O)(heterocyclyl), —C(O)(heteroaryl), —Y—($C_6$-$C_{10}$ aryl), —Y—(heteroaryl), —Y—(5 to 10 membered heterocyclic), —$SR^{6a}$, —$S(O)R^{6a}$, —$SO_2 R^{6a}$, wherein each of said $E^1$ are substituted with 1 to 5 independently selected $R^{38}$; and $R^{38}$ is selected from the group consisting of —$NR^{36}C(O)R^{39}$, —$NR^{36}R^{39}$, —$(CH_2)_j O(CH_2)_i NR^{36}R^{39}$, —$S(O)_j (C_1$-$C_6$alkyl), —$(CH_2)_j NR^{39}(CH_2)_i NR^{36}R^{39}$, —$(CH_2)_j NR^{39}(CH_2)_n R^{36}$, —$(CH_2)_n NR^{36}R^{39}$, wherein j is an integer ranging from 0 to 2, n is an integer ranging from 0 to 6, i is an integer ranging from 1 to 6, the —$(CH_2)_i$- and —$(CH_2)_n$-moieties of the foregoing $R^{38}$ groups optionally include a carbon-carbon double or triple bond where n is an integer between 2 and 6, and the alkyl, moieties of the foregoing $R^{38}$ groups are optionally substituted by one or more substituents independently selected from the group consisting of halo, cyano, nitro, trifluoromethyl, azido, —OH, —C(O)$R^{40}$, —C(O)O$R^{40}$, —OC(O)$R^{40}$, —OC(O)O$R^{40}$, —$NR^{36}C(O)R^{39}$, —C(O)$NR^{36}R^{39}$, —$(CH_2)_n NR^{36}R^{39}$, $C_1$-$C_6$ alkyl, $C_3$-$C_{10}$ cycloalkyl, —$(CH_2)_n (C_6$-$C_{10}$ aryl), —$(CH_2)_n (5$-10 membered heterocyclyl), —$(CH_2)_n O(CH_2)_i{}^2 OR^{37}$, and —$(CH_2)_n OR^{37}$, wherein n is an integer ranging from 0 to 6 and $i^2$ is an integer ranging from 2 to 6.

75. The compound according to claim 23, wherein X and $X^1$ are both hydrogen;
$R^1$ is fluorine;
L is CH;

$R^7$ is Y-Heteroaryl substituted with 1 to 5 independently selected $R^{38}$; and
Z is sulfur.

76. The compound according to claim 31, wherein $R^1$ is fluorine;
$R^7$ is —Y-(heteroaryl) substituted with 1 to 5 independently selected $R^{38}$;
$R^{38}$ is selected from the group consisting of —$(CH_2)_j NR^{39}(CH_2)_n R^{36}$, —$(CH_2)_j NR^{39}(CH_2)_i NR^{36}R^{39}$, and —$(CH_2)_j O(CH_2)_i NR^{36}R^{39}$, wherein n is an integer ranging from 0 to 6, is an integer ranging from 0 to 2, and i is an integer ranging from 1 to 6;
$R^{20}$ is selected from the group consisting of H, halogen, $OR^{17}$ and —C(O)O$R^{17}$;
X and $X^1$ are both H; and
$R^{17}$ is H or $C_1$-$C_6$alkyl.

77. The compound according to claim 1, selected from the group consisting of
1-(4-(2-(N-methoxy-N-methylcarbamoyl)thieno[3,2-b] pyridin-7yloxy)-3-fluorophenyl)-3-(2-phenylacetyl) thiourea,
7-[2-Fluoro-4-(3-phenylacetyl-thioureido)-phenoxy]-thieno[3,2-b]pyridine-2-carboxylic acid (2-diisopropylamino-ethyl)-amide, formate salt,
(R)-N-(3-Fluoro-4-(2-(3-Hydroxypyrrolidine-1-carbonyl)thieno[3,2-b]pyridin-7-yloxy)phenylcarbamothioyl)-2-phenylacetamide,
(S)-N-(3-Fluoro-4-(2-(3-hydroxypyrrolidine-1-carbonyl)thieno[3,2-b]pyridin-7-yloxy) phenylcarbamothioyl)-2-phenylacetamide,
7-[2-Fluoro-4-(3-phenylacetyl-thioureido)-phenoxy]-thieno[3,2-b]pyridine-2-carboxylic acid (2-dimethylamino-ethyl)-amide, formate salt,
7-[2-Fluoro-4-(3-phenylacetyl-thioureido)-phenoxy]-thieno[3,2-b]pyridine-2-carboxylic acid bis -(2-methoxy-ethyl)-amide,
7-[2-Fluoro-4-(3-phenylacetyl-thioureido)-phenoxy]-thieno[3,2-b]pyridine-2-carboxylic acid (2-cyanoethyl)-phenyl-amide,
N-(3-Fluoro-4-(2-(4-(methylsulfonyl)phenyl)thieno[3,2-b]pyridin-7-yloxy) phenylcarbamothioyl)-2-phenylacetamide,
1-(3-Fluoro-4-(2-(3-morpholinoprop-1-ynyl)thieno [3,2-b]pyridin-7-yloxy)phenyl)-3-(2-phenylacetyl)thiourea,
2-((4-7-(2-Fluoro-4-nitrophenoxy)thieno[3,2-b]pyridin-2-yl)phenyl)methylamino) ethanol, N-(3-Fluoro-4-(2-(3-((2-methoxyethylamino)methyl)phenyl)thieno[3,2] pyridin-7-yloxy)phenylcarbamothioyl)-2-phenylacetamide,
1-(3-Fluoro-4-(2-(2-((2-methoxyethylamino)methyl)phenyl)thieno[3,2-b]pyridin-7-yloxy)phenyl)-3-(2-phenylacetyl)thiourea,
1-(3-Fluoro-4-(2-(3-((2-morpholinoethylamino)methyl) phenyl)thieno [3,2-b]pyridin-7-yloxy)phenyl)-3-(2-phenylacetyl)thiourea,
N-(3-Fluoro-4-(2-(4((2-(methylamino)ethylamino)methyl)phenyl)thieno [3,2-b]pyridin-7-yloxy)phenylcarbamothioyl)-2-phenylacetamide
1-(3-Fluoro-4-(2(3-((2-methoxyethylamino)methyl)phenyl)thieno [3,2-b]pyridin-7 -yloxy)phenyl)-3-(2-phenyl acetyl)thiourea,
1-(3-Fluoro-4-(2-(3-(2-(methylamino)ethylamino)methyl)phenypthieno [3,2-b]pyridin- 7-yloxy)phenyl)-3-(2-phenylacetyl)thiourea,
1-(3-Fluoro-4-(2-(4-(((tetrahydrofuran-2-yl)methylamino)methyl)phenyl)thieno [3,2-b]pyridin-7-yloxy) phenyl)-3-(2-phenylacetyl)thiourea, 7[2-Fluoro-4-(3-phenylacetyl-thioureido)-phenoxy]-thieno [3,2-b]pyridine-2-sulfonic acid amide, (R)-N-(4-(2-(3-(Dimethylamino)pyrrolidine-1-carbonyl) thieno [3,2-b]pyridin-7-yloxy)-3- fluorophenylcarbamothioyl)-2-phenylacetamide, N-(3-Fluoro-4-(2-(4-hydroxyphenyl)thieno [3,2-b]pyridin-7-yloxy)phenylcarbamothioyl)-2-phenylacetamide, N-(3-Fluoro-4-(2-(2-hydroxyphenyl)thieno [3,2-b]pyridin-7-yloxy)phenylcarbamothioyl)-2-phenylacetamide, N-(3-Fluoro-4-(2-(3-hydroxyphenypthieno [3,2-b]pyridin-7-yloxy)phenylcarbamothioyl)-2-phenylacetamide, N-(4-(2-(4-(4-Aminobutoxy)phenyl)thieno [3,2-b]pyridin-7-yloxy)-3-fluorophenylcarbam othioyl)-2-phenylacetamide di-hydrochloride, N-(3-Fluoro-4-(2-(1-(2-(methylamino)ethyl)-1H-pyrazol-4-yl)thieno[3,2-b]pyridin-7-yloxy)phenylcarbamothioyl)-2-(2-methoxyphenyl)acetamide, N-(4-(2-(4-Hydroxyphenyl)thieno[3,2-b]pyridin-7-yloxy)phenylcarbamothioyl)-2-phenylacetamide, N-(3-Fluoro-4-(2-(3-hydroxyazetidine-1-carbonyl)thieno [3,2-b]pyridin-7-yloxy)phenylcarbamothioyl)-2-(2-methoxyphenyl)acetamide, and N-(4-(2-(4-(Dimethylamino)phenyl)thieno[3,2-b]pyridin-7-yloxy)-3-fluorophenylcarbamothioyl)-2-phenylacetamide.

* * * * *

UNITED STATES PATENT AND TRADEMARK OFFICE
CERTIFICATE OF CORRECTION

PATENT NO. : 7,772,247 B2
APPLICATION NO. : 11/191617
DATED : August 10, 2010
INVENTOR(S) : Vaisburg et al.

It is certified that error appears in the above-identified patent and that said Letters Patent is hereby corrected as shown below:

In Claim 1, Column 298, line 51, please cancel the text "-$NO_2$, -$OR^{17}$," and insert the following text -- -$NO_2$, -$NH_2$, -$OR^{17}$, --.

In Claim 1, Column 299, line 28, please cancel the text "-$NR^{6a}\ R^{6b}$" and insert the following text -- -$NR^{6a}R^{6b}$ --.

In Claim 1, Column 299, line 46 to line 47, please cancel the text "-$(CH_2)_j(CH_2)_iNR^{36}R^{39}$" and insert the following text -- -$(CH_2)_jO(CH_2)_iNR^{36}R^{39}$ --.

In Claim 1, Column 299, line 50, please cancel the text "-$(CH_2)_iNR^{39}(CH_2)_iS(O)_j(C_1\text{-}C_6 alkyl)$," and insert the following text -- -$(CH_2)_jNR^{39}(CH_2)_iS(O)_j(C_1\text{-}C_6 alkyl)$, --.

In Claim 1, Column 300, line 24, please cancel the text "-$NR,^{36}SO_2NR^{37}R^{41}$," and insert the following text -- -$NR^{36}SO_2NR^{37}R^{41}$, --.

In Claim 1, Column 300, line 29, please cancel the text "-$(CH_2)_jNR^{39}(CH^2)_i{}^2NR^{37}C(O)R^{40}$," and insert the following text -- -$(CH_2)_jNR^{39}(CH_2)_i{}^2NR^{37}C(O)R^{40}$, --.

In Claim 1, Column 300, line 35, please cancel the text "-$(CH_2)_i{}^2$-" and insert the following text -- -$(CH_2)_i$ --.

In Claim 1, Column 300, line 56 to line 57, please cancel the text "-$(CH_2)_nO(CH_2)_i{}^2OR^{37}$" and insert the following text -- -$(CH_2)_nOR^{37}$ --.

In Claim 1, Column 300, line 58, please cancel the text "$i^2$" and insert the following text -- i --.

In Claim 1, Column 300, line 66, please cancel the text "-$(CH_2)_nO(CH_2)_i{}^2OR^{37}$" and insert the following text -- -$(CH_2)_nO(CH_2)_iOR^{37}$ --.

Signed and Sealed this
Eighteenth Day of January, 2011

David J. Kappos
*Director of the United States Patent and Trademark Office*

CERTIFICATE OF CORRECTION (continued)

In Claim 1, Column 300, line 67, please cancel the text "$i^2$" and insert the following text -- $i$ --.

In Claim 1, Column 301, line 16, please cancel the text "$R^6a$ and $R^6b$" and insert the following text -- $R^{6a}$ and $R^{6b}$ --.

In Claim 1, Column 301, line 31 to line 35, please cancel the text "-N morpholino,)-$(CZ^9Z^{10})_rNH_2,)$-$(CZ^9Z^{10})_rNHZ^3$,-$(CZ^9Z^{10})_rNZ^7Z^8$,)-$X^6(CZ^9Z^{10})_r$-$(C_3$-$C_8)$cycloalkyl,)-$X^6(CZ^9Z^{1o}{}_r(C_5$-$C_8)$cycloalkenyl,)-$X^6(CZ^9Z^{1o}{}_r$aryl and -$X^6(CZ^9Z^{10})_r$_heterocycle," and insert the following text -- -N-morpholino, -$(CZ^9Z^{10})_rNH_2$, -$(CZ^9Z^{10})_rNHZ^3$, -$(CZ^9Z^{10})_rNZ^7Z^8$, -$X^6(CZ^9Z^{10})_r$-$(C_3$-$C_8)$cycloalkyl, -$X^6(CZ^9Z^{10})_r$-$(C_5$-$C_8)$cycloalkenyl, -$X^6(CZ^9Z^{10})_r$-aryl and -$X^6(CZ^9Z^{10})_r$-heterocycle, --.

In Claim 1, Column 301, line 41, please cancel the text "-$P(0)_3(Z^7)_2$" and insert the following text -- -$P(O)_3(Z^7)_2$ --.

In Claim 1, Column 301, line 43 to line 44, please cancel the text "-N morpholino,)-$(CZ^9Z^{10})_rNH_2,)$-$(CZ^9Z^{10})_rNHZ^3$," and insert the following text -- -N-morpholino, -$(CZ^9Z^{10})_rNH_2$, -$(CZ^9Z^{10})_rNHZ^3$, --.

In Claim 1, Column 301, line 46, please cancel the text "-$X(CZ^9Z^{10})_r(C_5$-$C_8)$cycloalkenyl," and insert the following text -- -$X^6(CZ^9Z^{10})_r$-$(C_5$-$C_8)$cycloalkenyl, --.

In Claim 1, Column 301, line 62, please cancel the text "$(C_i$-$C_{12})$alkyl," and insert the following text -- $(C_1$-$C_{12})$alkyl, --.

In Claim 1, Column 302, line 12 to line 13, please cancel the text "-$N[(C_1$-$C_4)$alkyl][$(C_I$-$C_4)$alkyl];" and insert the following text -- -$N[(C_1$-$C_4)$alkyl][$(C_1$-$C_4)$alkyl]; --.

In Claim 1, Column 302, line 14, please cancel the text "-$C{\equiv}C$-$(CR^{45}R^{45})_n{}^2$-$R^{46}$, $n^2$" and insert the following text -- -$C{\equiv}C$-$(CR^{45}R^{45})_n$-$R^{46}$, n --.

In Claim 1, Column 302, line 23, please cancel the text "$OC(O)0R^{49}$" and insert the following text -- $OC(O)OR^{49}$ --.

In Claim 1, Column 302, line 26, please cancel the text "–$(CH_2)_n0R^{50}$" and insert the following text -- -$(CH_2)_nOR^{50}$ --.

In Claim 1, Column 302, line 27, please cancel the text "$(CH_2),SR^{49}$" and insert the following text -- -$(CH_2)_nSR^{49}$ --.

In Claim 1, Column 302, line 28, please cancel the text "-$(CH_2),R^{49}$, -$(CH_2),CN$," and insert the following text -- -$(CH_2)_nR^{49}$, -$(CH_2)_nCN$, --.

CERTIFICATE OF CORRECTION (continued)

In Claim 1, Column 302, line 31, please cancel the text "-(CH$_2$)$_n$0R$^{49}$," and insert the following text -- -(CH$_2$)$_n$OR$^{49}$, --.

In Claim 1, Column 302, line 33, please cancel the text "-(CH$_2$)$_N$NR$^{50}$R$^{51}$," and insert the following text -- -(CH$_2$)$_n$NR$^{50}$R$^{51}$, --.

In Claim 1, Column 302, line 65, please cancel the text "-(Z$_{11}$)-(Z$^{12}$)$_m$-(Z$^{13}$)$_{m1}$," and insert the following text -- -(Z$^{11}$)-(Z$^{12}$)$_m$-(Z$^{13}$)$_{m1}$, --.

In Claim 13, Column 303, line 40, please cancel the text "E$^{\prime}$" and insert the following text -- E$^1$ --.

In Claim 13, Column 303, line 42 to line 43, please cancel the text "-C(O)(heteroaryl), -Y-(C$_6$-C$_{10}$membered heterocyclic)," and insert the following text -- -C(O)(heteroaryl), -Y-(C$_6$-C$_{10}$aryl), -Y-(heteroaryl), -Y-(5 to 10 membered heterocyclic), --.

In Claim 13, Column 303, line 44, please cancel the text "E$^{\prime}$" and insert the following text -- E$^1$ --.

In Claim 14, Column 303, line 48 to line 49, please cancel the text "-S(O)$_{,j}$(C$_1$-C$_6$alkyl)," and insert the following text -- -S(O)$_j$(C$_1$-C$_6$alkyl), --.

In Claim 14, Column 303, line 49, please cancel the text "-(C$_2$)$_n$R$^{36}$," and insert the following text -- -(CH$_2$)$_j$NR$^{39}$(CH$_2$)$_n$R$^{36}$, --.

In Claim 14, Column 303, line 58, please cancel the text "-C(O)R$^4$," and insert the following text -- -C(O)R$^{40}$, --.

In Claim 14, Column 303, line 62, please cancel the text "-(CH$_2$)$_n$0R$^{37}$," and insert the following text -- -(CH$_2$)$_n$OR$^{37}$, --.

In Claim 22, Column 304, line 35, please cancel the text "-C≡C-(CR$^{45}$R$^{45}$)$_n$-$^{R46}$," and insert the following text -- -C≡C-(CR$^{45}$R$^{45}$)$_n$-R$^{46}$, --.

In Claim 23, Column 305, line 28, please cancel the text "C$_I$-C$_6$ alkyl," and insert the following text -- C$_1$-C$_6$ alkyl, --.

In Claim 31, Column 306, line 3, please cancel the text "C$_1$-C$_6$ alkenyl" and insert the following text -- C$_1$-C$_6$alkyl, C$_2$-C$_6$ alkenyl, --.

In Claim 31, Column 306, line 14 to line 15, please cancel the text "-S  -(heteroaryl)," and insert the following text -- -S-(heteroaryl), --.

In Claim 31, Column 306, line 17, please cancel the text "-C≡C-(CR$^{45}$R$^{45}$)$_{n-R}$$^{46}$" and insert the following text -- -C≡C-(CR$^{45}$R$^{45}$)$_n$-R$^{46}$ --.

CERTIFICATE OF CORRECTION (continued)
U.S. Pat. No. 7,772,247 B2

In Claim 31, Column 306, line 26, please cancel the text "-$Y^1$-$CO_2$-$^{11}$," and insert the following text -- -$Y^1$-$CO_2$-$R^{11}$, --.

In Claim 36, Column 306, line 57, please cancel the text "-$(CH_2)_jNR^{39}(CH)_2)_iNR^{36}R^{39}$," and insert the following text -- -$(CH_2)_jNR^{39}(CH_2)_iNR^{36}R^{39}$ --.

In Claim 45, Column 308, line 7, please cancel the text "$C_1$-$C_6$ alkyl," and insert the following text -- $C_1$-$C_6$ alkyl, --.

In Claim 59, Column 309, line 10 to line 25, please cancel the chemical formula and insert the following chemical formula

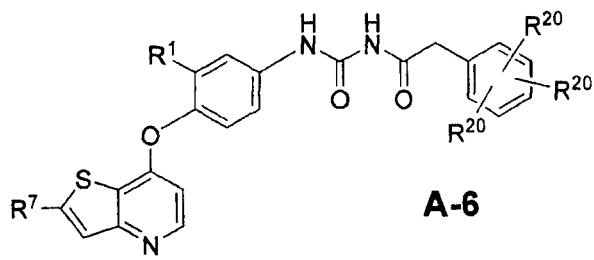

--                                           --.

In Claim 59, Column 309, line 36, please cancel the text "-$SO_2NR^9R^{10}CO_2R^9$," and insert the following text -- -$SO_2NR^9R^{10}$, $CO_2R^9$, --.

In Claim 59, Column 309, line 60, please cancel the text "-$(C(R^{11})(H)_t$-;" and insert the following text -- -$(C(R^{11})(H))_t$; --.

In Claim 73, Column 313, line 27, please cancel the text "and is an integer" and insert the following text -- and $i^2$ is an integer --.

In Claim 74, Column 313, line 38, please cancel the text "-$^{SO}2NR^{42}R^{43}$," and insert the following text -- -$SO_2NR^{42}R^{43}$, --.

In Claim 76, Column 314, line 11, please cancel the text "0 to 6, is an integer" and insert the following text -- 0 to 6, j is an integer --.

In Claim 76, Column 314, line 14, please cancel the text "-$C(O)0R^{17}$;" and insert the following text -- -$C(O)OR^{17}$; --.

In Claim 77, Column 314, line 25 to line 27, please cancel the text "(*R*)-N-(3-Fluoro-4-(2-(3-hydroxypyrrolidine-1-carbonyl)thieno[3,2-*b*]pyridin-7-yloxy)phenylearbamothioyl)-2-phenylacetamide," and insert the following text -- (*R*)-N-(3-Fluoro-4-(2-(3-hydroxypyrrolidine-1-carbonyl)thieno[3,2-*b*]pyridin-7-yloxy)phenylcarbamothioyl)-2-phenylacetamide, --.

In Claim 77, Column 314, line 46 to line 50, please cancel the text "N-(3-Fluoro-4-(2-(3-((2- methoxyethylamino)methyl)phenyl)thieno[3,2]pyridin-7-yloxy)phenylcarbamothioyl)-2-phenylacetamide," and insert the following text -- N-(3-Fluoro-4-(2-(3-((2-methoxyethylamino)methyl)phenyl)thieno[3,2-b]pyridin-7-yloxy)phenylcarbamothioyl)-2-phenylacetamide, --.

In Claim 77, Column 314, line 59 to line 61, please cancel the text "1-(3-Fluoro-4-(2-(3-((2-methoxyethylamino)methyl)phenyl)thieno[3,2-b]pyridin-7-yloxy)phenyl)-3-(2-phenylacetyl)thiourea," and insert the following text -- 1-(3-Fluoro-4-(2-(4-((2-methoxyethylamino)methyl)phenyl)thieno[3,2-b]pyridin-7-yloxy)phenyl)-3-(2-phenylacetyl)thiourea, --.

In Claim 77, Column 314, line 62 to line 64, please cancel the text "1-(3-Fluoro-4-(2-(3-(2-(methylamino)ethylamino)methyl)phenylthieno[3,2-b]pyridin-7-yloxy)phenyl)-3-(2-phenylacetyl)thiourea," and insert the following text -- 1-(3-Fluoro-4-(2-(3-((2-(methylamino)ethylamino)methyl)phenyl)thieno[3,2-b]pyridin-7-yloxy)phenyl)-3-(2-phenylacetyl)thiourea, --.

In Claim 77, Column 315, line 13 to line 15, please cancel the text "N-(3-Fluoro-4-(2-(3-hydroxyphenylthieno [3,2-b]pyridin-7-yloxy)phenylcarbamothioyl)-2-phenylacetamide," and insert the following text -- N-(3-Fluoro-4-(2-(3-hydroxyphenyl)thieno[3,2-b]pyridin-7-yloxy)phenylcarbamothioyl)-2-phenylacetamide, --.

In Claim 77, Column 316, line 1 to line 3, please cancel the text "N-(4-(2-(4-(4-Aminobutoxy)phenyl)thieno [3,2-b]pyridin-7-yloxy)-3-fluorophenylcarbam othioyl)-2-phenylacetamide di-hydrochloride," and insert the following text -- N-(4-(2-(4-(4-Aminobutoxy)phenyl)thieno[3,2-b]pyridin-7-yloxy)-3-fluorophenylcarbamothioyl)-2-phenylacetamide di-hydrochloride, --.